United States Patent
Pan et al.

(10) Patent No.: US 11,820,822 B2
(45) Date of Patent: Nov. 21, 2023

(54) METHODS FOR SENSITIZING CANCER CELLS TO T CELL-MEDIATED KILLING BY MODULATING MOLECULAR PATHWAYS

(71) Applicant: DANA-FARBER CANCER INSTITUTE, INC., Boston, MA (US)

(72) Inventors: Deng Pan, Boston, MA (US); Kai W. Wucherpfennig, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/612,935

(22) PCT Filed: Jun. 5, 2018

(86) PCT No.: PCT/US2018/036046
§ 371 (c)(1),
(2) Date: Nov. 12, 2019

(87) PCT Pub. No.: WO2018/226685
PCT Pub. Date: Dec. 13, 2018

(65) Prior Publication Data
US 2020/0095320 A1 Mar. 26, 2020

Related U.S. Application Data

(60) Provisional application No. 62/515,738, filed on Jun. 6, 2017.

(51) Int. Cl.
| | | |
|---|---|---|
| *C12N 15/11* | (2006.01) | |
| *C07K 16/28* | (2006.01) | |
| *A61P 35/00* | (2006.01) | |
| *A61K 31/7105* | (2006.01) | |
| *A61K 38/19* | (2006.01) | |
| *A61K 39/395* | (2006.01) | |
| *G01N 33/50* | (2006.01) | |
| *A61K 45/06* | (2006.01) | |
| *A61K 39/00* | (2006.01) | |

(52) U.S. Cl.
CPC ...... *C07K 16/2809* (2013.01); *A61K 31/7105* (2013.01); *A61K 38/19* (2013.01); *A61K 39/39558* (2013.01); *A61P 35/00* (2018.01); *C07K 16/2812* (2013.01); *C07K 16/2815* (2013.01); *G01N 33/5023* (2013.01); *A61K 45/06* (2013.01); *A61K 2039/51* (2013.01)

(58) Field of Classification Search
CPC . C12N 15/111; C12N 15/113; C12N 2310/14; C12N 2310/20; C12N 5/0636; C12N 2510/00; A61K 35/17; A61K 39/0011; A61K 2300/00; A61K 2039/505; A61K 39/39558; A61P 35/00; A61P 35/04
See application file for complete search history.

(56) References Cited

U.S. PATENT DOCUMENTS

| | | |
|---|---|---|
| 4,405,712 A | 9/1983 | Vande Woude et al. |
| 4,683,195 A | 7/1987 | Mullis et al. |
| 4,777,127 A | 10/1988 | Suni et al. |
| 4,816,397 A | 3/1989 | Boss et al. |
| 4,816,567 A | 3/1989 | Cabilly et al. |
| 4,861,719 A | 8/1989 | Miller |
| 4,873,316 A | 10/1989 | Meade et al. |
| 4,946,778 A | 8/1990 | Ladner et al. |
| 4,980,289 A | 12/1990 | Temin et al. |
| 4,987,071 A | 1/1991 | Cech et al. |
| 5,116,742 A | 5/1992 | Cech et al. |
| 5,219,740 A | 6/1993 | Miller et al. |
| 5,225,539 A | 7/1993 | Winter |
| 5,322,770 A | 6/1994 | Gelfand |
| 5,328,470 A | 7/1994 | Nabel et al. |
| 5,459,039 A | 10/1995 | Modrich et al. |
| 5,498,531 A | 3/1996 | Jarrell |
| 5,580,859 A | 12/1996 | Felgner et al. |
| 5,631,236 A | 5/1997 | Woo et al. |
| 5,665,549 A | 9/1997 | Pinkel et al. |
| 5,679,647 A | 10/1997 | Carson et al. |
| 5,698,520 A | 12/1997 | Honjo et al. |
| 5,830,645 A | 11/1998 | Pinkel et al. |
| 6,197,501 B1 | 3/2001 | Cremer et al. |
| 6,335,167 B1 | 1/2002 | Pinkel et al. |
| 6,379,897 B1 | 4/2002 | Weidenhammer et al. |

(Continued)

FOREIGN PATENT DOCUMENTS

| | | |
|---|---|---|
| EP | 0125023 | 11/1984 |
| EP | 0120694 | 7/1985 |

(Continued)

OTHER PUBLICATIONS

Hugo et al., Genomic and transcriptomic features of response to anti-PD-1 therapy in metastatic melanoma, Cell, vol. 165, pp. 35-44. (Year: 2016).*
International Search Report and Written Opinion for International Application No. PCT/US2018/036046 dated Nov. 26, 2018.
Lemon, Bryan, et al. "Selectivity of chromatin-remodelling cofactors for ligand-activated transcription." Nature 414.6866 (2001): 924-928.
Lennon GG. High-throughput gene expression analysis for drug discovery. Drug Discov Today. Feb. 2000;5(2):59-66.
Lerner, Felicitas, et al. "Structural and functional characterization of human NAD kinase." Biochemical and biophysical research communications 288.1 (2001): 69-74.

(Continued)

*Primary Examiner* — Dana H Shin
(74) *Attorney, Agent, or Firm* — Baker Donelson

(57) ABSTRACT

The present invention is based, in part, on the identification of biomarkers, and methods of modulate thereof, for sensitizing cancer cells to T cell-mediated killing. For example, the present invention, in part, comprises methods of sensitizing cancer cells in a subject afflicted with a cancer to cytotoxic T cell-mediated killing comprising administering to a subject a therapeutically effective amount of an agent that modulates the biomarker.

6 Claims, 47 Drawing Sheets

Specification includes a Sequence Listing.

(56) References Cited

U.S. PATENT DOCUMENTS

| | | | |
|---|---|---|---|
| 6,451,536 | B1 | 9/2002 | Fodor et al. |
| 6,664,377 | B1 | 12/2003 | Xu |
| 6,989,262 | B2 | 1/2006 | Bejanin et al. |
| 7,004,940 | B2 | 2/2006 | Ryan et al. |
| 8,440,432 | B2 | 5/2013 | Voytas et al. |
| 8,697,359 | B1 | 4/2014 | Zhang |
| 9,181,535 | B2 | 11/2015 | Liu et al. |
| 2003/0215858 | A1 | 11/2003 | Templeton |
| 2010/0203056 | A1* | 8/2010 | Irving ............... A61P 43/00 424/139.1 |
| 2016/0122829 | A1 | 5/2016 | Hammerman |
| 2016/0237429 | A1 | 8/2016 | Cubillos-Ruiz et al. |
| 2019/0201396 | A1* | 7/2019 | Fisher ............... A61K 31/711 |
| 2019/0338369 | A1* | 11/2019 | Van Allen ........... G01N 33/574 |

FOREIGN PATENT DOCUMENTS

| | | | |
|---|---|---|---|
| EP | 0194276 | | 9/1986 |
| EP | 0264166 | | 4/1988 |
| EP | 0239400 | | 4/1989 |
| EP | 0430402 | | 9/1991 |
| EP | 0451216 | | 10/1991 |
| EP | 0415731 | | 1/1992 |
| EP | 0519596 | | 12/1992 |
| GB | 2200651 | | 8/1988 |
| WO | WO86/01533 | | 3/1986 |
| WO | WO88/09810 | | 12/1988 |
| WO | WO89/02468 | | 3/1989 |
| WO | WO89/05349 | | 6/1989 |
| WO | WO89/10134 | | 11/1989 |
| WO | WO90/02806 | | 3/1990 |
| WO | WO90/07936 | | 7/1990 |
| WO | WO90/11092 | | 10/1990 |
| WO | WO91/02805 | | 3/1991 |
| WO | WO1993/10218 | | 5/1993 |
| WO | WO1993/11230 | | 6/1993 |
| WO | WO93/22461 | | 11/1993 |
| WO | WO93/25234 | | 12/1993 |
| WO | WO93/25698 | | 12/1993 |
| WO | WO94/02610 | | 2/1994 |
| WO | WO94/03622 | | 2/1994 |
| WO | WO94/16101 | | 7/1994 |
| WO | WO95/22618 | | 8/1995 |
| WO | WO00/08191 | | 2/2000 |
| WO | WO2003/014960 | | 2/2003 |
| WO | WO2008/020079 | | 2/2008 |
| WO | WO2010/101870 | | 9/2010 |
| WO | WO2012/177624 | | 12/2012 |
| WO | 2015/077382 | | 5/2015 |
| WO | WO2015/077414 | | 5/2015 |
| WO | WO2015/184061 | | 12/2015 |
| WO | WO-2016/038550 | A1 | 3/2016 |
| WO | 2016/100975 | | 6/2016 |
| WO | WO-2016/089883 | A1 | 6/2016 |
| WO | WO-2017/007941 | A2 | 1/2017 |
| WO | WO-2017151502 | A1 * | 9/2017 ............. A61P 35/04 |
| WO | WO-2018/226685 | A2 | 12/2018 |

OTHER PUBLICATIONS

Leschziner, Andres E., et al. "Structural studies of the human PBAF chromatin-remodeling complex." Structure 13.2 (2005): 267-275.

Lessard, Julie, et al. "An essential switch in subunit composition of a chromatin remodeling complex during neural development." Neuron 55.2 (2007): 201-215.

Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.

Li, Bo, et al. "Comprehensive analyses of tumor immunity: implications for cancer immunotherapy." Genome biology 17.1 (2016): 1-16.

Li, Guoqiang, et al. "SPOP promotes tumorigenesis by acting as a key regulatory hub in kidney cancer." Cancer cell 25.4 (2014): 455-468.

Li, Heng, and Richard Durbin. "Fast and accurate short read alignment with Burrows-Wheeler transform." bioinformatics 25.14 (2009): 1754-1760.

Li, Meng, et al. "Inactivating mutations of the chromatin remodeling gene ARID2 in hepatocellular carcinoma." Nature genetics 43.9 (2011): 828-829.

Li, Ting, et al. "Modularly assembled designer TAL effector nucleases for targeted gene knockout and gene replacement in eukaryotes." Nucleic acids research 39.14 (2011): 6315-6325.

Lin, Ming, et al. "dChipSNP: significance curve and clustering of SNP-array-based loss-of-heterozygosity data." Bioinformatics 20.8 (2004): 1233-1240.

Lin, Yanni, et al. "SAPTA: a new design tool for improving TALE nuclease activity." Nucleic acids research 42.6 (2014): e47-e47.

Love MI, Huber W, Anders S. Moderated estimation of fold change and dispersion for RNA-seq data with DESeq2. Genome Biol. 2014;15(12):550.

Luckow, Verne A., and Max D. Summers. "High level expression of nonfused foreign genes with Autographa californica nuclear polyhedrosis virus expression vectors." Virology 170.1 (1989): 31-39.

Mag, Matthias, and Joachim W. Engels. "Synthesis and selective cleavage of oligodeoxyribonucleotldes containing non-chiral internucieotlde phosphoramidate linkages." Nucleic acids research 17.15 (1989): 5973-5988.

Manguso, Robert T., et al. "In vivo CRISPR screening identifies Ptpn2 as a cancer immunotherapy target." Nature 647.7664 (2017): 413-418.

Mann, Richard, Richard C. Mulligan, and David Baltimore. "Construction of a retrovirus packaging mutant and its use to produce helper-free defective retrovirus." Cell 33.1 (1983): 153-159.

Marshall, R. L., et al. "Detection of HCV RNA by the asymmetric gap ligase chain reaction." Genome Research 4.2 (1994): 80-84.

Mascaro Jr, Jose M., and Jose M. Mascaro. "The Dermatologist's Position Concerning Nevi: A Vision Ranging From The Ugly Duckling to Little Red Riding Hood." Archives of dermatology 134.11 (1998): 1484-1485.

Maverakis, Emanual, et al. "Metastatic melanoma—a review of current and future treatment options." Acta dermato-venereologica 95.5 (2015): 516-527.

Maxam, Allan M., and Walter Gilbert. "A new method for sequencing DNA." Proceedings of the National Academy of Sciences 74.2 (1977): 560-564.

Messina, S., et al. "Dual-specificity phosphatase DUSP6 has tumor-promoting properties in human glioblastomas." Oncogene 30.35 (2011): 3813-3820.

Miao D, et al. Genomic correlates of response to immune checkpoint therapies in clear cell renal cell carcinoma. Science. Feb. 16, 2018;359(6377):801-806.

Miller, Jeffrey C., et al. "A TALE nuclease architecture for efficient genome editing." Nature biotechnology 29.2 (2011): 143-148.

Mohrmann, Lisette, and C. Peter Verrijzer. "Composition and functional specificity of SWI2/SNF2 class chromatin remodeling complexes." Biochimica et Biophysica Acta (BBA)—Gene Structure and Expression 1681.2-3 (2005): 59-73.

Mootha, Vamsi K., et al. "PGC-1a-responsive genes involved in oxidative phosphorylation are coordinately downregulated in human diabetes." Nature genetics 34.3 (2003): 267-273.

Moscou, Matthew J., and Adam J. Bogdanove. "A simple cipher governs DNA recognition by TAL effectors." Science 326.5959 (2009): 1501-1501.

Muppirala, Madhavi, Vijay Gupta, and Ghanshyam Swarup. "Tyrosine phosphorylation of a SNARE protein, syntaxin 17: implications for membrane trafficking in the early secretory pathway." Biochimica et Biophysica Acta (BBA)—Molecular Cell Research 1823.12 (2012): 2109-2119.

Murakami, Hiroshi, Lance Liotta, and Robert A. Star. "IF-LCM: Laser capture microdissection of immunofluorescently defined cells for mRNA analysis: Rapid Communication." Kidney international 58.3 (2000): 1346-1353.

(56) References Cited

OTHER PUBLICATIONS

Myers, Eugene W., and Webb Miller. "Optimal alignments in linear space." Bioinformatics 4.1 (1988): 11-17.
Myers, Richard M., et al. "Detection of single base substitutions in total genomic DNA." Nature 313.6002 (1985): 495-498.
Myers, Richard M., Zoia Larin, and Tom Maniatis. "Detection of single base substitutions by ribonuclease cleavage at mismatches in RNA: DNA duplexes." Science 230.4731 (1985): 1242-1246.
Nagl Jr, Norman G., et al. "Distinct mammalian SWI/SNF chromatin remodeling complexes with opposing roles in cell-cycle control." The EMBO journal 26.3 (2007): 752-763.
Nakazawa, Hisayoshi, et al. "UV and skin cancer: specific p53 gene mutation in normal skin as a biologically relevant exposure measurement." Proceedings of the National Academy of Sciences 91.1 (1994): 360-364.
Narang, Saran A. "DNA synthesis." Tetrahedron 39.1 (1983): 3-22.
Neigeborn, Lenore, and Marian Carlson. "Genes affecting the regulation of SUC2 gene expression by glucose repression in *Saccharomyces cerevisiae*." Genetics 108.4 (1984): 845-858.
Nguyen, Loc T., et al. "Cross-linking the B7 family molecule B7-DC directly activates immune functions of dendritic cells." Journal of Experimental Medicine 196.10 (2002): 1393-1398.
Nicolas, Robert H., and Graham H. Goodwin. "Molecular cloning of polybromo, a nuclear protein containing multiple domains including five bromodomains, a truncated HMG-box, and two repeats of a novel domain." Gene 175.1-2 (1996): 233-240.
Nie, Zuqin, et al. "A specificity and targeting subunit of a human SWI/SNF family-related chromatin-remodeling complex." Molecular and cellular biology 20.23 (2000): 8879-8888.
Nishimura, Hiroyuki, et al. "Developmentally regulated expression of the PD-1 protein on the surface of double-negative (CD4-CD8-) thymocytes." International immunology 8.5 (1996): 773-780.
Numata M, et al. The clinical significance of SWI/SNF complex in pancreatic cancer. Int J Oncol. Feb. 2013;42(2):403-10.
Ogston, Keith N., et al. "A new histological grading system to assess response of breast cancers to primary chemotherapy: prognostic significance and survival." The Breast 12.5 (2003): 320-327.
Orita, Masato, et al. "Detection of polymorphisms of human DNA by gel electrophoresis as single-strand conformation polymorphisms." Proceedings of the National Academy of Sciences 86.8 (1989): 2766-2770.
Osbourn, Jane K., et al. "Directed selection of MIP-1a neutralizing CCR5 antibodies from a phage display human antibody library." Nature biotechnology 16.8 (1998): 778-781.
Overwijk, Willem W., et al. "Tumor regression and autoimmunity after reversal of a functionally tolerant state of self-reactive CD8+ T cells." The Journal of experimental medicine 198.4 (2003): 569-580.
Pacher, Pál, et al. "Endothelial dysfunction in aging animals: the role of poly (ADP-ribose) polymerase activation." British journal of pharmacology 135.6 (2002): 1347-1350.
Park, Ji-Hye, et al. "Mammalian SWI/SNF complexes facilitate DNA double-strand break repair by promoting ?—H2AX induction." The EMBO journal 25.17 (2006): 3986-3997.
Parker, Belinda S., Jai Rautela, and Paul J. Hertzog. "Antitumour actions of interferons: implications for cancer therapy." Nature Reviews Cancer 16.3 (2016): 131-144.
Hoffman, Gregory R., et al. "Functional epigenetics approach identifies BRM/SMARCA2 as a critical synthetic lethal target in BRG1-deficient cancers." Proceedings of the National Academy of Sciences 111.8 (2014): 3128-3133.
Hogquist, Kristin A., et al. "T cell receptor antagonist peptides induce positive selection." Cell 76.1 (1994): 17-27.
Hohmann, Anja F., and Christopher R. Vakoc. "A rationale to target the SWI/SNF complex for cancer therapy." Trends in Genetics 30.8 (2014): 356-363.
Holliger, Philipp, Terence Prospero, and Greg Winter. ""Diabodies": small bivalent and bispecific antibody fragments." Proceedings of the National Academy of Sciences 90.14 (1993): 6444-6448.
Horikawa, Izumi, and J. Carl Barrett. "cDNA cloning of the human polybromo-1 gene on chromosome 3p21." DNA Sequence 13.4 (2002): 211-215.
Horwich, A. L., et al. "Synthesis of hepadnavirus particles that contain replication-defective duck hepatitis B virus genomes in cultured HuH7 cells." Journal of virology 64.2 (1990): 642-650.
Huang, Xuling, et al. "Coronary development is regulated by ATP-dependent SWI/SNF chromatin remodeling component BAF180." Developmental biology 319.2 (2008): 258-266.
Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.
Hyrup, Birgitte, and Peter E. Nielsen. "Peptide nucleic acids (PNA): synthesis, properties and potential applications." Bioorganic & medicinal chemistry 4.1 (1996): 5-23.
Ike, Yoshimasa, et al. "Solid phase synthesis of polynucleotides. VIII. Synthesis of mixed oligodeoxyribonucleotides by the phosphotriester solid phase method." Nucleic Acids Research 11.2 (1983): 477-488.
Innis, et al. (1990) PCR Protocols, A Guide to Nfethods and Applications, Academic Press, Inc. NY.
Inoue, Hideo, et al. "Sequence-dependent hydrolysis of RNA using modified oligonucleotide splints and RNase H." FEBS letters 215.2 (1987): 327-330.
Inoue, Hideo, et al. "Synthesis and hybridization studies on two complementary nona (2'-O-methyl) ribonucleotides." Nucleic acids research 15.15 (1987): 6131-6148.
Ishida, Yasumasa, et al. "Induced expression of PD-1, a novel member of the immunoglobulin gene superfamily, upon programmed cell death." The EMBO journal 11.11 (1992): 3887-3895.
Itakura, Keiichi, et al. "Expression in *Escherichia coli* of a chemically synthesized gene for the hormone somatostatin." Science 198.4321 (1977): 1056-1063.
Itakura, Keiichi, John J. Rossi, and R. Bruce Wallace. "Synthesis and use of synthetic oligonucleotides." Annual review of biochemistry 53.1 (1984): 323-356.
Iwai, Yoshiko, et al. "Involvement of PD-L1 on tumor cells in the escape from host immune system and tumor immunotherapy by PD-L1 blockade." Proceedings of the National Academy of Sciences 99.19 (2002): 12293-12297.
Jena, Prasanna K., et al. "Amplification of genes, single transcripts and cDNA libraries from one cell and direct sequence analysis of amplified products derived from one molecule." Journal of immunological methods 190.2 (1996): 199-213.
Johnson, Carol V., et al. "Isolation and mapping of human T-cell protein tyrosine phosphatase sequences: localization of genes and pseudogenes discriminated using fluorescence hybridization with genomic versus cDNA probes." Genomics 16.3 (1993): 619-629.
Kadam, Shilpa, and Beverly M. Emerson. "Transcriptional specificity of human SWI/SNF BRG1 and BRM chromatin remodeling complexes." Molecular cell 11.2 (2003): 377-389.
Kadoch, C., and G. R. Crabtree. "Mammalian SWI/SNF chromatin remodeling complexes and cancer: mechanistic insights gained from human genomics. Sci Adv 1: e1500447." (2015): 47.
Kadoch, Cigall, et al. "Dynamics of BAF-Polycomb complex opposition on heterochromatin in normal and oncogenic states." Nature genetics 49.2 (2017): 213-222.
Kadoch, Cigall, et al. "Proteomic and bioinformatic analysis of mammalian SWI/SNF complexes identifies extensive roles in human malignancy." Nature genetics 45.6 (2013): 592-601.
Kaiserman, Dion, and Phillip Ian Bird. "Control of granzymes by serpins." Cell Death & Differentiation 17.4 (2010): 586-595.
Kallioniemi, O. "P, Kallioniemi A, Kurisu W, Thor A, Chen L-C, Smith HS, Waldman FM, Pinkel D, Gray IW: erbB2 ampli?cation in breast cancer analyzed by ?uorescence in situ hybridization." Proc Natl Acad Sci USA 89 (1992): 5321-5325.
Kang, Sang-Mo, et al. "Transactivation by AP-1 is a molecular target of T cell clonal anergy." Science 257.5073 (1992): 1134-1138.
Kapur, Payal, et al. "Effects on survival of BAP1 and PBRM1 mutations in sporadic clear-cell renal-cell carcinoma: a retrospective analysis with independent validation." The lancet oncology 14.2 (2013): 159-167.

(56) References Cited

OTHER PUBLICATIONS

Karginov, Fedor V., and Gregory J. Hannon. "The CRISPR system: small RNA-guided defense in bacteria and archaea." Molecular cell 37.1 (2010): 7-19.
Karlin, Samuel, and Stephen F. Altschul. "Applications and statistics for multiple high-scoring segments in molecular sequences." Proceedings of the National Academy of Sciences 90.12 (1993): 5873-5877.
Karlin, Samuel, and Stephen F. Altschul. "Methods for assessing the statistical significance of molecular sequence features by using general scoring schemes." Proceedings of the National Academy of Sciences 87.6 (1990): 2264-2268.
Kaufman, Randal J., P. Murtha, and M. V. Davies. "Translational efficiency of polycistronic mRNAs and their utilization to express heterologous genes in mammalian cells." The EMBO journal 6.1 (1987): 187-193.
Keen, J., et al. "Rapid detection of single base mismatches as heteroduplexes on Hydrolink gels." Trends in genetics: TIG 7.1 (1991): 5-5.
Kessel, Michael, and Peter Gruss. "Murine developmental control genes." Science 249.4967 (1990): 374-379.
Khavari, Paul A., et al. "BRG1 contains a conserved domain of the SWI2/SNF2 family necessary for normal mitotic growth and transcription." Nature 366.6451 (1993): 170-174.
Kimura, Mitsuhiro, et al. "Detailed deletion mapping on chromosome arm 12q in human pancreatic adenocarcinoma: Identification of a 1-cM region of common allelic loss." Genes, Chromosomes and Cancer 17.2 (1996): 88-93.
Kipriyanov, Sergey M., et al. "Recombinant single-chain Fv fragments carrying C-terminal cysteine residues: production of bivalent and biotinylated miniantibodies." Molecular immunology 31.14 (1994): 1047-1058.
Kleppe, Maria, et al. "PTPN2 negatively regulates oncogenic JAK1 in T-cell acute lymphoblastic leukemia." Blood, The Journal of the American Society of Hematology 117.26 (2011): 7090-7098.
Kobayashi, Koichi S., and Peter J. Van Den Elsen. "NLRC5: a key regulator of MHC class I-dependent immune responses." Nature Reviews Immunology 12.12 (2012): 813-820.
Kontermann, Roland E. "Intrabodies as therapeutic agents." Methods 34.2 (2004): 163-170.
Koya, Richard C., et al. "BRAF inhibitor vemurafenib improves the antitumor activity of adoptive cell immunotherapy." Cancer research 72.16 (2012): 3928-3937.
Kozal, Michael J., et al. "Extensive polymorphisms observed in HIV-1 clade B protease gene using high-density oligonucleotide arrays." Nature medicine 2.7 (1996): 753-759.
Krauthammer, Michael, et al. "Exome sequencing identifies recurrent somatic RAC1 mutations in melanoma." Nature genetics 44.9 (2012): 1006-1014.
Kucherlapati, Raju. Gene Transfer (1986): New York: Plenum Press.
Kurjan, Janet, and Ira Herskowitz. "Structure of a yeast pheromone gene (MFa): a putative a-factor precursor contains four tandem copies of mature a-factor." Cell 30.3 (1982): 933-943.
Kwoh, D. Y., et al. "Transcription-based amplification system and detection of amplified human immunodeficiency virus type 1 with a bead-based sandwich hybridization format." Proceedings of the National Academy of Sciences 86.4 (1989): 1173-1177.
Kzhyshkowska J, Rusch A, Wolf H, Dobner T. Regulation of transcription by the heterogeneous nuclear ribonucleoprotein E1B-AP5 is mediated by complex formation with the novel bromodomain-containing protein BRD7. Biochem J. Apr. 15, 2003;371(Pt 2):385-93.
Landegren, Ulf, et al. "A ligase-mediated gene detection technique." Science 241.4869 (1988): 1077-1080.
Latchman, Yvette, et al. "PD-L2 is a second ligand for PD-1 and inhibits T cell activation." Nature immunology 2.3 (2001): 261-268.
Lechler R, Chai JG, Marelli-Berg F, Lombardi G. T-cell anergy and peripheral T-cell tolerance. Philos Trans R Soc Lond B Biol Sci. May 29, 2001;356(1409):625-37.
Lemaitre, Marc, Bernard Bayard, and Bernard Lebleu. "Specific antiviral activity of a poly (L-lysine)-conjugated bligodeoxyribonucleotide sequence complementary to vesicular stomatitis virus N protein mRNA initiation site." Proceedings of the National Academy of Sciences 84.3 (1987): 648-652.
Patel, Kedar G., and James R. Swartz. "Surface functionalization of virus-like particles by direct conjugation using azide-alkyne click chemistry." Bioconjugate chemistry 22.3 (2011): 376-387.
Paul, S., and P. J. Lombroso. "Receptor and nonreceptor protein tyrosine phosphatases in the nervous system." Cellular and Molecular Life Sciences CMLS 60.11 (2003): 2465-2482.
Pawlowski, Rafal, et al. "Loss of PBRM1 expression is associated with renal cell carcinoma progression." International journal of cancer 132.2 (2013): E11-E17.
Pazin, Michael J., and James T. Kadonaga. "SWI2/SNF2 and related proteins: ATP-driven motors that disrupt-protein-DNA interactions ?." Cell 88.6 (1997): 737-740.
Pearson, William R., and David J. Lipman. "Improved tools for biological sequence comparison." Proceedings of the National Academy of Sciences 85.8 (1988): 2444-2448.
Peña-Llopis, Samuel, et al. "BAP1 loss defines a new class of renal cell carcinoma." Nature genetics 44.7 (2012): 751-759.
Phelan, Michael L., et al. "Reconstitution of a core chromatin remodeling complex from SWI/SNF subunits." Molecular cell 3.2 (1999): 247-253.
Phoenix, Timothy N., and Sally Temple. "Spred1, a negative regulator of Ras-MAPK-ERK, is enriched in CNS germinal zones, dampens NSC proliferation, and maintains ventricular zone structure." Genes & development 24.1 (2010): 45-56.
Pinkel, D., et al. "Fluorescence in situ hybridization with human chromosome-specific libraries: detection of trisomy 21 and translocations of chromosome 4." Proceedings of the National Academy of Sciences 85.23 (1988): 9138-9142.
Pinkel, Daniel, et al. "High resolution analysis of DNA copy number variation using comparative genomic hybridization to microarrays." Nature genetics 20.2 (1998): 207-211.
Pinkert, Carl A., et al. "An albumin enhancer located 10 kb upstream functions along with its promoter to direct efficient, liver-specific expression in transgenic mice." Genes & development 1.3 (1987): 268-276.
Poljak, Roberto J. "Production and structure of diabodies." Structure 2.12 (1994): 1121-1123.
Prosser, Jane. "Detecting single-base mutations." Trends in biotechnology 11.6 (1993): 238-246.
Protocols for PCR and Illumina Sequencing: portals.broadinstitute.org/gpp/public/resources/protocols.
Queen, Cary, and David Baltimore. "Immunoglobulin gene transcription is activated by downstream sequence elements." Cell 33.3 (1983): 741-748.
Ram, Zvi, et al. "In situ retroviral-mediated gene transfer for the treatment of brain tumors in rats." Cancer research 53.1 (1993): 83-88.
Ratner, Nancy, and Shyra J. Miller. "A RASopathy gene commonly mutated in cancer: the neurofibromatosis type 1 tumour suppressor." Nature Reviews Cancer 15.5 (2015): 290-301.
Robert, Caroline, et al. "Ipilimumab plus dacarbazine for previously untreated metastatic melanoma." New England Journal of Medicine 364.26 (2011): 2517-2526.
Saiki, Randall K., et al. "Analysis of enzymatically amplified ß-globin and HLA-DQa DNA with allele-specific oligonucleotide probes." Nature 324.6093 (1986): 163-166.
Saiki, Randall K., et al. "Genetic analysis of amplified DNA with immobilized sequence-specific oligonucleotide probes." Proceedings of the National Academy of Sciences 86.16 (1989): 6230-6234.
Saleeba JA, Cotton RG. Chemical cleavage of mismatch to detect mutations. Methods Enzymol. 1993;217:286-95.
Sambrook, J., E. F. Fritsch, and T. Maniatis. "Molecular cloning, A laboratory manual 3rd edition, Book 2." (2001).
Sancak, Yasemin, et al. "Ragulator-Rag complex targets mTORC1 to the lysosomal surface and is necessary for its activation by amino acids." Cell 141.2 (2010): 290-303.

(56) References Cited

OTHER PUBLICATIONS

Sander, Jeffry D., and J. Keith Joung. "CRISPR-Cas systems for editing, regulating and targeting genomes." Nature biotechnology 32.4 (2014): 347-355.
Sanger F, Nicklen S, Coulson AR. DNA sequencing with chain-terminating inhibitors. Proc Natl Acad Sci U S A. Dec. 1977;74(12):5463-7.
Schena, Mark, et al. "Quantitative monitoring of gene expression patterns with a complementary DNA microarray." Science 270.5235 (1995): 467-470.
Schreiber, Valerie, et al. "Poly (ADP-ribose): novel functions for an old molecule." Nature reviews Molecular cell biology 7.7 (2006): 517-528.
Schultz, Loren D., et al. "Expression and secretion in yeast of a 400-kDa envelope glycoprotein derived from Epstein-Barr virus." Gene 54.1 (1987): 113-123.
Seed, Brian. "An LFA-3 cDNA encodes a phospholipid-linked membrane protein homologous to its receptor CD2." Nature 329. 6142 (1987): 840-842.
Seymour, Albert B., et al. "Allelotype of pancreatic adenocarcinoma." Cancer research 54.10 (1994): 2761-2764.
Shain AH, Pollack JR. The spectrum of SWI/SNF mutations, ubiquitous in human cancers. PLOS One. 2013;8(1): e55119.
Shain, A. Hunter, et al. "Convergent structural alterations define SWItch/Sucrose NonFermentable (SWI/SNF) chromatin remodeler as a central tumor suppressive complex in pancreatic cancer." Proceedings of the National Academy of Sciences 109.5 (2012): E252-E259.
Shaki-Loewenstein, Shelly, et al. "A universal strategy for stable intracellular antibodies." Journal of immunological methods 303. 1-2 (2005): 19-39.
Sharma, Padmanee, et al. "Primary, adaptive, and acquired resistance to cancer immunotherapy." Cell 168.4 (2017): 707-723.
Shin, Tahiro, et al. "In vivo costimulatory role of B7-DC in tuning T helper cell 1 and cytotoxic T lymphocyte responses." The Journal of experimental medicine 201.10 (2005): 1531-1541.
Shinohara, Takashi, et al. "Structure and chromosomal localization of the human PD-1 gene (PDCD1)." Genomics 23.3 (1994): 704-706.
Skarnes, William C., et al. "A conditional knockout resource for the genome-wide study of mouse gene function." Nature 474.7351 (2011): 337-342.
Smith DB, Johnson KS. Single-step purification of polypeptides expressed in Escherichia coli as fusions with glutathione S-transferase. Gene. Jul. 15, 1988;67(1):31-40.
Smith GE, Summers MD, Fraser MJ. Production of human beta interferon in insect cells infected with a baculovirus expression vector. Mol Cell Biol. Dec. 1983;3(12):2156-65.
Soriano, Francisco Garcia, et al. "Diabetic endothelial dysfunction: the role of poly (ADP-ribose) polymerase activation." Nature medicine 7.1 (2001): 108-113.
Staal, Ada, et al. "Molecular characterization of Celtix-1, a bromodomain protein interacting with the transcription factor interferon regulatory factor 2." Journal of cellular physiology 185.2 (2000): 269-279.
Stern M, Jensen R, Herskowitz I. Five SWI genes are required for expression of the HO gene in yeast. J Mol Biol. Oct. 5, 1984;178(4):853-68.
Stewart, Sheila A., et al. "Lentivirus-delivered stable gene silencing by RNAi in primary cells." Rna 9.4 (2003): 493-501.
Strobeck, Matthew W., et al. "Compensation of BRG-1 Function by Brm: Insight Into the Role of the Core SWI• SNF Subunits in Retinoblastoma Tumor Suppressor Signaling." Journal of Biological Chemistry 277.7 (2002): 4782-4789.
Subramanian, Aravind, et al. "Gene set enrichment analysis: a knowledge-based approach for interpreting genome-wide expression profiles." Proceedings of the National Academy of Sciences 102.43 (2005): 15545-15550.
Sudarsanam, Priya, and Fred Winston. "The Swi/Snf family: nucleosome-remodeling complexes and transcriptional control." Trends in Genetics 16.8 (2000): 345-351.
Swallow, Michelle M., Jeffrey J. Wallin, and C. Sha William. "B7h, a novel costimulatory homolog of B7. 1 and B7. 2, is induced by TNFa." Immunity 11.4 (1999): 423-432.
Symmans, W. Fraser, et al. "Measurement of residual breast cancer burden to predict survival after neoadjuvant chemotherapy." Journal of Clinical Oncology 25.28 (2007): 4414-4422.
Tang, Liling, Eva Nogales, and Claudio Ciferri. "Structure and function of SWI/SNF chromatin remodeling complexes and mechanistic implications for transcription." Progress in biophysics and molecular biology 102.2-3 (2010): 122-128.
Tanigawa N, Kern DH, Hikasa Y, Morton DL. Rapid assay for evaluating the chemosensitivity of human tumors in soft agar culture. Cancer Res. Jun. 1982;42(6):2159-64.
Abravaya, Klara, et al. "Detection of point mutations with a modified ligase chain reaction (Gap-LCR)." Nucleic Acids Research 23.4 (1995): 675-682.
Agata, Yasutoshi, et al. "Expression of the PD-1 antigen on the surface of stimulated mouse T and B lymphocytes." International immunology 8.5 (1996): 765-772.
Albertson, Donna G. "Localization of the ribosomal genes in Caenorhabditis elegans chromosomes by in situ hybridization using biotin-labeled probes." The EMBO journal 3.6 (1984): 1227-1234.
Alonso, Andres, et al. "Protein tyrosine phosphatases in the human genome." Cell 117.6 (2004): 699-711.
Alton, E. W. F. W., et al. "Non-invasive liposome-mediated gene delivery can correct the ion transport defect in cystic fibrosis mutant mice." Nature genetics 5.2 (1993): 135-142.
Altschul SF, Madden TL, Schäffer AA, Zhang J, Zhang Z, Miller W, Lipman DJ. Gapped BLAST and PSI-BLAST: a new generation of protein database search programs. Nucleic Acids Res. Sep. 1, 1997;25(17):3389-402.
Altschul, Stephen F., et al. "Basic local alignment search tool." Journal of molecular biology 215.3 (1990): 403-410.
Amann, Egon, Birgit Ochs, and Karl-Josef Abel. "Tightly regulated tac promoter vectors useful for the expression of unfused and fused proteins in Escherichia coli." Gene 69.2 (1988): 301-315.
Arafeh, Rand, et al. "Recurrent inactivating RASA2 mutations in melanoma." Nature genetics 47.12 (2015): 1408-1410.
Arkin, Adam P., and Douglas C. Youvan. "An algorithm for protein engineering: simulations of recursive ensemble mutagenesis." Proceedings of the National Academy of Sciences 89.16 (1992): 7811-7815.
Asturias, Francisco J., et al. "Structural analysis of the RSC chromatin-remodeling complex." Proceedings of the National Academy of Sciences 99.21 (2002): 13477-13480.
Augustin, M. A., W. Ankenbauer, and B. Angerer. "Progress towards single-molecule sequencing: enzymatic synthesis of nucleotide-specifically labeled DNA." Journal of biotechnology 86.3 (2001): 289-301.
Azoury SC, Lange JR. Epidemiology, risk factors, prevention, and early detection of melanoma. Surg Clin North Am. Oct. 2014;94(5):945-62.
Baichwal, Vijay R., and Bill Sugden. "Vectors for gene transfer derived from animal DNA viruses: transient and stable expression of transferred genes." Gene Transfer. Springer, Boston, MA, 1986. 117-148.
Baldari, C., et al. "A novel leader peptide which allows efficient secretion of a fragment of human interleukin 1 beta in Saccharomyces cerevisiae." The EMBO Journal 6.1 (1987): 229-234.
Banerji, Julian, Laura Olson, and Walter Schaffner. "A lymphocyte-specific cellular enhancer is located downstream of the joining region in immunoglobulin heavy chain genes." Cell 33.3 (1983): 729-740.
Barany, Francis. "Genetic disease detection and DNA amplification using cloned thermostable ligase." Proceedings of the National Academy of Sciences 88.1 (1991): 189-193.
Barford, David, Amit K. Das, and Marie-Pierre Egloff. "The structure and mechanism of protein phosphatases: insights into catalysis and regulation." Annual review of biophysics and biomolecular structure 27.1 (1998): 133-164.
Barr, Alastair J., et al. "Large-scale structural analysis of the classical human protein tyrosine phosphatome." Cell 136.2 (2009): 352-363.

(56) References Cited

OTHER PUBLICATIONS

Barringer, Kevin J., et al. "Blunt-end and single-strand ligations by *Escherichia coli* ligase: influence on an in vitro amplication scheme." Gene 89.1 (1990): 117-122.
Bartel, David P., and Jack W. Szostak. "Isolation of new ribozymes from a large pool of random sequences." Science 261.5127 (1993): 1411-1418.
Berge, Stephen M., Lyle D. Bighley, and Donald C. Monkhouse. "Pharmaceutical salts." Journal of pharmaceutical sciences 66.1 (1977): 1-19.
Besser, Michal J., et al. "Clinical responses in a phase II study using adoptive transfer of short-term cultured tumor infiltration lymphocytes in metastatic melanoma patients." Clinical cancer research 16.9 (2010): 2646-2655.
Bird, Robert E., et al. "Single-chain antigen-binding proteins." Science 242.4877 (1988): 423-426.
Blum, Janice S., Pamela A. Wearsch, and Peter Cresswell. "Pathways of antigen processing." Annual review of immunology 31 (2013): 443-473.
Boch, Jens, et al. "Breaking the code of DNA binding specificity of TAL-type III effectors." Science 326.5959 (2009): 1509-1512.
Boch, Jens. "TALEs of genome targeting." Nature biotechnology 29.2 (2011): 135-136.
Bonner, Robert F., et al. "Laser capture microdissection: molecular analysis of tissue." Science 278.5342 (1997): 1481-1483.
Bouchard, Veronique J., Michèle Rouleau, and Guy G. Poirier. "PARP-1, a determinant of cell survival in response to DNA damage." Experimental hematology 31.6 (2003): 446-454.
Bowman, Karen Julia, et al. "Differential effects of the poly (ADP-ribose) polymerase (PARP) inhibitor NU1025 on topoisomerase I and II inhibitor cytotoxicity in L1210 cells in vitro." British journal of cancer 84.1 (2001): 106-112.
Brown-Shimer, Sheryl, et al. "Molecular cloning and chromosome mapping of the human gene encoding protein phosphotyrosyl phosphatase 1B." Proceedings of the National Academy of Sciences 87.13 (1990): 5148-5152.
Brownlee, Peter M., et al. "Cancer and the bromodomains of BAF180." Biochemical Society transactions 40.2 (2012): 364-369.
Bryant, Helen E., et al. "Specific killing of BRCA2-deficient tumours with inhibitors of poly (ADP-ribose) polymerase." Nature 434.7035 (2005): 913-917.
Buenrostro, Jason D., et al. "ATAC-seq: a method for assaying chromatin accessibility genome-wide." Current protocols in molecular biology 109.1 (2015): 21-29.
Buenrostro, Jason D., et al. "Transposition of native chromatin for fast and sensitive epigenomic profiling of open chromatin, DNA-binding proteins and nucleosome position." Nature methods 10.12 (2013): 1213-1218.
Butte, Manish J., et al. "Programmed death-1 ligand 1 interacts specifically with the B7-1 costimulatory molecule to inhibit T cell responses." Immunity 27.1 (2007): 111-122.
Byrne GW, Ruddle FH. Multiplex gene regulation: a two-tiered approach to transgene regulation in transgenic mice. Proc Natl Acad Sci U S A. Jul. 1989;86(14):5473-7.
Calame, Kathryn, and Suzanne Eaton. "Transcriptional controlling elements in the immunoglobulin and T cell receptor loci." Advances in immunology 43 (1988): 235-275.
Camper, Sally A., and Shirley M. Tilghman. "Postnatal repression of the alpha-fetoprotein gene is enhancer independent." Genes & development 3.4 (1989): 537-546.
Cane, David E., Christopher T. Walsh, and Chaitan Khosla. "Harnessing the biosynthetic code: combinations, permutations, and mutations." Science 282.5386 (1998): 63-68.
Chapman, Paul B., et al. "Improved survival with vemurafenib in melanoma with BRAF V600E mutation." New England Journal of Medicine 364.26 (2011): 2507-2516.
Chen, Shihao, et al. "Combination of 4-1BB agonist and PD-1 antagonist promotes antitumor effector/memory CD8 T cells in a poorly immunogenic tumor model." Cancer immunology research 3.2 (2015): 149-160.

Chen, Shu-Hsia, et al. "Gene therapy for brain tumors: regression of experimental gliomas by adenovirus-mediated gene transfer in vivo." Proceedings of the National Academy of Sciences 91.8 (1994): 3054-3057.
Chen, Sidi, et al. "Genome-wide CRISPR screen in a mouse model of tumor growth and metastasis." Cell 160.6 (2015): 1246-1260.
Chirgwin, John M., et al. "Isolation of biologically active ribonucleic acid from sources enriched in ribonuclease." Biochemistry 18.24 (1979): 5294-5299.
Coburn, Glen A., and Bryan R. Cullen. "Potent and specific inhibition of human immunodeficiency virus type 1 replication by RNA interference." Journal of virology 76.18 (2002): 9225-9231.
Cohen, Pascale A., Jean-Claude Mani, and David P. Lane. "Characterization of a new intrabody directed against the N-terminal region of human p53." Oncogene 17.19 (1998): 2445-2456.
Compton J. Nucleic acid sequence-based amplification. Nature. Mar. 7, 1991;350(6313):91-2.
Cone, Roger D., and Richard C. Mulligan. "High-efficiency gene transfer into mammalian cells: generation of helper-free recombinant retrovirus with broad mammalian host range." Proceedings of the National Academy of Sciences 81.20 (1984): 6349-6353.
Cotton, R. G. H. "Current methods of mutation detection." Mutation Research/Fundamental and Molecular Mechanisms of Mutagenesis 285.1 (1993): 125-144.
Cotton, R. G., Nanda R. Rodrigues, and R. Duncan Campbell. "Reactivity of cytosine and thymine in single-base-pair mismatches with hydroxylamine and osmium tetroxide and its application to the study of mutations." Proceedings of the National Academy of Sciences 85.12 (1988): 4397-4401.
Coupar, Barbara EH, Marion E. Andrew, and David B. Boyle. "A general method for the construction of recombinant vaccinia viruses expressing multiple foreign genes." Gene 68.1 (1988): 1-10.
Cronin, Maureen T., et al. "Cystic fibrosis mutation detection by hybridization to light-generated DNA probe arrays." Human mutation 7.3 (1996): 244-255.
Curiel, David T., et al. "High-efficiency gene transfer mediated by adenovirus coupled to DNA-polylysine complexes." Human gene therapy 3.2 (1992): 147-154.
Current Protocols of Molecular Biology, John Wiley & Sons, N.Y. (1987).
De Murcia, Josiane Menissier, et al. "Requirement of poly (ADP-ribose) polymerase in recovery from DNA damage in mice and in cells." Proceedings of the National Academy of Sciences 94.14 (1997): 7303-7307.
Dechassa, Mekonnen Lemma, et al. "Architecture of the SWI/SNF-nucleosome complex." Molecular and cellular biology 28.19 (2008): 6010-6021.
Denu, John M., and Jack E. Dixon. "Protein tyrosine phosphatases: mechanisms of catalysis and regulation." Current opinion in chemical biology 2.5 (1998): 633-641.
Der Maur, Adrian Auf, Dominik Escher, and Alcide Barberis. "Antigen-independent selection of stable intracellular single-chain antibodies." FEBS letters 508.3 (2001): 407-412.
Doench, John G., et al. "Optimized sgRNA design to maximize activity and minimize off-target effects of CRISPR-Cas9." Nature biotechnology 34.2 (2016): 184-191.
Dong, Haidong, et al. "B7-H1, a third member of the B7 family, co-stimulates T-cell proliferation and interleukin-10 secretion." Nature medicine 5.12 (1999): 1365-1369.
Drost, Jarno, et al. "BRD7 is a candidate tumour suppressor gene required for p53 function." Nature cell biology 12.4 (2010): 380-389.
Dulac, Catherine. "14 Cloning of Genes from Single Neurons." Current topics in developmental biology 36 (1997): 245-258.
Ebert, Peter JR, et al. "MAP kinase inhibition promotes T cell and anti-tumor activity in combination with PD-L1 checkpoint blockade." Immunity 44.3 (2016): 609-621.
Edlund, Thomas, et al. "Cell-specific expression of the rat insulin gene: evidence for role of two distinct 5'flanking elements." Science 230.4728 (1985): 912-916.
Emmert-Buck, Michael R., et al. "Laser capture microdissection." Science 274.5289 (1996): 998-1001.

(56) References Cited

OTHER PUBLICATIONS

Euskirchen, Ghia, Raymond K. Auerbach, and Michael Snyder. "SWI/SNF chromatin-remodeling factors: multiscale analyses and diverse functions." Journal of Biological Chemistry 287.37 (2012): 30897-30905.
Farmer, Hannah, et al. "Targeting the DNA repair defect in BRCA mutant cells as a therapeutic strategy." Nature 434.7035 (2005): 917-921.
Felgner, Philip L., et al. "Improved cationic lipid formulations for in vivo gene therapy." Annals of the New York Academy of Sciences 772.1 (1995): 126-139.
Felgner, Philip L., et al. "Lipofection: a highly efficient, lipid-mediated DNA-transfection procedure." Proceedings of the National Academy of Sciences 84.21 (1987): 7413-7417.
Fend, Falko, et al. "Immuno-LCM: laser capture microdissection of immunostained frozen sections for mRNA analysis." The American journal of pathology 154.1 (1999): 61-66.
Finn, Patrick J., et al. "Synthesis and properties of DNA-PNA chimeric oligomers." Nucleic acids research 24.17 (1996): 3357-3363.
Flowers, Stephen, et al. "Antagonistic Roles for BRM and BRG1 SWI/SNF Complexes in Differentiation*." Journal of Biological Chemistry 284.15 (2009): 10067-10075.
Forbes, Nicole E., et al. "Exploiting tumor epigenetics to improve oncolytic virotherapy." Frontiers in genetics 4 (2013): 184.
Frederick, Dennie T., et al. "BRAF inhibition is associated with enhanced melanoma antigen expression and a more favorable tumor microenvironment in patients with metastatic melanoma." Clinical cancer research 19.5 (2013): 1225-1231.
Freeman, Gordon J., et al. "Engagement of the PD-1 immunoinhibitory receptor by a novel B7 family member leads to negative regulation of lymphocyte activation." The Journal of experimental medicine 192.7 (2000): 1027-1034.
Friedmann, Theodore. "Progress toward human gene therapy." Science 244.4910 (1989): 1275-1281.
Gao, Jianjun, et al. "Loss of IFN-? pathway genes in tumor cells as a mechanism of resistance to anti-CTLA-4 therapy." Cell 167.2 (2016): 397-404.
Gasparini, Paolo, et al. "Restriction site generating-polymerase chain reaction (RG-PCR) for the probeless detection of hidden genetic variation: application to the study of some common cystic fibrosis mutations." Molecular and cellular probes 6.1 (1992): 1-7.
Gautier C, Morvan F, Rayner B, Huynh-Dinh T, Igolen J, Imbach JL, Paoletti C, Paoletti J. Alpha-DNA. IV: Alpha-anomeric and beta-anomeric tetrathymidylates covalently linked to intercalating oxazolopyridocarbazole. Synthesis, physicochemical properties and poly (rA) binding. Nucleic Acids Res. Aug. 25, 1987;15(16):6625-41.
Gerhold, David, Thomas Rushmore, and C. Thomas Caskey. "DNA chips: promising toys have become powerful tools." Trends in biochemical sciences 24.5 (1999): 168-173.
Gibbs, Richard A., Phi-Nga Nguyen, and C. Thomas Caskey. "Detection of single DNA base differences by competitive oligonucleotide priming." Nucleic acids research 17.7 (1989): 2437-2448.
Ginzinger, David G., et al. "Measurement of DNA copy number at microsatellite loci using quantitative PCR analysis." Cancer research 60.19 (2000): 5405-5409.
Goeddel, Methods in Enzymology vol. 185, Academic Press, San Diego, CA, 1990.
Griffin, Hugh G., and Annette M. Griffin. "DNA sequencing." Applied biochemistry and biotechnology 38.1 (1993): 147-159.
Groom, Joanna R., and Andrew D. Luster. "CXCR3 ligands: redundant, collaborative and antagonistic functions." Immunology and cell biology 89.2 (2011): 207-215.
Guatelli, John C., et al. "Isothermal, in vitro amplification of nucleic acids by a multienzyme reaction modeled after retroviral replication." Proceedings of the National Academy of Sciences 87.5 (1990): 1874-1878.

Hahn SA, et al. Allelotype of pancreatic adenocarcinoma using xenograft enrichment. Cancer Res. Oct. 15, 1995;55(20):4670-5.
Hakimi, A. Ari, et al. "Clinical and pathologic impact of select chromatin-modulating tumor suppressors in clear cell renal cell carcinoma." European urology 63.5 (2013): 848-854.
Hale, Caryn R., et al. "RNA-guided RNA cleavage by a CRISPR RNA-Cas protein complex." Cell 139.5 (2009): 945-956.
Harte, Mary T., et al. "BRD7, a subunit of SWI/SNF complexes, binds directly to BRCA1 and regulates BRCA1-dependent transcription." Cancer research 70.6 (2010): 2538-2547.
Haseloff, Jim, and Wayne L. Gerlach. "Simple RNA enzymes with new and highly specific endoribonuclease activities." Nature 334. 6183 (1988): 585-591.
Hayashi, Kenshi. "PCR-SSCP: a method for detection of mutations." Genetic Analysis: Biomolecular Engineering 9.3 (1992): 73-79.
He, Rong-jun, et al. "Protein tyrosine phosphatases as potential therapeutic targets." Acta pharmacologica sinica 35.10 (2014): 1227-1246.
Heckman KL, Schenk EL, Radhakrishnan S, Pavelko KD, Hansen MJ, Pease LR. Fast-tracked CTL: rapid induction of potent anti-tumor killer T cells in situ. Eur J Immunol. Jul. 2007;37(7):1827-35.
Heinz, Sven, et al. "Simple combinations of lineage determining transcription factors prime cis-regulatory elements required for macrophage and B cell identities." Molecular cell 38.4 (2010): 576-589.
Helene, Claude, Nguyen T. Thuong, and Annick Harel. "Control of Gene Expression by Triple Helix-Forming Oligonucleotides. The Antigene Strategy a." Annals of the New York Academy of Sciences 660.1 (1992): 27-36.
Henry, Joelle, Marcia M. Miller, and Pierre Pontarotti. "Structure and evolution of the extended B7 family." Immunology today 20.6 (1999): 285-288.
Herceg, Zdenko, and Zhao-Qi Wang. "Functions of poly (ADP-ribose) polymerase (PARP) in DNA repair, genomic integrity and cell death." Mutation Research/Fundamental and Molecular Mechanisms of Mutagenesis 477.1-2 (2001): 97-110.
Hodis, Eran, et al. "A landscape of driver mutations in melanoma." Cell 150.2 (2012): 251-263.
Thompson, Martin. "Polybromo-1: the chromatin targeting subunit of the PBAF complex." Biochimie 91.3 (2009): 309-319.
Towbin H, Staehelin T, Gordon J. Electrophoretic transfer of proteins from polyacrylamide gels to nitrocellulose sheets: procedure and some applications. Proc Natl Acad Sci U S A. Sep. 1979;76(9):4350-4.
Trapnell, Cole, et al. "Transcript assembly and quantification by RNA-Seq reveals unannotated transcripts and isoform switching during cell differentiation." Nature biotechnology 28.5 (2010): 511-515.
Tsan MF, White JE, Shepard B. Lung-specific direct in vivo gene transfer with recombinant plasmid DNA. Am J Physiol. Jun. 1995;268(6 Pt 1):L1052-6.
Van Elsas, Andrea, Arthur A. Hurwitz, and James P. Allison. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation." Journal of Experimental Medicine 190.3 (1999): 355-366.
Varela, Ignacio, et al. "Exome sequencing identifies frequent mutation of the SWI/SNF complex gene PBRM1 in renal carcinoma." Nature 469.7331 (2011): 539-542.
Vignali, Marissa, et al. "ATP-dependent chromatin-remodeling complexes." Molecular and cellular biology 20.6 (2000): 1899-1910.
Vile RG, Hart IR. In vitro and in vivo targeting of gene expression to melanoma cells. Cancer Res. Mar. 1, 1993;53(5):962-7.
Vile, Richard G., and Ian R. Hart. "Use of tissue-specific expression of the herpes simplex virus thymidine kinase gene to inhibit growth of established murine melanomas following direct intratumoral injection of DNA." Cancer research 53.17 (1993): 3860-3864.
Vivier, Eric, and Marc Daeron. "Immunoreceptor tyrosine-based inhibition motifs." Immunology today 18.6 (1997): 286-291.

(56) References Cited

OTHER PUBLICATIONS

Wada, Ken-nosuke, et al. "Codon usage tabulated from the GenBank genetic sequence data." Nucleic acids research 20.Suppl (1992): 2111.
Walker, G. Terrance, et al. "Strand displacement amplification (SDA) and transient-state fluorescence polarization detection of Mycobacterium tuberculosis DNA." Clinical chemistry 42.1 (1996): 9-13.
Wang CY, Huang L. pH-sensitive immunoliposomes mediate target-cell-specific delivery and controlled expression of a foreign gene in mouse. Proc Natl Acad Sci U S A. Nov. 1987;84(22):7851-5.
Wang, Alice M., Michael V. Doyle, and David F. Mark. "Quantitation of mRNA by the polymerase chain reaction." Proceedings of the National Academy of Sciences 86.24 (1989): 9717-9721.
Wang, Su, et al. "Target analysis by integration of transcriptome and ChIP-seq data with BETA." Nature protocols 8.12 (2013): 2502-2515.
Wang, Weidong, et al. "Diversity and specialization of mammalian SWI/SNF complexes." Genes & development 10.17 (1996): 2117-2130.
Wang, Weidong, et al. "Purification and biochemical heterogeneity of the mammalian SWI-SNF complex." The EMBO journal 15.19 (1996): 5370-5382.
Wang, Zhao-Qi, et al. "PARP is important for genomic stability but dispensable in apoptosis." Genes & development 11.18 (1997): 2347-2358.
Wang, Zhigang C., et al. "Loss of heterozygosity and its correlation with expression profiles in subclasses of invasive breast cancers." Cancer research 64.1 (2004): 64-71.
Wang, Zhong, et al. "Polybromo protein BAF180 functions in mammalian cardiac chamber maturation." Genes & development 18.24 (2004): 3106-3116.
Ward, E. Sally, et al. "Binding activities of a repertoire of single immunoglobulin variable domains secreted from *Escherichia coli*." Nature 341.6242 (1989): 544-546.
Weber E, Gruetzner R, Werner S, Engler C, Marillonnet S. Assembly of designer TAL effectors by Golden Gate cloning. PLOS One. 2011;6(5):e19722.
Weisenthal LM, Shoemaker RH, Marsden JA, Dill PL, Baker JA, Moran EM. In vitro chemosensitivity assay based on the concept of total tumor cell kill. Recent Results Cancer Res. 1984;94:161-73.
Williams RS, et al. Introduction of foreign genes into tissues of living mice by DNA-coated microprojectiles. Proc Natl Acad Sci U S A. Apr. 1, 1991;88(7):2726-30.
Winoto, Astar, and David Baltimore. "A novel, inducible and T cell-specific enhancer located at the 3' end of the T cell receptor alpha locus." The EMBO journal 8.3 (1989): 729-733.
Winston, Fred, and Marian Carlson. "Yeast SNF/SWI transcriptional activators and the SPT/SIN chromatin connection." Trends in Genetics 8.11 (1992): 387-391.
Workman, J. L., and R. E. Kingston. "Alteration of nucleosome structure as a mechanism of transcriptional regulation." Annual review of biochemistry 67.1 (1998): 545-579.
Wu, Catherine H., James M. Wilson, and G. Y. Wu. "Targeting genes: delivery and persistent expression of a foreign gene driven by mammalian regulatory elements in vivo." Journal of Biological Chemistry 264.29 (1989): 16985-16987.
Wu, Dan Y., and R. Bruce Wallace. "The ligation amplification reaction (LAR)—amplification of specific DNA sequences using sequential rounds of template-dependent ligation." Genomics 4.4 (1989): 560-569.
Wu, Jiang I., Julie Lessard, and Gerald R. Crabtree. "Understanding the words of chromatin regulation." Cell 136.2 (2009): 200-206.
Xia, Wei, et al. "BAF180 is a critical regulator of p21 induction and a tumor suppressor mutated in breast cancer." Cancer research 68.6 (2008): 1667-1674.
Xue, Yutong, et al. "The human SWI/SNF-B chromatin-remodeling complex is related to yeast rsc and localizes at kinetochores of mitotic chromosomes." Proceedings of the National Academy of Sciences 97.24 (2000): 13015-13020.
Yan, Zhijiang, et al. "PBAF chromatin-remodeling complex requires a novel specificity subunit, BAF200, to regulate expression of selective interferon-responsive genes." Genes & development 19.14 (2005): 1662-1667.
Zagotta, William N., and Steven A. Siegelbaum. "Structure and function of cyclic nucleotide-gated channels." Annual review of neuroscience 19.1 (1996): 235-263.
Zaretsky, Jesse M., et al. "Mutations associated with acquired resistance to PD-1 blockade in melanoma." New England Journal of Medicine 375.9 (2016): 819-829.
Zhang Y, et al. Model-based analysis of ChIP-Seq (MACS). Genome Biol. 2008;9(9):R137.
Zhang, Feng, et al. "Programmable sequence-specific transcriptional regulation of mammalian genome using designer TAL effectors." Nature biotechnology 29.2 (2011): 149.
Zhang, Nu, and Michael J. Bevan. "CD8+ T cells: foot soldiers of the immune system." Immunity 35.2 (2011): 161-168.
Zhang, Qian, Michael J. Lenardo, and David Baltimore. "30 years of NF-?B: a blossoming of relevance to human pathobiology." Cell 168.1-2 (2017): 37-57.
Zhao, Hong, et al. "ARID2: a new tumor suppressor gene in hepatocellular carcinoma." Oncotarget 2.11 (2011): 886.
Zhong, Xuemei, et al. "PD-L2 expression extends beyond dendritic cells/macrophages to B1 cells enriched for VH11/VH12 and phosphatidylcholine binding." European journal of immunology 37.9 (2007): 2405-2410.
Zhou, Ming, et al. "Identification of nuclear localization signal that governs nuclear import of BRD7 and its essential roles in inhibiting cell cycle progression." Journal of cellular biochemistry 98.4 (2006): 920-930.
Zon, Gerald. "Oligonucleotide analogues as potential chemotherapeutic agents." Pharmaceutical Research 5.9 (1988): 539-549.
Inokawa et al., "Detection of doublecortin domain-containing 2 (DCDC2), a new candidate tumor suppressor gene of hepatocellular carcinoma, by triple combination array analysis", Journal of Experimental & Clinical Cancer Research, Biomed Central LTD, London UK, vol. 32, No. 1, Sep. 14, 2013.
Deng et al., "A major chromatin regulator determines resistance of tumor cells to T cell-mediated killing", Science, vol. 359, No. 6377, 2018.
Extended European Search Report dated Jun. 8, 2021.

* cited by examiner

A    Before T cell selection

After T cell selection

B

C

D

B

C

D

E

F

G

H

B

D

E

F

METHODS FOR SENSITIZING CANCER CELLS TO T CELL-MEDIATED KILLING BY MODULATING MOLECULAR PATHWAYS

CROSS-REFERENCE TO RELATED APPLICATIONS

This application is the U.S. national phase of International Patent Application No. PCT/US2018/036046, filed on 5 Jun. 2018, which claims the benefit of priority to U.S. Provisional Application Ser. No. 62/515,738, filed on 6 Jun. 2017; the entire contents of each of said applications are incorporated herein in their entirety by this reference.

STATEMENT OF RIGHTS

This invention was made with government support under grant number 1T32CA207021-01 and R01 CA173750 awarded by The National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jan. 25, 2022, is named 5031461-082US2 SL.txt and is 244,888 bytes in size.

BACKGROUND OF THE INVENTION

Cancer immunotherapies that target inhibitory receptors on T cells including the PD-1 receptor can induce durable responses, but the majority of patients do not respond (Sharma et al. (2017) *Cell* 168:707-723). The mechanisms that determine resistance to these immunotherapies remain poorly understood. Cytotoxic T cells are central effector cells of a protective anti-tumor immune response. It is well understood that this process requires recognition of MHC-bound peptides by the T cell receptor (Zhang et al. (2011) *Immunity* 35:161-168). This recognition event leads to release of cytotoxic granules, resulting in perforin-mediated pore formation in the target cell membrane, allowing granzymes to access the cytosol of target cells where they initiate apoptosis. T cell-mediated cytotoxicity can be remarkably efficient, but it is diminished when MHC class I expression by tumor cells is reduced. It is known that PD-L1 expression by tumor cells can inhibit T cell-mediated killing through PD-1 receptor signaling, and this interaction has become a major target for cancer immunotherapy (Iwai et al. (2002) *Proc. Natl. Acad. Sci. U.S.A.* 99:12293-12297). However, many of the genes whose products inhibit T cell mediated cytotoxicity remain unknown. Accordingly, there remains a great need in the art to identify molecular targets that enable sensitization of tumor cells to T cell mediated killing in order to better treat cancer of subjects in need thereof.

SUMMARY OF THE INVENTION

The present invention is based, at least in part, on the discovery that alterations in many genes and pathways sensitize tumor cells to T cell-mediated killing. The genes and pathways can be divided into two groups. Members of the first group confer resistance to T cell-mediated killing of tumor cells and members of the second group promote efficient T cell-mediated killing. Top genes in the first group determined as described herein include negative immune regulators such as CD274/PD-L1, Ptpn2, and Serpinb9. The first group also encompasses three major signaling pathways: the NF-kB pathway (including Otulin, Rela, Ikbkg, Ikbkb, Rnf31, Cflar and Sharpin), the mTORC1 pathway (including Rraga, Rragc and Lamtor 1), and the RIG-I like receptor signaling pathway (including Tbk1, Fadd, Atg5 and multiple components overlapped with NF-kB pathway). Moreover, the first group encompasses two major metabolic pathways: glycolysis (including Nsdhl, Gne, Gale, Ero11 and Cd44) and nicotinate/nicotinamide metabolism (including Nadk and Nampt). In particular, all three unique components of a SWI/SNF chromatin remodeling complex referred to as the PBAF complex (Arid2, Pbrm1 and Brd7) belong to this group, providing strong evidence that the presence of this complex conferred resistance to T cell-mediated killing. Sox4, Hdac5, and Ptpn11 are also included in this group. Inactivation of the first group of genes and pathways sensitizes tumor cells to T cell mediated killing. The second group includes key components of the MHC class I pathway required for presentation of tumor-derived peptides to T cells (including H2-D1, B2m, Tap1, Tap2 and Nlrc5), key components required for IFNγ and IFNα/β recognition and signaling (including Jak1, Jak2, Stat1, Ifngr1 and Ifngr2), and negative regulators of Ras/MAPK pathways (including Nf1, Dusp6, Spred1, Rasa2 and SPOP). Inactivation of the second group of genes and pathways increases resistance to T cell mediated cytotoxicity. Biomarkers of the present invention are provided, such as in Tables 1-9 or any combination thereof (e.g., Tables 1, 5, 7, and 9; and/or Tables 2, 4, 6, and 8), and can be used alone or in combination for any aspect and/or embodiment described herein.

For example, in one aspect, a method of sensitizing cancer cells in a subject afflicted with a cancer to cytotoxic T cell-mediated killing comprising administering to the subject a therapeutically effective amount of an agent that modulates the copy number, amount, and/or activity of at least one biomarker listed in Tables 1-9 in the cancer cells, thereby sensitizing the cancer cells in the subject to cytotoxic T cell-mediated killing, is provided.

Numerous embodiments are further provided that can be applied to any aspect of the present invention and/or combined with any other embodiment described herein. For example, in one embodiment, the agent downregulates the copy number, amount, and/or activity of at least one biomarker listed in Table 1, 5, 7 or 9. In another embodiment, the agent comprises or is a small molecule inhibitor, CRISPR guide RNA (gRNA), RNA interfering agent, antisense oligonucleotide, peptide or peptidomimetic inhibitor, aptamer, or intrabody. The RNA interfering agent, described herein, may comprise or be, e.g., a small interfering RNA (siRNA), CRISPR RNA (crRNA), a small hairpin RNA (shRNA), a microRNA (miRNA), or a piwi-interacting RNA (piRNA). For example, the RNA interfering agent comprises or is a CRISPR guide RNA (gRNA). In still another embodiment, the agent described herein comprises an antibody and/or intrabody, or an antigen binding fragment thereof, which specifically binds to the at least one biomarker listed in Table 1, 5, 7 or 9. In yet another embodiment, the intrabody, or antigen binding fragment thereof, is murine, chimeric, humanized, composite, or human. In another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the intrabody, or antigen binding fragment thereof, is conjugated to a cytotoxic agent. Such cytotoxic agent may be selected from the group consisting of a chemotherapeutic agent, a biologic agent, a toxin, and a radioactive isotope. In another embodiment, the agent described herein upregulates the copy number, amount, and/or activity of at least one biomarker listed in Table 2, 4, 6 or 8. In still another embodiment, the agent comprises or is a nucleic acid molecule encoding the one or more biomarkers listed in Table 2, 4, 6 or 8 or fragment thereof, a polypeptide of the one or more biomarkers listed in Table 2, 4, 6 or 8 or fragment(s) thereof, or a small molecule that binds to the one or more biomarkers listed in Table 2, 4, 6 or 8.

In one embodiment, the method further comprises treating the cancer in the subject by administering to the subject at least one immunotherapy. In another one embodiment, the immunotherapy is cell-based. In still another embodiment, the immunotherapy comprises an cancer vaccine adoptive T cell therapies, and/or virus. In yet another embodiment, the immunotherapy inhibits an immune checkpoint and/or inhibits TNF alpha.

For example, the immune checkpoint described in the instant disclosure may be any checkpoint proteins known in the art, such as one selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the immune checkpoint is selected from the group consisting of PD-1, PD-L1, PD-L2, and CTLA-4. In still another embodiment, the immune checkpoint is PD-1 or CTLA-4. In yet another embodiment, the agent reduces the number of proliferating cells in the cancer and/or reduces the volume or size of a tumor comprising the cancer cells. In another embodiment, the agent increases the amount of CD8+ T cells, CD4+ T cells, granzyme B+CD8+ T cells, and/or CD45+ immune cells in a tumor comprising the cancer cells. The CD45+ immune cells may express higher levels of genes (e.g., genes related to IFN-γ response, IFN-α response, and/or tumor necrosis factor α signaling via NF-κB) associated with productive antitumor immunity. In still another embodiment, the agent increases the percentage of dendritic cells within the CD45+ immune cells. In yet another embodiment, the agent increases the ratio of tumor-inhibitory M1-like macropahges to tumor-promoting M2-like macrophages within the CD45+ immune cells. In another embodiment, the agent increases the responsiveness of cancer cells to IFN-γ and/or IFN-α. In still another embodiment, the agent increases the production of chemokines (e.g., CXCL9 and/or CXCL10) in response to IFN-γ in cancer cells. In yet another embodiment, the agent increases cancer cell surface levels of $H2\text{-}K^b$ and/or PD-L1 in response to IFN-γ. In another embodiment, the agent increases chromatin accessibility for IFN-γ-responsive genes in cancer cells. In still another embodiment, the agent downregulates genes associated with mTORC1 pathway and/or cholesterol homeostasis in cancer cells. In yet another embodiment, the agent sensitizes cancer cells to immune checkpoint blockade therapy. In another embodiment, the immune checkpoint is PD-1 and/or CTLA-4. In still another embodiment, the agent is administered in a pharmaceutically acceptable formulation. In yet another embodiment, the method further comprises administering to the subject at least one additional therapeutic agent or regimen for treating the cancer.

In another aspect, a method of sensitizing cancer cells to cytotoxic T cell-mediated killing comprising contacting the cancer cells with 1) an agent that modulates the copy number, amount, and/or activity of at least one biomarker listed in Tables 1-9 in the cancer cells and 2) cytotoxic T cells, thereby sensitizing the cancer cells to cytotoxic T cell-mediated killing, is provided.

As described above, numerous embodiments are further provided that can be applied to any aspect of the present invention and/or combined with any other embodiment described herein. For example, in one embodiment, the agent described herein downregulates the copy number, amount, and/or activity of at least one biomarker listed in Table 1, 5, 7 or 9. In another embodiment, the agent comprises or is a small molecule inhibitor, CRISPR guide RNA (gRNA), RNA interfering agent, antisense oligonucleotide, peptide or peptidomimetic inhibitor, aptamer, or intrabody. The RNA interfering agent may comprise or be, e.g., a small interfering RNA (siRNA), CRISPR RNA (crRNA), a small hairpin RNA (shRNA), a microRNA (miRNA), or a piwi-interacting RNA (piRNA). For example, the RNA interfering agent comprises or is a CRISPR guide RNA (gRNA). In still another embodiment, the agent described herein comprises an antibody and/or intrabody, or an antigen binding fragment thereof, which specifically binds to the at least one biomarker listed in Table 1, 5, 7 or 9. In yet another embodiment, the intrabody, or antigen binding fragment thereof, is murine, chimeric, humanized, composite, or human. In another embodiment, the intrabody, or antigen binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the intrabody, or antigen binding fragment thereof, is conjugated to a cytotoxic agent. Such cytotoxic agent may be selected from the group consisting of a chemotherapeutic agent, a biologic agent, a toxin, and a radioactive isotope. In yet another embodiment, the agent upregulates the copy number, amount, and/or activity of at least one biomarker listed in Table 2, 4, 6 or 8. In another embodiment, the agent comprises or is a nucleic acid molecule encoding the one or more biomarkers listed in Table 2, 4, 6 or 8 or fragment thereof, a polypeptide of the one or more biomarkers listed in Table 2, 4, 6 or 8 or fragment(s) thereof, or a small molecule that binds to the one or more biomarkers listed in Table 2, 4, 6 or 8.

In one embodiment, the method further comprises contacting the cancer cells with at least one immunotherapy. In one embodiment, the immunotherapy is cell-based. In another embodiment, the immunotherapy comprises an cancer vaccine and/or virus. In still another embodiment, the immunotherapy inhibits an immune checkpoint and/or inhibits TNF alpha. For example, the immune checkpoint described in the instant disclosure may be any checkpoint proteins known in the art, such as one selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In one embodiment, the immune checkpoint is selected from the group consisting of PD-1, PD-L1, PD-L2, and CTLA-4. In another embodiment, the immune checkpoint is PD-1 or CTLA-4. In another embodiment, the agent reduces the number of proliferating cells in the cancer and/or reduces the volume or size of a tumor comprising the cancer cells. In still another embodiment, the agent increases the amount of CD8+ T cells, CD4+ T cells, granzyme B+CD8+ T cells, and/or CD45+ immune cells in a tumor comprising the cancer cells.

The CD45+ immune cells may express higher levels of genes (e.g., genes related to IFN-γ response, IFN-α response, and/or tumor necrosis factor α signaling via NF-κB) associated with productive antitumor immunity. In still another embodiment, the agent increases the percentage of dendritic cells within the CD45+ immune cells. In yet another embodiment, the agent increases the ratio of tumor-inhibitory M1-like macropahges to tumor-promoting M2-like macrophages within the CD45+ immune cells. In another embodiment, the agent increases the responsiveness of cancer cells to IFN-γ and/or IFN-α. In still another embodiment, the agent increases the production of chemokines (e.g., CXCL9 and/or CXCL10) in response to IFN-γ in cancer cells. In yet another embodiment, the agent increases cancer cell surface levels of H2-K$^b$ and/or PD-L1 in response to IFN-γ. In another embodiment, the agent increases chromatin accessibility for IFN-γ-responsive genes in cancer cells. In still another embodiment, the agent downregulates genes associated with mTORC1 pathway and/or cholesterol homeostasis in cancer cells. In yet another embodiment, the agent sensitizes cancer cells to immune checkpoint blockade therapy. In another embodiment, the immune checkpoint is PD-1 and/or CTLA-4. In yet another embodiment, the agent is administered in a pharmaceutically acceptable formulation. In another embodiment, a method further comprises contacting the cancer cells with at least one additional cancer therapeutic agent or regimen.

In still another aspect, a method of determining whether a subject afflicted with a cancer or at risk for developing a cancer would benefit from increasing sensitivity of the cancer cells to cytotoxic T cell-mediate killing by modulating the copy number, amount, and/or activity of at least one biomarker listed in Tables 1-9, the method comprising: a) obtaining a biological sample from the subject; b) determining the copy number, amount, and/or activity of at least one biomarker listed in Tables 1-9; c) determining the copy number, amount, and/or activity of the at least one biomarker in a control; and d) comparing the copy number, amount, and/or activity of the at least one biomarker detected in steps b) and c), wherein the presence of, or a significant increase in, the copy number, amount, and/or activity of, the at least one biomarker listed in Table 1, 5, 7 or 9 and/or the absence of, or a significant decrease in, the copy number, amount, and/or activity of, the at least one biomarker listed in Table 2, 4, 6 or 8, in the subject sample relative to the control copy number, amount, and/or activity of the at least one biomarker indicates that the subject afflicted with the cancer or at risk for developing the cancer would benefit from increasing sensitivity of the cancer cells to cytotoxic T cell-mediate killing by modulating the copy number, amount, and/or activity of the at least one biomarker listed in Tables 1-9, is provided.

In one embodiment, the method further comprises recommending, prescribing, or administering an agent that modulates the at least one biomarker listed in Tables 1-9 if the cancer is determined to benefit from the agent, optionally further administering at least one additional cancer therapeutic agent or regimen. In another embodiment, the method further comprises recommending, prescribing, or administering cancer therapy other than an agent that modulates the at least one biomarker listed in Tables 1-9 if the cancer is determined to not benefit from the agent. In still another embodiment, the cancer therapy is selected from the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells.

In yet another aspect, a method for predicting the clinical outcome of a subject afflicted with a cancer, the method comprising: a) determining the copy number, amount, and/or activity of at least one biomarker listed in Tables 1-9; b) determining the copy number, amount, and/or activity of the at least one biomarker in a sample from a control having a good clinical outcome; and d) comparing the copy number, amount, and/or activity of the at least one biomarker in the subject sample and in the sample from the control subject, wherein the presence of, or a significant increase in, the copy number, amount, and/or activity of, the at least one biomarker listed in Table 1, 5, 7 or 9 and/or the absence of, or a significant decrease in, the copy number, amount, and/or activity of, the at least one biomarker listed in Table 2, 4, 6 or 8, in the subject sample as compared to the copy number, amount and/or activity in the sample from the control subject, is an indication that the subject has a poor clinical outcome, is provided.

In another aspect, a method for monitoring the progression of a cancer in a subject, the method comprising: a) detecting in a subject sample at a first point in time the amount or activity of at least one biomarker listed in Tables 1-9; b) repeating step a) at a subsequent point in time; and c) comparing the amount or activity of at least one biomarker listed in Tables 1-9 detected in steps a) and b) to monitor the progression of the cancer in the subject, is provided.

In still another aspect, a method of assessing the efficacy of an agent for treating a cancer in a subject, comprising: a) detecting in a subject sample at a first point in time the copy number, amount, and/or or activity of at least one biomarker listed in Tables 1-9; b) repeating step a) during at least one subsequent point in time after administration of the agent; and c) comparing the copy number, amount, and/or activity detected in steps a) and b), wherein the absence of, or a significant decrease in, the copy number, amount, and/or activity of, the at least one biomarker listed in Table 1, 5, 7 or 9 and/or the presence of, or a significant increase in, the copy number, amount, and/or activity of, the at least one biomarker listed in Table 2, 4, 6 or 8, in the subsequent sample as compared to the copy number, amount, and/or activity in the sample at the first point in time, indicates that the agent treats the cancer in the subject, is provided.

As described above, numerous embodiments are further provided that can be applied to any aspect of the present invention and/or combined with any other embodiment described herein. For example, in one embodiment, the subject has undergone treatment, completed treatment, and/or is in remission for the cancer between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject. In another embodiment, the sample comprises cells, serum, peritumoral tissue, and/or intratumoral tissue obtained from the subject.

In yet another aspect, a cell-based assay for screening for agents that sensitize a cancer cell to cytotoxic T cell-mediated killing comprising contacting the cancer cell with cytotoxic T cells and a test agent, and determining the ability of the test agent to decrease the copy number, amount, and/or activity of at least one biomarker listed in Table 1, 5, 7 or 9 and/or increase the copy number, amount, and/or activity of the at least one biomarker listed in Table 2, 4, 6 or 8. In one embodiment, the step of contacting occurs in vivo, ex vivo, or in vitro, is provided.

As described above, numerous embodiments are further provided that can be applied to any aspect of the present invention and/or combined with any other embodiment described herein. For example, in one embodiment, the method or assay further comprises determining a reduction in the number of proliferating cells in the cancer and/or a reduction in the volume or size of a tumor comprising the cancer cells. In another embodiment, the method or assay further comprises determining an increased number of CD8+ T cells, CD4+ T cells, granzyme B+CD8+ T cells, and/or CD45+ immune cells infiltrating a tumor comprising the cancer cells. In still another embodiment, the method or assay further comprises determining an increased responsiveness of cancer cells to IFN-γ and/or IFN-α.

In yet another embodiment, the method or assay further comprises determining decreased expression levels of genes related to mTORC1 pathway and/or cholesterol hoeostasis. In another embodiment, the method or assay further comprises determining responsiveness to the agent that modulates the at least one biomarker listed in Tables 1-9 measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In still another embodiment, the method or assay further comprises contacting the cancer cells with at least one additional cancer therapeutic agent or regimen. In yet another embodiment, the at least one biomarker listed in Table 1, 5, 7 or 9 is selected from the group consisting of PD-L1, Ptpn2, Serpinb9, Otulin, Rela, Ikbkg, Ikbkb, Rnf31, Sharpin, Rraga, Rragc, Lamtor 1, Tbk1, Fadd, Atg5, Nsdhl, Gne, Gale, Ero1l, Cd44, Nadk, Nampt, Arid2, Pbrm1, Brd7, Sox4, Hdac5, Cflar, or Ptpn11, or a fragment thereof. In another embodiment, the at least one biomarker listed in Table 1, 5, 7 or 9 is Arid 2, Pbrm1, or Brd7, or a fragment thereof. In still another embodiment, the at least one biomarker listed in Table 2, 4, 6 or 8 is selected from the group consisting of human H2-D1, B2m, Tap1, Tap2, Nlrc5, Jak1, Jak2, Stat1, Ifngr1, Ifngr2, Nf1, Dusp6, Spred1, Rasa2, or SPOP, or a fragment thereof. In yet another embodiment, the cancer is selected from the group consisting of melanoma, head and neck squamous carcinoma, kidney cancer, colorectal cancer, gliomas, neuroblastoma, prostate cancer, breast cancer, pancreatic ductal carcinoma, epithelial ovarian cancer, B-CLL, leukemia, B cell lymphoma, renal cell carcinoma, lung adenocarcinoma and squamous carcinoma. In another embodiment, the cancer is resistant to blockade of at least one immune checkpoint. In still another embodiment, the subject to be treated is an animal model of the cancer, such as a mouse model. In yet another embodiment, the subject is a mammal, such as a mouse or a human. In another embodiment, the mammal is a human.

BRIEF DESCRIPTION OF THE DRAWINGS

FIG. 21, Panel D discloses SEQ ID NOS 992-993, respectively, in order of appearance. Panel E shows the direct target prediction and statistical significance analysis performed using BETA (Binding and Expression Target Analysis) based on ATAC-seq sites from clusters I and III and differentially expressed genes following IFNγ treatment in Pbrm1 deficient cells. Significant predicted targets for genes in FIG. 18C are shown.

Figure 15:
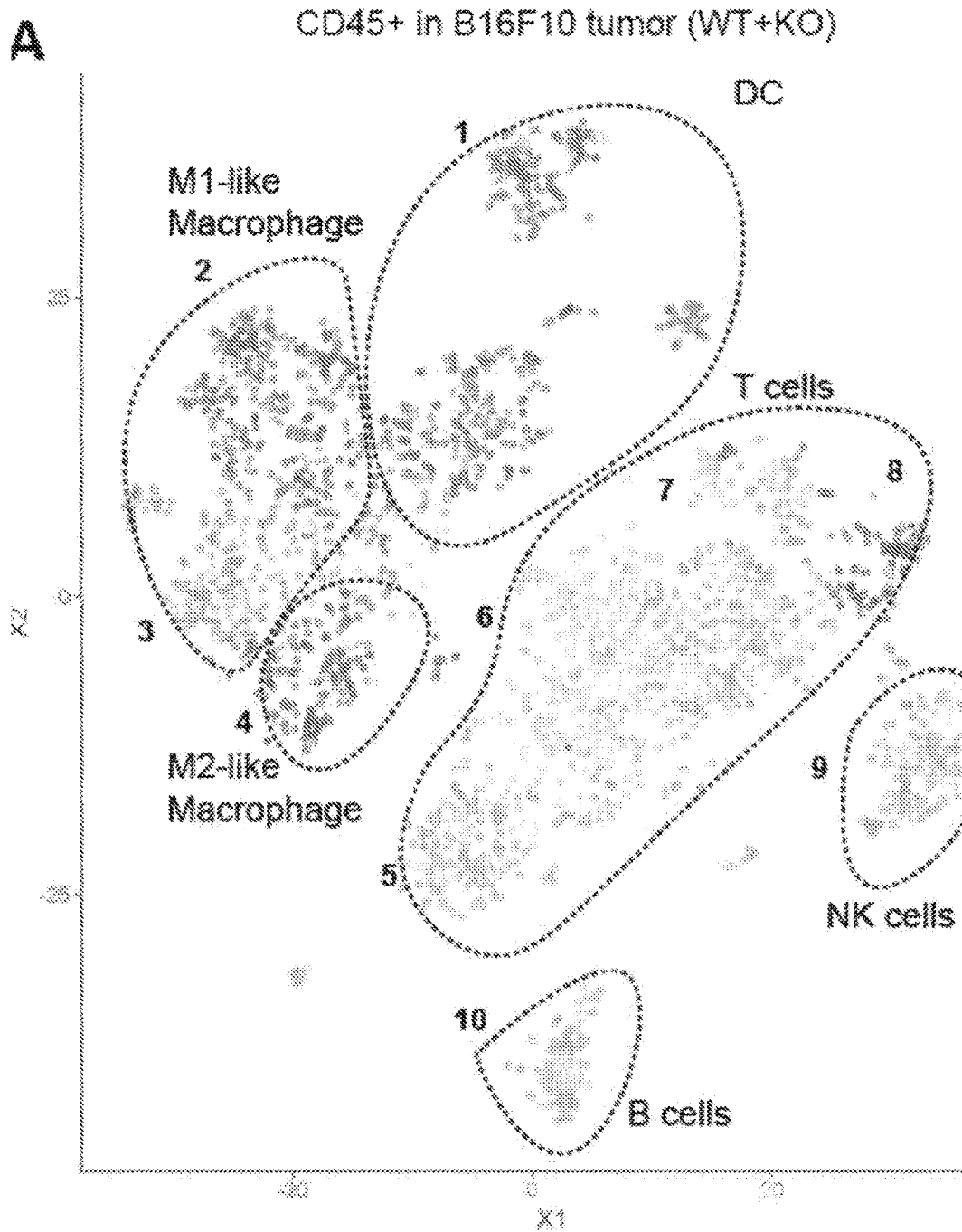
FIG. 15 includes 4 panels, identified as panels A, B, C, and D, which show the changes in tumor microenvironment in Pbrm1 deficient tumors. Panel A shows the tSNE projections of CD45+ cells (combined for Pbrm1 deficient and control B16F10 tumors). CD45+ cells were sorted and pooled (n=5) from either Pbrm1 deficient or control B16F10 tumors for single-cell RNA-seq. Cells are colored by k-means clusters, and the corresponding cell types are annotated based on expression of lineage-specific markers as illustrated in (Panel B). Panel B shows the heatmap that shows the gene expression level of markers for each cluster of cells separated by k-means clusters. Panel C shows the GSEA analysis (hallmark gene sets) performed on genes that were significantly overexpressed in Pbrm1 deficient compared to control B16F10 tumors for each k-means cluster shown in (Panel A). −$\log_{10}$ (FDR) for "IFNα response", "IFNγ response" and "TNFα signaling via NF-κB" gene sets are shown. Panel D shows the percentage of indicated cell clusters in total CD45+ cells in Pbrm1 deficient versus control B16F10 tumors.
Figure 15:
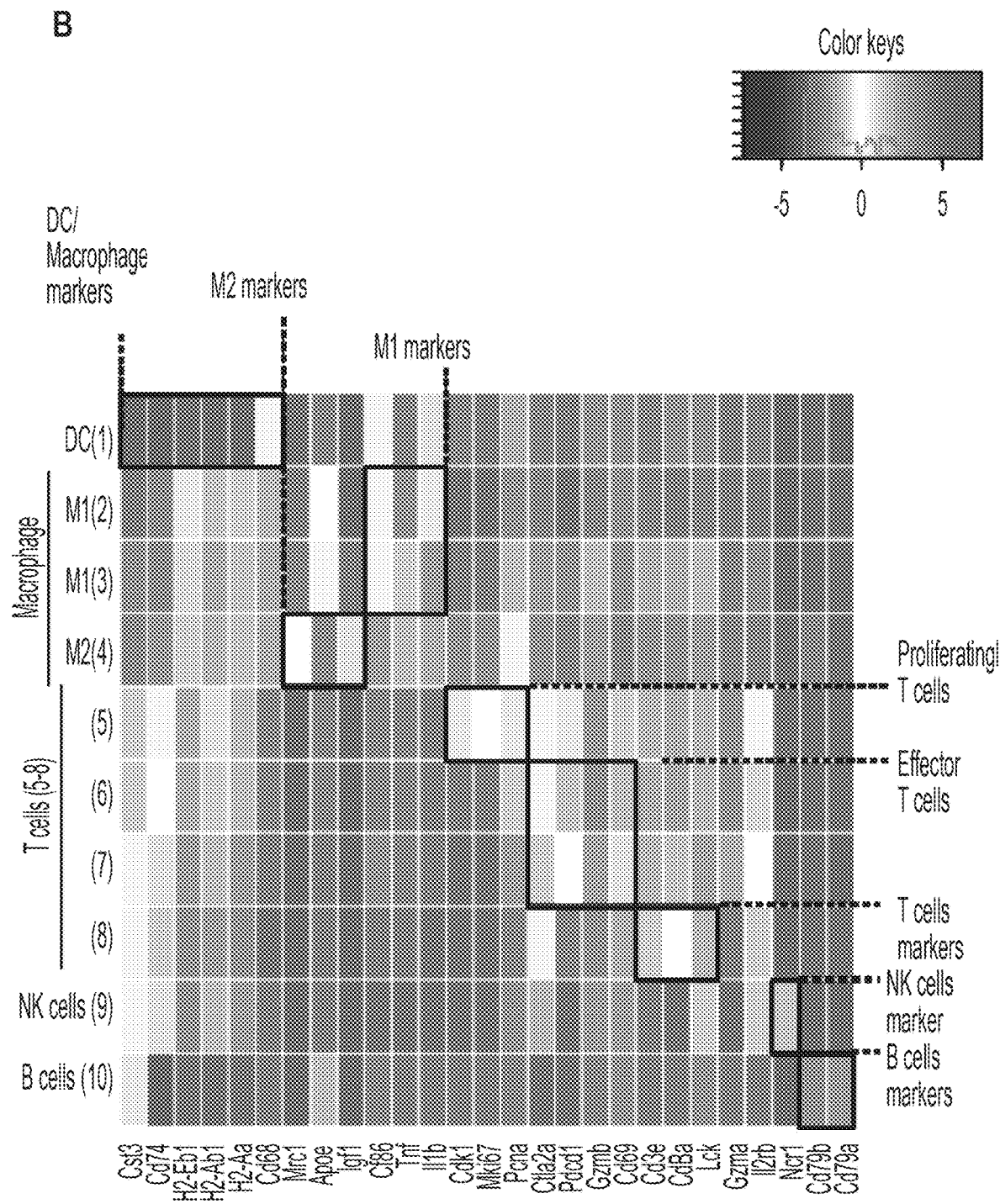
Figure 15:
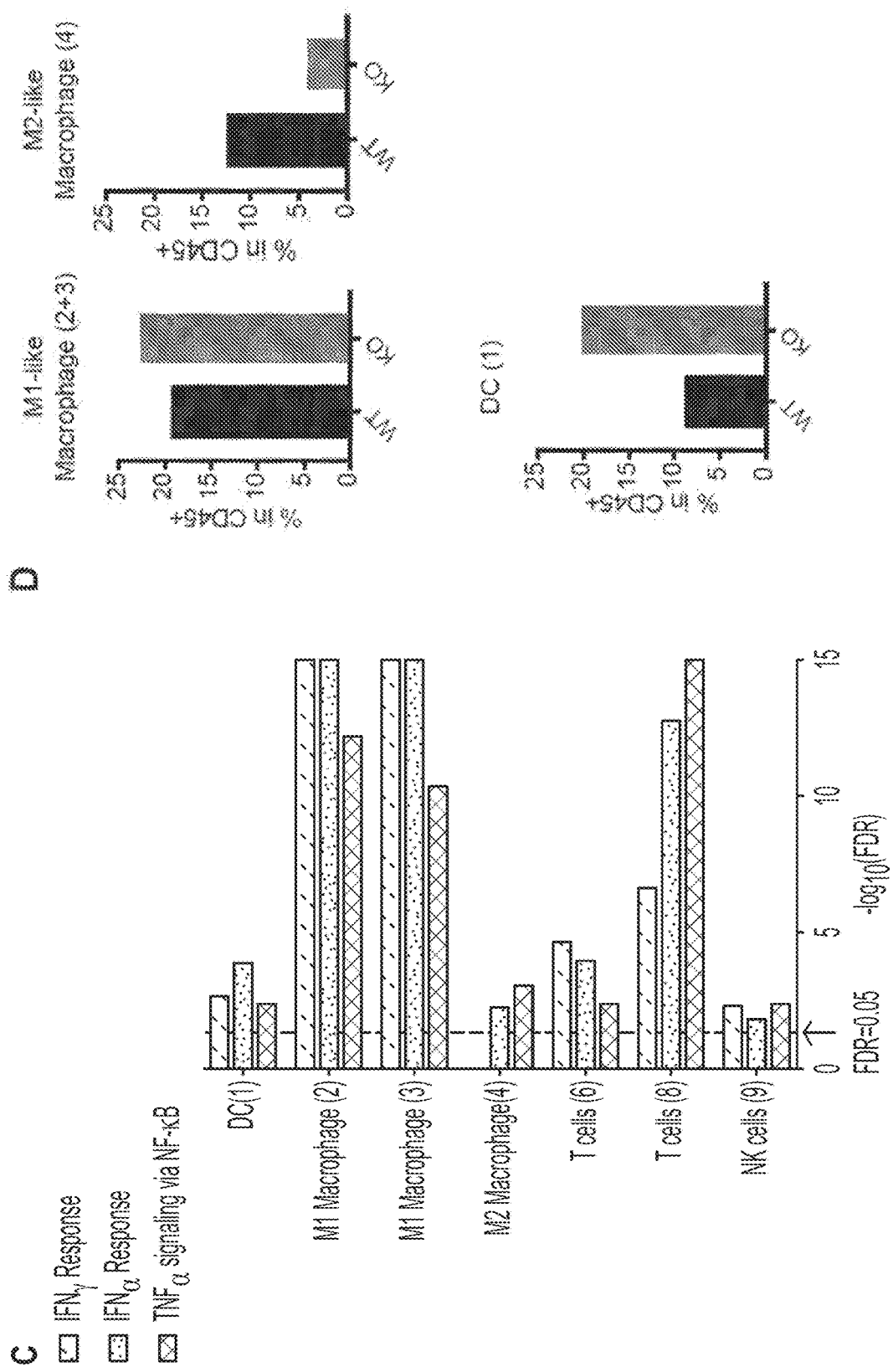

For any figure showing a bar histogram, curve, or other data associated with a legend, the bars, curve, or other data are generally presented from left to right for each indication correspond directly and in order to the boxes from top to bottom of the legend, except for FIG. 15C where the boxes for IFN-alpha appear before the boxes for IFN-gamma.

DETAILED DESCRIPTION OF THE INVENTION

It has been determined herein that multiple genes and pathways described herein, including components of NF-kB pathway, mTORC1 pathway, RIG-I like receptor signaling pathway, glycolysis and nicotinate/nicotinamide metabolism pathways, as well as components of a SWI/SNF chromatin remodeling complex (PBAF complex), such as those listed in the Tables and Examples, are regulators of T cell-mediated killing of cancer cells. Accordingly, the present invention relates, in part, to methods for sensitizing the cancer cells in a subject afflicted with a cancer to cytotoxic T cell-mediated killing by modulating the copy number, amount, and/or activity of these genes and pathways in the cancer cells.

I. Definitions

The articles "a" and "an" are used herein to refer to one or to more than one (i.e. to at least one) of the grammatical object of the article. By way of example, "an element" means one element or more than one element.

The term "administering" is intended to include routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples. In some embodiments, the level of the biomarker refers to the level of the biomarker itself, the level of a modified biomarker (e.g., phosphorylated biomarker), or to the level of a biomarker relative to another measured variable, such as a control (e.g., phosphorylated biomarker relative to an unphosphorylated biomarker).

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Figure 3:
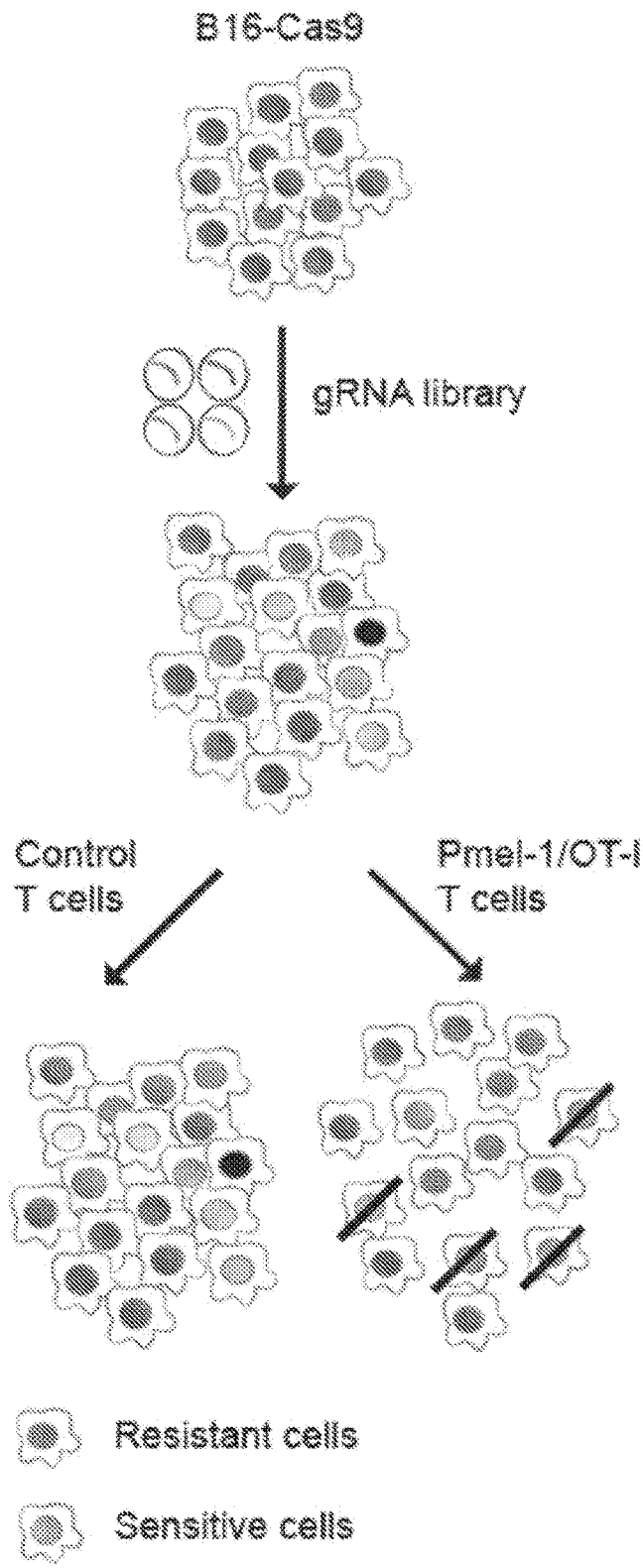
FIG. 3 includes 3 panels, identified as panels A, B and C which show the systematic discovery of genes and pathways regulating sensitivity and resistance of tumor cells to T cell-mediated killing. Panel A shows the screening strategy for identification of novel regulators of T cell-mediated killing. Cas9-expressing B16F10 cells were transduced with genomic gRNA library (four gRNAs/gene) consisting of ~80,000 gRNA targeting 20,000 genes. Edited B16F10 cells were co-cultured with activated cytotoxic T cells followed by Illumina sequencing of gRNA representation. Specific selection was performed with Pmel-1 T cells (specific for gp100 melanoma antigen) or OT-I T cells (specific for Ova peptide). Control selection was performed with T cells of irrelevant specificity. Panel B shows immune selection with antigen-specific CD8+ T cells in which the mutant pool of B16 cells was co-cultured and selected by CD8+ T cells isolated from two TCR transgenic strains: 1. Pmel1 T cells, which recognize endogenous antigen gp100, or 2. OT-1 T cells, which recognize exogenously pulsed antigen SIINFEKL[[L]] (SEQ ID NO: 1) with higher TCR-peptide-MHC affinity. The representation of gRNA is determined using Illumina sequencing from the remaining cells in post-immune selection. After selection by T cells, cells with enriched gRNA were expected to be more resistant to T cell-mediated killing. Cells with depleted gRNA were expected to be more sensitive to T cell-mediated killing. Panel B shows the top positively selected candidate genes in the Pmel1 screen using MaGeCK analysis. Candidate genes were plotted based on mean log 2 fold change of gRNA counts compared to control selection and P values computed by MaGeCK (Model-based Analysis of Genome-wide CRISPR-Cas9 Knockout). Dashed line indicates a FDR (False Discovery Rate)=0.05. Annotated genes represent MHC class I (red), interferon (yellow) and Ras/MAPK (blue) pathways. Genes involved in the MHC/antigen presentation pathway, type I/II interferon pathway and Ras/MAPK pathway were annotated. Panel C shows the top negatively selected candidate genes in the Pmel1 screen. Genes involved in the NF-kB pathway (blue), mTOR pathway (yellow), and PBAF form of SWI/SNF complex (red), and known negative immune regulators (green) were annotated.
Figure 3:
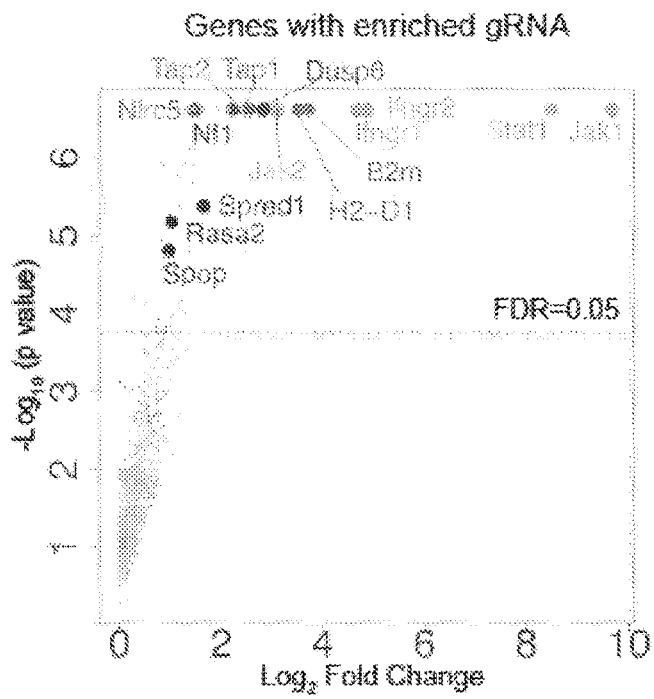
Figure 3:
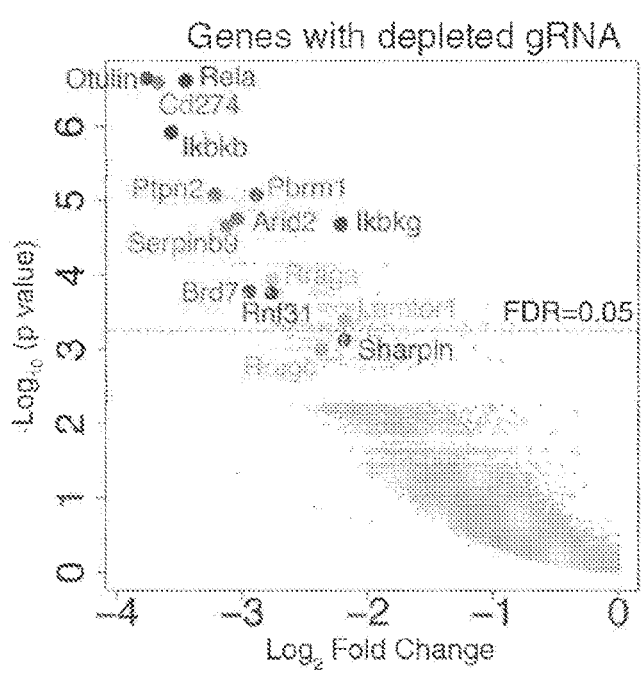
Figure 9:
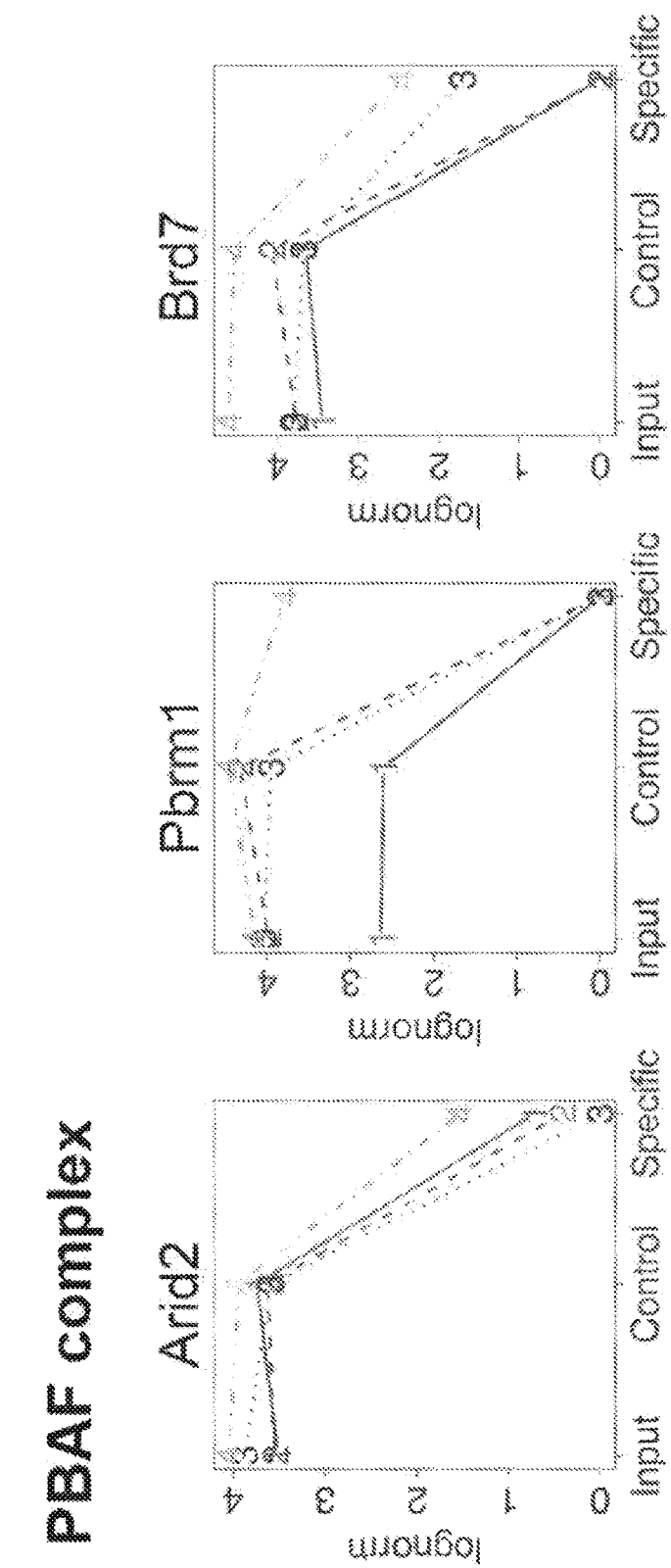
FIG. 9 includes 3 panels, identified as panels A, B and C, which show the analysis of gRNA representation in experimental and control screening conditions. gRNA frequencies were analyzed for key genes identified in the screen for which gRNAs were either depleted (Panels A, B) or enriched (Panel C) in the presence of tumor-specific cytotoxic T cells. These genes included all three unique members of the PBAF complex (Pbrm1, Arid2 and Brd7) (Panel A), and two representative members of major pathways presented in FIG. 5A (Panels B, C). For each gene, the frequencies of all four gRNAs in the primary screen were plotted for three conditions: Input tumor library (Input), control selection with T cells of irrelevant TCR specificity (Control) and experimental selection with tumor-specific Pmel-1 T cells (Specific); y-axis: Log normalized count for each condition.
Figure 9:
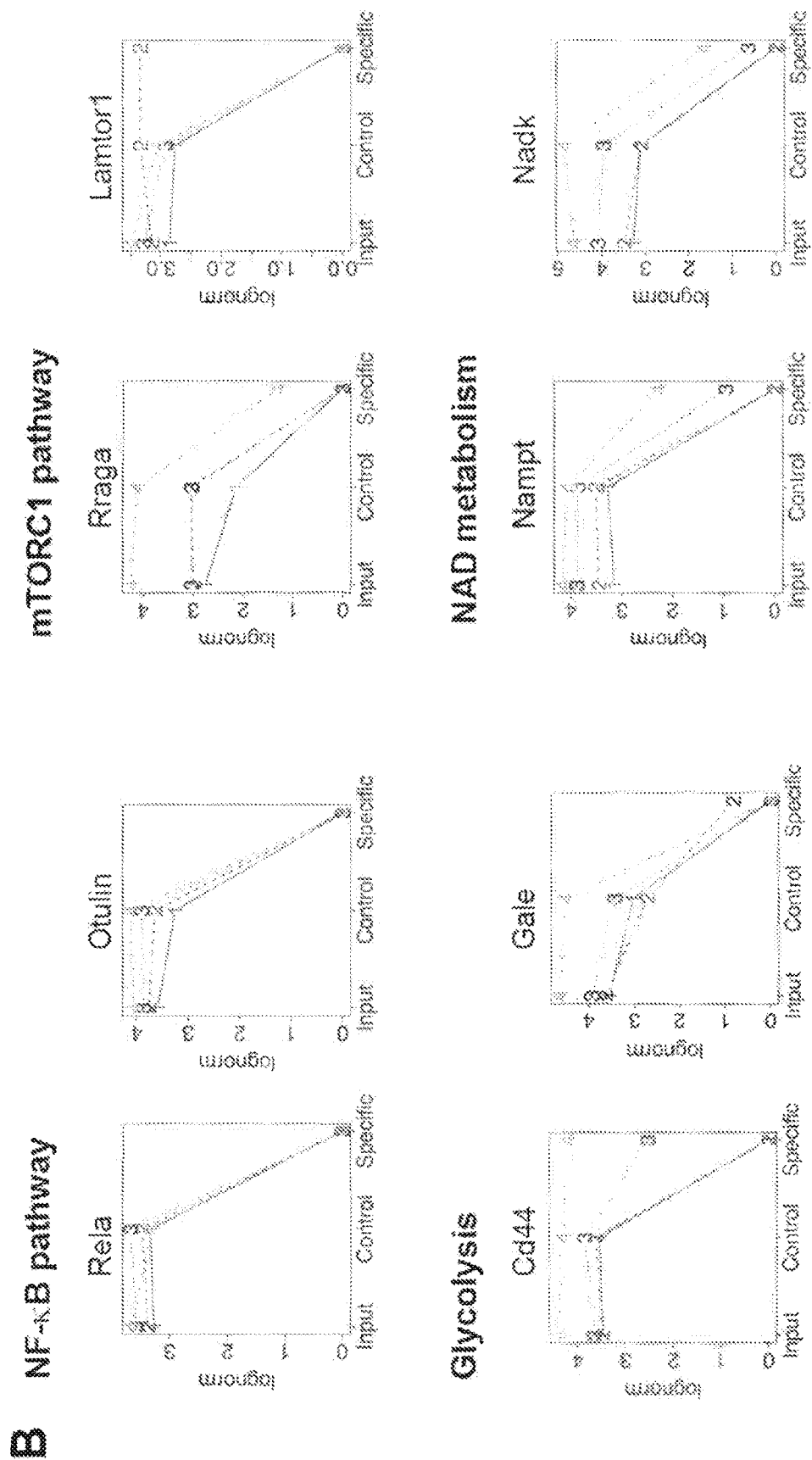
Figure 9:
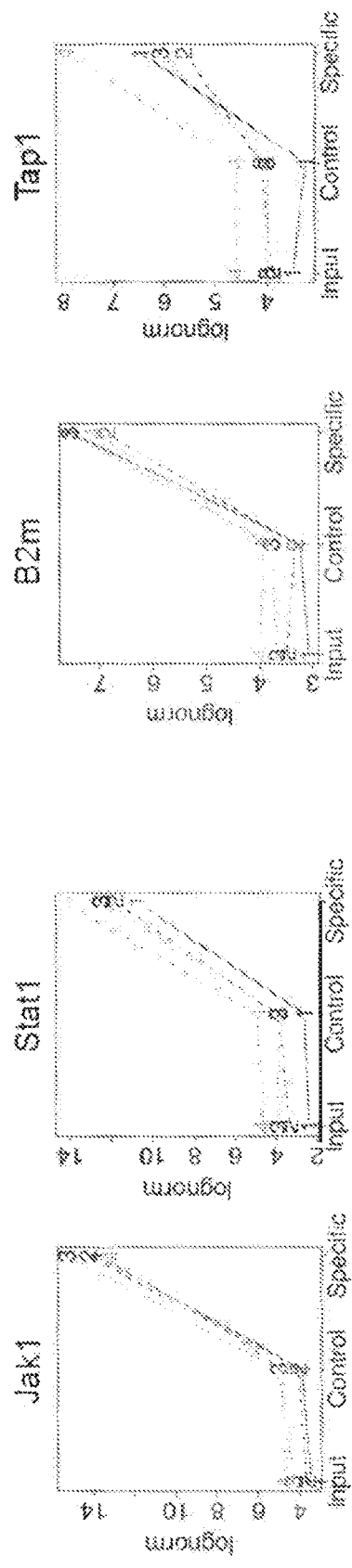
Figure 9:
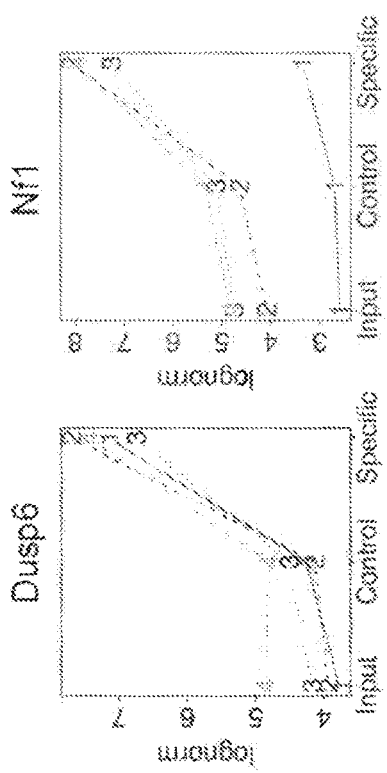

The term "SWI/SNF complex" refers to SWItch/Sucrose Non-Fermentable, a nucleosome remodeling complex found in both eukaryotes and prokaryotes (Neigeborn Carlson (1984) *Genetics* 108:845-858; Stern et al. (1984) *J. Mol. Biol.* 178:853-868). The SWI/SNF complex was first discovered in the yeast, *Saccharomyces cerevisiae*, named after yeast mating types switching (SWI) and sucrose nonfermenting (SNF) pathways (Workman and Kingston (1998) *Annu Rev Biochem.* 67:545-579; Sudarsanam and Winston (2000) *Trends Genet.* 16:345-351). It is a group of proteins comprising, at least, SWI1, SWI2/SNF2, SWI3, SWI5, and SWI6, as well as other polypeptides (Pazin and Kadonaga (1997) *Cell* 88:737-740). A genetic screening for suppressive mutations of the SWI/SNF phenotypes identified different histones and chromatin components, suggesting that these proteins were possibly involved in histone binding and chromatin organization (Winston and Carlson (1992) *Trends Genet.* 8:387-391). Biochemical purification of the SWI/SNF2p in *S. cerevisiae* demonstrated that this protein was part of a complex containing an additional 11 polypeptides, with a combined molecular weight over 1.5 MDa. The SWI/SNF complex contains the ATPase Swi2/Snf2p, two actin-related proteins (Arp7p and Arp9) and other subunits involved in DNA and protein-protein interactions. The purified SWI/SNF complex was able to alter the nucleosome structure in an ATP-dependent manner (Workman and Kingston (1998), *supra*; Vignali et al. (2000) *Mol Cell Biol.* 20:1899-1910). The structures of the SWI/SNF and RSC complexes are highly conserved but not identical, reflecting an increasing complexity of chromatin (e.g., an increased genome size, the presence of DNA methylation, and more complex genetic organization) through evolution. For this reason, the SWI/SNF complex in higher eukaryotes maintains core components, but also substitute or add on other components with more specialized or tissue-specific domains. Yeast contains two distinct and similar remodeling complexes, SWI/SNF and RSC (Remodeling the Structure of Chromatin). In *Drosophila*, the two complexes are called BAP (Brahma Associated Protein) and PBAP (Polybromo-associated BAP) complexes. The human analogs are BAF (Brg1 Associated Factors, or SWI/SNF-A) and PBAF (Polybromo-associated BAF, or SWI/SNF-B). As shown in FIG. 9, the BAF complex comprises, at least, BAF250A (ARID1A), BAF250B (ARID1B), BAF57 (SMARCE1), BAF190/BRM (SMARCA2), BAF47 (SMARCB1), BAF53A (ACTL6A), BRG1/BAF190 (SMARCA4), BAF155 (SMARCC1), and BAF170 (SMARCC2). The PBAF complex comprises, at last, BAF200 (ARID2), BAF180 (PBRM1), BRD7, BAF45A (PHF10), BRG1/BAF190 (SMARCA4), BAF155 (SMARCC1), and BAF170 (SMARCC2). As in *Drosophila*, human BAF and PBAF share the different core components BAF47, BAF57, BAF60, BAF155, BAF170, BAF45 and the two actins b-Actin and BAF53 (Mohrmann and Verrijzer (2005) *Biochim Biophys Acta.* 1681:59-73). The central core of the BAF and PBAF is the ATPase catalytic subunit BRG1/hBRM, which contains multiple domains to bind to other protein subunits and acetylated histones. For a summary of different complex subunits and their domain structure, see Tang et al. (2010) *Prog Biophys Mol Biol.* 102:122-128 (e.g., FIG. 3), Hohmann and Vakoc (2014) *Trends Genet.* 30:356-363 (e.g., FIG. 1), and Kadoch and Crabtree (2015) *Sci. Adv.* 1:e1500447. For chromatin remodeling, the SWI/SNF complex use the energy of ATP hydrolysis to slide the DNA around the nucleosome. The first step consists in the binding between the remodeler and the nucleosome. This binding occurs with nanomolar affinity and reduces the digestion of nucleosomal DNA by nucleases. The 3-D structure of the yeast RSC complex was first solved and imaged using negative stain electron microscopy (Asturias et al. (2002) *Proc Natl Acad Sci USA* 99:13477-13480). The first Cryo-EM structure of the yeast SWI/SNF complex was published in 2008 (Dechassa et al. 2008). DNA footprinting data showed that the SWI/SNF complex makes close contacts with only one gyre of nucleosomal DNA. Protein crosslinking showed that the ATPase SWI2/SNF2p and Swi5p (the homologue of Ini1p in human), Snf6, Swi29, Snfl1 and Sw82p (not conserved in human) make close contact with the histones. Several individual SWI/SNF subunits are encoded by gene families, whose protein products are mutually exclusive in the complex (Wu et al. (2009) *Cell* 136: 200-206). Thus, only one paralog is incorporated in a given SWI/SNF assembly. The only exceptions are BAF155 and BAF170, which are always present in the complex as homo- or hetero-dimers.

Combinatorial association of SWI/SNF subunits could in principle give rise to hundreds of distinct complexes, although the exact number has yet to be determined (Wu et al. (2009), *supra*). Genetic evidence suggests that distinct subunit configurations of SWI/SNF are equipped to perform specialized functions. As an example, SWI/SNF contains one of two ATPase subunits, BRG1 or BRM/SMARCA2, which share 75% amino acid sequence identity (Khavari et al. (1993) *Nature* 366:170-174). While in certain cell types BRG1 and BRM can compensate for loss of the other subunit, in other contexts these two ATPases perform divergent functions (Strobeck et al. (2002) *J Biol Chem.* 277: 4782-4789; Hoffman et al. (2014) *Proc Natl Acad Sci USA.* 111:3128-3133). In some cell types, BRG1 and BRM can even functionally oppose one another to regulate differentiation (Flowers et al. (2009) *J Biol Chem.* 284:10067-10075). The functional specificity of BRG1 and BRM has been linked to sequence variations near their N-terminus, which have different interaction specificities for transcription factors (Kadam and Emerson (2003)*Mol Cell.* 11:377-389). Another example of paralogous subunits that form mutually exclusive SWI/SNF complexes are ARID1A/BAF250A, ARID1B/BAF250B, and ARID2/BAF200. ARID1A and ARID1B share 60% sequence identity, but yet can perform opposing functions in regulating the cell cycle, with MYC being an important downstream target of each paralog (Nagl et al. (2007) *EMBO J.* 26:752-763). ARID2 has diverged considerably from ARID1A/ARID1B and exists in a unique SWI/SNF assembly known as PBAF (or SWI/SNF-B), which contains several unique subunits not found in ARID1A/B-containing complexes. The composition of SWI/SNF can also be dynamically reconfigured during cell fate transitions through cell type-specific expression patterns of certain subunits. For example, BAF53A/ACTL6A is repressed and replaced by BAF53B/ACTL6B during neuronal differentiation, a switch that is essential for proper neuronal functions in vivo (Lessard et al. (2007) *Neuron* 55:201-215). These studies stress that SWI/SNF in fact represents a collection of multi-subunit complexes whose integrated functions control diverse cellular processes, which is also incorporated in the scope of definitions of the instant disclosure. Two recently published meta-analyses of cancer genome sequencing data estimate that nearly 20% of human cancers harbor mutations in one (or more) of the genes encoding SWI/SNF (Kadoch et al. (2013) *Nat Genet.* 45:592-601; Shain and Pollack (2013) *PLoS One.* 8:e55119). Such mutations are generally loss-of-function, implicating SWI/SNF as a major tumor suppressor in diverse cancers. Specific SWI/SNF gene mutations are generally linked to a specific subset of cancer lineages: SNF5 is mutated in malignant rhabdoid tumors (MRT), PBRM1/BAF180 is frequently inactivated in renal carcinoma, and BRG1 is mutated in non-small cell lung cancer (NSCLC) and several other cancers. In the instant disclosure, the scope of "SWI/SNF complex" may cover at least one fraction or the whole complex (e.g., some or all subunit proteins/other components), either in the human BAF/PBAF forms or their homologs/orthologs in other species (e.g., the yeast and *drosophila* forms described herein). Preferably, a "SWI/SNF complex" described herein contains at least part of the full complex bio-functionality, such as binding to other subunits/components, binding to DNA/histone, catalyzing ATP, promoting chromatin remodeling, etc.

The term "BAF complex" refers to at least one type of mammalian SWI/SNF complexes. Its nucleosome remodeling activity can be reconstituted with a set of four core subunits (BRG1/SMARCA4, SNF5/SMARCB1, BAF155/SMARCC1, and BAF170/SMARCC2), which have orthologs in the yeast complex (Phelan et al. (1999) *Mol Cell.* 3:247-253). However, mammalian SWI/SNF contains several subunits not found in the yeast counterpart, which can provide interaction surfaces for chromatin (e.g. acetyl-lysine recognition by bromodomains) or transcription factors and thus contribute to the genomic targeting of the complex (Wang et al. (1996) *EMBO J.* 15:5370-5382; Wang et al. (1996) *Genes Dev.* 10:2117-2130; Nie et al. (2000)). A key attribute of mammalian SWI/SNF is the heterogeneity of subunit configurations that can exist in different tissues and even in a single cell type (e.g., as BAF, PBAF, neural progenitor BAF (npBAF), neuron BAF (nBAF), embryonic stem cell BAF (esBAF), etc.). In some embodiments, the BAF complex described herein refers to one type of mammalian SWI/SNF complexes, which is different from PBAF complexes.

The term "PBAF complex" refers to one type of mammalian SWI/SNF complexes originally known as SWI/SNF-B. It is highly related to the BAF complex and can be separated with conventional chromatographic approaches. For example, human BAF and PBAF complexes share multiple identical subunits (such as BRG, BAF170, BAF155, BAF60, BAF57, BAF53, BAF45, actin, SS18, and hSNF5/INI1, as illustrated in FIG. 9). However, while BAF contains BAF250 subunit, PBAF contains BAF180 and BAF200, instead (Lemon et al. (2001) *Nature* 414:924-998; Yan et al. (2005) *Genes Dev.* 19:1662-1667). Moreover, they do have selectivity in regulating interferon-responsive genes (Yan et al. (2005), *supra*, showing that BAF200, but not BAF180, is required for PBAF to mediate expression of IFITM1 gene induced by IFN-α, while the IFITM3 gene expression is dependent on BAF but not PBAF). Due to these differences, PBAF, but not BAF, was able to activate vitamin D receptor-dependent transcription on a chromatinzed template in vitro (Lemon et al. (2001), *supra*). The 3-D structure of human PBAF complex preserved in negative stain was found to be similar to yeast RSC but dramatically different from yeast SWI/SNF (Leschziner et al. (2005) *Structure* 13:267-275).

The term "BAF200" or "ARID2" refers to AT-rich interactive domain-containing protein 2, a subunit of the SWI/SNF complex, which can be found in PBAF but not BAF complexes. It facilitates ligand-dependent transcriptional activation by nuclear receptors. The ARID2 gene, located on chromosome 12q in humans, consists of 21 exons; orthologs are known from mouse, rat, cattle, chicken, and mosquito (Zhao et al. (2011) Oncotarget 2:886-891). A conditional knockout mouse line, called Arid2$^{tm1\alpha(EUCOMM)Wtsi}$ was generated as part of the International Knockout Mouse Consortium program, a high-throughput mutagenesis project to generate and distribute animal models of disease (Skames et al. (2011) *Nature* 474:337-342). Human ARID2 protein has 1835 amino acids and a molecular mass of 197391 Da. The ARID2 protein contains two conserved C-terminal C2H2 zinc fingers motifs, a region rich in the amino acid residues proline and glutamine, a RFX (regulatory factor X)-type winged-helix DNA-binding domain (e.g., amino acids 521-601 of ARID2), and a conserved N-terminal AT-rich DNA interaction domain (e.g., amino acids 19-101 of ARID2; Zhao et al. (2011), *supra*). Mutation studies have revealed ARID2 to be a significant tumor suppressor in many cancer subtypes. ARID2 mutations are prevalent in hepatocellular carcinoma (Li et al. (2011) *Nature Genetics.* 43:828-829) and melanoma (Hodis et al. (2012) *Cell* 150:251-263; Krauthammer et al. (2012) *Nature Genetics.* 44:1006-1014). Mutations are present in a smaller but significant fraction in a wide range of other tumors (Shain and Pollack (2013), *supra*). ARID2 mutations are enriched in hepatitis C virus-associated hepatocellular carcinoma in the U.S. and European patient populations compared with the overall mutation frequency (Zhao et al. (2011), *supra*). The known binding partners for ARID2 include, e.g., Serum Response Factor (SRF) and SRF cofactors MYOCD, NKX2-5 and SRFBP1.

The term "BAF200" or "ARID2" is intended to include fragments, variants (e.g., allelic variants), and derivatives thereof. Representative human ARID2 cDNA and human ARID2 protein sequences are well-known in the art and are publicly available from the National Center for Biotechnology Information (NCBI). For example, two different human ARID2 isoforms are known. Human ARID2 isoform A (NP_689854.2) is encodable by the transcript variant 1 (NM_152641.3), which is the longer transcript. Human ARID2 isoform B (NP_001334768.1) is encodable by the transcript variant 2 (NM_001347839.1), which differs in the 3' UTR and 3' coding region compared to isoform A. The encoded isoform B has a shorter C-terminus compared to isoform A. Nucleic acid and polypeptide sequences of ARID2 orthologs in organisms other than humans are well-known and include, for example, chimpanzee ARID2 (XM_016923581.1 and XP_016779070.1, and XM_016923580.1 and XP_016779069.1), Rhesus monkey ARID2 (XM_015151522.1 and XP_015007008.1), dog ARID2 (XM_003433553.2 and XP_003433601.2; and XM_014108583.1 and XP_013964058.1), cattle ARID2 (XM_002687323.5 and XP_002687369.1; and XM_015463314.1 and XP_015318800.1), mouse ARID2 (NM_175251.4 and NP_780460.3), rat ARID2 (XM_345867.8 and XP_345868.4; and XM_008776620.1 and XP_008774842.1), chicken ARID2 (XM_004937552.2 and XP_004937609.1, XM_004937551.2 and XP_004937608.1, XM_004937554.2 and XP_004937611.1, and XM_416046.5 and XP_416046.2), tropical clawed frog ARID2 (XM_002932805.4 and XP_002932851.1, XM_018092278.1 and XP_017947767.1, and XM_018092279.1 and XP_017947768.1), and zebrafish ARID2 (NM_001077763.1 and NP_001071231.1, and XM_005164457.3 and XP_005164514.1). Representative sequences of ARID2 orthologs are presented below in Table 1.

Anti-ARID2 antibodies suitable for detecting ARID2 protein are well-known in the art and include, for example, antibodies ABE316 and 04-080 (EMD Millipore, Billerica, MA), antibodies NBP1-26615, NBP2-43567, and NBP1-26614 (Novus Biologicals, Littleton, CO), antibodies ab51019, ab166850, ab113283, and ab56082 (AbCam, Cambridge, MA), antibodies Cat #: PA5-35857 and PA5-51258 (ThermoFisher Scientific, Waltham, MA), antibodies GTX129444, GTX129443, and GTX632011 (GeneTex, Irvine, CA), ARID2 (H-182) Antibody, ARID2 (H-182) X Antibody, ARID2 (5-13) Antibody, ARID2 (5-13) X Antibody, ARID2 (E-3) Antibody, and ARID2 (E-3) X Antibody (Santa Cruz Biotechnology), etc. In addition, reagents are well-known for detecting ARID2 expression. Multiple clinical tests of PBRM1 are available in NIH Genetic Testing Registry (GTR®) (e.g., GTR Test ID: GTR000541481.2, offered by Fulgent Clinical Diagnostics Lab (Temple City, CA)). Moreover, multiple siRNA, shRNA, CRISPR constructs for reducing ARID2 expression can be found in the commercial product lists of the above-referenced companies, such as siRNA product #SR316272, shRNA products #TR306601, TR505226, TG306601, SR420583, and CRISPR products #KN212320 and KN30154 from Origene Technologies (Rockville, MD), RNAi product H00196528-R01 (Novus Biologicals), CRISPR gRNA products from GenScript (Cat. #KN301549 and KN212320, Piscataway, NJ) and from Santa Cruz (sc-401863), and RNAi products from Santa Cruz (Cat #sc-96225 and sc-77400). It is to be noted that the term can further be used to refer to any combination of features described herein regarding ARID2 molecules. For example, any combination of sequence composition, percentage identify, sequence length, domain structure, functional activity, etc. can be used to describe an ARID2 molecule of the present invention.

The term "BRD7" refers to Bromodomain-containing protein 7, a subunit of the SWI/SNF complex, which can be found in PBAF but not BAF complexes. BRD7 is a transcriptional corepressor that binds to target promoters (e.g., the ESR1 promoter) and down-regulates the expression of target genes, leading to increased histone H3 acetylation at Lys-9 (H3K9ac). BRD7 can recruit other proteins such as BRCA1 and POU2F1 to, e.g., the ESR1 promoter for its function. BRD7 activates the Wnt signaling pathway in a DVL1-dependent manner by negatively regulating the GSK3B phosphotransferase activity, while BRD7 induces dephosphorylation of GSK3B at Tyr-216. BRD7 is also a coactivator for TP53-mediated activation of gene transcription and is required for TP53-mediated cell-cycle arrest in response to oncogene activation. BRD7 promotes acetylation of TP53 at Lys-382, and thereby promotes efficient recruitment of TP53 to target promoters. BRD7 also inhibits cell cycle progression from G1 to S phase. For studies on BRD7 functions, see Zhou et al. (2006) *J. Cell. Biochem.* 98:920-930; Harte et al. (2010) *Cancer Res.* 70:2538-2547; Drost et al. (2010) *Nat. Cell Biol.* 12:380-389. The known binding partners for BRD7 also include, e.g., Tripartite Motif Containing 24 (TRIM24), Protein Tyrosine Phosphatase, Non-Receptor Type 13 (PTPN13), Dishevelled Segment Polarity Protein 1 (DVL1), interferon regulatory factor 2 (IRF2) (Staal et al. (2000) *J. Cell. Physiol.* US 185:269-279) and heterogeneous nuclear ribonucleoprotein U-like protein 1 (HNRPUL1) (Kzhyshkowska et al. (2003) *Biochem. J.* England. 371:385-393). Human BRD7 protein has 651 amino acids and a molecular mass of 74139 Da, with a N-terminal nuclear localization signal (e.g., amino acids 65-96 of BRD7), a Bromo-BRD7-like domain (e.g., amino acids 135-232 of BRD7), and a DUF3512 domain (e.g., amino acids 287-533 of BRD7).

The term "BRD7" is intended to include fragments, variants (e.g., allelic variants), and derivatives thereof. Representative human BRD7 cDNA and human BRD7 protein sequences are well-known in the art and are publicly available from the National Center for Biotechnology Information (NCBI). For example, two different human BRD7 isoforms are known. Human BRD7 isoform A (NP_001167455.1) is encodable by the transcript variant 1 (NM_001173984.2), which is the longer transcript. Human BRD7 isoform B (NP_037395.2) is encodable by the transcript variant 2 (NM_013263.4), which uses an alternate in-frame splice site in the 3' coding region, compared to variant 1. The resulting isoform B lacks one internal residue, compared to isoform A. Nucleic acid and polypeptide sequences of BRD7 orthologs in organisms other than humans are well-known and include, for example, chimpanzee BRD7 (XM_009430766.2 and XP_009429041.1, XM_016929816.1 and XP_016785305.1, XM_016929815.1 and XP_016785304.1, and XM_003315094.4 and XP_003315142.1), Rhesus monkey BRD7 (XM_015126104.1 and XP_014981590.1, XM_015126103.1 and XP_014981589.1, XM_001083389.3 and XP_001083389.2, and XM_015126105.1 and XP_014981591.1), dog BRD7 (XM_014106954.1 and XP_013962429.1), cattle BRD7 (NM_001103260.2 and NP_001096730.1), mouse BRD7 (NM_012047.2 and NP_036177.1), chicken BRD7 (NM_001005839.1 and NP_001005839.1), tropical clawed frog BRD7 (NM_001008007.1 and NP_001008008.1), and zebrafish BRD7 (NM 213366.2 and NP_998531.2). Representative sequences of BRD7 orthologs are presented below in Table 1.

Anti-BRD7 antibodies suitable for detecting BRD7 protein are well-known in the art and include, for example, antibody TA343710 (Origene), antibody NBP1-28727 (Novus Biologicals, Littleton, CO), antibodies ab56036, ab46553, ab202324, and ab114061 (AbCam, Cambridge, MA), antibodies Cat #: 15125 and 14910 (Cell Signaling), antibody GTX118755 (GeneTex, Irvine, CA), BRD7 (P-13) Antibody, BRD7 (T-12) Antibody, BRD7 (H-77) Antibody, BRD7 (H-2) Antibody, and BRD7 (B-8) Antibody (Santa Cruz Biotechnology), etc. In addition, reagents are well-known for detecting BRD7 expression. A clinical test of BRD7 is available in NIH Genetic Testing Registry (GTR®) with GTR Test ID: GTR000540400.2, offered by Fulgent Clinical Diagnostics Lab (Temple City, CA)). Moreover, multiple siRNA, shRNA, CRISPR constructs for reducing BRD7 expression can be found in the commercial product lists of the above-referenced companies, such as shRNA product #TR100001 and CRISPR products #KN302255 and KN208734 from Origene Technologies (Rockville, MD), RNAi product H00029117-R01 (Novus Biologicals), and small molecule inhibitors BI 9564 and TP472 (Tocris Bioscience, UK). It is to be noted that the term can further be used to refer to any combination of features described herein regarding BRD7 molecules. For example, any combination of sequence composition, percentage identify, sequence length, domain structure, functional activity, etc. can be used to describe an BRD7 molecule of the present invention.

The term "PBRM1" or "BAF180" refers to protein Polybromo-1, which is a subunit of ATP-dependent chromatin-remodeling complexes. PBRM1 functions in the regulation of gene expression as a constituent of the evolutionary-conserved SWI/SNF chromatin remodeling complexes (Euskirchen et al. (2012) *J. Biol. Chem.* 287:30897-30905). Beside BRD7 and BAF200, PBRM1 is one of the unique components of the SWI/SNF-B complex, also known as polybromo/BRG1-associated factors (or PBAF), absent in the SWI/SNF-A (BAF) complex (Xue et al. (2000) *Proc Natl Acad Sci USA.* 97:13015-13020; Brownlee et al. (2012) *Biochem Soc Trans.* 40:364-369). On that account, and because it contains bromodomains known to mediate binding to acetylated histones, PBRM1 has been postulated to target PBAF complex to specific chromatin sites, therefore providing the functional selectivity for the complex (Xue et al. (2000), *supra*; Lemon et al. (2001) *Nature* 414:924-928; Brownlee et al. (2012), *supra*). Although direct evidence for PBRM1 involvement is lacking, SWI/SNF complexes have also been shown to play a role in DNA damage response (Park et al. (2006) *EMBO J.* 25:3986-3997). In vivo studies have shown that PBRM1 deletion leads to embryonic lethality in mice, where PBRM1 is required for mammalian cardiac chamber maturation and coronary vessel formation (Wang et al. (2004) *Genes Dev.* 18:3106-3116; Huang et al. (2008) *Dev Biol.* 319:258-266). PBRM1 mutations are most predominant in renal cell carcinomas (RCCs) and have been detected in over 40% of cases, placing PBRM1 second (after VHL) on the list of most frequently mutated genes in this cancer (Varela et al. (2011) *Nature* 469:539-542; Hakimi et al. (2013) *Eur Urol.* 63:848-854; Pena-Llopis et al. (2012) *Nat Genet.* 44:751-759; Pawlowski et al. (2013) *Int J Cancer.* 132:E11-E17). PBRM1 mutations have also been found in a smaller group of breast and pancreatic cancers (Xia et al. (2008) *Cancer Res.* 68:1667-1674; Shain et al. (2012) *Proc Natl Acad Sci USA.* 109:E252-E259; Numata et al. (2013) *Int J Oncol.* 42:403-410). PBRM1 mutations are more common in patients with advance stages (Hakimi et al. (2013), *supra*) and loss of PBRM1 protein expression has been associated with advanced tumour stage, low differentiation grade and worse patient outcome (Pawlowski et al. (2013), *supra*). In another study, no correlation between PBRM1 status and tumor grade was found (Pena-Llopis et al. (2012), *supra*). Although PBRM1-mutant tumors are associated with better prognosis than BAP1-mutant tumors, tumors mutated for both PBRM1 and BAP1 exhibit the greatest aggressiveness (Kapur et al. (2013) *Lancet Oncol.* 14:159-167). PBRM1 is ubiquitously expressed during mouse embryonic development (Wang et al. (2004), *supra*) and has been detected in various human tissues including pancreas, kidney, skeletal muscle, liver, lung, placenta, brain, heart, intestine, ovaries, testis, prostate, thymus and spleen (Xue et al. (2000), *supra*; Horikawa and Barrett (2002) *DNA Seq.* 13:211-215).

PBRM1 protein localizes to the nucleus of cells (Nicolas and Goodwin (1996) *Gene* 175:233-240). As a component of the PBAF chromatin-remodeling complex, it associates with chromatin (Thompson (2009) *Biochimie.* 91:309-319), and has been reported to confer the localization of PBAF complex to the kinetochores of mitotic chromosomes (Xue et al. (2000), *supra*). Human PBRM1 gene encodes a 1582 amino acid protein, also referred to as BAF180. Six bromodomains (BD1-6), known to recognize acetylated lysine residues and frequently found in chromatin-associated proteins, constitute the N-terminal half of PBRM1 (e.g., six BD domains at amino acid residue no. 44-156, 182-284, 383-484, 519-622, 658-762, and 775-882 of PBRM1). The C-terminal half of PBRM1 contains two bromo-adjacent homology (BAH) domains (BAH1 and BAH2, e.g., at amino acid residue no. 957-1049 and 1130-1248 of PBRM1), present in some proteins involved in transcription regulation. High mobility group (HMG) domain is located close to the C-terminus of PBRM1 (e.g., amino acid residue no. 1328-1377 of PBRM1). HMG domains are found in a number of factors regulating DNA-dependent processes where HMG domains often mediate interactions with DNA.

The term "PBRM1" is intended to include fragments, variants (e.g., allelic variants), and derivatives thereof. Representative human PBRM1 cDNA and human PBRM1 protein sequences are well-known in the art and are publicly available from the National Center for Biotechnology Information (NCBI). For example, two different human PBRM1 isoforms are known. Human PBRM1 transcript variant 2 (NM_181042.4) represents the longest transcript. Human PBRM1 transcript variant 1 (NM_018313.4) differs in the 5' UTR and uses an alternate exon and splice site in the 3' coding region, thus encoding a distinct protein sequence (NP_060783.3) of the same length as the isoform (NP_851385.1) encoded by variant 2. Nucleic acid and polypeptide sequences of PBRM1 orthologs in organisms other than humans are well-known and include, for example, mouse PBRM1 (NM_001081251.1 and NP_001074720.1), chicken PBRM1 (NM_205165.1 and NP_990496.1), tropical clawed frog PBRM1 (XM_018090224.1 and XP_017945713.1), zebrafish PBRM1 (XM_009305786.2 and XP_009304061.1, XM_009305785.2 and XP_009304060.1, and XM_009305787.2 and XP_009304062.1), fruit fly PBRM1 (NM_143031.2 and NP_651288.1), and worm PBRM1 (NM_001025837.3 and NP_001021008.1 and.NM_001025838.2 and NP_001021009.1). Representative sequences of PBRM1 orthologs are presented below in Table 1.

Anti-PBRM1 antibodies suitable for detecting PBRM1 protein are well-known in the art and include, for example, ABE70 (rabbit polyclonal antibody, EMD Millipore, Billerica, MA), TA345237 and TA345238 (rabbit polyclonal antibodies, OriGene Technologies, Rockville, MD), NBP2-30673 (mouse monoclonal) and other polyclonal antibodies (Novus Biologicals, Littleton, CO), ab196022 (rabiit mAb, AbCam, Cambridge, MA), PAH437Hu01 and PAH437Hu02 (rabbit polyclonal antibodies, Cloud-Clone Corp., Houston, TX), GTX100781 (GeneTex, Irvine, CA), 25-498 (ProSci, Poway, CA), sc-367222 (Santa Cruz Biotechnology, Dallas, TX), etc. In addition, reagents are well-known for detecting PBRM1 expression (see, for example, PBRM1 Hu-Cy3 or Hu-Cy5 SmartFlare™ RNA Detection Probe (EMD Millipore). Multiple clinical tests of PBRM1 are available in NIH Genetic Testing Registry (GTR©) (e.g., GTR Test ID: GTR000537378.2 which is offered by Fulgent Clinical Diagnostics Lab (Temple City, CA)). Moreover, multiple siRNA, shRNA, CRISPR constructs for reducing PBRM1 expression can be found in the commercial product lists of the above-referenced companies. Ribavirin and PFI 3 are known PBRM1 inhibitors. It is to be noted that the term can further be used to refer to any combination of features described herein regarding PBRM1 molecules. For example, any combination of sequence composition, percentage identify, sequence length, domain structure, functional activity, etc. can be used to describe an PBRM1 molecule of the present invention.

Protein tyrosine phosphatases (PTPs or PTPases) are a group of enzymes that remove phosphate groups from phosphorylated tyrosine residues on proteins (He et al. (2014) *Acta Pharmacol. Sin.* 35:1227-1246; Barr et al. (2009) *Cell* 136:352-363). Protein tyrosine (pTyr) phosphorylation is a common post-translational modification that can create novel recognition motifs for protein interactions and cellular localization, affect protein stability, and regulate enzyme activity. As a consequence, maintaining an appropriate level of protein tyrosine phosphorylation is essential for many cellular functions. Tyrosine-specific protein phosphatases (PTPase; EC 3.1.3.48) catalyze the removal of a phosphate group attached to a tyrosine residue, using a cysteinyl-phosphate enzyme intermediate. These enzymes are key regulatory components in signal transduction pathways (such as the MAP kinase pathway) and cell cycle control, and are important in the control of cell growth, proliferation, differentiation, transformation, and synaptic plasticity (Denu and Dixon (1998) *Curr. Opin. Chem. Biol.* 2:633-641; Lombroso (2003) *Cell. Mol. Life Sci.* 60:2465-2482). Together with tyrosine kinases, PTPs regulate the phosphorylation state of many important signaling molecules, such as the MAP kinase family. PTPs are increasingly viewed as integral components of signal transduction cascades. PTPs have been implicated in regulation of many cellular processes, including, but not limited to: cell growth, cellular differentiation, mitotic cycles, oncogenic transformation, receptor endocytosis, etc. The classification of PTPs can be achieved by mechanism or location. By mechanism, PTP activity can be found in four protein families, including: 1) class I PTPs, which is the largest group of PTPs comprising at least 99 members, such as at least 38 classical PTPs (21 receptor tyrosine phosphatase and 17 non-receptor-type PTPs) and 61 VH-1-like or dual-specific (dTyr and dSer/dThr) phosphatases (DSPs) (e.g., 11 MAPK phosphatases (MPKs), 3 Slingshots, 3 PRLs, 4 CDC14s, 19 atypical DSPs, 5 Phosphatase and tensin homologs (PTENs), and 16 Myotubularins); 2) class II PTP, comprising only one member low-molecular-weight phosphotyrosine phosphatase (LMPTP); 3) class III PTPs, comprising at least CDC25 A, B, and C proteins; and 4) Class IV PTPs, comprising at least Eya 1-4 proteins, which are pTyr-specific phosphatases and believed to have evolved separately from the other three classes. By cellular location, PTPs can be classified as receptor-like PTPs and non-receptor (intracellular) PTPs. The former are transmembrane receptors that contain PTPase domains. In terms of structure, all known receptor PTPases are made up of a variable-length extracellular domain, followed by a transmembrane region and a C-terminal catalytic cytoplasmic domain. Some of the receptor PTPases contain fibronectin type III (FN-III) repeats, immunoglobulin-like domains, MAM domains, or carbonic anhydrase-like domains in their extracellular region. In general, the cytoplasmic region contains two copies of the PTPase domain. The first has enzymatic activity, whereas the second is inactive (Sun et al. (2003) *Curr Top Med Chem.* 3:739-748; Alonso et al. (2004) *Cell* 117:699-711). All class I, II, and III PTPs carry a highly conserved active site motif C(X)$_5$R (PTP signature motif), employ a common catalytic mechanism, and possess a similar core structure made of a central parallel beta-sheet with flanking alpha-helices containing a beta-loop-alpha-loop that encompasses the PTP signature motif (Barford et al. (1998) *Annu. Rev. Biophys. Biomol. Struct.* 27:133-164). Functional diversity between PTPases is endowed by regulatory domains and subunits. For most PTPs, the consensus sequence (I/V)HCXAGXXR(S/T)G (SEQ ID NO: 991) (i.e., the C(X)$_5$RPTP signature motif) contains the catalytically essential Cys and Arg residues. Intracellular PTPs are often modular molecules containing structural motifs such as Src homology 2 (SH2) domains, PEST sequences, and band 4.1 domains on either the N- or C-terminal side of their catalytic domains.

Among non-receptor PTPs, tyrosine-protein phosphatase non-receptor type 2 (PTPN2) is an enzyme that in humans is encoded by the PTPN2 gene (Brown-Shimer et al. (1990) *Proc. Natl. Acad. Sci. USA* 87:5148-5152). Epidermal growth factor receptor and the adaptor protein Shc were reported to be substrates of this PTP, which suggests a role in growth factor-mediated cell signaling. Three alternatively spliced variants of this gene, which encode isoforms differing at their extreme C-termini, have been described. The different C-termini are thought to determine the substrate specificity, as well as the cellular localization of the isoforms. Two highly related but distinctly processed pseudogenes that localize to distinct human chromosomes have been reported. The human PTPN2 gene localizes to chromosome 18p11.2-p11.3, whereas pseudogenes (gene symbol PTPN2P1 and PTPN2P2) are mapped to chromosomes 1q22-q24 and 13q12-q13, respectively. A direct comparison of the specificity of genomic and cDNA probes demonstrated that under identical conditions the genomic probes (containing both exon and intron sequences) readily identified a single specific site of hybridization, whereas the cDNA identified sites of both the gene and its pseudogenes (Johnson et al. (1993) *Genomics* 16:619-629). Human PTPN2 exists as two forms generated by alternative splicing: a 48-kDa endoplasmic reticulum (ER)-associated form (TC48, 415 amino acid) and a 45-kDa nuclear form (TC45). The three-dimensional PDB structure of PTPN2 is also well-known and described in at least the OCA database (protein ID: 1L8K) at the Weizmann Institute of Science (Rehovot, Israel) available on the World Wide Web at oca.weizmann.ac.il/oca-bin/ocashort?id=1L8K. PTPN2 has a protein tryrosine phosphatase catalytic (PTPc) domain, for example, from amino acid residues 5 to 275 of PTPN2. The PTPc domain comprises different motifs for various functions, such as substrate binding (amino acid residues 216-222 of PTPN2), endoplasmic reticulum (ER) location (amino acid residues 346-415 of PTPN2), and STX17 interaction (amino acid residues 376-415 of PTPN2, also see Muppirala et al. (2012) *Biochim. Biophys. Acta* 1823:2109-2119).

The nucleic acid and amino acid sequences of a representative human PTPN2 is available to the public at the GenBank database (Gene ID 5771). Human PTPN2 isoforms include the longest isoform 1 (GenBank database numbers NM_002828.3 and NP_002819.2), and the shorter isoforms 2 (NM_080422.2 and NP_536347.1, which contains an alternate 3' region including a part of the C-terminal coding region, resulting in a shorter and distinct C-terminus, as compared to isoform 1), 3 (NM_080423.2 and NP_536348.1; which contains an alternate 3' region including a part of the C-terminal coding region, resulting in a shorter and distinct C-terminus, as compared to isoform 1), 4 (NM_001207013.1 and NP_001193942.1; which contains an additional in-frame exon in the middle coding region and an alternate 3' region including a part of the C-terminal coding region, resulting in an additional internal segment and a shorter and distinct C-terminus, as compared to isoform 1), and 5 (NM_001308287.1 and NP_001295216.1; which differs in the 5' UTR by lacking a portion of the 5' coding region and using an alternative start codon to initiates translation, resulting in a shorter and distinct N-terminus, as compared to isoform 1).

Nucleic acid and polypeptide sequences of PTPN2 orthologs in organisms other than humans are well-known and include, for example, chimpanzee (Pan troglodytes) PTPN2 (XM_009433614.2 and XP_009431889.2; XM_009433613.2 and XP_009431888.2; XM_009433615.2 and XP_009431890.2; XM_003953237.2 and XP_003953286.2; XM_001171536.4 and XP_001171536.2; XM_009433617.2 and XP_009431892.1; XM_016933257.1 and XP_016788746.1; XM_009433619.2 and XP_009431894.2; XM_009433618.2 and XP_009431893.2; XM_016933256.1 and XP_016788745.1; XM_016933258.1 and XP_016788747.1; and XM_009433620.2 and XP_009431895.2), dog PTPN2 (XM_014115598.1 and XP_013971073.1; XM_005623101.2 and XP_005623158.1; XM_005623100.2 and XP_005623157.1; and XM_005623099.2 and XP_005623156.1), mouse PTPN2 (NM_001127177.1 and NP_001120649.1, which represent the longer transcript, and NM_008977.3 and NP_033003.1, which differs in the 3' UTR and has multiple coding region differences, resulting in a distinct C-terminus and is shorter than the isoform encoded by the longer transcript), cattle PTPN2 (NM_001035431.2 and NP_001030508.1), Norway rat (*Rattus norvegicus*) PTPN2 (NM_053990.1 and NP_446442.1), chicken PTPN2 (NM_001199387.1 and NP_001186316.1), tropical clawed frog (*Xenopus tropicalis*) PTPN2 (XM_004915252.3 and XP_004915309.2; and XM_002936076.4 and XP_002936122.1); zebrafish (*Danio rerio*) PTPN2 (NM_200466.2 and NP_956760.2; and NM_212654.1 and NP_997819.1); and fruit fly (*Drosophila melanogaster*) PTPN2 (NM_167874.2 and NP_728600.1; NM_057340.4 and NP_476688.1; NM_001274324.2 and NP_001261253.1; NM_167875.2 and NP_728601.1; and NM_057339.5 and NP_476687.1).

Anti-Ptpn2 antibodies suitable for detecting Ptpn2 protein are well-known in the art and include, for example, antibody TA327184 (Origene), antibody MABS791 (EMD Millipore), antibodies MAB1930, and AF1930 (R&D systems), antibodies ab180764, ab129070, ab172266, ab171655, ab85330, ab1996, and ab102053 (AbCam, Cambridge, MA), antibody PAD585Hu01 (Cloud-Clone Corp, Katy, TX), Cat #: PA5-42722, and Cat #: MA5-17249 (ThermoFisher Scientific), antibody GTX130319, GTX54634, and GTX56114 (GeneTex, Irvine, CA), TC-PTP (F-8) Antibody, and TC-PTP (D-3) Antibody (Santa Cruz Biotechnology), etc. In addition, reagents are well-known for detecting Ptpn2 expression. Moreover, multiple siRNA, shRNA, CRISPR constructs for reducing Ptpn2 expression can be found in the commercial product lists of the above-referenced companies, such as shRNA product #TR310063, RNAi product SR303886 and CRISPR products #KN202161 and KN314212 from Origene Technologies (Rockville, MD). It is to be noted that the term can further be used to refer to any combination of features described herein regarding Ptpn2 molecules. For example, any combination of sequence composition, percentage identify, sequence length, domain structure, functional activity, etc. can be used to describe an Ptpn2 molecule of the present invention.

The term "Serpinb9" refers to serpin family B member 9, a member of the serine protease inhibitor family which are also known as serpins. Serpinb9 inhibits the activity of the effector molecule granzyme B. Overexpression of this protein may prevent cytotoxic T-lymphocytes from eliminating certain tumor cells. Human Serpinb9 protein has 376 amino acids and a molecular mass of 42404 Da.

The term "Serpinb9" is intended to include fragments, variants (e.g., allelic variants), and derivatives thereof. Representative human Serpinb9 cDNA and human Serpinb9 protein sequences are well-known in the art and are publicly available from the National Center for Biotechnology Information (NCBI). For example, one human Serpinb9 isoform is known. Human Serpinb9 isoform A (NP_004146.1) is encodable by the transcript variant 1 (NM_004155.5). Nucleic acid and polypeptide sequences of Serpinb9 orthologs in organisms other than humans are well-known and include, for example, monkey Serpinb9 (NM_001266993.1 and NP_001253922.1), dog Serpinb9 (XM_005639979.2 and XP_005640036.1), cattle Serpinb9 (NM_001075859.2 and NP_001069327.1), mouse Serpinb9 (NM_009256.3 and NP_033282.1), and rat Serpinb9 (NM_001007732.1 and NP_001007733.1). Representative sequences of Serpinb9 orthologs are presented below in Table 1.

Anti-Serpinb9 antibodies suitable for detecting Serpinb9 protein are well-known in the art and include, for example, antibodies AM01199PU-N, AM05390PU-N, TA318921, TA312970, TA303212, and AP26375PU-N(Origene), antibodies ab60265, ab112220, ab36624, ab150400, and ab110455 (AbCam, Cambridge, MA), antibody PAD390Hu01 (Cloud-Clone Corp, Katy, TX), Cat #: PA5-18686, Cat #: PA5-51038, Cat #: MA5-17648, Cat #: MA1-35771, and Cat #: MA5-17705 (ThermoFisher Scientific), antibody GTX54693, GTX39407, GTX59853, and GTX89125 (GeneTex, Irvine, CA), antibodies PI-9 (PI9-17), PI-9 (7D8), PI-9 (6D700), and PI-9 (C-10) (Santa Cruz Biotechnology), etc. In addition, reagents are well-known for detecting Serpinb9 expression. Moreover, multiple siRNA, shRNA, CRISPR constructs for reducing Serpinb9 expression can be found in the commercial product lists of the above-referenced companies, such as shRNA product #TL309527, RNAi product SR303506 and CRISPR products #KN200645 and KN315595 from Origene Technologies (Rockville, MD). It is to be noted that the term can further be used to refer to any combination of features described herein regarding Serpinb9 molecules. For example, any combination of sequence composition, percentage identify, sequence length, domain structure, functional activity, etc. can be used to describe an Serpinb9 molecule of the present invention.

The term "Otulin" refers to OTU deubiquitinase with linear linkage specificity, a member of the peptidase C65 family of ubiquitin isopeptidases. Members of this family remove ubiquitin from proteins. OTULIN specifically recognizes and removes M1(Met1)-linked, or linear, ubiquitin chains from protein substrates. Linear ubiquitin chains are known to regulate the NF-kappa B signaling pathway in the context of immunity and inflammation. Mutations in Otulin cause a potentially fatal autoinflammatory syndrome in human patients. Human Otulin protein has 352 amino acids and a molecular mass of 40263 Da.

The term "Otulin" is intended to include fragments, variants (e.g., allelic variants), and derivatives thereof. Representative human Otulin cDNA and human Otulin protein sequences are well-known in the art and are publicly available from the National Center for Biotechnology Information (NCBI). For example, one human Otulin isoform is known. Human Otulin isoform A (NP_612357.4) is encodable by the transcript variant 1 (NM_138348.5). Nucleic acid and polypeptide sequences of Otulin orthologs in organisms other than humans are well-known and include, for example, monkey Otulin (NM_001193800.1 and NP_001180729.1), dog Otulin (XM_014110329.1 and XP_013965804.1; XM_005639660.2 and XP_005639717.1; XM_005639659.2 and XP_005639716.1; XM_843160.4 and XP_848253.2), cattle Otulin (NM_001100328.1 and NP_001093798.1), mouse Otulin (NM_001013792.2 and NP_001013814.2), and rat Otulin (NM_001302889.1 and NP_001289818.1). Representative sequences of Otulin orthologs are presented below in Table 1.

Anti-Otulin antibodies suitable for detecting Serpinb9 protein are well-known in the art and include, for example, antibody ABC488 (EMD Millipore), antibody TA335406 (OriGene), antibody Cat #: 14127 (Cell Signaling), antibody NBP2-14722 (Novus Biologicals, Littleton, CO), antibodies ab151117, ab114137, and ab182598 (AbCam, Cambridge, MA), etc. In addition, reagents are well-known for detecting Otulin expression. Moreover, multiple siRNA, shRNA, CRISPR constructs for reducing Otulin expression can be found in the commercial product lists of the above-referenced companies, such as shRNA product #TR304698, and CRISPR products #KN224840 from Origene Technologies (Rockville, MD), and RNAi product Cat #: 14132 from Cell Signaling. It is to be noted that the term can further be used to refer to any combination of features described herein regarding Otulin molecules. For example, any combination of sequence composition, percentage identify, sequence length, domain structure, functional activity, etc. can be used to describe an Otulin molecule of the present invention.

The term "Rela" refers to RELA Proto-Oncogene, NF-κB Subunit. Members of this family remove ubiquitin from proteins. NF-κB is a ubiquitous transcription factor involved in several biological processes. It is held in the cytoplasm in an inactive state by specific inhibitors. Upon degradation of the inhibitor, NF-κB moves to the nucleus and activates transcription of specific genes. NF-κB is composed of NFKB1 or NFKB2 bound to either REL, RELA, or RELB. The most abundant form of NF-κB is NFKB1 complexed with the product of this gene, RELA. Human RELA protein has 551 amino acids and a molecular mass of 60219 Da.

The term "Rela" is intended to include fragments, variants (e.g., allelic variants), and derivatives thereof. Representative human Rela cDNA and human Rela protein sequences are well-known in the art and are publicly available from the National Center for Biotechnology Information (NCBI). Human Rela isoforms include the longest isoform 1 (NM_021975.3 and NP_068810.3), and the shorter isoforms 2 (NM_001145138.1 and NP_001138610.1, which uses an alternate in-frame acceptor splice site at one of the coding exons, resulting in a shorter isoform missing a 3 aa segment compared to isoform 1), 3 (NM_001243984.1 and NP_001230913.1; which uses an alternate in-frame splice site at the 5' end of the last exon, resulting isoform lacks an alternate internal segment compared to isoform 1), and 4 (NM_001243985.1 and NP_001230914.1; which lacks an alternate internal in-frame segment in the last exon, resulting isoform lacks an alternate internal segment compared to isoform 1). Nucleic acid and polypeptide sequences of Rela orthologs in organisms other than humans are well-known and include, for example, monkey Rela (XM_015113775.1 and XP_014969261.1), dog Rela (XM_005631473.2 and XP_005631530.1; XM_540850.5 and XP_540850.2; XM_005631474.2 and XP_005631531.1; XM_014121307.1 and XP_013976782.1; XM_005631472.2 and XP_005631529.1), cattle Rela (NM_001080242.2 and NP_001073711.1), mouse Rela (NM_009045.4 and NP_033071.1), and rat Rela (NM_199267.2 and NP_954888.1). Representative sequences of Rela orthologs are presented below in Table 1.

Anti-Rela antibodies suitable for detecting Rela protein are well-known in the art and include, for example, antibody ABE136 (EMD Millipore), antibody TA890002 (OriGene), antibody Cat #: 8242 (Cell Signaling), antibody NB100-56712 (Novus Biologicals, Littleton, CO), etc. In addition, reagents are well-known for detecting Rela expression. Moreover, multiple siRNA, shRNA, CRISPR constructs for reducing Rela expression can be found in the commercial product lists of the above-referenced companies, such as shRNA product #TR302038, and CRISPR products #KN220780 and #KN314656 from Origene Technologies (Rockville, MD), and RNAi products Cat #: 6261 and Cat #: 6534 from Cell Signaling. It is to be noted that the term can further be used to refer to any combination of features described herein regarding Rela molecules. For example, any combination of sequence composition, percentage identify, sequence length, domain structure, functional activity, etc. can be used to describe an Rela molecule of the present invention.

The term "Ikbkg" refers to inhibitor of nuclear factor kappa B kinase subunit gamma, the regulatory subunit of the inhibitor of kappaB kinase (IKK) complex, which activates NF-kappaB resulting in activation of genes involved in inflammation, immunity, cell survival, and other pathways. Mutations in this gene result in incontinentia pigmenti, hypohidrotic ectodermal dysplasia, and several other types of immunodeficiencies. A pseudogene highly similar to this locus is located in an adjacent region of the X chromosome. Human Ikbkg protein has 419 amino acids and a molecular mass of 48198 Da.

The term "Ikbkg" is intended to include fragments, variants (e.g., allelic variants), and derivatives thereof. Representative human Ikbkg cDNA and human Ikbkg protein sequences are well-known in the art and are publicly available from the National Center for Biotechnology Information (NCBI). Human Ikbkg isoforms include the longest isoform a (NM_001099857.2 and NP_001093327.1; NM_003639.4 and NP_003630.1; NM_001321396.1 and NP_001308325.1), and the shorter isoforms b (NM_001099856.4 and NP_001093326.2, which uses an alternate promoter and initiates translation from an alternate in-frame upstream start codon, resulting isoform (b) has a longer N-terminus compared to isoform a), c (NM_001145255.2 and NP_001138727.1; which lacks two in-frame exons in the central coding region compared, resulting isoform (c) lacks two internal protein segments compared to isoform a), d (NM_001321397.1 and NP_001308326.1). Nucleic acid and polypeptide sequences of Ikbkg orthologs in organisms other than humans are well-known and include, for example, monkey Ikbkg (XM_015128564.1 and XP_014984050.1; XM_002806446.2 and XP_002806492.1; XM_001095498.3 and XP_001095498.2; XM_015128566.1 and XP_014984052.1; XM_015128565.1 and XP_014984051.1), dog Ikbkg (XM_003640238.3 and XP_003640286.2; XM_005642038.2 and XP_005642095.1; XM_005642039.2 and XP_005642096.1; XM_014111627.1 and XP_013967102.1; XM_014111628.1 and XP_013967103.1), cattle Ikbkg (NM_174354.3 and NP_776779.1), mouse Ikbkg (NM_001136067.2 and NP_001129539.1; NM_001161421.1 and NP_001154893.1; NM_001161422.1 and NP_001154894.1; NM_001161423.1 and NP_001154895.1; NM_001161424.1 and NP_001154896.1; NM_010547.2 and NP_034677.2; NM_178590.4 and NP_848705.1), and rat Ikbkg (NM_199103.1 and NP_954534.1). Representative sequences of Ikbkg orthologs are presented below in Table 1.

Anti-Ikbkg antibodies suitable for detecting Ikbkg protein are well-known in the art and include, for example, antibody 05-631 (EMD Millipore), antibodies AM11080PU-N and AP07310PU-N(OriGene), antibodies Cat #: 2695 and Cat #: 2685 (Cell Signaling), antibodies NB100-56542 and NB100-56532 (Novus Biologicals, Littleton, CO), antibodies ab178872, ab137363, and ab188569 (AbCam, Cambridge, MA), etc. In addition, reagents are well-known for detecting Ikbkg expression. Moreover, multiple siRNA, shRNA, CRISPR constructs for reducing Ikbkg expression can be found in the commercial product lists of the above-referenced companies, such as shRNA product #TL312203, RNAi products SR305587, and CRISPR products #KN201743 and #KN308212 from Origene Technologies (Rockville, MD). It is to be noted that the term can further be used to refer to any combination of features described herein regarding Ikbkg molecules. For example, any combination of sequence composition, percentage identify, sequence length, domain structure, functional activity, etc. can be used to describe an Ikbkg molecule of the present invention.

The term "Ikbkb" refers to inhibitor of nuclear factor kappa B kinase subunit beta. Ikbkb phosphorylates the inhibitor in the inhibitor/NF-kappa-B complex, causing dissociation of the inhibitor and activation of NF-kappa-B. The encoded protein itself is found in a complex of proteins. Human Ikbkb protein has 756 amino acids and a molecular mass of 86564 Da.

The term "Ikbkb" is intended to include fragments, variants (e.g., allelic variants), and derivatives thereof. Representative human Ikbkb cDNA and human Ikbkb protein sequences are well-known in the art and are publicly available from the National Center for Biotechnology Information (NCBI). Human Ikbkb isoforms include the longest isoform 1 (NM_001556.2 and NP_001547.1), and the shorter isoforms 2 (NM_001190720.2 and NP_001177649.1, which lacks an exon in the 5' region, resulting in an upstream AUG start codon, as compared to variant 1. The resulting isoform (2) is slightly shorter and has a different N-terminus, as compared to isoform 1), and 5 (NM_001242778.1 and NP_001229707.1; which lacks an alternate exon in the 5' coding region and uses an alternate start codon, resulting isoform (5) has a shorter and distinct N-terminus, compared to variant 1). Nucleic acid and polypeptide sequences of Ikbkb orthologs in organisms other than humans are well-known and include, for example, monkey Ikbkb (NM_001265946.1 and NP_001252875.1), dog Ikbkb (XM_539954.5 and XP_539954.2; XM_014120063.1 and XP_013975538.1; XM_014120062.1 and XP_013975537.1), cattle Ikbkb (NM_174353.2 and NP_776778.1), mouse Ikbkb (NM_001159774.1 and NP_001153246.1; NM_010546.2 and NP_034676.1), and rat Ikbkb (NM_053355.2 and NP_445807.2). Representative sequences of Ikbkb orthologs are presented below in Table 1.

Anti-Ikbkb antibodies suitable for detecting Ikbkb protein are well-known in the art and include, for example, antibodies 07-1479 and 05-535 (EMD Millipore), antibodies AM06154SU-N and AM06155SU-N(OriGene), antibody Cat #: 2684 (Cell Signaling), antibodies NB100-56509 and NB100-56513 (Novus Biologicals, Littleton, CO), antibodies ab32135, and ab124957 (AbCam, Cambridge, MA), etc. In addition, reagents are well-known for detecting Ikbkb expression. Moreover, multiple siRNA, shRNA, CRISPR constructs for reducing Ikbkb expression can be found in the commercial product lists of the above-referenced companies, such as shRNA product #TL320385, and CRISPR products #KN308210 and #KN219154 from Origene Technologies (Rockville, MD), and RNAi products Cat #: 6377 from Cell Signaling. It is to be noted that the term can further be used to refer to any combination of features described herein regarding Ikbkb molecules. For example, any combination of sequence composition, percentage identify, sequence length, domain structure, functional activity, etc. can be used to describe an Ikbkb molecule of the present invention.

The term "Rnf31" refers to ring finger protein 31. RNF31 contains a RING finger, a motif present in a variety of functionally distinct proteins and known to be involved in protein-DNA and protein-protein interactions. It is the E3 ubiquitin-protein ligase component of the LUBAC complex (linear ubiquitin chain assembly complex) which conjugates linear (Met-1-linked) polyubiquitin chains to substrates and plays a key role in NF-kappa-B activation and regulation of inflammation. LUBAC conjugates linear polyubiquitin to IKBKG and RIPK1 and is involved in activation of the canonical NF-kappa-B and the JNK signaling pathways. Linear ubiquitination mediated by the LUBAC complex interferes with TNF-induced cell death and thereby prevents inflammation. LUBAC is proposed to be recruited to the TNF-R1 signaling complex (TNF-RSC) following polyubiquitination of TNF-RSC components by BIRC2 and/or BIRC3 and to conjugate linear polyubiquitin to IKBKG and possibly other components contributing to the stability of the complex. Together with otulin, the LUBAC complex regulates the canonical Wnt signaling during angiogenesis. Human Rnf31 protein has 1072 amino acids and a molecular mass of 119652 Da.

The term "Rnf31" is intended to include fragments, variants (e.g., allelic variants), and derivatives thereof. Representative human Rnf31 cDNA and human Rnf31 protein sequences are well-known in the art and are publicly available from the National Center for Biotechnology Information (NCBI). Human Rnf31 isoforms include the longest isoform 1 (NM_017999.4 and NP_060469.4), and the shorter isoforms 2 (NM_001310332.1 and NP_001297261.1, which uses an alternate first exon and an alternate splice site in a 5' exon, resulting isoform (2) has a shorter and distinct N-terminus compared to isoform 1). Nucleic acid and polypeptide sequences of Rnf31 orthologs in organisms other than humans are well-known and include, for example, monkey Rnf31 (XM_001112195.3 and XP_001112195.1; XM_015143429.1 and XP_014998915.1), dog Rnf31 (XM_005623255.2 and XP_005623312.1; XM_005623256.2 and XP_005623313.1; XM_537383.5 and XP_537383.2; XM_005623257.2 and XP_005623314.1), mouse Rnf31 (NM_194346.2 and NP_919327.2), and rat Rnf31 (NM_001108868.1 and NP_001102338.2). Representative sequences of Rnf31 orthologs are presented below in Table 1.

Anti-Rnf31 antibodies suitable for detecting Rnf31 protein are well-known in the art and include, for example, antibodies TA302821 and TA329873 (OriGene), antibodies MAB8039, AF8039, NBP2-27290 and NB100-1094 (Novus Biologicals, Littleton, CO), antibodies ab46322, ab85294, and ab187976 (AbCam, Cambridge, MA), etc. In addition, reagents are well-known for detecting Rnf31 expression. Moreover, multiple siRNA, shRNA, CRISPR constructs for reducing Rnf31 expression can be found in the commercial product lists of the above-referenced companies, such as shRNA product #TL320708, RNAi products SR310467, and CRISPR products #KN314948 and #KN204117 from Origene Technologies (Rockville, MD). It is to be noted that the term can further be used to refer to any combination of features described herein regarding Rnf31 molecules. For example, any combination of sequence composition, percentage identify, sequence length, domain structure, functional activity, etc. can be used to describe an Rnf31 molecule of the present invention.

The term "Sharpin" refers to SHANK associated RH domain interactor, a component of the LUBAC complex which conjugates linear polyubiquitin chains in a head-to-tail manner to substrates and plays a key role in NF-kappa-B activation and regulation of inflammation. Human Sharpin protein has 387 amino acids and a molecular mass of 39949 Da.

The term "Sharpin" is intended to include fragments, variants (e.g., allelic variants), and derivatives thereof. Representative human Sharpin cDNA and human Sharpin protein sequences are well-known in the art and are publicly available from the National Center for Biotechnology Information (NCBI). Human Sharpin has one isoform (NM 030974.3 and NP_112236.3). Nucleic acid and polypeptide sequences of Sharpin orthologs in organisms other than humans are well-known and include, for example, monkey Sharpin (XM_015146259.1 and XP_015001745.1; XM_015146260.1 and XP_015001746.1; XM_015146263.1 and XP_015001749.1; XM_015146261.1 and XP_015001747.1; XM_015146258.1 and XP_015001744.1), dog Sharpin (XM_005628075.2 and XP_005628132.1; XM_532352.5 and XP_532352.3; XM 014118748.1 and XP_013974223.1), cattle Sharpin (NM_001109766.1 and NP_001103236.1), mouse Sharpin (NM_025340.2 and NP_079616.2), and rat Sharpin (NM_031153.2 and NP_112415.1.

Anti-Sharpin antibodies suitable for detecting Sharpin protein are well-known in the art and include, for example, antibody ABF128 (EMD Millipore), antibody TA342597 (OriGene), antibodies Cat #: 12541 (Cell Signaling), antibodies AF8100 and NBP1-92386 (Novus Biologicals, Littleton, CO), antibodies ab197853, ab125188, and ab174545 (AbCam, Cambridge, MA), etc. In addition, reagents are well-known for detecting Sharpin expression. Moreover, multiple siRNA, shRNA, CRISPR constructs for reducing Sharpin expression can be found in the commercial product lists of the above-referenced companies, such as shRNA product #TL317564, RNAi products SR313114, and CRISPR products #KN315736 and #KN222012 from Origene Technologies (Rockville, MD). It is to be noted that the term can further be used to refer to any combination of features described herein regarding Sharpin molecules. For example, any combination of sequence composition, percentage identify, sequence length, domain structure, functional activity, etc. can be used to describe an Sharpin molecule of the present invention.

The term "Rraga" refers to Ras related GTP binding A, a guanine nucleotide-binding protein that plays a crucial role in the cellular response to amino acid availability through regulation of the mTORC1 signaling cascade. It forms heterodimeric Rag complexes with RRAGC or RRAGD and cycles between an inactive GDP-bound and an active GTP-bound form. In its active form participates in the relocalization of mTORC1 to the lysosomes and its subsequent activation by the GTPase RHEB. Rraga is involved in the RCC1/Ran-GTPase pathway. It may play a direct role in a TNF-alpha signaling pathway leading to induction of cell death, or may alternatively act as a cellular target for adenovirus E3-14.7K, an inhibitor of TNF-alpha functions, thereby affecting cell death. Human Rraga protein has 313 amino acids and a molecular mass of 36566 Da.

The term "Rraga" is intended to include fragments, variants (e.g., allelic variants), and derivatives thereof. Representative human Rraga cDNA and human Rraga protein sequences are well-known in the art and are publicly available from the National Center for Biotechnology Information (NCBI). Human Rraga has one isoform (NM_006570.4 and NP_006561.1). Nucleic acid and polypeptide sequences of Rraga orthologs in organisms other than humans are well-known and include, for example, monkey Rraga (NM_001194800.1 and NP_001181729.1), dog Rraga (XM_003639357.3 and XP_003639405.2), cattle Rraga (NM_001035499.1 and NP_001030576.1), mouse Rraga (NM_178376.3 and NP_848463.1), and rat Rraga (NM_053973.2 and NP_446425.1). Representative sequences of Rraga orthologs are presented below in Table 1.

Anti-Rraga antibodies suitable for detecting Rraga protein are well-known in the art and include, for example, antibody TA350374 and TA315091 (OriGene), antibodies Cat #: 4357 (Cell Signaling), antibody ab128196 (AbCam, Cambridge, MA), etc. In addition, reagents are well-known for detecting Rraga expression. Moreover, multiple siRNA, shRNA, CRISPR constructs for reducing Rraga expression can be found in the commercial product lists of the above-referenced companies, such as shRNA product #TL309705, RNAi products SR307279, and CRISPR products #KN203493 and #KN315129 from Origene Technologies (Rockville, MD). It is to be noted that the term can further be used to refer to any combination of features described herein regarding Rraga molecules. For example, any combination of sequence composition, percentage identify, sequence length, domain structure, functional activity, etc. can be used to describe an Rraga molecule of the present invention.

The term "Rragb" refers to Ras related GTP binding B, a guanine nucleotide-binding protein that plays a crucial role in the cellular response to amino acid availability through regulation of the mTORC1 signaling cascade. It forms heterodimeric Rag complexes with RRAGC or RRAGD and cycles between an inactive GDP-bound and an active GTP-bound form. In its active form participates in the relocalization of mTORC1 to the lysosomes and its subsequent activation by the GTPase RHEB. Rragb is involved in the RCC1/Ran-GTPase pathway. Human Rragb protein has 374 amino acids and a molecular mass of 43250 Da.

The term "Rragb" is intended to include fragments, variants (e.g., allelic variants), and derivatives thereof. Representative human Rragb cDNA and human Rragb protein sequences are well-known in the art and are publicly available from the National Center for Biotechnology Information (NCBI). Human Rragb isoforms include the longest isoform a (NM_016656.3 and NP_057740.2), the shorter isoform b (NM_006064.4 and NP_006055.3, which lacks an alternate exon in the coding region, resulting isoform (b) is shorter than isoform a), c (NM_001354011.1 and NP_001340940.1), and d (NM_001354013.1 and NP_001340942.1). Nucleic acid and polypeptide sequences of Rragb orthologs in organisms other than humans are well-known and include, for example, chimpanzee Rragb (XM_003317489.4 and XP_003317537.1; XM_001148126.5 and XP_001148126.2; XM_016943767.2 and XP_016799256.1; XM_016943766.2 and XP_016799255.1), monkey Rragb (NM_001257444.1 and NP_001244373.1), dog Rragb (XM_022415838.1 and XP_022271546.1; XM_022415834.1 and XP_022271542.1; XM_022415836.1 and XP_022271544.1; XM_846980.5 and XP_852073.1; XM_005641400.3 and XP_005641457.1; XM_005641401.3 and XP_005641458.1; XM_022415837.1 and XP_022271545.1), cattle Rragb (NM_001075279.1 and NP_001068747.1), and mouse Rragb (NM_001004154.2 and NP_001004154.1).

Anti-Rragb antibodies suitable for detecting Rragb protein are well-known in the art and include, for example, antibody TA331223 (OriGene), antibodies Cat #: 8150 (Cell Signaling), antibody ab103671 (AbCam, Cambridge, MA), etc. In addition, reagents are well-known for detecting Rragb expression. Moreover, multiple siRNA, shRNA, CRISPR constructs for reducing Rragb expression can be found in the commercial product lists of the above-referenced companies, such as shRNA products #TF301903, #TL301903 and #TG301903 (OriGene), RNAi products #SR306997 (OriGene) and #ABIN3346754 (Genomics-online), and CRISPR products #KN201860 (OriGene) and #K6999908 (AbCam, Cambridge, MA). It is to be noted that the term can further be used to refer to any combination of features described herein regarding Rragb molecules. For example, any combination of sequence composition, percentage identify, sequence length, domain structure, functional activity, etc. can be used to describe an Rragb molecule of the present invention.

The term "Rragc" refers to Ras related GTP binding C, a member of the GTR/RAG GTP-binding protein family. Rragc is a monomeric guanine nucleotide-binding protein which forms a heterodimer with RRAGA and RRAGB and promotes intracellular localization of the mTOR complex. It forms heterodimeric Rag complexes required for the amino acid-induced relocalization of mTORC1 to the lysosomes and its subsequent activation by the GTPase RHEB. This is a crucial step in the activation of the TOR signaling cascade by amino acids. Human Rragc protein has 399 amino acids and a molecular mass of 44224 Da.

The term "Rragc" is intended to include fragments, variants (e.g., allelic variants), and derivatives thereof. Representative human Rragc cDNA and human Rragc protein sequences are well-known in the art and are publicly available from the National Center for Biotechnology Information (NCBI). Human Rragc isoforms include a longer isoform 1 (NM_022157.3 and NP_071440.1), and a shorter isoforms 2 (NM_001271851.1 and NP_001258780.1, which uses an alternate in-frame splice site in the coding region and encodes isoform 2 which is shorter than isoform 1). Nucleic acid and polypeptide sequences of Rragc orthologs in organisms other than humans are well-known and include, for example, monkey Rragc (XM_001113124.3 and XP_001113124.1), dog Rragc (XM_003431952.3 and XP_003432000.1), cattle Rragc (NM_001076456.1 and NP_001069924.1), mouse Rragc (NM_017475.2 and NP_059503.2), and rat Rragc (NM_001048184.1 and NP_001041649.1).

Anti-Rragc antibodies suitable for detecting Rragc protein are well-known in the art and include, for example, antibody AP53748PU-N(OriGene), antibodies Cat #: 3360 (Cell Signaling), antibodies NBP1-83699, NBP2-32202 and NBP2-56218 (Novus Biologicals, Littleton, CO), antibodies ab168819, ab206864, ab187705, and ab76577 (AbCam, Cambridge, MA), etc. In addition, reagents are well-known for detecting Rragc expression. Moreover, multiple siRNA, shRNA, CRISPR constructs for reducing Rragc expression can be found in the commercial product lists of the above-referenced companies, such as shRNA product #TL301902, CRISPR products #KN203834 and #KN315131 from Origene Technologies (Rockville, MD), and RNAi products H00064121-R02 from Novus Biologicals (Littleton, CO). It is to be noted that the term can further be used to refer to any combination of features described herein regarding Rragc molecules. For example, any combination of sequence composition, percentage identify, sequence length, domain structure, functional activity, etc. can be used to describe an Rragc molecule of the present invention.

The term "Lamtor 1" refers to late endosomal/lysosomal adaptor, MAPK and MTOR activator 1. As a part of the Ragulator complex, it is involved in amino acid sensing and activation of mTORC1, a signaling complex promoting cell growth in response to growth factors, energy levels, and amino acids. Activated by amino acids through a mechanism involving the lysosomal V-ATPase, the Ragulator functions as a guanine nucleotide exchange factor activating the small GTPases Rag. Activated Ragulator and Rag GTPases function as a scaffold recruiting mTORC1 to lysosomes where it is in turn activated. LAMTOR1 is directly responsible for anchoring the Ragulator complex to membranes. Diseases associated with Lamtor 1 include Bone Benign Neoplasm and Connective Tissue Benign Neoplasm. Human Lamtor 1 protein has 161 amino acids and a molecular mass of 17745 Da.

The term "Lamtor 1" is intended to include fragments, variants (e.g., allelic variants), and derivatives thereof. Representative human Lamtor 1 cDNA and human Lamtor 1 protein sequences are well-known in the art and are publicly available from the National Center for Biotechnology Information (NCBI). Human Lamtor 1 has one isoform (NM_017907.2 and NP_060377.1). Nucleic acid and polypeptide sequences of Lamtor 1 orthologs in organisms other than humans are well-known and include, for example, monkey Lamtor 1 (NM_001194634.2 and NP_001181563.1), dog Lamtor 1 (XM_542329.5 and XP_542329.2), cattle Lamtor 1 (NM_001034769.1 and NP_001029941.1), mouse Lamtor 1 (NM_025605.3 and NP_079881.2), and rat Lamtor 1 (NM_199102.1 and NP_954533.1). Representative sequences of Lamtor 1 orthologs are presented below in Table 1.

Anti-Lamtor 1 antibodies suitable for detecting Lamtor 1 protein are well-known in the art and include, for example, antibodies TA309727 and TA326713 (OriGene), antibodies Cat #: 8975 (Cell Signaling), antibodies NBP1-71689 and NBP1-89909 (Novus Biologicals, Littleton, CO), antibodies ab121157, and ab181017 (AbCam, Cambridge, MA), etc. In addition, reagents are well-known for detecting Lamtor 1 expression. Moreover, multiple siRNA, shRNA, CRISPR constructs for reducing Lamtor 1 expression can be found in the commercial product lists of the above-referenced companies, such as shRNA product #SR310417, RNAi products SR310417, and CRISPR products #KN200159 from Origene Technologies (Rockville, MD). It is to be noted that the term can further be used to refer to any combination of features described herein regarding Lamtor 1 molecules. For example, any combination of sequence composition, percentage identify, sequence length, domain structure, functional activity, etc. can be used to describe an Lamtor 1 molecule of the present invention.

The term "Atg5" refers to autophagy related 5. In combination with autophagy protein 12, Atg5 functions as an E1-like activating enzyme in an ubiquitin-like conjugating system. Atg5 is involved in several cellular processes, including autophagic vesicle formation, mitochondrial quality control after oxidative damage, negative regulation of the innate antiviral immune response, lymphocyte development and proliferation, MHC II antigen presentation, adipocyte differentiation, and apoptosis. Human Atg5 protein has 275 amino acids and a molecular mass of 32447 Da.

The term "Atg5" is intended to include fragments, variants (e.g., allelic variants), and derivatives thereof. Representative human Atg5 cDNA and human Atg5 protein sequences are well-known in the art and are publicly available from the National Center for Biotechnology Information (NCBI). Human Atg5 isoforms include the longest isoform a (NM_004849.3 and NP_004840.1; NM_001286106.1 and NP_001273035.1), and the shorter isoform b (NM_001286107.1 and NP_001273036.1, which lacks an exon in the 5' coding region and initiates translation at an alternate start codon, resulting isoform (b) has a distinct N-terminus and is shorter than isoform a), c (NM_001286108.1 and NP_001273037.1, which uses an alternate splice site that causes a frameshift in the 3' coding region, resulting isoform (c) has a distinct C-terminus and is shorter than isoform a), and d (NM_001286111.1 and NP_001273040.1, which lacks three alternate exons in the 5' coding region, resulting isoform (d) has the same N-terminus but is otherwise distinct and shorter than isoform a). Nucleic acid and polypeptide sequences of Atg5 orthologs in organisms other than humans are well-known and include, for example, monkey Atg5 (XM_015137011.1 and XP_014992497.1; XM_015137015.1 and XP_014992501.1; XM_001088300.2 and XP_001088300.1; XM_015137016.1 and XP_014992502.1; XM_015137017.1 and XP_014992503.1; XM_015137018.1 and XP_014992504.1; XM_015137012.1 and XP_014992498.1; XM_015137013.1 and XP_014992499.1; XM_015137014.1 and XP_014992500.1; XM_001088076.2 and XP_001088076.1), dog Atg5 (XM_005627675.2 and XP_005627732.1; XM_005627676.2 and XP_005627733.1; XM_014118180.1 and XP_013973655.1; XM_849201.4 and XP_854294.1), cattle Atg5 (NM_001034579.2 and NP_001029751.2), and mouse Atg5 (NM_001314013.1 and NP_001300942.1; NM_053069.6 and NP_444299.1). Representative sequences of Rraga orthologs are presented below in Table 1.

Anti-Atg5 antibodies suitable for detecting Atg5 protein are well-known in the art and include, for example, antibodies MAB2605, ABC14 and MABC137 (EMD Millipore), antibodies AM20205PU-N and AM20206PU-N (OriGene), antibodies Cat #: 2630 (Cell Signaling), antibodies NB110-53818, MAB5294, and NBP2-24389 (Novus Biologicals, Littleton, CO), antibodies ab108327, and ab109490 (AbCam, Cambridge, MA), etc. In addition, reagents are well-known for detecting Atg5 expression. Moreover, multiple siRNA, shRNA, CRISPR constructs for reducing Atg5 expression can be found in the commercial product lists of the above-referenced companies, such as shRNA product #TR314610, RNAi products SR306286 and TR314610, and CRISPR products #KN301740 and #KN210563 from Origene Technologies (Rockville, MD). It is to be noted that the term can further be used to refer to any combination of features described herein regarding Atg5 molecules. For example, any combination of sequence composition, percentage identify, sequence length, domain structure, functional activity, etc. can be used to describe an Atg5 molecule of the present invention.

The term "Fadd" refers to Fas associated via death domain, an adaptor molecule that interacts with various cell surface receptors and mediates cell apoptotic signals. Through its C-terminal death domain, Fadd can be recruited by TNFRSF6/Fas-receptor, tumor necrosis factor receptor, TNFRSF25, and TNFSF10/TRAIL-receptor, and thus it participates in the death signaling initiated by these receptors. Interaction of Fadd with the receptors unmasks the N-terminal effector domain of Fadd, which allows it to recruit caspase-8, and thereby activate the cysteine protease cascade. Knockout studies in mice also suggest the importance of Fadd in early T cell development. Human Fadd protein has 208 amino acids and a molecular mass of 23279 Da.

The term "Fadd" is intended to include fragments, variants (e.g., allelic variants), and derivatives thereof. Representative human Fadd cDNA and human Fadd protein sequences are well-known in the art and are publicly available from the National Center for Biotechnology Information (NCBI). Human Fadd has one isoform (NM_003824.3 and NP_003815.1). Nucleic acid and polypeptide sequences of Fadd orthologs in organisms other than humans are well-known and include, for example, monkey Fadd (XM_001100468.3 and XP_001100468.2), cattle Fadd (NM_001007816.1 and NP_001007817.1), mouse Fadd (NM_010175.5 and NP_034305.1), and rat Fadd (NM_152937.2 and NP_690920.1). Representative sequences of Fadd orthologs are presented below in Table 1.

Anti-Fadd antibodies suitable for detecting Fadd protein are well-known in the art and include, for example, antibodies 05-486, 06-711 and AB3102 (EMD Millipore), antibodies AM00163PU-N and AM08189PU-N(OriGene), antibodies Cat #: 2782 (Cell Signaling), antibodies NBP1-81831, AF2938, and NBP2-16406 (Novus Biologicals, Littleton, CO), antibodies ab24533, ab124812 and ab108601 (AbCam, Cambridge, MA), etc. In addition, reagents are well-known for detecting Fadd expression. Moreover, multiple siRNA, shRNA, CRISPR constructs for reducing Fadd expression can be found in the commercial product lists of the above-referenced companies, such as shRNA product #TL320593, RNAi product SR305777, and CRISPR products #KN201805 and #KN305495 from Origene Technologies (Rockville, MD). It is to be noted that the term can further be used to refer to any combination of features described herein regarding Fadd molecules. For example, any combination of sequence composition, percentage identify, sequence length, domain structure, functional activity, etc. can be used to describe an Fadd molecule of the present invention.

The term "Tbk1" refers to TANK binding kinase 1. Tbk1 plays an essential role in regulating inflammatory responses to foreign agents. Following activation of toll-like receptors by viral or bacterial components, Tbk1 associates with TRAF3 and TANK and phosphorylates interferon regulatory factors (IRFs) IRF3 and IRF7 as well as DDX3X. This activity allows subsequent homodimerization and nuclear translocation of the IRFs leading to transcriptional activation of pro-inflammatory and antiviral genes including IFNA and IFNB. In order to establish such an antiviral state, TBK1 forms several different complexes whose composition depends on the type of cell and cellular stimuli. Thus, several scaffolding molecules including FADD, TRADD, MAVS, AZI2, TANK or TBKBP1/SINTBAD can be recruited to the TBK1-containing-complexes. Under particular conditions, Tbk1 functions as a NF-kappa-B effector by phosphorylating NF-kappa-B inhibitor alpha/NFKBIA, IKBKB or RELA to translocate NF-Kappa-B to the nucleus. Human Tbk1 protein has 729 amino acids and a molecular mass of 83642 Da.

The term "Tbk1" is intended to include fragments, variants (e.g., allelic variants), and derivatives thereof. Representative human Tbk1 cDNA and human Tbk1 protein sequences are well-known in the art and are publicly available from the National Center for Biotechnology Information (NCBI). Human Tbk1 has one isoform (NM_013254.3 and NP_037386.1). Nucleic acid and polypeptide sequences of Tbk1 orthologs in organisms other than humans are well-known and include, for example, monkey Tbk1 (NM_001261193.1 and NP_001248122.1), dog Tbk1 (XM_538266.5 and XP_538266.3), cattle Tbk1 (NM 001192755.1 and NP_001179684.1), mouse Tbk1 (NM_019786.4 and NP_062760.3), and rat Tbk1 (NM_001106786.1 and NP_001100256.1). Representative sequences of Tbk1 orthologs are presented below in Table 1.

Anti-Tbk1 antibodies suitable for detecting Tbk1 protein are well-known in the art and include, for example, antibodies 04-387, and 04-856 (EMD Millipore), antibodies TA336453 and TA334469 (OriGene), antibodies Cat #: 3013 (Cell Signaling), antibodies NB100-56705, NB100-421, and NBP2-13416 (Novus Biologicals, Littleton, CO), antibodies ab40676, ab109735 and ab186470 (AbCam, Cambridge, MA), etc. In addition, reagents are well-known for detecting Tbk1 expression. Moreover, multiple siRNA, shRNA, CRISPR constructs for reducing Tbk1 expression can be found in the commercial product lists of the above-referenced companies, such as shRNA product #TL320685, RNAi products SR309210, and CRISPR products #KN205238 and #KN3172714 from Origene Technologies (Rockville, MD). It is to be noted that the term can further be used to refer to any combination of features described herein regarding Tbk1 molecules. For example, any combination of sequence composition, percentage identify, sequence length, domain structure, functional activity, etc. can be used to describe an Tbk1 molecule of the present invention.

The term "Nsdhl" refers to NAD(P) dependent steroid dehydrogenase-like. Nsdhl is localized in the endoplasmic reticulum and is involved in cholesterol biosynthesis. Mutations in Nsdhl are associated with CHILD syndrome, which is a X-linked dominant disorder of lipid metabolism with disturbed cholesterol biosynthesis, and typically lethal in males. Human Nsdhl protein has 373 amino acids and a molecular mass of 41900 Da.

The term "Nsdhl" is intended to include fragments, variants (e.g., allelic variants), and derivatives thereof. Representative human Nsdhl cDNA and human Nsdhl protein sequences are well-known in the art and are publicly available from the National Center for Biotechnology Information (NCBI). Human Nsdhl has two transcript variants which encode the same protein: the variant 1 NM_015922.2 encodes NP_057006.1, and the variant 2 NM_001129765.1 encodes NP_001123237.1. Nucleic acid and polypeptide sequences of Nsdhl orthologs in organisms other than humans are well-known and include, for example, monkey Nsdhl (NM_001265710.1 and NP_001252639.1), dog Nsdhl (XM_014111859.1 and XP_013967334.1; XM_014111861.1 and XP_013967336.1; XM_005641965.2 and XP_005642022.1; XM_014111860.1 and XP_013967335.1), cattle Nsdhl (NM_001035482.2 and NP_001030559.1), mouse Nsdhl (NM_010941.3 and NP_035071.3), and rat Nsdhl (NM_001009399.1 and NP_001009399.1). Representative sequences of Nsdhl orthologs are presented below in Table 1.

Anti-Nsdhl antibodies suitable for detecting Nsdhl protein are well-known in the art and include, for example, antibody TA341986 (OriGene), antibodies NBP1-83306, NBP1-83307, and H00050814-M01 (Novus Biologicals, Littleton, CO), antibodies ab190353, ab199730 and ab102805 (Ab-Cam, Cambridge, MA), etc. In addition, reagents are well-known for detecting Nsdhl expression. Moreover, multiple siRNA, shRNA, CRISPR constructs for reducing Nsdhl expression can be found in the commercial product lists of the above-referenced companies, such as shRNA product #TR302882, RNAi products SR324001, and CRISPR products #KN311254 and #KN203225 from Origene Technologies (Rockville, MD). It is to be noted that the term can further be used to refer to any combination of features described herein regarding Nsdhl molecules. For example, any combination of sequence composition, percentage identify, sequence length, domain structure, functional activity, etc. can be used to describe an Nsdhl molecule of the present invention.

The term "Gne" refers to glucosamine (UDP-N-acetyl)-2-epimerase/N-acetylmannosamine kinase. Gne is a bifunctional enzyme that initiates and regulates the biosynthesis of N-acetylneuraminic acid (NeuAc), a precursor of sialic acids. It is a rate-limiting enzyme in the sialic acid biosynthetic pathway. Sialic acid modification of cell surface molecules is crucial for their function in many biologic processes, including cell adhesion and signal transduction. Differential sialylation of cell surface molecules is also implicated in the tumorigenicity and metastatic behavior of malignant cells. Mutations in Gne are associated with sialuria, autosomal recessive inclusion body myopathy, and Nonaka myopathy. Human Gne protein has 722 amino acids and a molecular mass of 79275 Da.

The term "Gne" is intended to include fragments, variants (e.g., allelic variants), and derivatives thereof. Representative human Gne cDNA and human Gne protein sequences are well-known in the art and are publicly available from the National Center for Biotechnology Information (NCBI). Human Gne isoforms include the longest isoform 1 (NM_001128227.2 and NP_001121699.1), and the shorter isoform 2 (NM_005476.5 and NP_005467.1, which contains a different 5' terminal exon, resulting in translation initiation from an in-frame downstream AUG, and a protein (isoform 2) with a shorter N-terminus compared to isoform 1), 3 (NM_001190388.1 and NP_001177317.1, which lacks a 5' coding segment, resulting in the use of an upstream alternate start codon, and a protein (isoform 3) with a shorter and distinct N-terminus compared to isoform 1), 4 (NM_001190383.1 and NP_001177312.1, which contains a different 5' terminal exon and lacks a 3' coding region segment, resulting in translation initiation from an in-frame downstream AUG and a shorter protein (isoform 4) compared to isoform 1), and 5 (NM_001190384.1 and NP_001177313.1, which contains a different 5' terminal exon and lacks two alternate 5' coding region segments, resulting in translation initiation from an in-frame downstream AUG and a shorter protein (isoform 5) compared to isoform 1). Nucleic acid and polypeptide sequences of Gne orthologs in organisms other than humans are well-known and include, for example, monkey Gne (XM_015117449.1 and XP_014972935.1; XM_015117448.1 and XP_014972934.1; XM_015117445.1 and XP_014972931.1; XM_015117446.1 and XP_014972932.1; XM_015117447.1 and XP_014972933.1), dog Gne (XM_003431575.3 and XP_003431623.1; XM_005626808.2 and XP_005626865.1; XM_005626809.2 and XP_005626866.1), cattle Gne (NM_001191143.3 and NP_001178072.2), mouse Gne (NM_001190414.1 and NP_001177343.1; NM_015828.3 and NP_056643.3), and rat Gne (NM_053765.2 and NP_446217.1). Representative sequences of Gne orthologs are presented below in Table 1.

Anti-Gne antibodies suitable for detecting Gne protein are well-known in the art and include, for example, antibodies TA890043, TA315006 and AP51881PU-N(OriGene), antibodies NBP1-81621, NBP1-81622, and H00010020-D01P (Novus Biologicals, Littleton, CO), antibodies ab189927, ab184963 and ab199416 (AbCam, Cambridge, MA), etc. In addition, reagents are well-known for detecting Gne expression. Moreover, multiple siRNA, shRNA, CRISPR constructs for reducing Gne expression can be found in the commercial product lists of the above-referenced companies, such as shRNA product #TL312714, CRISPR products #KN307080 and #KN222626 from Origene Technologies (Rockville, MD), and RNAi product H00010020-R02 from Novus Biologicals (Littleton, CO). It is to be noted that the term can further be used to refer to any combination of features described herein regarding Gne molecules. For example, any combination of sequence composition, percentage identify, sequence length, domain structure, functional activity, etc. can be used to describe an Gne molecule of the present invention.

The term "Gale" refers to UDP-galactose-4-epimerase. Gale catalyzes two distinct but analogous reactions: the reversible epimerization of UDP-glucose to UDP-galactose and the reversible epimerization of UDP-N-acetylglucosamine to UDP-N-acetylgalactosamine. The reaction with UDP-Gal plays a critical role in the Leloir pathway of galactose catabolism in which galactose is converted to the glycolytic intermediate glucose 6-phosphate. Gale contributes to the catabolism of dietary galactose and enables the endogenous biosynthesis of both UDP-Gal and UDP-GalNAc when exogenous sources are limited. Both UDP-sugar interconversions are important in the synthesis of glycoproteins and glycolipids. Mutations in this gene result in epimerase-deficiency galactosemia, also referred to as galactosemia type 3, a disease characterized by liver damage, early-onset cataracts, deafness and mental retardation, with symptoms ranging from mild ('peripheral' form) to severe ('generalized' form). Human Gale protein has 348 amino acids and a molecular mass of 38282 Da.

The term "Gale" is intended to include fragments, variants (e.g., allelic variants), and derivatives thereof. Representative human Gale cDNA and human Gale protein sequences are well-known in the art and are publicly available from the National Center for Biotechnology Information (NCBI). Human Gale has three transcript variants which encode the same protein: the variant 1 NM_000403.3 encodes NP_000394.2, and the variant 2 NM_001008216.1 encodes NP_001008217.1, and the variant 3 NM_001127621.1 encodes NP_001121093.1. Nucleic acid and polypeptide sequences of Gale orthologs in organisms other than humans are well-known and include, for example, monkey Gale (NM_001261703.1 and NP_001248632.1), dog Gale (XM_003638903.3 and XP_003638951.1), cattle Gale (NM_001206208.1 and NP_001193137.1), mouse Gale (NM_178389.3 and NP_848476.1), and rat Gale (NM_080783.2 and NP_542961.2). Representative sequences of Gale orthologs are presented below in Table 1.

Anti-Gale antibodies suitable for detecting Gale protein are well-known in the art and include, for example, antibody ABS591 (EMD Millipore), antibodies AP17410PU-N and TA334924 (OriGene), antibodies NBP1-87066, NBP2-03390, and NBP2-59421 (Novus Biologicals, Littleton, CO), antibodies ab155997, ab210807 and ab155277 (AbCam, Cambridge, MA), etc. In addition, reagents are well-known for detecting Gale expression. Moreover, multiple siRNA, shRNA, CRISPR constructs for reducing Gale expression can be found in the commercial product lists of the above-referenced companies, such as shRNA product #TL312852, RNAi product SR301721, and CRISPR products #KN306269 and #KN201561 from Origene Technologies (Rockville, MD). It is to be noted that the term can further be used to refer to any combination of features described herein regarding Gale molecules. For example, any combination of sequence composition, percentage identify, sequence length, domain structure, functional activity, etc. can be used to describe an Gale molecule of the present invention.

The term "Ero1l" refers to endoplasmic reticulum oxidoreductase 1 alpha. Ero1l is involved in disulfide bond formation in the endoplasmic reticulum. It efficiently reoxidizes P4HB/PDI, the enzyme catalyzing protein disulfide formation, in order to allow P4HB to sustain additional rounds of disulfide formation. Following P4HB reoxidation, Ero1l passes its electrons to molecular oxygen via FAD, leading to the production of reactive oxygen species (ROS) in the cell. Ero1l is required for the proper folding of immunoglobulins. Ero1l is involved in the release of the unfolded cholera toxin from reduced P4HB/PDI in case of infection by V.cholerae, thereby playing a role in retrotranslocation of the toxin. It also plays an important role in ER stress-induced, CHOP-dependent apoptosis by activating the inositol 1,4,5-trisphosphate receptor IP3R1. Diseases associated with Ero1l include Cholera. Human Ero1l protein has 468 amino acids and a molecular mass of 54393 Da.

The term "Ero1l" is intended to include fragments, variants (e.g., allelic variants), and derivatives thereof. Representative human Ero1l cDNA and human Ero1l protein sequences are well-known in the art and are publicly available from the National Center for Biotechnology Information (NCBI). Human Ero1l has one isoform (NM_014584.2 and NP_055399.1). Nucleic acid and polypeptide sequences of Ero1l orthologs in organisms other than humans are well-known and include, for example monkey Ero1l (NM_001266764.1 and NP_001253693.1), dog Ero1l (XM_547813.3 and XP_547813.2), cattle Ero1l (NM_001103348.1 and NP_001096818.1), mouse Ero1l (NM_015774.3 and NP_056589.1), and rat Ero1l (NM_138528.1 and NP_612537.1). Representative sequences of Ero1l orthologs are presented below in Table 1.

Anti-Ero1l antibodies suitable for detecting Ero1l protein are well-known in the art and include, for example, antibody MABT376 (EMD Millipore), antibodies TA311424 and TA309644 (OriGene), Cat #3264 (Cell Signaling Technology), antibodies NB100-2525, H00030001-M01, and NBP1-84799 (Novus Biologicals, Littleton, CO), antibodies ab177156, ab172954 and ab81959 (AbCam, Cambridge, MA), etc. In addition, reagents are well-known for detecting Ero1l expression. Moreover, multiple siRNA, shRNA, CRISPR constructs for reducing Ero1l expression can be found in the commercial product lists of the above-referenced companies, such as shRNA product #TL313168, RNAi product SR309340, and CRISPR products #KN203840 from Origene Technologies (Rockville, MD). It is to be noted that the term can further be used to refer to any combination of features described herein regarding Ero1l molecules. For example, any combination of sequence composition, percentage identify, sequence length, domain structure, functional activity, etc. can be used to describe an Ero1l molecule of the present invention.

The term "Cd44" refers to CD44 molecule (Indian blood group). Cd44 is a cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs). Cd44 participates in a wide variety of cellular functions including lymphocyte activation, recirculation and homing, hematopoiesis, and tumor metastasis. Altered expression or dysfunction of Cd44 causes numerous pathogenic phenotypes. Human Cd44 protein has 742 amino acids and a molecular mass of 81538 Da.

The term "Cd44" is intended to include fragments, variants (e.g., allelic variants), and derivatives thereof. Representative human Cd44 cDNA and human Cd44 protein sequences are well-known in the art and are publicly available from the National Center for Biotechnology Information (NCBI). Human Cd44 isoforms include the longest isoform 1 (NM_000610.3 and NP_000601.3), and the shorter isoform 2 (NM_001001389.1 and NP_001001389.1, which lacks an in-frame coding exon, resulting isoform (2) lacks an internal region, as compared to isoform 1), 3 (NM_001001390.1 and NP_001001390.1, which lacks multiple coding-exons but remains in-frame, resulting isoform (3) lacks an internal segment, as compared to isoform 1), 4 (NM_001001391.1 and NP_001001391.1, which lacks multiple coding-exons but remains in-frame, resulting isoform (3) lacks an internal segment, as compared to isoform 1), 5 (NM_001001392.1 and NP_001001392.1, which lacks multiple coding-exons and leads to frame-shift, resulting isoform (5) has a distinct and shorter C-terminus, as compared to isoform 1), 6 (NM_001202555.1 and NP_001189484.1, which lacks multiple coding-exons and remains in-frame, resulting isoform (6) lacks an internal segment, as compared to isoform 1), 7 (NM_001202556.1 and NP_001189485.1, which lacks multiple coding-exons and remains in-frame, resulting isoform (7) lacks an internal segment, as compared to isoform 1), 8 (NM_001202557.1 and NP_001189486.1, which lacks multiple in-frame coding-exons and differs in the 3' UTR and coding sequence, resulting isoform (8) lacks an internal segment and has a shorter and distinct C-terminus, as compared to isoform 1). Nucleic acid and polypeptide sequences of Cd44 orthologs in organisms other than humans are well-known and include, for example, monkey Cd44 (XM_015114538.1 and XP_014970024.1; XM_001115390.3 and XP_001115390.1; XM_015114531.1 and XP_014970017.1; XM_015114527.1 and XP_014970013.1; XM_015114537.1 and XP_014970023.1; XM_015114536.1 and XP_014970022.1; XM_015114535.1 and XP_014970021.1; XM_015114534.1 and XP_014970020.1; XM_015114530.1 and XP_014970016.1; XM_015114532.1 and XP_014970018.1; XM_015114533.1 and XP_014970019.1; XM_015114529.1 and XP_014970015.1; XM_015114528.1 and XP_014970014.1; XM_001115359.3 and XP_001115359.2); , dog Cd44 (NM_001197022.1 and NP_001183951.1), cattle Cd44 (NM_174013.3 and NP_776438.2), mouse Cd44 (NM_001039150.1 and NP_001034239.1; NM_001039151.1 and NP_001034240.1;

NM_001177785.1 and NP_001171256.1; NM_001177786.1 and NP_001171257.1; NM_001177787.1 and NP_001171258.1; NM_009851.2 and NP_033981.2), and rat Cd44 (NM_012924.2 and NP_037056.2). Representative sequences of Cd44 orthologs are presented below in Table 1.

Anti-Cd44 antibodies suitable for detecting Gale protein are well-known in the art and include, for example, antibody MAB4073 (EMD Millipore), antibodies AM00699FC-N and AM01076FC-T (OriGene), antibody Cat #3578 (Cell Signaling Technology), antibodies NBP1-47386, BBA10, and AF6127 (Novus Biologicals, Littleton, CO), antibodies ab34229, and ab119365 (AbCam, Cambridge, MA), etc. In addition, reagents are well-known for detecting Cd44 expression. Moreover, multiple siRNA, shRNA, CRISPR constructs for reducing Cd44 expression can be found in the commercial product lists of the above-referenced companies, such as shRNA product #TL314080, RNAi product #SR300683, and CRISPR products #KN302920 and #KN202455 from Origene Technologies (Rockville, MD). It is to be noted that the term can further be used to refer to any combination of features described herein regarding Cd44 molecules. For example, any combination of sequence composition, percentage identify, sequence length, domain structure, functional activity, etc. can be used to describe an Cd44 molecule of the present invention.

The term "Nadk" refers to NAD kinase. NADK catalyzes the transfer of a phosphate group from ATP to NAD to generate NADP, which in its reduced form acts as an electron donor for biosynthetic reactions (Lerner et al., 2001 [PubMed 11594753]). Human Nadk protein has 446 amino acids and a molecular mass of 49228 Da.

The term "Nadk" is intended to include fragments, variants (e.g., allelic variants), and derivatives thereof. Representative human Nadk cDNA and human Nadk protein sequences are well-known in the art and are publicly available from the National Center for Biotechnology Information (NCBI). Human Nadk isoforms include the longest isoform 1 encoded by two different transcript variants (NM_001198993.1, which encodes NP_001185922.1, and NM_023018.4, which encodes NP_075394.3), and the shorter isoform 2 (NM_001198994.1 and NP_001185923.1, which differs in the 5' UTR and CDS, resulting an isoform with two additional internal segments, as compared to isoform 1), 3 (NM_001198995.1 and NP_001185924.1, which lacks three exons from the 5' end and has an alternate 5' exon, resulting an isoform with a shorter and distinct N-terminus, as compared to isoform 1). Nucleic acid and polypeptide sequences of Nadk orthologs in organisms other than humans are well-known and include, for example, monkey Nadk (XM_015133300.1 and XP_014988786.1; XM_015133396.1 and XP_014988882.1; XM_015133361.1 and XP_014988847.1), dog Nadk (XM_005620403.2 and XP_005620460.1; XM_014113829.1 and XP_013969304.1), cattle Nadk (XM_005217071.2 and XP_005217128.1; XM_010813336.2 and XP_010811638.2; XM_015475143.1 and XP_015330629.1; XM_015475144.1 and XP_015330630.1), mouse Nadk (NM_001159637.1 and NP_001153109.1; NM_138671.2 and NP_619612.2), and rat Nadk (NM_001109678.1 and NP_001103148.1). Representative sequences of Nadk orthologs are presented below in Table 1.

Anti-Nadk antibodies suitable for detecting Nadk protein are well-known in the art and include, for example, antibodies AF8009, H00065220-M01, and NBP2-58769 (Novus Biologicals, Littleton, CO), antibodies ab220484, ab172675 and ab128604 (AbCam, Cambridge, MA), etc. In addition, reagents are well-known for detecting Nadk expression. Moreover, multiple siRNA, shRNA, CRISPR constructs for reducing Nadk expression can be found in the commercial product lists of the above-referenced companies, such as shRNA product #TL303056, RNAi product SR312226, and CRISPR products #KN200544 and #KN310701 from Origene Technologies (Rockville, MD). It is to be noted that the term can further be used to refer to any combination of features described herein regarding Nadk molecules. For example, any combination of sequence composition, percentage identify, sequence length, domain structure, functional activity, etc. can be used to describe an Nadk molecule of the present invention.

The term "Nampt" refers to nicotinamide phosphoribosyltransferase. Nampt catalyzes the condensation of nicotinamide with 5-phosphoribosyl-1-pyrophosphate to yield nicotinamide mononucleotide, one step in the biosynthesis of nicotinamide adenine dinucleotide. Nampt belongs to the nicotinic acid phosphoribosyltransferase (NAPRTase) family and is thought to be involved in many important biological processes, including metabolism, stress response and aging. Human Nampt protein has 491 amino acids and a molecular mass of 55521 Da.

The term "Nampt" is intended to include fragments, variants (e.g., allelic variants), and derivatives thereof. Representative human Nampt cDNA and human Nampt protein sequences are well-known in the art and are publicly available from the National Center for Biotechnology Information (NCBI). Human Nampt has one isoform (NM_005746.2 and NP_005737.1). Nucleic acid and polypeptide sequences of Nampt orthologs in organisms other than humans are well-known and include, for example, monkey Nampt (XM_015134665.1 and XP_014990151.1; XM_015134666.1 and XP_014990152.1), dog Nampt (XM_014120762.1 and XP_013976237.1), cattle Nampt (NM_001244141.1 and NP_001231070.1), mouse Nampt (NM_021524.2 and NP_067499.2), and rat Nampt (NM_177928.3 and NP_808789.1). Representative sequences of Nampt orthologs are presented below in Table 1.

Anti-Nampt antibodies suitable for detecting Nampt protein are well-known in the art and include, for example, antibodies AM06217SU-N and AM09041PU-N(OriGene), antibodies Cat #61122 and Cat #86634 (Cell Signaling Technology), antibodies NB100-594, NBP2-23795, and NBP2-23667 (Novus Biologicals, Littleton, CO), antibodies ab45890, ab24149 and ab58640 (AbCam, Cambridge, MA), etc. In addition, reagents are well-known for detecting Nampt expression. Moreover, multiple siRNA, shRNA, CRISPR constructs for reducing Nampt expression can be found in the commercial product lists of the above-referenced companies, such as shRNA product #TR302662, RNAi product SR306835, and CRISPR products #KN310718 and #KN210707 from Origene Technologies (Rockville, MD). It is to be noted that the term can further be used to refer to any combination of features described herein regarding Nampt molecules. For example, any combination of sequence composition, percentage identify, sequence length, domain structure, functional activity, etc. can be used to describe an Nampt molecule of the present invention.

The term "Sox4" refers to SRY-box 4, a member of the SOX (SRY-related HMG-box) family of transcription factors involved in the regulation of embryonic development and in the determination of cell fate. Sox4 is believed to act as a transcriptional regulator after forming a protein complex with other proteins, such as syndecan binding protein (syntenin). It is also believed to function in the apoptosis pathway leading to cell death, tumorigenesis, and mediation of downstream effects of parathyroid hormone (PTH) and PTH-related protein (PTHrP) in bone development. It binds with high affinity to the T-cell enhancer motif 5-AACAAAG-3 motif. Human Sox4 protein has 474 amino acids and a molecular mass of 47263 Da.

The term "Sox4" is intended to include fragments, variants (e.g., allelic variants), and derivatives thereof. Representative human Sox4 cDNA and human Sox4 protein sequences are well-known in the art and are publicly available from the National Center for Biotechnology Information (NCBI). Human Sox4 has one isoform (NM_003107.2 and NP_003098.1). Nucleic acid and polypeptide sequences of Sox4 orthologs in organisms other than humans are well-known and include, for example, monkey Sox4 (XM_001098923.3 and XP_001098923.1), dog Sox4 (XM_005640161.2 and XP_005640218.1), cattle Sox4 (NM_001078128.1 and NP_001071596.1), mouse Sox4 (NM_009238.2 and NP_033264.2), and rat Sox4 (NM_001271205.1 and NP_001258134.1). Representative sequences of Sox4 orthologs are presented below in Table 1.

Anti-Sox4 antibodies suitable for detecting Sox4 protein are well-known in the art and include, for example, antibody AB5803 (EMD Millipore), antibodies AP22737PU-N and TA324704 (OriGene), antibodies NBP1-89506, H00006659-A01, and NBP1-50776 (Novus Biologicals, Littleton, CO), antibodies ab86809, ab80261 and ab70598 (AbCam, Cambridge, MA), etc. In addition, reagents are well-known for detecting Sox4 expression. Moreover, multiple siRNA, shRNA, CRISPR constructs for reducing Sox4 expression can be found in the commercial product lists of the above-referenced companies, such as shRNA product #TR315513, RNAi product #SR304530, and CRISPR products #KN209139 and #KN316499 from Origene Technologies (Rockville, MD). It is to be noted that the term can further be used to refer to any combination of features described herein regarding Sox4 molecules. For example, any combination of sequence composition, percentage identify, sequence length, domain structure, functional activity, etc. can be used to describe an Sox4 molecule of the present invention.

The term "Hdac5" refers to histone deacetylase 5. Histones play a critical role in transcriptional regulation, cell cycle progression, and developmental events. Histone acetylation/deacetylation alters chromosome structure and affects transcription factor access to DNA. The Hdac5 protein belongs to the class II histone deacetylase/acuc/apha family. It possesses histone deacetylase activity and represses transcription when tethered to a promoter. It co-immunoprecipitates only with HDAC3 family member and might form multi-complex proteins. It also interacts with myocyte enhancer factor-2 (MEF2) proteins, resulting in repression of MEF2-dependent genes. Hdac5 gene is thought to be associated with colon cancer. Hdac5 is also involved in the MTA1-mediated epigenetic regulation of ESR1 expression in breast cancer. Human Hdac5 protein has 1122 amino acids and a molecular mass of 121978 Da.

The term "Hdac5" is intended to include fragments, variants (e.g., allelic variants), and derivatives thereof. Representative human Hdac5 cDNA and human Hdac5 protein sequences are well-known in the art and are publicly available from the National Center for Biotechnology Information (NCBI). Human Hdac5 isoforms include a longer isoform 3 (NM_001015053.1 and NP_001015053.1), and a shorter isoform 1 (NM_005474.4 and NP_005465.2, which uses an alternate in-frame splice site compared to variant 3, resulting isoform (1) has the same N- and C-termini but is 1 aa shorter compared to isoform 3). Nucleic acid and polypeptide sequences of Hdac5 orthologs in organisms other than humans are well-known and include, for example, monkey Hdac5 (NM_001258098.1 and NP_001245027.1), dog Hdac5 (XM_014116523.1 and XP_013971998.1; XM 014116525.1 and XP 013972000.1; XM 005624409.2 and XP 005624466.1; XM_005624410.2 and XP_005624467.1; XM_014116524.1 and XP_013971999.1; XM_014116521.1 and XP_013971996.1; XM_014116526.1 and XP_013972001.1), cattle Hdac5 (NM_001038025.2 and NP_001033114.2), mouse Hdac5 (NM_001077696.1 and NP_001071164.1; NM_001284248.1 and NP_001271177.1; NM_001284249.1 and NP_001271178.1; NM_001284250.1 and NP_001271179.1; NM_010412.3 and NP_034542.3), and rat Hdac5 (NM_053450.1 and NP_445902.1). Representative sequences of Hdac5 orthologs are presented below in Table 1.

Anti-Hdac5 antibodies suitable for detecting Hdac5 protein are well-known in the art and include, for example, antibody 07-045 (EMD Millipore), antibodies AP00274PU-N and AP01598PU-N(OriGene), antibodies Cat #20458 (Cell Signaling Technology), antibodies NBP2-22152, NBP2-03988, and NBP1-83436 (Novus Biologicals, Littleton, CO), antibodies ab1439, ab55403 and ab47283 (AbCam, Cambridge, MA), etc. In addition, reagents are well-known for detecting Hdac5 expression. Moreover, multiple siRNA, shRNA, CRISPR constructs for reducing Hdac5 expression can be found in the commercial product lists of the above-referenced companies, such as shRNA product #TR312492, RNAi product SR306740, and CRISPR products #KN208656 and #KN307620 from Origene Technologies (Rockville, MD). It is to be noted that the term can further be used to refer to any combination of features described herein regarding Hdac5 molecules. For example, any combination of sequence composition, percentage identify, sequence length, domain structure, functional activity, etc. can be used to describe an Hdac5 molecule of the present invention.

The term "Ptpn11" refers to protein tyrosine phosphatase, non-receptor type 11, a member of the protein tyrosine phosphatase (PTP) family. PTPs are known to be signaling molecules that regulate a variety of cellular processes including cell growth, differentiation, mitotic cycle, and oncogenic transformation. Ptpn11 contains two tandem Src homology-2 domains, which function as phospho-tyrosine binding domains and mediate the interaction of this PTP with its substrates. Ptpn11 is widely expressed in most tissues and plays a regulatory role in various cell signaling events that are important for a diversity of cell functions, such as mitogenic activation, metabolic control, transcription regulation, and cell migration. Mutations in Ptpn11 are a cause of Noonan syndrome as well as acute myeloid leukemia. Human Ptpn11 protein has 597 amino acids and a molecular mass of 68436 Da.

The term "Ptpn11" is intended to include fragments, variants (e.g., allelic variants), and derivatives thereof. Representative human Ptpn11 cDNA and human Ptpn11 protein sequences are well-known in the art and are publicly available from the National Center for Biotechnology Information (NCBI). Human Ptpn11 isoforms include isoform 1 (NM_002834.4 and NP_002825.3), isoform 2 (NM_080601.2 and NP_542168.1, which differs in the 3' UTR and coding sequence, resulting an isoform with a shorter and distinct N-terminus compared to isoform 1), and isoform 3 (NM_001330437.1 and NP_001317366.1, which uses an alternate in-frame splice site in the 3' coding region, resulting an isoform with the same N- and C-termini but longer than isoform 1). Nucleic acid and polypeptide sequences of Ptpn11 orthologs in organisms other than humans are well-known and include, for example, monkey Ptpn11 (NM_001261109.1 and NP_001248038.1), dog Ptpn11 (XM_005636250.1 and XP_005636307.1; XM_005636251.1 and XP_005636308.1), cattle Ptpn11 (XM_010814056.2 and XP_010812358.1; XM_002694590.5 and XP_002694636.2; XM_010814055.2 and XP_010812357.1), mouse Ptpn11 (NM_001109992.1 and NP_001103462.1; NM_011202.3 and NP_035332.1), and rat Ptpn11 (NM_001177593.1 and NP_001171064.1; NM_013088.2 and NP_037220.2). Representative sequences of Ptpn11 orthologs are presented below in Table 1.

Anti-Ptpn11 antibodies suitable for detecting Ptpn11 protein are well-known in the art and include, for example, antibodies AM06217SU-N and AM09041PU-N(OriGene), antibodies Cat #61122 and Cat #86634 (Cell Signaling Technology), antibodies NB100-594, NBP2-23795, and NBP2-23667 (Novus Biologicals, Littleton, CO), antibodies ab45890, ab24149 and ab58640 (AbCam, Cambridge, MA), etc. In addition, reagents are well-known for detecting Ptpn11 expression. Moreover, multiple siRNA, shRNA, CRISPR constructs for reducing Ptpn11 expression can be found in the commercial product lists of the above-referenced companies, such as shRNA product #TR302662, RNAi product SR306835, and CRISPR products #KN310718 and #KN210707 from Origene Technologies (Rockville, MD). It is to be noted that the term can further be used to refer to any combination of features described herein regarding Ptpn11 molecules. For example, any combination of sequence composition, percentage identify, sequence length, domain structure, functional activity, etc. can be used to describe an Ptpn11 molecule of the present invention.

Unless otherwise specified here within, the terms "antibody" and "antibodies" broadly encompass naturally-occurring forms of antibodies (e.g. IgG, IgA, IgM, IgE) and recombinant antibodies, such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., 1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Poljak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "biomarker" refers to a measurable entity of the present invention that has been determined to be predictive of cancer therapy (e.g., at least one modulator of biomarkers listed in Tables 1-9) effects. Biomarkers can include, without limitation, nucleic acids (e.g., genomic nucleic acids and/or transcribed nucleic acids) and proteins, particularly those involved shown in Tables 1-9. Many biomarkers listed in Tables 1-9 are also useful as therapeutic targets. In one embodiment, such targets are negative regulators of T cell-mediated cytotoxicity shown in Table 1, 3, 5, 7, or 9, and/or positive regulators of T cell-mediated cytotoxicity shown in Table 2, 4, 6 or 8.

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of immune checkpoint proteins, such as PD-1, PD-L1, and/or CTLA-4.

Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses melanoma. The term "melanoma" as used herein, is generally meant to include cancers that develop from the pigment-containing cells, known as melanocytes, in the basal layer of the epidermis. Melanomas typically occur in the skin but may rarely occur in the mouth, intestines, or eye. In women they most commonly occur on the legs, while in men they are most common on the back. Sometimes they develop from a mole with concerning changes including an increase in size, irregular edges, change in color, itchiness, or skin breakdown. Thus, the term "melanoma" also includes cancers developing from these cells, tissues, and organs.

Melanomas are among the most dangerous forms of skin cancer and develop when unrepaired DNA damage to skin cells (most often caused by ultraviolet radiation from sunshine or tanning beds) triggers gene mutations that lead the skin cells to multiply rapidly and form malignant tumors. The primary cause of melanoma is ultraviolet light (UV)

exposure in those with low levels of skin pigment. Melanomas often resemble moles; some develop from moles. Those with many moles, a history of affected family members, and who have poor immune function are at greater risk. A number of rare genetic defects such as xeroderma pigmentosum also increase risk (Azoury and Lange, 2014 *Surg Clin North Am.* 2014 94:945-962).

Melanoma can be divided into different types, including, at least, lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, melanoma with small nevus-like cells, melanoma with features of a Spitz nevus, uveal melanoma, etc. (see James, et al., 2006 *Andrews' Diseases of the Skin: clinical Dermatology.* Saunders Elsevier. pp. 694-9).

Diagnosis is by biopsy of any concerning skin lesion, including, at least, shave (tangential) biopsy, punch biopsy, incisional and excisional biopsies, "optical" biopsies (e.g., by reflectance confocal microscopy (RCM)), fine needle aspiration (FNA) biopsy, surgical lymph node biopsy, sentinel lymph node biopsy, etc. In addition, visual inspection may also be used for diagnosis, such as a popular method for the signs and symptoms of melanoma as mnemonic "ABCDE": Asymmetrical skin lesion, Border of the lesion is irregular, Color: melanomas usually have multiple colors, Diameter: moles greater than 6 mm are more likely to be melanomas than smaller moles, and Enlarging: Enlarging or evolving. Another method as the "ugly duckling sign" is also known in the art (Mascaro and Mascaro, 1998 *Arch Dermatol.* 134: 1484-1485).

Treatment of melanoma includes surgery, chemotherapy (such as temozolomide, dacarbazine (also termed DTIC), etc.), radiation therapy, oncolytic virotherapy (e.g., see Forbes et al., 2013 *Front. Genet.* 4:184), and immunotherapy (e.g., interleukin-2 (IL-2), interferon, etc.). Targeted therapies (e.g., as in Maverakis et al., 2015 *Acta Derm Venereol.* 95: 516-524) may include: 1) adoptive cell therapy (ACT) using TILs immune cells (tumor infiltrating lymphocytes) isolated from a person's own melanoma tumor). Cells are grown in large numbers in a laboratory and returned to the patient after a treatment that temporarily reduces normal T cells in the patient's body. TIL therapy following lymphodepletion can result in durable complete response in a variety of setups (Besser et al., 2010 *Clin. Cancer Res.* 16:2646-2655); and 2) adoptive transfer of genetically altered (expressing T cell receptors (TCRs)) autologous lymphocytes into patient's lymphocytes, where the altered lymphocytes recognize and bind to the surface of melanoma cells and kill them. Other therapies include, at least, B-Raf inhibitors (such as vemurafenib, see Chapman et al., 2011 *N. Engl. J. Med.* 364:2507-2516) and ipilimumab (alone or in combination with dacarbazine, see, e.g., Robert et al. (2011) *N. Engl. J. Med.* 364:2517-2526).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The terms "conjoint therapy" and "combination therapy," as used herein, refer to the administration of two or more therapeutic substances, e.g., combinations of anti-immune checkpoint therapies, multiple inhibitors of an immune checkpoint of interest, combinations of immune checkpoint therapy with an inhibitor of PBRM1 (ARID2, BRD7, PHF10, KDM6A, ARID1A, ARID1B, BRG1, BRM, CRB1, EGFR, and the like), and combinations thereof. The different agents comprising the combination therapy may be administered concomitant with, prior to, or following the administration of one or more therapeutic agents.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

Conventional T cells, also known as Tconv or Teffs, have effector functions (e.g., cytokine secretion, cytotoxic activity, anti-self-recognition, and the like) to increase immune responses by virtue of their expression of one or more T cell receptors. Tcons or Teffs are generally defined as any T cell population that is not a Treg and include, for example, naïve T cells, activated T cells, memory T cells, resting Tcons, or Tcons that have differentiated toward, for example, the Th1 or Th2 lineages. In some embodiments, Teffs are a subset of non-Treg T cells. In some embodiments, Teffs are CD4+ Teffs or CD8+ Teffs, such as CD4+ helper T lymphocytes (e.g., Th0, Th1, Tfh, or Th17) and CD8+ cytotoxic T lymphocytes. As described further herein, cytotoxic T cells are CD8+ T lymphocytes. "Naïve Tcons" are CD4+ T cells that have differentiated in bone marrow, and successfully underwent a positive and negative processes of central selection in a thymus, but have not yet been activated by exposure to an antigen. Naïve Tcons are commonly characterized by surface expression of L-selectin (CD62L), absence of activation markers such as CD25, CD44 or CD69, and absence of memory markers such as CD45RO. Naïve Tcons are therefore believed to be quiescent and non-dividing, requiring interleukin-7 (IL-7) and interleukin-15 (IL-15) for homeostatic survival (see, at least WO 2010/101870). The presence and activity of such cells are undesired in the context of suppressing immune responses. Unlike Tregs, Tcons are not anergic and can proliferate in response to antigen-based T cell receptor activation (Lechler et al. (2001) *Philos. Trans. R. Soc. Lond. Biol. Sci.* 356:625-637). In tumors, exhausted cells can present hallmarks of anergy.

The term "immunotherapy" or "immunotherapies" refer to any treatment that uses certain parts of a subject's immune system to fight diseases such as cancer. The subject's own immune system is stimulated (or suppressed), with or without administration of one or more agent for that purpose. Immunotherapies that are designed to elicit or amplify an immune response are referred to as "activation immunotherapies." Immunotherapies that are designed to reduce or suppress an immune response are referred to as "suppression immunotherapies." Any agent believed to have an immune system effect on the genetically modified transplanted cancer cells can be assayed to determine whether the agent is an immunotherapy and the effect that a given genetic modification has on the modulation of immune response. In some embodiments, the immunotherapy is cancer cell-specific. In some embodiments, immunotherapy can be "untargeted," which refers to administration of agents that do not selectively interact with immune system cells, yet modulates immune system function. Representative examples of untargeted therapies include, without limitation, chemotherapy, gene therapy, and radiation therapy.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

Immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

In some embodiments, immunotherapy comprises inhibitors of one or more immune checkpoints. The term "immune checkpoint" refers to a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein. In one embodiment, the immune checkpoint is PD-1.

Immune checkpoints and their sequences are well-known in the art and representative embodiments are described below. For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) Int. Immunol. 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) Int. Immunol. 8:773).

The nucleic acid and amino acid sequences of a representative human PD-1 biomarker is available to the public at the GenBank database under NM_005018.2 and NP_005009.2 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) EMBO J. 11:3887; Shinohara et al. (1994) Genomics 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) Immunol. Today 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) Immunol. Today 20(6):285-8). Nucleic acid and polypeptide sequences of PD-1 orthologs in organisms other than humans are well-known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) J. Exp. Med. 192:1027-1034) and PD-L2 (Latchman et al. (2001) Nat. Immunol. 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) Immunity 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two R sheets, each consisting of anti-parallel R strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of p strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-LIS. The second form is a cell-associated polypeptide, i.e., having a transmembrane and cytoplasmic domain, referred to herein as PD-L1M. The nucleic acid and amino acid sequences of representative human PD-L1 biomarkers regarding PD-LIM are also available to the public at the GenBank database under NM_014143.3 and NP_054862.1. PD-L1 proteins comprise a signal sequence, and an IgV domain and an IgC domain. The signal sequence of PD-L1S is from about amino acid 1 to about amino acid 18. The signal sequence of PD-L1M is from about amino acid 1 to about amino acid 18. The IgV domain of PD-L1S is from about amino acid 19 to about amino acid 134 and the IgV domain of PD-L1M is from about amino acid 19 to about amino acid 134. The IgC domain of PD-L1 S is from about amino acid 135 to about amino acid 227 and the IgC domain of PD-L1M is from about amino acid 135 to about amino acid 227. The hydrophilic tail of the PD-L1 exemplified in PD-L1 S comprises a hydrophilic tail shown from about amino acid 228 to about amino acid 245. The PD-L1 polypeptide of PD-L1M comprises a transmembrane domain from about amino acids 239 to about amino acid 259 of PD-L1M and a cytoplasmic domain shown from about amino acid 260 to about amino acid 290 of PD-L1M. In addition, nucleic acid and polypeptide sequences of PD-L1 orthologs in organisms other than humans are well-known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well-known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of PD-L2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two β sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well-known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra-or intercellular signaling, 3) modulate activation of immune cells, e.g., T lymphocytes, and 4) modulate the immune response of an organism, e.g., a mouse or human organism.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof, as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM, IgG1, IgG2C, and the like) that is encoded by heavy chain constant region genes.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to modulators of T-cell mediated cytotoxicity alone or in combination with immunotherapy (e.g., treatment with a combination of an inhibitor of at least one biomarker described herein and an immunotherapy, such as an immune checkpoint inhibitor). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular modulator of T-cell mediated cytotoxicity alone or in combination with immunotherapy or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "cancer response," "response to immunotherapy," or "response to modulators of T-cell mediated cytotoxicity/immunotherapy combination therapy" relates to any response of the hyperproliferative disorder (e.g., cancer) to an cancer agent, such as a modulator of T-cell mediated cytotoxicity, and an immunotherapy, preferably to a change in tumor mass and/or volume after initiation of neoadjuvant or adjuvant therapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for which biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive. The reduction in response can be measured by comparing with the same cancer sample or mammal before the resistance is acquired, or by comparing with a different cancer sample or a mammal that is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a biomarker of interest. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the therapies. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 5%, 10%, 15%, 20%, 25%, 30%, 35%, 40%, 45%, 50%, 55%, 60%, 65%, 70%, 75%, 80%, 85%, 90%, 95%, 100%, or more, such 2-fold, 3-fold, 4-fold, 5-fold, 10-fold, 15-fold, 20-fold or more, or any range in between, inclusive, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* Apr; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "small molecule" is a term of the art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. (1998) Science 282:63), and natural product extract libraries. In another embodiment, the compounds are small, organic non-peptidic compounds. In a further embodiment, a small molecule is not biosynthetic.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using an antigen of interest as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen." Selective binding is a relative term referring to the ability of an antibody to discriminate the binding of one antigen over another.

The term "subject" refers to any healthy animal, mammal or human, or any animal, mammal or human afflicted with a cancer, e.g., brain, lung, ovarian, pancreatic, liver, breast, prostate, and/or colorectal cancers, melanoma, multiple myeloma, and the like. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "synergistic effect" refers to the combined effect of two or more cancer agents (e.g., a modulator of biomarkers listed in Tables 1-9 and immunotherapy combination therapy) can be greater than the sum of the separate effects of the cancer agents/therapies alone.

The term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells), as well as other antigen presenting cells (e.g., keratinocytes, endothelial cells, astrocytes, fibroblasts, and oligodendrocytes).

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1 and 2) are well-known in the art and readily available on publicly available databases, such as the National Center for Biotechnology Information (NCBI). For example, exemplary nucleic acid and amino acid sequences derived from publicly available sequence databases are provided below.

TABLE 1

| Gene Symbol | Marker ID | NCBI Entrez Gene ID | NCBI GenBank ID |
|---|---|---|---|
| 2700049A03Rik | MGI: 1924217 | 76967 | NM_029818.1 |
| 2700049A03Rik | MGI: 1924217 | 76967 | NP_001156850.1 |
| 2700049A03Rik | MGI: 1924217 | 76967 | NP_084094.1 |
| KIAA0586 | HGNC: 19960 | 9786 | NP_001231119.1 |
| KIAA0586 | HGNC: 19960 | 9786 | NM_001244191.1 |

TABLE 1-continued

| Gene Symbol | Marker ID | NCBI Entrez Gene ID | NCBI GenBank ID |
|---|---|---|---|
| Actr3 | MGI: 1921367 | 74117 | NM_001205385.1 |
| Actr3 | MGI: 1921367 | 74117 | NM_001205386.1 |
| Actr3 | MGI: 1921367 | 74117 | NM_023735.2 |
| Actr3 | MGI: 1921367 | 74117 | NP_001192314.1 |
| Actr3 | MGI: 1921367 | 74117 | NP_001192315.1 |
| Actr3 | MGI: 1921367 | 74117 | NP_076224.1 |
| ACTR3 | HGNC: 170 | 10096 | NP_001264069.1 |
| ACTR3 | HGNC: 170 | 10096 | NM_001277140.1 |
| Aip | MGI: 109622 | 11632 | NM_001276284.1 |
| Aip | MGI: 109622 | 11632 | NM_016666.3 |
| Aip | MGI: 109622 | 11632 | NP_001263213.1 |
| Aip | MGI: 109622 | 11632 | NP_057875.1 |
| AIP | HGNC: 358 | 9049 | NP_003968.3 |
| AIP | HGNC: 358 | 9049 | NM_001302960.1 |
| Ak2 | MGI: 87978 | 11637 | NM_001033966.4 |
| Ak2 | MGI: 87978 | 11637 | NM_016895.4 |
| Ak2 | MGI: 87978 | 11637 | NP_001029138.1 |
| Ak2 | MGI: 87978 | 11637 | NP_058591.2 |
| Ak2 | MGI: 87978 | 11637 | NR_138540.1 |
| AK2 | HGNC: 362 | 204 | NP_037543.1 |
| AK2 | HGNC: 362 | 204 | NM_001319139.1 |
| Akt1 | MGI: 87986 | 11651 | NM_001165894.1 |
| Akt1 | MGI: 87986 | 11651 | NM_001331107.1 |
| Akt1 | MGI: 87986 | 11651 | NM_009652.3 |
| Akt1 | MGI: 87986 | 11651 | NP_001159366.1 |
| Akt1 | MGI: 87986 | 11651 | NP_001318036.1 |
| Akt1 | MGI: 87986 | 11651 | NP_033782.1 |
| AKT1 | HGNC: 391 | 207 | NP_005154.2 |
| AKT1 | HGNC: 391 | 207 | NM_001014431.1 |
| Alg8 | MGI: 2141959 | 381903 | NM_199035.2 |
| Alg8 | MGI: 2141959 | 381903 | NP_950200.2 |
| ALG8 | HGNC: 23161 | 79053 | NP_076984.2 |
| ALG8 | HGNC: 23161 | 79053 | NM_001007027.2 |
| Ankrd11 | MGI: 1924337 | 77087 | NM_001081379.2 |
| Ankrd11 | MGI: 1924337 | 77087 | NP_001074848.2 |
| Ankrd11 | MGI: 1924337 | 77087 | NR_037865.1 |
| ANKRD11 | HGNC: 21316 | 29123 | XP_016878674.1 |
| ANKRD11 | HGNC: 21316 | 29123 | NM_001256183.1 |
| Ankrd46 | MGI: 1916089 | 68839 | NM_175134.4 |
| Ankrd46 | MGI: 1916089 | 68839 | NP_780343.1 |
| ANKRD46 | HGNC: 27229 | 157567 | NP_001257306.1 |
| ANKRD46 | HGNC: 27229 | 157567 | NM_001270378.1 |
| Aprt | MGI: 88061 | 11821 | NM_009698.2 |
| Aprt | MGI: 88061 | 11821 | NP_033828.2 |
| APRT | HGNC: 626 | 353 | NP_000476.1 |
| APRT | HGNC: 626 | 353 | NM_001030018.1 |
| Ar | MGI: 88064 | 11835 | NM_013476.4 |
| Ar | MGI: 88064 | 11835 | NP_038504.1 |
| AR | HGNC: 644 | 367 | NP_000035.2 |
| AR | HGNC: 644 | 367 | NM_001348061.1 |
| Arf3 | MGI: 99432 | 11842 | NM_007478.3 |
| Arf3 | MGI: 99432 | 11842 | NP_031504.1 |
| ARF3 | HGNC: 654 | 377 | XP_005268913.1 |
| ARF3 | HGNC: 654 | 377 | NM_001659.2 |
| Arf6 | MGI: 99435 | 11845 | NM_007481.3 |
| Arf6 | MGI: 99435 | 11845 | NP_031507.1 |
| ARF6 | HGNC: 659 | 382 | NP_001654.1 |
| ARF6 | HGNC: 659 | 382 | NM_001663.3 |
| Arhgap11a | MGI: 2444300 | 228482 | NM_181416.3 |
| Arhgap11a | MGI: 2444300 | 228482 | NP_852081.2 |
| ARHGAP11A | HGNC: 15783 | 9824 | NP_001273409.1 |
| ARHGAP11A | HGNC: 15783 | 9824 | NM_014783.5 |
| Arhgap21 | MGI: 1918685 | 71435 | NM_001081364.3 |
| Arhgap21 | MGI: 1918685 | 71435 | NM_001128084.2 |
| Arhgap21 | MGI: 1918685 | 71435 | NP_001074833.3 |
| Arhgap21 | MGI: 1918685 | 71435 | NP_001121556.2 |
| ARHGAP21 | HGNC: 23725 | 57584 | NP_065875.3 |
| ARHGAP21 | HGNC: 23725 | 57584 | NM_020824.3 |
| Arid1a | MGI: 1935147 | 93760 | NM_001080819.1 |
| Arid1a | MGI: 1935147 | 93760 | NP_001074288.1 |
| ARID1A | HGNC: 11110 | 8289 | NP_624361.1 |
| ARID1A | HGNC: 11110 | 8289 | NM_018450.4 |
| Arid2 | MGI: 1924294 | 77044 | NM_175251.4 |
| Arid2 | MGI: 1924294 | 77044 | NP_780460.3 |
| ARID2 | HGNC: 18037 | 196528 | XP_006719335.1 |
| ARID2 | HGNC: 18037 | 196528 | NM_001347839.1 |
| Arid4a | MGI: 2444354 | 238247 | XM_006515834.3 |
| Arid4a | MGI: 2444354 | 238247 | NP_001074664.1 |
| ARID4A | HGNC: 9885 | 5926 | XP_016877052.1 |
| ARID4A | HGNC: 9885 | 5926 | NM_002892.3 |
| Asnsd1 | MGI: 1917646 | 70396 | NM_001290984.1 |
| Asnsd1 | MGI: 1917646 | 70396 | NM_133728.3 |
| Asnsd1 | MGI: 1917646 | 70396 | NP_001277913.1 |
| Asnsd1 | MGI: 1917646 | 70396 | NP_598489.2 |
| ASNSD1 | HGNC: 24910 | 54529 | XP_016859870.1 |
| ASNSD1 | HGNC: 24910 | 54529 | NM_019048.2 |
| Asxl2 | MGI: 1922552 | 75302 | NG_032909.1 |
| Asxl2 | MGI: 1922552 | 75302 | NM_001270988.1 |
| Asxl2 | MGI: 1922552 | 75302 | NM_172421.5 |
| Asxl2 | MGI: 1922552 | 75302 | NP_001257917.1 |
| Asxl2 | MGI: 1922552 | 75302 | NP_766009.2 |
| ASXL2 | HGNC: 23805 | 55252 | XP_011531253.1 |
| ASXL2 | HGNC: 23805 | 55252 | NM_018263.5 |
| Atg13 | MGI: 1196429 | 51897 | NM_145528.3 |
| Atg13 | MGI: 1196429 | 51897 | NP_663503.1 |
| ATG13 | HGNC: 29091 | 9776 | NP_001192050.1 |
| ATG13 | HGNC: 29091 | 9776 | NM_001346324.1 |
| Atg16l1 | MGI: 1924290 | 77040 | NM_001205391.1 |
| Atg16l1 | MGI: 1924290 | 77040 | NM_301205392.1 |
| Atg16l1 | MGI: 1924290 | 77040 | NM_029846.4 |
| Atg16l1 | MGI: 1924290 | 77040 | NP_001192320.1 |
| Atg16l1 | MGI: 1924290 | 77040 | NP_001192321.1 |
| Atg16l1 | MGI: 1924290 | 77040 | NP_084122.2 |
| ATG16L1 | HGNC: 21498 | 55054 | NP_060444.3 |
| ATG16L1 | HGNC: 21498 | 55054 | NM_198890.2 |
| Atg5 | MGI: 1277186 | 11793 | NM_001314013.1 |
| Atg5 | MGI: 1277186 | 11793 | NM_053069.6 |
| Atg5 | MGI: 1277186 | 11793 | NP_001300942.1 |
| Atg5 | MGI: 1277186 | 11793 | NP_444299.1 |
| ATG5 | HGNC: 589 | 9474 | NP_001273037.1 |
| ATG5 | HGNC: 589 | 9474 | NM_001286111.1 |
| Atp6v1h | MGI: 1914864 | 108664 | NM_001310442.1 |
| Atp6v1h | MGI: 1914864 | 108664 | NM_133826.5 |
| Atp6v1h | MGI: 1914864 | 108664 | NP_001297371.1 |
| Atp6v1h | MGI: 1914864 | 108664 | NP_598587.2 |
| ATP6V1H | HGNC: 18303 | 51606 | NP_057025.2 |
| ATP6V1H | HGNC: 18303 | 51606 | NM_015941.3 |
| Atr | MGI: 108028 | 245000 | NM_019864.1 |
| Atr | MGI: 108028 | 245000 | NP_063917.1 |
| ATR | HGNC: 882 | 545 | XP_011521226.1 |
| ATR | HGNC: 882 | 545 | NM_001184.3 |
| Batf2 | MGI: 1921731 | 74481 | NM_328967.1 |
| Batf2 | MGI: 1921731 | 74481 | NP_083243.1 |
| BATF2 | HGNC: 25163 | 116071 | NP_001287737.1 |
| BATF2 | HGNC: 25163 | 116071 | NM_138456.3 |
| Becn1 | MGI: 1891828 | 56208 | NM_019584.3 |
| Becn1 | MGI: 1891828 | 56208 | NP_062530.2 |
| BECN1 | HGNC: 1034 | 8678 | XP_011523723.1 |
| BECN1 | HGNC: 1034 | 8678 | NM_003766.4 |
| Birc2 | MGI: 1197009 | 11797 | NM_001291503.1 |
| Birc2 | MGI: 1197009 | 11797 | NM_007465.3 |
| Birc2 | MGI: 1197009 | 11797 | NP_001278432.1 |
| Birc2 | MGI: 1197009 | 11797 | NP_031491.2 |
| BIRC2 | HGNC: 590 | 329 | NP_001243095.1 |
| BIRC2 | HGNC: 590 | 329 | NM_001166.4 |
| Boll | MGI: 1922638 | 75388 | NM_001113367.1 |
| Boll | MGI: 1922638 | 75388 | NM_029657.3 |
| Boll | MGI: 1922638 | 75388 | NP_001106838.1 |
| Boll | MGI: 1922638 | 75388 | NP_083543.2 |
| BOLL | HGNC: 14273 | 66037 | XP_011509994.1 |
| BOLL | HGNC: 14273 | 66037 | NM_197970.2 |
| Bptf | MGI: 2444008 | 207165 | NM_176850.2 |
| Bptf | MGI: 2444008 | 207165 | NP_789820.2 |
| BPTF | HGNC: 3581 | 2186 | XP_005257209.1 |
| BPTF | HGNC: 3581 | 2186 | NM_182641.3 |
| Brd7 | MGI: 1349766 | 26992 | NM_012047.2 |
| Brd7 | MGI: 1349766 | 26992 | NP_036177.1 |
| BRD7 | HGNC: 14310 | 29117 | NP_001167455.1 |
| BRD7 | HGNC: 14310 | 29117 | NM_013263.4 |
| Brinp2 | MGI: 2443333 | 240843 | XM_006496836.1 |
| Brinp2 | MGI: 2443333 | 240843 | NP_997466.2 |
| BRINP2 | HGNC: 13746 | 57795 | NP_066988.1 |
| BRINP2 | HGNC: 13746 | 57795 | NM_021165.3 |
| Brwd3 | MGI: 3029414 | 382236 | NM_001081477.1 |

TABLE 1-continued

| Gene Symbol | Marker ID | NCBI Entrez Gene ID | NCBI GenBank ID |
|---|---|---|---|
| Brwd3 | MGI: 3029414 | 382236 | NP_001074946.1 |
| BRWD3 | HGNC: 17342 | 254065 | XP_016884873.1 |
| BRWD3 | HGNC: 17342 | 254065 | NM_153252.4 |
| BC030336 | MGI: 2446240 | 233812 | XM_006507689.2 |
| BC030336 | MGI: 2446240 | 233812 | NP_001158052.1 |
| C16orf52 | HGNC: 27087 | 730094 | NP_001158051.1 |
| C16orf52 | HGNC: 27087 | 730094 | NM_173501.1 |
| C330007P06Rik | MGI: 1924894 | 77644 | NM_029951.1 |
| C330007P06Rik | MGI: 1924894 | 77644 | NP_084227.1 |
| CXorf56 | HGNC: 26239 | 63932 | NP_001164041.1 |
| CXorf56 | HGNC: 26239 | 63932 | NM_022101.3 |
| C330027C09Rik | MGI: 2146335 | 224171 | NM_172616.2 |
| C330027C09Rik | MGI: 2146335 | 224171 | NP_766204.2 |
| KIAA1524 | HGNC: 29302 | 57650 | NP_065941.2 |
| KIAA1524 | HGNC: 29302 | 57650 | NM_020890.2 |
| Calr | MGI: 88252 | 12317 | NM_007591.3 |
| Calr | MGI: 88252 | 12317 | NP_031617.1 |
| CALR | HGNC: 1455 | 811 | NP_004334.1 |
| CALR | HGNC: 1455 | 811 | NM_004343.3 |
| Carm1 | MGI: 1913208 | 59035 | NM_021531.6 |
| Carm1 | MGI: 1913208 | 59035 | NM_153141.1 |
| Carm1 | MGI: 1913208 | 59035 | NP_067506.2 |
| Carm1 | MGI: 1913208 | 59035 | NP_694781.1 |
| CARM1 | HGNC: 23393 | 10498 | XP_011525940.1 |
| CARM1 | HGNC: 23393 | 10498 | NM_199141.1 |
| Ccdc134 | MGI: 1923707 | 76457 | NM_001326588.1 |
| Ccdc134 | MGI: 1923707 | 76457 | NM_172428.2 |
| Ccdc134 | MGI: 1923707 | 76457 | NP_001313517.1 |
| Ccdc134 | MGI: 1923707 | 76457 | NP_766016.2 |
| Ccdc134 | MGI: 1923707 | 76457 | NR_137170.1 |
| CCDC134 | HGNC: 26185 | 79879 | NP_001291726.1 |
| CCDC134 | HGNC: 26185 | 79879 | NM_024821.3 |
| Ccdc137 | MGI: 1914541 | 67291 | NM_152807.3 |
| Ccdc137 | MGI: 1914541 | 67291 | NP_690020.1 |
| CCDC137 | HGNC: 33451 | 339230 | XP_016880062.1 |
| CCDC137 | HGNC: 33451 | 339230 | NM_199287.2 |
| Ccdc155 | MGI: 2687329 | 384619 | NM_201374.2 |
| Ccdc155 | MGI: 2687329 | 384619 | NP_958762.2 |
| CCDC155 | HGNC: 26520 | 147872 | XP_011524797.1 |
| CCDC155 | HGNC: 26520 | 147872 | NM_144688.4 |
| Ccna2 | MGI: 108069 | 12428 | NM_009828.2 |
| Ccna2 | MGI: 108069 | 12428 | NP_033958.2 |
| CCNA2 | HGNC: 1578 | 890 | NP_001228.1 |
| CCNA2 | HGNC: 1578 | 890 | NM_001237.4 |
| Ccnc | MGI: 1858199 | 51813 | NM_001122982.2 |
| Ccnc | MGI: 1858199 | 51813 | NM_001290420.1 |
| Ccnc | MGI: 1858199 | 51813 | NM_001290422.1 |
| Ccnc | MGI: 1858199 | 51813 | NM_016746.4 |
| Ccnc | MGI: 1858199 | 51813 | NP_001116454.1 |
| Ccnc | MGI: 1858199 | 51813 | NP_001277349.1 |
| Ccnc | MGI: 1858199 | 51813 | NP_001277351.1 |
| Ccnc | MGI: 1858199 | 51813 | NP_058026.2 |
| CCNC | HGNC: 1581 | 892 | NP_001013417.1 |
| CCNC | HGNC: 1581 | 892 | NM_005190.3 |
| Ccs | MGI: 1333783 | 12460 | NM_016892.3 |
| Ccs | MGI: 1333783 | 12460 | NP_058588.1 |
| CCS | HGNC: 1613 | 9973 | NP_005116.1 |
| CCS | HGNC: 1613 | 9973 | NM_005125.1 |
| Cd274 | MGI: 1926446 | 60533 | NM_021893.3 |
| Cd274 | MGI: 1926446 | 60533 | NP_068693.1 |
| CD274 | HGNC: 17635 | 29126 | NP_054862.1 |
| CD274 | HGNC: 17635 | 29126 | NM_014143.3 |
| Cd36 | MGI: 107899 | 12491 | NM_001159555.1 |
| Cd36 | MGI: 107899 | 12491 | NM_001159556.1 |
| Cd36 | MGI: 107899 | 12491 | NM_001159557.1 |
| Cd36 | MGI: 107899 | 12491 | NM_001159558.1 |
| Cd36 | MGI: 107899 | 12491 | NM_007643.4 |
| Cd36 | MGI: 107899 | 12491 | NP_001153027.1 |
| Cd36 | MGI: 107899 | 12491 | NP_001153028.1 |
| Cd36 | MGI: 107899 | 12491 | NP_001153029.1 |
| Cd36 | MGI: 107899 | 12491 | NP_001153030.1 |
| Cd36 | MGI: 107899 | 12491 | NP_031669.3 |
| CD36 | HGNC: 1663 | 948 | XP_005250770.1 |
| CD36 | HGNC: 1663 | 948 | NM_001127443.1 |
| Cd44 | MGI: 88338 | 12505 | NM_001039150.1 |
| Cd44 | MGI: 88338 | 12505 | NM_001039151.1 |
| Cd44 | MGI: 88338 | 12505 | NM_001177785.1 |
| Cd44 | MGI: 88338 | 12505 | NM_001177786.1 |
| Cd44 | MGI: 88338 | 12505 | NM_001177787.1 |
| Cd44 | MGI: 88338 | 12505 | NM_009851.2 |
| Cd44 | MGI: 88338 | 12505 | NP_001034239.1 |
| Cd44 | MGI: 88338 | 12505 | NP_001034240.1 |
| Cd44 | MGI: 88338 | 12505 | NP_001171256.1 |
| Cd44 | MGI: 88338 | 12505 | NP_001171257.1 |
| Cd44 | MGI: 88338 | 12505 | NP_001171258.1 |
| Cd44 | MGI: 88338 | 12505 | NP_033981.2 |
| CD44 | HGNC: 1681 | 960 | NP_001001392.1 |
| CD44 | HGNC: 1681 | 960 | NM_001001391.1 |
| Cdk2 | MGI: 104772 | 12566 | NM_016756.4 |
| Cdk2 | MGI: 104772 | 12566 | NM_183417.3 |
| Cdk2 | MGI: 104772 | 12566 | NP_058036.1 |
| Cdk2 | MGI: 104772 | 12566 | NP_904326.1 |
| CDK2 | HGNC: 1771 | 1017 | NP_001277159.1 |
| CDK2 | HGNC: 1771 | 1017 | NM_001290230.1 |
| Cdk5 | MGI: 101765 | 12568 | NM_007668.3 |
| Cdk5 | MGI: 101765 | 12568 | NP_031694.1 |
| CDK5 | HGNC: 1774 | 1020 | NP_001157882.1 |
| CDK5 | HGNC: 1774 | 1020 | NM_001164410.2 |
| Cflar | MGI: 1336166 | 12633 | NM_001289704.2 |
| Cflar | MGI: 1336166 | 12633 | NM_001293804.1 |
| Cflar | MGI: 1336166 | 12633 | NM_001293805.1 |
| Cflar | MGI: 1336166 | 12633 | NM_009805.4 |
| Cflar | MGI: 1336166 | 12633 | NM_207653.5 |
| Cflar | MGI: 1336166 | 12633 | NP_001276633.1 |
| Cflar | MGI: 1336166 | 12633 | NP_001280733.1 |
| Cflar | MGI: 1336166 | 12633 | NP_001280734.1 |
| Cflar | MGI: 1336166 | 12633 | NP_033935.2 |
| Cflar | MGI: 1336166 | 12633 | NP_997536.1 |
| CFLAR | HGNC: 1876 | 8837 | NP_001338522.1 |
| CFLAR | HGNC: 1876 | 8837 | NM_001308042.2 |
| Chic2 | MGI: 1921527 | 74277 | NM_028850.5 |
| Chic2 | MGI: 1921527 | 74277 | NP_083126.1 |
| CHIC2 | HGNC: 1935 | 26511 | XP_011532684.1 |
| CHIC2 | HGNC: 1935 | 26511 | NM_012110.3 |
| Chmp5 | MGI: 1924209 | 76959 | NM_029814.1 |
| Chmp5 | MGI: 1924209 | 76959 | NP_084090.1 |
| CHMP5 | HGNC: 26942 | 51510 | NP_057494.3 |
| CHMP5 | HGNC: 26942 | 51510 | NM_016410.5 |
| Chtf8 | MGI: 2443370 | 214987 | NM_145412.3 |
| Chtf8 | MGI: 2443370 | 214987 | NP_663387.3 |
| CHTF8 | HGNC: 24353 | 54921 | XP_011521470.1 |
| CHTF8 | HGNC: 24353 | 54921 | NM_001040145.1 |
| Cks1b | MGI: 1889208 | 54124 | NM_016904.1 |
| Cks1b | MGI: 1889208 | 54124 | NP_058600.1 |
| CKS1B | HGNC: 19083 | 1163 | NP_001817.1 |
| CKS1B | HGNC: 19083 | 1163 | NM_001826.2 |
| Cmip | MGI: 1921690 | 74440 | NM_001163262.1 |
| Cmip | MGI: 1921690 | 74440 | NM_028941.1 |
| Cmip | MGI: 1921690 | 74440 | NP_001156734.1 |
| Cmip | MGI: 1921690 | 74440 | NP_083217.1 |
| CMIP | HGNC: 24319 | 80790 | XP_005256238.1 |
| CMIP | HGNC: 24319 | 80790 | NM_030629.2 |
| Cnot11 | MGI: 106580 | 52846 | NM_028043.2 |
| Cnot11 | MGI: 106580 | 52846 | NP_082319.1 |
| CNOT11 | HGNC: 25217 | 55571 | NP_060016.3 |
| CNOT11 | HGNC: 25217 | 55571 | NM_017546.4 |
| Cnot8 | MGI: 1916375 | 69125 | NM_026949.3 |
| Cnot8 | MGI: 1916375 | 69125 | NP_081225.1 |
| CNOT8 | HGNC: 9207 | 9337 | NP_001288011.1 |
| CNOT8 | HGNC: 9207 | 9337 | NM_001301082.1 |
| Creb1 | MGI: 88494 | 12912 | NM_001037726.1 |
| Creb1 | MGI: 88494 | 12912 | NM_009952.2 |
| Creb1 | MGI: 88494 | 12912 | NM_133828.2 |
| Creb1 | MGI: 88494 | 12912 | NP_001032815.1 |
| Creb1 | MGI: 88494 | 12912 | NP_034082.1 |
| Creb1 | MGI: 88494 | 12912 | NP_598589.2 |
| CREB1 | HGNC: 2345 | 1385 | XP_011508951.1 |
| CREB1 | HGNC: 2345 | 1385 | NM_001320793.1 |
| Crkl | MGI: 104686 | 12929 | NM_001077231.1 |
| Crkl | MGI: 104686 | 12929 | NM_007764.5 |
| Crkl | MGI: 104686 | 12929 | NP_001264160.1 |
| Crkl | MGI: 104686 | 12929 | NP_031790.2 |
| CRKL | HGNC: 2363 | 1399 | NP_005198.1 |
| CRKL | HGNC: 2363 | 1399 | NM_005207.3 |

TABLE 1-continued

| Gene Symbol | Marker ID | NCBI Entrez Gene ID | NCBI GenBank ID |
|---|---|---|---|
| Crlf3 | MGI: 1860086 | 54394 | NM_001277106.1 |
| Crlf3 | MGI: 1860086 | 54394 | NM_018776.2 |
| Crlf3 | MGI: 1860086 | 54394 | NP_001264035.1 |
| Crlf3 | MGI: 1860086 | 54394 | NP_061246.1 |
| CRLF3 | HGNC: 17177 | 51379 | NP_057070.3 |
| CRLF3 | HGNC: 17177 | 51379 | NM_015986.3 |
| Crocc | MGI: 3529431 | 230872 | NM_001145958.1 |
| Crocc | MGI: 3529431 | 230872 | NM_172122.2 |
| Crocc | MGI: 3529431 | 230872 | NP_001139430.1 |
| Crocc | MGI: 3529431 | 230872 | NP_742120.2 |
| CROCC | HGNC: 21299 | 9696 | XP_016858403.1 |
| CROCC | HGNC: 21299 | 9696 | NM_014675.4 |
| Cwc27 | MGI: 1914535 | 67285 | XM_011244690.2 |
| Cwc27 | MGI: 1914535 | 67285 | NP_080348.1 |
| CWC27 | HGNC: 10664 | 10283 | NP_005860.2 |
| CWC27 | HGNC: 10664 | 10283 | NM_005869.3 |
| Cwf19l1 | MGI: 1919752 | 72502 | XM_006527364.2 |
| Cwf19l1 | MGI: 1919752 | 72502 | NP_001074546.1 |
| CWF19L1 | HGNC: 25613 | 55280 | NP_060764.3 |
| CWF19L1 | HGNC: 25613 | 55280 | NM_018294.5 |
| Ddi2 | MGI: 1917244 | 68817 | NM_001017966.2 |
| Ddi2 | MGI: 1917244 | 68817 | NP_001017966.1 |
| DDI2 | HGNC: 24578 | 84301 | NP_115717.3 |
| DDI2 | HGNC: 24578 | 84301 | NM_032341.4 |
| Ddx20 | MGI: 1858415 | 53975 | NM_017397.3 |
| Ddx20 | MGI: 1858415 | 53975 | NP_059093.3 |
| DDX20 | HGNC: 2743 | 11218 | NP_009135.4 |
| DDX20 | HGNC: 2743 | 11218 | NM_007204.4 |
| Ddx42 | MGI: 1919297 | 72047 | NM_028074.4 |
| Ddx42 | MGI: 1919297 | 72047 | NP_082350.3 |
| DDX42 | HGNC: 18676 | 11325 | XP_016879601.1 |
| DDX42 | HGNC: 18676 | 11325 | NM_203499.2 |
| Dlst | MGI: 1926170 | 78920 | NM_030225.4 |
| Dlst | MGI: 1926170 | 78920 | NP_084501.1 |
| DLST | HGNC: 2911 | 1743 | NP_001231812.1 |
| DLST | HGNC: 2911 | 1743 | NM_001244883.1 |
| Dnaja2 | MGI: 1931882 | 56445 | NM_019794.4 |
| Dnaja2 | MGI: 1931882 | 56445 | NP_062768.1 |
| DNAJA2 | HGNC: 14884 | 10294 | NP_005871.1 |
| DNAJA2 | HGNC: 14884 | 10294 | NM_005880.3 |
| Dpf2 | MGI: 109529 | 19708 | NM_001291078.1 |
| Dpf2 | MGI: 109529 | 19708 | NM_011262.5 |
| Dpf2 | MGI: 109529 | 19708 | NP_001278007.1 |
| Dpf2 | MGI: 109529 | 19708 | NP_035392.1 |
| DPF2 | HGNC: 9964 | 5977 | XP_016873590.1 |
| DPF2 | HGNC: 9964 | 5977 | NM_001330308.1 |
| Dscc1 | MGI: 1919357 | 72107 | NM_183089.2 |
| Dscc1 | MGI: 1919357 | 72107 | NP_898912.2 |
| DSCC1 | HGNC: 24453 | 79075 | XP_005251122.1 |
| DSCC1 | HGNC: 24453 | 79075 | NM_024094.2 |
| Dtx3l | MGI: 2656973 | 209200 | NM_001013371.2 |
| Dtx3l | MGI: 2656973 | 209200 | NP_001013389.2 |
| DTX3L | HGNC: 30323 | 151636 | NP_612144.1 |
| DTX3L | HGNC: 30323 | 151636 | NM_138287.3 |
| Eefsec | MGI: 2137092 | 65967 | NM_023060.3 |
| Eefsec | MGI: 2137092 | 65967 | NP_075547.1 |
| EEFSEC | HGNC: 24614 | 60678 | NP_068756.2 |
| EEFSEC | HGNC: 24614 | 60678 | NM_021937.4 |
| Ei24 | MGI: 108090 | 13663 | NM_001199494.1 |
| Ei24 | MGI: 108090 | 13663 | NM_007915.5 |
| Ei24 | MGI: 108090 | 13663 | NP_001186423.1 |
| Ei24 | MGI: 108090 | 13663 | NP_031941.1 |
| EI24 | HGNC: 13276 | 9538 | NP_001317348.1 |
| EI24 | HGNC: 13276 | 9538 | NM_001290135.1 |
| Eif2ak3 | MGI: 1341830 | 13666 | NM_001313918.1 |
| Eif2ak3 | MGI: 1341830 | 13666 | NM_010121.3 |
| Eif2ak3 | MGI: 1341830 | 13666 | NP_001300847.1 |
| Eif2ak3 | MGI: 1341830 | 13666 | NP_034251.2 |
| EIF2AK3 | HGNC: 3255 | 9451 | NP_004827.4 |
| EIF2AK3 | HGNC: 3255 | 9451 | NM_001313915.1 |
| Eif2ak4 | MGI: 1353427 | 27103 | NM_001177806.1 |
| Eif2ak4 | MGI: 1353427 | 27103 | NM_013719.3 |
| Eif2ak4 | MGI: 1353427 | 27103 | NP_001171277.1 |
| Eif2ak4 | MGI: 1353427 | 27103 | NP_038747.2 |
| EIF2AK4 | HGNC: 19687 | 440275 | XP_011519901.1 |
| EIF2AK4 | HGNC: 19687 | 440275 | NM_001013703.3 |
| Elmo2 | MGI: 2153045 | 140579 | NM_001302752.1 |
| Elmo2 | MGI: 2153045 | 140579 | NM_001302754.1 |
| Elmo2 | MGI: 2153045 | 140579 | NM_080287.2 |
| Elmo2 | MGI: 2153045 | 140579 | NM_207706.1 |
| Elmo2 | MGI: 2153045 | 140579 | NP_001289681.1 |
| Elmo2 | MGI: 2153045 | 140579 | NP_001289683.1 |
| Elmo2 | MGI: 2153045 | 140579 | NP_525026.2 |
| Elmo2 | MGI: 2153045 | 140579 | NP_997589.1 |
| ELMO2 | HGNC: 17233 | 63916 | XP_005260553.1 |
| ELMO2 | HGNC: 17233 | 63916 | NM_022086.6 |
| Epc1 | MGI: 1278322 | 13831 | NM_001276350.1 |
| Epc1 | MGI: 1278322 | 13831 | NM_007935.2 |
| Epc1 | MGI: 1278322 | 13831 | NM_027497.3 |
| Epc1 | MGI: 1278322 | 13831 | NP_001263279.1 |
| Epc1 | MGI: 1278322 | 13831 | NP_031961.1 |
| Epc1 | MGI: 1278322 | 13831 | NP_081773.1 |
| EPC1 | HGNC: 19876 | 80314 | NP_001269320.1 |
| EPC1 | HGNC: 19876 | 80314 | NM_025209.3 |
| Epg5 | MGI: 1918673 | 100502841 | NM_001195633.1 |
| Epg5 | MGI: 1918673 | 100502841 | NP_001182562.1 |
| EPG5 | HGNC: 29331 | 57724 | XP_016881380.1 |
| EPG5 | HGNC: 29331 | 57724 | NM_020964.2 |
| Eri1 | MGI: 1914526 | 67276 | NM_026067.3 |
| Eri1 | MGI: 1914526 | 67276 | NP_080343.4 |
| ERI1 | HGNC: 23994 | 90459 | XP_011542153.1 |
| ERI1 | HGNC: 23994 | 90459 | NM_153332.3 |
| ERO1A | HGNC: 13280 | 30001 | NP_055399.1 |
| ERO1A | HGNC: 13280 | 30001 | NM_014584.2 |
| Ero1l | MGI: 1354385 | 50527 | NM_015774.3 |
| Ero1l | MGI: 1354385 | 50527 | NP_056589.1 |
| Exoc7 | MGI: 1859270 | 53413 | NM_001286872.1 |
| Exoc7 | MGI: 1859270 | 53413 | NM_001347636.1 |
| Exoc7 | MGI: 1859270 | 53413 | NM_016857.2 |
| Exoc7 | MGI: 1859270 | 53413 | NP_001156344.1 |
| Exoc7 | MGI: 1859270 | 53413 | NP_001334565.1 |
| Exoc7 | MGI: 1859270 | 53413 | NP_058553.2 |
| EXOC7 | HGNC: 23214 | 23265 | NP_001269242.1 |
| EXOC7 | HGNC: 23214 | 23265 | NM_015219.4 |
| Fadd | MGI: 109324 | 14082 | NM_010175.5 |
| Fadd | MGI: 109324 | 14082 | NP_034305.1 |
| FADD | HGNC: 3573 | 8772 | NP_003815.1 |
| FADD | HGNC: 3573 | 8772 | NM_003824.3 |
| Fam170b | MGI: 2145650 | 105511 | NM_001164485.1 |
| Fam170b | MGI: 2145650 | 105511 | NP_001157957.1 |
| FAM170B | HGNC: 19736 | 170370 | NP_001157956.1 |
| FAM170B | HGNC: 19736 | 170370 | NM_001164484.1 |
| Fam234b | MGI: 1921775 | 74525 | NM_028982.4 |
| Fam234b | MGI: 1921775 | 74525 | NP_083258.2 |
| FAM234B | HGNC: 29288 | 57613 | XP_016875195.1 |
| FAM234B | HGNC: 29288 | 57613 | NM_020853.1 |
| Faxc | MGI: 1923382 | 76132 | NM_175234.4 |
| Faxc | MGI: 1923382 | 76132 | NP_780443.2 |
| FAXC | HGNC: 20742 | 84553 | NP_001333460.1 |
| FAXC | HGNC: 20742 | 84553 | NM_001346530.1 |
| Fhod3 | MGI: 1925847 | 225288 | NM_001289654.1 |
| Fhod3 | MGI: 1925847 | 225288 | NM_001289655.1 |
| Fhod3 | MGI: 1925847 | 225288 | NM_175276.4 |
| Fhod3 | MGI: 1925847 | 225288 | NP_001276583.1 |
| Fhod3 | MGI: 1925847 | 225288 | NP_001276584.1 |
| Fhod3 | MGI: 1925847 | 225288 | NP_780485.2 |
| FHOD3 | HGNC: 26178 | 80206 | XP_016881495.1 |
| FHOD3 | HGNC: 26178 | 80206 | NM_001281739.2 |
| Fis1 | MGI: 1913687 | 66437 | NM_001163243.1 |
| Fis1 | MGI: 1913687 | 66437 | NM_001347504.1 |
| Fis1 | MGI: 1913687 | 66437 | NM_025562.3 |
| Fis1 | MGI: 1913687 | 66437 | NP_001156715.1 |
| Fis1 | MGI: 1913687 | 66437 | NP_001334433.1 |
| Fis1 | MGI: 1913687 | 66437 | NP_079838.1 |
| FIS1 | HGNC: 21689 | 51024 | NP_057152.2 |
| FIS1 | HGNC: 21689 | 51024 | NM_016068.2 |
| Fitm2 | MGI: 2444508 | 228859 | NM_173397.4 |
| Fitm2 | MGI: 2444508 | 228859 | NP_775573.1 |
| FITM2 | HGNC: 16135 | 128486 | NP_001077941.1 |
| FITM2 | HGNC: 16135 | 128486 | NM_001080472.3 |
| Fnbp4 | MGI: 1860513 | 55935 | NM_018828.2 |
| Fnbp4 | MGI: 1860513 | 55935 | NP_061298.1 |
| FNBP4 | HGNC: 19752 | 23360 | NP_001305268.1 |
| FNBP4 | HGNC: 19752 | 23360 | NM_015308.4 |

TABLE 1-continued

| Gene Symbol | Marker ID | NCBI Entrez Gene ID | NCBI GenBank ID |
|---|---|---|---|
| Foxb1 | MGI: 1927549 | 64290 | NM_022378.3 |
| Foxb1 | MGI: 1927549 | 64290 | NP_071773.2 |
| FOXB1 | HGNC: 3799 | 27023 | NP_036314.2 |
| FOXB1 | HGNC: 3799 | 27023 | NM_012182.2 |
| Gabpb1 | MGI: 95611 | 14391 | NM_001271467.1 |
| Gabpb1 | MGI: 95611 | 14391 | NM_001271468.1 |
| Gabpb1 | MGI: 95611 | 14391 | NM_001271469.1 |
| Gabpb1 | MGI: 95611 | 14391 | NM_001271470.1 |
| Gabpb1 | MGI: 95611 | 14391 | NM_001271492.1 |
| Gabpb1 | MGI: 95611 | 14391 | NM_010249.2 |
| Gabpb1 | MGI: 95611 | 14391 | NM_207669.2 |
| Gabpb1 | MGI: 95611 | 14391 | NP_001258396.1 |
| Gabpb1 | MGI: 95611 | 14391 | NP_001258397.1 |
| Gabpb1 | MGI: 95611 | 14391 | NP_001258398.1 |
| Gabpb1 | MGI: 95611 | 14391 | NP_001258399.1 |
| Gabpb1 | MGI: 95611 | 14391 | NP_001258421.1 |
| Gabpb1 | MGI: 95611 | 14391 | NP_034379.1 |
| Gabpb1 | MGI: 95611 | 14391 | NP_997552.1 |
| Gabpb1 | MGI: 95611 | 14391 | NR_073183.1 |
| GABPB1 | HGNC: 4074 | 2553 | NP_005245.2 |
| GABPB1 | HGNC: 4074 | 2553 | NM_001320910.1 |
| Gabrb3 | MGI: 95621 | 14402 | NM_001038701.2 |
| Gabrb3 | MGI: 95621 | 14402 | NM_008071.3 |
| Gabrb3 | MGI: 95621 | 14402 | NP_001033790.1 |
| Gabrb3 | MGI: 95621 | 14402 | NP_032097.1 |
| GABRB3 | HGNC: 4083 | 2562 | NP_001265560.1 |
| GABRB3 | HGNC: 4083 | 2562 | NM_000814.5 |
| Gale | MGI: 1921496 | 74246 | NM_178389.3 |
| Gale | MGI: 1921496 | 74246 | NP_848476.1 |
| GALE | HGNC: 4116 | 2582 | NP_000394.2 |
| GALE | HGNC: 4116 | 2582 | NM_000403.3 |
| Galnt15 | MGI: 1926004 | 78754 | NM_030166.3 |
| Galnt15 | MGI: 1926004 | 78754 | NP_084442.1 |
| GALNT15 | HGNC: 21531 | 117248 | NP_473451.3 |
| GALNT15 | HGNC: 21531 | 117248 | NM_001319052.1 |
| Gigyf2 | MGI: 2138584 | 227331 | NM_001110212.2 |
| Gigyf2 | MGI: 2138584 | 227331 | NM_146112.4 |
| Gigyf2 | MGI: 2138584 | 227331 | NP_001103682.1 |
| Gigyf2 | MGI: 2138584 | 227331 | NP_666224.3 |
| GIGYF2 | HGNC: 11960 | 26058 | NP_001096616.1 |
| GIGYF2 | HGNC: 11960 | 26058 | NM_001103146.1 |
| Gml | MGI: 3644767 | 625599 | NM_001177524.1 |
| Gml | MGI: 3644767 | 625599 | NP_001170995.1 |
| GML | HGNC: 4375 | 2765 | NP_002057.1 |
| GML | HGNC: 4375 | 2765 | NM_002066.2 |
| Gnb2 | MGI: 95784 | 14693 | NM_010312.4 |
| Gnb2 | MGI: 95784 | 14693 | NP_034442.1 |
| GNB2 | HGNC: 4398 | 2783 | NP_005264.2 |
| GNB2 | HGNC: 4398 | 2783 | NM_005273.3 |
| Gne | MGI: 1354951 | 50798 | NM_001190414.1 |
| Gne | MGI: 1354951 | 50798 | NM_015828.3 |
| Gne | MGI: 1354951 | 50798 | NP_001177343.1 |
| Gne | MGI: 1354951 | 50798 | NP_056643.3 |
| GNE | HGNC: 23657 | 10020 | NP_001177313.1 |
| GNE | HGNC: 23657 | 10020 | NM_001128227.2 |
| Gpaa1 | MGI: 1202392 | 14731 | NM_010331.2 |
| Gpaa1 | MGI: 1202392 | 14731 | NP_034461.1 |
| GPAA1 | HGNC: 4446 | 8733 | NP_003792.1 |
| GPAA1 | HGNC: 4446 | 8733 | NM_003801.3 |
| GPI | HGNC: 4458 | 2821 | NP_001171651.1 |
| GPI | HGNC: 4458 | 2821 | NM_001329910.1 |
| Gpi1 | MGI: 95797 | 14751 | NM_008155.4 |
| Gpi1 | MGI: 95797 | 14751 | NP_032181.2 |
| GPR31 | HGNC: 4486 | 2853 | NP_005290.2 |
| GPR31 | HGNC: 4486 | 2853 | NM_005299.2 |
| Gpr31b | MGI: 1354372 | 436440 | NM_001013832.2 |
| Gpr31b | MGI: 1354372 | 436440 | NP_001013854.2 |
| Gpx4 | MGI: 104767 | 625249 | NM_001037741.3 |
| Gpx4 | MGI: 104767 | 625249 | NM_008162.3 |
| Gpx4 | MGI: 104767 | 625249 | NP_001032830.2 |
| Gpx4 | MGI: 104767 | 625249 | NP_032188.3 |
| Gpx4 | MGI: 104767 | 625249 | NR_110342.1 |
| GPX4 | HGNC: 4556 | 2879 | NP_001034937.1 |
| GPX4 | HGNC: 4556 | 2879 | NM_001039848.3 |
| Gss | MGI: 95852 | 14854 | NM_001291111.1 |
| Gss | MGI: 95852 | 14854 | NM_008180.2 |
| Gss | MGI: 95852 | 14854 | NP_001278040.1 |
| Gss | MGI: 95852 | 14854 | NP_032206.1 |
| GSS | HGNC: 4624 | 2937 | NP_001309424.1 |
| GSS | HGNC: 4624 | 2937 | NM_001322494.1 |
| Gtf2i | MGI: 1202722 | 14886 | NM_001080746.2 |
| Gtf2i | MGI: 1202722 | 14886 | NM_001080747.2 |
| Gtf2i | MGI: 1202722 | 14886 | NM_001080748.2 |
| Gtf2i | MGI: 1202722 | 14886 | NM_001080749.2 |
| Gtf2i | MGI: 1202722 | 14886 | NM_010365.4 |
| Gtf2i | MGI: 1202722 | 14886 | NP_001074215.1 |
| Gtf2i | MGI: 1202722 | 14886 | NP_001074216.1 |
| Gtf2i | MGI: 1202722 | 14886 | NP_001074217.1 |
| Gtf2i | MGI: 1202722 | 14886 | NP_001074218.1 |
| Gtf2i | MGI: 1202722 | 14886 | NP_034495.2 |
| GTF2I | HGNC: 4659 | 2969 | NP_001509.3 |
| GTF2I | HGNC: 4659 | 2969 | NM_033001.3 |
| Hdac5 | MGI: 1333784 | 15184 | NM_001077696.1 |
| Hdac5 | MGI: 1333784 | 15184 | NM_001284248.1 |
| Hdac5 | MGI: 1333784 | 15184 | NM_001284249.1 |
| Hdac5 | MGI: 1333784 | 15184 | NM_001284250.1 |
| Hdac5 | MGI: 1333784 | 15184 | NM_010412.3 |
| Hdac5 | MGI: 1333784 | 15184 | NP_001071164.1 |
| Hdac5 | MGI: 1333784 | 15184 | NP_001271177.1 |
| Hdac5 | MGI: 1333784 | 15184 | NP_001271178.1 |
| Hdac5 | MGI: 1333784 | 15184 | NP_001271179.1 |
| Hdac5 | MGI: 1333784 | 15184 | NP_034542.3 |
| HDAC5 | HGNC: 14068 | 10014 | XP_005256965.1 |
| HDAC5 | HGNC: 14068 | 10014 | NM_001015053.1 |
| Hes7 | MGI: 2135679 | 84653 | NM_033041.4 |
| Hes7 | MGI: 2135679 | 84653 | NP_149030.2 |
| HES7 | HGNC: 15977 | 84667 | NP_115969.2 |
| HES7 | HGNC: 15977 | 84667 | NM_032580.3 |
| Hipk2 | MGI: 1314872 | 15258 | NM_001136065.2 |
| Hipk2 | MGI: 1314872 | 15258 | NM_001294143.1 |
| Hipk2 | MGI: 1314872 | 15258 | NM_001294144.1 |
| Hipk2 | MGI: 1314872 | 15258 | NM_010433.2 |
| Hipk2 | MGI: 1314872 | 15258 | NP_001129537.1 |
| Hipk2 | MGI: 1314872 | 15258 | NP_001281072.1 |
| Hipk2 | MGI: 1314872 | 15258 | NP_001281073.1 |
| Hipk2 | MGI: 1314872 | 15258 | NP_034563.2 |
| HIPK2 | HGNC: 14402 | 28996 | XP_011514379.1 |
| HIPK2 | HGNC: 14402 | 28996 | NM_022740.4 |
| Hnrnpf | MGI: 2138741 | 98758 | NM_001166427.1 |
| Hnrnpf | MGI: 2138741 | 98758 | NM_001166428.1 |
| Hnrnpf | MGI: 2138741 | 98758 | NM_001166429.1 |
| Hnrnpf | MGI: 2138741 | 98758 | NM_001166430.1 |
| Hnrnpf | MGI: 2138741 | 98758 | NM_001166431.1 |
| Hnrnpf | MGI: 2138741 | 98758 | NM_001166432.1 |
| Hnrnpf | MGI: 2138741 | 98758 | NM_133834.2 |
| Hnrnpf | MGI: 2138741 | 98758 | NP_001159899.1 |
| Hnrnpf | MGI: 2138741 | 98758 | NP_001159900.1 |
| Hnrnpf | MGI: 2138741 | 98758 | NP_001159901.1 |
| Hnrnpf | MGI: 2138741 | 98758 | NP_001159902.1 |
| Hnrnpf | MGI: 2138741 | 98758 | NP_001159903.1 |
| Hnrnpf | MGI: 2138741 | 98758 | NP_001159904.1 |
| Hnrnpf | MGI: 2138741 | 98758 | NP_598595.1 |
| HNRNPF | HGNC: 5039 | 3185 | NP_001091677.1 |
| HNRNPF | HGNC: 5039 | 3185 | NM_001098205.1 |
| Hsd17b12 | MGI: 1926967 | 56348 | NM_019657.4 |
| Hsd17b12 | MGI: 1926967 | 56348 | NP_062631.1 |
| HSD17B12 | HGNC: 18646 | 51144 | XP_011518458.1 |
| HSD17B12 | HGNC: 18646 | 51144 | NM_016142.2 |
| Hsd17b4 | MGI: 105089 | 15488 | NM_008292.4 |
| Hsd17b4 | MGI: 105089 | 15488 | NP_032318.2 |
| HSD17B4 | HGNC: 5213 | 3295 | NP_001186220.1 |
| HSD17B4 | HGNC: 5213 | 3295 | NM_000414.3 |
| Hspa13 | MGI: 1309463 | 110920 | NM_030201.3 |
| Hspa13 | MGI: 1309463 | 110920 | NP_084477.1 |
| Hspa13 | MGI: 1309463 | 110920 | NR_027492.1 |
| HSPA13 | HGNC: 11375 | 6782 | NP_008879.3 |
| HSPA13 | HGNC: 11375 | 6782 | NM_006948.4 |
| Ice1 | MGI: 2385865 | 218333 | NM_144837.3 |
| Ice1 | MGI: 2385865 | 218333 | NP_659026.2 |
| ICE1 | HGNC: 29154 | 23379 | XP_016864774.1 |
| ICE1 | HGNC: 29154 | 23379 | NM_015325.2 |
| Icosl | MGI: 1354701 | 50723 | NM_015790.3 |
| Icosl | MGI: 1354701 | 50723 | NP_056605.1 |
| ICOSLG | HGNC: 17087 | 23308 | NP_001269981.1 |

TABLE 1-continued

| Gene Symbol | Marker ID | NCBI Entrez Gene ID | NCBI GenBank ID |
|---|---|---|---|
| ICOSLG | HGNC: 17087 | 23308 | NM_001283052.1 |
| Ikbkb | MGI: 1338071 | 16150 | NM_001159774.1 |
| Ikbkb | MGI: 1338071 | 16150 | NM_010546.2 |
| Ikbkb | MGI: 1338071 | 16150 | NP_001153246.1 |
| Ikbkb | MGI: 1338071 | 16150 | NP_034676.1 |
| IKBKB | HGNC: 5960 | 3551 | XP_005273552.1 |
| IKBKB | HGNC: 5960 | 3551 | NM_001190722.1 |
| Ikbkg | MGI: 1338074 | 16151 | NM_001136067.2 |
| Ikbkg | MGI: 1338074 | 16151 | NM_001161421.1 |
| Ikbkg | MGI: 1338074 | 16151 | NM_001161422.1 |
| Ikbkg | MGI: 1338074 | 16151 | NM_001161423.1 |
| Ikbkg | MGI: 1338074 | 16151 | NM_001161424.1 |
| Ikbkg | MGI: 1338074 | 16151 | NM_010547.2 |
| Ikbkg | MGI: 1338074 | 16151 | NM_178590.4 |
| Ikbkg | MGI: 1338074 | 16151 | NP_001129539.1 |
| Ikbkg | MGI: 1338074 | 16151 | NP_001154893.1 |
| Ikbkg | MGI: 1338074 | 16151 | NP_001154894.1 |
| Ikbkg | MGI: 1338074 | 16151 | NP_001154895.1 |
| Ikbkg | MGI: 1338074 | 16151 | NP_001154896.1 |
| Ikbkg | MGI: 1338074 | 16151 | NP_034677.2 |
| Ikbkg | MGI: 1338074 | 16151 | NP_848705.1 |
| IKBKG | HGNC: 5961 | 8517 | NP_001093327.1 |
| IKBKG | HGNC: 5961 | 8517 | NM_003639.4 |
| Ilk | MGI: 1195267 | 16202 | NM_001161724.1 |
| Ilk | MGI: 1195267 | 16202 | NM_010562.2 |
| Ilk | MGI: 1195267 | 16202 | NP_001155196.1 |
| Ilk | MGI: 1195267 | 16202 | NP_034692.2 |
| ILK | HGNC: 6040 | 3611 | NP_001265371.1 |
| ILK | HGNC: 6040 | 3611 | NM_001014794.2 |
| Impg1 | MGI: 1926876 | 63859 | NM_022016.3 |
| Impg1 | MGI: 1926876 | 63859 | NP_071299.3 |
| IMPG1 | HGNC: 6055 | 3617 | NP_001269297.1 |
| IMPG1 | HGNC: 6055 | 3617 | NM_001282368.1 |
| Ipo11 | MGI: 2442377 | 76582 | NM_029665.3 |
| Ipo11 | MGI: 2442377 | 76582 | NP_083941.2 |
| IPO11 | HGNC: 20628 | 51194 | NP_001128251.1 |
| IPO11 | HGNC: 20628 | 51194 | NM_016338.4 |
| Iqsec1 | MGI: 1196356 | 232227 | NM_001134383.1 |
| Iqsec1 | MGI: 1196356 | 232227 | NM_001134384.1 |
| Iqsec1 | MGI: 1196356 | 232227 | NP_001127855.1 |
| Iqsec1 | MGI: 1196356 | 232227 | NP_001127856.1 |
| IQSEC1 | HGNC: 29112 | 9922 | NP_001127854.1 |
| IQSEC1 | HGNC: 29112 | 9922 | NM_014869.6 |
| Ireb2 | MGI: 1928268 | 64602 | XM_006511335.3 |
| Ireb2 | MGI: 1928268 | 64602 | NP_073146.2 |
| IREB2 | HGNC: 6115 | 3658 | NP_001307870.1 |
| IREB2 | HGNC: 6115 | 3658 | NM_004136.3 |
| Irf1 | MGI: 96590 | 16362 | NM_001159393.1 |
| Irf1 | MGI: 96590 | 16362 | NM_001159396.1 |
| Irf1 | MGI: 96590 | 16362 | NM_008390.2 |
| Irf1 | MGI: 96590 | 16362 | NP_001152865.1 |
| Irf1 | MGI: 96590 | 16362 | NP_001152868.1 |
| Irf1 | MGI: 96590 | 16362 | NP_032416.1 |
| IRF1 | HGNC: 6116 | 3659 | XP_011541681.1 |
| IRF1 | HGNC: 6116 | 3659 | NM_002198.2 |
| IRGM | HGNC: 29597 | 345611 | NP_001139277.1 |
| IRGM | HGNC: 29597 | 345611 | NM_001145805.1 |
| Irgm2 | MGI: 1926262 | 54396 | NM_019440.3 |
| Irgm2 | MGI: 1926262 | 54396 | NP_062313.3 |
| Itgav | MGI: 96608 | 16410 | NM_008402.3 |
| Itgav | MGI: 96608 | 16410 | NP_032428.2 |
| ITGAV | HGNC: 6150 | 3685 | NP_002201.1 |
| ITGAV | HGNC: 6150 | 3685 | NM_002210.4 |
| Jmjd6 | MGI: 1858910 | 107817 | NM_033398.2 |
| Jmjd6 | MGI: 1858910 | 107817 | NP_203971.2 |
| JMJD6 | HGNC: 19355 | 23210 | NP_055982.2 |
| JMJD6 | HGNC: 19355 | 23210 | NM_001081461.1 |
| Keap1 | MGI: 1858732 | 50868 | NM_001110305.1 |
| Keap1 | MGI: 1858732 | 50868 | NM_001110306.1 |
| Keap1 | MGI: 1858732 | 50868 | NM_001110307.1 |
| Keap1 | MGI: 1858732 | 50868 | NM_016679.4 |
| Keap1 | MGI: 1858732 | 50868 | NP_001103775.1 |
| Keap1 | MGI: 1858732 | 50868 | NP_001103776.1 |
| Keap1 | MGI: 1858732 | 50868 | NP_001103777.1 |
| Keap1 | MGI: 1858732 | 50868 | NP_057888.1 |
| KEAP1 | HGNC: 23177 | 9817 | NP_987096.1 |
| KEAP1 | HGNC: 23177 | 9817 | NM_203500.1 |
| Kmt2c | MGI: 2444959 | 231051 | NM_001081383.1 |
| Kmt2c | MGI: 2444959 | 231051 | NP_001074852.1 |
| KMT2C | HGNC: 13726 | 58508 | XP_011514754.1 |
| KMT2C | HGNC: 13726 | 58508 | NM_021230.2 |
| Krit1 | MGI: 1930618 | 79264 | NM_001170552.1 |
| Krit1 | MGI: 1930618 | 79264 | NM_030675.3 |
| Krit1 | MGI: 1930618 | 79264 | NP_001164023.1 |
| Krit1 | MGI: 1930618 | 79264 | NP_109600.2 |
| Krit1 | MGI: 1930618 | 79264 | NR_033173.1 |
| KRIT1 | HGNC: 1573 | 889 | XP_005250719.1 |
| KRIT1 | HGNC: 1573 | 889 | NM_001350678.1 |
| Lamtor1 | MGI: 1913758 | 66508 | NM_025605.3 |
| Lamtor1 | MGI: 1913758 | 66508 | NP_079881.2 |
| LAMTOR1 | HGNC: 26068 | 55004 | NP_060377.1 |
| LAMTOR1 | HGNC: 26068 | 55004 | NM_017907.2 |
| Larp4 | MGI: 2443114 | 207214 | NM_001024526.2 |
| Larp4 | MGI: 2443114 | 207214 | NM_001080948.2 |
| Larp4 | MGI: 2443114 | 207214 | NM_001284521.1 |
| Larp4 | MGI: 2443114 | 207214 | NM_001284522.1 |
| Larp4 | MGI: 2443114 | 207214 | NM_001284523.1 |
| Larp4 | MGI: 2443114 | 207214 | NP_001019697.2 |
| Larp4 | MGI: 2443114 | 207214 | NP_001074417.1 |
| Larp4 | MGI: 2443114 | 207214 | NP_001271450.1 |
| Larp4 | MGI: 2443114 | 207214 | NP_001271451.1 |
| Larp4 | MGI: 2443114 | 207214 | NP_001271452.1 |
| LARP4 | HGNC: 24320 | 113251 | XP_011536146.1 |
| LARP4 | HGNC: 24320 | 113251 | NM_001170808.1 |
| Lemd2 | MGI: 2385045 | 224640 | NM_146075.2 |
| Lemd2 | MGI: 2385045 | 224640 | NP_666187.2 |
| LEMD2 | HGNC: 21244 | 221496 | NP_851853.1 |
| LEMD2 | HGNC: 21244 | 221496 | NM_001348710.1 |
| Lman2 | MGI: 1914140 | 66890 | NM_025828.3 |
| Lman2 | MGI: 1914140 | 66890 | NP_080104.2 |
| LMAN2 | HGNC: 16986 | 10960 | NP_006807.1 |
| LMAN2 | HGNC: 16986 | 10960 | NM_006816.2 |
| Lrp10 | MGI: 1929480 | 65107 | NM_022993.3 |
| Lrp10 | MGI: 1929480 | 65107 | NP_075369.2 |
| LRP10 | HGNC: 14553 | 26020 | NP_054764.2 |
| LRP10 | HGNC: 14553 | 26020 | NM_001329226.1 |
| Lrrn3 | MGI: 106036 | 16981 | NM_001271708.1 |
| Lrrn3 | MGI: 106036 | 16981 | NM_001271709.1 |
| Lrrn3 | MGI: 106036 | 16981 | NM_010733.3 |
| Lrrn3 | MGI: 106036 | 16981 | NP_001258637.1 |
| Lrrn3 | MGI: 106036 | 16981 | NP_001258638.1 |
| Lrrn3 | MGI: 106036 | 16981 | NP_034863.1 |
| LRRN3 | HGNC: 17200 | 54674 | NP_001093130.1 |
| LRRN3 | HGNC: 17200 | 54674 | NM_018534.4 |
| Maea | MGI: 1891748 | 59003 | NM_021500.2 |
| Maea | MGI: 1891748 | 59003 | NP_067475.2 |
| MAEA | HGNC: 13731 | 10296 | NP_005873.2 |
| MAEA | HGNC: 13731 | 10296 | NM_001297430.1 |
| Man2a1 | MGI: 104669 | 17158 | NM_008549.2 |
| Man2a1 | MGI: 104669 | 17158 | NP_032575.2 |
| MAN2A1 | HGNC: 6824 | 4124 | NP_002363.2 |
| MAN2A1 | HGNC: 6824 | 4124 | NM_002372.3 |
| Matr3 | MGI: 1298379 | 17184 | NM_010771.6 |
| Matr3 | MGI: 1298379 | 17184 | NP_034901.2 |
| MATR3 | HGNC: 6912 | 9782 | NP_061322.2 |
| MATR3 | HGNC: 6912 | 9782 | NM_199189.2 |
| Mcl1 | MGI: 101769 | 17210 | NM_008562.3 |
| Mcl1 | MGI: 101769 | 17210 | NP_032588.1 |
| MCL1 | HGNC: 6943 | 4170 | NP_001184249.1 |
| MCL1 | HGNC: 6943 | 4170 | NM_021960.4 |
| Med7 | MGI: 1913463 | 66213 | NM_001104530.1 |
| Med7 | MGI: 1913463 | 66213 | NM_001104556.1 |
| Med7 | MGI: 1913463 | 66213 | NM_001104557.1 |
| Med7 | MGI: 1913463 | 66213 | NM_025426.3 |
| Med7 | MGI: 1913463 | 66213 | NP_001098000.1 |
| Med7 | MGI: 1913463 | 66213 | NP_001098026.1 |
| Med7 | MGI: 1913463 | 66213 | NP_001098027.1 |
| Med7 | MGI: 1913463 | 66213 | NP_079702.3 |
| MED7 | HGNC: 2378 | 9443 | NP_001094286.1 |
| MED7 | HGNC: 2378 | 9443 | NM_001100816.1 |
| Megf8 | MGI: 2446294 | 269878 | NM_001160400.1 |
| Megf8 | MGI: 2446294 | 269878 | NP_001153872.1 |
| MEGF8 | HGNC: 3233 | 1954 | NP_001258867.1 |
| MEGF8 | HGNC: 3233 | 1954 | NM_178121.2 |

TABLE 1-continued

| Gene Symbol | Marker ID | NCBI Entrez Gene ID | NCBI GenBank ID |
|---|---|---|---|
| Meioc | MGI: 2686410 | 268491 | XM_006533415.1 |
| Meioc | MGI: 2686410 | 268491 | NP_001121048.1 |
| MEIOC | HGNC: 26670 | 284071 | NP_001138552.2 |
| MEIOC | HGNC: 26670 | 284071 | NM_001033659.2 |
| Memo1 | MGI: 1924140 | 76890 | NM_133771.2 |
| Memo1 | MGI: 1924140 | 76890 | NP_598532.1 |
| MEMO1 | HGNC: 14014 | 51072 | XP_011531194.1 |
| MEMO1 | HGNC: 14014 | 51072 | NM_001137602.2 |
| Mprip | MGI: 1349438 | 26936 | NM_012027.2 |
| Mprip | MGI: 1349438 | 26936 | NM_201245.3 |
| Mprip | MGI: 1349438 | 26936 | NP_036157.2 |
| Mprip | MGI: 1349438 | 26936 | NP_957697.1 |
| MPRIP | HGNC: 30321 | 23164 | NP_958431.2 |
| MPRIP | HGNC: 30321 | 23164 | NM_015134.3 |
| Mrps21 | MGI: 1913542 | 66292 | NM_078479.3 |
| Mrps21 | MGI: 1913542 | 66292 | NP_510964.1 |
| MRPS21 | HGNC: 14046 | 54460 | NP_061870.1 |
| MRPS21 | HGNC: 14046 | 54460 | NM_031901.5 |
| Mtch1 | MGI: 1929261 | 56462 | NM_001347335.1 |
| Mtch1 | MGI: 1929261 | 56462 | NM_019880.3 |
| Mtch1 | MGI: 1929261 | 56462 | NP_001334264.1 |
| Mtch1 | MGI: 1929261 | 56462 | NP_063933.1 |
| MTCH1 | HGNC: 17586 | 23787 | XP_005249035.1 |
| MTCH1 | HGNC: 17586 | 23787 | NM_014341.2 |
| N4bp1 | MGI: 2136825 | 80750 | NM_030563.2 |
| N4bp1 | MGI: 2136825 | 80750 | NP_085040.2 |
| N4BP1 | HGNC: 29850 | 9683 | XP_011521784.1 |
| N4BP1 | HGNC: 29850 | 9683 | NM_153029.3 |
| Nadk | MGI: 2183149 | 192185 | NM_001159637.1 |
| Nadk | MGI: 2183149 | 192185 | NM_138671.2 |
| Nadk | MGI: 2183149 | 192185 | NP_001153109.1 |
| Nadk | MGI: 2183149 | 192185 | NP_619612.2 |
| NADK | HGNC: 29831 | 65220 | NP_075394.3 |
| NADK | HGNC: 29831 | 65220 | NM_023018.4 |
| Nampt | MGI: 1929865 | 59027 | NM_021524.2 |
| Nampt | MGI: 1929865 | 59027 | NP_067499.2 |
| NAMPT | HGNC: 30092 | 10135 | XP_005250157.1 |
| NAMPT | HGNC: 30092 | 10135 | NM_005746.2 |
| Nans | MGI: 2149820 | 94181 | NM_053179.3 |
| Nans | MGI: 2149820 | 94181 | NP_444409.1 |
| NANS | HGNC: 19237 | 54187 | XP_016870300.1 |
| NANS | HGNC: 19237 | 54187 | NM_018946.3 |
| Nckap1 | MGI: 1355333 | 50884 | NM_001290745.1 |
| Nckap1 | MGI: 1355333 | 50884 | NM_016965.3 |
| Nckap1 | MGI: 1355333 | 50884 | NP_001277674.1 |
| Nckap1 | MGI: 1355333 | 50884 | NP_058661.1 |
| NCKAP1 | HGNC: 7666 | 10787 | NP_038464.1 |
| NCKAP1 | HGNC: 7666 | 10787 | NM_013436.4 |
| Nepro | MGI: 2384836 | 212547 | NM_145972.4 |
| Nepro | MGI: 2384836 | 212547 | NP_666084.1 |
| NEPRO | HGNC: 24496 | 25871 | NP_001306041.1 |
| NEPRO | HGNC: 24496 | 25871 | NM_001319109.1 |
| Neurl3 | MGI: 2429944 | 214854 | NM_153408.2 |
| Neurl3 | MGI: 2429944 | 214854 | NP_700457.1 |
| NEURL3 | HGNC: 25162 | 93082 | XP_011510480.1 |
| NEURL3 | HGNC: 25162 | 93082 | NM_001285486.1 |
| Nfix | MGI: 97311 | 18032 | NM_001081981.2 |
| Nfix | MGI: 97311 | 18032 | NM_001081982.2 |
| Nfix | MGI: 97311 | 18032 | NM_001297601.1 |
| Nfix | MGI: 97311 | 18032 | NM_010906.3 |
| Nfix | MGI: 97311 | 18032 | NP_001075450.1 |
| Nfix | MGI: 97311 | 18032 | NP_001075451.1 |
| Nfix | MGI: 97311 | 18032 | NP_001284530.1 |
| Nfix | MGI: 97311 | 18032 | NP_035036.1 |
| NFIX | HGNC: 7788 | 4784 | XP_006722823.1 |
| NFIX | HGNC: 7788 | 4784 | NM_001271043.2 |
| Nprl2 | MGI: 1914482 | 56032 | NM_018879.2 |
| Nprl2 | MGI: 1914482 | 56032 | NP_061367.1 |
| NPRL2 | HGNC: 24969 | 10641 | NP_006536.3 |
| NPRL2 | HGNC: 24969 | 10641 | NM_006545.4 |
| Nprl3 | MGI: 109258 | 17168 | NM_001284359.1 |
| Nprl3 | MGI: 109258 | 17168 | NM_001284360.1 |
| Nprl3 | MGI: 109258 | 17168 | NM_181569.3 |
| Nprl3 | MGI: 109258 | 17168 | NP_001271288.1 |
| Nprl3 | MGI: 109258 | 17168 | NP_001271289.1 |
| Nprl3 | MGI: 109258 | 17168 | NP_853547.1 |
| Nprl3 | MGI: 109258 | 17168 | NR_104306.1 |
| NPRL3 | HGNC: 14124 | 8131 | NP_001230176.1 |
| NPRL3 | HGNC: 14124 | 8131 | NM_012075.1 |
| Nrbf2 | MGI: 1354950 | 641340 | NM_001036293.2 |
| Nrbf2 | MGI: 1354950 | 641340 | NP_001031370.1 |
| NRBF2 | HGNC: 19692 | 29982 | XP_006717873.1 |
| NRBF2 | HGNC: 19692 | 29982 | NM_001282405.1 |
| Nsdhl | MGI: 1099438 | 18194 | NM_010941.3 |
| Nsdhl | MGI: 1099438 | 18194 | NP_035071.3 |
| NSDHL | HGNC: 13398 | 50814 | XP_016885053.1 |
| NSDHL | HGNC: 13398 | 50814 | NM_015922.2 |
| Nudcd2 | MGI: 1277103 | 52653 | NM_001290697.1 |
| Nudcd2 | MGI: 1277103 | 52653 | NM_026023.5 |
| Nudcd2 | MGI: 1277103 | 52653 | NP_001277626.1 |
| Nudcd2 | MGI: 1277103 | 52653 | NP_080299.4 |
| NUDCD2 | HGNC: 30535 | 134492 | NP_660309.1 |
| NUDCD2 | HGNC: 30535 | 134492 | NM_145266.5 |
| Oprk1 | MGI: 97439 | 18387 | NM_001204371.1 |
| Oprk1 | MGI: 97439 | 18387 | NM_001318751.1 |
| Oprk1 | MGI: 97439 | 18387 | NM_011011.2 |
| Oprk1 | MGI: 97439 | 18387 | NP_001191300.1 |
| Oprk1 | MGI: 97439 | 18387 | NP_001305664.1 |
| Oprk1 | MGI: 97439 | 18387 | NP_035141.1 |
| OPRK1 | HGNC: 8154 | 4986 | NP_000903.2 |
| OPRK1 | HGNC: 8154 | 4986 | NM_000912.4 |
| Otulin | MGI: 3577015 | 432940 | NM_001013792.2 |
| Otulin | MGI: 3577015 | 432940 | NP_001013814.2 |
| OTULIN | HGNC: 25118 | 90268 | XP_016865504.1 |
| OTULIN | HGNC: 25118 | 90268 | NM_138348.5 |
| Padi4 | MGI: 1338898 | 18602 | NM_011061.2 |
| Padi4 | MGI: 1338898 | 18602 | NP_035191.2 |
| PADI4 | HGNC: 18368 | 23569 | XP_011539455.1 |
| PADI4 | HGNC: 18368 | 23569 | NM_012387.2 |
| Pak2 | MGI: 1339984 | 224105 | NM_177326.3 |
| Pak2 | MGI: 1339984 | 224105 | NP_796300.1 |
| PAK2 | HGNC: 8591 | 5062 | NP_002568.2 |
| PAK2 | HGNC: 8591 | 5062 | NM_002577.4 |
| Paox | MGI: 1916983 | 212503 | NM_001346725.1 |
| Paox | MGI: 1916983 | 212503 | NM_153783.4 |
| Paox | MGI: 1916983 | 212503 | NP_001333654.1 |
| Paox | MGI: 1916983 | 212503 | NP_722478.2 |
| PAOX | HGNC: 20837 | 196743 | NP_997011.1 |
| PAOX | HGNC: 20837 | 196743 | NM_207125.1 |
| Parn | MGI: 1921358 | 74108 | NM_028761.3 |
| Parn | MGI: 1921358 | 74108 | NP_083037.1 |
| PARN | HGNC: 8609 | 5073 | XP_011520815.1 |
| PARN | HGNC: 8609 | 5073 | NM_001242992.1 |
| Pax3 | MGI: 97487 | 18505 | NM_001159520.1 |
| Pax3 | MGI: 97487 | 18505 | NM_008781.4 |
| Pax3 | MGI: 97487 | 18505 | NP_001152992.1 |
| Pax3 | MGI: 97487 | 18505 | NP_032807.3 |
| PAX3 | HGNC: 8617 | 5077 | NP_000429.2 |
| PAX3 | HGNC: 8617 | 5077 | NM_181457.3 |
| Pbrm1 | MGI: 1923998 | 66923 | NM_001081251.1 |
| Pbrm1 | MGI: 1923998 | 66923 | NP_001074720.1 |
| PBRM1 | HGNC: 30064 | 55193 | XP_016862125.1 |
| PBRM1 | HGNC: 30064 | 55193 | NM_001350079.1 |
| Pcgf6 | MGI: 1918291 | 71041 | NM_027654.3 |
| Pcgf6 | MGI: 1918291 | 71041 | NP_081930.1 |
| Pcgf6 | MGI: 1918291 | 71041 | NR_133574.1 |
| PCGF6 | HGNC: 21156 | 84108 | NP_001011663.1 |
| PCGF6 | HGNC: 21156 | 84108 | NM_001011663.1 |
| Pde7a | MGI: 1202402 | 18583 | NM_001122759.2 |
| Pde7a | MGI: 1202402 | 18583 | NM_008802.3 |
| Pde7a | MGI: 1202402 | 18583 | NP_001116231.1 |
| Pde7a | MGI: 1202402 | 18583 | NP_032828.2 |
| PDE7A | HGNC: 8791 | 5150 | XP_016869027.1 |
| PDE7A | HGNC: 8791 | 5150 | NM_001242318.2 |
| Pigk | MGI: 1913863 | 329777 | NM_025662.5 |
| Pigk | MGI: 1913863 | 329777 | NM_178016.3 |
| Pigk | MGI: 1913863 | 329777 | NP_079938.1 |
| Pigk | MGI: 1913863 | 329777 | NP_821135.1 |
| PIGK | HGNC: 8965 | 10026 | NP_005473.1 |
| PIGK | HGNC: 8965 | 10026 | NM_005482.2 |
| Pigs | MGI: 2687325 | 276846 | NM_201406.1 |
| Pigs | MGI: 2687325 | 276846 | NP_958808.1 |
| PIGS | HGNC: 14937 | 94005 | NP_149975.1 |
| PIGS | HGNC: 14937 | 94005 | NM_033198.3 |

TABLE 1-continued

| Gene Symbol | Marker ID | NCBI Entrez Gene ID | NCBI GenBank ID |
|---|---|---|---|
| Pigu | MGI: 3039607 | 228812 | NM_001004721.1 |
| Pigu | MGI: 3039607 | 228812 | NP_001004721.1 |
| PIGU | HGNC: 15791 | 128869 | NP_536724.1 |
| PIGU | HGNC: 15791 | 128869 | NM_080476.4 |
| Pih1d1 | MGI: 1916095 | 68845 | NM_001278207.1 |
| Pih1d1 | MGI: 1916095 | 68845 | NM_001285904.1 |
| Pih1d1 | MGI: 1916095 | 68845 | NM_029406.4 |
| Pih1d1 | MGI: 1916095 | 68845 | NP_001265136.1 |
| Pih1d1 | MGI: 1916095 | 68845 | NP_001272833.1 |
| Pih1d1 | MGI: 1916095 | 68845 | NP_083682.1 |
| PIH1D1 | HGNC: 26075 | 55011 | NP_060386.1 |
| PIH1D1 | HGNC: 26075 | 55011 | NM_017916.2 |
| Pip5k1c | MGI: 1298224 | 18717 | NM_001146687.2 |
| Pip5k1c | MGI: 1298224 | 18717 | NM_001293646.1 |
| Pip5k1c | MGI: 1298224 | 18717 | NM_001293647.1 |
| Pip5k1c | MGI: 1298224 | 18717 | NM_008844.3 |
| Pip5k1c | MGI: 1298224 | 18717 | NP_001140159.1 |
| Pip5k1c | MGI: 1298224 | 18717 | NP_001280575.1 |
| Pip5k1c | MGI: 1298224 | 18717 | NP_001280576.1 |
| Pip5k1c | MGI: 1298224 | 18717 | NP_032870.2 |
| PIP5K1C | HGNC: 8996 | 23396 | XP_011526155.1 |
| PIP5K1C | HGNC: 8996 | 23396 | NM_012398.2 |
| Pitx2 | MGI: 109340 | 18741 | NM_001042502.2 |
| Pitx2 | MGI: 109340 | 18741 | NM_001042504.2 |
| Pitx2 | MGI: 109340 | 18741 | NM_001286942.1 |
| Pitx2 | MGI: 109340 | 18741 | NM_001287048.1 |
| Pitx2 | MGI: 109340 | 18741 | NM_011098.4 |
| Pitx2 | MGI: 109340 | 18741 | NP_001035967.1 |
| Pitx2 | MGI: 109340 | 18741 | NP_001035969.1 |
| Pitx2 | MGI: 109340 | 18741 | NP_001273871.1 |
| Pitx2 | MGI: 109340 | 18741 | NP_001273977.1 |
| Pitx2 | MGI: 109340 | 18741 | NP_035228.2 |
| PITX2 | HGNC: 9005 | 5308 | NP_700476.1 |
| PITX2 | HGNC: 9005 | 5308 | NM_001204399.1 |
| Plpp2 | MGI: 1354945 | 50784 | NM_001302389.1 |
| Plpp2 | MGI: 1354945 | 50784 | NM_001302390.1 |
| Plpp2 | MGI: 1354945 | 50784 | NM_001302442.1 |
| Plpp2 | MGI: 1354945 | 50784 | NM_015817.3 |
| Plpp2 | MGI: 1354945 | 50784 | NP_001289318.1 |
| Plpp2 | MGI: 1354945 | 50784 | NP_001289319.1 |
| Plpp2 | MGI: 1354945 | 50784 | NP_001289371.1 |
| Plpp2 | MGI: 1354945 | 50784 | NP_056632.2 |
| PLPP2 | HGNC: 9230 | 8612 | NP_803545.1 |
| PLPP2 | HGNC: 9230 | 8612 | NM_177543.2 |
| Ppcs | MGI: 1915237 | 106564 | NM_026494.3 |
| Ppcs | MGI: 1915237 | 106564 | NP_080770.2 |
| PPCS | HGNC: 25686 | 79717 | NP_001274440.1 |
| PPCS | HGNC: 25686 | 79717 | NM_001287511.1 |
| Ppp4r2 | MGI: 3027896 | 232314 | NM_182939.4 |
| Ppp4r2 | MGI: 3027896 | 232314 | NP_891984.1 |
| PPP4R2 | HGNC: 18296 | 151987 | NM_001304956.1 |
| PPP4R2 | HGNC: 18296 | 151987 | NM_001318025.1 |
| Prdm10 | MGI: 2682952 | 382066 | NM_001080817.1 |
| Prdm10 | MGI: 2682952 | 382066 | NP_001074286.1 |
| PRDM10 | HGNC: 13995 | 56980 | NP_955470.1 |
| PRDM10 | HGNC: 13995 | 56980 | NM_199439.1 |
| Prdx1 | MGI: 99523 | 18477 | NM_011034.4 |
| Prdx1 | MGI: 99523 | 18477 | NP_035164.1 |
| PRDX1 | HGNC: 9352 | 5052 | NP_002565.1 |
| PRDX1 | HGNC: 9352 | 5052 | NM_002574.3 |
| Prkcq | MGI: 97601 | 18761 | NM_008859.2 |
| Prkcq | MGI: 97601 | 18761 | NP_032885.1 |
| PRKCQ | HGNC: 9410 | 5588 | NP_001269573.1 |
| PRKCQ | HGNC: 9410 | 5588 | NM_001282645.1 |
| Prrc2a | MGI: 1915467 | 53761 | NM_001199044.1 |
| Prrc2a | MGI: 1915467 | 53761 | NM_020027.3 |
| Prrc2a | MGI: 1915467 | 53761 | NP_001185973.1 |
| Prrc2a | MGI: 1915467 | 53761 | NP_064411.2 |
| PRRC2A | HGNC: 13918 | 7916 | NP_004629.3 |
| PRRC2A | HGNC: 13918 | 7916 | NM_080686.2 |
| Psmb8 | MGI: 1346527 | 16913 | NM_010724.2 |
| Psmb8 | MGI: 1346527 | 16913 | NM_034854.2 |
| PSMB8 | HGNC: 9545 | 5696 | NP_004150.1 |
| PSMB8 | HGNC: 9545 | 5696 | NM_004159.4 |
| Psme1 | MGI: 1096367 | 19186 | NM_011189.1 |
| Psme1 | MGI: 1096367 | 19186 | NP_035319.1 |
| PSME1 | HGNC: 9568 | 5720 | NP_006254.1 |
| PSME1 | HGNC: 9568 | 5720 | NM_006263.3 |
| Psme2 | MGI: 1096365 | 19188 | NM_001029855.1 |
| Psme2 | MGI: 1096365 | 19188 | NM_011190.3 |
| Psme2 | MGI: 1096365 | 19188 | NP_001025026.1 |
| Psme2 | MGI: 1096365 | 19188 | NP_035320.1 |
| PSME2 | HGNC: 9569 | 5721 | XP_006720276.1 |
| PSME2 | HGNC: 9569 | 5721 | NM_002818.2 |
| Ptar1 | MGI: 1921875 | 72351 | NM_028208.1 |
| Ptar1 | MGI: 1921875 | 72351 | NP_082484.1 |
| PTAR1 | HGNC: 30449 | 375743 | XP_005252034.1 |
| PTAR1 | HGNC: 30449 | 375743 | NM_001099666.1 |
| Ptpn11 | MGI: 99511 | 19247 | NM_001109992.1 |
| Ptpn11 | MGI: 99511 | 19247 | NM_011202.3 |
| Ptpn11 | MGI: 99511 | 19247 | NP_001103462.1 |
| Ptpn11 | MGI: 99511 | 19247 | NP_035332.1 |
| PTPN11 | HGNC: 9644 | 5781 | NP_002825.3 |
| PTPN11 | HGNC: 9644 | 5781 | NM_080601.2 |
| Ptpn2 | MGI: 97806 | 19255 | NM_001127177.1 |
| Ptpn2 | MGI: 97806 | 19255 | NM_008977.3 |
| Ptpn2 | MGI: 97806 | 19255 | NP_001120649.1 |
| Ptpn2 | MGI: 97806 | 19255 | NP_033003.1 |
| PTPN2 | HGNC: 9650 | 5771 | XP_016871377.1 |
| PTPN2 | HGNC: 9650 | 5771 | NM_080423.2 |
| Rab13 | MGI: 1927232 | 68328 | NM_001293741.1 |
| Rab13 | MGI: 1927232 | 68328 | NM_026677.4 |
| Rab13 | MGI: 1927232 | 68328 | NP_001280670.1 |
| Rab13 | MGI: 1927232 | 68328 | NP_080953.1 |
| RAB13 | HGNC: 9762 | 5872 | NP_001258967.1 |
| RAB13 | HGNC: 9762 | 5872 | NM_001272038.1 |
| Rab1a | MGI: 97842 | 19324 | NM_308996.3 |
| Rab1a | MGI: 97842 | 19324 | NP_033022.1 |
| RAB1A | HGNC: 9758 | 5861 | NP_056358.1 |
| RAB1A | HGNC: 9758 | 5861 | NM_004161.4 |
| Rab25 | MGI: 1858203 | 53868 | NM_016899.4 |
| Rab25 | MGI: 1858203 | 53868 | NP_058595.2 |
| RAB25 | HGNC: 18238 | 57111 | NP_065120.2 |
| RAB25 | HGNC: 18238 | 57111 | NM_020387.3 |
| Rab7 | MGI: 105068 | 19349 | NM_001293652.1 |
| Rab7 | MGI: 105068 | 19349 | NM_001293653.1 |
| Rab7 | MGI: 105068 | 19349 | NM_001293654.1 |
| Rab7 | MGI: 105068 | 19349 | NM_001293655.1 |
| Rab7 | MGI: 105068 | 19349 | NM_009005.3 |
| Rab7 | MGI: 105068 | 19349 | NP_001280581.1 |
| Rab7 | MGI: 105068 | 19349 | NP_001280582.1 |
| Rab7 | MGI: 105068 | 19349 | NP_001280583.1 |
| Rab7 | MGI: 105068 | 19349 | NP_001280584.1 |
| Rab7 | MGI: 105068 | 19349 | NP_033031.2 |
| RAB7A | HGNC: 9788 | 7879 | NP_004628.4 |
| RAB7A | HGNC: 9788 | 7879 | NM_004637.5 |
| Rad51d | MGI: 1261809 | 19364 | NM_001277938.1 |
| Rad51d | MGI: 1261809 | 19364 | NM_001277939.1 |
| Rad51d | MGI: 1261809 | 19364 | NM_001277941.1 |
| Rad51d | MGI: 1261809 | 19364 | NM_001277942.1 |
| Rad51d | MGI: 1261809 | 19364 | NM_011235.4 |
| Rad51d | MGI: 1261809 | 19364 | NP_001264867.1 |
| Rad51d | MGI: 1261809 | 19364 | NP_001264868.1 |
| Rad51d | MGI: 1261809 | 19364 | NP_001264870.1 |
| Rad51d | MGI: 1261809 | 19364 | NP_001264871.1 |
| Rad51d | MGI: 1261809 | 19364 | NP_035365.1 |
| Rad51d | MGI: 1261809 | 19364 | NR_102717.1 |
| Rad51d | MGI: 1261809 | 19364 | NR_102718.1 |
| Rad51d | MGI: 1261809 | 19364 | NR_102719.1 |
| Rad51d | MGI: 1261809 | 19364 | NR_102720.1 |
| RAD51D | HGNC: 9823 | 5892 | NM_001116043.1 |
| RAD51D | HGNC: 9823 | 5892 | NM_001142571.1 |
| Raf1 | MGI: 97847 | 110157 | NM_029780.3 |
| Raf1 | MGI: 97847 | 110157 | NP_084056.1 |
| RAF1 | HGNC: 9829 | 5894 | XP_005265412.1 |
| RAF1 | HGNC: 9829 | 5894 | NM_002880.3 |
| Rbm34 | MGI: 1098653 | 52202 | NM_172762.2 |
| Rbm34 | MGI: 1098653 | 52202 | NP_766350.2 |
| RBM34 | HGNC: 28965 | 23029 | XP_016856210.1 |
| RBM34 | HGNC: 28965 | 23029 | NM_001161533.1 |
| Rela | MGI: 103290 | 19697 | NM_009045.4 |
| Rela | MGI: 103290 | 19697 | NP_033071.1 |
| RELA | HGNC: 9955 | 5970 | NP_001230914.1 |
| RELA | HGNC: 9955 | 5970 | NM_001145138.1 |

TABLE 1-continued

| Gene Symbol | Marker ID | NCBI Entrez Gene ID | NCBI GenBank ID |
|---|---|---|---|
| Rer1 | MGI: 1915080 | 67830 | NM_026395.1 |
| Rer1 | MGI: 1915080 | 67830 | NP_080671.1 |
| RER1 | HGNC: 30309 | 11079 | XP_011538845.1 |
| RER1 | HGNC: 30309 | 11079 | NM_007033.4 |
| Rfwd2 | MGI: 1347046 | 26374 | NM_011931.3 |
| Rfwd2 | MGI: 1347046 | 26374 | NP_036061.1 |
| RFWD2 | HGNC: 17440 | 64326 | XP_016557568.1 |
| RFWD2 | HGNC: 17440 | 64326 | NM_001001740.3 |
| Rfx6 | MGI: 2445208 | 320995 | NM_001159389.1 |
| Rfx6 | MGI: 2445208 | 320995 | NM_177306.3 |
| Rfx6 | MGI: 2445208 | 320995 | NP_001152861.1 |
| Rfx6 | MGI: 2445208 | 320995 | NP_796280.1 |
| RFX6 | HGNC: 21478 | 222546 | NP_775831.2 |
| RFX6 | HGNC: 21478 | 222546 | NM_173560.3 |
| Rgmb | MGI: 1916049 | 68799 | NM_178615.3 |
| Rgmb | MGI: 1916049 | 68799 | NP_848730.2 |
| RGMB | HGNC: 26896 | 285704 | XP_016864879.1 |
| RGMB | HGNC: 26896 | 285704 | NM_001012761.2 |
| Rgp1 | MGI: 1915956 | 242406 | NM_172866.3 |
| Rgp1 | MGI: 1915956 | 242406 | NP_766454.1 |
| RGP1 | HGNC: 21965 | 9827 | NP_001073965.2 |
| RGP1 | HGNC: 21965 | 9827 | NM_001080496.2 |
| Rhbdl2 | MGI: 3608413 | 230726 | NM_183163.2 |
| Rhbdl2 | MGI: 3608413 | 230726 | NP_898986.2 |
| RHBDL2 | HGNC: 16083 | 54933 | NP_001291675.1 |
| RHBDL2 | HGNC: 16083 | 54933 | NM_017821.4 |
| Rnf31 | MGI: 1934704 | 268749 | NP_919327.2 |
| RNF31 | HGNC: 16031 | 55072 | NP_001297261.1 |
| RNF31 | HGNC: 16031 | 55072 | NM_017999.4 |
| Rnf38 | MGI: 1920719 | 73469 | NM_001038993.3 |
| Rnf38 | MGI: 1920719 | 73469 | NM_175201.5 |
| Rnf38 | MGI: 1920719 | 73469 | NP_001034082.1 |
| Rnf38 | MGI: 1920719 | 73469 | NP_780410.2 |
| RNF38 | HGNC: 18052 | 152006 | XP_016869784.1 |
| RNF38 | HGNC: 18052 | 152006 | NM_194328.2 |
| Rraga | MGI: 1915691 | 68441 | NM_178376.3 |
| Rraga | MGI: 1915691 | 68441 | NP_848463.1 |
| RRAGA | HGNC: 16963 | 10670 | NP_006561.1 |
| RRAGA | HGNC: 16963 | 10670 | NM_006570.4 |
| Rsf1 | MGI: 2682305 | 233532 | NM_001081267.2 |
| Rsf1 | MGI: 2682305 | 233532 | NP_001074736.1 |
| RSF1 | HGNC: 18118 | 51773 | XP_016873412.1 |
| RSF1 | HGNC: 18118 | 51773 | NM_016578.3 |
| Rsph1 | MGI: 1194909 | 22092 | NM_025290.3 |
| Rsph1 | MGI: 1194909 | 22092 | NP_079566.1 |
| RSPH1 | HGNC: 12371 | 89765 | XP_005261265.1 |
| RSPH1 | HGNC: 12371 | 89765 | NM_080861.3 |
| Sepsecs | MGI: 1098791 | 211006 | NM_172490.3 |
| Sepsecs | MGI: 1098791 | 211006 | NP_766078.1 |
| SEPSECS | HGNC: 30605 | 51091 | XP_016863767.1 |
| SEPSECS | HGNC: 30605 | 51091 | NM_016570.3 |
| Serpinb9 | MGI: 106603 | 20723 | NM_009256.3 |
| Serpinb9 | MGI: 106603 | 20723 | NP_033282.1 |
| SERPINB9 | HGNC: 8955 | 5272 | XP_016866432.1 |
| SERPINB9 | HGNC: 8955 | 5272 | NM_004155.5 |
| Setd2 | MGI: 1918177 | 235626 | NM_001081340.2 |
| Setd2 | MGI: 1918177 | 235626 | NP_001074809.2 |
| SETD2 | HGNC: 18420 | 29072 | XP_016861759.1 |
| SETD2 | HGNC: 18420 | 29072 | NM_012271.1 |
| Slc2a1 | MGI: 95755 | 20525 | NM_011400.3 |
| Slc2a1 | MGI: 95755 | 20525 | NP_035530.2 |
| SLC2A1 | HGNC: 11005 | 6513 | NP_006507.2 |
| SLC2A1 | HGNC: 11005 | 6513 | NM_006516.2 |
| Slc35a1 | MGI: 1345622 | 24060 | NM_011895.3 |
| Slc35a1 | MGI: 1345622 | 24060 | NP_036025.2 |
| SLC35A1 | HGNC: 11021 | 10559 | NP_001161870.1 |
| SLC35A1 | HGNC: 11021 | 10559 | NM_006416.4 |
| Slc7a11 | MGI: 1347355 | 26570 | NM_011990.2 |
| Slc7a11 | MGI: 1347355 | 26570 | NP_036120.1 |
| SLC7A11 | HGNC: 11059 | 23657 | NP_055146.1 |
| SLC7A11 | HGNC: 11059 | 23657 | NM_014331.3 |
| Smarce1 | MGI: 1927347 | 57376 | NM_020618.4 |
| Smarce1 | MGI: 1927347 | 57376 | NP_065643.1 |
| SMARCE1 | HGNC: 11109 | 6605 | NP_003070.3 |
| SMARCE1 | HGNC: 11109 | 6605 | NM_003079.4 |
| Snapin | MGI: 1333745 | 20615 | NM_133854.3 |
| Snapin | MGI: 1333745 | 20615 | NP_598615.1 |
| SNAPIN | HGNC: 17145 | 23557 | NP_036569.1 |
| SNAPIN | HGNC: 17145 | 23557 | NM_012437.5 |
| Sod2 | MGI: 98352 | 20656 | NM_013671.3 |
| Sod2 | MGI: 98352 | 20656 | NP_038699.2 |
| SOD2 | HGNC: 11180 | 6648 | NP_001019637.1 |
| SOD2 | HGNC: 11180 | 6648 | NM_001322817.1 |
| Sox11 | MGI: 98359 | 20666 | NM_009234.6 |
| Sox11 | MGI: 98359 | 20666 | NP_033260.4 |
| SOX11 | HGNC: 11191 | 6664 | NP_003099.1 |
| SOX11 | HGNC: 11191 | 6664 | NM_003108.3 |
| Sox4 | MGI: 98366 | 20677 | NM_009238.2 |
| Sox4 | MGI: 98366 | 20677 | NP_033264.2 |
| SOX4 | HGNC: 11200 | 6659 | NP_003098.1 |
| SOX4 | HGNC: 11200 | 6659 | NM_003107.2 |
| Spen | MGI: 1891706 | 56381 | NM_001347235.1 |
| Spen | MGI: 1891706 | 56381 | NM_019763.2 |
| Spen | MGI: 1891706 | 56381 | NP_001334164.1 |
| Spen | MGI: 1891706 | 56381 | NP_062737.2 |
| SPEN | HGNC: 17575 | 23013 | NP_055816.2 |
| SPEN | HGNC: 17575 | 23013 | NM_015001.2 |
| Spns1 | MGI: 1920908 | 73658 | NM_023712.3 |
| Spns1 | MGI: 1920908 | 73658 | NP_076201.2 |
| Spns1 | MGI: 1920908 | 73658 | NR_045537.1 |
| SPNS1 | HGNC: 30621 | 83985 | XP_016879247.1 |
| SPNS1 | HGNC: 30621 | 83985 | NM_001142448.1 |
| Sptlc1 | MGI: 1099431 | 268656 | NM_009269.2 |
| Sptlc1 | MGI: 1099431 | 268656 | NP_033295.2 |
| SPTLC1 | HGNC: 11277 | 10558 | NP_001268232.1 |
| SPTLC1 | HGNC: 11277 | 10558 | NM_006415.3 |
| Sptlc2 | MGI: 108074 | 20773 | NM_011479.4 |
| Sptlc2 | MGI: 108074 | 20773 | NP_035609.1 |
| SPTLC2 | HGNC: 11278 | 9517 | XP_011535686.1 |
| SPTLC2 | HGNC: 11278 | 9517 | NM_004863.3 |
| Srrd | MGI: 1917368 | 70118 | NM_027323.2 |
| Srrd | MGI: 1917368 | 70118 | NP_081599.2 |
| SRRD | HGNC: 33910 | 402055 | XP_011528480.1 |
| SRRD | HGNC: 33910 | 402055 | NM_001013694.2 |
| Stat3 | MGI: 103038 | 20848 | NM_011486.5 |
| Stat3 | MGI: 103038 | 20848 | NM_213659.3 |
| Stat3 | MGI: 103038 | 20848 | NM_213660.3 |
| Stat3 | MGI: 103038 | 20848 | NP_035616.1 |
| Stat3 | MGI: 103038 | 20848 | NP_998824.1 |
| Stat3 | MGI: 103038 | 20848 | NP_998825.1 |
| STAT3 | HGNC: 11364 | 6774 | XP_016880463.1 |
| STAT3 | HGNC: 11364 | 6774 | NM_003150.3 |
| Strada | MGI: 1919399 | 72149 | NM_001252448.1 |
| Strada | MGI: 1919399 | 72149 | NM_001252449.1 |
| Strada | MGI: 1919399 | 72149 | NM_028126.3 |
| Strada | MGI: 1919399 | 72149 | NP_001239377.1 |
| Strada | MGI: 1919399 | 72149 | NP_001239378.1 |
| Strada | MGI: 1919399 | 72149 | NP_082402.1 |
| STRADA | HGNC: 30172 | 92335 | XP_016880803.1 |
| STRADA | HGNC: 30172 | 92335 | NM_001165970.1 |
| Stub1 | MGI: 1891731 | 56424 | NM_019719.3 |
| Stub1 | MGI: 1891731 | 56424 | NP_062693.1 |
| STUB1 | HGNC: 11427 | 10273 | NP_001280126.1 |
| STUB1 | HGNC: 11427 | 10273 | NM_001293197.1 |
| Tacc3 | MGI: 1341163 | 21335 | NM_001040435.3 |
| Tacc3 | MGI: 1341163 | 21335 | NM_001310541.1 |
| Tacc3 | MGI: 1341163 | 21335 | NP_001035545.1 |
| Tacc3 | MGI: 1341163 | 21335 | NP_001297470.1 |
| TACC3 | HGNC: 11524 | 10460 | XP_005247986.1 |
| TACC3 | HGNC: 11524 | 10460 | NM_006342.2 |
| Tbc1d10b | MGI: 1915699 | 68449 | NM_144520.5 |
| Tbc1d10b | MGI: 1915699 | 68449 | NP_653105.3 |
| TBC1D10B | HGNC: 24510 | 26000 | XP_011544092.1 |
| TBC1D10B | HGNC: 24510 | 26000 | NM_015527.3 |
| Tbk1 | MGI: 1929658 | 56480 | NM_019786.4 |
| Tbk1 | MGI: 1929658 | 56480 | NP_062760.3 |
| TBK1 | HGNC: 11584 | 29110 | NP_037386.1 |
| TBK1 | HGNC: 11584 | 29110 | NM_013254.3 |
| Tcea1 | MGI: 1196624 | 21399 | NM_001159750.1 |
| Tcea1 | MGI: 1196624 | 21399 | NM_001159751.1 |
| Tcea1 | MGI: 1196624 | 21399 | NM_011541.4 |
| Tcea1 | MGI: 1196624 | 21399 | NP_001153222.1 |
| Tcea1 | MGI: 1196624 | 21399 | NP_001153223.1 |
| Tcea1 | MGI: 1196624 | 21399 | NP_035671.1 |

TABLE 1-continued

| Gene Symbol | Marker ID | NCBI Entrez Gene ID | NCBI GenBank ID |
|---|---|---|---|
| TCEA1 | HGNC: 11612 | 6917 | XP_006716530.1 |
| TCEA1 | HGNC: 11612 | 6917 | NM_201437.2 |
| Tcof1 | MGI: 892003 | 21453 | NM_001198984.1 |
| Tcof1 | MGI: 892003 | 21453 | NM_011552.3 |
| Tcof1 | MGI: 892003 | 21453 | NP_001185913.1 |
| Tcof1 | MGI: 892003 | 21453 | NP_035682.1 |
| TCOF1 | HGNC: 11654 | 6949 | XP_016865282.1 |
| TCOF1 | HGNC: 11654 | 6949 | NM_001135244.1 |
| Ten1 | MGI: 1916785 | 69535 | NM_027107.1 |
| Ten1 | MGI: 1916785 | 69535 | NP_081383.1 |
| TEN1 | HGNC: 37242 | 100134934 | NP_001106795.2 |
| TEN1 | HGNC: 37242 | 100134934 | NM_001113324.2 |
| Tgif1 | MGI: 1194497 | 21815 | NM_001164074.1 |
| Tgif1 | MGI: 1194497 | 21815 | NM_001164075.1 |
| Tgif1 | MGI: 1194497 | 21815 | NM_001164076.1 |
| Tgif1 | MGI: 1194497 | 21815 | NM_001164077.1 |
| Tgif1 | MGI: 1194497 | 21815 | NM_009372.3 |
| Tgif1 | MGI: 1194497 | 21815 | NP_001157546.1 |
| Tgif1 | MGI: 1194497 | 21815 | NP_001157547.1 |
| Tgif1 | MGI: 1194497 | 21815 | NP_001157548.1 |
| Tgif1 | MGI: 1194497 | 21815 | NP_001157549.1 |
| Tgif1 | MGI: 1194497 | 21815 | NP_033398.2 |
| TGIF1 | HGNC: 11776 | 7050 | NP_775301.1 |
| TGIF1 | HGNC: 11776 | 7050 | NM_170695.3 |
| Tgif2 | MGI: 1915299 | 228839 | NM_001291124.1 |
| Tgif2 | MGI: 1915299 | 228839 | NM_173396.3 |
| Tgif2 | MGI: 1915299 | 228839 | NP_001278053.1 |
| Tgif2 | MGI: 1915299 | 228839 | NP_775572.1 |
| TGIF2 | HGNC: 15764 | 60436 | NP_068581.1 |
| TGIF2 | HGNC: 15764 | 60436 | NM_001199514.1 |
| Tial1 | MGI: 107913 | 21843 | NM_001347640.1 |
| Tial1 | MGI: 107913 | 21843 | NM_001347641.1 |
| Tial1 | MGI: 107913 | 21843 | NM_009383.2 |
| Tial1 | MGI: 107913 | 21843 | NP_001334569.1 |
| Tial1 | MGI: 107913 | 21843 | NP_001334570.1 |
| Tial1 | MGI: 107913 | 21843 | NP_033409.1 |
| TIAL1 | HGNC: 11804 | 7073 | NP_001310893.1 |
| TIAL1 | HGNC: 11804 | 7073 | NM_001323970.1 |
| Tiparp | MGI: 2159210 | 99929 | NM_178892.5 |
| Tiparp | MGI: 2159210 | 99929 | NP_849223.2 |
| TIPARP | HGNC: 23696 | 25976 | NP_001171646.1 |
| TIPARP | HGNC: 23696 | 25976 | NM_001184717.1 |
| Tk1 | MGI: 98763 | 21877 | NM_001271729.1 |
| Tk1 | MGI: 98763 | 21877 | NM_009387.2 |
| Tk1 | MGI: 98763 | 21877 | NP_001258658.1 |
| Tk1 | MGI: 98763 | 21877 | NP_033413.2 |
| TK1 | HGNC: 11830 | 7083 | XP_016880481.1 |
| TK1 | HGNC: 11830 | 7083 | NM_001346663.1 |
| Tk2 | MGI: 1913266 | 57813 | NM_021028.3 |
| Tk2 | MGI: 1913266 | 57813 | NP_066356.3 |
| Tk2 | MGI: 1913266 | 57813 | NR_045642.1 |
| TK2 | HGNC: 11831 | 7084 | NP_001166114.1 |
| TK2 | HGNC: 11831 | 7084 | NM_001271934.1 |
| Tlcd1 | MGI: 1915572 | 68385 | NM_001291235.1 |
| Tlcd1 | MGI: 1915572 | 68385 | NM_001291236.1 |
| Tlcd1 | MGI: 1915572 | 68385 | NM_001291237.1 |
| Tlcd1 | MGI: 1915572 | 68385 | NM_026708.2 |
| Tlcd1 | MGI: 1915572 | 68385 | NP_001278164.1 |
| Tlcd1 | MGI: 1915572 | 68385 | NP_001278165.1 |
| Tlcd1 | MGI: 1915572 | 68385 | NP_001278166.1 |
| Tlcd1 | MGI: 1915572 | 68385 | NP_080984.1 |
| TLCD1 | HGNC: 25177 | 116238 | XP_011522580.1 |
| TLCD1 | HGNC: 25177 | 116238 | NM_001160407.1 |
| Tm2d1 | MGI: 2137022 | 94043 | NM_053157.2 |
| Tm2d1 | MGI: 2137022 | 94043 | NP_444387.1 |
| TM2D1 | HGNC: 24142 | 83941 | NP_114416.1 |
| TM2D1 | HGNC: 24142 | 83941 | NM_032027.2 |
| Tm2d3 | MGI: 1915884 | 68634 | NM_026795.3 |
| Tm2d3 | MGI: 1915884 | 68634 | NM_178056.3 |
| Tm2d3 | MGI: 1915884 | 68634 | NP_081071.1 |
| Tm2d3 | MGI: 1915884 | 68634 | NP_835157.1 |
| TM2D3 | HGNC: 24128 | 80213 | NP_079417.2 |
| TM2D3 | HGNC: 24128 | 80213 | NM_078474.2 |
| Tmed10 | MGI: 1915831 | 68581 | NM_026775.4 |
| Tmed10 | MGI: 1915831 | 68581 | NP_081051.1 |
| TMED10 | HGNC: 16998 | 10972 | NP_006818.3 |
| TMED10 | HGNC: 16998 | 10972 | NM_006827.5 |
| Tmed2 | MGI: 1929269 | 56334 | NM_019770.2 |
| Tmed2 | MGI: 1929269 | 56334 | NP_062744.1 |
| TMED2 | HGNC: 16996 | 10959 | NP_001308374.1 |
| TMED2 | HGNC: 16996 | 10959 | NM_001321445.1 |
| Tmem165 | MGI: 894407 | 21982 | NM_011626.2 |
| Tmem165 | MGI: 894407 | 21982 | NP_035756.2 |
| TMEM165 | HGNC: 30760 | 55858 | NP_060945.2 |
| TMEM165 | HGNC: 30760 | 55858 | NM_018475.4 |
| Tmem41b | MGI: 1289225 | 233724 | NM_153525.5 |
| Tmem41b | MGI: 1289225 | 233724 | NP_705745.3 |
| TMEM41B | HGNC: 28948 | 440026 | NP_001158502.1 |
| TMEM41B | HGNC: 28948 | 440026 | NM_015012.3 |
| Tmx2 | MGI: 1914208 | 66958 | NM_001290751.1 |
| Tmx2 | MGI: 1914208 | 66958 | NM_025868.4 |
| Tmx2 | MGI: 1914208 | 66958 | NP_001277680.1 |
| Tmx2 | MGI: 1914208 | 66958 | NP_080144.1 |
| TMX2 | HGNC: 30739 | 51075 | NP_001334821.1 |
| TMX2 | HGNC: 30739 | 51075 | NM_001347896.1 |
| Traf2 | MGI: 101835 | 22030 | NM_001290413.1 |
| Traf2 | MGI: 101835 | 22030 | NM_009422.3 |
| Traf2 | MGI: 101835 | 22030 | NP_001277342.1 |
| Traf2 | MGI: 101835 | 22030 | NP_033448.2 |
| TRAF2 | HGNC: 12032 | 7186 | XP_016870583.1 |
| TRAF2 | HGNC: 12032 | 7186 | NM_021138.3 |
| Traf3 | MGI: 108041 | 22031 | NM_001286122.1 |
| Traf3 | MGI: 108041 | 22031 | NM_011632.3 |
| Traf3 | MGI: 108041 | 22031 | NP_001273051.1 |
| Traf3 | MGI: 108041 | 22031 | NP_035762.2 |
| TRAF3 | HGNC: 12033 | 7187 | XP_016877106.1 |
| TRAF3 | HGNC: 12033 | 7187 | NM_001199427.1 |
| Trex1 | MGI: 1328317 | 22040 | NM_001012236.1 |
| Trex1 | MGI: 1328317 | 22040 | NM_011637.6 |
| Trex1 | MGI: 1328317 | 22040 | NP_001012236.1 |
| Trex1 | MGI: 1328317 | 22040 | NP_035767.4 |
| TREX1 | HGNC: 12269 | 11277 | NP_057465.1 |
| TREX1 | HGNC: 12269 | 11277 | NM_033629.4 |
| Trip11 | MGI: 1924393 | 109181 | NM_028446.1 |
| Trip11 | MGI: 1924393 | ` | NP_082722.1 |
| TRIP11 | HGNC: 12305 | 9321 | NM_001308780.1 |
| TRIP11 | HGNC: 12305 | 9321 | NM_001321851.1 |
| Trip13 | MGi: 1916966 | 69716 | NM_027182.2 |
| Trip13 | MGI: 1916966 | 69716 | NP_081458.1 |
| TRIP13 | HGNC: 12307 | 9319 | NP_004228.1 |
| TRIP13 | HGNC: 12307 | 9319 | NM_004237.3 |
| Tsc2 | MGI: 102548 | 22084 | NM_001039363.2 |
| Tsc2 | MGI: 102548 | 22084 | NM_001286713.1 |
| Tsc2 | MGI: 102548 | 22084 | NM_001286714.1 |
| Tsc2 | MGI: 102548 | 22084 | NM_001286716.1 |
| Tsc2 | MGI: 102548 | 22084 | NM_001286718.1 |
| Tsc2 | MGI: 102548 | 22084 | NM_001286720.1 |
| Tsc2 | MGI: 102548 | 22084 | NM_011647.3 |
| Tsc2 | MGI: 102548 | 22084 | NP_001034452.1 |
| Tsc2 | MGI: 102548 | 22084 | NP_001273642.1 |
| Tsc2 | MGI: 102548 | 22084 | NP_001273643.1 |
| Tsc2 | MGI: 102548 | 22084 | NP_001273645.1 |
| Tsc2 | MGI: 102548 | 22084 | NP_001273647.1 |
| Tsc2 | MGI: 102548 | 22084 | NP_001273649.1 |
| Tsc2 | MGI: 102548 | 22084 | NP_035777.2 |
| TSC2 | HGNC: 12363 | 7249 | NP_001305761.1 |
| TSC2 | HGNC: 12363 | 7249 | NM_021056.1 |
| Ttc33 | MGI: 1914765 | 67515 | NM_026213.3 |
| Ttc33 | MGI: 1914765 | 67515 | NP_080489.1 |
| TTC33 | HGNC: 29959 | 23548 | NP_036514.1 |
| TTC33 | HGNC: 29959 | 23548 | NM_012382.2 |
| Tubb2b | MGI: 1920960 | 73710 | NM_023716.2 |
| Tubb2b | MGI: 1920960 | 73710 | NP_076205.1 |
| TUBB2B | HGNC: 30829 | 347733 | NP_821080.1 |
| TUBB2B | HGNC: 30829 | 347733 | NM_178012.4 |
| Tvp23b | MGI: 1914760 | 67510 | NM_026210.4 |
| Tvp23b | MGI: 1914760 | 67510 | NP_080486.1 |
| TVP23B | HGNC: 20399 | 51030 | NP_001303849.1 |
| TVP23B | HGNC: 20399 | 51030 | NM_001316921.1 |
| Txndc15 | MGI: 1916922 | 69672 | NM_175150.3 |
| Txndc15 | MGI: 1916922 | 69672 | NP_780359.2 |
| TXNDC15 | HGNC: 20652 | 79770 | NP_078991.3 |
| TXNDC15 | HGNC: 20652 | 79770 | NM_024715.3 |
| Uba6 | MGI: 1913894 | 231380 | NM_172712.2 |

TABLE 1-continued

| Gene Symbol | Marker ID | NCBI Entrez Gene ID | NCBI GenBank ID |
|---|---|---|---|
| Uba6 | MGI: 1913894 | 231380 | NP_766300.1 |
| UBA6 | HGNC: 25581 | 55236 | NP_060697.4 |
| UBA6 | HGNC: 25581 | 55236 | NM_018227.5 |
| Ube2h | MGI: 104632 | 22214 | NM_001169576.1 |
| Ube2h | MGI: 104632 | 22214 | NM_001169577.1 |
| Ube2h | MGI: 104632 | 22214 | NM_009459.3 |
| Ube2h | MGI: 104632 | 22214 | NP_001163047.1 |
| Ube2h | MGI: 104632 | 22214 | NP_001163048.1 |
| Ube2h | MGI: 104632 | 22214 | NP_033485.1 |
| UBE2H | HGNC: 12484 | 7328 | NP_001189427.1 |
| UBE2H | HGNC: 12484 | 7328 | NM_001202498.1 |
| Ube2j2 | MGI: 2153608 | 140499 | NM_001039157.2 |
| Ube2j2 | MGI: 2153608 | 140499 | NM_001039158.2 |
| Ube2j2 | MGI: 2153608 | 140499 | NM_001039159.2 |
| Ube2j2 | MGI: 2153608 | 140499 | NM_001284312.1 |
| Ube2j2 | MGI: 2153608 | 140499 | NM_001284314.1 |
| Ube2j2 | MGI: 2153608 | 140499 | NM_021402.6 |
| Ube2j2 | MGI: 2153608 | 140499 | NP_001034246.1 |
| Ube2j2 | MGI: 2153608 | 140499 | NP_001034247.1 |
| Ube2j2 | MGI: 2153608 | 140499 | NP_001034248.1 |
| Ube2j2 | MGI: 2153608 | 140499 | NP_001271241.1 |
| Ube2j2 | MGI: 2153608 | 140499 | NP_001271243.1 |
| Ube2j2 | MGI: 2153608 | 140499 | NP_067377.4 |
| UBE2J2 | HGNC: 19268 | 118424 | XP_016855728.1 |
| UBE2J2 | HGNC: 19268 | 118424 | NM_194315.1 |
| Ube2k | MGI: 1858216 | 53323 | NM_001310618.1 |
| Ube2k | MGI: 1858216 | 53323 | NM_001310619.1 |
| Ube2k | MGI: 1858216 | 53323 | NM_016786.4 |
| Ube2k | MGI: 1858216 | 53323 | NP_001297547.1 |
| Ube2k | MGI: 1858216 | 53323 | NP_001297548.1 |
| Ube2k | MGI: 1858216 | 53323 | NP_058066.2 |
| Ube2k | MGI: 1858216 | 53323 | NR_144566.1 |
| UBE2K | HGNC: 4914 | 3093 | NP_001104582.1 |
| UBE2K | HGNC: 4914 | 3093 | NM_001312647.1 |
| Ube2n | MGI: 1934835 | 93765 | NM_080560.3 |
| Ube2n | MGI: 1934835 | 93765 | NP_542127.1 |
| UBE2N | HGNC: 12492 | 7334 | XP_016875407.1 |
| UBE2N | HGNC: 12492 | 7334 | NM_003348.3 |
| Ube2r2 | MGI: 1914865 | 67615 | NM_026275.4 |
| Ube2r2 | MGI: 1914865 | 67615 | NP_080551.1 |
| UBE2R2 | HGNC: 19907 | 54926 | XP_016870349.1 |
| UBE2R2 | HGNC: 19907 | 54926 | NM_017811.3 |
| Ubr4 | MGI: 1916366 | 69116 | NM_001160319.1 |
| Ubr4 | MGI: 1916366 | 69116 | NP_001153791.1 |
| UBR4 | HGNC: 30313 | 23352 | XP_011539413.1 |
| UBR4 | HGNC: 30313 | 23352 | NM_020765.2 |
| Ubtd1 | MGI: 2385092 | 226122 | NM_145500.3 |
| Ubtd1 | MGI: 2385092 | 226122 | NP_663475.1 |
| UBTD1 | HGNC: 25683 | 80019 | NP_079230.1 |
| UBTD1 | HGNC: 25683 | 80019 | NM_024954.4 |
| Uggt1 | MGI: 2443162 | 320011 | NM_198899.2 |
| Uggt1 | MGI: 2443162 | 320011 | NP_942602.2 |
| UGGT1 | HGNC: 15663 | 56886 | XP_016859997.1 |
| UGGT1 | HGNC: 15663 | 56886 | NM_020120.3 |
| Ugp2 | MGI: 2183447 | 216558 | NM_001290634.1 |
| Ugp2 | MGI: 2183447 | 216558 | NM_139297.6 |
| Ugp2 | MGI: 2183447 | 216558 | NP_001277563.1 |
| Ugp2 | MGI: 2183447 | 216558 | NP_647458.1 |
| UGP2 | HGNC: 12527 | 7360 | XP_016860346.1 |
| UGP2 | HGNC: 12527 | 7360 | NM_001001521.1 |
| Usp18 | MGI: 1344364 | 24110 | NM_011909.2 |
| Usp18 | MGI: 1344364 | 24110 | NP_036039.2 |
| USP18 | HGNC: 12616 | 11274 | NP_059110.2 |
| USP18 | HGNC: 12616 | 11274 | NM_017414.3 |
| Usp19 | MGI: 1918722 | 71472 | NM_001168371.2 |
| Usp19 | MGI: 1918722 | 71472 | NM_001168372.2 |
| Usp19 | MGI: 1918722 | 71472 | NM_001168373.2 |
| Usp19 | MGI: 1918722 | 71472 | NM_027804.4 |
| Usp19 | MGI: 1918722 | 71472 | NM_145407.3 |
| Usp19 | MGI: 1918722 | 71472 | NP_001161843.1 |
| Usp19 | MGI: 1918722 | 71472 | NP_001161844.1 |
| Usp19 | MGI: 1918722 | 71472 | NP_001161845.1 |
| Usp19 | MGI: 1918722 | 71472 | NP_082080.3 |
| Usp19 | MGI: 1918722 | 71472 | NP_663382.2 |
| USP19 | HGNC: 12617 | 10869 | XP_006713013.1 |
| USP19 | HGNC: 12617 | 10869 | NM_001199161.1 |
| Usp24 | MGI: 1919936 | 329908 | NM_183225.2 |
| Usp24 | MGI: 1919936 | 329908 | NP_899048.2 |
| USP24 | HGNC: 12623 | 23358 | XP_016856325.1 |
| USP24 | HGNC: 12623 | 23358 | NM_015306.2 |
| Vps11 | MGI: 1918982 | 71732 | XM_017313598.1 |
| Vps11 | MGI: 1918982 | 71732 | NP_082165.1 |
| VPS11 | HGNC: 14583 | 55823 | NP_001277114.1 |
| VPS11 | HGNC: 14583 | 55823 | NM_001290185.1 |
| Vps16 | MGI: 2136772 | 80743 | NM_030559.3 |
| Vps16 | MGI: 2136772 | 80743 | NP_085036.3 |
| VPS16 | HGNC: 14584 | 64601 | NP_536338.1 |
| VPS16 | HGNC: 14584 | 64601 | NM_080413.2 |
| Vps29 | MGI: 1928344 | 56433 | NM_001347453.1 |
| Vps29 | MGI: 1928344 | 56433 | NM_019780.1 |
| Vps29 | MGI: 1928344 | 56433 | NP_001334382.1 |
| Vps29 | MGI: 1928344 | 56433 | NP_062754.1 |
| VPS29 | HGNC: 14340 | 51699 | XP_006719523.1 |
| VPS29 | HGNC: 14340 | 51699 | NM_016226.4 |
| Vps33a | MGI: 1924823 | 77573 | NM_029929.3 |
| Vps33a | MGI: 1924823 | 77573 | NP_084205.3 |
| VPS33A | HGNC: 18179 | 65082 | NP_001337950.1 |
| VPS33A | HGNC: 18179 | 65082 | NM_001351019.1 |
| Vps4b | MGI: 1100499 | 20479 | NM_009190.2 |
| Vps4b | MGI: 1100499 | 20479 | NP_033216.2 |
| VPS4B | HGNC: 10895 | 9525 | XP_006722645.1 |
| VPS4B | HGNC: 10895 | 9525 | NM_004869.3 |
| Wdr26 | MGI: 1923825 | 226757 | NM_145514.5 |
| Wdr26 | MGI: 1923825 | 226757 | NP_663489.4 |
| WDR26 | HGNC: 21208 | 80232 | XP_016857885.1 |
| WDR26 | HGNC: 21208 | 80232 | NM_025160.6 |
| Xrcc1 | MGI: 99137 | 22594 | NM_009532.4 |
| Xrcc1 | MGI: 99137 | 22594 | NP_033558.3 |
| XRCC1 | HGNC: 12828 | 7515 | NP_006288.2 |
| XRCC1 | HGNC: 12828 | 7515 | NM_006297.2 |
| Xrcc2 | MGI: 1927345 | 57434 | NM_020570.2 |
| Xrcc2 | MGI: 1927345 | 57434 | NP_065595.2 |
| XRCC2 | HGNC: 12829 | 7516 | NP_005422.1 |
| XRCC2 | HGNC: 12829 | 7516 | NM_005431.1 |
| Xrcc4 | MGI: 1333799 | 108138 | NM_028012.4 |
| Xrcc4 | MGI: 1333799 | 108138 | NP_082288.1 |
| XRCC4 | HGNC: 12831 | 7518 | NP_003392.1 |
| XRCC4 | HGNC: 12831 | 7518 | NM_022406.3 |
| Xrcc5 | MGI: 104517 | 22596 | NM_009533.2 |
| Xrcc5 | MGI: 104517 | 22596 | NP_033559.2 |
| XRCC5 | HGNC: 12833 | 7520 | NP_066964.1 |
| XRCC5 | HGNC: 12833 | 7520 | NM_021141.3 |
| Ypel5 | MGI: 1916937 | 383295 | XM_006524538.1 |
| Ypel5 | MGI: 1916937 | 383295 | NP_081442.1 |
| YPEL5 | HGNC: 18329 | 51646 | XP_016859810.1 |
| YPEL5 | HGNC: 18329 | 51646 | NM_001127399.1 |
| Ywhaz | MGI: 109484 | 22631 | NM_001253805.1 |
| Ywhaz | MGI: 109484 | 22631 | NM_001253806.1 |
| Ywhaz | MGI: 109484 | 22631 | NM_001253807.1 |
| Ywhaz | MGI: 109484 | 22631 | NM_011740.3 |
| Ywhaz | MGI: 109484 | 22631 | NP_001240734.1 |
| Ywhaz | MGI: 109484 | 22631 | NP_001240735.1 |
| Ywhaz | MGI: 109484 | 22631 | NP_001240736.1 |
| Ywhaz | MGI: 109484 | 22631 | NP_035870.1 |
| YWHAZ | HGNC: 12855 | 7534 | XP_016869301.1 |
| YWHAZ | HGNC: 12855 | 7534 | NM_001135699.1 |
| Zc3h18 | MGI: 1923264 | 76014 | NM_001029993.1 |
| Zc3h18 | MGI: 1923264 | 76014 | NM_001029994.1 |
| Zc3h18 | MGI: 1923264 | 76014 | NM_001310650.1 |
| Zc3h18 | MGI: 1923264 | 76014 | NP_001025164.1 |
| Zc3h18 | MGI: 1923264 | 76014 | NP_001025165.1 |
| Zc3h18 | MGI: 1923264 | 76014 | NP_001297579.1 |
| ZC3H18 | HGNC: 25091 | 124245 | NP_653205.3 |
| ZC3H18 | HGNC: 25091 | 124245 | NM_144604.3 |
| Zfp148 | MGI: 1332234 | 22661 | NM_011749.4 |
| Zfp148 | MGI: 1332234 | 22661 | NP_035879.1 |
| ZNF148 | HGNC: 12933 | 7707 | NP_001335353.1 |
| ZNF148 | HGNC: 12933 | 7707 | NM_001348436.1 |
| Zfp273 | MGI: 3036278 | 212569 | NM_198322.3 |
| Zfp273 | MGI: 3036278 | 212569 | NP_938081.2 |
| ZNF676 | HGNC: 20429 | 163223 | NP_001001411.2 |
| ZNF676 | HGNC: 20429 | 163223 | NM_001001411.2 |
| Zfp281 | MGI: 3029290 | 226442 | NM_001160251.1 |
| Zfp281 | MGI: 3029290 | 226442 | NM_177643.4 |

TABLE 1-continued

| Gene Symbol | Marker ID | NCBI Entrez Gene ID | NCBI GenBank ID |
|---|---|---|---|
| Zfp281 | MGI: 3029290 | 226442 | NP_001153723.1 |
| Zfp281 | MGI: 3029290 | 226442 | NP_808311.1 |
| ZNF281 | HGNC: 13075 | 23528 | NP_036614.1 |
| ZNF281 | HGNC: 13075 | 23528 | NM_001281294.1 |
| Zfp473 | MGI: 2442697 | 243963 | NM_001289836.1 |
| Zfp473 | MGI: 2442697 | 243963 | NM_001289837.1 |
| Zfp473 | MGI: 2442697 | 243963 | NM_001289838.1 |
| Zfp473 | MGI: 2442697 | 243963 | NM_001289839.1 |
| Zfp473 | MGI: 2442697 | 243963 | NM_178734.4 |
| Zfp473 | MGI: 2442697 | 243963 | NP_001276765.1 |
| Zfp473 | MGI: 2442697 | 243963 | NP_001276766.1 |
| Zfp473 | MGI: 2442697 | 243963 | NP_001276767.1 |
| Zfp473 | MGI: 2442697 | 243963 | NP_001276768.1 |
| Zfp473 | MGI: 2442697 | 243963 | NP_848849.2 |
| ZNF473 | HGNC: 23239 | 25888 | XP_016882063.1 |
| ZNF473 | HGNC: 23239 | 25888 | NM_001308424.2 |
| Zfp827 | MGI: 2444807 | 622675 | NM_001294279.1 |
| Zfp827 | MGI: 2444807 | 622675 | NM_178267.3 |
| Zfp827 | MGI: 2444807 | 622675 | NP_001281208.1 |
| Zfp827 | MGI: 2444807 | 622675 | NP_839998.2 |
| ZNF827 | HGNC: 27193 | 152485 | XP_016863262.1 |
| ZNF827 | HGNC: 27193 | 152485 | NM_001306215.1 |

TABLE 2

| Gene Symbol | Marker ID | NCBI Entrez Gene ID | NCBI GenBank ID |
|---|---|---|---|
| B2m | MGI: 88127 | 12010 | NM_009735.3 |
| B2m | MGI: 88127 | 12010 | NP_033865.2 |
| B2M | HGNC: 914 | 567 | NP_004039.1 |
| B2M | HGNC: 914 | 567 | NM_004048.2 |
| Derl2 | MGI: 2151483 | 116891 | NM_001291146.1 |
| Derl2 | MGI: 2151483 | 116891 | NM_001291147.1 |
| Derl2 | MGI: 2151483 | 116891 | NM_001291148.1 |
| Derl2 | MGI: 2151483 | 116891 | NM_033562.4 |
| Derl2 | MGI: 2151483 | 116891 | NP_001278075.1 |
| Derl2 | MGI: 2151483 | 116891 | NP_001278076.1 |
| Derl2 | MGI: 2151483 | 116891 | NP_001278077.1 |
| Derl2 | MGI: 2151483 | 116891 | NP_291040.1 |
| DERL2 | HGNC: 17943 | 51009 | NP_001291708.1 |
| DERL2 | HGNC: 17943 | 51009 | NM_001304779.1 |
| Dusp6 | MGI: 1914853 | 67603 | NM_026268.3 |
| Dusp6 | MGI: 1914853 | 67603 | NP_080544.1 |
| DUSP6 | HGNC: 3072 | 1848 | NP_073143.2 |
| DUSP6 | HGNC: 3072 | 1848 | NM_022652.3 |
| H2-D1 | MGI: 95896 | 14964 | NM_010380.3 |
| H2-D1 | MGI: 95896 | 14964 | NP_034510.3 |
| HLA-A | HGNC: 4931 | 3105 | NP_001229687.1 |
| HLA-A | HGNC: 4931 | 3105 | NM_001242758.1 |
| Ifngr1 | MGI: 107655 | 15979 | NM_010511.3 |
| Ifngr1 | MGI: 107655 | 15979 | NP_034644.1 |
| IFNGR1 | HGNC: 5439 | 3459 | XP_006715534.1 |
| IFNGR1 | HGNC: 5439 | 3459 | NM_000416.2 |
| Ifngr2 | MGI: 107654 | 15980 | NM_008338.3 |
| Ifngr2 | MGI: 107654 | 15980 | NP_032364.1 |
| IFNGR2 | HGNC: 5440 | 3460 | XP_011527855.1 |
| IFNGR2 | HGNC: 5440 | 3460 | NM_001329128.1 |
| Jak1 | MGI: 96628 | 16451 | NM_146145.2 |
| Jak1 | MGI: 96628 | 16451 | NP_666257.2 |
| JAK1 | HGNC: 6190 | 3716 | NP_001320783.1 |
| JAK1 | HGNC: 6190 | 3716 | NM_001320923.1 |
| Jak2 | MGI: 96629 | 16452 | NM_001048177.2 |
| Jak2 | MGI: 96629 | 16452 | NM_008413.3 |
| Jak2 | MGI: 96629 | 16452 | NP_001041642.1 |
| Jak2 | MGI: 96629 | 16452 | NP_032439.2 |
| JAK2 | HGNC: 6192 | 3717 | NP_001309128.1 |
| JAK2 | HGNC: 6192 | 3717 | NM_001322204.1 |
| Lztr1 | MGI: 1914113 | 66863 | NM_001331226.1 |
| Lztr1 | MGI: 1914113 | 66863 | NM_001331227.1 |
| Lztr1 | MGI: 1914113 | 66863 | NM_025808.4 |
| Lztr1 | MGI: 1914113 | 66863 | NP_001318155.1 |
| Lztr1 | MGI: 1914113 | 66863 | NP_001318156.1 |
| Lztr1 | MGI: 1914113 | 66863 | NP_080084.2 |
| LZTR1 | HGNC: 6742 | 8216 | NP_006758.2 |
| LZTR1 | HGNC: 6742 | 8216 | NM_006767.3 |
| Mbnl1 | MGI: 1928482 | 56758 | NM_001253708.2 |
| Mbnl1 | MGI: 1928482 | 56758 | NM_001253709.2 |
| Mbnl1 | MGI: 1928482 | 56758 | NM_001253710.2 |
| Mbnl1 | MGI: 1928482 | 56758 | NM_001253711.2 |
| Mbnl1 | MGI: 1928482 | 56758 | NM_001253713.2 |
| Mbnl1 | MGI: 1928482 | 56758 | NM_001310514.1 |
| Mbnl1 | MGI: 1928482 | 56758 | NM_020007.4 |
| Mbnl1 | MGI: 1928482 | 56758 | NP_001240637.1 |
| Mbnl1 | MGI: 1928482 | 56758 | NP_001240638.1 |
| Mbnl1 | MGI: 1928482 | 56758 | NP_001240639.1 |
| Mbnl1 | MGI: 1928482 | 56758 | NP_001240640.1 |
| Mbnl1 | MGI: 1928482 | 56758 | NP_001240642.1 |
| Mbnl1 | MGI: 1928482 | 56758 | NP_001297443.1 |
| Mbnl1 | MGI: 1928482 | 56758 | NP_064391.2 |
| MBNL1 | HGNC: 6923 | 4154 | XP_005247534.1 |
| MBNL1 | HGNC: 6923 | 4154 | NM_207293.1 |
| Nf1 | MGI: 97306 | 18015 | NM_010897.2 |
| Nf1 | MGI: 97306 | 18015 | NP_035027.1 |
| NF1 | HGNC: 7765 | 4763 | NP_001035957.1 |
| NF1 | HGNC: 7765 | 4763 | NM_000267.3 |
| Stat1 | MGI: 103063 | 20846 | NM_001205313.1 |
| Stat1 | MGI: 103063 | 20846 | NM_001205314.1 |
| Stat1 | MGI: 103063 | 20846 | NM_009283.4 |
| Stat1 | MGI: 103063 | 20846 | NP_001192242.1 |
| Stat1 | MGI: 103063 | 20846 | NP_001192243.1 |
| Stat1 | MGI: 103063 | 20846 | NP_033309.3 |
| STAT1 | HGNC: 11362 | 6772 | XP_006712781.1 |
| STAT1 | HGNC: 11362 | 6772 | NM_139266.2 |
| Syvn1 | MGI: 1921376 | 74126 | NM_001164709.1 |
| Syvn1 | MGI: 1921376 | 74126 | NM_028769.5 |
| Syvn1 | MGI: 1921376 | 74126 | NP_001158181.1 |
| Syvn1 | MGI: 1921376 | 74126 | NP_083045.4 |
| SYVN1 | HGNC: 20738 | 84447 | XP_011543605.1 |
| SYVN1 | HGNC: 20738 | 84447 | NM_032431.2 |
| Tap1 | MGI: 98483 | 21354 | NM_001161730.1 |
| Tap1 | MGI: 98483 | 21354 | NM_013683.2 |
| Tap1 | MGI: 98483 | 21354 | NP_001155202.1 |
| Tap1 | MGI: 98483 | 21354 | NP_038711.2 |
| TAP1 | HGNC: 43 | 6890 | NP_000584.2 |
| TAP1 | HGNC: 43 | 6890 | NM_001292022.1 |
| Tap2 | MGI: 98484 | 21355 | NM_011530.1 |
| Tap2 | MGI: 98484 | 21355 | NP_035660.3 |
| TAP2 | HGNC: 44 | 6891 | NP_000535.3 |
| TAP2 | HGNC: 44 | 6891 | NM_000544.3 |
| Ube2g2 | MGI: 1343188 | 22213 | NM_019803.3 |
| Ube2g2 | MGI: 1343188 | 22213 | NP_062777.2 |
| UBE2G2 | HGNC: 12483 | 7327 | NP_001189418.1 |
| UBE2G2 | HGNC: 12483 | 7327 | NM_182688.2 |

\* The nucleic acid and polypeptide sequences of the biomarkers of the present invention listed in Table 2 have been submitted at GenBank under the unique identifier provided herein and each such uniquely identified sequence submitted at GenBank is hereby incorporated in its entirety by reference.
\* Included in Table 2 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any publicly available sequence listed in Table 2, or a portion thereof. Such nucleic acid molecules can have a function of the full-length nucleic acid as described further herein.
\* Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any publicly available sequence listed in Table 2, or a portion thereof. Such polypeptides can have a function of the full-length polypeptide as described further herein.
\* Included in Table 2 are any known components of the MHC class I pathway required for presentation of tumor-derived peptides to T cells (including H2-D1, B2m, Tap1, and Tap2), any known component of the IFγ and IFNα/β recognition and signaling pathway (including Jak1, Jak2, Stat1, Ifngr 1 and Infngr 2), and negative regulators of Ras/MAPK pathways (including Nf1 and Dusp6), as well as orthologs of the pathway components and nucleic acid and amino acid variants having the recited homology described in the immediately preceding paragraphs and elsewhere herein.

II. Subjects

In one embodiment, the subject for whom an agent sensitizing cancer cells to T cell mediated killing is administered (e.g., at least one modulator of biomarkers listed in Tables 1-9), or whose predicted likelihood of efficacy of the agent for treating a cancer is determined, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to cancer therapy (e.g., at least one modulator of biomarkers listed in Tables 1-9) of many different cancers in subjects such as those described herein. In one embodiment, the cancers are melanoma, head and neck squamous carcinoma, kidney cancer, and lung adenocarcinoma and squamous carcinoma.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to cancer therapy (e.g., at least one modulator of biomarkers listed in Tables 1-9), and/or evaluate a response to a combination cancer therapy (e.g., at least one modulator of biomarkers listed in Tables 1-9 in combination of at least one immunotherapy). A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of cancer therapy. Post-treatment biomarker measurement can be made at any time after initiation of cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of cancer therapy, and even longer toward indefinitely for continued monitoring. Treatment can comprise cancer therapy, such as a therapeutic regimen comprising one or more modulators of at least one biomarker listed in Tables 1-9 alone or in combination with other cancer agents, such as with immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N Y, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of Current Protocols in Molecular Biology, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood-or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al. (1987) *Nucleic Acids Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach (1988) *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak (1993) *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al. (1996) *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), *supra*; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), *supra*; or as probes or primers for DNA sequence and hybridization (Hyrup (1996), *supra*; Perry-O'Keefe et al. (1996) *Proc. Natl. Acad. Sci. USA* 93:14670-14675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), *supra*). The synthesis of PNA-DNA chimeras can be performed as described in Hyrup (1996), *supra*, and Finn et al. (1996) *Nucleic Acids Res.* 24(17):3357-3363. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973-5988). PNA monomers are then coupled in a step-wise manner to produce a chimeric molecule with a 5' PNA segment and a 3' DNA segment (Finn et al. (1996) *Nucleic Acids Res.* 24:3357-3363). Alternatively, chimeric molecules can be synthesized with a 5' DNA segment and a 3' PNA segment (Peterser et al. (1975) *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958-976) or intercalating agents (see, e.g., Zon (1988) *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See www.ncbi.nlm-.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan (1992) *Proc. Natl. Acad. Sci. USA* 89:7811-7815; Delgrave et al. 91993) *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, *supra*. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al. (1988) *Gene* 69:301-315) and pET 11d (Studier et al., p. 60-89, In *Gene Expression Technology: Methods in Enzymology* vol. 185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, *In Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al. (1987) *EMBO J.* 6:229-234), pMFa (Kurjan and Herskowitz (1982) *Cell* 30:933-943), pJRY88 (Schultz et al. (1987) *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al. (1983)*Mol. Cell Biol.* 3:2156-2165) and the pVL series (Lucklow and Summers (1989) *Virology* 170:31-39).

In yet another embodiment, a nucleic acid of the present invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., *supra*.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Camper and Tilghman (1989) *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al. (1986) *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (*supra*), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number and/or Genomic Nucleic Acid Mutations

Methods of evaluating the copy number and/or genomic nucleic acid status (e.g., mutations) of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. In some embodiments, the increased copy number of at least one biomarker listed in Table 1, 5, 7 or 9, and/or the decreased copy number of at least one biomarker listed in Table 2, 4, 6 or 8 is predictive of poor outcome of cancer therapy (e.g., at least one modulator of biomarkers listed in Tables 1-9). A copy number of at least 3, 4, 5, 6, 7, 8, 9, or 10 of at least one biomarker listed in Tables 1-9 is predictive of likely responsive to cancer therapy (e.g., at least one modulator of biomarkers listed in Tables 1-9).

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., *supra*, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., *supra*, and Jena et al., *supra*).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to a modulator of T cell mediated cytotoxicity alone or in combination with an immunotherapy treatment. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as to not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (un-labeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect T cell mediated killing of cancer cells.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) *supra*. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992)*Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Cancer Therapies

The efficacy of cancer therapy (e.g., at least one modulator of biomarkers listed in Tables 1-9) is predicted according to biomarker presence, absence, amount and/or activity associated with a cancer in a subject according to the methods described herein. In one embodiment, such cancer therapy (e.g., at least one modulator of biomarkers listed in Tables 1-9) or combinations of therapies (e.g., at least one modulator of biomarkers listed in Tables 1-9, in combination with at least one immunotherapy) can be administered to a desired subject or once a subject is indicated as being a likely responder to cancer therapy (e.g., at least one modulator of biomarkers listed in Tables 1-9). In another embodiment, such cancer therapy (e.g., at least one modulator of biomarkers listed in Tables 1-9) can be avoided once a subject is indicated as not being a likely responder to the cancer therapy (e.g., at least one modulator of biomarkers listed in Tables 1-9) and an alternative treatment regimen, such as targeted and/or untargeted cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without cancer therapy (e.g., at least one modulator of biomarkers listed in Tables 1-9).

The exemplary agents useful for modulating biomarkers listed in Tables 1-9, have been described above.

The term "targeted therapy" refers to administration of agents that selectively interact with a chosen biomolecule to thereby treat cancer. For example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" referes to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et.al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with cancer therapy (e.g., at least one modulator of biomarkers listed in Tables 1-9) may vary according to the particular modulator of biomarkers listed in Tables 1-9 or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well-known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector.

Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al.(1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Clinical Efficacy

Clinical efficacy can be measured by any method known in the art. For example, the response to an cancer therapy (e.g., at least one modulator of biomarkers listed in Tables 1-9), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) Breast (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular modulator of biomarkers listed in Tables 1-9 therapeutic regimen is at least 25%, 30%, 35%, 40%, 45%, 50%, 55%, 60%, 65%, 70%, 75%, 80%, 85%, or more.

Additional criteria for evaluating the response to cancer therapy (e.g., e.g., at least one modulator of biomarkers listed in Tables 1-9) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular modulator of biomarkers listed in Tables 1-9 therapeutic regimen can be administered to a population of subjects and the outcome can be correlated to biomarker measurements that were determined prior to administration of any cancer therapy (e.g., e.g., at least one modulator of biomarkers listed in Tables 1-9). The outcome measurement may be pathologic response to therapy given in the neoadjuvant setting. Alternatively, outcome measures, such as overall survival and disease-free survival can be monitored over a period of time for subjects following cancer therapy (e.g., at least one modulator of biomarkers listed in Tables 1-9) for whom biomarker measurement values are known. In certain embodiments, the same doses of the agent modulating at least one biomarkers listed in Tables 1-9 are administered to each subject. In related embodiments, the doses administered are standard doses known in the art for the agent modulating at least one biomarkers listed in Tables 1-9. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an cancer therapy (e.g., at least one modulator of biomarkers listed in Tables 1-9) can be determined using methods such as those described in the Examples section.

VIII. Further Uses and Methods of the Present Invention

The compositions described herein can be used in a variety of diagnostic, prognostic, and therapeutic applications regarding biomarkers described herein, such as those listed in Tables 1 and 2. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell based assays. In one embodiment, the assays provide a method for identifying whether a cancer is likely to respond to cancer therapy (e.g., at least one modulator of biomarkers listed in Tables 1-9) and/or whether an agent can inhibit the growth of or kill a cancer cell that is unlikely to respond to cancer therapy (e.g., at least one modulator of biomarkers listed in Tables 1-9).

In one embodiment, the invention relates to assays for screening test agents which bind to, or modulate the biological activity of, at least one biomarker listed in Tables 1-9. In one embodiment, a method for identifying such an agent entails determining the ability of the agent to modulate, e.g. inhibit, the at least one biomarker listed in Tables 1-9.

In one embodiment, an assay is a cell-free or cell-based assay, comprising contacting at least one biomarker listed in Tables 1-9, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting the cancer cell with cytotoxic T cells and a test agent, and determining the ability of the test agent to decrease the copy number, amount, and/or activity of at least one biomarker listed in Table 1, 5, 7 or 9, and/or increase the copy number, amount, and/or activity of the at least one biomarker listed in Table 2, 4, 6 or 8, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the biomarkers listed in Tables 1-9.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the presence, absence, amount, and/or activity level of a biomarker described herein, such as those listed in Tables 1-9, in the context of a biological sample (e.g., blood, serum, cells, or tissue) to thereby determine whether an individual afflicted with a cancer is likely to respond to cancer therapy (e.g., at least one modulator of biomarkers listed in Tables 1-9), whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Tables 1-9.

Another aspect of the present invention pertains to monitoring the influence of agents (e.g., drugs, compounds, and small nucleic acid-based molecules) on the expression or activity of a biomarker listed in Tables 1-9. These and other agents are described in further detail in the following sections.

The skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to cancer therapy (e.g., at least one modulator of biomarkers listed in Tables 1-9). In some embodiments, the present invention is useful for classifying a sample (e.g., from a subject) as associated with or at risk for responding to or not responding to cancer therapy (e.g., at least one modulator of biomarkers listed in Tables 1-9) using a statistical algorithm and/or empirical data (e.g., the amount or activity of at least one biomarker listed in Tables 1-9).

An exemplary method for detecting the amount or activity of a biomarker listed in Tables 1-9, and thus useful for classifying whether a sample is likely or unlikely to respond to cancer therapy (e.g., at least one modulator of biomarkers listed in Tables 1-9) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely cancer therapy (e.g., at least one modulator of biomarkers listed in Tables 1-9) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%0, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to cancer therapy (e.g., at least one modulator of biomarkers listed in Tables 1-9), a biological sample from the subject during remission, or a biological sample from the subject during treatment for developing a cancer progressing despite cancer therapy (e.g., at least one modulator of biomarkers listed in Tables 1-9).

d. Prognostic Assays

The diagnostic methods described herein can furthermore be utilized to identify subjects having or at risk of developing a cancer that is likely or unlikely to be responsive to cancer therapy (e.g., at least one modulator of biomarkers listed in Tables 1-9). The assays described herein, such as the preceding diagnostic assays or the following assays, can be utilized to identify a subject having or at risk of developing a disorder associated with a misregulation of the amount or activity of at least one biomarker described in, for example, Tables 1-9, such as in cancer. Alternatively, the prognostic assays can be utilized to identify a subject having or at risk for developing a disorder associated with a misregulation of the at least one biomarker described in Tables 1-9, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the invention pertains to methods of modulating the expression or activity of one or more biomarkers described herein (e.g., those listed in Tables 1-9, and the Examples, or fragments thereof,) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods of the invention involve contacting a cell with one or more modulators of a biomarker of the invention, including one or more biomarkers of the invention, including one or more biomarkers listed in Tables 1-9, and the Examples, or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Tables 1-9, and the Examples, or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 2, 4, 6, or 8 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Tables 1-9 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

IX. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., *supra*).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1: Materials and Methods for Examples 2-7 a. Cell Culture

B16F10 cells were maintained in complete DMEM media (10% FBS and 50 U/ml of Penicillin-Streptomycin). B16F10-Cas9 cells were maintained in complete DMEM media with 2.5-5 ug/ml of blasticidin. CD8 T cells isolated from mice were cultured in complete RPMI 1640 media (10% FBS, 20 nM HEPES, 1 mM sodium pyruvate, 0.05 mM 2-mercaptoethanol, 2 mM L-glutamine, and 50 U/ml streptomycin and penicillin).

b. Generation of Murine B16F10-Cas9 Cell Lines

Lentiviral Cas9-Blast (Addgene #52962) vector was co-transfected with lentiviral packaging plasmids pCMV-dR8.91 and pCMV-VSV-G (Addgene #8454) to HEK293T cells. Transfection was done by using TransIT-293 (Mirus, MIR2700) following the manufacturer's protocol. Virus was harvested at 48 hrs post-transfection, titered, and stored at −80° C. B16F10 cells were infected with Cas9-Blast lentivirus overnight. Forty-eight hours post-infection, cells were selected with 5 ug/ml of blasticidin (Life Technologies R21001).

To acquire clones with high Cas9 activity, B16F10-Cas9 cells were single-cell sorted into 96-well plates. Multiple were infected with lentivirus driving expression of a gRNA specific for Cd274 and mCherry. Ten days post-infection, each individual clone was stimulated with 10 ng/ml of IFNγ for 24 hours and the expression of PD-L1 was determined by fluorescence-activated cells sorting (FACS) using an anti-Cd274 antibody (clone 10F.9G2, BioLegend, #124311). Cas9 efficiency was determined by the percentage of PD-L1 negative cells in the transduced (mCherry+) population. Clone 4, which showed an editing efficiency >95% was selected for subsequent screen.

c. Development of the Screen System

Generation of positive controls: Two positive control B16F10-Cas9 cells were generated for optimizing the screen system: (1) Positive control for resistance to T cell mediated cytotoxicity: B2m−/− (GFP+) B16F10-Cas9 cells and (2) positive control for sensitization to T cell mediated killing: Cd274$^{-/-}$ (mCherry+) B16F10-Cas9 cells. These cells were generated by infecting B16F10-Cas9 cells with lentivirus containing GFP and gRNA against B2m or lentivirus containing mCherry and gRNA against Cd274. Ten days after infection, these cells were stimulated with 10 ng/ml of IFNγ for 24 hours and B2m$^{-/-}$ cells (GFP+H2Kb−) and Cd274$^{-/-}$ cells mCherry+PD-L1− populations were sorted by FACS.

Isolation and in vitro activation of CD8+ T cells: Pmel-1 and OT-I TCR transgenic mice were purchased from Jackson Laboratory (stock #005023 for Pmel-1 and 003831 for OT-1). CD8+ T cells were isolated from spleen and lymph nodes from Pmel1 or OT-I transgenic mice by using the EasySep® mouse CD8+ T cell isolation kit (STEMCELL #19753) following the manufacturer's protocol. Fresh isolated CD8+ T cells were stimulated with anti-CD3/CD28 beads (ThermoFisher #11452D) at a ratio of 1 bead to 2 T cells. Recombinant mouse IL-2 (Biolegend, #575406) was added to the culture at 20 ng/ml on day 3. T cells were used for co-culture with B16F10 cells after at least 6 days of in vitro activation.

Testing B16/T cell co-culture with positive controls: Positive controls were mixed with parental B16F10-Cas9 cells at ~1% for B2m$^{-/-}$ and ~10% for Cd274$^{-/-}$ cells. For optimization of selection, these cells were co-cultured with in vitro activated OT-I or Pmel1 CD8+ T cells with various of experimental conditions. For selection with OT-I T cells, B16F10 cells were pulsed with SIINFEKL peptide (SEQ ID NO: 1) (1 ng/ml) at 37° C. for 2 hours prior to co-culture with OT-I T cells. For optimal killing by Pmel1 T cells, B16F10 cells were pre-treated with 10 ng/ml of IFNγ for 24 hours to enhance surface MHC class I expression (which is very low in the absence of IFNγ) prior to co-culture with Pmel1 T cells. After 1-3 days of selection, tumor cells were detached and the percentage of B2m$^{-/-}$ (GFP+) and Cd274$^{-/-}$ (mCherry+) cells was determined by FACS following gating on the DAPI− CD45− CD3− population. Fold enrichment and depletion was calculated by comparing the ratio of positive control cells to parental cells before and after selection.

d. Genome-Scale CRIPSR-Cas9 Screen in B16F10 Cells gRNA pool library production: Mouse CRISPR Brie lentiviral-pooled libraries consisting of 79,637 gRNA were co-transfected with packaging plasmids (psPAX2 #12260 and pCMV-VSV-G #8454) to HEK293T cells using the TransIT®-LT1 Transfection Reagent (Mirus Bio. Cat. #MIR2305) following the manufacture's protocol. Briefly, 37 µg of library DNA, 46 µg of psPAX2 DNA, and 4.62 µg of VSV-G DNA were mixed and transfected to 293T cells in a T162 flask (Corning Cat. #3151). Six hours after transfection, media was removed and 60 ml of virus production media (DMEM media with 20% of FBS) was added. Forty-eight hours post-transfection, lentiviral media was harvested and stored in −80° C.

Virus titer determination: One million B16F10-Cas9 cells were plated into each well of a 6-well plate. B16F10 cells were infected with different amount of "Bire" lentivirus overnight in the presence of absence of 8 ug/ml of polybrene. The next day, 100,000 infected B16 cells from each condition were seeded per well into a 6-well plate (in duplicates). After 24 hours of infection, 1 µg/ml of puromycin was added to one of the duplicated wells. After forty-eight hours of selection, all uninfected cells were dead and infected cells in each wells were counted. The percentage of survival for each of the viral concentration was calculated as follows (Chen et al. (2015) Cell 160:1246-1260):

$$Psurvival = \frac{Cell\# \text{ with puromycin}}{Cell\# \text{ without puromycin}} \times 100$$

MOI(m) was calculated using following formula:

$$P_{survival} = P(n>0) = 1-P(n=0) = 1-e^{-m}$$

Single gRNA infection (SIP) rate was calculated using the following formula:

$$SIP = \frac{(1-P_{survival})\ln(1-P_{survival})}{P_{survival}}$$

The MOI for screen was 0.06, which corresponds to a SIP rate of >95%.

Pmel1 screen: B16F10-Cas9 (clone4) cells were infected with "Brie" lentivirus at MOI of 0.06 and selected with puromycin for at least 10 days prior to selection with T cells. B16F10 cells were pre-treated with 10 ng/ml of IFNγ for 24 hours prior to co-culture with Pmel1 T cells to increase MHC class I expression. A total of approximately 8×10$^7$ B16F10 cells was prepared for each of three replicates for the Pmel-1 screen: (1) 40 million B16F10 cells were harvested for genomic DNA isolation prior to selection; (2) 1×10⁷ B16F10 cells were co-cultured with control OT-I T cells at a 1:1 ratio (control condition, OT-I T cells were not stimulated because B16F10 cells were not pulsed with Ova peptide); (3) 1×10⁷ B16F10 cells were co-cultured with Pmel-1 T cells at a 1:1 ratio (experimental condition). B16F10 and Pmel1 T cells were co-cultured in T162 flasks for three days before T cells were removed from the culture by gentle washing of the adherent tumor cells. Genomic DNA was harvested from cells regrown after removing the T cells. Genomic DNA was isolated by using Blood & Cell Culture DNA Maxi/Midi Kit (Qiagen #13362,13343) following the manufacturer's protocol. Genomic DNA was submitted to the Genetic Perturbation Platform at the Broad Institute for next generation sequencing. The Genetic Perturbation Platform at the Broad Institute of MIT and Harvard (Cambridge, MA) performed PCR amplification of the gRNA cassette for Illumina sequencing of gRNA representation. Protocols for PCR and Illumina sequencing are available online (available on the World Wide Web at portals.broadinstitute.org/gpp/public/resources/protocols).

OT-I screen: For OT-I selection, B16F10 cells were pulsed with 1 ng/ml of Ova peptide (SIINFEKL (SEQ ID NO: 1)) at 37-C for 2 hours prior to co-culture with OT-I T cells. A total of approximately 3×10⁸ B16F10 cells were prepared for each of three replicates for the OT-I screen: (1) 8×10⁷ B16F10 cells were harvested for genomic DNA isolation prior to the screen; (2) 9×10⁷ non-pulsed B16F10 cells were co-cultured with OT-I T cells at a 1:1 ratio (control condition, no SIINFEKL peptide (SEQ ID NO: 1) pulse); (3) 9×10⁷ SIINFEKL (SEQ ID NO: 1) pulsed B16F10 cells were co-cultured with OT-I T cells at a 1:1 ratio (experimental condition). Given that killing of tumor cells by OT-I was rapid, B16F10 and OT-I T cells were co-cultured for one day before T cells were removed from the culture. Genomic DNA was extracted from cells regrown following T cell removal, and the gRNA cassette was sequenced as described above.

e. Screen Data Analysis

For a direct comparison of enriched and depleted gRNA, the average normalized gRNA count in each condition were compared and plotted using R. For candidate gene discovery, the normalized gRNA count table was loaded to MaGeCK (Model-based Analysis of Genome-wide CRISPR-Cas9 Knockout) (Li et al. (2014) *Genome Biol.* 15:550) by comparing the condition for OT-I/Pmel1 selection versus selection with control T cells. Top genes were determined based on median Log(2) fold change for all gRNAs and false discovery rate (FDR). Log(2) fold changes >|2| and FDR<0.05 was used as a cutoff for significant genes. In order to identify significant pathways enriched or depleted in the screen, a hypergeometric distribution was computed by using overlapped genes sets with top positively selected or negative selected genes (Hallmark and Biological Process gene sets). Genes included in each pathway were based on MSIgDB (Molecular signature database), available on the World Wide Web at software.broadinstitute.org/gsea/msigdb/search.jsp) and relevant literature.

Table 3 provided below lists the top single-stranded guide RNAs (sgRNAs) identified in the screen.

TABLE 3

| Gene | sgRNA | OT1 | Pmel+ |
|---|---|---|---|
| Psmb8 | ACATGATGCTGCAGTACCGG | -0.78 | -4.53 |
| Psmb8 | AGGTTGTATTATCTTCGGAA | -1.06 | -3.78 |
| Psmb8 | CCGGAGCTCGCACTTCCCCG | -1.26 | -3.40 |
| Psmb8 | CTCGCCTTCAAGTTCCAGCA | -1.02 | -4.01 |
| Otulin | AACAGAACCCAGGTTAAGTG | -2.54 | -3.90 |
| Otulin | AGTATACCTGGATCAAGCAG | -3.37 | -3.65 |
| Otulin | GGAACTTCACAGCTTCGTAG | -0.79 | -3.25 |
| Otulin | TGATAACTACTGTGCACTGA | -2.87 | -4.11 |
| Cd274 | CTCAGCACAGCAACTTCAGG | -0.99 | -3.48 |
| Cd274 | GCTTGCGTTAGTGGTGTACT | 0.06 | -4.05 |
| Cd274 | TCCAAAGGACTTGTACGTGG | -0.35 | -3.66 |
| Cd274 | TGCTGCATAATCAGCTACGG | 0.07 | -3.62 |
| Ikbkb | ATGTGGCACCCTCGGCAAAG | -0.60 | -5.03 |
| Ikbkb | CAAGATCCATGTCCAACGTG | -1.18 | -3.60 |
| Ikbkb | GAAGCCAGTGATGCACTCGA | -1.56 | -3.74 |
| Ikbkb | TCACACATACCCCGTGACGG | -2.91 | -1.89 |
| Psme1 | AAAGGGGACGAAGACGACAA | 0.27 | -2.49 |
| Psme1 | CCGTGAAGACCTGTGTAGCA | -0.57 | -3.40 |
| Psme1 | CTGCAACCAGGTAGTGACCT | 0.89 | -4.18 |
| Psme1 | GAACTGCAATGAGAAGATTG | -0.48 | -4.05 |
| Fadd | AAGCTGGAGCGCGTGCAGAG | -0.26 | -2.42 |
| Fadd | GCGCCTGGACGACTTCGAGG | -3.96 | -4.05 |
| Fadd | TAGATCGTGTCGGCGCAGCG | -1.15 | -4.00 |
| Fadd | TTCGTTTGCTCACGCGCTCG | -2.25 | -3.34 |
| Rela | GATTCCGCTATAAATGCGAG | -3.44 | -3.34 |
| Rela | GCCCAGACCGCAGTATCCAT | -1.32 | -3.30 |
| Rela | TATCAAAAATCGGATGTGAG | -1.78 | -3.48 |
| Rela | TCACCAAGGATCCACCTCAC | -3.53 | -3.67 |
| Creb1 | ACAGATTGCCACATTAGCCC | 0.75 | -3.83 |
| Creb1 | ACAGCTGGCTAACAATGGTA | 0.24 | -3.59 |
| Creb1 | ACTGCTAGTTTGGTAAATGG | 0.16 | -3.35 |
| Creb1 | GAAGGGAAATCCTTTCAAGG | 0.71 | -2.81 |
| Ypel5 | AAAAAGAAATGCTCTACCAG | -2.86 | -2.66 |
| Ypel5 | AGCTCACATCTCGAACCATG | -2.86 | -3.44 |
| Ypel5 | AGTACAGTGAAGTTCAAGAT | -1.70 | -3.67 |
| Ypel5 | ATCTTTCTTGACCATATCGG | -0.94 | -3.68 |
| Fitm2 | CACAATCATGAGCGCACAGA | -3.54 | -2.86 |
| Fitm2 | CCCGATGCACTCACACGTTG | -3.84 | -3.31 |
| Fitm2 | CTTACCAACTACCACCTGAC | -3.25 | -3.54 |
| Fitm2 | GAGGTAGCTCTCGGGCAGCG | -1.48 | -3.63 |

TABLE 3-continued

| Gene | sgRNA | OT1 | Pmel+ |
|---|---|---|---|
| Tcea1 | ACATACCTGTAGCAATTCTA | 0.10 | -3.58 |
| Tcea1 | AGAACTGGGATCTCAGATTG | -0.81 | -3.68 |
| Tcea1 | GATGAGAGACTTGGCTAGAG | -1.25 | -2.37 |
| Tcea1 | GCTGCAGCTCTTCGGACAGG | -0.96 | -3.61 |
| Psme2 | GAATTCAGAGACTTACCTCC | -0.43 | -3.97 |
| Psme2 | GGATGTCCAGAGGAGCCCGG | 1.00 | -3.03 |
| Psme2 | TCCTCCACCCAAGGATGACG | 0.09 | -2.87 |
| Psme2 | TTTCTCTTAGTCCCTAAGTG | 0.19 | -3.30 |
| Usp18 | ACAGCTCTCGCAGCACATGT | -1.87 | -2.94 |
| Usp18 | CAGGCACTGAACGAGCTCCG | -2.85 | -2.94 |
| Usp18 | CATCATGAACACTTGAAGCA | -3.58 | -3.42 |
| Usp18 | TGTACAGCCCACGCAAATCA | -3.49 | -3.80 |
| Spns1 | ACAGCCAGCACTCCTAGACC | -1.16 | -3.08 |
| Spns1 | AGGAAGAGCATGAATCTCCA | -0.18 | -2.31 |
| Spns1 | CCATTCGACCCTCATAGTGG | -0.49 | -4.31 |
| Spns1 | GGATGATCCCAGTGTCACCA | 0.97 | -3.27 |
| Gale | AGAACTTGGACTTGCCGTAG | -3.46 | -3.44 |
| Gale | ATCTTCACCGATGCGCCCAG | -0.18 | -4.51 |
| Gale | CTGGGGGTTCCCGTACACGG | -1.10 | -3.03 |
| Gale | TTAACTCTATAGTAGTCCAG | -2.79 | -1.90 |
| Ptpn2 | AAGAAGTTACATCTTAACAC | -3.44 | -3.15 |
| Ptpn2 | CACTCTATGAGGATAGTCAT | -3.05 | -2.65 |
| Ptpn2 | CTCACTTCCATTATACCACC | -3.96 | -3.58 |
| Ptpn2 | TGCAGTGATCCATTGCAGTG | -4.06 | -3.50 |
| Nprl2 | CATACTCCTGCGCAACAGGA | -1.95 | -2.62 |
| Nprl2 | CTCGCGAGATGAAATCCTCA | 0.29 | -3.43 |
| Nprl2 | GGCCGGCTACTTGACCACGG | -3.09 | -2.90 |
| Nprl2 | TGGTGTTGGGCAATACACAT | -0.29 | -3.85 |
| Tcof1 | ACCTGCTAAACCAGCCAGGG | -1.08 | -3.48 |
| Tcof1 | GTCCCATTGTAAGGCAGGAG | -3.55 | -3.10 |
| Tcof1 | TGAGGACGATTCTGATAGTG | -2.26 | -3.45 |
| Tcof1 | TTCTCCAGATAAAACCTGTG | -1.68 | -2.75 |
| Tk1 | AGGACTCCTGGGTCACATCG | -0.19 | -3.30 |
| Tk1 | CAGGCCCAGCCTCTTCGTGT | -0.92 | -2.77 |
| Tk1 | GTAATTGTGGCAGCGCTGGA | -0.47 | -2.71 |
| Tk1 | TAGGACTGACCGATCATGTG | -1.41 | -3.96 |
| Nadk | AAGTTCTGCACGTTCCGTGA | -3.11 | -3.32 |
| Nadk | AATGAAGTGGTGATCGACAG | -0.17 | -3.12 |
| Nadk | AGCTACAATCACCCTATCCG | -1.44 | -3.10 |
| Nadk | TAAACTCACATGATGGTCTG | -0.74 | -3.19 |
| Tiparp | AAAGTTATGGATTATGTACC | -0.03 | -2.92 |
| Tiparp | CTCTCCGGAAGAATGAGTTG | -0.18 | -2.66 |
| Tiparp | CTGAATTTGACCAACTACGA | -1.06 | -2.62 |
| Tiparp | TGCCTGTCCTGATTCCTGAT | 0.26 | -4.52 |
| Wdr26 | ACGTTAGAAGGACATGCGTA | -1.36 | -3.87 |
| Wdr26 | CCTCTTACCACAATAGCGTG | -1.37 | -2.03 |
| Wdr26 | GACATCCTGACTCTTGCATG | -1.46 | -3.12 |
| Wdr26 | GAGAGTCTGTAAACGCCGTG | -0.12 | -3.68 |
| Sox4 | ACAACCCCAGTGGATCACTG | -0.43 | -3.34 |
| Sox4 | CCAAGCGGCTAGGCAAACGC | -3.18 | -1.86 |
| Sox4 | CCACGCTAAGCTGGCTCCGG | 0.02 | -4.24 |
| Sox4 | CCACGGCCGTCTACAAGGTG | 0.05 | -3.25 |
| Srrd | ACCTCAGTCTGACTGAACAG | -2.47 | -3.83 |
| Srrd | CACTAGGCAACGATGAGCCA | -1.84 | -2.64 |
| Srrd | CGAGTGTCTTAGGAAACAGT | -1.69 | -2.62 |
| Srrd | GCACACACTTCACATGGG | -0.91 | -3.45 |
| Krit1 | AGCAACAGTGAAATAGCACA | 1.22 | -3.57 |
| Krit1 | CATGCTTTAGTTCAACAGAA | -3.57 | -3.15 |
| Krit1 | TATGGTTAGAGAACGACAGT | 0.35 | -2.58 |
| Krit1 | TTTGTCTTTATCCGTTCAAG | 0.32 | -3.03 |
| Serpinb9 | CAGAAAGTACTCTCTTAGAG | -0.12 | -3.36 |
| Serpinb9 | CAGGCAACACATAAACACAT | -3.62 | -3.42 |
| Serpinb9 | GCTCCGTCGATTCAGAAACC | -0.49 | -2.41 |
| Serpinb9 | TAACCTCGCCTATGTGAAGG | -0.46 | -3.13 |
| Memo1 | ATGCGGGATACACATACTGT | -0.56 | -4.20 |
| Memo1 | GAGAGTGCACATCGAGACAG | -1.17 | -3.05 |
| Memo1 | TCAATACGAAGATCATACAG | -0.86 | -3.59 |
| Arid2 | ACTTGCAGTAAATTAGCTCG | -1.30 | -2.42 |
| Arid2 | GCTGAACCGTCTGACCGGCA | -3.68 | -3.03 |
| Arid2 | GTTGCCTTAACGACTTCACA | -1.06 | -3.21 |
| Arid2 | TTTACTGCTCGCTAATGCGG | -0.70 | -3.58 |
| Crkl | CTTACGTTGAAAAGCTTGTG | -0.76 | -3.75 |
| Crkl | GGGCGCCGGTTCGATTAAGG | -2.68 | -2.64 |
| Crkl | GGTCCCCGATCTTAAAGCGG | -0.63 | -3.96 |
| Itgav | ATAATAACCAATTAGCAACA | -2.95 | -3.48 |
| Itgav | CCTGCATGGAGCATACTCAA | -3.17 | -3.07 |
| Itgav | TCATGGACCGAGGTTCCGAT | -1.94 | -3.69 |
| Mprip | CAAGACACAGAATGTCCACG | -3.24 | -3.42 |

TABLE 3-continued

| Gene | sgRNA | OT1 | Pme1+ |
|---|---|---|---|
| Mprip | CCATCAAGTGACACTCGTCA | -0.70 | -3.65 |
| Mprip | CCATGACATCTGGCATACGA | -0.74 | -3.30 |
| Hdac5 | AACTCTGGTCCAAAGAAGCG | 0.17 | -3.79 |
| Hdac5 | CGTGCCCTGTACTTACGGTG | -0.28 | -4.26 |
| Hdac5 | CTTTCTGTAGAGCCTTCCCG | -2.29 | -1.96 |
| Maea | CAATGAACTCCTGAATCCTG | -0.25 | -3.72 |
| Maea | CATGAGCATTACCTTGTATG | -3.00 | -3.10 |
| Maea | GCAGGAGTACCCGACCCTCA | -2.79 | -3.22 |
| Ptpn11 | AAGGAGCTGAAATACGACGT | 0.22 | -3.63 |
| Ptpn11 | AGAGAACGAAGTCTCCGGGG | -0.49 | -3.54 |
| Ptpn11 | AGTATTACATGGAACACCAT | -0.62 | -3.50 |
| Cflar | ATGATCAAGCAGATTCCTAG | 0.61 | -3.06 |
| Cflar | CCAAAATTACTTACTGGACT | -1.01 | -3.49 |
| Cflar | CTTACCTATAATCAGAAACC | -3.08 | -1.94 |
| Cflar | TGGGTTATGTCATGTGACTT | -1.52 | -3.43 |
| Fis1 | AGGCTCTAAAGTATGTGCGA | -0.81 | -2.33 |
| Fis1 | GCACGCAATTTGAATATGCC | -2.82 | -4.16 |
| Fis1 | GGTTCGAAGCAAATACAATG | -0.56 | -3.60 |
| Tgif1 | GACACACCTGTCCACACTAC | 0.32 | -2.25 |
| Tgif1 | GTTCACGATTTCCCGCCGTG | 0.10 | -3.14 |
| Tgif1 | TGGGTTGGGTCCAACTACGC | 0.90 | -3.60 |
| Tgif1 | TGGTATGGCAGATCACTGAC | -0.22 | -2.88 |
| Jmjd6 | AGTTCGTGGAGCGCTACGAG | -2.15 | -3.14 |
| Jmjd6 | CTGCTATCGAAGATGTAAAG | -2.26 | -2.53 |
| Jmjd6 | TAGTTCAGGGTCACAAGCGG | -2.66 | -3.15 |
| Jmjd6 | TGAATCCCAGTTCCAGAACG | -1.03 | -2.97 |
| Brd7 | AGCTCGTTAGCCAAACAAGA | 0.50 | -4.07 |
| Brd7 | CAGGAGGCAAGCTAACACGG | 0.27 | -2.08 |
| Brd7 | CTGGAGTGAACACTCTGCAG | -0.59 | -3.65 |
| Usp19 | GTGATTGTTAAGCTGCGCGT | -0.33 | -3.18 |
| Usp19 | TCTGTCCTGGACCATAACCG | 0.50 | -2.59 |
| Usp19 | TGGAGGGGTTGAATCCAAAG | -1.09 | -2.03 |
| Usp19 | TTAACTACAATAACCCATTG | -1.27 | -3.89 |
| Gpi1 | ACTTACCGTGTTCGTAGACA | -0.04 | -2.99 |
| Gpi1 | CGGCAAAGATGTGATGCCGG | -1.37 | -2.55 |
| Gpi1 | GTACACTGGCAAATCCATCA | -1.05 | -3.27 |
| Gpi1 | TTAGAGACAAACCAGACACG | -3.25 | -2.82 |
| Gabpb1 | AGAGAAATGCCCATACTGTG | -0.94 | -3.63 |
| Gabpb1 | CAGTGGTGTCCGGTCCACTT | -0.75 | -3.34 |
| Gabpb1 | CGTAGCTAATACTGACGTAG | 0.71 | -2.26 |
| Gabpb1 | GTTCATCATTGGACCCGGAG | -1.89 | -2.39 |
| Ube2h | ACGCTTCATCAATGTTGGGA | -1.18 | -3.33 |
| Ube2h | CACCATTGAGAGGATCTATG | 0.46 | -2.60 |
| Ube2h | CGGCAAGAGGCGGATGGACA | -1.51 | -2.93 |
| Ube2h | GTTACAGCACCATATGAAGG | -2.57 | -2.73 |
| Atg5 | AAATGTACTGTGATGTTCCA | -3.55 | -3.28 |
| Atg5 | AAGAGTCAGCTATTTGACGT | -2.85 | -2.54 |
| Atg5 | CCTTCTACACTGTCCATCCA | -4.15 | -3.93 |
| Pbrm1 | AATAAAAGAGCAGTCCAAGG | 0.92 | -2.60 |
| Pbrm1 | ACAAGCAGCTTTATACTCAG | 0.12 | -3.95 |
| Pbrm1 | CAATGCCAGGCACTACAATG | -0.74 | -4.32 |
| Eri1 | AGTACTGTATACTAACAGAT | -3.59 | -3.33 |
| Eri1 | ATACGTTTCAGCAGTATGTG | -3.70 | -3.77 |
| Eri1 | CGGTCTTACTGGAATCACTC | -3.18 | -2.86 |
| Eri1 | GTCATAGTAACTGTCCCCAG | -2.27 | -1.58 |
| Nampt | AATGCGTGTGAGAAAATATG | -3.09 | -3.27 |
| Nampt | CAGACCATCTAAGTTACCAG | -0.28 | -2.91 |
| Nampt | CTAGTACCATAACGGCTTGG | -0.29 | -3.51 |
| Pcgf6 | ATGAAGACACTCTGTAATGG | -0.18 | -3.38 |
| Pcgf6 | CAAATTAGTGATCAATCTAG | -0.55 | -2.66 |
| Pcgf6 | CCTCGAAGCGGCCTCTCAAG | 0.06 | -2.81 |
| Pcgf6 | TGTAGGGGGTCAGCTCGACA | -0.32 | -2.60 |
| Chmp5 | ATAGGACTTACAAGACCAGC | -0.29 | -3.08 |
| Chmp5 | CAGTCCGTCAAGCTAGGTGG | -1.09 | -2.74 |
| Chmp5 | GGCCCAACAGTCCTTTAACA | -3.17 | -2.78 |
| Chmp5 | TTACACCATCCAGTCACTAA | -1.16 | -2.69 |
| Man2a1 | ACAATCCCTTTGAACAAGAA | -0.30 | -3.31 |
| Man2a1 | AGGAACCGCGAAAGACTGGG | -2.21 | -3.39 |
| Man2a1 | CAGCTGGAAATTGTGACCGG | -1.46 | -3.19 |
| Man2a1 | TGCGTCGAAATAATCTGACA | -2.14 | -1.32 |
| C330027C09Rik | AAATTGCTGATTATCTGACC | -0.89 | -2.62 |
| C330027C09Rik | AGGTAGCCGATTCTGAGTTG | 0.40 | -3.05 |
| C330027C09Rik | GGTCACAAAATGGTCAGTTA | -2.66 | -2.45 |
| C330027C09Rik | TTTGCCAATAGTCCTAGACA | -2.61 | -3.09 |
| Hipk2 | ACAGGTCAATGAACTCCCGT | -0.63 | -2.37 |
| Hipk2 | ACTGGGCGAATATACTTGAG | -0.23 | -3.02 |
| Hipk2 | TTAGGTTATGTGGTCCACCG | 0.31 | -3.28 |
| Hipk2 | TTCAGCAATGACACAACCAA | 0.51 | -2.54 |

TABLE 3-continued

| Gene | sgRNA | OT1 | Pme1+ |
|---|---|---|---|
| Cnot11 | ATCACAGAGTCTTTAGTCAG | -0.84 | -2.98 |
| Cnot11 | TCCATCAAGGCAATCTGGCG | -1.21 | -3.06 |
| Cnot11 | TGGCGGCGAGCGGCTCGGTG | 0.16 | -3.26 |
| Gss | ACAGCTGGCTGGGACTAAGA | -3.22 | -1.44 |
| Gss | AGTCAGTATAATTCACAGGT | -1.41 | -2.85 |
| Gss | GTTCTCTGGACCAAAACCGA | -2.37 | -3.01 |
| Gss | TCAGATTACATGTTCCAGTG | -3.96 | -3.88 |
| Epg5 | ACAGCCGACTCGTTGTAACA | -3.60 | -3.10 |
| Epg5 | GAAACGCTGTCTTACACAAG | -2.34 | -1.76 |
| Epg5 | TCGAGCCAGAAGAACCAATG | -3.19 | -3.10 |
| Epg5 | TGGGTACCATACCCATATTG | -1.24 | -3.21 |
| Prkcq | ATGGGAGACCAATTTCAACT | -2.83 | -3.29 |
| Prkcq | CCACCACCGATGCCAGACAA | -3.36 | -2.57 |
| Prkcq | TTTGACGCCCACATTAACAA | -2.69 | -2.12 |
| Prkcq | TTTGCACTGCATCAGCGCCG | -0.16 | -3.17 |
| Rnf31 | CTACCTCAACACCCTATCCA | -4.69 | -4.50 |
| Rnf31 | GAACTATGAGTTGTTGGACG | -3.28 | -3.35 |
| Rnf31 | GGAGGAACCAAGGTGTTGTG | -3.84 | -2.86 |
| Rraga | AAAGATGATCGACCTCATGC | -0.26 | -3.02 |
| Rraga | GATCAGCTGATAGACGATGC | -2.68 | -2.14 |
| Rraga | GGTTCCCCAAGAATCGGACG | -0.40 | -3.05 |
| Rraga | TTCATCAGCCTCAATAATCT | -0.74 | -2.83 |
| Dpf2 | AGAGGCGGGCGTTATAATTG | 0.81 | -3.50 |
| Dpf2 | AGTGGTAACTGAGGCCAGGT | -0.33 | -3.28 |
| Dpf2 | GAAGATACGCCAAAGCGTCG | 0.02 | -2.01 |
| Dpf2 | TGGATGGAAAAGCGACACCG | -3.33 | -2.24 |
| Pde7a | ACGGAAGTCAATGTACGGAT | -0.73 | -3.27 |
| Pde7a | GAAACGGCTGATTAACACCT | -1.26 | -2.75 |
| Pde7a | GGCACCCCGAAAAACTCGTG | -0.64 | -2.13 |
| Pde7a | TACTTAAAGGAACCTAAGGT | -0.84 | -2.88 |
| Eif2ak4 | ATTCTGGCAGAGCACGTCAG | 0.53 | -3.24 |
| Eif2ak4 | CTGCAAGCAGACACTTCCGC | -0.13 | -3.45 |
| Eif2ak4 | CTGCGGGACACCATTGACCA | -0.27 | -3.15 |
| Actr3 | ACGGGTACAGTAATAGACAG | -0.86 | -3.15 |
| Actr3 | ATGACACCGATGGGTCAAAG | 0.22 | -2.47 |
| Actr3 | TAATAGTGGCCAATTCGCCA | -0.15 | -2.69 |
| Actr3 | TTTCCAAGGACTGCTCAGGA | 0.08 | -2.70 |
| Zfp273 | AAATGTGACCAGGTATGGCT | 0.24 | -2.05 |
| Zfp273 | AGTGTGGAAAGGCCTTTGAT | -3.58 | -3.47 |
| Zfp273 | CAACACCAACAGATTCATAG | -0.92 | -2.69 |
| Zfp273 | GCACCAGCGAACTCATACTG | 0.42 | -2.78 |
| Arid1a | CCTGCTGGCCATACGCACTG | -2.96 | -2.21 |
| Arid1a | GCAGCTGCGAAGATATCGGG | -0.56 | -2.78 |
| Arid1a | TACCCAAATATGAATCAAGG | -1.38 | -2.39 |
| Arid1a | TGGTCGTGCGAGTTCTGCTG | -2.09 | -3.59 |
| Ddi2 | ATGCTACTGAAGTCAATCCG | -1.72 | -2.51 |
| Ddi2 | GAGCCCGGAGAGAACAAGAA | -0.23 | -2.65 |
| Ddi2 | TCAGCAAGGACAACTCATGC | -2.73 | -2.76 |
| Ddi2 | TCTGTCACCTGAGTCGACAA | -3.46 | -2.99 |
| Tk2 | CTCCAATACAACAGACGTCG | 0.55 | -3.84 |
| Tk2 | TACCATGATGCCAGCCGATG | 0.77 | -2.10 |
| Tk2 | TTGAGGGCAATATTGCAAGT | -1.09 | -3.48 |
| Irf1 | CGGAGCTGGGCCATTCACAC | -3.91 | -3.49 |
| Irf1 | CTGTAGGTTATACAGATCAG | -1.26 | -3.54 |
| Irf1 | TTAATTCCAACCAAATCCCA | -2.87 | -3.08 |
| Ten1 | CAAATCCATCCCCTCCACAC | -0.69 | -2.25 |
| Ten1 | GGTCCCCAAGAACCATGTAC | -0.18 | -3.84 |
| Ten1 | TGGCCGTCACTGACCTCCCA | -1.41 | -3.72 |
| Nrbf2 | ATGGCTCACCTGCTCAGACT | -4.07 | -3.82 |
| Nrbf2 | CTAACAAACGGTCTGCTCGG | -2.72 | -2.21 |
| Nrbf2 | TGAGAAGCAGCTGTTTCATG | -3.28 | -3.05 |
| Strada | AAGTCCGATATCTACAGTGT | -1.58 | -2.12 |
| Strada | GAGAGTATGTGACAGTACGA | -0.96 | -2.14 |
| Strada | GATACGGTACTATATTGGGA | 0.70 | -3.23 |
| Strada | GTCACATCATTTATGGCGTA | -1.00 | -3.32 |
| Epc1 | CTATGAGTCCATATACCCTG | -1.73 | -2.95 |
| Epc1 | TATCGACTAGTATCTGACTG | -0.88 | -2.45 |
| Epc1 | TGTTAGTAATCGGGATGATG | -2.14 | -3.50 |
| Ccs | CAGGCTGTACTCAAGGGTAT | -0.90 | -3.21 |
| Ccs | CCCTGATGGAGCATCTCATG | -3.35 | -3.00 |
| Ccs | TTGATTGAGGGAACCATCGA | -3.67 | -3.46 |
| Dtx31 | GAACGGGAGCAGAAACGGAA | -0.49 | -3.03 |
| Dtx31 | TCTATGAACTCTAGTCTACC | 0.97 | -3.06 |
| Dtx31 | TGGGTACACGACGGGCATCG | -0.23 | -3.54 |
| Raf1 | ACCTGGCGATTGTGACTCAG | -0.23 | -2.94 |
| Raf1 | GAGAGACTCGAGTTATTACT | -3.20 | -2.69 |
| Raf1 | GCCGAATAAGCAAAGGACTG | -2.76 | -2.06 |
| Raf1 | GGGTGTAGAGTATCTGTGCT | -0.15 | -3.05 |

TABLE 3-continued

| Gene | sgRNA | OT1 | Pme1+ |
|---|---|---|---|
| Lrp10 | AAGTACAAGGCACTTTACAG | -0.01 | -3.23 |
| Lrp10 | AGGTGAGCGTTGCTATAGCG | 0.57 | -3.34 |
| Lrp10 | GAGGCTACGTAGCAGTCGAG | -2.00 | -3.07 |
| Iqsec1 | AGTTCCACGGAGCTATCACT | -1.69 | -3.74 |
| Iqsec1 | GCACAATGCGACGTGACATG | -0.20 | -3.51 |
| Iqsec1 | TGAGTCTGACTACTCAGATG | -0.03 | -3.69 |
| Mtch1 | AAGGCGTTGGACATAAGGCG | -3.03 | -2.83 |
| Mtch1 | AGTGATCTCGATGCGATGCA | -2.10 | -2.23 |
| Mtch1 | CTCACTCAAGAAAGTTGTGA | -3.46 | -2.51 |
| Mtch1 | GGACAACGCCCCGACCACCG | -2.89 | -3.16 |
| Nprl3 | GCAGGACAGTAGCAATTCGG | -3.30 | -3.45 |
| Nprl3 | GCTGCATAGTGGATCTTGTG | -0.32 | -2.10 |
| Nprl3 | TGTCTCACTCAGATAAACCA | -1.42 | -3.97 |
| Vps4b | GGAAAGCGGACACCTTGGAG | -3.47 | -3.19 |
| Vps4b | GGCTGCACGGAGAATTAAGA | -2.97 | -2.61 |
| Vps4b | TAAAGCCAAGCAAAGTATCA | -3.67 | -3.37 |
| Dnaja2 | AAATGGCAGAAGAAGAGGCG | -2.86 | -1.64 |
| Dnaja2 | AAGGCATGAAACATGGACAG | -0.51 | -3.02 |
| Dnaja2 | CAGAAATGCAGCGCTTGTCG | -1.39 | -3.62 |
| Dnaja2 | CTTACCTTCTCCATTACAGT | -2.41 | -2.39 |
| Trex1 | ACACAGAAGGTACCATCTAG | -3.32 | -2.64 |
| Trex1 | AGCTTGTCCACCACACGGGG | -2.18 | -4.08 |
| Trex1 | GGAGCAGAGGAAAGTCATAG | -3.14 | -2.87 |
| Gabrb3 | CCTGGTAGATGGCTACACTA | 0.88 | -2.94 |
| Gabrb3 | CGAAAACTCAATGAAAGTCG | -0.83 | -3.51 |
| Gabrb3 | CGCCTGAGACCCGACTTCGG | -0.36 | -2.88 |
| Paox | CTTCACACTCCACCAATACG | 0.55 | -2.66 |
| Paox | TACCGAAGCAGCGTTCCGAG | 0.12 | -3.64 |
| Paox | TGGGCAAGGAAGCCAGTATG | -2.69 | -2.80 |
| Tacc3 | AGTTTAAGGAGTCGGCCTGG | -1.05 | -2.32 |
| Tacc3 | TAACATGACCAATAAGCGTG | 0.07 | -3.44 |
| Tacc3 | TCAGGGACTAGAACCTGTCG | -2.74 | -2.80 |
| Boll | AAGGATAAGAAACTCAACAT | 0.77 | -2.79 |
| Boll | AGGTTCTAGTCTCATGCCAG | 0.45 | -2.46 |
| Boll | GAATCACTTACAGGCCAAGA | -0.54 | -2.95 |
| Boll | GGTGACACAGGATTAGGGGA | 0.28 | -2.32 |
| Gpr31b | GACGGTAAAAGAAGGTCCAG | 1.15 | -2.47 |
| Gpr31b | GATGAGGCCACTGTTGCAGA | -0.72 | -2.61 |
| Gpr31b | GGAAGGCTACTCCCACACCA | 1.13 | -2.31 |
| Gpr31b | TGTCTACCTGTTCAACCTGG | 0.84 | -3.08 |
| Ilk | CCTCGGAGAAGCTCTCTAAG | -2.06 | -2.44 |
| Ilk | CTTCCTGTTAGATTTCGTTG | -2.29 | -1.75 |
| Ilk | GATTAATGTGATGAATCGTG | -2.01 | -3.53 |
| Ilk | TCAGTGTCCCACCTGAGCCG | -0.84 | -2.74 |
| Slc2a1 | CAAACATGGAACCACCGCTA | -2.80 | -1.10 |
| Slc2a1 | CCTGCTCATCAATCGTAACG | 0.22 | -3.73 |
| Slc2a1 | GTGTCACCTACAGCTCTACG | -0.39 | -3.71 |
| Becn1 | ACACAGCGGGTGATCCACAT | -0.72 | -3.64 |
| Becn1 | GGAAGAGGCTAACTCAGGAG | 0.20 | -2.57 |
| Becn1 | GGATGACGAACTCAAGAGTG | -2.81 | -1.93 |
| Becn1 | TGTGGAAAAGAACCGCAAGG | -2.81 | -2.30 |
| Zfp281 | CGAACAGCCCCCATAGTGG | -1.70 | -3.73 |
| Zfp281 | TTGAAGCACAGGCGCACGTG | -0.70 | -4.25 |
| Ywhaz | AAAACGTTGTAGGAGCCCGT | -0.37 | -2.20 |
| Ywhaz | ATGAAGTCTGTCACTGAGCA | -0.58 | -2.63 |
| Ywhaz | GTTGCATTATCTAGGAATTG | -0.64 | -2.50 |
| Ywhaz | TTTCTGGTTGCGAAGCATTG | -0.16 | -3.09 |
| Cnot8 | ACCCGTCTGGAATCAACACA | -0.33 | -3.68 |
| Cnot8 | GCAGTTCCAGAAACACGAGG | -2.92 | -3.12 |
| Cnot8 | GGTGTGGGCCAGCAATCTTG | -0.86 | -2.79 |
| Cmip | CCTTCAAGACAACCTCCCAG | -3.41 | -3.10 |
| Cmip | CGGTCTCCAGTCATCGTAGT | -1.57 | -3.21 |
| Cmip | GAGCTGTAAACAGTACTTCG | 0.70 | -2.75 |
| Cdk5 | CCAGAACCTGCTCATAAACA | -0.56 | -2.44 |
| Cdk5 | TGAGTAGACAGATCTCCCGG | -0.17 | -3.21 |
| Cdk5 | TGTGTTCAAGGCTAAAAACC | -2.26 | -3.00 |
| 2700049A03Rik | AACACATTTGTTTCTAAACG | -0.55 | -2.10 |
| 2700049A03Rik | AGTTTACAAGTCCACCTGTG | 0.65 | -3.63 |
| 2700049A03Rik | TTACCTAAGAGGATTGCCAT | -0.34 | -3.49 |
| Tsc2 | CACAGGGTGATAATGAACAG | -2.90 | -2.65 |
| Tsc2 | CTGATCCTAGCACACATGTG | 0.04 | -2.96 |
| Tsc2 | TGAACCACATGGCTATGACG | -3.20 | -2.95 |
| Tm2d3 | AACTACAATACTTACGACAC | 0.99 | -2.24 |
| Tm2d3 | GACACTTCGTCATGTAAGGA | -0.38 | -2.78 |
| Tm2d3 | GCGCTGCCGAGGGCAAGCCA | 0.49 | -2.52 |
| Tm2d3 | GGACAGGAAAAGCAGCACGC | 0.77 | -2.80 |
| Rgmb | AGTGATCCTTGAAAGTTCGA | -0.06 | -3.27 |
| Rgmb | CGTTCGTCACTTGAACCGAA | 1.55 | -2.76 |

TABLE 3-continued

| Gene | sgRNA | OT1 | Pmel+ |
|---|---|---|---|
| Rgmb | CTCAGAGTCAAACCCATCAG | -0.48 | -2.53 |
| Zfp148 | CAGTGCTGACATCGATCAAG | -0.38 | -3.39 |
| Zfp148 | GAACGAACTATCACTTACAG | -1.43 | -3.46 |
| Tbk1 | CGGGAACAACTCAATACCGT | -3.71 | -1.79 |
| Tbk1 | CTTCTCGCTACAACACATGA | -2.16 | -3.80 |
| Tbk1 | TGCCGTTTAGACCCTTCGAG | -0.72 | -2.79 |
| Zfp473 | CAATAAAATCCACACCATCG | 0.00 | -2.89 |
| Zfp473 | GTTAAAAGTCCTGGCACACA | 0.23 | -2.75 |
| Zfp473 | TCTACGAAACCACTCTGCAA | -3.29 | -3.31 |
| Ccdc155 | CTGTAGAGGAGCATCAGGAG | 0.55 | -3.73 |
| Ccdc155 | GCAAGAGATCTCAAACCTGG | 0.26 | -3.20 |
| Ccdc155 | TTTGATACAGGGGATTAGAG | 0.32 | -3.08 |
| Rob25 | ACCCCATACAGGTACTATCG | -0.10 | -2.64 |
| Rob25 | CACGAGCATGACAACAATCG | 0.11 | -2.87 |
| Rob25 | CGGTGCCCAGCATTACAGTG | -3.16 | -3.28 |
| Pitx2 | CTCGCGAAGAAATCGCCGTG | -0.46 | -3.50 |
| Pitx2 | GGGCCAGCAAGGAAAGAATG | 0.97 | -2.32 |
| Pitx2 | GGTTTGGTTCAAGAATCGCC | -3.56 | -3.64 |
| March5 | AGGCAAAATGATTCGCTGGG | -0.56 | -3.96 |
| March5 | TGTCACTGCTCCATAAGTCA | -1.45 | -4.12 |
| Meioc | ACGAAGACAATGTAGACCTA | 0.14 | -2.43 |
| Meioc | GTTGGGGAAAATCTGAAGAG | 0.48 | -3.25 |
| Meioc | TGAGAGATAGATGTATCTAC | -3.10 | -2.66 |
| Xrcc1 | CATTGCCAATGTCCACACTG | -1.05 | -3.38 |
| Xrcc1 | CCGGATTGTGCGTAAAGAGT | 0.71 | -2.52 |
| Xrcc1 | TGTGAAACTTCACAAAACTC | 0.98 | -2.44 |
| Fam170b | CTGAGAGTAGGACTGATACT | 0.57 | -3.56 |
| Fam170b | GCCGCGCACAGTCTGCACGT | -1.10 | -3.54 |
| Fam170b | GGAGGAATGAGTCATCTCCG | 0.47 | -3.03 |
| Ptar1 | ACATCACCAACGCCTTCCGA | -2.33 | -1.40 |
| Ptar1 | CTGTAAAACCCAGATGCGAT | -2.01 | -3.81 |
| Ptar1 | GGCGATAGTGAAATCCACTG | -3.19 | -2.54 |
| Ptar1 | GGTTGAGAACAAACTTGGTG | -1.85 | -2.37 |
| Sod2 | ACAAACCTGAGCCCTAAGGG | -0.14 | -2.71 |
| Sod2 | ATGATCTGCGCGTTAATGTG | -2.71 | -3.22 |
| Sod2 | CCTGCACTGAAGTTCAATGG | 0.36 | -3.02 |
| Tgif2 | CCTGGGGAGAGCCACATCAG | 0.00 | -2.55 |
| Tgif2 | CTCTTACCTGCAGCACCGAG | -0.36 | -2.38 |
| Tgif2 | TTAGCTTCTCCTGCTCTGAG | -0.72 | -3.55 |
| Elmo2 | CTGAAGGACATACAGCTGAT | -3.38 | -2.88 |
| Elmo2 | GAGTGGGACTGAAAAGCGCA | 0.44 | -3.20 |
| Elmo2 | TCATCAAGGAGGTGTGCGAT | -2.79 | -2.19 |
| Crlf3 | CAGGGTACATCAACTAGCAA | -2.05 | -1.31 |
| Crlf3 | CTGGAGGCATCATAGTGCGA | -1.41 | -3.71 |
| Crlf3 | GAAGCTATTGGATGAGCGAT | 0.62 | -3.48 |
| Rfwd2 | AAGCTCCTTCTCCATCACAC | -0.06 | -3.11 |
| Rfwd2 | ATCACTAGCATAAGACAATG | -1.43 | -2.87 |
| Rfwd2 | GATGGTCTTACCAAAAGCTG | 0.67 | -2.69 |
| Pigk | AAAGAGTATTTGCAACATGT | -2.33 | -3.15 |
| Pigk | AGGGCGCGTCCATGTACGAG | -2.18 | -3.47 |
| Pigk | CTCTGCCGCTGGACACATCG | -3.67 | -1.84 |
| Pigk | TTTGAGCGAGGGGTACTGGG | -2.31 | -1.58 |
| Arhgap21 | ACTGGGGTGTCACTTCAACG | -0.21 | -3.32 |
| Arhgap21 | CTGATGCTAAGACTCTGGCG | 1.03 | -2.82 |
| Arhgap21 | GAGCGCAGCAGACTATAACC | -1.13 | -2.95 |
| Ar | ACCAGGATACCACACTTCGG | -3.38 | -0.96 |
| Ar | GACTTGGGTAGTCTACATGG | -0.26 | -3.09 |
| Ar | GCTCCTGGGAGGTCCACCCG | -0.39 | -2.86 |
| Ar | GGTGGAAAGTAATAGTCGAT | 0.52 | -3.07 |
| Arhgap11a | GAGTCCATCAATACCTAACA | -2.63 | -2.68 |
| Arhgap11a | TGGAACGACTGAATGAGGCA | -2.23 | -2.72 |
| Arhgap11a | TTAATTCTGTACTGACCAAG | -0.74 | -3.29 |
| Tbc1d10b | CAGAGAGAGCTCTATTCCGG | -0.70 | -3.49 |
| Tbc1d10b | GCAGTACCTGTCTAATAGCA | -2.45 | -2.90 |
| Tbc1d10b | TACCATCTACAGGCCTGACG | -3.62 | -3.49 |
| Ttc33 | GCGTAACCCACACTCGTGGG | -0.01 | -2.97 |
| Ttc33 | TAACAACTGCAGATACAAGG | -0.36 | -3.29 |
| Ttc33 | TGATTTCATCTCATAAAGGG | -1.53 | -2.82 |
| Sox11 | GAAGATCCCGTTCATCAGGG | -0.29 | -2.77 |
| Sox11 | GTACAGGCTCGCGCCCTCGG | -0.03 | -2.49 |
| Sox11 | TGTGGTCCAAGATCGAGCGC | -0.17 | -2.75 |
| Oprk1 | AAATACCACAGAGTAGACAG | -0.62 | -2.15 |
| Oprk1 | AGCACTCTGAAAGGGCATAG | -1.84 | -3.04 |
| Oprk1 | TGGGCAGAATCCGACAGTAA | -2.43 | -3.04 |
| Atg16l1 | CATACTTACGAAGACATACG | 0.53 | -2.66 |
| Atg16l1 | CGAACTGCACAAGAAGCGTG | -2.62 | -3.45 |
| Atg16l1 | GAAACTGAGGAAAACTACTG | -2.60 | -2.59 |
| Ankrd11 | CTGATGGCACTCGAGCCGTA | -0.16 | -2.56 |

TABLE 3-continued

| Gene | sgRNA | OT1 | Pmel+ |
|---|---|---|---|
| Ankrd11 | GCAGGCTCTTCTCGACATCG | -0.36 | -2.76 |
| Ankrd11 | GCTGGGGCACGACACTACTG | -1.64 | -2.68 |
| Pax3 | CCCAGACATTTACACCAGGG | -3.34 | -3.11 |
| Pax3 | GTTAATGGACCCAGTACCTG | -2.65 | -2.14 |
| Pax3 | TGCCGCCGATGGCACCAGGT | -0.49 | -2.77 |
| Keap1 | CATGTACCAGATTGACAGCG | -0.48 | -2.33 |
| Keap1 | GGCACGCTCATAGAGGCACA | -1.05 | -2.14 |
| Keap1 | GGGCCGCCTCATCTACACAG | 0.59 | -2.52 |
| Keap1 | TCAAATACGACTGCCCGCAG | -1.67 | -2.90 |
| Traf2 | AGATAACGCTGCCCGCAGAG | -3.59 | -3.05 |
| Traf2 | AGTACAAACCTTGTTACTCA | -2.28 | -3.41 |
| Traf2 | CACAGGTTAAGGGAAACTTG | -3.32 | -0.88 |
| Traf2 | CGGACCAGGCCTTTACATGC | -2.71 | -2.51 |
| Xrcc5 | CAAATCCATGCACACAATCA | -1.09 | -3.47 |
| Xrcc5 | GAATGATATCACTTCCGTAG | -1.65 | -2.17 |
| Xrcc5 | GAGCTTGGTAAAGAAAAACG | -1.95 | -2.04 |
| Xrcc5 | GTCATAAGCATATCGGACGA | -1.32 | -2.16 |
| Hspa13 | GACAATTCATCAGTCTGCCC | 0.13 | -2.23 |
| Hspa13 | GAGGACAAGACTTCAATCAG | 0.71 | -2.49 |
| Hspa13 | GTGTTGGTCATAGACTTGGG | -0.24 | -3.43 |
| Neurl3 | GGAGGAGCAGAGTCCCACGT | -2.36 | -1.93 |
| Neurl3 | GGCTGAACACGATACCATCG | -0.34 | -3.01 |
| Neurl3 | TGGAAACTAAGGGCCTCGCG | -2.29 | -3.18 |
| Nfix | TAAACAAAATCACCATGACC | 0.57 | -3.98 |
| Nfix | TGTGATGTGGCTGGACACAC | -1.00 | -3.78 |
| Zc3h18 | GCAACACCGAGACCGAGACA | -2.15 | -3.29 |
| Zc3h18 | TTCCCTAGGAAACTGCACGT | -3.03 | -2.80 |
| Ero1l | CTGAAGGAGAAGGCCCACGA | -1.20 | -3.42 |
| Ero1l | CTTAACCCTGAGCGCTACAC | -0.31 | -4.09 |
| Gigyf2 | AACAGGAGGAAATCCTTCGG | 0.89 | -2.83 |
| Gigyf2 | GGTGATATCATGAAAATGTG | -0.57 | -2.87 |
| Gigyf2 | TGACACAGACCTAGTTACTG | -0.14 | -3.26 |
| Rab13 | CATGGCTCCACGGTAATAGG | 0.72 | -2.92 |
| Rab13 | CTGGATGAAAAGCATCAAAG | 0.17 | -2.47 |
| Rab13 | TGATTTCAAGATCCGAACCG | 1.17 | -2.61 |
| Galnt15 | CTGCAGCAGCACCCTACAAG | -0.35 | -3.59 |
| Galnt15 | GCTACCAGTTCATCAAACAC | 0.32 | -3.42 |
| Arid4a | TCCATCCGTAGTAGTGCACT | 0.05 | -3.81 |
| Arid4a | TTGGAGCTATTGTAGAAACA | 0.41 | -4.40 |

TABLE 3-continued

| Gene | sgRNA | OT1 | Pmel+ |
|---|---|---|---|
| Nsdhl | CCTGTGTACCCACAGAAATG | -2.54 | -2.93 |
| Nsdhl | CTTGGGCCGAAAATGCCATG | -3.94 | -1.65 |
| Nsdhl | TAGGCTTCATGGCGTAAGGG | -0.27 | -3.24 |
| Ube2j2 | GAAGATTTAAGTGCAACACA | -0.78 | -2.95 |
| Ube2j2 | GTTATCATGTAAATACTAGG | -1.11 | -2.77 |
| Ube2j2 | TGGAGAAAGGCCCCACCCTG | -3.30 | -3.25 |
| Gml | AATAGAAGGTGTTATGCTCC | 0.37 | -2.61 |
| Gml | ACATATCCACTATTGTGACA | -0.63 | -2.69 |
| Gml | GTATTCGACAACACTACTGG | -2.69 | -2.36 |
| Gml | TGTAGACATAGAGCAGCCGA | -0.45 | -2.01 |
| Nckap1 | AAATACAAGTACTCACGCGT | -2.49 | -2.01 |
| Nckap1 | GCAGGATTAAGCATTGTGCT | 0.22 | -2.77 |
| Nckap1 | GGGAGCACACCTTCACGCCG | -0.93 | -2.41 |
| Nckap1 | TTCCACCAACATTTCAACCA | -1.20 | -2.47 |
| Trip13 | ACTACTCGGATAGCATCTGA | -2.89 | -2.97 |
| Trip13 | GGATAGCCTCGTGTATGATG | -2.42 | -1.02 |
| Trip13 | TGAACTAGGAATTTACCTGA | -0.63 | -3.03 |
| Trip13 | TTTGGGCTAATGCCTTACAA | -1.10 | -2.59 |
| Snapin | AGAACTGTGCCGGATCAATG | -2.93 | -2.46 |
| Snapin | CCTGGAGTTCCTGCGACCCG | -1.68 | -2.52 |
| Snapin | GCCTGTGGGCCCGCCACTG | -2.79 | -2.36 |
| Snapin | GCTCGACTCTCACGTGCACG | -0.80 | -2.25 |
| Ccdc137 | CCTGCGCTGTCCGGGCAGTG | 0.82 | -2.68 |
| Ccdc137 | GAATTGCAAGCCTAAGAACC | -2.17 | -2.45 |
| Ccdc137 | GGTGGCTTTCAAGAAGACGT | -0.45 | -2.69 |
| Stub1 | CGTGGGCCGCAAGTACCCGG | -2.59 | -1.97 |
| Stub1 | GAAGCGCTGGAACAGTATCG | -2.71 | -2.45 |
| Stub1 | GGAGATGGAGAGTTATGATG | -2.98 | -2.69 |
| Stub1 | GGCAGTGTACTACACTAACC | -2.89 | -2.47 |
| Foxb1 | ACCGCCCAGGTTGTACGCAG | 0.40 | -3.57 |
| Foxb1 | GTAGTTAACTGGTTAGGGAG | -2.82 | -1.73 |
| Foxb1 | TATCGAGAACATCATCGCTA | 0.20 | -3.39 |
| Xrcc4 | ACTGGAATGATGTTCAAGGC | 0.00 | -3.25 |
| Xrcc4 | GCCGAGACTCCTTAGAAAAG | -0.74 | -2.86 |
| Xrcc4 | TTTGTTATTACACTTACTGA | -0.12 | -3.64 |
| Ice1 | AAGTACACTTATAACCTCGG | 0.90 | -3.13 |
| Ice1 | CTGAGCCCTGCTGTAAATGG | -2.02 | -2.35 |
| Ice1 | GATACAAACCCTGTGGACTG | -2.64 | -1.74 |
| Ice1 | GCTGCACATATGCCTGACTG | -2.40 | -2.33 |

TABLE 3-continued

| Gene | sgRNA | OT1 | Pmel+ |
|---|---|---|---|
| Fhod3 | GAAAAGCTGTACAACTCCAG | 0.29 | -2.98 |
| Fhod3 | GAGAAGCCAATAAATTACCG | 0.75 | -3.38 |
| Fhod3 | GGAATATCTAGACAAAAGGG | -0.39 | -3.02 |
| Ube2r2 | CCTAACACCCTCTACGAAGG | 0.21 | -3.49 |
| Ube2r2 | TCAGATTCTTGACCAAAATG | -1.00 | -3.38 |
| Ube2r2 | TGAGTCCGACCTCTACAACT | -0.20 | -2.61 |
| Slc7a11 | ACAGGCAGACCAGAAAACCA | -3.53 | -3.44 |
| Slc7a11 | GAAGAGACACAAGTCTAATG | -3.14 | -2.91 |
| Slc7a11 | GGGCTACGTACTGACAAACG | -2.39 | -1.29 |
| Padi4 | AGAATTCTCATCGGGAATAG | 0.19 | -2.93 |
| Padi4 | CTACCATAACTCGCTTGACA | -0.82 | -2.70 |
| Padi4 | CTGGACAAGTCTAACCCGGT | -2.42 | -2.01 |
| Rfx6 | GGACATAGGATGTCTCCACG | -0.37 | -3.14 |
| Rfx6 | TGAGCATAAAGAATGCACCG | -0.22 | -3.02 |
| Pigu | AACACAAGACAAGATCGTGT | -3.76 | -3.08 |
| Pigu | GAGAAGTCCTGGGGCAAACA | -3.42 | -2.24 |
| Pigu | GAGTACGCCATGATGTACAC | -3.22 | -1.88 |
| Pigu | TGGCCGAGTTCATTTCCGAG | -0.73 | -2.29 |
| Cdk2 | ACCTGCTTATCAATGCAGAG | -0.04 | -2.99 |
| Cdk2 | CAAGTTGACGGGAGAAGTTG | -2.30 | -1.94 |
| Cdk2 | CATGAGTGTAAGTTCGGACA | -1.07 | -2.66 |
| Txndc15 | CCAAGTGTTGGAAACGCCCG | 0.90 | -2.69 |
| Txndc15 | TGTGTATCTGCATGAAGAGG | -0.10 | -3.23 |
| Txndc15 | TTGGGTTTAGGAAATCCATG | -0.69 | -3.68 |
| Gpx4 | CATGCCCGATATGCTGAGTG | -2.71 | -2.64 |
| Gpx4 | CGTGTGCATCGTCACCAACG | -3.57 | -3.61 |
| Gpx4 | TGGTCTGGCAGGCACCATGG | -2.83 | -2.83 |
| Hsd17b4 | ACCAAACCGTACCAGTCACG | 0.15 | -2.14 |
| Hsd17b4 | TCTAACATAGGCTCTTCACG | -1.56 | -2.21 |
| Hsd17b4 | TGCAGTGAACGACTTAGGAG | 0.35 | -2.38 |
| Hsd17b4 | TGGGCGCCATCGTCAGAAAG | -1.48 | -2.71 |
| Hes7 | CCAAGCGAAGCAGGCACTCG | 0.06 | -3.41 |
| Hes7 | GGAGAAAAGCTGGGAGCGTG | -1.76 | -2.90 |
| Hes7 | GGCCCGAGGCCGTAGATCCA | -0.18 | -3.35 |
| Rsf1 | GATGAACCTTGCAAAAAGTG | -0.27 | -2.17 |
| Rsf1 | GTGTGGGTCGAACTTTAAGA | -1.37 | -2.26 |
| Rsf1 | TGGCCCCAGCCATCGAGAGT | -0.38 | -3.24 |
| Fam234b | CCTGTGAAGTATAACATCGT | 0.41 | -3.23 |
| Fam234b | CTTGTCGGGTTGTAATCAGG | -0.46 | -3.10 |
| Fam234b | GCAGAGCAATACCAGAACCA | -1.48 | -3.60 |
| Uba6 | CTATCGAACATACTATCCAG | -2.81 | -1.66 |
| Uba6 | CTGGACCCATATTTACATGG | -3.11 | -2.85 |
| Uba6 | TTCATGCCCAGGATTGCCTA | -3.42 | -3.00 |
| Tm2d1 | ATAACTTGTAAGGATTTGAG | 0.49 | -3.01 |
| Tm2d1 | TGTACAAACTACACAGCTCA | 0.33 | -2.58 |
| Rab7 | ACGGTTCCAGTCTCTTGGTG | -2.35 | -2.73 |
| Rab7 | CGACAGACTTGTTACCATGC | -0.46 | -2.79 |
| Rab7 | GGAAGTTCTCGGGATCCCGG | -2.15 | -2.17 |
| Matr3 | ACACCGTGGAGATACGACC | -0.32 | -3.08 |
| Matr3 | AGCCACCATACAGAGTACCT | -0.65 | -3.60 |
| Matr3 | CTTCCATGGACTCTTACCGA | -0.02 | -2.65 |
| Asxl2 | AGAACCGACATGAGGGAAAA | -1.55 | -2.93 |
| Asxl2 | AGTCAGTCAGAACCGACATG | -1.04 | -3.47 |
| Asxl2 | GTCAGTCAGAACCGACATGA | -0.89 | -3.05 |
| Faxc | CAGTTTGCAAGACCTAACAA | -1.00 | -2.87 |
| Faxc | GTGGAGCAGATACGCAGCCG | -2.14 | -3.00 |
| Faxc | TAACAAAGGAATTGTGAAG | -0.17 | -3.25 |
| Ei24 | AAAATTCTACTAACAATACG | -2.73 | -2.14 |
| Ei24 | ACTTTGCTAAGCACAAACAG | -3.62 | -2.63 |
| Ei24 | TGGCATTTGAAGTATCAGGG | -3.61 | -3.05 |
| Ube2k | AGGTTTACAATACCTTAGGG | -2.65 | -1.83 |
| Ube2k | CCTTCATACGGTGTGTCTGG | -1.79 | -2.17 |
| Ube2k | GTCATTGCAAGCGCTGTTGG | -0.80 | -3.17 |
| Ube2k | TAATATTAGTTCCGTCACAG | -1.58 | -2.10 |
| Pak2 | AGGAACTATTGTGAGCATAG | -2.15 | -2.53 |
| Pak2 | GGTGTGCTCAAAATCAGATG | -1.94 | -2.08 |
| Pak2 | TATCTCTGCAGATTTACACA | -2.04 | -2.95 |
| Cwf19l1 | ATATCTTACTCACGTCCCCG | -1.02 | -4.11 |
| Cwf19l1 | TGTGCTTGGTGCCAATAACG | -2.39 | -3.46 |
| Larp4 | AAGTAGTTAACTTACCCTCA | -2.47 | -2.35 |
| Larp4 | TACCAGAAACATCATAGAGT | -1.39 | -2.31 |
| Larp4 | TCAGTTCGTCCCAATATGGA | -2.00 | -2.54 |
| Larp4 | TGGTCCATCCCCCAATGACA | -2.38 | -1.99 |
| Batf2 | GATCACAGTCCACTCTGCAC | -0.06 | -2.23 |
| Batf2 | GCAGCCATTGTATCCAAGAG | -1.02 | -2.91 |
| Batf2 | GTGATGATGCAGACAGGACA | 1.08 | -2.09 |
| Birc2 | AATCTTGTCAAATTGGACAA | -1.02 | -3.68 |
| Birc2 | GAGTTCTTGATACGGATGAA | -3.68 | -0.14 |

TABLE 3-continued

| Gene | sgRNA | OT1 | Pmel+ |
|---|---|---|---|
| Birc2 | GGCTGAACAGGAACACTAGG | -3.87 | -1.32 |
| Birc2 | TGAATGCCACCTCGTTCCAG | -1.40 | -3.97 |
| Impg1 | CTTACCTAAATCCTAATACA | 0.52 | -3.66 |
| Impg1 | TCAAGCCTAGGCTCAACGAA | 0.54 | -3.52 |
| Bptf | CGATGACTCCGATTATCCGG | 1.75 | -2.92 |
| Bptf | GACTCCTTAAGAATCAAACG | 0.35 | -3.09 |
| Bptf | TGAGTTCCGATCTGGACAAG | 0.54 | -3.04 |
| Xrcc2 | CAGACTCTCGCAAAGCTCCG | -1.80 | -2.56 |
| Xrcc2 | CGAGCCGTAGCATGTCAAAG | -3.40 | -1.85 |
| Xrcc2 | TGGATAGACCGAGTCAGTGG | -0.64 | -2.56 |
| Xrcc2 | TTCATGGTCCAGAAGGAACG | -0.78 | -2.06 |
| Gtf2i | CTTACTTCTTAATCACGAAG | 0.41 | -2.87 |
| Gtf2i | TCACTCCTCAGAAGGCAACG | -0.06 | -2.99 |
| Gtf2i | TCTTGGGATTCCATACCACG | 1.40 | -3.20 |
| Lemd2 | GCAGCCTTAAACCTCGAAGA | -2.46 | -2.55 |
| Lemd2 | TGACGAGGATACACGAACGC | -0.92 | -3.03 |
| Icosl | AGAGACTGAAGTCGGTGCAA | -3.04 | -2.44 |
| Icosl | GGACAATAGCCTAATAGACA | 0.03 | -2.97 |
| Ak2 | GGTAGGACCGGCCACTCTTG | -0.63 | -2.35 |
| Ak2 | TCAGCCAGTTTGGGTGCCTG | -1.70 | -2.46 |
| Ak2 | TCCGAACCGGAGATTCCGAA | -2.32 | -2.32 |
| Ak2 | TGAAGGCGACAATGGATGCA | -2.42 | -1.76 |
| Spen | CAGGCCGTATCTCTCCTCGG | -0.44 | -2.69 |
| Spen | GAGCCCACATAAATGCCGGT | -0.71 | -2.00 |
| Spen | GCTCGGCCGTGACACTACCA | -2.87 | -1.64 |
| Spen | TGACGCCACTCAGAACGCTG | -3.17 | -2.56 |
| Ikbkg | AAGGATCGGCAAGCTTTAGA | -1.74 | -2.36 |
| Ikbkg | AGGCTGCCTTGCGAATGGAG | -0.45 | -4.58 |
| Ikbkg | GCTCAGGTGACATCATTGCT | -4.18 | -0.92 |
| Eif2ak3 | AAAGTTCCCTACAAGCCCAA | -0.91 | -2.93 |
| Eif2ak3 | GAATATACCGAAGTTCAAAG | -0.51 | -2.37 |
| Rnf38 | CTCCTACACGGTAACTACGG | -0.80 | -2.58 |
| Rnf38 | GAGGAGGCACACTACAGACG | -0.58 | -2.34 |
| Vps11 | AGTTGTCACGACAAACAAGT | -2.92 | -1.92 |
| Vps11 | GACCACCCTGCACATATGGA | -4.13 | -3.00 |
| Vps11 | GCAGCTTCCCGATATACCGA | -2.53 | -1.39 |
| Vps11 | TCAGAGCCTCCCGATCGCCT | -0.39 | -2.50 |
| Nans | GAGATCACCATAGGACGACC | -2.89 | -2.31 |
| Nans | TATGTGACGTTCCAACACCT | 0.02 | -2.64 |
| Nans | TCGTGCCCGGAATACCCGAT | 0.38 | -2.18 |
| Zfp827 | AATAATTCCAAGGACTGAGG | -0.94 | -2.71 |
| Zfp827 | CTGAACACGTAGCTGGAGCG | -2.64 | -2.96 |
| Zfp827 | TGACGTCTAACACGCCAGAG | 0.21 | -2.99 |
| Cd36 | TAGGATATGGAACCAAACTG | -3.70 | -3.41 |
| Lamtor1 | CATCTGTGCGAGCTGAAGGT | 0.37 | -2.91 |
| Lamtor1 | CTCACCTAGCTGTCTTGGCA | -1.91 | -3.05 |
| Lamtor1 | TGGACCGGGCAAGGCAGTAC | -1.95 | -2.76 |
| Irgm2 | CAGGCTTAAAGACAGATACC | -2.83 | -2.91 |
| Irgm2 | CTTGGTAAAGGGTTTCGACG | -0.24 | -2.82 |
| Irgm2 | GACGGCAATACTTTATCTGT | -1.23 | -2.88 |
| Irgm2 | TTCGTGTCCGATGAGCCTAA | -2.82 | -0.03 |
| Arf6 | CCCCACGGTGGGCTTCAACG | -2.76 | -2.24 |
| Arf6 | CGACCGCGACCGCATCGACG | -2.50 | -2.20 |
| Arf6 | TCTGGCGGCATTACTACACC | -2.37 | -2.25 |
| Cd44 | CAGTCCGGGAGATACTGTAG | -1.31 | -3.56 |
| Cd44 | TCTGTGCGGGCAGAAACCCG | -0.96 | -3.64 |
| Rsph1 | GAAAGCACGACTGCCCAACG | -2.54 | -1.88 |
| Rsph1 | GACTTACAAATTTAAGAATG | -2.93 | -2.21 |
| Rsph1 | GATATTGGATGCGAACAGCA | 0.90 | -2.64 |
| Vps16 | AGGTGAGAGGGATCCCAATG | -1.05 | -2.58 |
| Vps16 | ATGTCAGAGTATGAAACACC | -2.17 | -2.25 |
| Carm1 | CAATCTGACAGACCGCATCG | 0.10 | -2.25 |
| Carm1 | GGTTCTGCAGGATCGCACGC | -2.89 | -2.10 |
| Carm1 | TGAGTACTTCCGGCAACCTG | -0.42 | -2.46 |
| Tmem165 | ACATAGTATGTATACACCCT | -0.91 | -4.31 |
| Tmem165 | GGCATTAGAATGCTTCGGGA | -1.33 | -2.45 |
| Tmem165 | GTCATCATAGTGTCCGAACT | -2.60 | -2.55 |
| Pip5k1c | GCCATGGAGTCTATCCAGGG | -0.29 | -2.40 |
| Pip5k1c | TGGTGGCAAGAACATCCGCG | -2.06 | -1.46 |
| Pip5k1c | TTACCAAATAGTCATCTGGA | 0.57 | -4.41 |
| Prdx1 | ACTGAAAGCAATGATCTCCG | -0.19 | -2.63 |
| Prdx1 | TCAATAATAAAAAGGCCCCT | -1.61 | -2.92 |
| Prdx1 | TCTTACCTTTGTATTCACTT | -0.08 | -2.64 |
| Ppp4r2 | CAAACCATTTGTTGTCAAGG | -3.01 | -2.06 |
| Ppp4r2 | CTCTATACTTACTCTGAGGA | -0.49 | -2.25 |
| Ppp4r2 | GCGGCTATGTGAATTGCTAA | 0.16 | -2.23 |
| Setd2 | GCATTCGCTTAATATCCCGG | 3.44 | -2.09 |
| Setd2 | TGCTCATGCTCAGAGTGACG | 2.43 | -2.58 |

TABLE 3-continued

| Gene | sgRNA | OT1 | Pmel+ |
|---|---|---|---|
| Setd2 | TTGCTTATGATCGAATCCAA | 3.37 | -2.66 |
| Rgp1 | ACTGACTGACCCCGAAAGGA | -2.97 | -2.75 |
| Rgp1 | CAGACTTGGCGAAGACGTGG | -2.72 | -2.93 |
| Rgp1 | CTCTCTCTCTAACCTCGGTG | -0.44 | -3.11 |
| Stat3 | CAAAGAGTCACATGCCACGT | -1.72 | -3.49 |
| Stat3 | GTTTACCACGAAAGTCAGGT | -0.46 | -3.52 |
| Kmt2c | AAAAGGCCCATTACCCAATG | -0.17 | -3.01 |
| Kmt2c | AAGCATTACCTGAATCCATG | -2.25 | -3.30 |
| Kmt2c | GGTGAAATGGATGATAGTCG | 0.60 | -2.69 |
| Gne | ACGTCCAACTCAAAGAACGC | -2.82 | -2.24 |
| Gne | CCTCTTGTTAAACGAGATCA | -3.02 | -2.30 |
| Gne | GCTCCACACGATTGTTAGAG | -2.75 | -1.66 |
| Gne | TTGCAGCTCAAAGATATATG | -0.49 | -2.02 |
| Tubb2b | AGCCTCATTATCGATGCAGT | -0.35 | -2.71 |
| Tubb2b | AGGTAATAAATATGTGCCTA | -0.96 | -2.77 |
| Tubb2b | CTCCATGGTAACTTCCAGTG | 0.21 | -2.94 |
| Lrrn3 | CGTCGTCTGGTATTTCCGTG | -0.61 | -3.48 |
| Lrrn3 | GGTGAATGTAAGACAATCTG | 0.48 | -3.43 |
| Tmem41b | GGAACCCGGAGAGTATACTG | -2.56 | -1.88 |
| Tmem41b | TATACTTACTCACTAAGCTG | -0.56 | -2.42 |
| Tial1 | AATGCAATTGTGCATATGGG | 0.47 | -2.28 |
| Arf3 | CCTCTACAAGCTGAAACTCG | -1.44 | -3.14 |
| Arf3 | GAAGAGCCTAATCGGCAAGA | -2.67 | -3.01 |
| Arf3 | TGATCGGGAGCGAGTGAACG | -3.33 | -1.84 |
| Arf3 | TTCACAGTCTGGGACGTAGG | -2.40 | 0.00 |
| Gpaa1 | CCGCAGGATGCCATACACGT | -1.64 | -2.54 |
| Gpaa1 | GTCCCTCCACTGTCACATCG | -2.68 | -3.71 |
| Gpaa1 | GTGGAGGCACTAACCCTACG | -3.58 | -1.89 |
| Brwd3 | AGACATTACTAGGTGTCGGT | -2.67 | -1.22 |
| Brwd3 | ATGGTATCCAAGATCCACTG | -2.18 | -1.89 |
| Brwd3 | GCTGTGGAAGGTCTTTACGA | -1.29 | -2.31 |
| Brwd3 | TAGCCTTTGATCGAAGCGGG | -2.21 | -2.50 |
| Tlcd1 | ATACTTTATCCACGACACAG | -0.58 | -2.22 |
| Tlcd1 | GCAGGCGACAGAGCACGCGC | -2.65 | -2.84 |
| Tlcd1 | TGGTGGAGATTGAAACAGCG | -3.51 | -0.45 |
| Tlcd1 | TTACCATGACATGATGAACA | -3.59 | -1.92 |
| Dscc1 | ATGCTACGGAAAGAGATACG | -2.44 | -2.24 |
| Dscc1 | CGGTACCTCCGTGTGAACGA | -2.59 | -2.43 |
| Dscc1 | CTAATGGAAAATACCTACGA | -2.76 | -2.42 |
| Dscc1 | GGGGACTCTATCCAAAGACC | -3.01 | -0.33 |
| Cwc27 | ACATAGAATCAAGAGTTGTG | -2.85 | -2.43 |
| Cwc27 | CCTGGCTTTATAGTCCAAGG | -2.79 | -1.44 |
| Cwc27 | GAGATATTGACATAGAGTTG | -2.50 | -1.67 |
| Cwc27 | GGGAGCCTACCTGACTGACT | -2.57 | -1.70 |
| Rbm34 | AGGAGAAGGTCTCAGTCTCG | -2.57 | -0.15 |
| Rbm34 | AGGAGCGGTTAAAAAACGAG | -2.54 | -2.67 |
| Rbm34 | TACCACAGAACGAAATCGTA | -2.26 | -2.39 |
| Rbm34 | TGTCTTTATAACTAGAAATG | -2.37 | -1.89 |
| Mcl1 | CGGCCGACGCGGTGACGTCG | -3.01 | -1.99 |
| Mcl1 | CGTGCAGCGCAACCACGAGA | -2.60 | -1.90 |
| Mcl1 | CTCCTCCGGAGACACGATGG | -3.31 | -1.97 |
| Fnbp4 | CAGACATGTATACAAAGGAG | -3.15 | -1.03 |
| Fnbp4 | CATCTCAGGACGGAGTGCGT | -2.30 | -2.42 |
| Pih1d1 | CTTGCATCCAGCTCCGCGTG | -2.74 | -2.35 |
| Pih1d1 | TCAATAGCAACTTCTACCTG | -3.06 | -1.57 |
| Pih1d1 | TCCTCAGTCACGTCGGCCGG | -3.08 | -2.08 |
| Pigs | ACCATAATGCCACCCCAGCG | -4.05 | -0.21 |
| Pigs | CTACCTAAGCTGGACTTGAG | -1.68 | -2.16 |
| Pigs | GATCTCTCGCTCATGCACAA | -3.02 | -1.16 |
| Pigs | GGGCGACCTGGACTATGCGA | -3.27 | -3.20 |
| Sptlc1 | AATGTGCCATAGAACCCTCG | -3.01 | -0.89 |
| Sptlc1 | CCCTCCAACCCACAACATCG | -2.81 | -3.10 |
| Sptlc1 | TCCTGCGTACTCTAAGAGAG | -2.79 | -1.79 |
| Prdm10 | AAAGAGTGACGACGGAACAC | -2.02 | -1.62 |
| Prdm10 | GTTCCAAGACCTTCAAACCA | -2.16 | -2.08 |
| Prdm10 | TACATAGATAGGTTCCTCGG | -2.07 | -1.21 |
| Prdm10 | TTATTGTTGTGTAATACACA | -2.31 | -1.41 |
| Aprt | CGCACCTGAACAGCACGCCC | -3.15 | -0.42 |
| Aprt | CTAACAGGTCTAGACTCCAG | -2.01 | -2.18 |
| Aprt | GAGTCCGGGTCTTTCAAGAG | -2.88 | -2.14 |
| Aprt | TGTGTGCTCATCCGGAAACA | -3.27 | -1.40 |
| Crocc | CGGCAGGAACAGGACCGGGT | -2.40 | -0.76 |
| Crocc | GCTTCAGGAACAGACAACCC | -1.63 | -2.59 |
| Crocc | GGTGGCCGAGGCGCTAACCA | -2.08 | -1.47 |
| Crocc | TCTGAGCGAGGACATACGCA | -2.99 | -1.23 |
| C330007P06Rik | AGGAGACTACTTATCTTCGG | -2.82 | -1.42 |
| C330007P06Rik | CTCAGACACCCGGGACCGCG | -3.51 | -2.87 |
| Traf3 | AGTGACTGCACGTGGCCTCG | -3.85 | -1.25 |

TABLE 3-continued

| Gene | sgRNA | OT1 | Pmel+ |
|---|---|---|---|
| Traf3 | CAGGTTCACGTGCTGTACCG | -2.41 | -1.75 |
| Traf3 | GCTTTGAGATCGAGATTGAG | -3.75 | -2.57 |
| Akt1 | ACACACGCTCTCGAGACAGG | -3.16 | -1.63 |
| Akt1 | ACGGTTCTCAGTAAGCGTGT | -3.10 | -0.73 |
| Akt1 | CTCACCCAGTGACAACTCAG | -2.51 | -2.23 |
| Sptlc2 | AATCTCGAAGATATCCAAAG | -2.58 | -1.82 |
| Sptlc2 | ACAACTATCTTGGATTTGCG | -2.70 | -2.45 |
| Sptlc2 | GTTGTGTTTGAAGATTCGAA | -2.21 | 0.44 |
| Sptlc2 | TGAGAGCAATCACTTCAGGA | -3.00 | -1.94 |
| Ugp2 | AAGGGACCGTCTGTGGACTG | -2.90 | -0.26 |
| Ugp2 | GAAGCGCTGTGAGTTTGTCA | -3.48 | -2.37 |
| Ugp2 | TCTACACCTTCAATCAAAGC | -2.02 | -2.23 |
| Med7 | ACATCTTAATAAGAAGTCCT | -3.14 | -3.08 |
| Med7 | GCCTCCAATGCAGTACATCA | -2.33 | -0.89 |
| Gnb2 | ACAGGCCACAAAGTTCCCTG | -2.47 | -1.83 |
| Gnb2 | GGACGCCAGAAAAGCATGCG | -2.30 | -1.91 |
| Aip | ATAGATGACAGCCGAACACG | -3.27 | 1.36 |
| Aip | CAGCGTCCGAAAGTGGAACG | -2.72 | -2.83 |
| Aip | GGGCAACCGGTTGTACCGTG | -2.79 | -2.06 |
| Exoc7 | AGCAGACAGAGAACCTACAG | -2.04 | -0.08 |
| Exoc7 | GAATACAACATGCCTAAAGA | -2.37 | -2.32 |
| Exoc7 | GCTGGCTGGTGGAATATGGT | -2.18 | -1.27 |
| Tmx2 | CAACCCGTGTGACTTTGACT | -2.04 | -2.31 |
| Tmx2 | GCCAGCCATCGAGAAAGCCG | -2.43 | -1.72 |
| Tmx2 | GTCACTGTGGAGCAACATGT | -2.77 | -1.35 |
| Tmx2 | TCAGTGTGCATACTCACTTG | -3.43 | -0.03 |
| Rhbdl2 | AGAGGGAAAGGAAGAACCGG | -2.99 | -1.52 |
| Rhbdl2 | GCTCCCACAAGAGACTTGAG | -2.55 | -3.45 |
| Rhbdl2 | GGTCCACAAAGGCCTCCGAG | -2.94 | -0.78 |
| Atg13 | ACAGTTCGAGTTGGAACAGT | -2.78 | -0.95 |
| Atg13 | TGTGGGGCGATCTATGTGTG | -3.96 | -0.94 |
| Ireb2 | AATTTGGCAGAAATCGAGAG | -2.38 | -1.40 |
| Ireb2 | TAAGCTGTCCCATGGATCCG | -2.71 | -2.00 |
| Ireb2 | TCTAAGAAGCTTCCATGTCG | -3.20 | -2.70 |
| Calr | CAAGAATGTGCTGATCAACA | -3.39 | -0.25 |
| Calr | GCGGCCAGACAACACCTATG | -3.42 | -2.96 |
| Calr | TATGTTTGGATTCGACCCAG | -2.99 | -0.56 |
| Tvp23b | CAATATGATTCCACCAACGC | -2.53 | -0.79 |
| Tvp23b | TAGCCAAAAGATTCTTGACT | -3.45 | -1.34 |
| Tvp23b | TGCTACTGAGCAGCTCGCAA | -2.74 | -1.02 |
| Uggt1 | CAAGTGGGTCAACAACCTAG | -2.11 | -2.42 |
| Uggt1 | GGAGAAGAAGTACCCGTACG | -2.58 | 0.78 |
| Uggt1 | TCGTGTGACAGGGTCAACAA | -3.23 | -3.30 |
| Ccna2 | ATAGACATATCCATAGCATG | -2.56 | -1.34 |
| Ccna2 | CATGCTCATCGTTTATAGGA | -2.84 | -2.35 |
| Ccna2 | GCCTGCCTTCACCATTCATG | -3.07 | -1.28 |
| Tmed10 | AAACATGTCATAGTCTTCCG | -3.29 | -3.06 |
| Tmed10 | AGAGGCGAAAAATTATGAAG | -3.19 | -0.46 |
| Tmed10 | CTCTCGCAAGTGTCTCCGAG | -2.75 | -1.13 |
| Eefsec | ACATAAGGAATGGTCCGAG | -3.00 | -1.47 |
| Eefsec | GCAGGGGTCCTCGGAAGTAA | -2.98 | -1.23 |
| Eefsec | GGGTGCACCGATTATTCCCG | -2.72 | -1.42 |
| Eefsec | GGGTGTATGGAACATCTGCA | -2.95 | -0.77 |
| Prrc2a | AAAGCTCAAATTCAGCGATG | -1.96 | -2.93 |
| Prrc2a | GAGGAATCATCATCCAGCGG | -3.13 | -1.22 |
| Prrc2a | TCAGTACGATTCTCTCTCCG | -2.22 | 0.56 |
| Sgol1 | CAGCATTGACAATACGACCA | -3.84 | 0.62 |
| Sgol1 | GCTGTTACTCCAGAGACACA | -0.23 | -2.27 |
| Sgol1 | TTACCCCCTACTACACTGGA | -2.56 | -2.24 |
| Sgol1 | TTTACAATCCTCCAAAGTCG | -3.13 | -0.68 |
| Ankrd46 | GAAGTAAAGGGATTTAACAG | -2.59 | -0.84 |
| Ankrd46 | TTAGTTCTGGCAAAGCGCCG | -2.23 | -2.54 |
| Ddx20 | CGGCCCGCCGATGTCGTGTG | -3.19 | -0.25 |
| Ddx20 | GCCAACATCTGCTTACTCGC | -2.55 | -1.97 |
| Ddx20 | TCTTGAAAACTATAGTACTC | -2.40 | -2.12 |
| Chtf8 | GCCCTTTACTTTCAGTACGG | -2.52 | -0.93 |
| Chtf8 | GGAATCCCTGTGCTGATCGT | -2.76 | -0.49 |
| Chtf8 | TGTAATGTAGGTCTCCCAGG | -3.77 | -1.35 |
| Vps29 | GAGATCTGCACATTCCGCAC | -2.69 | -0.78 |
| Vps29 | GCTGCAGAGGCAGTTTGATG | -3.06 | -0.70 |
| Vps29 | GGACACCAAGTTATTCCGTG | -3.20 | -2.89 |
| Brinp2 | CCATATCCAAATAGCCACAG | -3.59 | -2.19 |
| Brinp2 | CCTGGGCTAGCACATAACCA | -3.35 | 0.10 |
| Trip11 | TACTGATCATAAACGAACCA | -3.34 | 0.25 |
| Trip11 | TTATTGAGTCAAGAAAAGGT | -3.67 | -1.87 |
| Hsd17b12 | AAAAATTCAACGTTGAAACA | -1.37 | -3.43 |
| Hsd17b12 | AGATTGTCAACAATGGAACT | -2.17 | 0.00 |
| Hsd17b12 | TGTTTGCAGTTAGCAAAACG | -2.49 | 0.00 |

TABLE 3-continued

| Gene | sgRNA | OT1 | Pme1+ |
|---|---|---|---|
| Plpp2 | AGTTGGATCGCGAATAAAGA | -2.70 | -2.35 |
| Plpp2 | CATAGCCAGAACAGTTGACC | -2.44 | -0.66 |
| Plpp2 | CATGCAATACATGCCAAAGG | -2.39 | -0.22 |
| Slc35a1 | ATAGCACCAAAGCCTAACAA | -2.27 | 0.00 |
| Slc35a1 | GAACACTCAGCAAATTACAG | -2.58 | -0.81 |
| Slc35a1 | TCTTAAAGCTACGGTGTAAG | -2.41 | -0.87 |
| Slc35a1 | TGCACAGCATACACTAGTGA | -2.96 | -1.65 |
| Ubr4 | CCTCCGACATTCCGTAACTG | -2.32 | -1.90 |
| Ubr4 | CTCAGCTGGATACAACCAGG | -2.27 | 0.00 |
| Ubr4 | CTGAGCATGTCTAACACGAG | -2.99 | -0.37 |
| Atr | CTTCAGATCTCTCTCGAATG | -2.84 | -2.11 |
| Atr | CTTGTGACGGTAATTCTGAA | -2.48 | 0.00 |
| Atr | TTCAAAGCAAGGCTCTACTG | -2.28 | -0.93 |
| Chic2 | GCTCAAGTACTCGCCCGACC | -2.85 | -0.69 |
| Nudcd2 | GGTTCCTTGCGGGACTCCGT | -3.31 | -2.53 |
| Alg8 | ACAGCCTCCCAATATCTCAG | -3.56 | -0.54 |
| Alg8 | AGTTTGGAGCCCAGTAGGCA | -2.77 | -2.19 |
| Alg8 | CCGCAGCAGATAGACACCAT | -2.54 | -0.11 |
| Alg8 | TTGTCCGCGTTACTTCCCTG | -2.50 | 0.07 |
| Rad51d | AGAGATCTGCGCCATTTAAG | -3.28 | -0.91 |
| Rad51d | GATATGCTACAGGACCTTCG | -2.83 | 0.44 |
| Rad51d | TGATGCTGGCCTCTATACTG | -3.28 | -1.90 |
| Dlst | AATGCTGACGACTTTCAATG | -2.31 | 0.00 |
| Dlst | GCAGGGGTCTCCTTATGTCG | -2.67 | -1.13 |
| Dlst | GGTTCGCTTCTTCCAAACCA | -2.41 | -2.08 |
| N4bp1 | CCATTGTATAACTGTCTGCG | -3.02 | -1.14 |
| N4bp1 | GAGTTGCAGCCAGATACGCG | -3.25 | -1.28 |
| N4bp1 | TTACTGAGGCTCGATTGGGA | -3.59 | 0.41 |
| Ipo11 | ATGGGATTGATCGTTACTGG | -2.32 | 0.00 |
| Ipo11 | CCAAACACCCCACATATGGT | -2.24 | -0.79 |
| Ipo11 | GTATAAGCCATTACGACGCA | -2.81 | -1.52 |
| Sepsecs | CACCGGATCGTCCAATTCCG | -2.82 | -0.88 |
| Sepsecs | CAGGACTTCTGGTCTATCCG | -3.14 | -1.47 |
| Sepsecs | TAAGCGTTGTTGACTACATG | -3.02 | 0.00 |
| Asnsd1 | CCTGGGTACCAACTGACGAA | -2.91 | -2.96 |
| Asnsd1 | TGATAATAGATAAACGACCA | -3.36 | 0.05 |
| Asnsd1 | TTGTGCCTAAACAAAAAACA | -2.52 | 0.85 |
| Ube2n | CTGTTACCTTCATAGATAAG | -2.50 | 0.00 |
| Ube2n | GCTGCCCCGCAGGATCATCA | -2.94 | -2.00 |
| Ube2n | TAAAAGTCCCTCCCTCAAAG | -2.56 | 0.00 |
| Ubtd1 | CAGCAGCAAGTTCACAGGTG | -3.04 | -1.37 |
| Ubtd1 | TGAAGCTAATGACCATGAGC | -2.77 | -0.59 |
| Ubtd1 | TGTGAATGCTATGACGAGCT | -2.59 | 0.02 |
| Ccnc | ATTTCAAGAGATTCTATGCT | -2.59 | 1.73 |
| Ccnc | GTTTCTGGCATCCAAAGTAG | -2.50 | 0.80 |
| Ccnc | TCTGTTGAAAGAGCGCCAAA | -0.71 | -3.36 |
| Ccnc | TGGTCTAGTTACCATGCAAG | -3.50 | -0.83 |
| Parn | AAAACGGTCTCAAGCCAATG | -3.05 | 1.05 |
| Parn | AAGACATATAGTTATCAGCA | -2.22 | -1.83 |
| Parn | GGTCATACTTAAAAGCACAA | -2.07 | -0.81 |
| Ccdc134 | GCCAGCTTTCTCGCACGTGG | -0.61 | -2.01 |
| Ccdc134 | TGGAACCTCCTGATCCGCTG | -4.60 | 0.12 |
| Ccdc134 | TGGAATTATGGTCAAAGTAG | -2.20 | 0.96 |
| Nepro | CAAGAGCCAGACCTTGGATG | -2.86 | 0.41 |
| Nepro | CCTTTAGTAGCAGAAGCCGC | -2.95 | 0.73 |
| Nepro | GTCTTGTGCAAAAAGCCCGA | -2.54 | -0.15 |
| Nepro | TCAGCAACTGAGAACTCACT | -1.37 | -2.37 |
| Vps33a | ACACAACGCTAAGACAGTCG | -3.60 | -0.22 |
| Vps33a | GCAAGAGGTTATCAAACACG | -2.17 | -0.79 |
| Vps33a | GCCTGTACCACGCAGCCAAG | -2.37 | 0.00 |
| Vps33a | TAATTGCTGAGAATGTACTC | -2.54 | 0.00 |
| Cks1b | ACGACGAGGAGTTCGAATAC | -2.76 | -0.86 |
| Cks1b | GAATCTGAATGGAGGAACCT | -2.21 | 0.00 |
| Cks1b | TTCAGATTCAGACATCAGAT | -2.07 | 0.00 |
| Cks1b | TTCGGACAAATACGACGACG | -2.32 | 0.00 |
| Atp6v1h | CTGCAGCATATCGTCAACCA | -2.30 | -0.72 |
| Atp6v1h | GAATGATATTATAGCGACGA | -2.20 | 0.59 |
| Atp6v1h | GGATCCTGGCGATTCAACAT | -3.11 | 0.74 |
| Atp6v1h | TCATAGCCAGAGCATACTCT | -3.24 | -1.33 |
| Rer1 | ACGCAATGAAAAGGTTTAGG | -2.24 | 2.19 |
| Rer1 | AGGTCACAATGTACCAACCC | -1.71 | -2.61 |
| Rer1 | CAGTGTCACAACCCACCGGA | -2.75 | 0.23 |
| Rer1 | GAAAAATCTGTACACCACCG | -2.64 | -0.30 |
| BC030336 | CCCGGACTGGATCAACACCG | -3.76 | -0.09 |
| BC030336 | GCTCGATGGATAGCATTCAC | -3.98 | 0.17 |
| Megf8 | CACACCCTTACTGCCCGTCG | -2.48 | -1.34 |
| Megf8 | GAATTGCAACGCCCACACCG | -3.93 | 0.39 |
| Megf8 | GATGTGTCCCTAGTCTACCG | -3.40 | -0.24 |

TABLE 3-continued

| Gene | sgRNA | OT1 | Pmel+ |
|---|---|---|---|
| Megf8 | TGTTCTAGGAAACTACATGG | -2.76 | 1.10 |
| Hnrnpf | ACAGGGAAAGCATGGGACAC | -2.35 | 0.76 |
| Hnrnpf | AGAAGGCAGGCAGAGTGGTG | -2.13 | -0.75 |
| Hnrnpf | TTGTGAGGCAAACTGAACGA | -2.11 | -0.86 |
| Mrps21 | GCGTCGTCGACTTATGACTT | -3.36 | -0.05 |
| Ppcs | AACTTCAGTAGCGGGCGACG | -2.23 | 0.00 |
| Ppcs | ATAGAAATCTGACACTGCCG | -2.12 | 0.00 |
| Ppcs | ATGCAGATAATCCGCCAAAG | -2.49 | 0.00 |
| Rab1a | ACTTCTGATTGGCGATTCTG | -3.78 | -2.49 |
| Rab1a | ATACACAACTATGATGCCAT | -1.48 | 5.64 |
| Rab1a | CCTTCAATAACGTTAAACAG | -2.79 | -0.26 |
| Lman2 | ACTTCAAAGTCCATGGCACA | -2.45 | -0.63 |
| Lman2 | CCCGGGAATAGCGTACAGCT | -2.71 | 0.70 |
| Lman2 | GCAAATGTAGAAATGTCGTG | -2.34 | -0.65 |
| Smarce1 | ATGAGGTACAGCAGAAAGGT | -2.05 | 0.90 |
| Smarce1 | CAGCCTGCTGAGGATCCAGA | -2.33 | -1.07 |
| Smarce1 | GAATACGAAGCAGAAAAGGT | -2.50 | 0.00 |
| Tmed2 | CCGCTCGAAGAAGCACTCCT | -3.04 | 0.95 |
| Tmed2 | CTTCCTGGACATCGACGTGG | -2.12 | 0.56 |
| Tmed2 | GGACAAGACATGGAGACAGA | -2.11 | 0.83 |
| Ddx42 | AAACAAGAGCACACTCCCCG | -2.06 | 1.49 |
| Ddx42 | ACATTGATACGCACACTCAC | -2.37 | 1.41 |
| Ddx42 | ACCTCCGAATGATCAATGGG | -2.52 | -0.84 |
| Ddx42 | AGCGTATAATCTTCGATCAG | -2.46 | 1.35 |
| Usp24 | CATGAGGTAGAATAGTTCGT | -0.65 | 2.15 |
| Usp24 | TATGGAGCGGTGTATGCCCG | -3.33 | 1.27 |
| Usp24 | TCACTGCGTACGCGTCACTG | -3.44 | 0.81 |
| Mbnl1 | CTGCACCAATGTTGGTCACG | 0.32 | 2.82 |
| Mbnl1 | GCTCACCACGGGCTGCAACG | 0.43 | 2.34 |
| Syvn1 | AAGGGCCACTTACAATTAGG | -0.44 | 2.10 |
| Syvn1 | CTTGGTCAAATACACTACAG | 1.61 | 2.66 |
| Syvn1 | TCAGGATGCTGTGATAAGCG | -0.67 | 2.98 |
| Nf1 | GACAAGATGACAAACCTGGT | 1.65 | 3.45 |
| Nf1 | GGAAACGTGGCATGTCTCGG | 1.93 | 2.66 |
| Nf1 | GGACGAGAGCAACATAAACA | -0.03 | 2.15 |
| Derl2 | CAAAGTCTGCTGTCCGACCT | 0.41 | 2.57 |
| Derl2 | CAATAATGCTGGTCTACGTG | 0.89 | 2.58 |
| Derl2 | GAAGACCAAAGAAGTTCATG | -0.52 | 2.37 |
| Derl2 | GCTGGGGAACTCAATTATAG | -0.78 | 2.03 |
| Tap2 | AGAAGCCACTCGGACTACTG | -0.30 | 2.77 |
| Tap2 | GCTGTGGGGACTGCTAAAAG | -1.12 | 2.22 |
| Tap2 | TTACACGACCCGAATAGCGA | -2.14 | 3.22 |
| Tap1 | ACTAATGGACTCGCACACGT | -0.42 | 2.09 |
| Tap1 | GTCTCTAGCAAAGTCCACGC | -0.40 | 3.25 |
| Tap1 | TGGACATGAGCCATATGTTG | -0.14 | 3.35 |
| Dusp6 | ACTCGTACAGCTCCTGTGGT | 0.67 | 2.62 |
| Dusp6 | CACTGCGAGACCAATCTAGA | 1.44 | 2.24 |
| Dusp6 | CCGAGACCCCAATAGTGCAA | 0.71 | 2.89 |
| Dusp6 | CTCTTCCAACACGTCCAAGT | 0.64 | 3.56 |
| Ube2g2 | ATCACCTGGAGCATGCAGGA | -0.29 | 2.72 |
| Ube2g2 | GAATCCTCCAGAAGGAATCG | 0.26 | 2.99 |
| Ube2g2 | GCACTGCTCTCATAACCCAT | -0.77 | 3.01 |
| Ube2g2 | TCATCTTCGGAGGGCTCAAG | 0.18 | 2.75 |
| Lztr1 | ATGTTGCCATCGTCACTGCA | 0.41 | 3.04 |
| Lztr1 | CCCACGAATTCGTCACAGGG | 1.32 | 2.63 |
| Lztr1 | CGGATGGCCACACGTAACAG | 0.20 | 3.00 |
| Lztr1 | GTAGACAACAACATTCGCAG | 0.33 | 2.97 |
| Jak2 | AAGTCCTAGATAAAGCACAT | 3.13 | 3.43 |
| Jak2 | ACAGATACGGAGTGTCCCGT | 2.85 | 1.90 |
| Jak2 | CGGGTATTACAGACTAACTG | 2.71 | 3.20 |
| Jak2 | TCTTCAGGAGAGAATACCAT | 3.69 | 3.86 |
| H2-D1 | CGACGCAAGTGGGAGCAGAG | -2.09 | 3.91 |
| H2-D1 | GGCCCCGACTCAGACCCGCG | 5.15 | 3.60 |
| H2-D1 | GTGAGCCTGAGGAACCTGCT | 1.01 | 3.08 |
| H2-D1 | TAGCCGACAGAGATGTACCG | 0.05 | 3.52 |
| B2m | ACTCACTCTGGATAGCATAC | 5.27 | 3.80 |
| B2m | ATTTGGATTTCAATGTGAGG | 5.19 | 3.20 |
| B2m | TCGGCTTCCCATTCTCCGGT | 5.48 | 4.33 |
| B2m | TGAGTATACTTGAATTTGAG | 5.51 | 3.55 |
| Ifngr1 | GGTATTCCCAGCATACGACA | 3.32 | 5.25 |
| Ifngr1 | TATACCAATACGCAAATACC | 4.07 | 4.34 |
| Ifngr1 | TATGTGGAGCATAACCGGAG | 2.95 | 3.80 |
| Ifngr1 | TTCAGGGTGAAATACGAGGA | 3.43 | 5.32 |
| Ifngr2 | AGGGAACCTCACTTCCAAGT | 3.12 | 4.83 |
| Ifngr2 | TCCCTTTGATGTGTTCCACG | 3.40 | 4.23 |
| Ifngr2 | TGATGAGCAGATTCTAACTT | 3.81 | 5.03 |
| Ifngr2 | TGGACCTCCGAAAAACATCT | 3.78 | 5.37 |
| Stat1 | GAAAAGCAAGCGTAATCTCC | 2.70 | 8.13 |

TABLE 3-continued

| Gene  | sgRNA            | OT1  | Pmel+ |
|-------|------------------|------|-------|
| Stat1 | GGATAGACGCCCAGCCACTG | 3.32 | 9.31  |
| Stat1 | TGTGATGTTAGATAAACAGA | 1.50 | 7.91  |
| Stat1 | TTAATGACGAGCTCGTGGAG | 2.25 | 8.60  |
| Jak1  | AAACATATAGTGTACCTCTA | 2.36 | 10.21 |
| Jak1  | CGATGCCATTCGAATGACAG | 1.57 | 8.40  |
| Jak1  | TCCGAACCGAATCATCACTG | 3.59 | 10.23 |
| Jak1  | TGAATAAATCCATCAGACAG | 2.46 | 9.92  |

Tables 4-5 provided below lists the top sgRNAs identified in the screen.

TABLE 4

| Pathways | Direction | Genes |
|---|---|---|
| Jak Stat signaling pathway | Enriched | Jak1, Jak2, Stat1, Ifngr1, Ifngr2 |
| Antigen processing and presentation | Enriched | Tap1, Tap2, B2m, Nlrc5, H2-D1 |
| Negative regulation of MAPK pathway | Enriched | Nf1, Dusp6, Spred1, Spop, Rasa2 |

TABLE 5

| Pathways | Direction | Genes |
|---|---|---|
| NF-kB pathway | Depleted | RelA, Ikbkb, Ikbkg, Rnf31, Otulin, Sharpin, Cflar |
| Autophagy | Depleted | Atg5, Atg13 |
| mTORC1 signaling pathway | Depleted | Rraga, Rragb, Rragc, Lamtor1 |
| Amino sugar and nnucleotide sugar metabolism | Depleted | Gpi, Gale, Gne, Nans, |
| Nicotinate and nicotinamide metabolism | Depleted | Nampt, Nadk |
| Glycolysis | Depleted | Cd44, Ero1l, Gale, Gne, Nsdhl |
| PBAF complex | Depleted | Arid2, Brd7, Pbrm1 | f. In Vitro Validation of Genes of the PBAF Complex

Guide RNA sequences against Arid2, Brd7 and Pbrm1 were cloned into a PLKO3G-GFP vector and confirmed by sequencing. gRNA constructs were co-transfected with pCMV-dR8.91 and pCMV-VSV-G (Addgene #8454) to HEK293T cells. Transfection was done by using TransIT®-293 (Mirus, MIR2700) following the manufacturer's protocol. Virus was harvested at 48 hors post-transfection and stored at −80° C. B16F10-Cas9 cells (clone4) were infected with a gRNA lentivirus driving expression of a single gRNA overnight to inactivate Arid2, Brd7 or Pbrm1 genes individually. Infected cells were sorted based on GFP expression by BD FACS Aria II. Cells were edited for at least ten days prior to validation experiment.

For in vitro validation, Arid2, Brd7 or Pbrm1 deficient B16F10 cells (GFP positive) were mixed with control B16F10 cells (GFP negative) at a 1:1 ratio. These cells were stimulated with 10 ng/ml of IFNγ and co-cultured with in vitro activated Pmel1 T cells at different effector to target ratios in a 6-well plate (triplicated wells for each gRNA). After a three-day co-culture with T cells, fold depletion of mutant B16F10 cells in the presence or absence of T cells was determined by FACS, comparing the percentage of mutant cells (GFP positive) to control B16F10 cells (GFP negative).

g. In Vivo Experiment with Pbrm1-Deficient B16F10 Cells

Two hundred and fifty thousand control (non-targeting gRNA) or Pbrm1-deficient B16F10-Cas9 (clone4) cells were subcutaneously injected into 7 to 8-week-old male C57BL/6 mice (The Jackson Laboratory, #000664). Three treatment groups were compared for mice implanted with control or Pbrm1 deficient B16F10 tumor cells: CD8 depletion (n=5-8 mice/group), checkpoint blockade therapy (αCTLA-4+αPD-1) (n=10 mice/group) and isotype control antibody (n=5-7 mice/group). For the CD8 depletion group, CD8β mAb (clone53-5.8, #BE0223, 100 µg/mouse) was given on day −1, day 0, and every four days. For checkpoint blockade treatment group (α-PD-1: clone 29F.1A12, #BE0273, 200 µg/mouse; α-CTLA-4: clone 9H10, #BP0131, 100 µg/mouse) mAbs were administered on day 4 and then every $3^{rd}$ day. For isotype control group (2A3 and polyclonal syrian hamster IgG, 200 µg/mouse and 100 µg/mouse, respectively), antibodies were given starting on day 4, and every three days. Tumor size were measured with digital calipers every 2-3 days. Mice were sacrificed when tumor reached 20 mm in diameter. All experiments were performed in compliance with federal laws and institutional guidelines and were approved by the Animal Care and Use Committee of the Dana-Farber Cancer Institute.

h. Validation Screen

Top hits were selected from the genome-scale screen for validation based on the following criteria: (1) |LFC|>2, (2) FDR<0.05, and (3) known human homologs. The mini-pool gRNA library was synthesized by the Genetic Perturbation Platform at the Broad Institute and included 1,878 gene-targeting gRNAs (6 gRNAs/gene) and 2,000 control gRNAs for data normalization. Lentivirus for the mini-pool gRNA library was produced as described above, and a low MOI was used for the validation screen (MOI=0.08). Pmel-1 and OT-I screens were performed as described for the genome-scale screen with a representation (cell number/gRNA) of >5,000. For both Pmel-1 and OT-I screens, B16F10 cells and T cells were co-cultured for 3 and 1 days respectively, before T cells were removed from the culture. An Ova peptide concentration of 0.1 ng/ml was used in the validation screen with OT-I T cells. Genomic DNA was extracted from cells regrown after T cell removal, and gRNA representation was quantified as described above.

i. Western Blot Analysis of Mutant Cell Lines

Cells were lysed in RIPA buffer (50 mM Tris-HCl, pH7.4, 150 mM NaCl, 0.25% deoxycholic acid, 1% NP-40, 1 mM EDTA). Protein concentrations were quantified with the Pierce™ BCA Protein Assay Kit (Thermo Fisher Scientific). For Western blotting, equal amounts of protein were heat denatured in the presence of a reducing agent and separated on 4-12% Bis Tris NuPage gels or 3-8% Tris-Acetate NuPage gels (Thermo Fisher Scientific), and transferred to PVDF membranes. Antibodies used for Western blotting were as follows: BRD7 (Cell Signaling, clone D9K2T), PBRM1 (Cell Signaling, clone D3F70), ARID2 (Abcam, ab51019) and GAPDH (Cell Signaling, clone D16H11), OTULIN (Cell Signaling, #14127), DUSP6 (Abcam, #ab76310) and NF1 (Cell Signaling, #14623). Proteins were detected using ECL Plus (GE Healthcare Life Sciences) using the ChemiDoc™ Imaging System (Bio-Rad). For total protein measurement, whole cell lysates were loaded to TGX Stain-Free gel (BIO-RAD) and ChemiDoc™ Imaging System (Bio-Rad) was used for image acquisition.

j. FACS Analysis with Tumor Infiltrating T Cells

Five times $10^5$ control (non-targeting gRNA) or Pbrm1 deficient B16F10-Cas9 cells were subcutaneously injected into 7 to 8 week old male C57BL/6 mice. Mice were administrated with checkpoint blockade therapy (αCTLA-4 plus αPD-1) starting from day 3 and then every third day. Tumors were harvested on day 15, and single cell suspensions were stained with the following antibodies: anti-CD3 (17A2, BV510), anti-CD4 (RM4-5, BV785), anti-CD8 (53-6.7, BV650), anti-CD45 (30-F11, APC), anti-B220 (RA3-6B2, FITC), anti-NK1.1 (PK136, FITC) (Biolegend), anti-CD19 (MB19-1, FITC), anti-granzyme B (NGZB, PE-Cy7) (Thermo Fisher Scientific) and with fixable Zombie UV™ viability dye (Biolegend). BD LSRFortessa™ X-20 was used for data acquisition and FlowJo (Tree Star) was used for data analysis.

k. Analysis of MHC Class I and PD-L1 Expression by Flow Cytometry

Control (non-targeting gRNA), Arid2, Pbrm1 and Brd7 deficient B16F10 cells were treated with different doses (0, 0.1, 0.5, 1, 5 or 10 ng/ml) of IFNγ for 24 hours in triplicates. Cells were then stained with anti-H2-K$^b$ (AF6-88.5, APC, Biolegend) or anti-PD-L1 (10F.9G2, APC, Biolegend) antibodies followed by FACS analysis. BD LSRFortessa™ X-20 was used for data acquisition and FlowJo (Tree Star) was used for data analysis. Geometric mean fluorescence intensity (gMFI) was calculated using FlowJo software.

l. RNA-Seq Analysis

Total RNA was extracted from control (non-targeting gRNA), Arid2, Pbrm1 and Brd7 deficient B16F10 cells cultured in complete DMEM in triplicates. Cells were stimulated with IFNγ (10 ng/ml) or vehicle control for 24 hours. RNA extraction was performed using the RNeasy® Plus Mini Kit (Qiagen, #74134) following the manufacturer's protocol. Total RNA was submitted to the Molecular Biology Core Facility at DFCI for sequencing. Standard mRNA library preparation kit (RS-122-2101, Illumina) was used for library preparation. Single-end 75 bp sequencing was done on Illumina NextSeq™ 500. Statistics for differentially expressed genes were calculated by DESeq2 (version 3.5) (Love et al. (2014) *Genome Biol.* 15:550) and Cufflinks (Trapnell et al. (2010) *Nat. Biotechnol.* 28: 511-515).

m. ATAC-seq

Control (non-targeting gRNA) and Pbrm1 deficient B16F10 cells were cultured in complete DMEM media in 10 cm dishes. Cells were treated with 10 ng/ml IFNγ or vehicle control for 24 hours. ATAC-seq was performed on triplicates (200,000 cells) by the Center for Functional Cancer Epigenetics at DFCI as previously described (Buenrostro et al. (2015) *Curr. Protoc. Mol. Biol.* 109:21-29; Buenrostro et al. (2013) *Nat. Methods* 10:1213-1218). For data analysis, Burrows-Wheeler Aligner (BWA) (Li et al. (2009) *Bioinformatics* 25:1754-1760) was used to map sequencing reads to the reference genome and MACS2 (Zhang et al. (2008) *Genome Biol.* 9:R137) for peak calling. DESeq2 (Love et al. (2014) *Genome Biol.* 15:550) was applied to identify the differentially accessible regions with or without IFNγ treatment from ATAC-seq data. Binding and expression target analysis (BETA) (Wang et al. (2013) *Nat. Protoc.* 8:2502-2515) was used to integrate ATAC-seq data on accessible chromatin sites with differential gene expression data to infer directly targeted genes.

n. Gene Sets Enrichment Analysis (GSEA)

For gene set identification, the hypergeometric overlap statistic tool (available on the World Wide Web at software-.broadinstitute.org/gsea/msigdb/annotate.jsp) was used to calculate the overlap between a gene list and pathways in MSIgDB (Molecular signature database) (Subramanian et al. (2005) *Proc. Natl. Acad. Sci. U.S.A.* 102:15545-15550; Mootha et al. (2003) *Nat. Genet.* 34:267-273). GSEA on gene expression data was performed by loading cufflink count table for each comparison into the GSEA package.

o. Single-Cell RNA-Seq

Five times $10^5$ control (non-targeting gRNA) or Pbrm1 deficient B16F10-Cas9 cells were subcutaneously injected into 7 to 8 week old male C57BL/6 mice (n=5 for each group). Mice were administrated with checkpoint blockade therapy (αCTLA-4 plus αPD-1) starting from day 3 and then every third day. On day 15, tumors were harvested and 9,000 CD45+ live (DAPI negative) cells were sorted from each individual tumor by BD FACS Aria II. Sorted CD45+ cells were then combined for each group (total ~45,000 CD45+ cells for each genotype) and washed with 0.04% RNase-free BSA (Thermo Fisher Scientific) in PBS. Five thousand cells per condition were targeted for the 10× Genomics 3' single cell assay (10× Genomics). Reverse transcription, cDNA amplification and library preparation were performed according to manufacturer's protocols. Completed libraries were sequenced on an Illumina HiSeq 2500 on rapid-run mode, yielding >40,000 reads per cell.

Single-cell RNA-seq data analysis was performed using the Cell Ranger Single-Cell Software Suite provided by 10× Genomics: available on the World Wide Web at support. 10×genomics.com/single-cell-gene-expression/software/downloads/latest. Briefly, UMI counts were obtained by sequence alignment followed by barcode demultiplexing. The gene expression matrix was filtered to include only genes with at least one UMI count in at least one cell. Raw UMI counts were normalized by the total counts in each cell. The 1,000 genes with highest dispersion values (defined as the variance divided by the mean) were selected for further analysis. The UMI counts were log-transformed and z-score normalized for each gene. tSNE analysis was carried out based on the first 50 principal components obtained from PCA analysis. Distinct cell subpopulations were identified using k-means clustering. Differential expression analyses were performed by using the zlm.SingleCellAssay function in the R MAST package with method "glm". Hypergeometric overlap statistic tool (available on the World Wide Web at software.broadinstitute.org/gsea/msigdb/annotate.jsp) was used for GSEA analysis for single cell data.

p. ELISA

Cells (1×10$^6$) were plated in 6-well plates with complete growth medium. On the following day, cells were washed with serum-free medium three times and treated with IFNγ at indicated concentrations for 24 hrs. Chemokines were measured in supernatants using mouse CXCL9 (MIG) ELISA Kit and mouse CRG-2 (CXCL10) ELISA Kit (Thermo Fisher Scientific) according to the manufacturer's protocol.

q. Quantitative Real-Time PCR

Cells were treated with indicated concentrations of IFNγ for 24 hours and total RNA was isolated by RNeasy® Plus Mini Kit (Qiagen). cDNAs were synthesized from 1 μg of total RNA using the PrimeScript™ RT reagent Kit (Takara) and were amplified by SYBR® Premix Ex Taq™ II (Takara) using CFX96 Real-Time PCR System (Bio-Rad) according to the manufacturer's protocols. Primers for Cxcl9 and Gapdh were as follows: Cxcl9; 5'-AGTCCGCTGTTCTTTTCCTC-3' (SEQ ID NO: 985) and 5'-TGAGGTCTTTGAGGGATTTGTAG-3' (SEQ ID NO: 986), Gapdh; 5'-GTGTTCCTACCCCCAATGTGT-3' (SEQ ID NO: 987) and 5'-ATTGTCATACCAGGAAAT- GAGCTT-3' (SEQ ID NO: 988). Relative mRNA expression was evaluated after normalization for Gapdh expression.

r. Growth Competition Assay

PBAF mutant (GFP+) and control B16F10-Cas9 cells (GFP−) were mixed at 1:1 ratio. The mixture of cells was then seeded in 10 cm dish in complete growth medium. Cells were passaged every three or four days and were analyzed by flow cytometry for changes of the ratio of GFP+/GFP− cells.

s. Doxorubicin-Induced Cell Death

Figure 11:
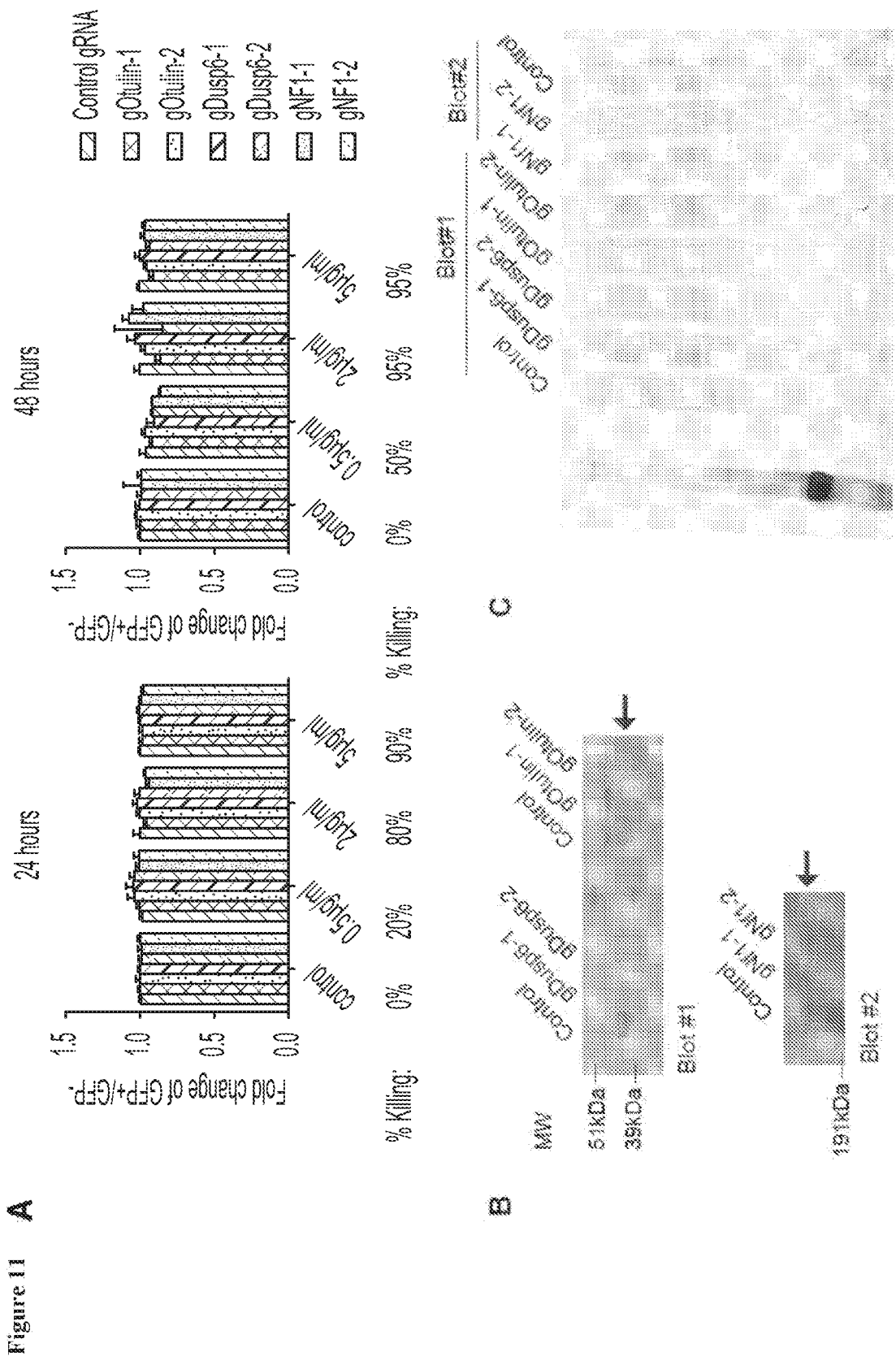
FIG. 11 includes 3 panels, identified as panels A, B, and C, which show testing of the cell death threshold for Otulin, Dups6 and Nf1 deficient B16F10 cells. Panel A shows the sensitivity to doxorubicin induced cell death of Otulin, Dusp6 and Nf1 deficient B16F10 cells (two gRNAs for each gene). GFP expressing Otulin, Dusp6 and Nf1 deficient B16 B16F10 cells were mixed with GFP-negative control B16 cells at a 1:1 ratio. Cells were treated with different concentrations of doxorubicin or vehicle control for 24 (left) or 48 (right) hours. Fold change of the percentage of GFP+ cells following doxorubicin treatment was measured by FACS. The total % killing of tumor cells in response to doxorubicin is indicated below the graphs. Panel B shows the protein levels of Dusp6, Otulin and Nf1 in control and indicated knockout cell lines by Western blot. Panel C shows the amount of total protein in each sample by loading the same cell lysates as in panel B on a TGX stain-free gel (Bio-Rad). Data shown in panel A are representative of two independent experiments.

Two knockout B16F10 cell lines with independent gRNAs were generated for Otulin, Dusp6 and Nf1 using the same protocol as described for PBAF complex. The knockout cell lines (GFP+) were mixed with control cells (GFP−) at 1:1 ratio. The mixture of cells was then seeded at 200,000 cells/well in a 6-well plate. Eighteen hours after seeding, different doses of doxorubicin (Sigma-Aldrich, D1515) as indicated in FIG. 11 were added to the cell culture (triplicate wells per condition). After 24 or 48 hours, cells were harvested and stained with DAPI (5 µg/ml) for 5 minutes in PBS with 2% FBS at room temperature. The ratio of GFP+/GFP−was determined by FACS (gated on DAPI− for live cells).

Figure 1:
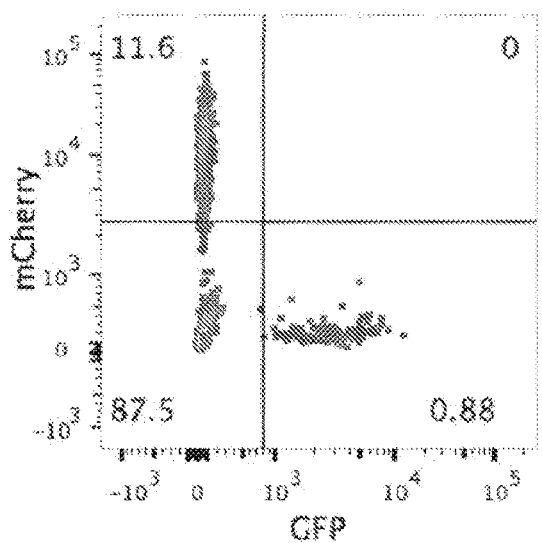
FIG. 1 includes 3 panels, identified as panels A, B, and C, which show the positive controls for discovery of positive and negative immune regulators expressed by tumor cells. Panel A shows representative FACS plots of B16F10 cell populations before and after co-culture with T cells. B2m deficient (GFP+) and Cd274 (PD-L1) deficient (mCherry+) B16F10 cells were mixed with unmodified B16F10 cells (targeting a composition of ~1% GFP+ and 10% mCherry+ cells prior to co-culture with T cells). Tumor cells were pulsed with 1 ng/ml of SIINFEKL peptide (SEQ ID NO: 1) for two hours. These tumor cell populations were then co-cultured with OT-I T cells at different tumor to T cell ratios for one day or three days. Panels B and C show summary of results (fold change) for B2m$^{-/-}$ (Panel B) and Cd274$^{-/-}$ (Panel C) B16F10 tumor cells after selection by OT-1 T cells depending on the following experimental variables: (1) B16F10 tumor to OT-1 T cell ratio; (2) time period of co-culture, and (3) pretreatment of B16F10 cells with or without 10 ng/ml of IFNγ prior to co-culturing with T cells to increase H2-K$^b$ expression by tumor cells. Data are representative of at least two independent experiments.
Figure 1:
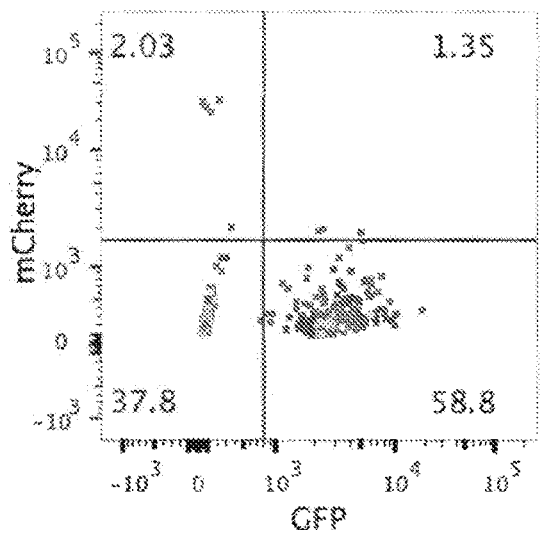
Figure 1:
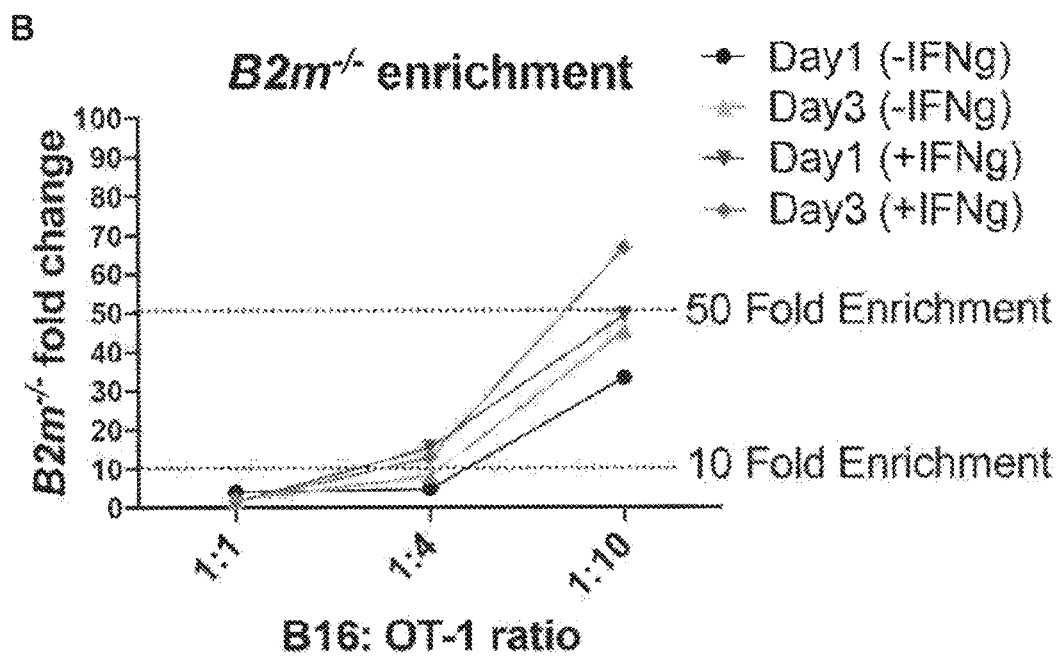
Figure 1:
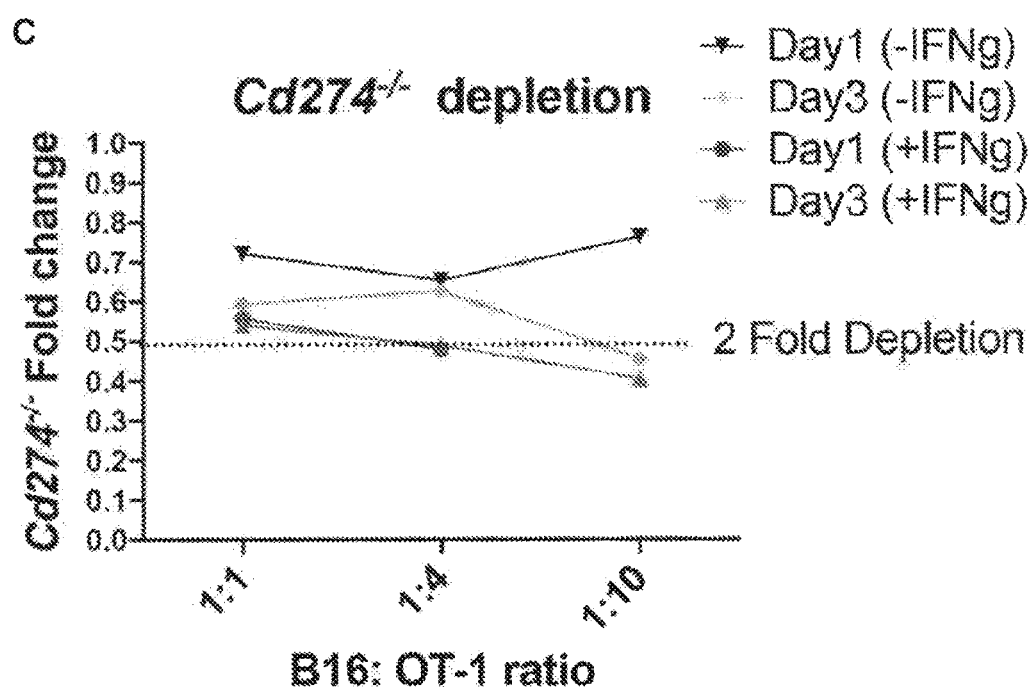

Example 2: Genome-Scale Screen to Discover Regulators of T Cell Mediated Killing In order to establish a screening system that allows for the identification of immune regulators in murine melanoma B16F10 tumor cells, the CRIPSR/Cas9 system was used to generate positive controls that are either more resistant (GFP+, B2m$^{-/-}$) or more sensitive (mCherry+, Cd274$^{-/-}$) to T cell-mediated killing. The murine B16F10 melanoma cell line was used for this screen because it is resistant to checkpoint blockade with antibodies targeting the PD-1 and/or CTLA-4 receptors (van Elsas et al. (1999) *J. Exp. Med.* 190:355-366; Chen et al. (2015) *Cancer Immunol. Res.* 3:149-160). Inactivation of resistance genes resulted in depletion of the corresponding gRNAs, but such depletion could only be detected with sufficient sensitivity when most tumor cells had sufficient Cas9 activity. Therefore, a B16F10-Cas9 clone with high editing efficiency was selected (FIG. 2) and tested with positive controls that were either more resistant (B2m$^{-/-}$) or sensitive (Cd274$^{-/-}$) to T cell-mediated cytotoxicity (FIG. 1).

Figure 2:
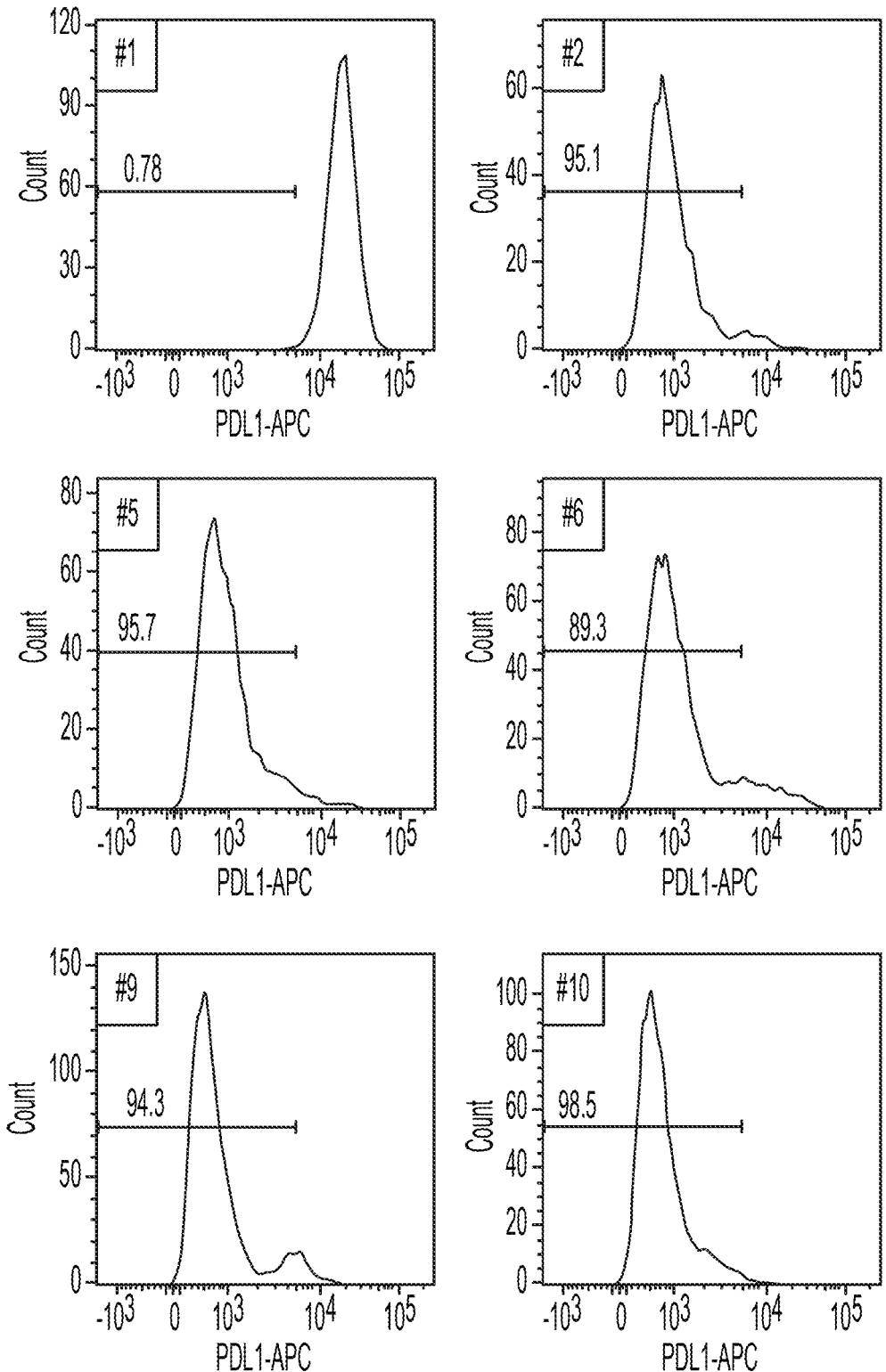
FIG. 2 shows the selection of B16F10 clones with high Cas9 editing activity. B16F10 cells were transduced with a lentiviral vector driving Cas9 expression and individual cells were sorted into 96 well plates based on co-expression of a GFP marker. Each of the B16F10 clones was independently transduced with a lentivirus encoding a gRNA targeting PD-L1. Ten days post-transduction, Cas9 efficiency was determined based on the percentage of PD-L1-negative cells after treatment with IFNγ (10 ng/ml) for 24 hours. Clone 4, which shows an efficiency of >95%, was selected for the screen to enable sensitive detection of depleted gRNAs in the screen. High editing efficiency is important in such a screen because non-edited tumor cells would mask detection of depleted gRNAs.
Figure 2:
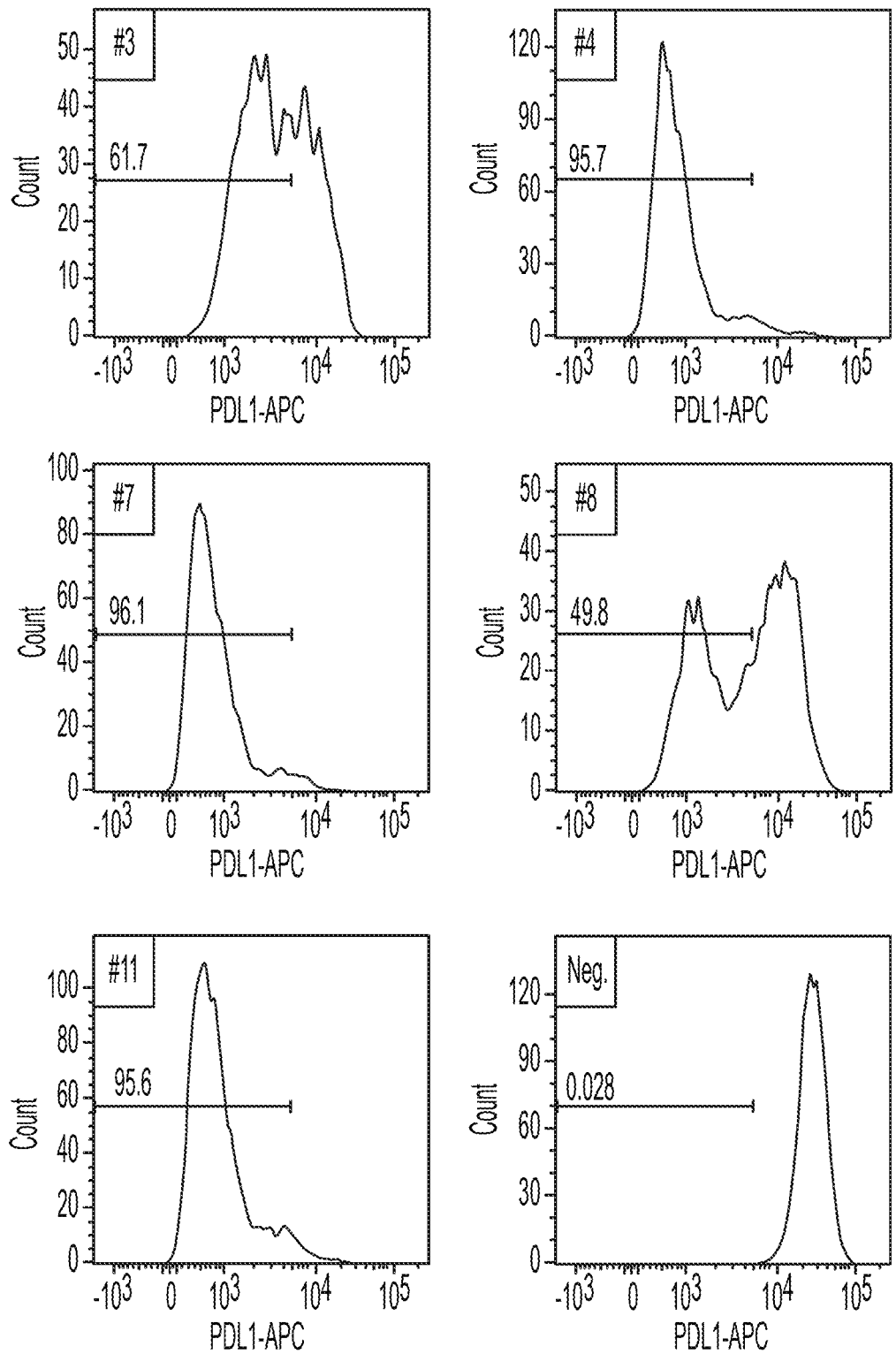

These controls were mixed with parental cells followed by selection with in vitro activated OT-1 T cells. B2m$^{-/-}$ cells were strongly enriched and Cd274$^{-/-}$ were noticeably depleted after 1-3 days of selection by the T cells (FIG. 1), indicating that both positive and negative regulators can be identified by using this approach. Identification of negative regulators requires efficient depletion of gRNAs during the selection process, which requires sufficient Cas9 activity in the vast majority of cells because non-edited cells are resistant to selection. Accordingly, Cas9 was introduced into the B16 cells and clones from sorted single cells for Cas9 activity by introducing a gRNA targeting PD-L1 were tested. Treatment of tumor cells with IFNγ results in strong upregulation of PD-L1 expression, which allowed for the identification of Cas9-expressing B16F10 clones with high editing efficiency. Similar results were obtained for multiple clones, and one of these clones (clone #4) was selected for the screen (FIG. 2).

This B16F10-Cas9 clone was then transduced with a genome-scale gRNA library in a lentiviral vector (Doench et al. (2016) *Nat. Biotechnol.* 34:184-191). These tumor cells were transduced with a genome-scale gRNA library in a lentiviral vector, and transduced cells were selected using puromycin. CD8 T cells from two TCR transgenic strains were used for selection: 1. Pmel1 T cells that recognize an endogenous melanoma antigen, gp100; and 2. OT-I T cells that recognize an ovalbumin-derived peptide. The OT-I TCR has a higher affinity for its peptide-MHC ligand that Pmel1 T cells. Selection was performed either with Pmel-1 T cells which have a relatively low TCR affinity for an endogenous melanoma antigen (Overwijk et al. (2003) *J. Exp. Med.* 198:569-580) or high-affinity OT-I T cells (Hogquist et al. (1994) *Cell* 76:17-27). Following a three-day co-culture of CD8 T cells with edited tumor cells, T cells were removed and remaining tumor cells were grown up for isolation of genomic DNA. Edited tumors cells were selected by three-day co-culture with Pmel-1 CD8 T cells (or one day for OT-I T cells), and the representation of all gRNAs was then determined following Illumina sequencing of the gRNA cassette (FIG. 3A). The specificity of gRNA enrichment/depletion was demonstrated by comparing selection with tumor-specific T cells versus control T cells of irrelevant specificity (FIG. 9). This comparison also controlled for potential effects of gRNAs on cell proliferation/viability.

Figure 4:
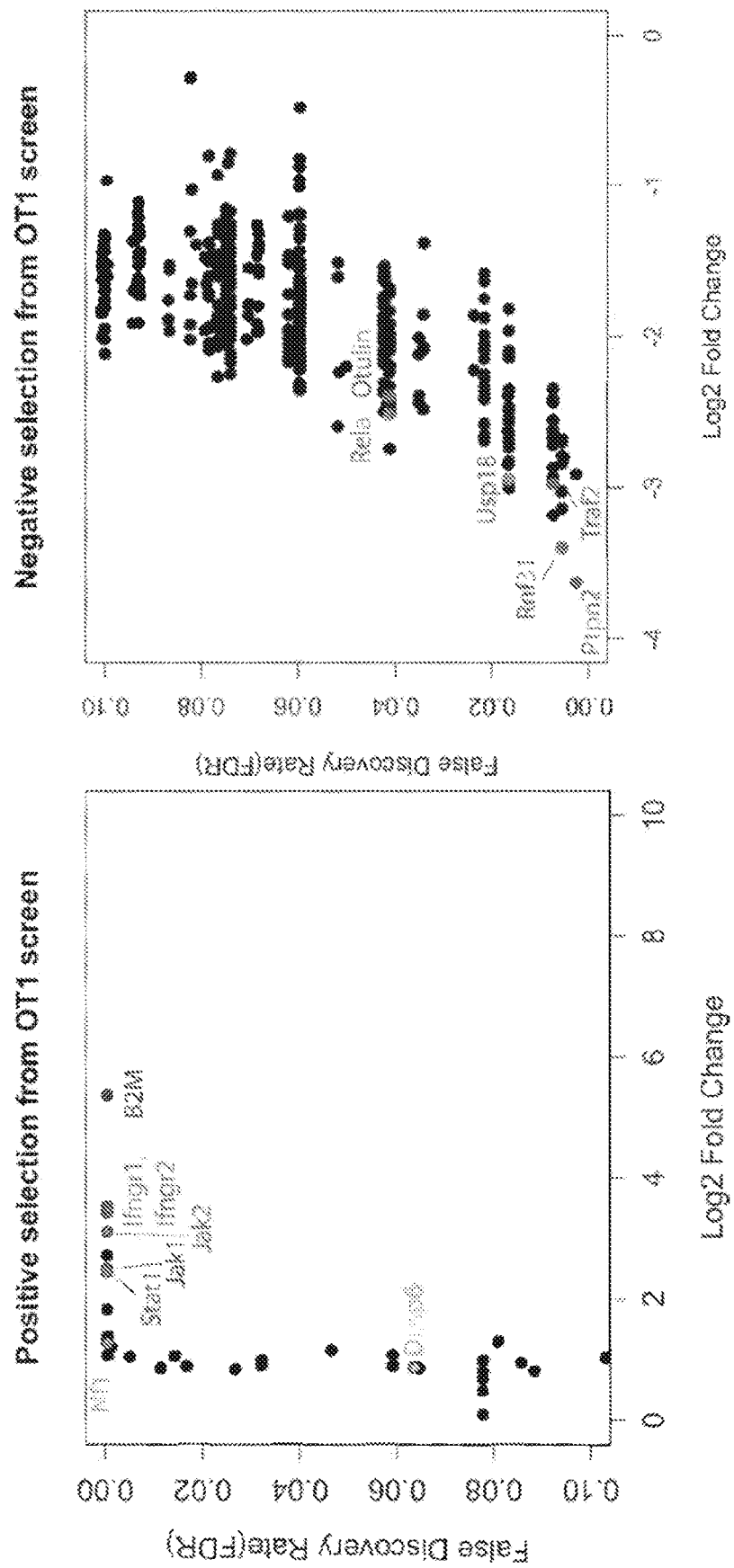
FIG. 4 shows the top candidate genes selected by OT-I T cells. The top positively selected (left) and negatively selected (right) candidate genes were identified using MaGeCK analysis.

In this screen, enriched gRNAs correspond to genes that are required for efficient T cell-mediated killing of the tumor cells. In fact, a number of well-known genes required for T cell-mediated tumor immunity were identified among the enriched gRNAs in both Pmel-1 and OT-1 screens (FIG. 3B, FIG. 10A, and Tables 6-9), including key genes in the MHC class I and IFNγ signaling pathways (Blum et al. (2013) *Annu. Rev. Immunol.* 31:443-473; Kobayashi et al. (2012) *Nat. Rev. Immunol.* 12:813-820; Parker et al. (2016) *Nat. Rev. Cancer* 16:131-144). These included the key components of the MHC class I pathway required for presentation of tumor-derived peptides to T cells, including H2-D1 (MHC class I heavy chain), B2m (subunit of MHC class I proteins), Tap1 and Tap2 (transporters for peptides from cytosol to ER) and Nlrc5 (key transcription factor for MHC class I genes). Furthermore, key components required for IFNγ and IFNα/β recognition and signaling were identified, including Jak1, Jak2, Stat1, Ifngr1 and Ifngr2, which are important for interferon-mediated upregulation of MHC pathway genes (FIGS. 3B and 4). In fact, mutations in both MHC and interferon pathway genes were shown to confer resistance to immunotherapy in cancer patients, indicating that these genes are relevant for tumor immunity in humans (Gao et al. (2016) *Cell* 167:397-404; Zaretsky et al. (2016) *N. Engl. J Med.* 375:819-829). T cell-based CRISPR/Cas9 screens have been described by two other laboratories. One of these studies performed an in vivo screen covering 2,368 murine genes and highlighted the phosphatase Ptpn2 as a novel target for immunotherapy (Manguso et al. (2017) *Nature* 547:413-418). The second study focused on human tumor cells and T cells and reported that mutations in APLNR render tumor cells resistant to T cell mediated cytotoxicity (Patel et al. (2011) *Bioconjugate Chem.* 22:376-387). This approach emphasized sensitive detection of depleted gRNAs in a genome-wide manner, which allowed discovery of additional mechanisms conferring resistance to immunotherapy.

A striking result was that a much larger number of gRNAs were depleted (Tables 6-9), indicating that inactivation of these genes sensitized tumor cells to killing by T cells. Top genes in this group included known negative immune regulators, including CD274 (encoding PD-L1 (Dong et al. (1999) *Nat. Med.* 5:1365-1369; Freeman et al. (2000) *J. Exp. Med.* 192:1027-1034)), the phosphatase Ptpn2 (Kleppe et al. (2011) *Blood* 117:7090-7098), and *granzyme B inhibitor*

Figure 10:
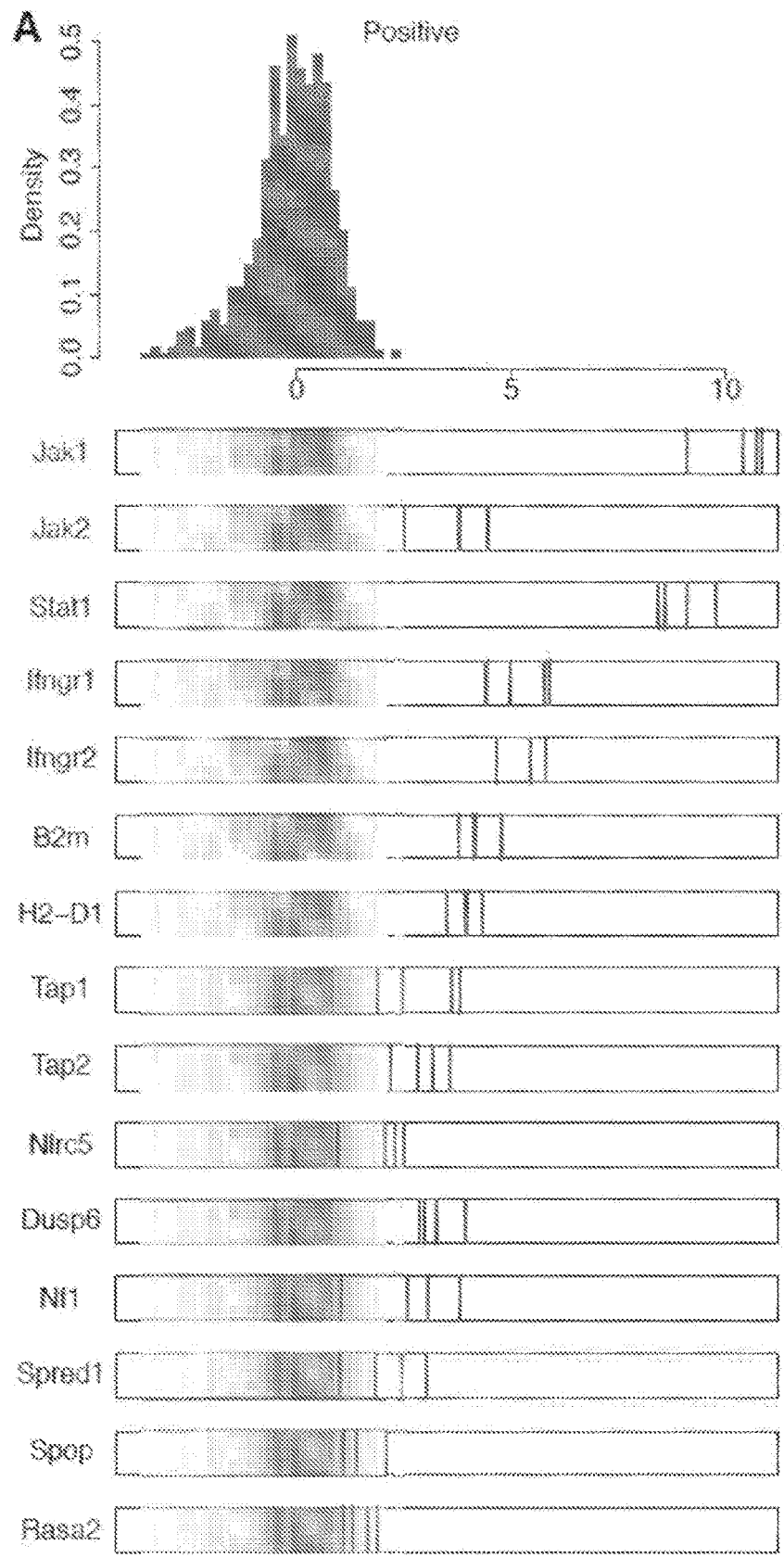
FIG. 10 includes 2 panels, identified as panels A and B, which show the frequency histograms of enriched and depleted gRNAs. In Pmel1 primary screen, Log 2 fold change of enriched (Panel A) or depleted (Panel B) gRNAs for each gene presented in FIG. 5A are labelled with red lines. Distribution of 1,000 non-targeting control gRNAs is also indicated in both histograms (grey scale).
Figure 10:
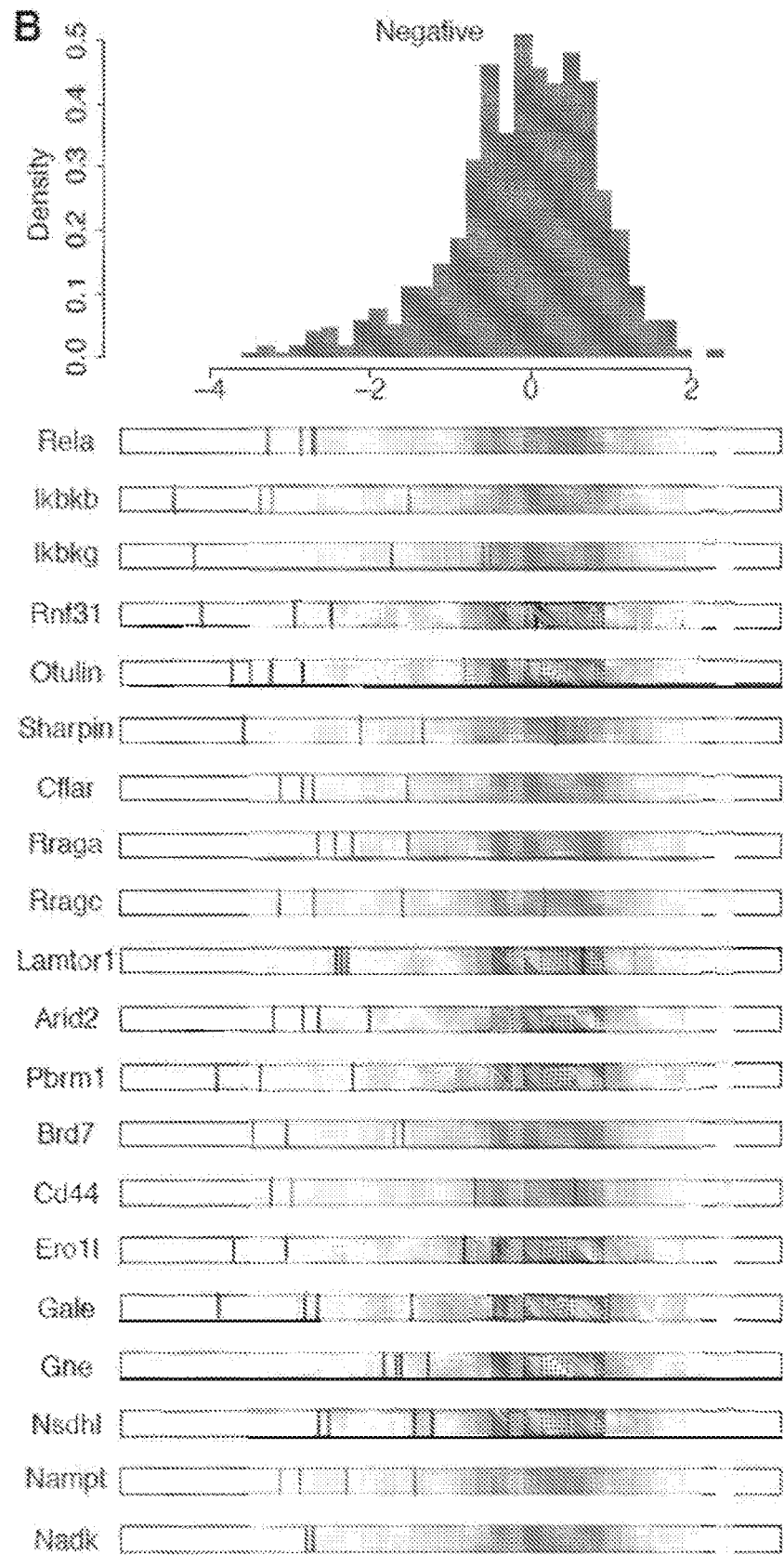

*Serpinb9* (Kaiserman et al. (2010) *Cell Death Differ.* 17:586-595) indicating the depleted gRNA well identified negative regulators of T cell-mediated killing in tumor cells (FIGS. 3C and 10B). However, the vast majority of identified genes had not been previously implicated in resistance to T cell mediated killing (Tables 6-9).

TABLE 6

List of top candidate genes enriched in Pmel-1 screen (FDR < 0.05)

| Gene | logFC | Positive selection | | Negative selection | |
|---|---|---|---|---|---|
| | | p value | FDR | p value | FDR |
| Jak1 | 9.69 | 2.39E−07 | 1.50E−04 | 1.00E+00 | 1.00E+00 |
| Stat1 | 8.49 | 2.39E−07 | 1.50E−04 | 1.00E+00 | 1.00E+00 |
| Ifngr2 | 4.87 | 2.39E−07 | 1.50E−04 | 1.00E+00 | 1.00E+00 |
| Ifngr1 | 4.68 | 2.39E−07 | 1.50E−04 | 1.00E+00 | 1.00E+00 |
| B2m | 3.72 | 2.39E−07 | 1.50E−04 | 1.00E+00 | 1.00E+00 |
| H2-D1 | 3.53 | 2.39E−07 | 1.50E−04 | 1.00E+00 | 1.00E+00 |
| Jak2 | 3.10 | 2.39E−07 | 1.50E−04 | 1.00E+00 | 1.00E+00 |
| Lztr1 | 2.91 | 2.39E−07 | 1.50E−04 | 1.00E+00 | 1.00E+00 |
| Ube2g2 | 2.87 | 2.39E−07 | 1.50E−04 | 1.00E+00 | 1.00E+00 |
| Dusp6 | 2.83 | 2.39E−07 | 1.50E−04 | 1.00E+00 | 1.00E+00 |
| Tap1 | 2.55 | 2.39E−07 | 1.50E−04 | 1.00E+00 | 1.00E+00 |
| Tap2 | 2.51 | 2.39E−07 | 1.50E−04 | 1.00E+00 | 1.00E+00 |
| Derl2 | 2.39 | 2.39E−07 | 1.50E−04 | 1.00E+00 | 1.00E+00 |
| Nf1 | 2.23 | 2.39E−07 | 1.50E−04 | 1.00E+00 | 1.00E+00 |
| Syvn1 | 2.15 | 2.39E−07 | 1.50E−04 | 1.00E+00 | 1.00E+00 |
| Mbnl1 | 2.15 | 2.39E−07 | 1.50E−04 | 1.00E+00 | 1.00E+00 |
| Cic | 1.94 | 2.39E−07 | 1.50E−04 | 1.00E+00 | 1.00E+00 |
| Tbl1x | 1.93 | 2.39E−07 | 1.50E−04 | 1.00E+00 | 1.00E+00 |
| Aup1 | 1.93 | 2.39E−07 | 1.50E−04 | 1.00E+00 | 1.00E+00 |
| Ube2j1 | 1.91 | 2.39E−07 | 1.50E−04 | 1.00E+00 | 1.00E+00 |
| Ints10 | 1.91 | 2.39E−07 | 1.50E−04 | 1.00E+00 | 1.00E+00 |
| Vgll4 | 1.65 | 2.39E−07 | 1.50E−04 | 1.00E+00 | 1.00E+00 |
| Spred1 | 1.64 | 4.07E−06 | 1.91E−03 | 1.00E+00 | 1.00E+00 |
| Fus | 1.64 | 2.39E−07 | 1.50E−04 | 1.00E+00 | 1.00E+00 |
| Cbx4 | 1.62 | 2.39E−07 | 1.50E−04 | 1.00E+00 | 1.00E+00 |
| Pmel | 1.53 | 2.39E−07 | 1.50E−04 | 1.00E+00 | 1.00E+00 |
| Fbrs | 1.51 | 2.39E−07 | 1.50E−04 | 1.00E+00 | 1.00E+00 |
| Nlrc5 | 1.48 | 2.39E−07 | 1.50E−04 | 1.00E+00 | 1.00E+00 |
| Sel1l | 1.48 | 7.18E−07 | 4.24E−04 | 9.99E−01 | 1.00E+00 |
| Xpnpep1 | 1.47 | 2.39E−07 | 1.50E−04 | 1.00E+00 | 1.00E+00 |
| Mbnl2 | 1.46 | 2.16E−06 | 1.11E−03 | 1.00E+00 | 1.00E+00 |
| Swi5 | 1.46 | 2.39E−07 | 1.50E−04 | 1.00E+00 | 1.00E+00 |
| Asun | 1.46 | 1.56E−05 | 6.57E−03 | 1.00E+00 | 1.00E+00 |
| Usp24 | 1.45 | 1.20E−06 | 6.51E−04 | 1.00E+00 | 1.00E+00 |
| Ifnar1 | 1.42 | 2.39E−07 | 1.50E−04 | 1.00E+00 | 1.00E+00 |
| Cdkn1a | 1.38 | 2.39E−07 | 1.50E−04 | 1.00E+00 | 1.00E+00 |
| Ifnar2 | 1.37 | 7.18E−07 | 4.24E−04 | 1.00E+00 | 1.00E+00 |
| Rfxank | 1.37 | 2.42E−05 | 8.93E−03 | 1.00E+00 | 1.00E+00 |
| Edem3 | 1.35 | 2.39E−07 | 1.50E−04 | 9.99E−01 | 1.00E+00 |
| Nf2 | 1.33 | 3.59E−06 | 1.77E−03 | 1.00E+00 | 1.00E+00 |
| Med13 | 1.29 | 2.39E−07 | 1.50E−04 | 1.00E+00 | 1.00E+00 |
| Usp22 | 1.28 | 0.00010081 | 3.16E−02 | 1.00E+00 | 1.00E+00 |
| Pvr | 1.26 | 1.20E−06 | 6.51E−04 | 9.99E−01 | 1.00E+00 |
| Ipo13 | 1.24 | 9.27E−05 | 2.95E−02 | 1.00E+00 | 1.00E+00 |
| Kdm1a | 1.20 | 4.07E−06 | 1.91E−03 | 9.99E−01 | 1.00E+00 |
| Bbx | 1.19 | 1.68E−06 | 8.89E−04 | 9.98E−01 | 1.00E+00 |
| Chrac1 | 1.15 | 0.00016834 | 4.70E−02 | 1.00E+00 | 1.00E+00 |
| Eloa | 1.14 | 7.02E−05 | 2.34E−02 | 9.99E−01 | 1.00E+00 |
| 2310033P09Rik | 1.08 | 2.08E−05 | 7.98E−03 | 9.99E−01 | 1.00E+00 |
| Cdkn2c | 1.08 | 2.75E−05 | 9.65E−03 | 9.99E−01 | 1.00E+00 |
| Kirrel | 1.07 | 2.75E−05 | 9.65E−03 | 9.99E−01 | 1.00E+00 |
| Lta4h | 1.07 | 3.59E−06 | 1.77E−03 | 9.99E−01 | 1.00E+00 |
| Alkbh8 | 1.06 | 2.61E−05 | 9.47E−03 | 1.00E+00 | 1.00E+00 |
| Cdc73 | 1.03 | 0.00011135 | 3.44E−02 | 9.95E−01 | 1.00E+00 |
| Cdk12 | 1.02 | 1.84E−05 | 7.47E−03 | 1.00E+00 | 1.00E+00 |
| Gosr2 | 1.02 | 0.00014583 | 4.19E−02 | 9.98E−01 | 1.00E+00 |
| Rasa2 | 1.01 | 6.47E−06 | 2.97E−03 | 9.99E−01 | 1.00E+00 |
| Senp1 | 0.99 | 0.00014583 | 4.19E−02 | 9.97E−01 | 1.00E+00 |
| Fgf12 | 0.98 | 9.27E−05 | 2.95E−02 | 9.94E−01 | 1.00E+00 |
| Creb3l2 | 0.98 | 6.15E−05 | 2.12E−02 | 9.97E−01 | 1.00E+00 |
| Men1 | 0.96 | 2.08E−05 | 7.98E−03 | 9.99E−01 | 1.00E+00 |
| Spop | 0.96 | 1.51E−05 | 6.50E−03 | 9.99E−01 | 1.00E+00 |
| Cbll1 | 0.91 | 0.00014439 | 4.19E−02 | 9.99E−01 | 1.00E+00 |
| Ankrd24 | 0.90 | 1.75E−05 | 7.23E−03 | 9.98E−01 | 1.00E+00 |
| Edem2 | 0.90 | 0.00016594 | 4.70E−02 | 9.98E−01 | 1.00E+00 |
| Pcif1 | 0.87 | 2.42E−05 | 8.93E−03 | 9.98E−01 | 1.00E+00 |
| 4921507P07Rik | 0.86 | 0.00017169 | 4.73E−02 | 9.93E−01 | 1.00E+00 |
| Ddx42 | 0.85 | 1.20E−06 | 6.51E−04 | 9.79E−01 | 1.00E+00 |
| Otud5 | 0.84 | 1.89E−05 | 7.52E−03 | 9.71E−01 | 1.00E+00 |

TABLE 6-continued

List of top candidate genes enriched in Pmel-1 screen (FDR < 0.05)

| Gene | logFC | Positive selection | | Negative selection | |
|---|---|---|---|---|---|
| | | p value | FDR | p value | FDR |
| Dppa5a | 0.84 | 1.13E−05 | 5.06E−03 | 9.96E−01 | 1.00E+00 |
| Kif3a | 0.77 | 0.00011949 | 3.63E−02 | 9.82E−01 | 1.00E+00 |
| Sec22a | 0.72 | 0.00014583 | 4.19E−02 | 9.92E−01 | 1.00E+00 |
| Furin | 0.71 | 0.00017648 | 4.80E−02 | 9.92E−01 | 1.00E+00 |
| Ankrd6 | 0.49 | 7.40E−05 | 2.43E−02 | 7.32E−01 | 9.14E−01 |
| Lsm12 | 0.29 | 6.44E−05 | 2.18E−02 | 4.65E−01 | 7.50E−01 |
| Marcksl1 | 0.20 | 1.46E−05 | 6.43E−03 | 9.86E−02 | 4.84E−01 |

LogFC, Log(2) fold change; FDR, False Discovery rate. FDR and p value calculated by MaGeCK.

TABLE 7

List of top candidate genes depleted in Pmel-1 screen (FDR < 0.05)

| Gene | logFC | Positive selection | | Negative selection | |
|---|---|---|---|---|---|
| | | p value | FDR | p value | FDR |
| Atg3 | −0.85 | 0.020985 | 4.20E−01 | 4.64E−04 | 4.63E−02 |
| Dbp | −1.05 | 0.0016874 | 2.49E−01 | 2.59E−04 | 4.17E−02 |
| Nln | −1.05 | 0.36437 | 1.00E+00 | 4.69E−04 | 4.63E−02 |
| Xylb | −1.09 | 0.48935 | 1.00E+00 | 4.83E−04 | 4.63E−02 |
| Pstpip2 | −1.22 | 0.78233 | 1.00E+00 | 4.83E−04 | 4.63E−02 |
| Olfr1463 | −1.33 | 0.83086 | 1.00E+00 | 5.01E−04 | 4.63E−02 |
| Pus7l | −1.37 | 0.79036 | 1.00E+00 | 2.74E−04 | 4.17E−02 |
| Bpnt1 | −1.45 | 0.24093 | 1.00E+00 | 3.10E−04 | 4.18E−02 |
| Ttll5 | −1.47 | 0.89188 | 1.00E+00 | 5.46E−04 | 4.63E−02 |
| Olfr523 | −1.47 | 0.5871 | 1.00E+00 | 2.89E−04 | 4.17E−02 |
| Cyb5r2 | −1.57 | 0.84605 | 1.00E+00 | 5.53E−04 | 4.63E−02 |
| Crygc | −1.58 | 0.85002 | 1.00E+00 | 2.81E−04 | 4.17E−02 |
| Phf12 | −1.70 | 0.87576 | 1.00E+00 | 5.60E−04 | 4.63E−02 |
| Al314180 | −1.79 | 0.84838 | 1.00E+00 | 5.53E−04 | 4.63E−02 |
| Pik3ca | −1.80 | 0.73094 | 1.00E+00 | 5.31E−04 | 4.63E−02 |
| Sec23b | −1.80 | 0.77773 | 1.00E+00 | 4.83E−04 | 4.63E−02 |
| Hagh | −1.83 | 0.42794 | 1.00E+00 | 4.71E−04 | 4.63E−02 |
| Olfr237-ps1 | −1.83 | 0.9129 | 1.00E+00 | 5.60E−04 | 4.63E−02 |
| Tas2r104 | −1.84 | 0.80913 | 1.00E+00 | 2.55E−04 | 4.17E−02 |
| Erap1 | −1.85 | 0.39007 | 1.00E+00 | 7.16E−05 | 2.00E−02 |
| Sept3 | −1.86 | 0.22664 | 1.00E+00 | 4.83E−04 | 4.63E−02 |
| Zfand6 | −1.89 | 0.97729 | 1.00E+00 | 5.55E−04 | 4.63E−02 |
| C3ar1 | −1.90 | 0.37623 | 1.00E+00 | 5.30E−04 | 4.63E−02 |
| Mylip | −1.92 | 0.88336 | 1.00E+00 | 1.75E−04 | 3.68E−02 |
| Gosr1 | −1.92 | 0.99198 | 1.00E+00 | 1.85E−04 | 3.68E−02 |
| Pcp4 | −1.93 | 0.91935 | 1.00E+00 | 5.24E−04 | 4.63E−02 |
| Cachd1 | −1.95 | 0.81897 | 1.00E+00 | 1.80E−05 | 9.79E−03 |
| Rfxap | −1.96 | 0.93257 | 1.00E+00 | 2.55E−04 | 4.17E−02 |
| Slc12a2 | −1.96 | 0.96301 | 1.00E+00 | 5.53E−04 | 4.63E−02 |
| Ube2a | −1.97 | 0.8566 | 1.00E+00 | 4.66E−04 | 4.63E−02 |
| Tgif2lx1 | −1.98 | 0.95558 | 1.00E+00 | 5.06E−04 | 4.63E−02 |
| Strn4 | −1.98 | 0.9735 | 1.00E+00 | 5.46E−04 | 4.63E−02 |
| Nudt11 | −1.99 | 0.96227 | 1.00E+00 | 5.13E−04 | 4.63E−02 |
| Tial1 | −2.01 | 0.9539 | 1.00E+00 | 3.17E−04 | 4.18E−02 |
| Tmem41b | −2.02 | 0.96579 | 1.00E+00 | 3.96E−04 | 4.63E−02 |
| Lrrn3 | −2.03 | 0.98067 | 1.00E+00 | 5.06E−04 | 4.63E−02 |
| Tubb2b | −2.04 | 0.86216 | 1.00E+00 | 4.69E−04 | 4.63E−02 |
| Gne | −2.06 | 0.95715 | 1.00E+00 | 5.45E−04 | 4.63E−02 |
| Rsl1 | −2.06 | 0.94016 | 1.00E+00 | 4.06E−04 | 4.63E−02 |
| Zfp942 | −2.07 | 0.97317 | 1.00E+00 | 4.12E−04 | 4.63E−02 |
| Kmt2c | −2.08 | 0.59541 | 1.00E+00 | 4.83E−04 | 4.63E−02 |
| Stat3 | −2.08 | 0.99048 | 1.00E+00 | 4.06E−04 | 4.63E−02 |
| Rgp1 | −2.09 | 0.76343 | 1.00E+00 | 4.12E−04 | 4.63E−02 |
| Ppp4r2 | −2.11 | 0.95069 | 1.00E+00 | 2.80E−04 | 4.17E−02 |
| Prdx1 | −2.12 | 0.99041 | 1.00E+00 | 5.24E−04 | 4.63E−02 |
| Pip5k1c | −2.12 | 0.99136 | 1.00E+00 | 2.55E−04 | 4.17E−02 |
| Tmem165 | −2.13 | 0.48032 | 1.00E+00 | 4.57E−04 | 4.63E−02 |
| Carm1 | −2.13 | 0.96937 | 1.00E+00 | 4.93E−04 | 4.63E−02 |
| Vps16 | −2.14 | 0.9762 | 1.00E+00 | 3.96E−04 | 4.63E−02 |
| Rsph1 | −2.15 | 0.97941 | 1.00E+00 | 2.89E−04 | 4.17E−02 |
| Cd44 | −2.15 | 0.98583 | 1.00E+00 | 2.63E−04 | 4.17E−02 |
| Arf6 | −2.16 | 0.95126 | 1.00E+00 | 2.59E−04 | 4.17E−02 |
| Irgm2 | −2.16 | 0.98195 | 1.00E+00 | 2.83E−04 | 4.17E−02 |
| Lamtor1 | −2.18 | 0.95816 | 1.00E+00 | 3.97E−04 | 4.63E−02 |

TABLE 7-continued

List of top candidate genes depleted in Pmel-1 screen (FDR < 0.05)

| Gene | logFC | Positive selection | | Negative selection | |
| --- | --- | --- | --- | --- | --- |
| | | p value | FDR | p value | FDR |
| Cd36 | −2.18 | 0.99451 | 1.00E+00 | 5.13E−04 | 4.63E−02 |
| Zfp827 | −2.19 | 0.98737 | 1.00E+00 | 4.69E−04 | 4.63E−02 |
| Olfr512 | −2.19 | 0.9518 | 1.00E+00 | 2.61E−05 | 1.02E−02 |
| Nans | −2.20 | 0.97933 | 1.00E+00 | 5.53E−04 | 4.63E−02 |
| Rnf38 | −2.20 | 0.97671 | 1.00E+00 | 2.63E−04 | 4.17E−02 |
| Eif2ak3 | −2.20 | 0.99073 | 1.00E+00 | 5.13E−04 | 4.63E−02 |
| Ikbkg | −2.21 | 0.9944 | 1.00E+00 | 2.08E−05 | 9.79E−03 |
| Spen | −2.22 | 0.98152 | 1.00E+00 | 5.55E−04 | 4.63E−02 |
| Ak2 | −2.22 | 0.96937 | 1.00E+00 | 4.71E−04 | 4.63E−02 |
| Icosl | −2.24 | 0.99186 | 1.00E+00 | 5.30E−04 | 4.63E−02 |
| Krtap1-5 | −2.24 | 0.98152 | 1.00E+00 | 1.56E−05 | 9.75E−03 |
| Lemd2 | −2.25 | 0.9933 | 1.00E+00 | 5.45E−04 | 4.63E−02 |
| Gtf2i | −2.25 | 0.94313 | 1.00E+00 | 2.62E−04 | 4.17E−02 |
| Xrcc2 | −2.26 | 0.97576 | 1.00E+00 | 3.05E−04 | 4.18E−02 |
| Bptf | −2.26 | 0.97193 | 1.00E+00 | 1.84E−04 | 3.68E−02 |
| Impg1 | −2.27 | 0.99352 | 1.00E+00 | 2.89E−04 | 4.17E−02 |
| Birc2 | −2.28 | 0.98877 | 1.00E+00 | 1.13E−04 | 2.86E−02 |
| Batf2 | −2.30 | 0.98999 | 1.00E+00 | 2.58E−04 | 4.17E−02 |
| Larp4 | −2.30 | 0.97355 | 1.00E+00 | 2.55E−04 | 4.17E−02 |
| Cwf19l1 | −2.30 | 0.91546 | 1.00E+00 | 4.83E−04 | 4.63E−02 |
| Tgtp1 | −2.30 | 0.90076 | 1.00E+00 | 7.30E−05 | 2.00E−02 |
| Pak2 | −2.30 | 0.9912 | 1.00E+00 | 5.46E−04 | 4.63E−02 |
| Ube2k | −2.32 | 0.99548 | 1.00E+00 | 3.17E−04 | 4.18E−02 |
| Faxc | −2.33 | 0.99186 | 1.00E+00 | 2.59E−04 | 4.17E−02 |
| Asxl2 | −2.33 | 0.9296 | 1.00E+00 | 1.82E−04 | 3.68E−02 |
| Matr3 | −2.33 | 0.97193 | 1.00E+00 | 5.01E−04 | 4.63E−02 |
| Rab7 | −2.34 | 0.98577 | 1.00E+00 | 5.45E−04 | 4.63E−02 |
| Arl14epl | −2.34 | 0.99093 | 1.00E+00 | 3.03E−04 | 4.18E−02 |
| Tm2d1 | −2.34 | 0.99258 | 1.00E+00 | 2.81E−04 | 4.17E−02 |
| Uba6 | −2.35 | 0.9925 | 1.00E+00 | 5.46E−04 | 4.63E−02 |
| Fam234b | −2.35 | 0.72319 | 1.00E+00 | 7.06E−05 | 2.00E−02 |
| Rsf1 | −2.35 | 0.99657 | 1.00E+00 | 4.83E−04 | 4.63E−02 |
| Hes7 | −2.36 | 0.89628 | 1.00E+00 | 2.55E−04 | 4.17E−02 |
| Hsd17b4 | −2.36 | 0.98272 | 1.00E+00 | 1.13E−04 | 2.86E−02 |
| Gpx4 | −2.36 | 0.99594 | 1.00E+00 | 5.24E−04 | 4.63E−02 |
| Txndc15 | −2.37 | 0.92739 | 1.00E+00 | 4.83E−04 | 4.63E−02 |
| Cdk2 | −2.37 | 0.99215 | 1.00E+00 | 2.83E−04 | 4.17E−02 |
| Pigu | −2.37 | 0.99418 | 1.00E+00 | 2.83E−04 | 4.17E−02 |
| Rfx6 | −2.37 | 0.99498 | 1.00E+00 | 5.46E−04 | 4.63E−02 |
| Padi4 | −2.38 | 0.99068 | 1.00E+00 | 3.10E−04 | 4.18E−02 |
| Ube2r2 | −2.38 | 0.98387 | 1.00E+00 | 5.46E−04 | 4.63E−02 |
| Fhod3 | −2.39 | 0.98998 | 1.00E+00 | 1.68E−04 | 3.68E−02 |
| Ice1 | −2.39 | 0.99477 | 1.00E+00 | 4.83E−04 | 4.63E−02 |
| Xrcc4 | −2.39 | 0.90778 | 1.00E+00 | 2.69E−04 | 4.17E−02 |
| Foxb1 | −2.39 | 0.99902 | 1.00E+00 | 5.55E−04 | 4.63E−02 |
| Stub1 | −2.39 | 0.98149 | 1.00E+00 | 2.58E−04 | 4.17E−02 |
| Ccdc137 | −2.39 | 0.98149 | 1.00E+00 | 4.66E−04 | 4.63E−02 |
| Snapin | −2.40 | 0.97303 | 1.00E+00 | 7.11E−05 | 2.00E−02 |
| Trip13 | −2.40 | 0.99343 | 1.00E+00 | 5.56E−04 | 4.63E−02 |
| Nckap1 | −2.42 | 0.9851 | 1.00E+00 | 1.85E−04 | 3.68E−02 |
| Gml | −2.42 | 0.98162 | 1.00E+00 | 1.85E−04 | 3.68E−02 |
| Ube2j2 | −2.42 | 0.99665 | 1.00E+00 | 3.18E−04 | 4.18E−02 |
| Nsdhl | −2.42 | 0.99658 | 1.00E+00 | 5.53E−04 | 4.63E−02 |
| Arid4a | −2.43 | 0.80658 | 1.00E+00 | 1.84E−05 | 9.79E−03 |
| Galnt15 | −2.43 | 0.99902 | 1.00E+00 | 5.13E−04 | 4.63E−02 |
| Rab13 | −2.44 | 0.99042 | 1.00E+00 | 4.83E−04 | 4.63E−02 |
| Gigyf2 | −2.44 | 0.99705 | 1.00E+00 | 2.81E−04 | 4.17E−02 |
| Ero1l | −2.44 | 0.99887 | 1.00E+00 | 5.06E−04 | 4.63E−02 |
| Olfr912 | −2.45 | 0.99066 | 1.00E+00 | 5.13E−04 | 4.63E−02 |
| Zc3h18 | −2.45 | 0.99723 | 1.00E+00 | 4.68E−04 | 4.63E−02 |
| Nfix | −2.45 | 0.9959 | 1.00E+00 | 2.08E−05 | 9.79E−03 |
| Neurl3 | −2.45 | 0.99577 | 1.00E+00 | 5.01E−04 | 4.63E−02 |
| Hspa13 | −2.46 | 0.99844 | 1.00E+00 | 5.13E−04 | 4.63E−02 |
| Xrcc5 | −2.46 | 0.9979 | 1.00E+00 | 1.75E−04 | 3.68E−02 |
| Prl2c3 | −2.47 | 0.99614 | 1.00E+00 | 1.75E−04 | 3.68E−02 |
| Keap1 | −2.47 | 0.98993 | 1.00E+00 | 1.13E−04 | 2.86E−02 |
| Pax3 | −2.47 | 0.99466 | 1.00E+00 | 2.92E−04 | 4.18E−02 |
| Ankrd11 | −2.47 | 0.98473 | 1.00E+00 | 2.80E−04 | 4.17E−02 |
| Atg16l1 | −2.48 | 0.99847 | 1.00E+00 | 5.60E−04 | 4.63E−02 |
| Oprk1 | −2.48 | 0.99358 | 1.00E+00 | 5.24E−04 | 4.63E−02 |
| Sox11 | −2.48 | 0.98494 | 1.00E+00 | 2.80E−04 | 4.17E−02 |
| Ttc33 | −2.48 | 0.99723 | 1.00E+00 | 2.83E−04 | 4.17E−02 |
| Tbc1d10b | −2.48 | 0.98395 | 1.00E+00 | 2.55E−04 | 4.17E−02 |
| Arhgap11a | −2.49 | 0.99723 | 1.00E+00 | 4.90E−04 | 4.63E−02 |

TABLE 7-continued

List of top candidate genes depleted in Pmel-1 screen (FDR < 0.05)

| Gene | logFC | Positive selection | | Negative selection | |
| --- | --- | --- | --- | --- | --- |
| | | p value | FDR | p value | FDR |
| Ar | −2.49 | 0.99435 | 1.00E+00 | 2.67E−04 | 4.17E−02 |
| Arhgap21 | −2.50 | 0.99764 | 1.00E+00 | 2.83E−04 | 4.17E−02 |
| Rfwd2 | −2.51 | 0.99466 | 1.00E+00 | 4.83E−04 | 4.63E−02 |
| Crlf3 | −2.52 | 0.99906 | 1.00E+00 | 4.11E−04 | 4.63E−02 |
| Elmo2 | −2.52 | 0.99593 | 1.00E+00 | 3.12E−04 | 4.18E−02 |
| Tgif2 | −2.53 | 0.99901 | 1.00E+00 | 5.60E−04 | 4.63E−02 |
| Sod2 | −2.53 | 0.99643 | 1.00E+00 | 4.69E−04 | 4.63E−02 |
| Fam170b | −2.54 | 0.9833 | 1.00E+00 | 1.13E−04 | 2.86E−02 |
| Xrcc1 | −2.54 | 0.99811 | 1.00E+00 | 3.12E−04 | 4.18E−02 |
| Meioc | −2.54 | 0.99689 | 1.00E+00 | 3.17E−04 | 4.18E−02 |
| March5 | −2.55 | 0.99799 | 1.00E+00 | 7.90E−06 | 7.00E−03 |
| Pitx2 | −2.56 | 0.99902 | 1.00E+00 | 3.12E−04 | 4.18E−02 |
| Rab25 | −2.56 | 0.99719 | 1.00E+00 | 5.13E−04 | 4.63E−02 |
| Ccdc155 | −2.56 | 0.99257 | 1.00E+00 | 7.16E−05 | 2.00E−02 |
| Zfp473 | −2.56 | 0.99762 | 1.00E+00 | 4.12E−04 | 4.63E−02 |
| Tbk1 | −2.58 | 0.99959 | 1.00E+00 | 4.57E−04 | 4.63E−02 |
| Zfp148 | −2.58 | 0.99863 | 1.00E+00 | 5.60E−04 | 4.63E−02 |
| Rgmb | −2.58 | 0.99711 | 1.00E+00 | 4.79E−04 | 4.63E−02 |
| Tm2d3 | −2.59 | 0.98635 | 1.00E+00 | 7.16E−05 | 2.00E−02 |
| Tsc2 | −2.59 | 0.99145 | 1.00E+00 | 4.56E−04 | 4.63E−02 |
| 2700049A03Rik | −2.59 | 0.99917 | 1.00E+00 | 4.00E−04 | 4.63E−02 |
| Cdk5 | −2.60 | 0.99621 | 1.00E+00 | 4.90E−04 | 4.63E−02 |
| Cmip | −2.60 | 0.99622 | 1.00E+00 | 4.12E−04 | 4.63E−02 |
| Ccdc187 | −2.60 | 0.99705 | 1.00E+00 | 2.80E−04 | 4.17E−02 |
| Cnot8 | −2.60 | 0.99918 | 1.00E+00 | 3.10E−04 | 4.18E−02 |
| Dspp | −2.60 | 0.99548 | 1.00E+00 | 3.12E−04 | 4.18E−02 |
| Ywhaz | −2.60 | 0.99438 | 1.00E+00 | 7.26E−05 | 2.00E−02 |
| Cfhr2 | −2.61 | 0.9925 | 1.00E+00 | 7.16E−05 | 2.00E−02 |
| Zfp281 | −2.61 | 0.99865 | 1.00E+00 | 6.97E−05 | 2.00E−02 |
| Becn1 | −2.61 | 0.99906 | 1.00E+00 | 2.69E−04 | 4.17E−02 |
| Slc2a1 | −2.61 | 0.99946 | 1.00E+00 | 7.21E−05 | 2.00E−02 |
| Ilk | −2.62 | 0.9989 | 1.00E+00 | 4.83E−04 | 4.63E−02 |
| Gpr31b | −2.62 | 0.99422 | 1.00E+00 | 2.56E−05 | 1.02E−02 |
| Sprr2e | −2.62 | 0.99665 | 1.00E+00 | 5.24E−04 | 4.63E−02 |
| Boll | −2.63 | 0.99136 | 1.00E+00 | 2.56E−05 | 1.02E−02 |
| Tacc3 | −2.63 | 0.99846 | 1.00E+00 | 2.55E−04 | 4.17E−02 |
| Paox | −2.66 | 0.99923 | 1.00E+00 | 5.00E−04 | 4.63E−02 |
| Gabrb3 | −2.66 | 0.99887 | 1.00E+00 | 2.59E−04 | 4.17E−02 |
| Trex1 | −2.67 | 0.99964 | 1.00E+00 | 5.24E−04 | 4.63E−02 |
| Dnaja2 | −2.67 | 0.99907 | 1.00E+00 | 5.53E−04 | 4.63E−02 |
| Vps4b | −2.68 | 0.9981 | 1.00E+00 | 5.46E−04 | 4.63E−02 |
| Nprl3 | −2.68 | 0.99974 | 1.00E+00 | 4.90E−04 | 4.63E−02 |
| Mtch1 | −2.68 | 0.99534 | 1.00E+00 | 7.16E−05 | 2.00E−02 |
| Iqsec1 | −2.68 | 0.89653 | 1.00E+00 | 7.42E−06 | 7.00E−03 |
| Lrp10 | −2.68 | 0.99784 | 1.00E+00 | 7.21E−05 | 2.00E−02 |
| Raf1 | −2.69 | 0.99392 | 1.00E+00 | 1.74E−04 | 3.68E−02 |
| Dtx3l | −2.69 | 0.999 | 1.00E+00 | 1.13E−04 | 2.86E−02 |
| Ccs | −2.70 | 0.99858 | 1.00E+00 | 1.68E−04 | 3.68E−02 |
| Epc1 | −2.70 | 0.99881 | 1.00E+00 | 2.74E−04 | 4.17E−02 |
| Strada | −2.70 | 0.9977 | 1.00E+00 | 1.68E−04 | 3.68E−02 |
| Nrbf2 | −2.70 | 0.99964 | 1.00E+00 | 4.83E−04 | 4.63E−02 |
| Ten1 | −2.72 | 0.99964 | 1.00E+00 | 7.11E−05 | 2.00E−02 |
| Irf1 | −2.72 | 0.999 | 1.00E+00 | 7.21E−05 | 2.00E−02 |
| Vmn2r72 | −2.72 | 0.99853 | 1.00E+00 | 1.74E−04 | 3.68E−02 |
| Tk2 | −2.73 | 0.99964 | 1.00E+00 | 4.63E−04 | 4.63E−02 |
| Ddi2 | −2.73 | 0.99216 | 1.00E+00 | 1.46E−05 | 9.44E−03 |
| Arid1a | −2.74 | 0.99903 | 1.00E+00 | 7.21E−05 | 2.00E−02 |
| Zfp273 | −2.75 | 0.99863 | 1.00E+00 | 1.75E−04 | 3.68E−02 |
| Actr3 | −2.75 | 0.99505 | 1.00E+00 | 1.75E−05 | 9.79E−03 |
| Eif2ak4 | −2.75 | 0.99846 | 1.00E+00 | 2.56E−05 | 1.02E−02 |
| Pde7a | −2.76 | 0.99715 | 1.00E+00 | 1.62E−04 | 3.68E−02 |
| Dpf2 | −2.76 | 0.99881 | 1.00E+00 | 1.85E−04 | 3.68E−02 |
| Rraga | −2.76 | 0.99382 | 1.00E+00 | 1.13E−04 | 2.86E−02 |
| Rnf31 | −2.77 | 0.99534 | 1.00E+00 | 1.74E−04 | 3.68E−02 |
| Smgc | −2.78 | 0.99719 | 1.00E+00 | 2.56E−05 | 1.02E−02 |
| Prkcq | −2.79 | 0.99731 | 1.00E+00 | 1.68E−04 | 3.68E−02 |
| Epg5 | −2.79 | 0.99622 | 1.00E+00 | 7.06E−05 | 2.00E−02 |
| Gss | −2.79 | 0.99969 | 1.00E+00 | 2.74E−04 | 4.17E−02 |
| Cnot11 | −2.80 | 0.99704 | 1.00E+00 | 1.68E−04 | 3.68E−02 |
| Hipk2 | −2.80 | 0.99722 | 1.00E+00 | 2.51E−05 | 1.02E−02 |
| C330027C09Rik | −2.80 | 0.99439 | 1.00E+00 | 1.80E−05 | 9.79E−03 |
| Man2a1 | −2.80 | 0.99812 | 1.00E+00 | 2.04E−05 | 9.79E−03 |
| Chmp5 | −2.82 | 0.99418 | 1.00E+00 | 7.90E−06 | 7.00E−03 |
| Pcgf6 | −2.86 | 0.99811 | 1.00E+00 | 9.34E−06 | 7.00E−03 |

TABLE 7-continued

List of top candidate genes depleted in Pmel-1 screen (FDR < 0.05)

| Gene | logFC | Positive selection p value | Positive selection FDR | Negative selection p value | Negative selection FDR |
|---|---|---|---|---|---|
| Nampt | −2.87 | 0.99887 | 1.00E+00 | 2.54E−04 | 4.17E−02 |
| Eri1 | −2.88 | 0.99964 | 1.00E+00 | 2.67E−04 | 4.17E−02 |
| Pbrm1 | −2.89 | 0.99881 | 1.00E+00 | 8.38E−06 | 7.00E−03 |
| Atg5 | −2.89 | 0.99974 | 1.00E+00 | 4.12E−04 | 4.63E−02 |
| Ube2h | −2.90 | 0.99771 | 1.00E+00 | 9.34E−06 | 7.00E−03 |
| Gabpb1 | −2.91 | 0.99907 | 1.00E+00 | 7.06E−05 | 2.00E−02 |
| Gpi1 | −2.91 | 0.9971 | 1.00E+00 | 1.41E−05 | 9.42E−03 |
| Usp19 | −2.92 | 0.99969 | 1.00E+00 | 1.81E−04 | 3.68E−02 |
| Brd7 | −2.94 | 0.99974 | 1.00E+00 | 1.68E−04 | 3.68E−02 |
| Jmjd6 | −2.95 | 0.99505 | 1.00E+00 | 1.41E−05 | 9.42E−03 |
| Tgif1 | −2.97 | 0.99906 | 1.00E+00 | 7.11E−05 | 2.00E−02 |
| Fis1 | −2.98 | 0.99995 | 1.00E+00 | 1.85E−04 | 3.68E−02 |
| Cflar | −2.98 | 0.99875 | 1.00E+00 | 7.21E−05 | 2.00E−02 |
| Ptpn11 | −2.99 | 0.99917 | 1.00E+00 | 7.42E−06 | 7.00E−03 |
| Maea | −3.00 | 0.99946 | 1.00E+00 | 6.97E−05 | 2.00E−02 |
| Hdac5 | −3.00 | 0.99969 | 1.00E+00 | 2.04E−05 | 9.79E−03 |
| Mprip | −3.01 | 0.99923 | 1.00E+00 | 9.82E−06 | 7.00E−03 |
| Itgav | −3.02 | 0.99936 | 1.00E+00 | 7.21E−05 | 2.00E−02 |
| Crkl | −3.06 | 0.99974 | 1.00E+00 | 2.56E−05 | 1.02E−02 |
| Arid2 | −3.06 | 0.99902 | 1.00E+00 | 1.89E−05 | 9.79E−03 |
| Memo1 | −3.07 | 0.99995 | 1.00E+00 | 7.26E−05 | 2.00E−02 |
| Serpinb9 | −3.08 | 0.99831 | 1.00E+00 | 2.04E−05 | 9.79E−03 |
| Krit1 | −3.08 | 0.99902 | 1.00E+00 | 9.82E−06 | 7.00E−03 |
| Srrd | −3.13 | 0.99964 | 1.00E+00 | 9.34E−06 | 7.00E−03 |
| Sox4 | −3.17 | 0.99996 | 1.00E+00 | 1.75E−05 | 9.79E−03 |
| Wdr26 | −3.17 | 0.99969 | 1.00E+00 | 2.61E−05 | 1.02E−02 |
| Tiparp | −3.18 | 0.99969 | 1.00E+00 | 9.34E−06 | 7.00E−03 |
| Nadk | −3.18 | 0.99764 | 1.00E+00 | 1.20E−06 | 3.54E−03 |
| Tk1 | −3.18 | 0.99974 | 1.00E+00 | 7.90E−06 | 7.00E−03 |
| Tcof1 | −3.20 | 0.99865 | 1.00E+00 | 7.90E−06 | 7.00E−03 |
| Nprl2 | −3.20 | 0.99969 | 1.00E+00 | 9.34E−06 | 7.00E−03 |
| Ptpn2 | −3.22 | 0.99902 | 1.00E+00 | 8.38E−06 | 7.00E−03 |
| Gale | −3.22 | 0.99996 | 1.00E+00 | 7.35E−05 | 2.00E−02 |
| Spns1 | −3.24 | 0.99995 | 1.00E+00 | 2.56E−05 | 1.02E−02 |
| Usp18 | −3.28 | 0.99964 | 1.00E+00 | 1.68E−06 | 4.33E−03 |
| Psme2 | −3.29 | 0.99974 | 1.00E+00 | 7.42E−06 | 7.00E−03 |
| Tcea1 | −3.31 | 0.99925 | 1.00E+00 | 1.20E−06 | 3.54E−03 |
| Fitm2 | −3.33 | 0.99917 | 1.00E+00 | 7.42E−06 | 7.00E−03 |
| Ypel5 | −3.36 | 0.9993 | 1.00E+00 | 7.90E−06 | 7.00E−03 |
| Creb1 | −3.40 | 0.99964 | 1.00E+00 | 7.42E−06 | 7.00E−03 |
| Rela | −3.45 | 0.99924 | 1.00E+00 | 2.39E−07 | 1.24E−03 |
| Fadd | −3.45 | 0.99995 | 1.00E+00 | 7.42E−06 | 7.00E−03 |
| Psme1 | −3.53 | 0.99996 | 1.00E+00 | 7.42E−06 | 7.00E−03 |
| Ikbkb | −3.57 | 1 | 1.00E+00 | 1.20E−06 | 3.54E−03 |
| Cd274 | −3.70 | 0.99995 | 1.00E+00 | 2.39E−07 | 1.24E−03 |
| Otulin | −3.73 | 0.99995 | 1.00E+00 | 2.39E−07 | 1.24E−03 |
| Psmb8 | −3.93 | 1 | 1.00E+00 | 2.39E−07 | 1.24E−03 |

LogFC, Log(2) fold change; FDR, False Discovery rate. FDR and p value calculated by MaGeCK.

TABLE 8

List of top candidate genes enriched in OT-I screen (FDR < 0.05)

| Gene | logFC | Positive selection p value | Positive selection FDR | Negative selection p value | Negative selection FDR |
|---|---|---|---|---|---|
| B2m | 5.36 | 2.39E−07 | 3.81E−04 | 1.00E+00 | 1.00E+00 |
| Ifngr2 | 3.53 | 2.39E−07 | 3.81E−04 | 1.00E+00 | 1.00E+00 |
| Ifngr1 | 3.44 | 2.39E−07 | 3.81E−04 | 1.00E+00 | 1.00E+00 |
| Jak2 | 3.10 | 2.39E−07 | 3.81E−04 | 1.00E+00 | 1.00E+00 |
| Setd2 | 2.72 | 2.39E−07 | 3.81E−04 | 1.00E+00 | 1.00E+00 |
| Jak1 | 2.50 | 2.39E−07 | 3.81E−04 | 1.00E+00 | 1.00E+00 |
| Stat1 | 2.44 | 2.39E−07 | 3.81E−04 | 1.00E+00 | 1.00E+00 |
| Kmt2b | 1.82 | 2.39E−07 | 3.81E−04 | 1.00E+00 | 1.00E+00 |
| Alad | 1.38 | 2.39E−07 | 3.81E−04 | 1.00E+00 | 1.00E+00 |
| Wdr48 | 1.37 | 2.39E−07 | 3.81E−04 | 9.99E−01 | 1.00E+00 |
| Wdr20 | 1.34 | 2.39E−07 | 3.81E−04 | 1.00E+00 | 1.00E+00 |
| Nf1 | 1.27 | 2.39E−07 | 3.81E−04 | 9.99E−01 | 1.00E+00 |
| Cs | 1.20 | 7.18E−07 | 1.06E−03 | 1.00E+00 | 1.00E+00 |
| Ubr5 | 1.15 | 4.96E−05 | 4.66E−02 | 1.00E+00 | 1.00E+00 |
| Kctd5 | 1.07 | 2.39E−07 | 3.81E−04 | 9.96E−01 | 1.00E+00 |
| Hnrnph1 | 1.06 | 1.17E−05 | 1.43E−02 | 9.99E−01 | 1.00E+00 |
| Wdr24 | 1.04 | 3.59E−06 | 4.95E−03 | 9.97E−01 | 1.00E+00 |
| Olfr600 | 0.99 | 3.28E−05 | 3.23E−02 | 9.90E−01 | 1.00E+00 |
| Lrrc8a | 0.91 | 3.23E−05 | 3.23E−02 | 9.99E−01 | 1.00E+00 |
| Naa30 | 0.89 | 1.46E−05 | 1.68E−02 | 9.97E−01 | 1.00E+00 |
| Sult6b1 | 0.86 | 8.86E−06 | 1.14E−02 | 9.81E−01 | 1.00E+00 |
| Cep57l1 | 0.84 | 2.47E−05 | 2.68E−02 | 9.90E−01 | 1.00E+00 |

LogFC, Log2 fold change; FDR, False Discovery rate. FDR and p value calculated by MaGeCK.

TABLE 9

| | | \multicolumn{2}{c}{Positive selection} | \multicolumn{2}{c}{Negative selection} |
|---|---|---|---|---|---|

List of top candidate genes depleted in OT-I screen (FDR < 0.05)

| Gene | logFC | p value | FDR | p value | FDR |
|---|---|---|---|---|---|
| Olfr1450 | −1.38 | 9.01E−01 | 1.00E+00 | 1.42E−04 | 3.41E−02 |
| Pstpip2 | −1.53 | 9.83E−01 | 1.00E+00 | 2.56E−04 | 4.22E−02 |
| Lrrtm4 | −1.55 | 9.62E−01 | 1.00E+00 | 2.96E−04 | 4.22E−02 |
| Nmt2 | −1.58 | 5.03E−01 | 1.00E+00 | 2.71E−04 | 4.22E−02 |
| Lamtor4 | −1.59 | 9.74E−01 | 1.00E+00 | 8.02E−05 | 2.15E−02 |
| Tert | −1.61 | 8.82E−01 | 1.00E+00 | 3.02E−04 | 4.22E−02 |
| Rce1 | −1.63 | 8.71E−01 | 1.00E+00 | 2.33E−04 | 4.19E−02 |
| Socs1 | −1.64 | 1.38E−01 | 9.49E−01 | 8.07E−05 | 2.15E−02 |
| Ropn1 | −1.64 | 2.64E−01 | 1.00E+00 | 2.44E−04 | 4.22E−02 |
| Alk | −1.64 | 5.06E−01 | 1.00E+00 | 8.21E−05 | 2.15E−02 |
| Ctps | −1.69 | 9.67E−01 | 1.00E+00 | 2.16E−04 | 4.11E−02 |
| Mogs | −1.71 | 9.75E−01 | 1.00E+00 | 2.20E−04 | 4.11E−02 |
| Rars2 | −1.72 | 9.66E−01 | 1.00E+00 | 2.16E−04 | 4.11E−02 |
| Vmn1r2 | −1.74 | 9.83E−01 | 1.00E+00 | 3.02E−04 | 4.22E−02 |
| Gpx1 | −1.74 | 5.03E−01 | 1.00E+00 | 2.51E−04 | 4.22E−02 |
| Pdzph1 | −1.75 | 9.13E−01 | 1.00E+00 | 8.07E−05 | 2.15E−02 |
| Rwdd1 | −1.76 | 9.81E−01 | 1.00E+00 | 2.63E−04 | 4.22E−02 |
| Med23 | −1.77 | 5.68E−01 | 1.00E+00 | 2.47E−04 | 4.22E−02 |
| Rpl22l1 | −1.80 | 5.92E−01 | 1.00E+00 | 2.96E−04 | 4.22E−02 |
| B3glct | −1.82 | 8.87E−01 | 1.00E+00 | 3.76E−05 | 1.65E−02 |
| Hsd17b10 | −1.83 | 9.88E−01 | 1.00E+00 | 2.21E−04 | 4.11E−02 |
| Kctd2 | −1.85 | 9.85E−01 | 1.00E+00 | 1.42E−04 | 3.41E−02 |
| Slc33a1 | −1.86 | 9.73E−01 | 1.00E+00 | 9.27E−05 | 2.37E−02 |
| Pak2 | −1.86 | 9.77E−01 | 1.00E+00 | 2.85E−04 | 4.22E−02 |
| Atf4 | −1.87 | 9.85E−01 | 1.00E+00 | 8.07E−05 | 2.15E−02 |
| Scyl1 | −1.88 | 9.89E−01 | 1.00E+00 | 2.86E−04 | 4.22E−02 |
| Gramd1b | −1.90 | 9.75E−01 | 1.00E+00 | 2.43E−04 | 4.22E−02 |
| Rnd2 | −1.91 | 7.48E−01 | 1.00E+00 | 2.96E−04 | 4.22E−02 |
| Olfr220 | −1.91 | 9.79E−01 | 1.00E+00 | 2.96E−04 | 4.22E−02 |
| Olfr969 | −1.91 | 8.31E−01 | 1.00E+00 | 2.96E−04 | 4.22E−02 |
| Osgepl1 | −1.91 | 9.40E−01 | 1.00E+00 | 2.21E−04 | 4.11E−02 |
| Rbbp4 | −1.92 | 9.89E−01 | 1.00E+00 | 2.16E−04 | 4.11E−02 |
| Alg3 | −1.94 | 9.88E−01 | 1.00E+00 | 3.08E−04 | 4.22E−02 |
| Rbck1 | −1.96 | 9.30E−01 | 1.00E+00 | 2.85E−05 | 1.65E−02 |
| Ylpm1 | −1.97 | 5.12E−01 | 1.00E+00 | 2.86E−04 | 4.22E−02 |
| Ssu72 | −1.98 | 9.88E−01 | 1.00E+00 | 2.75E−04 | 4.22E−02 |
| Cyld | −1.98 | 9.94E−01 | 1.00E+00 | 2.16E−04 | 4.11E−02 |
| Mc1r | −1.99 | 9.90E−01 | 1.00E+00 | 8.07E−05 | 2.15E−02 |
| Anp32b | −1.99 | 9.97E−01 | 1.00E+00 | 2.47E−04 | 4.22E−02 |
| Ccs | −1.99 | 9.94E−01 | 1.00E+00 | 2.85E−04 | 4.22E−02 |
| Hsd17b12 | −2.00 | 9.88E−01 | 1.00E+00 | 2.37E−04 | 4.22E−02 |
| Prl2c3 | −2.01 | 9.97E−01 | 1.00E+00 | 1.53E−04 | 3.50E−02 |
| Ankrd46 | −2.02 | 9.90E−01 | 1.00E+00 | 2.16E−04 | 4.11E−02 |
| Ikbkg | −2.03 | 9.98E−01 | 1.00E+00 | 3.08E−04 | 4.22E−02 |
| Ddx20 | −2.03 | 9.89E−01 | 1.00E+00 | 2.85E−04 | 4.22E−02 |
| Akt1 | −2.04 | 6.94E−01 | 1.00E+00 | 2.16E−04 | 4.11E−02 |
| Exoc7 | −2.05 | 9.85E−01 | 1.00E+00 | 8.07E−05 | 2.15E−02 |
| Larp4 | −2.06 | 9.88E−01 | 1.00E+00 | 2.24E−04 | 4.11E−02 |
| Ubtd1 | −2.07 | 9.71E−01 | 1.00E+00 | 1.42E−04 | 3.41E−02 |
| Brwd3 | −2.09 | 9.92E−01 | 1.00E+00 | 3.08E−04 | 4.22E−02 |
| Nudcd2 | −2.09 | 9.98E−01 | 1.00E+00 | 8.02E−05 | 2.15E−02 |
| Ppcs | −2.09 | 9.88E−01 | 1.00E+00 | 1.40E−04 | 3.41E−02 |
| Mrps21 | −2.09 | 9.99E−01 | 1.00E+00 | 2.24E−04 | 4.11E−02 |
| Gnb2 | −2.09 | 9.88E−01 | 1.00E+00 | 7.40E−05 | 2.15E−02 |
| Chic2 | −2.09 | 9.95E−01 | 1.00E+00 | 3.90E−05 | 1.65E−02 |
| Fnbp4 | −2.09 | 9.98E−01 | 1.00E+00 | 2.16E−04 | 4.11E−02 |
| Plpp2 | −2.10 | 9.93E−01 | 1.00E+00 | 2.85E−04 | 4.22E−02 |
| Trip11 | −2.11 | 9.99E−01 | 1.00E+00 | 2.96E−04 | 4.22E−02 |
| Ccna2 | −2.12 | 9.89E−01 | 1.00E+00 | 1.53E−04 | 3.50E−02 |
| Brinp2 | −2.12 | 9.97E−01 | 1.00E+00 | 2.86E−04 | 4.22E−02 |
| Hnrnpf | −2.12 | 9.84E−01 | 1.00E+00 | 3.57E−05 | 1.65E−02 |
| Ccdc134 | −2.12 | 9.99E−01 | 1.00E+00 | 3.90E−05 | 1.65E−02 |
| Prdm10 | −2.14 | 9.83E−01 | 1.00E+00 | 2.80E−05 | 1.65E−02 |
| Smarce1 | −2.15 | 9.88E−01 | 1.00E+00 | 7.06E−05 | 2.15E−02 |
| Tmed2 | −2.15 | 9.97E−01 | 1.00E+00 | 2.75E−04 | 4.22E−02 |
| Usp24 | −2.15 | 9.99E−01 | 1.00E+00 | 3.02E−04 | 4.22E−02 |
| Ipo11 | −2.17 | 9.95E−01 | 1.00E+00 | 2.96E−04 | 4.22E−02 |
| Arf6 | −2.18 | 9.94E−01 | 1.00E+00 | 2.96E−04 | 4.22E−02 |
| Prrc2a | −2.19 | 9.98E−01 | 1.00E+00 | 2.20E−04 | 4.11E−02 |
| Rhbdl2 | −2.19 | 9.97E−01 | 1.00E+00 | 2.10E−04 | 4.11E−02 |
| Lman2 | −2.20 | 9.93E−01 | 1.00E+00 | 3.67E−04 | 4.99E−02 |
| Parn | −2.22 | 9.97E−01 | 1.00E+00 | 9.27E−05 | 2.37E−02 |
| Tvp23b | −2.24 | 9.98E−01 | 1.00E+00 | 2.16E−04 | 4.11E−02 |
| Vmn1r167 | −2.25 | 7.30E−01 | 1.00E+00 | 8.12E−05 | 2.15E−02 |

TABLE 9-continued

List of top candidate genes depleted in OT-I screen (FDR < 0.05)

| | | Positive selection | | Negative selection | |
|---|---|---|---|---|---|
| Gene | logFC | p value | FDR | p value | FDR |
| Med7 | −2.25 | 9.98E−01 | 1.00E+00 | 7.73E−05 | 2.15E−02 |
| Prkcq | −2.26 | 9.97E−01 | 1.00E+00 | 8.07E−05 | 2.15E−02 |
| Gne | −2.27 | 9.97E−01 | 1.00E+00 | 8.02E−05 | 2.15E−02 |
| Aip | −2.27 | 9.99E−01 | 1.00E+00 | 8.07E−05 | 2.15E−02 |
| Crocc | −2.27 | 9.97E−01 | 1.00E+00 | 8.02E−05 | 2.15E−02 |
| Uggt1 | −2.31 | 9.98E−01 | 1.00E+00 | 3.02E−04 | 4.22E−02 |
| Atr | −2.32 | 9.95E−01 | 1.00E+00 | 7.45E−05 | 2.15E−02 |
| Ccnc | −2.33 | 9.99E−01 | 1.00E+00 | 2.20E−04 | 4.11E−02 |
| Rer1 | −2.34 | 9.93E−01 | 1.00E+00 | 7.40E−05 | 2.15E−02 |
| Cks1b | −2.34 | 9.94E−01 | 1.00E+00 | 7.90E−06 | 7.22E−03 |
| Ptar1 | −2.35 | 9.98E−01 | 1.00E+00 | 3.71E−05 | 1.65E−02 |
| Dlst | −2.35 | 9.92E−01 | 1.00E+00 | 2.80E−05 | 1.65E−02 |
| Ubr4 | −2.35 | 9.97E−01 | 1.00E+00 | 3.86E−05 | 1.65E−02 |
| Ddx42 | −2.35 | 9.89E−01 | 1.00E+00 | 8.38E−06 | 7.22E−03 |
| C330007P06Rik | −2.35 | 9.99E−01 | 1.00E+00 | 2.69E−04 | 4.22E−02 |
| Vps29 | −2.37 | 9.98E−01 | 1.00E+00 | 8.07E−05 | 2.15E−02 |
| Atg13 | −2.37 | 1.00E+00 | 1.00E+00 | 2.88E−04 | 4.22E−02 |
| Rab1a | −2.39 | 1.00E+00 | 1.00E+00 | 1.53E−04 | 3.50E−02 |
| Rad51d | −2.39 | 9.97E−01 | 1.00E+00 | 4.19E−05 | 1.67E−02 |
| Otulin | −2.39 | 9.99E−01 | 1.00E+00 | 2.16E−04 | 4.11E−02 |
| Gpaa1 | −2.40 | 9.99E−01 | 1.00E+00 | 8.02E−05 | 2.15E−02 |
| Pih1d1 | −2.41 | 9.98E−01 | 1.00E+00 | 8.02E−05 | 2.15E−02 |
| Nrbf2 | −2.41 | 8.58E−01 | 1.00E+00 | 8.07E−05 | 2.15E−02 |
| BC030336 | −2.42 | 9.89E−01 | 1.00E+00 | 7.90E−06 | 7.22E−03 |
| Nepro | −2.43 | 9.96E−01 | 1.00E+00 | 2.16E−04 | 4.11E−02 |
| Rbm34 | −2.44 | 9.90E−01 | 1.00E+00 | 6.47E−06 | 7.22E−03 |
| Ireb2 | −2.44 | 9.98E−01 | 1.00E+00 | 2.16E−04 | 4.11E−02 |
| Sgol1 | −2.44 | 9.98E−01 | 1.00E+00 | 1.53E−04 | 3.50E−02 |
| Ugp2 | −2.45 | 9.99E−01 | 1.00E+00 | 2.29E−04 | 4.15E−02 |
| Arf3 | −2.46 | 9.99E−01 | 1.00E+00 | 2.16E−04 | 4.11E−02 |
| Itgav | −2.47 | 9.98E−01 | 1.00E+00 | 3.86E−05 | 1.65E−02 |
| Ube2n | −2.47 | 9.96E−01 | 1.00E+00 | 3.62E−05 | 1.65E−02 |
| Mcl1 | −2.48 | 9.99E−01 | 1.00E+00 | 1.42E−04 | 3.41E−02 |
| Map3k7 | −2.48 | 9.98E−01 | 1.00E+00 | 3.57E−05 | 1.65E−02 |
| Vps11 | −2.49 | 9.99E−01 | 1.00E+00 | 2.16E−04 | 4.11E−02 |
| Birc2 | −2.49 | 1.00E+00 | 1.00E+00 | 3.62E−05 | 1.65E−02 |
| Vmn1r202 | −2.50 | 9.99E−01 | 1.00E+00 | 2.71E−04 | 4.22E−02 |
| Rela | −2.51 | 9.99E−01 | 1.00E+00 | 2.16E−04 | 4.11E−02 |
| N4bp1 | −2.54 | 9.99E−01 | 1.00E+00 | 2.80E−05 | 1.65E−02 |
| Slc35a1 | −2.55 | 9.96E−01 | 1.00E+00 | 6.47E−06 | 7.22E−03 |
| Gm7534 | −2.57 | 9.99E−01 | 1.00E+00 | 3.86E−05 | 1.65E−02 |
| Tmed10 | −2.58 | 9.99E−01 | 1.00E+00 | 8.02E−05 | 2.15E−02 |
| Tlcd1 | −2.58 | 1.00E+00 | 1.00E+00 | 8.07E−05 | 2.15E−02 |
| Sptlc2 | −2.62 | 9.97E−01 | 1.00E+00 | 6.94E−06 | 7.22E−03 |
| Sepsecs | −2.62 | 9.98E−01 | 1.00E+00 | 4.19E−05 | 1.67E−02 |
| Pigk | −2.62 | 9.99E−01 | 1.00E+00 | 6.94E−06 | 7.22E−03 |
| Sptlc1 | −2.64 | 9.97E−01 | 1.00E+00 | 3.14E−05 | 1.65E−02 |
| Asnsd1 | −2.65 | 9.99E−01 | 1.00E+00 | 3.86E−05 | 1.65E−02 |
| Gpx4 | −2.65 | 9.99E−01 | 1.00E+00 | 8.07E−05 | 2.15E−02 |
| Uba6 | −2.66 | 9.99E−01 | 1.00E+00 | 7.02E−05 | 2.15E−02 |
| Vps33a | −2.67 | 1.00E+00 | 1.00E+00 | 7.42E−06 | 7.22E−03 |
| Tmx2 | −2.67 | 9.99E−01 | 1.00E+00 | 8.38E−06 | 7.22E−03 |
| Cwc27 | −2.68 | 9.95E−01 | 1.00E+00 | 1.92E−06 | 5.45E−03 |
| Chtf8 | −2.69 | 1.00E+00 | 1.00E+00 | 7.45E−05 | 2.15E−02 |
| Kmt2d | −2.69 | 9.99E−01 | 1.00E+00 | 3.76E−05 | 1.65E−02 |
| Atg5 | −2.69 | 9.98E−01 | 1.00E+00 | 3.90E−05 | 1.65E−02 |
| Dscc1 | −2.70 | 9.97E−01 | 1.00E+00 | 2.63E−06 | 5.45E−03 |
| Atp6v1h | −2.71 | 9.98E−01 | 1.00E+00 | 6.94E−06 | 7.22E−03 |
| Slc7a11 | −2.73 | 9.99E−01 | 1.00E+00 | 3.71E−05 | 1.65E−02 |
| Gss | −2.74 | 1.00E+00 | 1.00E+00 | 2.21E−04 | 4.11E−02 |
| Pigu | −2.78 | 1.00E+00 | 1.00E+00 | 2.63E−06 | 5.45E−03 |
| Stub1 | −2.79 | 9.97E−01 | 1.00E+00 | 7.18E−07 | 4.95E−03 |
| Calr | −2.82 | 9.99E−01 | 1.00E+00 | 2.85E−05 | 1.65E−02 |
| Aprt | −2.83 | 9.99E−01 | 1.00E+00 | 2.80E−05 | 1.65E−02 |
| Alg8 | −2.84 | 9.99E−01 | 1.00E+00 | 2.16E−06 | 5.45E−03 |
| Ei24 | −2.85 | 1.00E+00 | 1.00E+00 | 4.14E−05 | 1.67E−02 |
| Mtch1 | −2.87 | 9.99E−01 | 1.00E+00 | 7.90E−06 | 7.22E−03 |
| Eefsec | −2.91 | 9.97E−01 | 1.00E+00 | 2.39E−07 | 2.48E−03 |
| Traf3 | −2.94 | 1.00E+00 | 1.00E+00 | 7.90E−06 | 7.22E−03 |
| Usp18 | −2.95 | 9.99E−01 | 1.00E+00 | 3.71E−05 | 1.65E−02 |
| Vps4b | −2.97 | 1.00E+00 | 1.00E+00 | 2.90E−05 | 1.65E−02 |
| Traf2 | −2.98 | 1.00E+00 | 1.00E+00 | 6.47E−06 | 7.22E−03 |
| Pigs | −3.01 | 1.00E+00 | 1.00E+00 | 2.75E−05 | 1.65E−02 |
| Fitm2 | −3.03 | 1.00E+00 | 1.00E+00 | 2.63E−06 | 5.45E−03 |

TABLE 9-continued

List of top candidate genes depleted in OT-I screen (FDR < 0.05)

| Gene | logFC | Positive selection | | Negative selection | |
|---|---|---|---|---|---|
| | | p value | FDR | p value | FDR |
| Megf8 | −3.14 | 1.00E+00 | 1.00E+00 | 2.16E−06 | 5.45E−03 |
| Eri1 | −3.18 | 1.00E+00 | 1.00E+00 | 6.47E−06 | 7.22E−03 |
| Rnf31 | −3.40 | 1.00E+00 | 1.00E+00 | 2.16E−06 | 5.45E−03 |
| Ptpn2 | −3.63 | 1.00E+00 | 1.00E+00 | 2.39E−07 | 2.48E−03 |

LogFC, Log2 fold change; FDR, False Discovery rate. FDR and p value calculated by MaGeCK.

Example 3: Pathway Identification and Clinical Correlations

Figure 5:
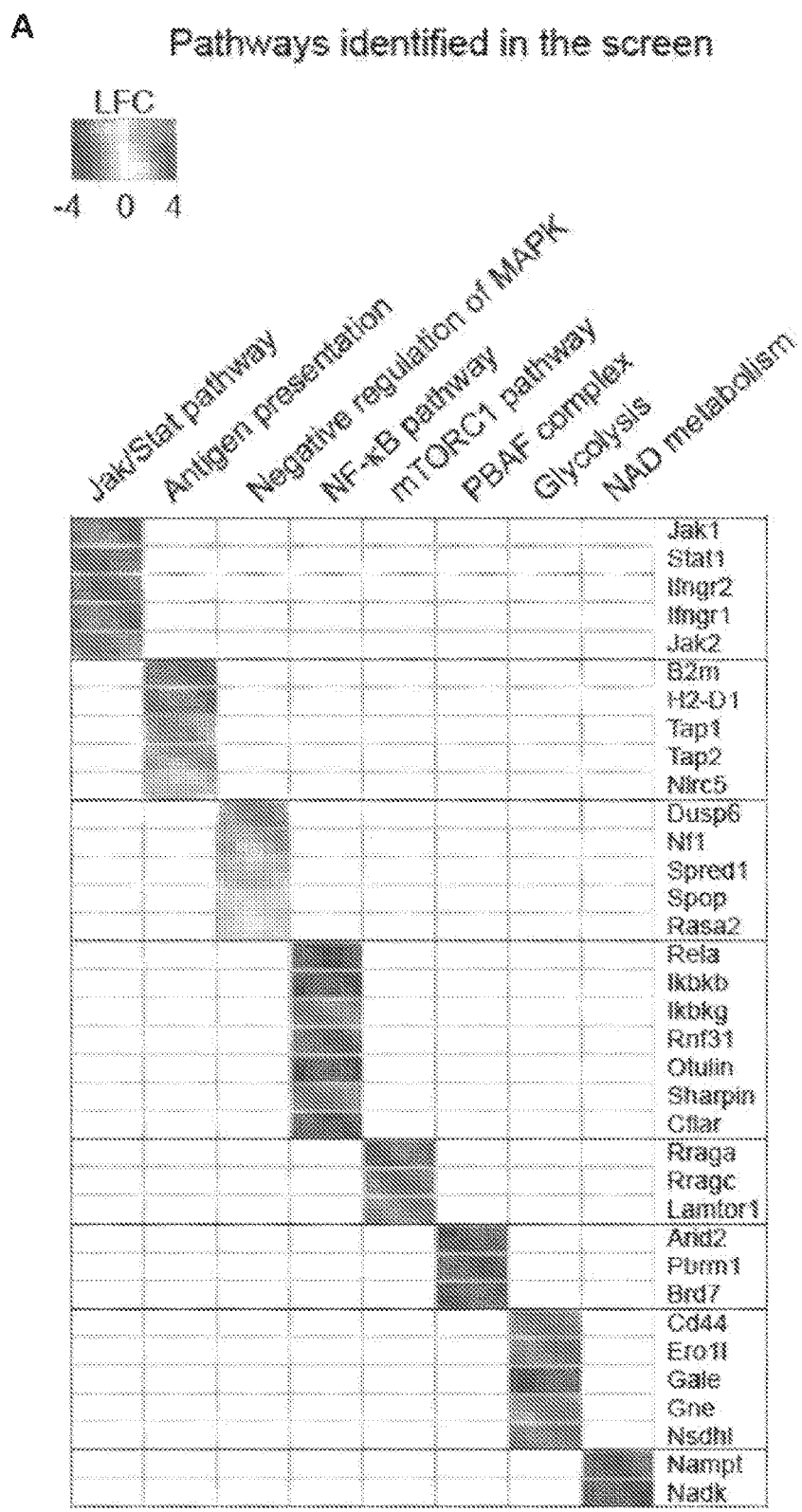
FIG. 5 includes 4 panels, identified as panels A, B, C, and D, which show pathways identified and correlated with clinical data. Panel A provides a heat map showing the most significant pathways and corresponding genes identified in the Pmel1 screen by gene set enrichment analysis (GSEA) using a molecular signature data base. Color scale represents log 2 fold change of average gRNA representation. Panel B shows the impact of discovered gene sets on survival of melanoma patients. For each patient in the TCGA melanoma study, the Pearson correlation value is computed between gene expression values in melanomas for all genes identified in the OT-I or Pmel-1 screens and log 2 fold enrichment/depletion of gRNAs for genes identified in CRISPR/Cas9 screen. The overall survival (OS) durations were shown for patients with positive and negative correlations. Comparison of survival between groups were done through two-sided Ward test in CoxPH. Panel C shows the correlation of CRISPR screening data with estimated CD8 T cell infiltration in TCGA melanoma data. For each patient in TCGA melanoma study, the average value of CD8A+CD8B mRNA level (X-axis, marker of CD8 T cell infiltration) was plotted against correlation value (Y-axis) determined in (Panel A) for CRISPR screening data (log 2 fold ratios). Panel D shows the correlation of ARID2 expression level with survival of melanoma patients depending on calculated level of CD8 T cell infiltration. All patients in TCGA melanoma study were divided according to the expression level of ARID2 (higher or lower than mean expression value of all patients). The impact of ARID2 expression level on survival is shown for patients whose tumors had higher (>1 SD) or lower (<1SD) expression of CD8 [(CD8A+CD8B)/2].
Figure 5:
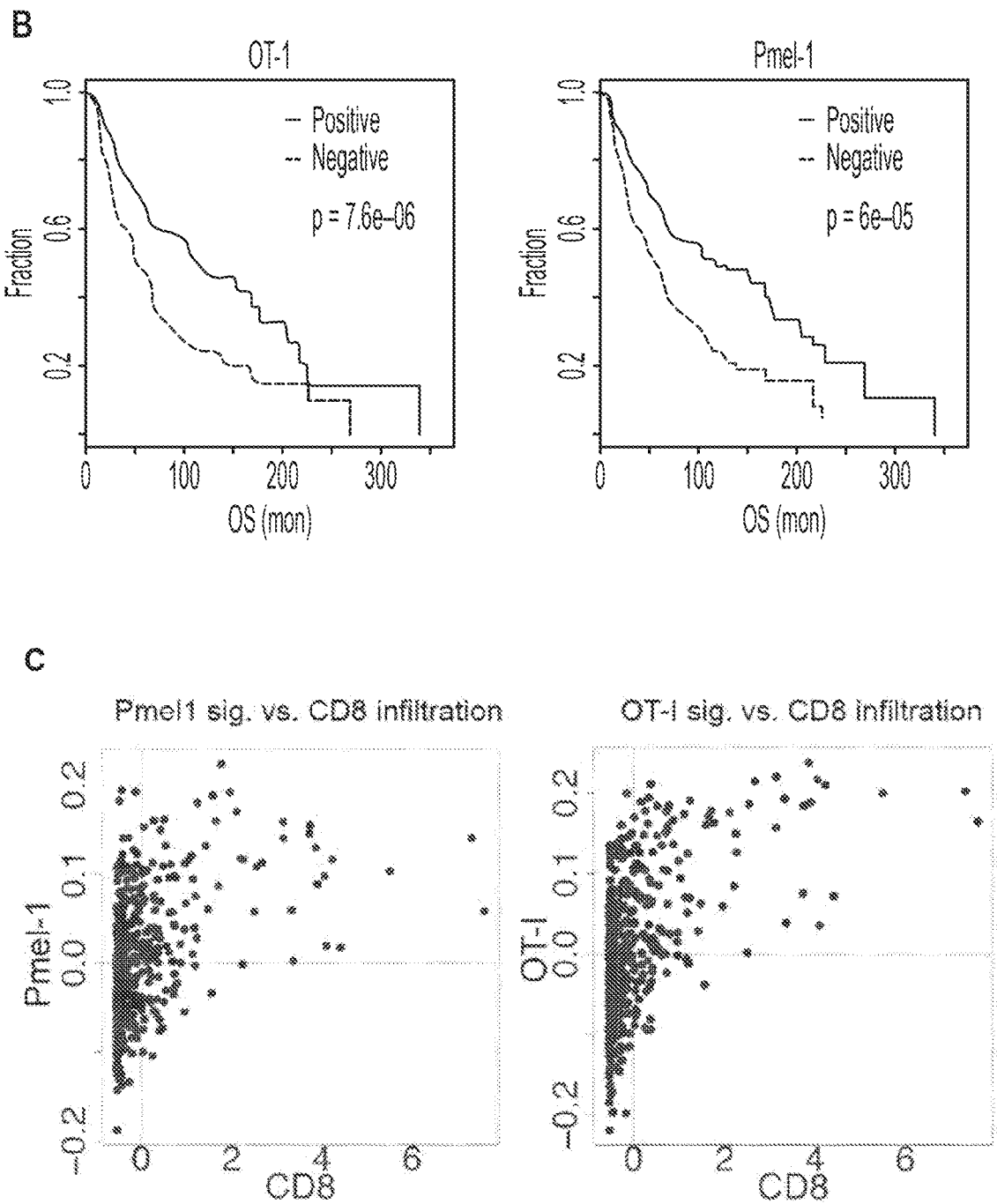
Figure 5:
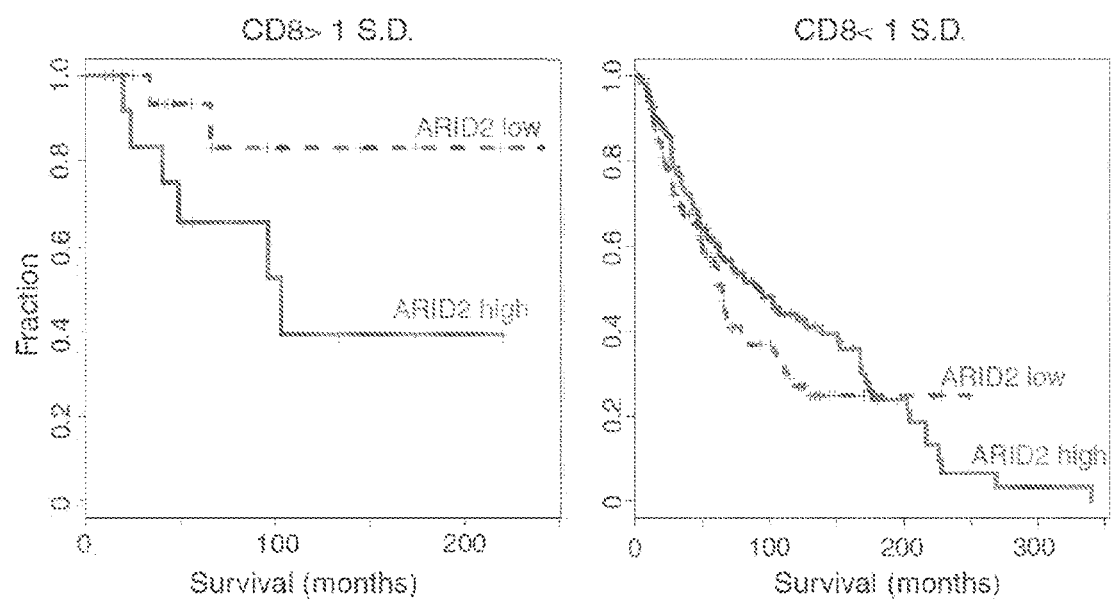

Gene set enrichment analysis was performed to identify known gene sets/pathways for genes corresponding to enriched or depleted gRNA (Tables 10 and 11). Pathway analysis based on the most significant hits indicates that multiple pathways regulate the sensitivity to T cell-mediated killing. The enriched hits from the screen recaptured essential pathways required for T cell-mediated killing. In addition to interferon and antigen presentation pathways, a number of negative regulators of Ras/MAPK pathways were identified among enriched gRNAs, including Nf1 (inhibitor of Ras activation) (Ratner et al. (2015) *Nat. Rev. Cancer* 15:290-301) and Dusp6 (phosphatase that dephosphorylates Erk1/2 downstream of Ras) (Messina et al. (2011) *Oncogene* 30:3813-3820), as well as Spred1 (Phoenix et al. (2010) *Genes Dev.* 24:45-56), Rasa2 (Arafeh et al. (2015) *Nat. Genet.* 47:1408-1410), and SPOP (Li et al.(2014) *Cancer Cell* 25:455-468) (FIG. 5A). These data indicate that Ras pathway activation increases resistance to T cell-mediated cytotoxicity. This hypothesis is supported by the clinical finding that BRAF inhibition in patients with melanoma (which is upstream of the Ras pathway) is associated with CD8 T cell infiltration. Ras pathway activation is very common among human cancers and may not only promote tumor cell growth but also attenuate tumor immunity. Braf is immediately downstream of Ras, and small molecule inhibitors of mutant BRAF$^{V600E}$ elicit stronger cytotoxic T cell responses in melanoma patients and murine tumor models (Frederick et al. (2013) *Clin. Cancer Res.* 19:1225-1231; Ebert et al. (2016) *Immunity* 44:609-621; Koya et al. (2012) *Cancer Res.* 72:3928-3937).

TABLE 10

Gene sets (Hallmark and KEGG gene sets) significantly enriched (FDR < 0.05) in Pmel-1 or OT-I screen

| Gene Set Name | Screen | p-value | q-value |
|---|---|---|---|
| KEGG_JAK_STAT_SIGNALING_PATHWAY | Pmel1 | 8.69E−11 | 2.36E−08 |
| HALLMARK_ALLOGRAFT_REJECTION | Pmel1 | 6.61E−10 | 8.99E−08 |
| KEGG_LEISHMANIA_INFECTION | Pmel1 | 1.21E−09 | 1.41E−07 |
| HALLMARK_INTERFERON_GAMMA_RESPONSE | Pmel1 | 2.06E−08 | 1.68E−06 |
| HALLMARK_IL6_JAK_STAT3_SIGNALING | Pmel1 | 8.89E−06 | 4.84E−04 |
| KEGG_ANTIGEN_PROCESSING_AND_PRESENTATION | Pmel1 | 9.73E−06 | 4.96E−04 |
| KEGG_PRIMARY_IMMUNODEFICIENCY | Pmel1 | 1.96E−05 | 8.89E−04 |
| KEGG_NATURAL_KILLER_CELL_MEDIATED_CYTOTOXICITY | Pmel1 | 5.31E−05 | 2.17E−03 |
| HALLMARK_COMPLEMENT | Pmel1 | 2.28E−04 | 6.00E−03 |
| HALLMARK_INFLAMMATORY_RESPONSE | Pmel1 | 2.28E−04 | 6.00E−03 |
| KEGG_TOLL_LIKE_RECEPTOR_SIGNALING_PATHWAY | Pmel1 | 4.79E−04 | 1.12E−02 |
| KEGG_CYTOKINE_CYTOKINE_RECEPTOR_INTERACTION | Pmel1 | 6.78E−04 | 1.47E−02 |
| KEGG_MAPK_SIGNALING_PATHWAY | Pmel1 | 6.78E−04 | 1.47E−02 |
| KEGG_UBIQUITIN_MEDIATED_PROTEOLYSIS | Pmel1 | 1.15E−03 | 2.13E−02 |
| KEGG_PATHWAYS_IN_CANCER | Pmel1 | 1.45E−03 | 2.63E−02 |
| HALLMARK_APOPTOSIS | Pmel1 | 1.79E−03 | 3.10E−02 |
| KEGG_LEISHMANIA_INFECTION | OT-I | 1.25E−10 | 1.02E−07 |
| KEGG_JAK_STAT_SIGNALING_PATHWAY | OT-I | 6.09E−09 | 2.48E−06 |
| HALLMARK_ALLOGRAFT_REJECTION | OT-I | 2.18E−08 | 5.94E−06 |
| HALLMARK_IL6_JAK_STAT3_SIGNALING | OT-I | 7.30E−06 | 1.49E−03 |
| HALLMARK_INTERFERON_GAMMA_RESPONSE | OT-I | 8.76E−05 | 8.94E−03 |
| KEGG_PANCREATIC_CANCER | OT-I | 4.27E−04 | 3.87E−02 |

Gene sets related to FIG. 5A are highlighted.

TABLE 11

Gene sets (Hallmark and KEGG gene sets) significantly depleted (LFC > 2, FDR q < 0.05) in Pmel-1 or OT-I screens

| Gene Set Name | Screen | p-value | q-value |
|---|---|---|---|
| HALLMARK_INTERFERON_GAMMA_RESPONSE | Pmel1 | 4.00E−11 | 9.44E−09 |
| KEGG_ADIPOCYTOKINE_SIGNALING_PATHWAY | Pmel1 | 3.15E−10 | 3.72E−08 |
| KEGG_UBIQUITIN_MEDIATED_PROTEOLYSIS | Pmel1 | 5.60E−09 | 4.40E−07 |
| HALLMARK_TNFA_SIGNALING_VIA_NFKB | Pmel1 | 1.02E−08 | 4.66E−07 |
| KEGG_PATHWAYS_IN_CANCER | Pmel1 | 1.11E−08 | 4.66E−07 |
| HALLMARK_PI3K_AKT_MTOR_SIGNALING | Pmel1 | 1.18E−08 | 4.66E−07 |
| KEGG_PROSTATE_CANCER | Pmel1 | 7.97E−08 | 2.69E−06 |
| HALLMARK_INTERFERON_ALPHA_RESPONSE | Pmel1 | 1.45E−07 | 4.27E−06 |
| KEGG_RIG_I_LIKE_RECEPTOR_SIGNALING_PATHWAY | Pmel1 | 4.52E−07 | 1.19E−05 |
| KEGG_CHRONIC_MYELOID_LEUKEMIA | Pmel1 | 5.34E−07 | 1.26E−05 |
| KEGG_SMALL_CELL_LUNG_CANCER | Pmel1 | 1.23E−06 | 2.64E−05 |
| HALLMARK_IL6_JAK_STAT3_SIGNALING | Pmel1 | 1.51E−06 | 2.85E−05 |
| KEGG_APOPTOSIS | Pmel1 | 1.62E−06 | 2.85E−05 |
| HALLMARK_MTORC1_SIGNALING | Pmel1 | 1.69E−06 | 2.85E−05 |
| KEGG_CYTOSOLIC_DNA_SENSING_PATHWAY | Pmel1 | 3.24E−06 | 5.10E−05 |
| HALLMARK_APOPTOSIS | Pmel1 | 4.42E−06 | 6.34E−05 |
| KEGG_ACUTE_MYELOID_LEUKEMIA | Pmel1 | 4.57E−06 | 6.34E−05 |
| KEGG_T_CELL_RECEPTOR_SIGNALING_PATHWAY | Pmel1 | 5.34E−06 | 7.00E−05 |
| KEGG_PANCREATIC_CANCER | Pmel1 | 9.80E−06 | 1.16E−04 |
| KEGG_RENAL_CELL_CARCINOMA | Pmel1 | 9.80E−06 | 1.16E−04 |
| KEGG_NEUROTROPHIN_SIGNALING_PATHWAY | Pmel1 | 1.29E−05 | 1.46E−04 |
| KEGG_FOCAL_ADHESION | Pmel1 | 1.88E−05 | 2.01E−04 |
| KEGG_AMINO_SUGAR_AND_NUCLEOTIDE_SUGAR_METABOLISM | Pmel1 | 3.04E−05 | 3.12E−04 |
| KEGG_TOLL_LIKE_RECEPTOR_SIGNALING_PATHWAY | Pmel1 | 6.08E−05 | 5.98E−04 |
| HALLMARK_PEROXISOME | Pmel1 | 6.67E−05 | 6.30E−04 |
| KEGG_NOD_LIKE_RECEPTOR_SIGNALING_PATHWAY | Pmel1 | 1.18E−04 | 1.07E−03 |
| KEGG_CHEMOKINE_SIGNALING_PATHWAY | Pmel1 | 1.28E−04 | 1.12E−03 |
| KEGG_EPITHELIAL_CELL_SIGNALING_IN_HELICOBACTER_PYLORI_INFECTION | Pmel1 | 1.69E−04 | 1.33E−03 |
| HALLMARK_ESTROGEN_RESPONSE_EARLY | Pmel1 | 1.70E−04 | 1.33E−03 |
| HALLMARK_INFLAMMATORY_RESPONSE | Pmel1 | 1.70E−04 | 1.33E−03 |
| KEGG_B_CELL_RECEPTOR_SIGNALING_PATHWAY | Pmel1 | 2.47E−04 | 1.88E−03 |
| KEGG_REGULATION_OF_ACTIN_CYTOSKELETON | Pmel1 | 2.57E−04 | 1.89E−03 |
| KEGG_PEROXISOME | Pmel1 | 2.87E−04 | 2.06E−03 |
| KEGG_FC_GAMMA_R_MEDIATED_PHAGOCYTOSIS | Pmel1 | 6.58E−04 | 4.57E−03 |
| KEGG_MAPK_SIGNALING_PATHWAY | Pmel1 | 7.84E−04 | 5.29E−03 |
| KEGG_ENDOCYTOSIS | Pmel1 | 9.09E−04 | 5.96E−03 |
| KEGG_PROTEASOME | Pmel1 | 9.72E−04 | 6.20E−03 |
| HALLMARK_REACTIVE_OXIGEN_SPECIES_PATHWAY | Pmel1 | 1.03E−03 | 6.41E−03 |
| HALLMARK_GLYCOLYSIS | Pmel1 | 1.35E−03 | 7.96E−03 |
| HALLMARK_HYPOXIA | Pmel1 | 1.35E−03 | 7.96E−03 |
| KEGG_NON_HOMOLOGOUS_END_JOINING | Pmel1 | 1.42E−03 | 8.18E−03 |
| KEGG_INSULIN_SIGNALING_PATHWAY | Pmel1 | 2.35E−03 | 1.32E−02 |
| KEGG_P53_SIGNALING_PATHWAY | Pmel1 | 2.77E−03 | 1.52E−02 |
| HALLMARK_FATTY_ACID_METABOLISM | Pmel1 | 3.92E−03 | 2.06E−02 |
| HALLMARK_UV_RESPONSE_UP | Pmel1 | 3.92E−03 | 2.06E−02 |
| KEGG_NICOTINATE_AND_NICOTINAMIDE_METABOLISM | Pmel1 | 4.20E−03 | 2.15E−02 |
| KEGG_ECM_RECEPTOR_INTERACTION | Pmel1 | 4.81E−03 | 2.42E−02 |
| KEGG_ERBB_SIGNALING_PATHWAY | Pmel1 | 5.31E−03 | 2.61E−02 |
| KEGG_ANTIGEN_PROCESSING_AND_PRESENTATION | Pmel1 | 5.66E−03 | 2.72E−02 |
| KEGG_REGULATION_OF_AUTOPHAGY | Pmel1 | 8.79E−03 | 3.97E−02 |
| KEGG_SMALL_CELL_LUNG_CANCER | OT-I | 1.44E−11 | 3.39E−09 |
| KEGG_GLYCOSYLPHOSPHATIDYLINOSITOL_GPI_ANCHOR_BIOSYNTHESIS | OT-I | 2.58E−07 | 3.01E−05 |
| KEGG_ADIPOCYTOKINE_SIGNALING_PATHWAY | OT-I | 3.83E−07 | 3.01E−05 |
| KEGG_RIG_I_LIKE_RECEPTOR_SIGNALING_PATHWAY | OT-I | 5.12E−07 | 3.02E−05 |
| KEGG_PATHWAYS_IN_CANCER | OT-I | 6.51E−07 | 3.07E−05 |
| KEGG_APOPTOSIS | OT-I | 1.50E−06 | 5.89E−05 |
| HALLMARK_PROTEIN_SECRETION | OT-I | 2.30E−06 | 7.77E−05 |
| KEGG_T_CELL_RECEPTOR_SIGNALING_PATHWAY | OT-I | 4.12E−06 | 1.21E−04 |
| KEGG_TOLL_LIKE_RECEPTOR_SIGNALING_PATHWAY | OT-I | 7.61E−05 | 2.00E−03 |
| HALLMARK_PI3K_AKT_MTOR_SIGNALING | OT-I | 8.52E−05 | 2.01E−03 |
| KEGG_UBIQUITIN_MEDIATED_PROTEOLYSIS | OT-I | 2.44E−04 | 5.24E−03 |
| KEGG_MAPK_SIGNALING_ PATHWAY | OT-I | 3.06E−04 | 5.68E−03 |
| KEGG_ACUTE_MYELOID_LEUKEMIA | OT-I | 3.13E−04 | 5.68E−03 |
| KEGG_NOD_LIKE_RECEPTOR_SIGNALING_PATHWAY | OT-I | 3.44E−04 | 5.81E−03 |
| KEGG_EPITHELIAL_CELL_SIGNALING_IN_HELICOBACTER_PYLORI_INFECTION | OT-I | 4.52E−04 | 7.11E−03 |
| KEGG_PANCREATIC_CANCER | OT-I | 4.92E−04 | 7.26E−03 |
| KEGG_CHRONIC_MYELOID_LEUKEMIA | OT-I | 5.57E−04 | 7.73E−03 |
| KEGG_B_CELL_RECEPTOR_SIGNALING_PATHWAY | OT-I | 6.02E−04 | 7.90E−03 |
| KEGG_CHEMOKINE_SIGNALING_PATHWAY | OT-I | 8.14E−04 | 1.01E−02 |
| KEGG_PROSTATE_CANCER | OT-I | 9.91E−04 | 1.13E−02 |
| KEGG_FOCAL_ADHESION | OT-I | 1.00E−03 | 1.13E−02 |
| HALLMARK_UNFOLDED_PROTEIN_RESPONSE | OT-I | 1.97E−03 | 2.11E−02 |

TABLE 11-continued

Gene sets (Hallmark and KEGG gene sets) significantly depleted (LFC > 2, FDR q < 0.05) in Pmel-1 or OT-I screens

| Gene Set Name | Screen | p-value | q-value |
| --- | --- | --- | --- |
| KEGG_SPHINGOLIPID_METABOLISM | OT-I | 3.46E−03 | 3.55E−02 |
| KEGG_AMINO_SUGAR_AND_NUCLEOTIDE_SUGAR_METABOLISM | OT-I | 4.18E−03 | 4.11E−02 |
| HALLMARK_DNA_REPAIR | OT-I | 4.37E−03 | 4.13E−02 |
| HALLMARK_APOPTOSIS | OT-I | 5.32E−03 | 4.69E−02 |
| KEGG_GLUTATHIONE_METABOLISM | OT-I | 5.36E−03 | 4.69E−02 |

Gene sets related to FIG. 5A are highlighted.

Figure 12:
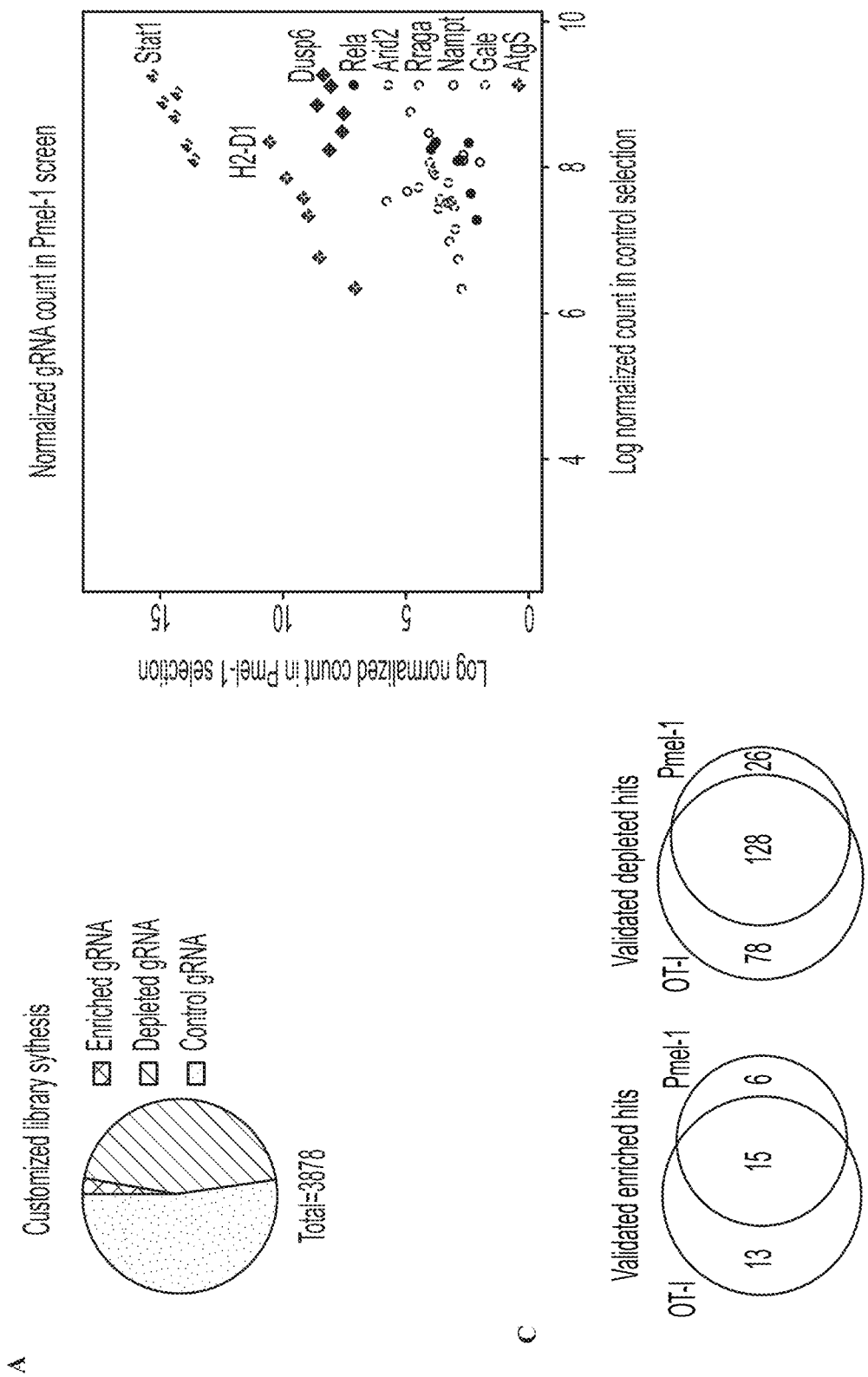
FIG. 12 includes 5 panels, identified as panels A, B, C, D, and E, which show the validation of candidate genes by screening of a mini-pool gRNA library. Panel A illustrates the mini-pool library design. The most significant hits (LFC>2 and FDR<0.05) from Pmel-1 and OT-I screens (total of 313 genes) were included in the mini-pool gRNA library. The library contained 6 gRNAs for each candidate gene (total 1,878 targeting gRNAs) and 2,000 non-targeting control gRNAs. Panel B shows the normalized counts for each gRNA with Pmel-1 selection (Y-axis) or control T cell selection (X-axis). Examples of enriched and depleted gRNAs were annotated. Panel C shows a summary of validation screen. Venn diagram illustrating validated genes for enriched gRNAs (n=15 genes) and depleted gRNAs (n=128 genes) that were positive in both Pmel-1 and OT-I screens (FDR<0.05 in MaGeCK analysis). Panel D shows the correlation between different screening results. The log-fold change (log FC) ratios of primary screens are plotted on the X-axis, while the log FC of the validation screen is on the Y-axis. The OT1 and Pmel-1 conditions are shown separately. Panel E shos the correlation between OT-I and Pmel1 validation screens. The log-fold change (log FC) ratios of OT1 screens are plotted on the X-axis, with the Pmel1 screen log FC on the Y-axis.
Figure 12:
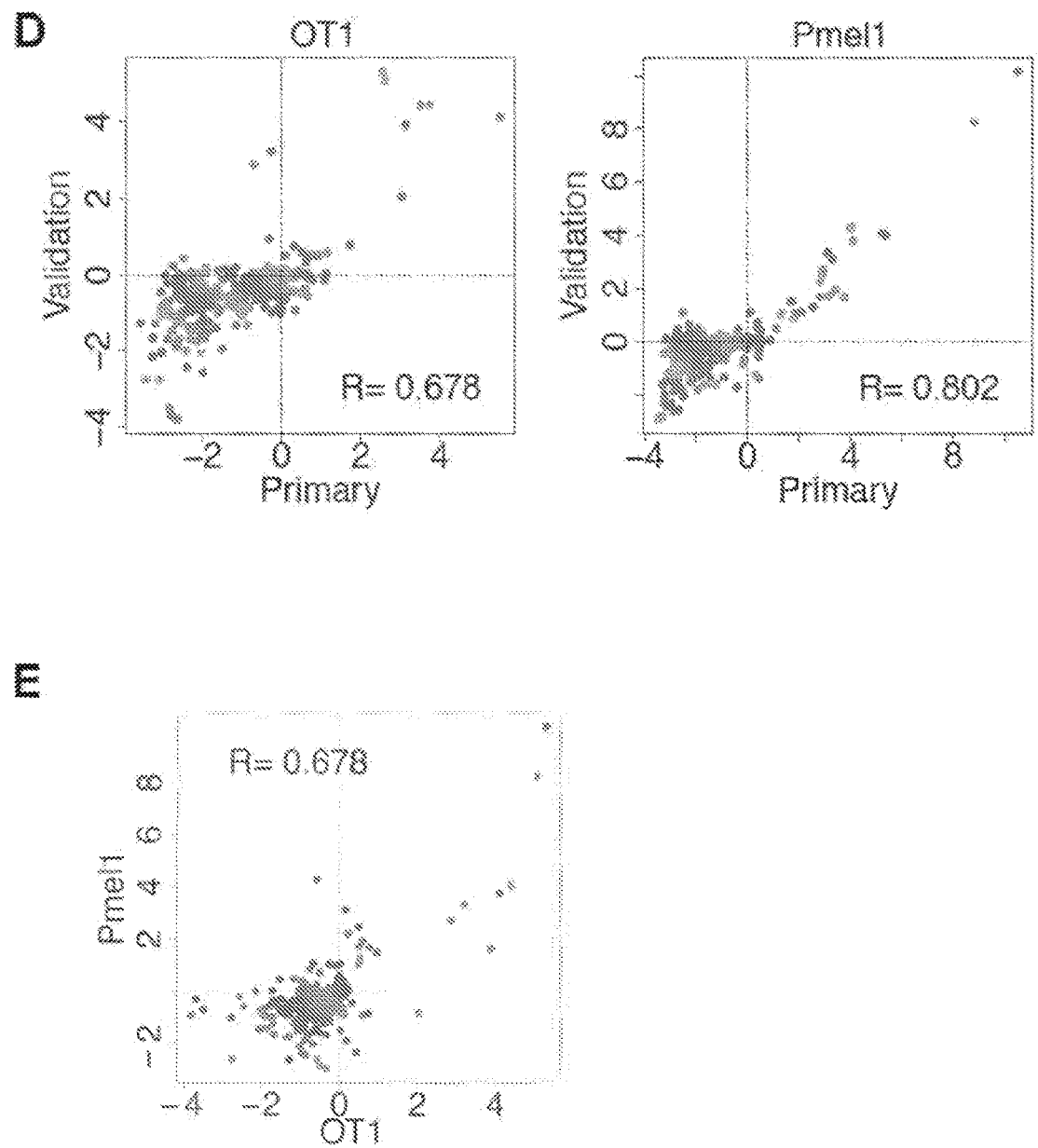
Figure 13:
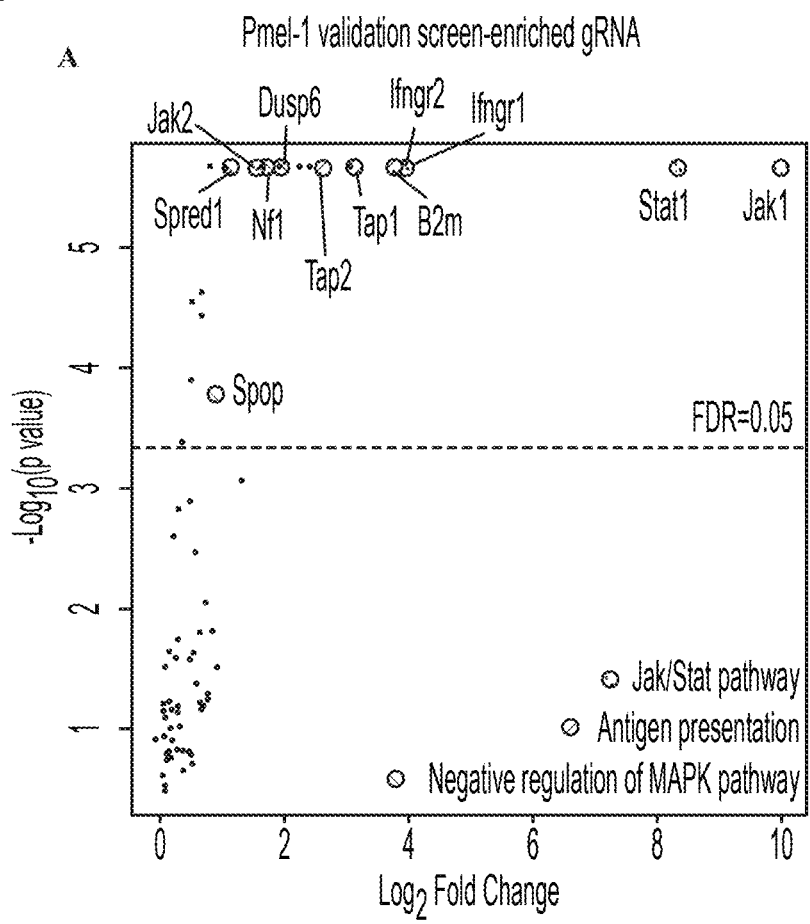
FIG. 13 includes 4 panels, identified as panels A, B, C, and D, which show the genes validated in screens with Pmel-1 and OT-I T cells. Panels A and B show the validation data for genes with enriched gRNAs in screens with Pmel-1 (Panel A) and OT-I (Panel B) T cells analyzed using MaGeCK software. Candidate genes were plotted based on mean log 2 fold change of gRNA counts and p values. Genes involved in MHC/antigen presentation pathway (red), type I/II interferon pathways (yellow) and Ras/MAPK pathway (blue) were annotated. Panels C and D show the validation data for top genes with depleted gRNAs in screens with Pmel-1 (Panel C) and OT-I (Panel D) T cells. Selected genes involved in NF-kB (blue), mTORC1 pathway (yellow), PBAF form of SWI/SNF complex (red), NAD metabolism (black), and glycolysis (green) were highlighted.
Figure 13:
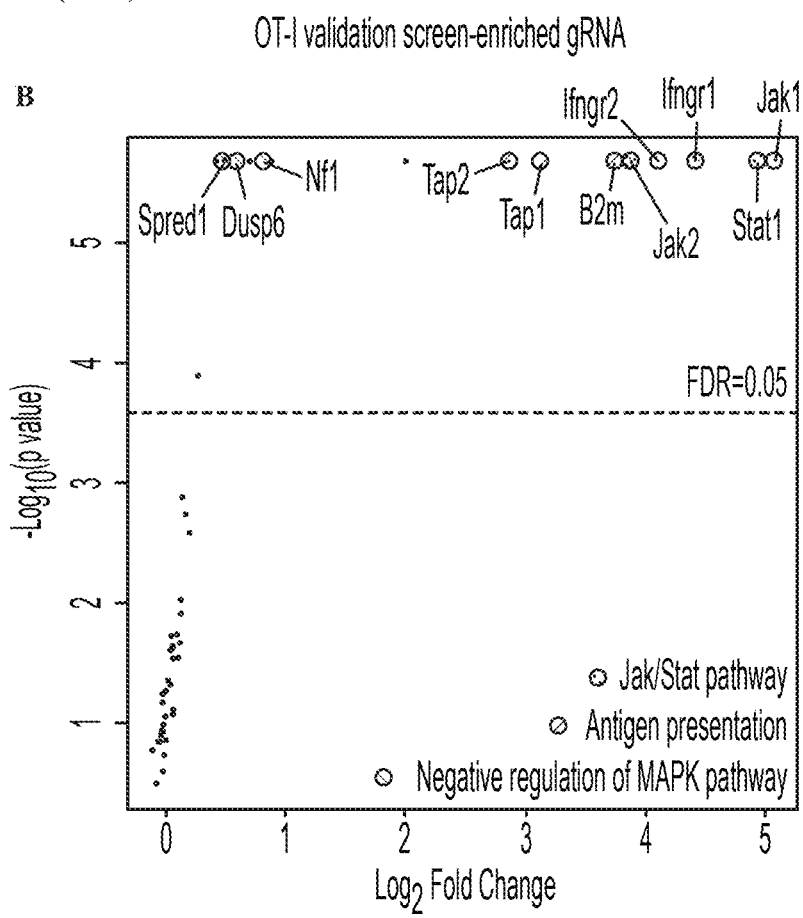
Figure 13:
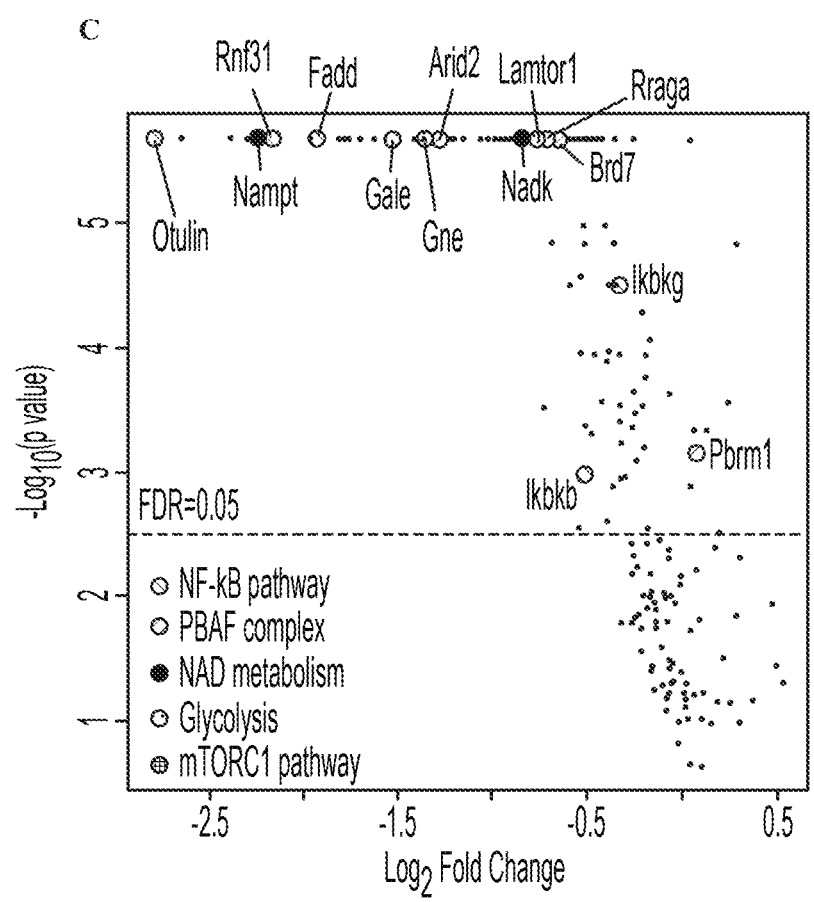
Figure 13:
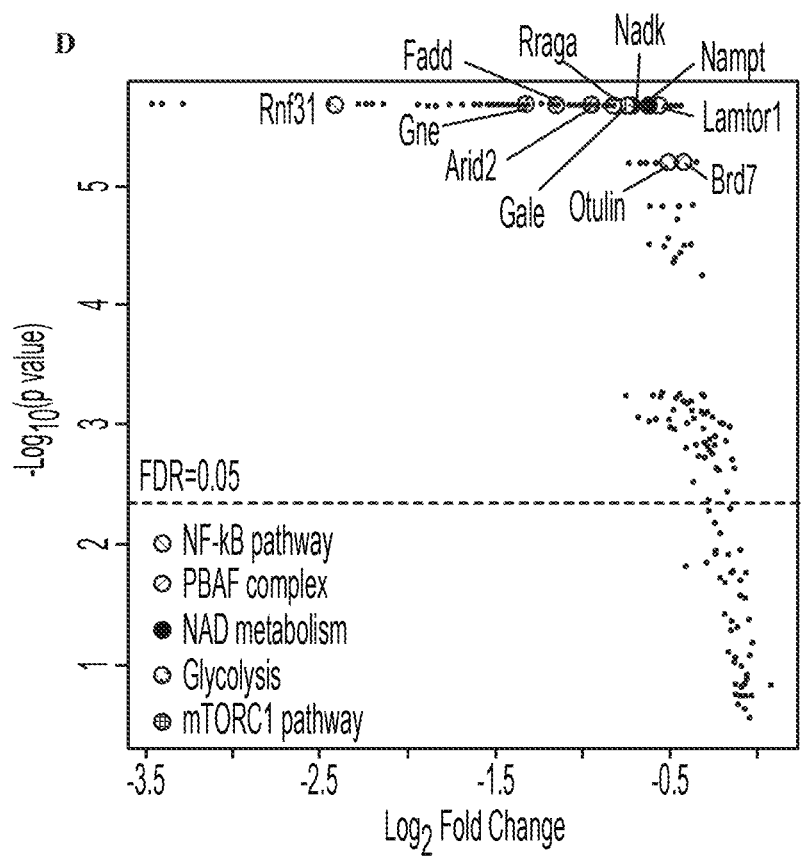

Analysis of depleted gRNAs revealed a number of resistance pathways to T cell mediated killing (FIGS. 3C and 5A and Table 11). Importantly, a number of pathways whose inactivation sensitized tumor cells to T cell-mediated killing were also identified. Three major signaling pathways were identified: NF-kB pathway (Zhang et al. (2017) Cell 168: 37-57) (including Otulin, Rela, Ikbkg, Ikbkb, Rnf31 and Sharpin), mTORC1 pathways (including Rraga, Rragc and Lamtor 1 which are required for mTORC1 recruitment to lysosomes (Sancak et al. (2010) Cell 141:290-303)), and RIG-I like receptor signaling pathway (including Tbk1, Fadd, Atg5 and multiple components overlapped with NF-kB pathway). In addition, depleted gRNA enriched in two major metabolic pathways were also identified: glycolysis (including Nsdhl, Gne, Gale, Ero11 and Cd44) and nicotinate/nicotinamide metabolism (including Nadk and Nampt). Moreover, all three unique components of a SWI/SNF chromatin remodeling complex, referred to as the PBAF complex (Kadoch et al. (2015) Sci. Adv. 1:e1500447; Lemon et al. (2001) Nature 414:924-928), were also strongly depleted (Arid2, Pbrm1 and Brd7), providing strong evidence that the presence of this complex conferred resistance to T cell-mediated killing (FIG. 5A). The NF-kB pathway was also identified as a resistance mechanism by Manguso et al (2017) Nature 547:413-418). Control experiments demonstrated that inactivation of such genes did not merely increase sensitivity to cell death; inactivation of representative genes (Otulin, Dusp6 or Nf1) in B16F10-Cas9 cells did not render them more sensitive to doxorubicin induced cell death (FIG. 11). The majority of identified genes (253 of 313 genes) were validated in a secondary screen (FIG. 12) which also confirmed the major pathways described above (FIG. 13).

Figure 6:
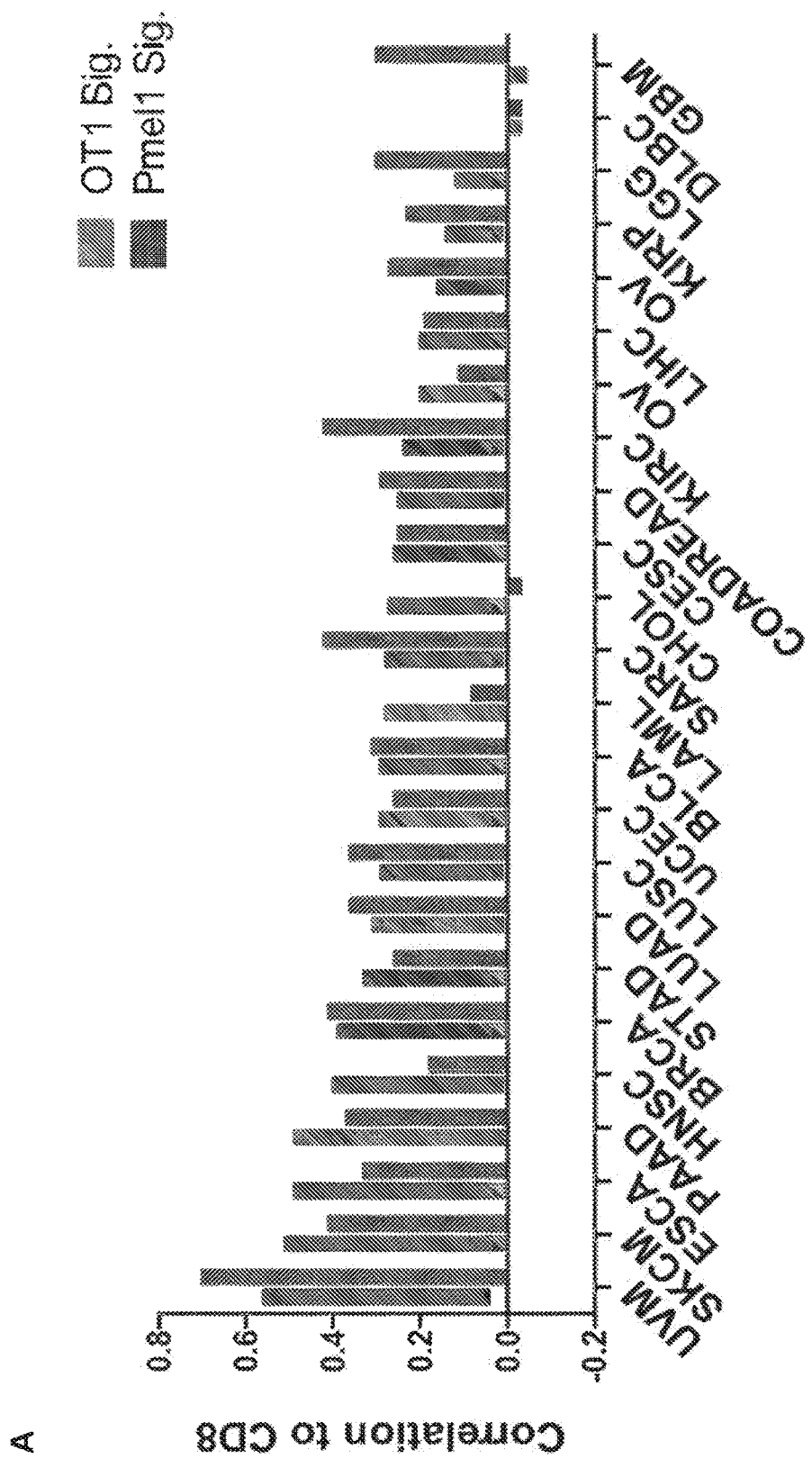
FIG. 6 includes 2 panels, identified as panels A and B which show the analysis of discovered genes in TCGA datasets of human cancer. Panel A shows correlation values between CD8 expression and CRISPR screen signatures shown in FIG. 5C computed for all cancer types studied in TCGA. For each patient in TCGA, a correlation signature between gene expression profile and log 2 fold change of top CRISPR gene hits was computed. This patient signature was related to average value of CD8A+CD8B mRNA level across patients in each cancer type through Pearson correlation. Panel B shows correlation of expression level of each of the top hits to GZMB or PRF1 expression level. For each of the top hits identified in the screen, Spearman's correlation of its expression level to GZMB or PRF1 expression level in TCGA melanoma patients were computed and plotted. Examples with positive (red) and negative (blue) correlations were annotated.
Figure 6:
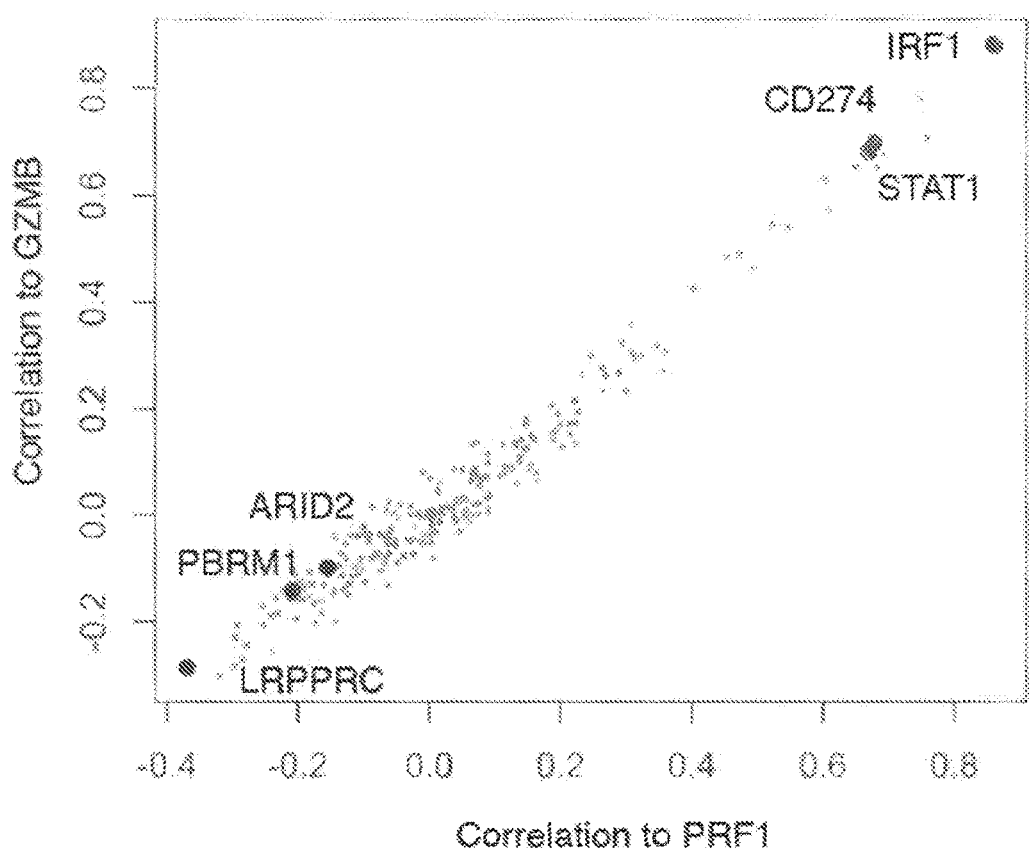

Several different approaches were used to investigate the clinical relevance of these findings. First, it was determined whether the entire set of genes from both Pmel1 and OT-I screens were associated with a survival benefit in patients with melanoma using a TCGA dataset. It was found that both the OT-I and Pmel1 gene sets were associated with improved survival, indicating that these genes sets reflect immunological mechanisms that are also relevant in humans (FIG. 5B). Second, it was determined whether these genes sets were associated with enhanced CD8 T cell infiltration into human cancers. Both Pmel1 and OT-I gene sets were both strongly associated with increased CD8 T cell infiltration into many human cancers, in particular melanoma (SKCM), head and neck squamous carcinoma (HNSC), kidney cancer (KIRC), and lung adenocarcinoma and squamous carcinoma (LUAD and LUSC) (FIGS. 5C and 6). Third, the potential clinical impact of inactivating mutation of the SWI/SNF complex was examined. Since ARID2 gene inactivation is rather common in patients with melanoma, TCGA data were examined to determine whether inactivation of this gene conferred a survival benefit in the presence of tumor-infiltrating CD8 T cells. RNA-seq data were used to infer the level of CD8 T cell infiltration based on expression of genes that are specifically expressed in this immune cell population. The melanoma cases in the TCGA database which were the top and bottom quartile in terms of CD8 T cell infiltration were first identified. For both of these patient populations, the survival benefit of ARID2 expression level was assessed. It was determined that ARID2 did not confer a survival benefit in melanoma patients with a low density of tumor-infiltrating CD8 T cells. However, a substantial survival benefit was observed for patients with low ARID2 expressing tumors with a high degree of CD8 T cell infiltration (FIG. 5D). These data indicate that low level of ARID2 enhances immune mediated control of melanoma growth. Similar results were obtained for BRD7 mutant melanomas, but the number of cases with this mutation was smaller compared to ARID2.

Example 4: Validation of PBAF Complex

Figure 7:
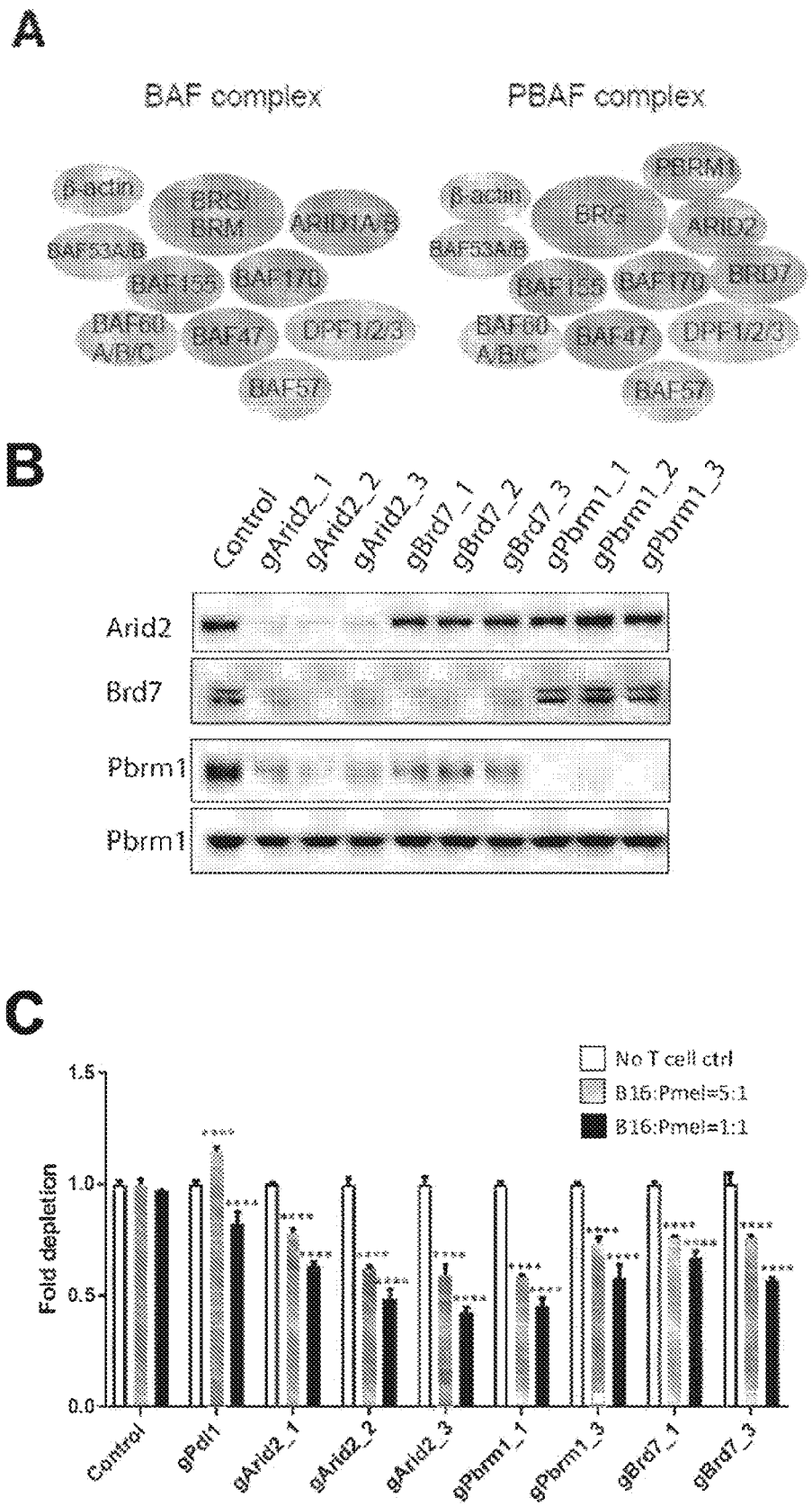
FIG. 7 includes 9 panels, identified as panels A, B, C, D, E, F, G, H, and I, which show that knocking out the PBAF complex sensitizes tumor cell to T cell-mediated killing and synergizes with checkpoint blockade therapy in vivo. Panel A is a schematic showing the composition of the BAF and PBAF versions of SWI/SNF complex distinguished by Arid1a/b or Arid2, Brd7 and Pbrm1. Panel B shows protein expression level of Arid2, Brd7, Pbrm1, and Gapdh (loading control) in control and knockout cell lines by Western blot. Panel C shows the depletion of GFP-expressing Arid2-, Pbrm1-, or Brd7-deficient B16F10 cells after co-culture with wild-type cells in the presence of Pmel1 CD8+ T cells. Panel D shows that control or Pbrm1-deficient B16F10 cells were transplanted into wild-type B6 mice and were administrated with either anti-CD8, isotype control, or anti-PD-1/CTLA-4 antibodies. Panel E shows the tumor growth curve from each individual mouse treated with checkpoint blockade. Panel F shows the depletion of GFP-positive Arid2-, Pbrm1- or Brd7-deficient B16F10 cells after co-culture with Pmel-1 T cells. GFP-positive Arid2-, Pbrm1- or Brd7-deficient B16F10 cells were mixed with GFP-negative control B16F10 cells at approximately 1:1 ratio. Tumor cells were co-cultured with Pmel-1 T cells at indicated effector to target ratios for 3 days in triplicates; the fold change of % GFP+ tumor cells was determined by FACS. Two-way ANOVA was used for determine statistical significance (****p<0.0001). Values represents mean+/−SD. Panel G shows the tumor size after treatment with α-PD-1 plus α-CTLA-4 antibodies. Mice bearing control (n=10) or Pbrm1-deficient B16F10 tumors (n=10) were treated with anti-PD-1 (α-PD-1, 200 μg/mouse) plus anti-CTLA-4 (α-CTLA-4, 100 μg/mouse) and tumor size was measured. Two-way ANOVA was used to determine statistical significance for time points when all mice were viable for tumor measurement. Panel H shows the survival of mice after tumor implantation. Survival of mice inoculated with control (n=10) or Pbrm1-deficient B16F10 cells (n=10) and treated with α-PD-1 plus α-CTLA-4 antibodies. Log-rank (Mantel-Cox) test was used to determine statistical significance. Panel I shows flow cytometric analysis of immune cell infiltration in Pbrm1 deficient and control B16F10 tumors. The number of CD45+, CD4+, CD8+ and Granzyme B+CD8+ T cells was determined per gram of tumor. Mann-Whitney test was used to determine significance (*p<0.05, **p<0.01). Values represents mean+/−SD. Data in Panel F to Panel I are representative of two independent experiments.
Figure 7:
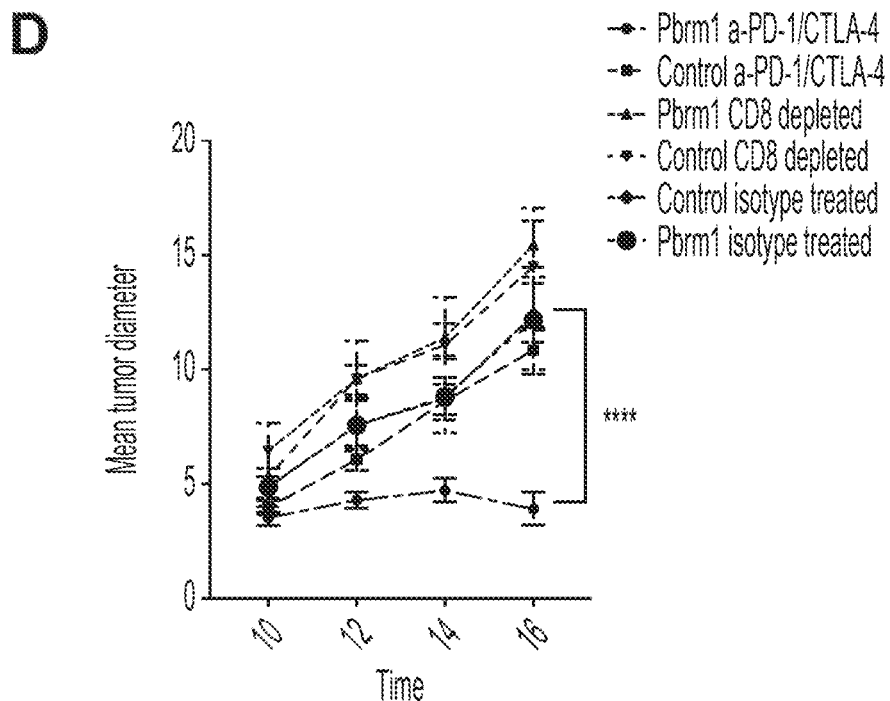
Figure 7:
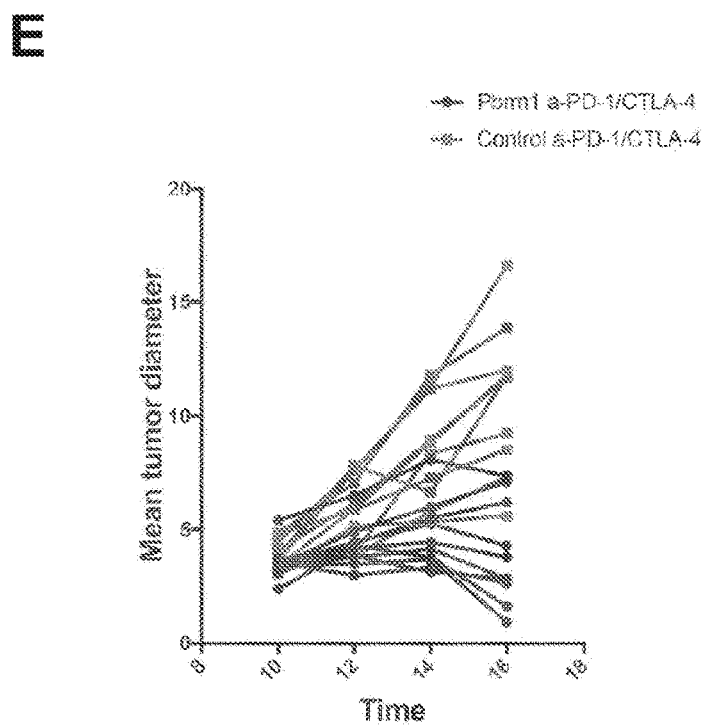
Figure 7:
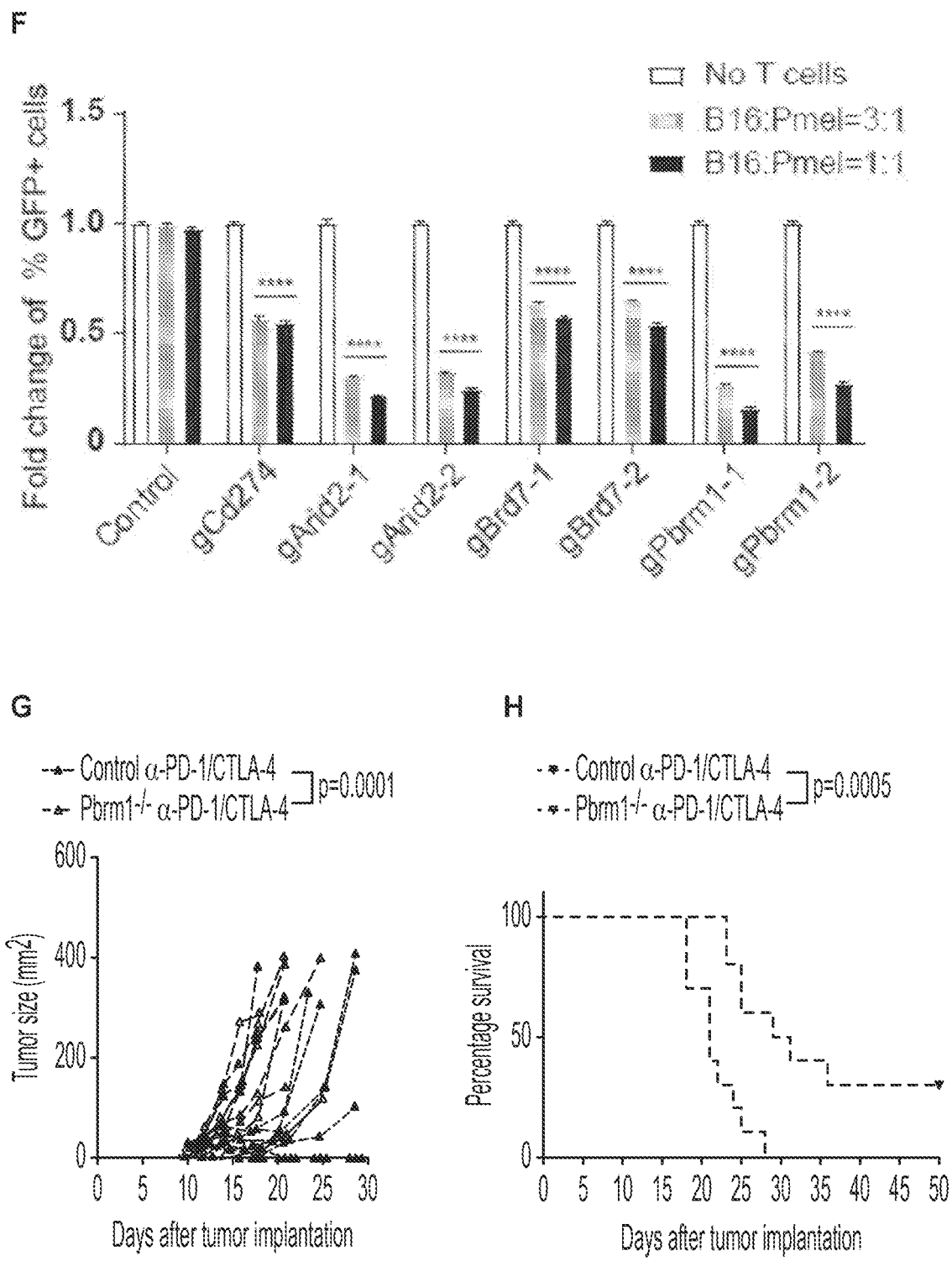
Figure 7:
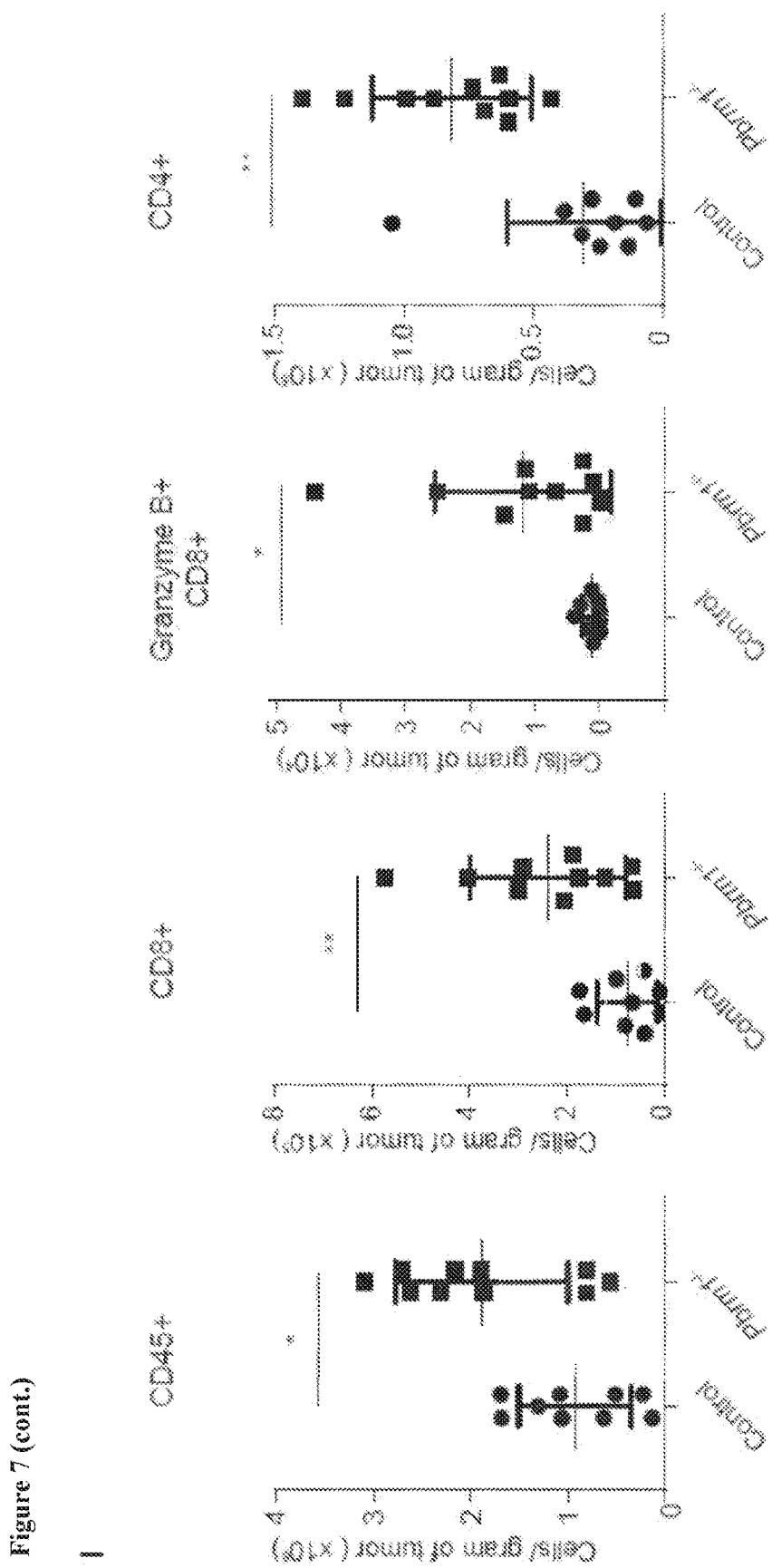
Figure 14:
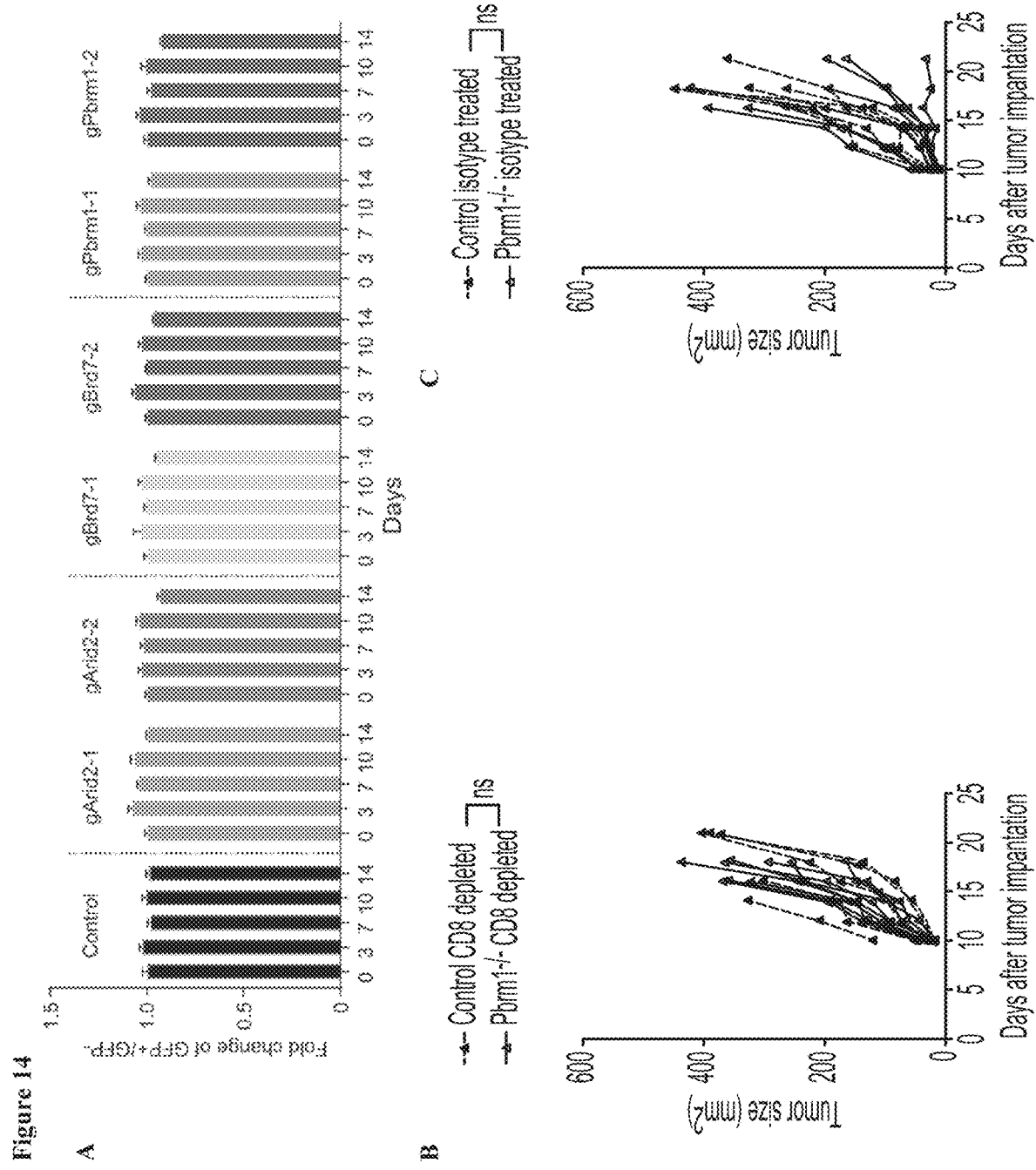
FIG. 14 includes 4 panels, identified as panels A, B, C, and D, which show the characterization of Pbrm1 deficient B16F10 tumor cells in vitro and in vivo. Panel A shows the ratio of GFP-positive vs. GFP-negative cells at different time points to determine if inactivation of the PBAF complex had an impact on tumor cell growth or survival in vitro. GFP-expressing Arid2, Pbrm1 or Brd7 deficient B16F10 cells were mixed with GFP-negative control B16F10 cells at a 1:1 ratio and grown in vitro for 2 weeks. Values represents mean+/−SD. Panels B and C show the tumor size in the mice. Related to FIG. 7G, mice bearing control or Pbrm1-deficient B16F10 tumors (n=5-8) were treated with CD8 depleting mAb (B) or isotype control antibody (2A3 and polyclonal Syrian hamster IgG) (C), and tumor size was measured. Two-way ANOVA was used to determine statistical significance for time points when all mice were viable for tumor measurement. "ns" indicates not significant. Panel D shows flow cytometry plots. Related to FIG. 7I, flow cytometric analysis of granzyme B expression by tumor-infiltrating CD8 T cells in Pbrm1 deficient and control B16F10 tumors. All data shown in this figure are representative of two independent experiments.
Figure 14:
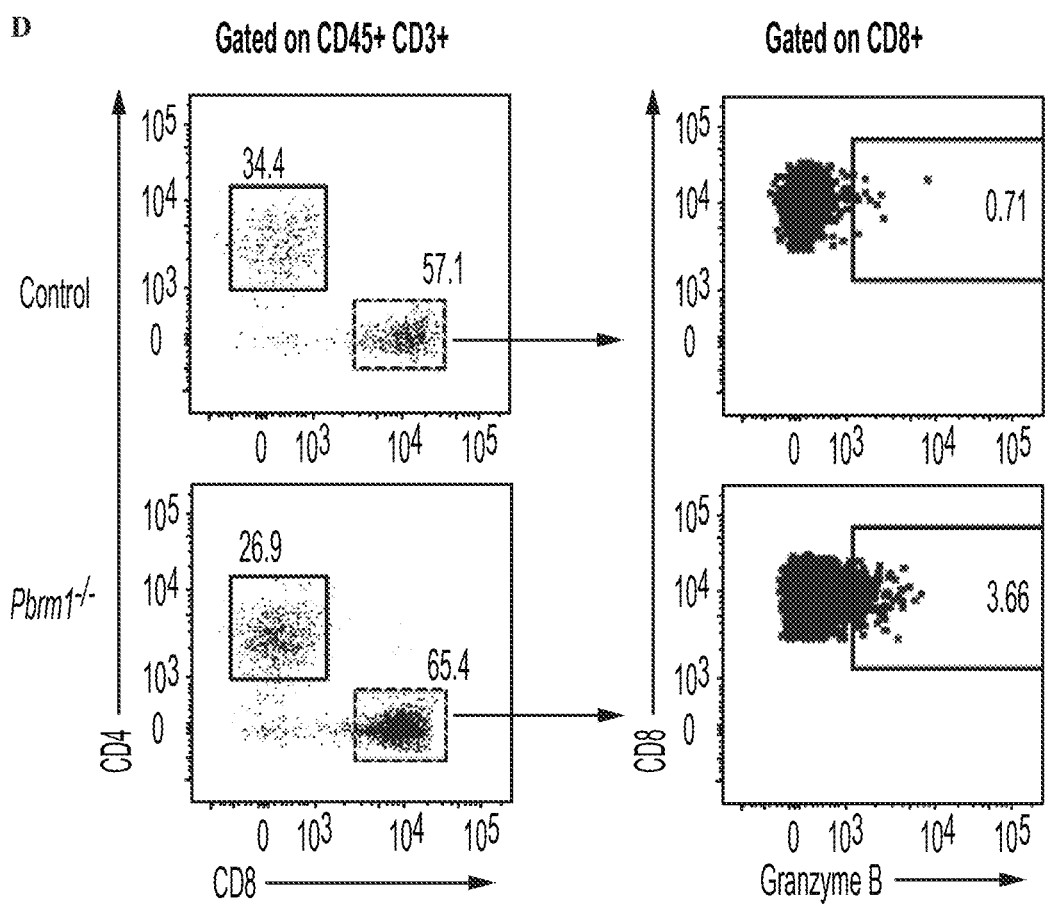

The SWI/SNF complex regulates chromatin accessibility for transcription factors. The BAF version of SWI/SNF induces dissociation of polycomb repressive complex 1 and 2 (PRC1 and PRC2) (Kadoch et al. (2017) Nat. Genet. 49:213-222), but the PBAF complex may operate through a different biochemical mechanism. The major forms of the SWI/SNF chromatin remodeling complex, referred to as BAF and PBAF, share core subunits, but they can be distinguished by the presence of ARID1A/B in the BAF (BRG1-associated factors) complex, as well as ARID2, PBRM1 and BRD7 in the PBAF complex (FIG. 7A) (Kadoch et al. (2015) Sci. Adv. 1:e1500447). In order to validate the role of PBAF complex in regulating sensitivity to T cell-mediated killing, B16F10 tumor cell lines were generated in which each of these three genes encoding the unique members of the PBAF complex were individually mutated by CRISPR/Cas9. Western blotting experiments confirmed greatly diminished levels of these corresponding proteins in the three mutant cell lines (FIG. 7B). Inactivation of Arid2 diminished protein levels of Brd7 and Pbrm1, consistent with a prior study (Yan et al. (2005) Genes Dev. 19:1662-1667), while inactivation of Pbrm1 did not affect protein levels of Arid2 or Brd7. Partial complexes with some chromatin remodeling activity may therefore remain in some of these knockout cell lines. Co-culture of Arid2, Pbrm1 or Brd7 mutant tumor cells with cytotoxic T cells resulted in enhanced depletion of PBAF mutant cell lines compared to B16F10 tumor cells transduced with a control gRNA (referred to as control B16F10 tumor cells) in a three-day co-culture assay (FIG. 7C). However, inactivation of Arid2, Pbrm1 or Brd7 genes did not alter cell proliferation over a two-week period (FIG. 14A).

B16F10 tumor cells are resistant to checkpoint blockade with PD-1 and/or CTLA-4 antibodies. Accordingly, it was asked whether inactivation of the PBAF complex by loss of Pbrm1 would enhance the sensitivity of B16F10 tumor cells to checkpoint blockade with PD-1 and CTLA-4 antibodies. Checkpoint blockade was ineffective when administered to mice bearing subcutaneous B16F10 tumors transduced with a control gRNA. However, checkpoint blockade conferred significant therapeutic benefit in mice with Pbrm1-mutant B16F10 tumors compared mice with WT B16F10 tumors (FIGS. 7D-7E and 14B-14C). Significantly increased numbers of CD45+ immune cells, CD4 and CD8 T cells, as well as granzyme B+CD8 T cells were present in Pbrm1-deficient compared to control B16F10 tumors treated with PD-1 plus CTLA-4 checkpoint blockade (FIGS. 7I and 14D). Single-cell RNA-seq analysis of sorted CD45+ immune cells showed that gene expression signatures associated with productive anti-tumor immunity (IFNγ response, IFNα response and TNFα signaling via NF-κB) were significantly enriched in Pbrm1 deficient compared to control B16F10 tumors for both myeloid cells (dendritic cells and M1-like macrophages) as well as lymphoid cells (T cells and NK cells) (FIGS. 15A-15C). These single cell data also identified an increased percentage of dendritic cells and a higher ratio of tumor-inhibitory M1-like macrophages to tumor-promoting M2-like macrophages in Pbrm1 deficient compared to control B16F10 tumors (FIG. 15D). Thus, inactivation of Pbrm1 not only sensitizes tumor cells to T cell-mediated cytotoxicity but also results in a more favorable tumor microenvironment. This result is significant because inactivating mutations in genes encoding the three unique members of the PBAF complex are quite common in human cancers.

Figure 8:
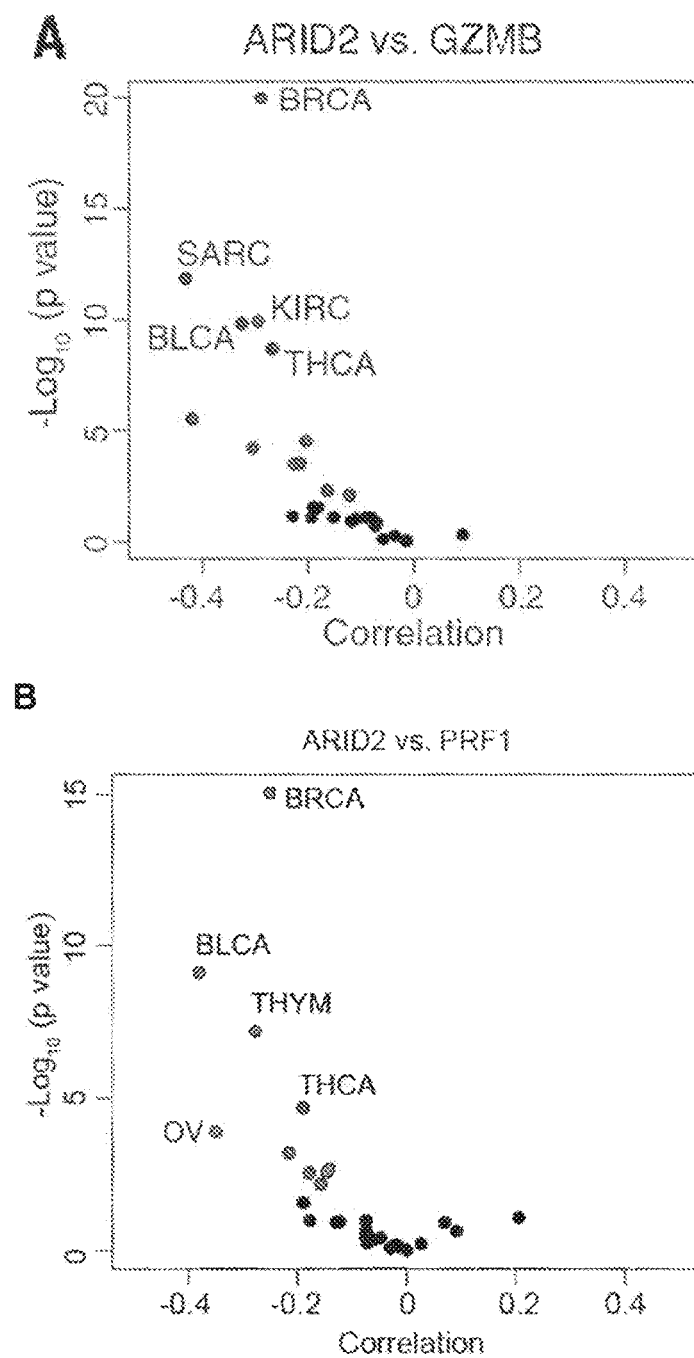
FIG. 8 includes 8 panels, identified as panels A, B, C, D, E, F, G, and H, which show that expression of Arid2 and Pbrm1 are correlated with T cell cytotoxicity markers across many cancer types. Panels A and C show correlation of ARID2 and PBRM1 mRNA levels with GZMB mRNA levels in indicated cancers, respectively. Volcano plots show the Spearman's correlation and estimated significance of ARID2 (Panel A) or PBRM1 (Panel C), with GZMB mRNA levels from RNA-seq data across TCGA cancer types calculated by TIMER (Tumor Immune Estimation Resource) and adjusted for tumor purity (Li et al. (2016) *Genome Biol* 17:174). Each dot represents a cancer type in the TCGA and red dots, including all those labeled, indicate significant correlations (p<0.01). Panels B and D show volcano plots showing the Spearman's correlation and estimated significance (log 10 p-value) of ARID2 (Panel B) or PBRM1 (Panel D) expression with PRF1 (perforin) expression across all TCGA cancer types using Tumor Immune Estimation Resource (TIMER) (tumor purity adjusted) (Li et al. (2016) *Genome Biol* 17:174). Each dot represents a cancer type in TCGA, with red dots indicating a significant correlation (p<0.01). Panels E and F show analysis of ARID2 and PBRM1 mRNA levels in relationship to GZMB and CD8A as cytotoxicity and CD8 T cell infiltration markers, respectively. Spearman's correlation of ARID2 (Panel E) and PBRM1 (Panel F) mRNA levels to GZMB/CD8A mRNA ratio in TCGA melanoma dataset was shown. Panels G and H show the relative contribution of CD8 T cells and NK cells to the immune-mediated cytotoxicity. Panel G shows the correlation between the estimated CD8 T cell or NK cell infiltration and immune cytotoxicity markers. Panel H shows the comparison of relative contribution to immune cytotoxicity between CD8 T and NK cells, with the line of equal contribution on the diagonal. In each cancer type, the CD8 T cell level was estimated through the expression sum of CD8A and CD8B. The NK cell level was estimated through expression of NCR1 (NKp46). Immune cytotoxicity was estimated through expression sum of GZMA, GZMB and PRF1. In each cancer, a linear regression was fitted with CD8 T, NK cell levels as the covariates and immune cytotoxicity as the outcome. The t-values of T cells and NK cells, representing their relative contribution to the immune cytotoxicity, were plotted across all TCGA cancer types. This analysis indicates that cytotoxicity markers are more closely associated with estimated T cell than NK cell infiltration.
Figure 8:
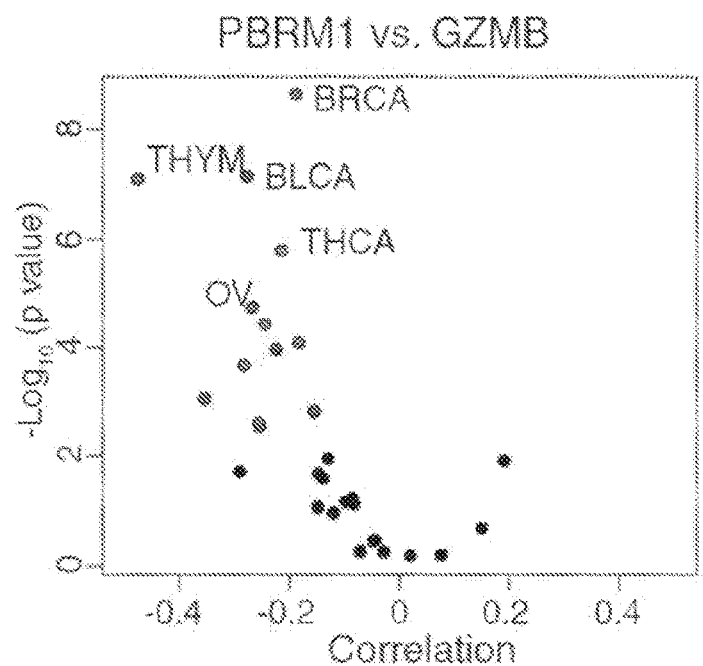
Figure 8:
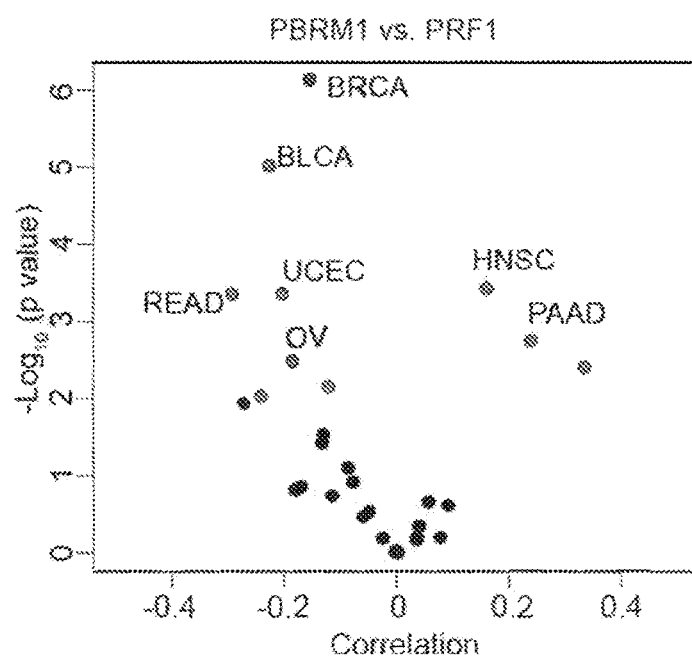
Figure 8:
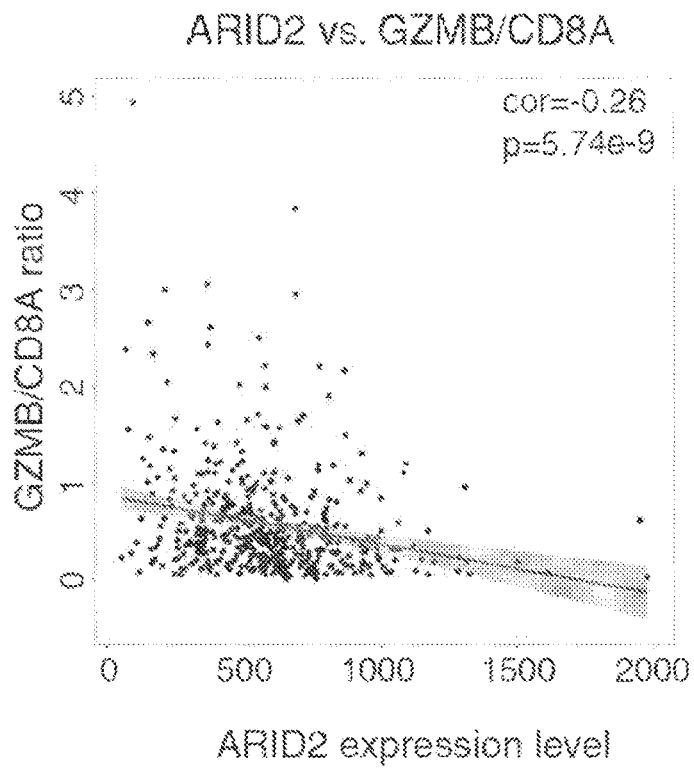
Figure 8:
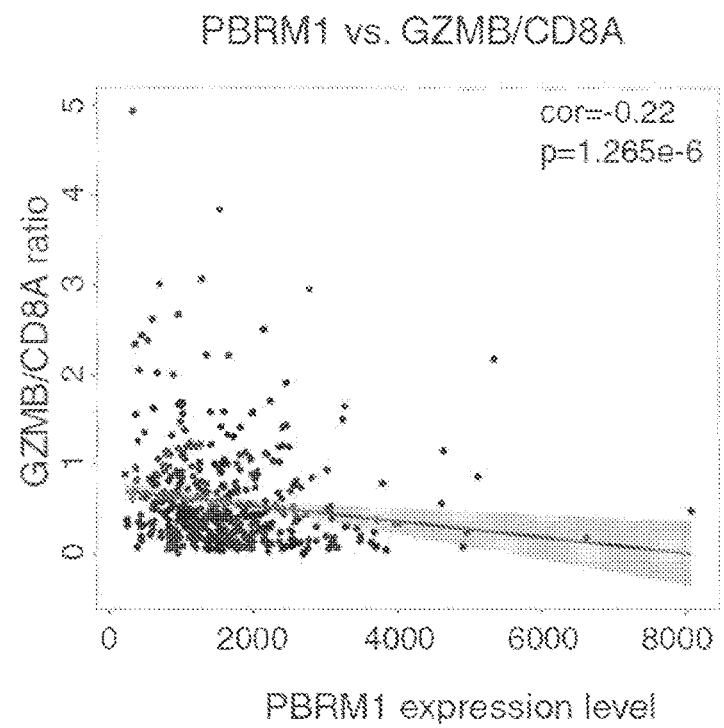
Figure 8:
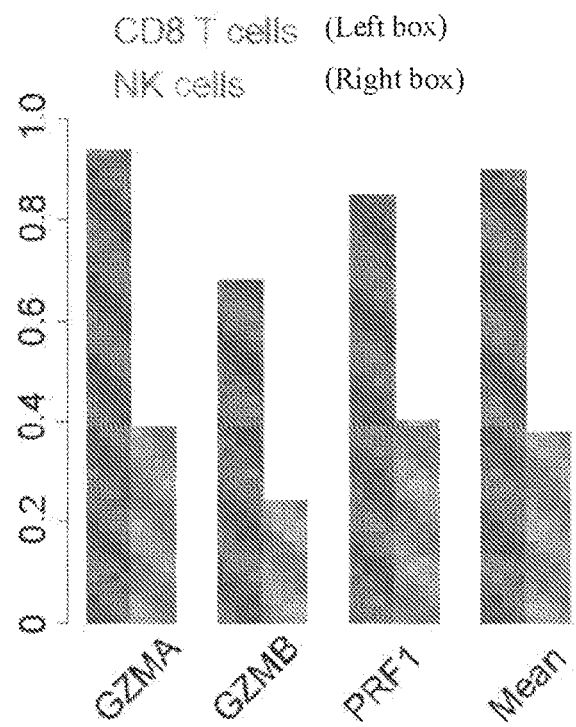
Figure 8:
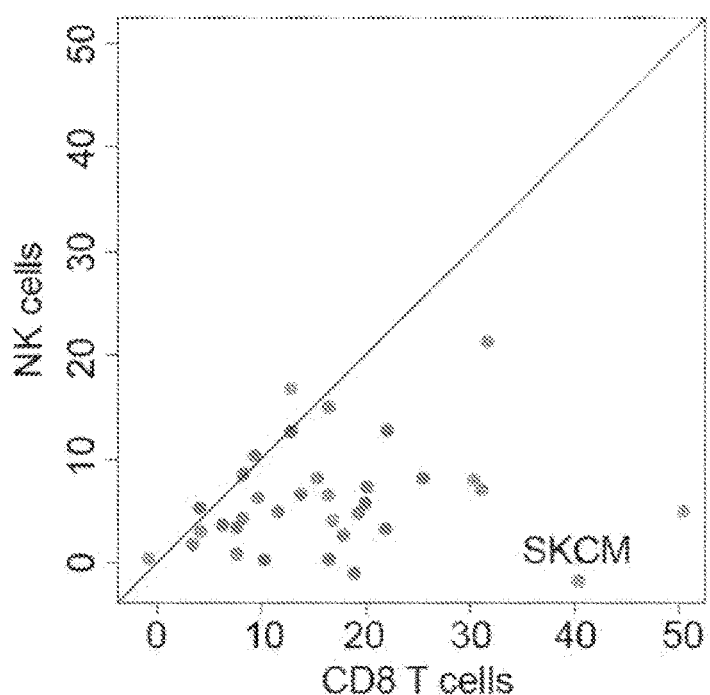

TCGA RNA-seq datasets and TIMER (Li et al. (2016) *Genome Biol.* 17:174) were used to examine the relevance of the CRIPSR screen (FIGS. 5B-5C and 6A-6B) and PBAF complex in human cancers. It was found that the mRNA levels of Arid2 and Pbrm1 negatively correlates with T cell cytotoxicity markers granzyme B and perforin mRNA levels across many cancer types in the TCGA database (FIGS. 8A-8D and Table 12), indicating that lower expression of ARID2 and PBRM1 is correlated with higher cytotoxic activity contributed by CD8 T cells (FIGS. 8G-8H) in human cancers. These clinical data support the hypothesis that Arid2 and Pbrm1 suppress anti-tumor immunity. Since both T cell infiltration level and cytotoxicity could contribute to granzyme B expression, the correlation of the ratio of GZMB/CD8A with ARID2 and PBRM1 expression in melanoma patients was calculated. A consistently strong negative correlation of GZMB/CD8A ratio to ARID2 and PBRM1 expression was found, indicating that ARID2 negatively correlates with T cell cytotoxicity rather than T cell infiltration in melanoma patient. This correlation was not merely explained by the degree of CD8 T cell infiltration because ARID2 and PBRM1 mRNA levels were also negatively associated with the GZMB/CD8A ratio (FIGS. 8E-8F). In addition, it was found that low ARID2 mRNA levels were associated with a substantial survival benefit in melanoma patients, but only for those tumors with a higher degree of infiltration by CD8 T cells (based on CD8 expression) (FIG. 5D). These data indicate that ARID2 and PBRM1 affect tumor immunity in a variety of human cancers.

TABLE 12

Correlation of ARID2 or PBRM1 mRNA expression level (tumor purity adjusted) to GZMB or PRF1 mRNA expression level in TCGA data
Cor., Spearman's correlation; p, p value calculated by TIMER (Li et al. (2016) *Genome Biol.* 17: 174

| Cancer type | ARID2 vs GZMB Cor. | p value | ARID2 vs. PRF1 Cor. | p value | PBRM1 vs. GZMB Cor. | p value | PBRM1 vs. PRF1 Cor. | p value |
|---|---|---|---|---|---|---|---|---|
| ACC | −0.016 | 8.90E−01 | 0.206 | 8.05E−02 | 0.15 | 2.04E−01 | 0.334 | 3.88E−03 |
| BLCA | −0.326 | 1.42E−10 | −0.277 | 6.25E−08 | −0.277 | 6.79E−08 | −0.228 | 9.69E−06 |
| BRCA | −0.29 | 1.01E−20 | −0.251 | 8.88E−16 | −0.188 | 2.29E−09 | −0.156 | 7.40E−07 |
| CESC | −0.216 | 2.89E−04 | −0.178 | 2.98E−03 | −0.245 | 3.70E−05 | −0.131 | 2.94E−02 |
| COAD | −0.09 | 7.15E−02 | −0.021 | 6.75E−01 | −0.047 | 3.49E−01 | −0.078 | 1.19E−01 |
| DLBC | −0.058 | 7.17E−01 | −0.03 | 8.53E−01 | 0.077 | 6.34E−01 | 0.077 | 6.31E−01 |
| ESCA | −0.119 | 1.11E−01 | −0.059 | 4.35E−01 | −0.12 | 1.09E−01 | 0.036 | 6.34E−01 |
| GBM | −0.191 | 2.52E−02 | −0.189 | 2.73E−02 | −0.148 | 8.47E−02 | −0.115 | 1.81E−01 |
| HNSC | −0.081 | 7.40E−02 | 0.07 | 1.22E−01 | 0.02 | 6.54E−01 | 0.16 | 3.65E−04 |
| KICH | −0.23 | 6.56E−02 | −0.072 | 5.70E−01 | −0.29 | 1.92E−02 | −0.18 | 1.52E−01 |
| KIRC | −0.295 | 1.12E−10 | −0.142 | 2.17E−03 | −0.183 | 8.07E−05 | −0.049 | 2.91E−01 |
| KIRP | −0.108 | 8.36E−02 | −0.074 | 2.37E−01 | −0.139 | 2.54E−02 | −0.06 | 3.40E−01 |
| LGG | −0.122 | 7.65E−03 | −0.074 | 1.06E−01 | −0.044 | 3.38E−01 | −0.003 | 9.46E−01 |
| LIHC | −0.073 | 1.74E−01 | −0.047 | 3.81E−01 | −0.098 | 6.82E−02 | −0.025 | 6.47E−01 |
| LUAD | −0.014 | 7.54E−01 | −0.02 | 6.58E−01 | −0.085 | 5.95E−02 | 0.001 | 9.81E−01 |
| LUSC | −0.07 | 1.29E−01 | −0.013 | 7.76E−01 | −0.028 | 5.46E−01 | 0.056 | 2.19E−01 |
| MESO | −0.194 | 7.49E−02 | −0.177 | 1.05E−01 | −0.355 | 8.67E−04 | −0.273 | 1.14E−02 |
| OV | −0.227 | 3.14E−04 | −0.215 | 6.55E−04 | −0.268 | 1.77E−05 | −0.186 | 3.20E−03 |
| PAAD | −0.013 | 8.70E−01 | 0.092 | 2.32E−01 | 0.191 | 1.22E−02 | 0.238 | 1.73E−03 |
| PCPG | −0.305 | 6.26E−05 | −0.122 | 1.16E−01 | −0.283 | 2.10E−04 | 0.091 | 2.43E−01 |
| PRAD | −0.204 | 2.87E−05 | −0.146 | 2.80E−03 | −0.155 | 1.47E−03 | −0.086 | 7.86E−02 |
| READ | −0.152 | 7.36E−02 | −0.075 | 3.79E−01 | −0.255 | 2.41E−03 | −0.294 | 4.35E−04 |
| SARC | −0.433 | 1.34E−12 | −0.381 | 7.34E−10 | −0.147 | 2.12E−02 | −0.133 | 3.80E−02 |
| SKCM | −0.078 | 9.65E−02 | 0 | 9.95E−01 | −0.083 | 7.46E−02 | 0.002 | 9.62E−01 |
| STAD | −0.036 | 4.81E−01 | 0.027 | 6.03E−01 | −0.13 | 1.11E−02 | 0.039 | 4.51E−01 |
| TGCT | −0.182 | 2.76E−02 | −0.129 | 1.19E−01 | −0.254 | 2.76E−03 | 0.035 | 6.70E−01 |
| THCA | −0.268 | 1.84E−09 | −0.191 | 2.06E−05 | −0.215 | 1.58E−06 | −0.122 | 6.93E−03 |
| THYM | −0.42 | 3.01E−06 | −0.35 | 1.24E−04 | −0.476 | 7.77E−08 | −0.242 | 9.21E−03 |
| UCEC | −0.164 | 4.76E−03 | −0.157 | 6.93E−03 | −0.224 | 1.08E−04 | −0.204 | 4.28E−04 |
| UVM | 0.093 | 4.20E−01 | −0.028 | 8.08E−01 | −0.071 | 5.40E−01 | −0.17 | 1.39E−01 |

Example 5: TNF Signaling in T Cell Mediated Killing of Tumor Cells

Experiments are performed to determine whether TNF signaling in tumor cells confers resistance to T cell mediated killing, and to determine whether a major source of TNF alpha originates from activated cytotoxic T cells. In vitro experiments are carried out by co-culturing B16-Ova tumor cells with OT-I T cells that recognize the Ova antigen, and monitoring T cell mediated killing of tumor cells over a time course of 4-48 hours. This experiment is performed in the presence of a TNF alpha neutralizing antibody or isotype control antibody. The same experimental design is also used to examine Pbrm1-mutant and wild type tumor cells to determine if the PBAF complex impacts sensitivity to TNF-alpha. Other mutant tumor cells can be tested as well, including mutants in which key signaling molecules in the TNF pathway have been inactivated, such as Rela. B16F10 tumor cells are treated with TNF alpha for 4-12 hours and RNA-seq is performed. Transcriptional profiles of wild type and mutant tumor cells, including Pbrm1 mutant cells, are compared. These in vitro experiments are followed by in vivo experiments. B16F10 tumor cells are implanted into C57BL/6 mice. Mice are treated with PD-1 or PD-1+ CTLA-4 antibodies, in the presence of TNF alpha neutralizing antibody or isotype control antibody. The experiment can also be performed with Pbrm1 mutant or WT tumor cells. Additional mutants can also be tested, such as tumors with mutations in Rela, a key signaling molecule in the TNF pathway.

Example 6: Regulation of IFNγ and mTORC1 Pathways by the PBAF Complex

Figure 16:
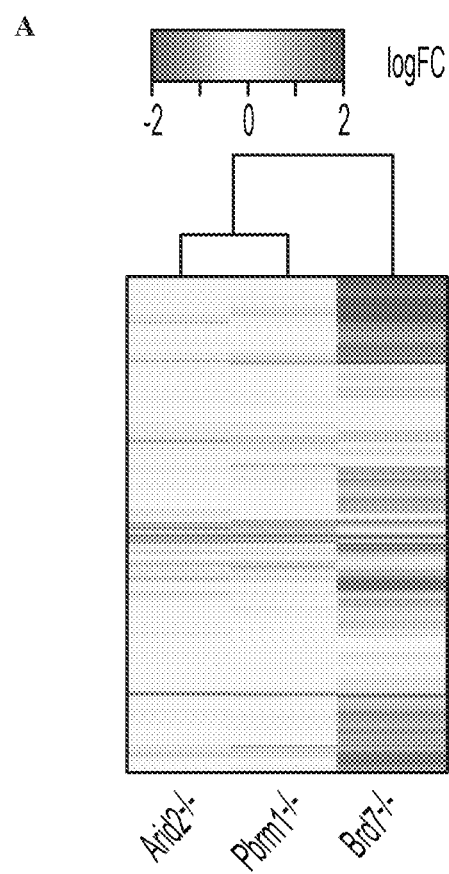
FIG. 16 includes 4 panels, identified as panels A, B, C, and D, which show the gene expression profiles of Arid2, Pbrm1 and Brd7 deficient B16F10 tumor cells. RNA-seq was performed on Arid2, Brd7 or Pbrm1 deficient cells as well as control B16F10 cells. Panel A shows a heat map and clustering that shows the overall log 2 fold change in gene expression in Arid2, Pbrm1 and Brd7 deficient B16F10 cells compared to control B16F10 cells (transduced with non-targeting gRNA). Panel B shows venn diagrams that show the number of genes that were upregulated or downregulated in Arid2 and/or Pbrm1 deficient B16F10 cells compared to control B16F10 cells in RNA-seq data. Panel C shows FDR q-values for top-ranked mTORC1 and several other metabolic genes sets. Hypergeometric overlap statistics were used to test which Hallmark and KEGG gene sets were enriched among genes that were significantly downregulated in both Arid2 and Pbrm1 deficient cells compared to control B16F10 cells. Panel D shows heat maps that show the expression value (z-score based on cufflink count) for genes in mTORC1 and cholesterol homeostasis gene sets for control, Arid2 or Pbrm1 deficient B16F10 cells.
Figure 16:
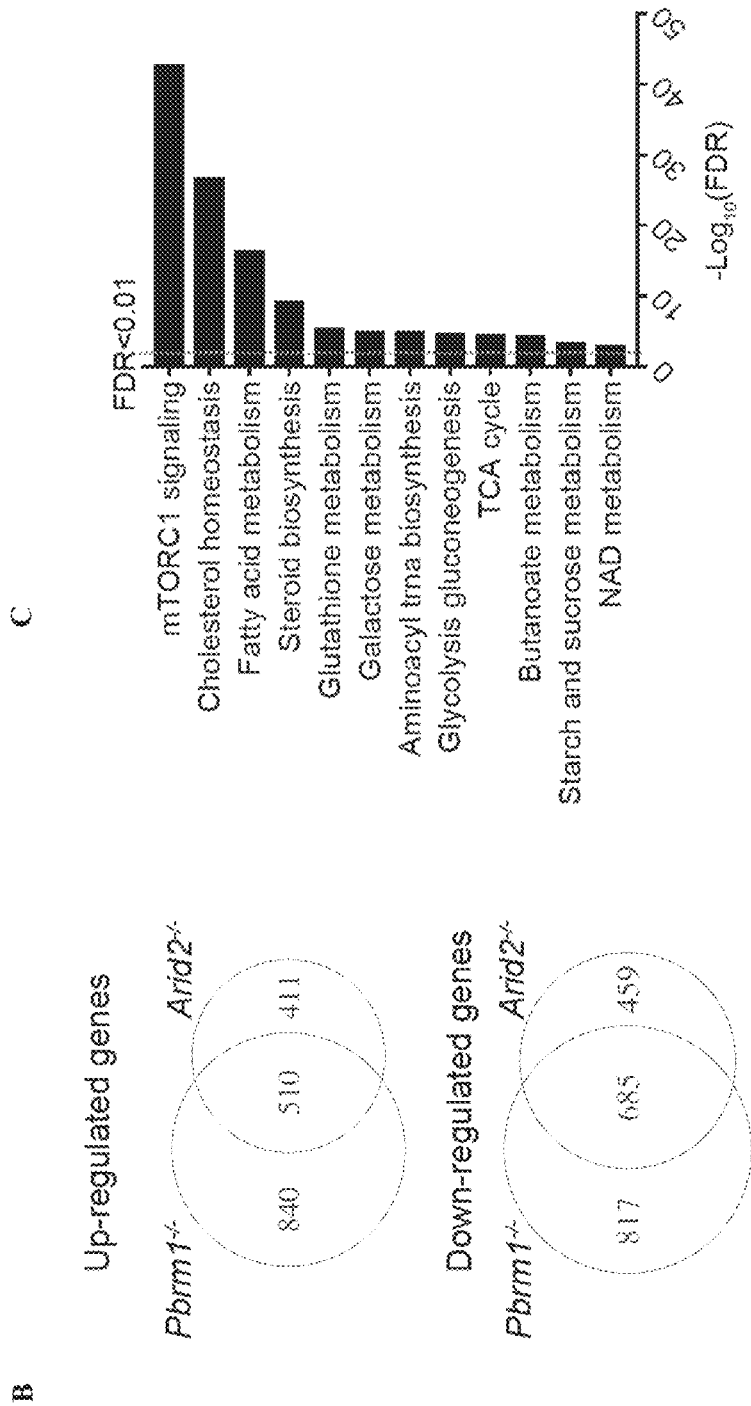
Figure 16:
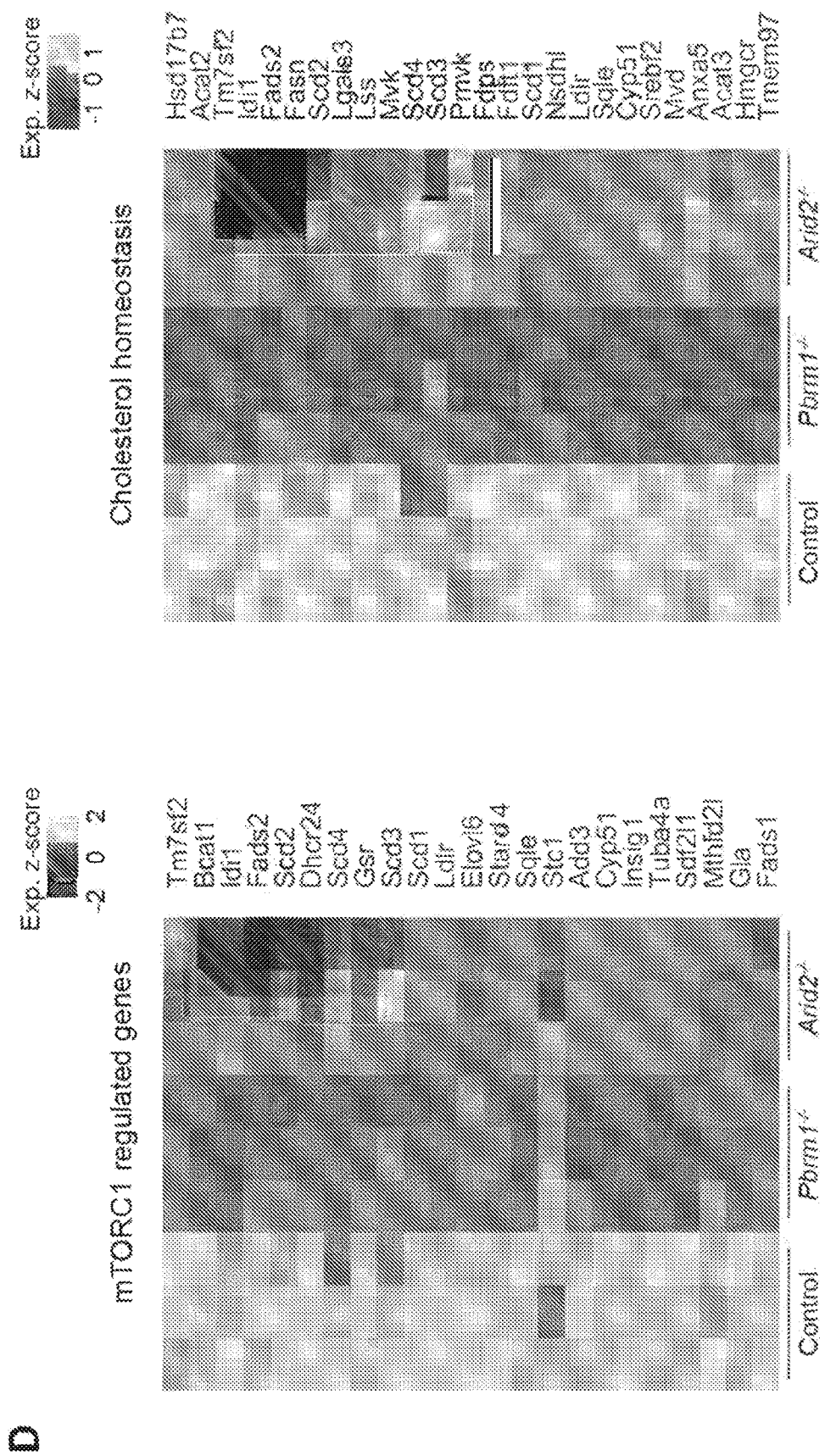
Figure 17:
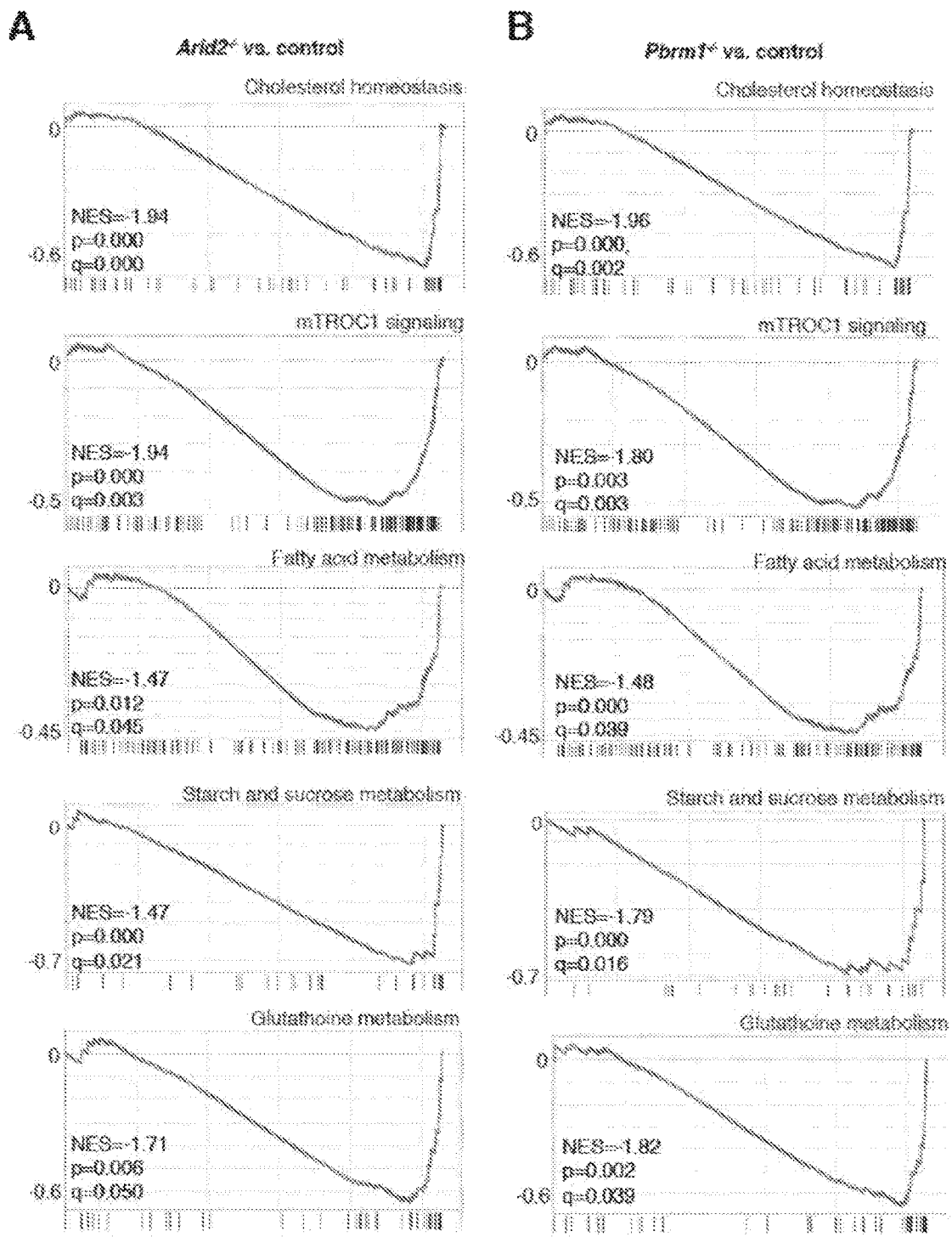
FIG. 17 includes 2 panels, identified as panels A and B, which show the GSEA analysis on Arid2 and Pbrm1 deficient cells. Panel A shows the GSEA analysis of differentially expressed genes (RNA-seq datasets) in Arid2 deficient cells versus control B16F10 cells. Panel B shows the GSEA analysis of differentially expressed genes (RNA-seq datasets) in Pbrm1 deficient cells versus control B16F10 cells. Gene sets for mTORC1 and several other metabolic pathways negatively enriched in Arid2 and Pbrm1 deficient cells are shown.

To investigate the molecular mechanisms by which the PBAF complex regulates the sensitivity of B16F10 tumor cells to T cell-mediated killing, the transcriptome of PBAF deficient B16F10 cells was examined by RNA-seq. Arid2- and Pbrm1-deficient B16F10 cells shared similar gene expression profiles (FIG. 16A-B), consistent with their critical role in the PBAF complex. The transcriptome of Brd7 mutant B16F10 cells was more distinct, indicating that Brd7 may also have PBAF-independent functions (FIG. 16A). mRNAs for a number of metabolic pathways were concordantly downregulated in Arid2 and Pbrm1 mutant cells compared to control B16F10 tumor cells, in particular gene sets associated with mTORC1 activation and cholesterol homeostasis (FIG. 16C-D and FIG. 17). mTORC1 was also a major resistance pathway for T cell-mediated cytotoxicity in the CRISPR/Cas9 screen (FIG. 5A).

Figure 18:
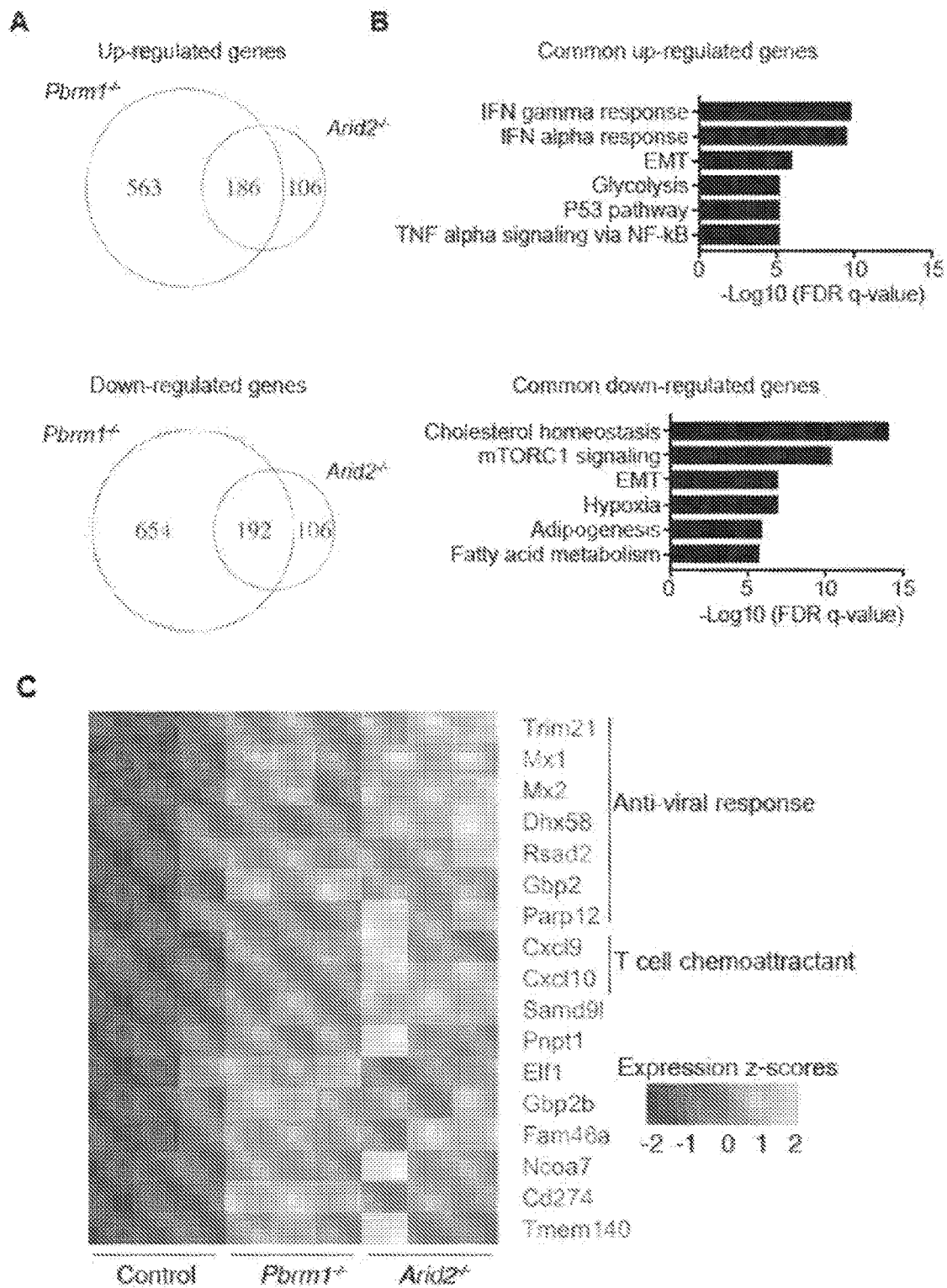
FIG. 18 includes 6 panels, identified as panels A, B, C, D, E and F, which show the enhanced responsiveness to IFNγ stimulation by Arid2 and Pbrm1 deficient tumor cells. Panels A to C show the RNA-seq analysis of Arid2 or Pbrm1 deficient cells and control B16F10 cells treated with IFNγ (10 ng/ml) for 24 hours. Panel A are venn diagrams that show differentially regulated mRNAs in the presence of IFNγ. Panel B shows the hallmark gene sets enriched for commonly up- or down-regulated mRNAs in both Arid2 and Pbrm1 deficient cells compared to control B16F10 cells in the presence of IFNγ treatment (as shown in Panel A). Panel C is a heat map which shows expression value (z-score based on cufflink count) of interferon-responsive genes in control, Arid2 and Pbrm1 deficient B16F10 cells following IFNγ treatment. Panels D and E show Cxcl9 mRNA level (Panel D) and Cxcl9 protein secretion (Panel E) comparing Pbrm1-deficient and control B16F10 tumor cells stimulated with IFNγ (10 ng/ml) for 24 hours. Values represents mean+/−SD. Panel F shows the Cxcl10 secretion by Pbrm1-deficient and control B16F10 tumor cells stimulated with IFNγ (0, 0.5 and 1 ng/ml) for 24 hours. Values represents mean+/−SD. One-way ANOVA (Panels D and E) and two-way ANOVA were used to determine significance (Panel F). $p<0.01$, **$p<0.0001$. Data in Panel D and Panel F are representative of two independent experiments.
Figure 18:
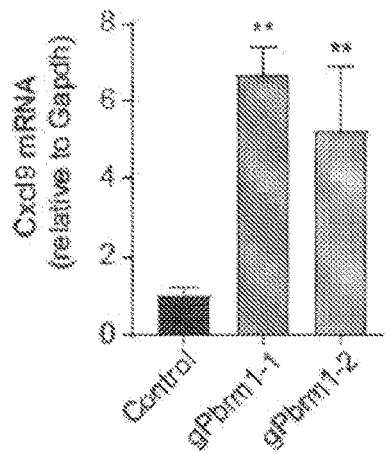
Figure 18:
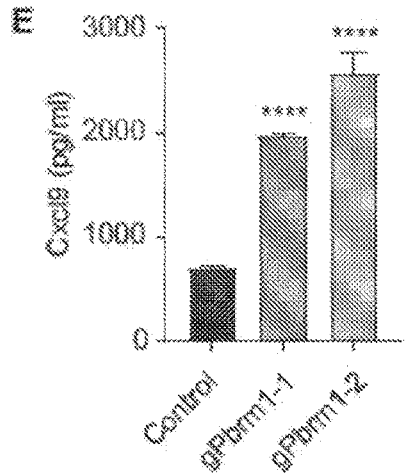
Figure 18:
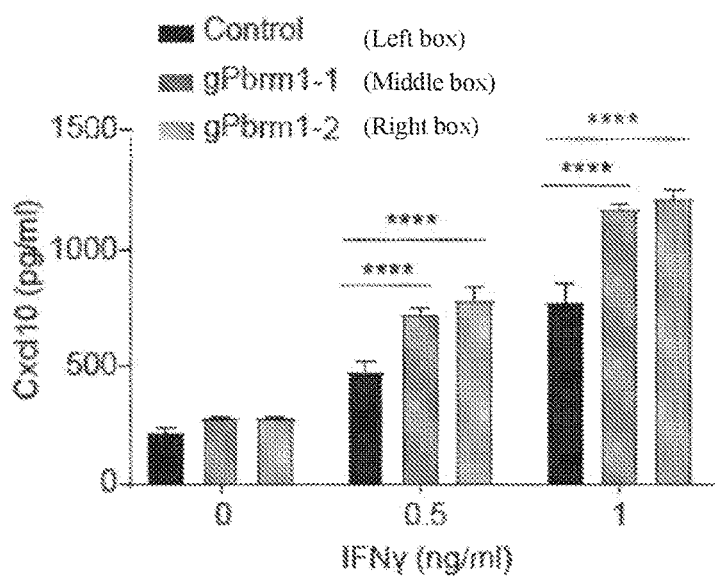
Figure 19:
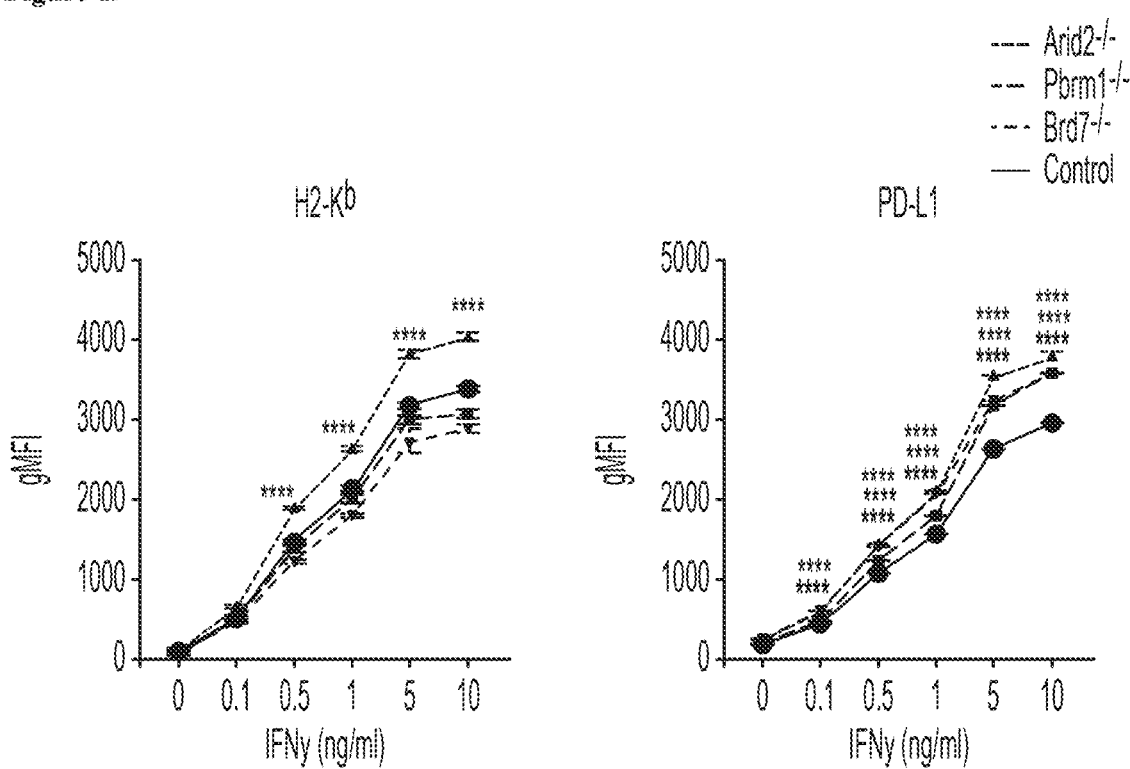
FIG. 19 shows the effect of PBAF complex on IFNγ induced expression of H2-$K^b$ and PD-L1 induction. Arid2, Pbrm1 and Brd7 deficient cells and control B16F10 cells were treated with different doses of IFNγ and surface expression of H2-$K^b$ and PD-L1 (geometric mean fluorescence intensity, gMFI) was determined by FACS after 24 hours. Two-way ANOVA was used to determine statistical significance (****$p<0.0001$). Data shown are representative of two independent experiments.

Silencing of BAF200 (Arid2) with a siRNA was shown to reduce the expression of Interferon Induced Transmembrane Protein 1 (IFITM1) by IFNα, but not other interferon-regulated genes (Yan et al. (2005) *Genes Dev.* 19:1662-1667). It was systematically examined whether the PBAF complex regulates gene expression in response to IFNγ, given the importance of this T cell-derived cytokine for tumor immunity (Gao et al. (2016) *Cell* 167:397-404). RNA-seq analysis showed that gene sets related to IFNγ and IFNα response were significantly enriched among genes concordantly upregulated in Arid2- and Pbrm1-deficient cells compared to B16F10 control cells treated with IFNγ (FIGS. 18A-18B), indicating that Arid2 and Pbrm1 suppressed the expression of IFNγ responsive genes. Many of the IFNγ responsive genes suppressed by Arid2 and Pbrm1 were relevant to innate immunity or encoded chemokines (Cxcl9 and Cxcl10) (FIG. 18C) (Groom et al. (2011) *Immunol. Cell Biol.* 89:207-215). Pbrm1-deficient tumor cells also secreted substantially larger amounts of Cxcl9 and Cxcl10 compared to control B16F10 cells following IFNγ stimulation (FIGS. 18D-18F) which are key chemokines for recruitment of effector T cells that express the Cxcr3 chemokine receptor (Groom et al. (2011) *Immunol. Cell Biol.* 89:207-215). Arid2-deficient cells had significantly increased surface levels of H2-K$^b$ over a range of IFNγ concentrations compared to control B16F10 cells. Also, all three mutants showed increased surface levels of PD-L1 in response to IFNγ (FIG. 19). Brd7- and Pbrm1-deficient cells only showed enhanced surface expression of PD-L1 but not H2-K$^b$ in response to IFNγ stimulation (FIG. 19) which is believed to be due to partial complexes that retain some activity. These data demonstrate that Arid2 and Pbrm1 attenuate the responsiveness of B16F10 tumor cells to IFNγ, a key cytokine for the interaction of tumor cells and T cells.

Figure 20:
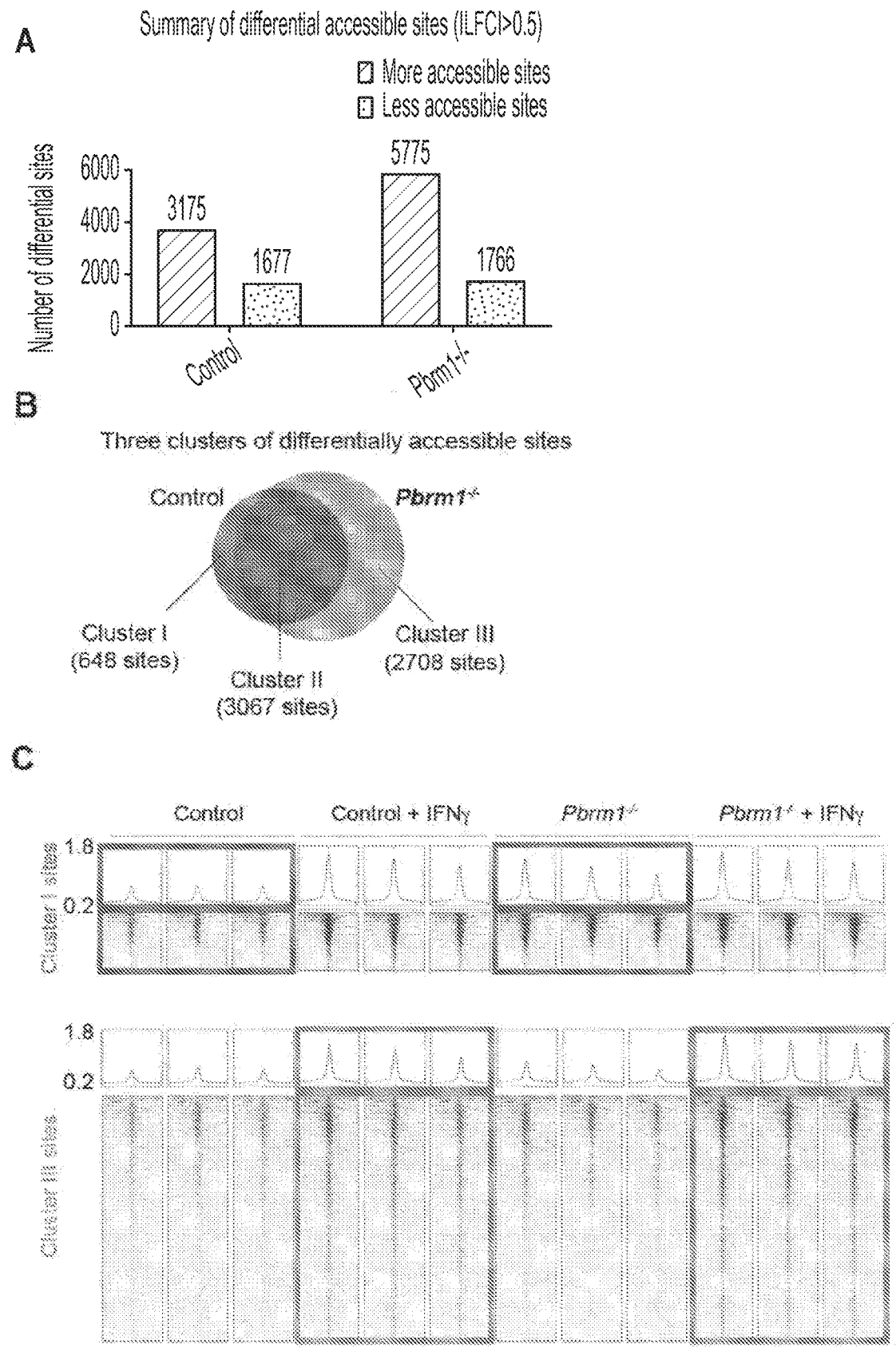
FIG. 20 includes 3 panels, identified as panels A, B and C, which show the enhanced chromatin accessibility for IFNγ responsive genes in Pbrm1-deficient tumor cells. ATAC-seq was performed on Pbrm1-deficient and control B16F10 cells with or without IFNγ stimulation (10 ng/ml) for 24 hours. Panel A shows the genome-wide analysis of differentially accessible chromatin sites (|$\log_2$ fold change|>0.5) following IFNγ stimulation in control versus Pbrm1-deficient B16F10 tumor cells. Panel B is a venn diagram which illustrates accessible sites gained following IFNγ treatment in control (blue) and Pbrm1-deficient (red) cells. Panel C are chromatin accessibility heat maps for all sites in clusters I (top panel) and III (bottom panel). Aggregated reads within 2 kb of center of differentially accessible regions are shown above heat maps.
Figure 21:
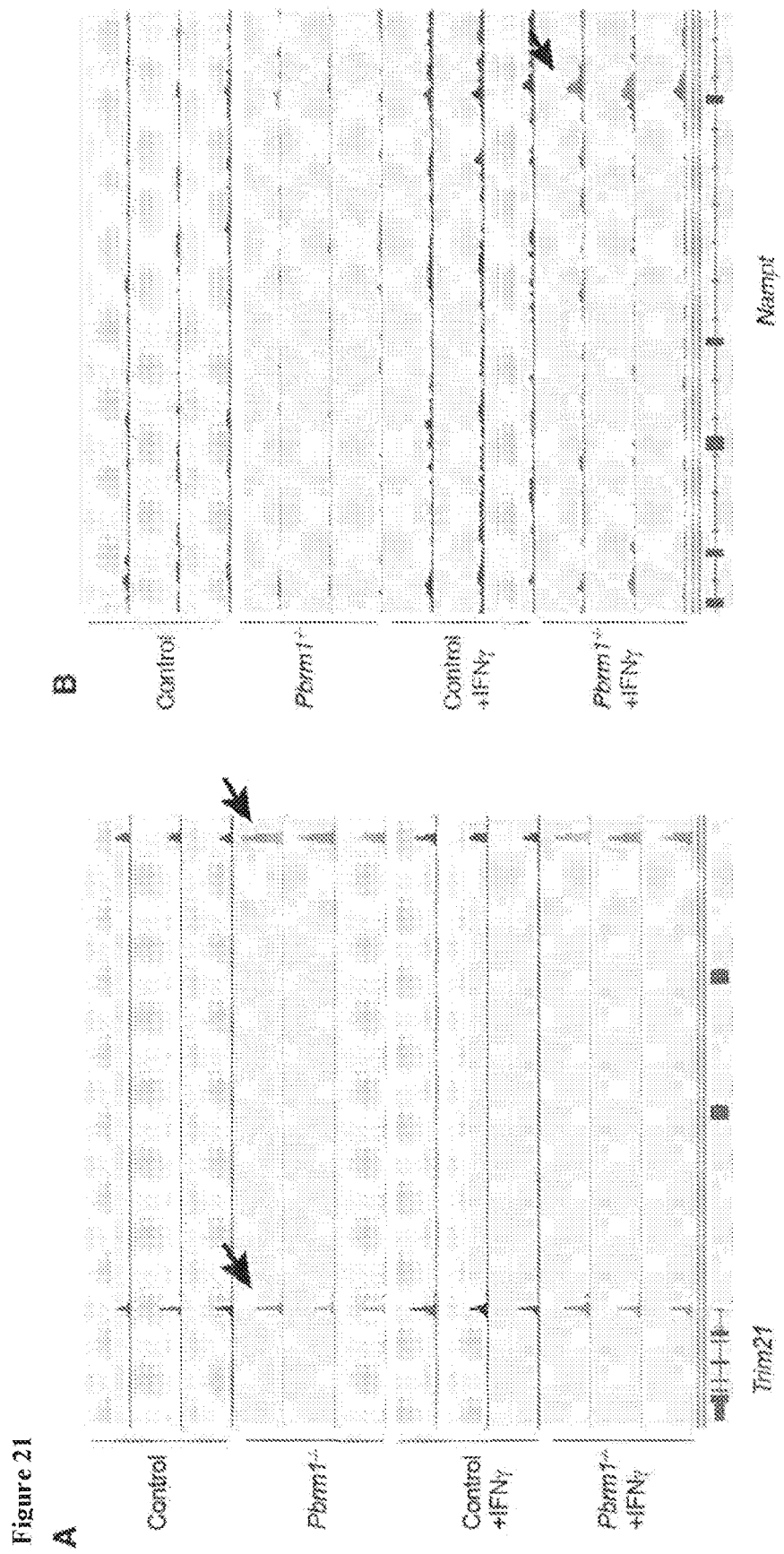
FIG. 21 includes 5 panels, identified as panels A, B, C, D and E, which show the analysis of chromatin accessibility in Pbrm1 deficient and control cells. Panel A shows accessible sites near Trim21 as example of interferon-responsive sites that were more accessible in Pbrm1 deficient cells prior to IFNγ stimulation (arrows). Panel B shows an example of a cluster III site (as defined in FIG. 20B), which became more accessible in Pbrm1 deficient cells compared to control B16F10 cells following IFNγ treatment (arrow). Panel C shows IFNγ and IFNγ response gene sets. Hypergeometric overlap statistics were used to define Hallmark gene sets enriched in nearby genes for cluster I, II and III sites. Panel D shows the IRF2 and IRSE motifs. IRF2 and IRSE were the most significant motifs (computed by HOMER (Heinz et al. (2010) *Mol Cell* 38:576-589) enriched in clusters I, II and III ($p<1e-37$).
Figure 21:
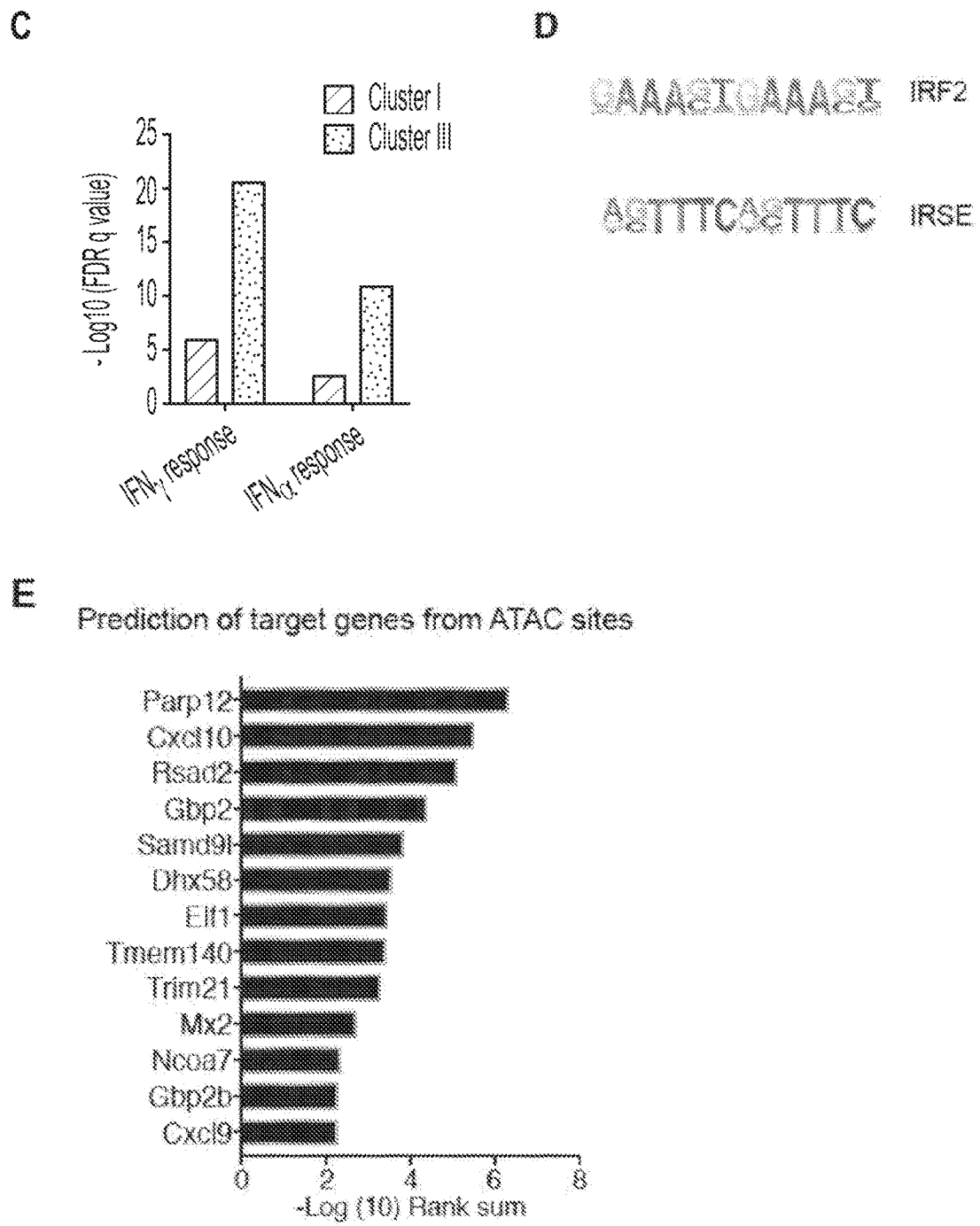

Example 7: The PBAF Complex Regulates Chromatin Accessibility of IFNγ Induced Genes The major function of the SWI/SNF complex is to regulate chromatin accessibility for transcription factors. ATAC-seq was therefore performed to directly assess chromatin accessibility in Pbrm1-deficient and control B16F10 tumor cells with and without IFNγ treatment for 24 hours. Following IFNγ treatment, a substantially larger number of genomic sites were accessible in Pbrm1-deficient than control B16F10 cells, consistent with the RNA-seq data (FIG. 20A). Sites in cluster 1 (648 sites) were more accessible prior to IFNγ treatment in Pbrm1 deficient compared to control cells, indicating that the corresponding genes were poised to respond to IFNγ (FIGS. 20B-20 and 21A). Also, 2,708 sites (cluster III) showed enhanced accessibility following IFNγ exposure in Pbrm1 mutant compared to control B16F10 cells, but their accessibility was similar between the two cell lines in the absence of IFNγ (FIGS. 20B-20C and 21B). Motif and target gene prediction analysis suggests these sites were highly enriched with IRF motifs and associated with IFN regulated genes (FIGS. 21C-21E). Thus, inactivation of Pbrm1 enhances chromatin accessibility for transcription factors at promoters/enhancers of many IFNγ induced genes.

These data demonstrate that resistance to T cell-mediated cytotoxicity is regulated by many genes and pathways in tumor cells. The corresponding gene products represent targets for immunotherapy because inactivating mutations sensitize tumor cells to T cell-mediated attack. The interaction between T cells and tumor cells is dynamically regulated at many levels, including innate immune and metabolic pathways within tumor cells. The PBAF complex is of particular interest because it regulates chromatin accessibility for both IFNγ and mTORC1 pathways within tumor cells and thereby increases resistance to T cell-mediated cytotoxicity.

The PBAF complex is a tumor suppressor and inactivating mutations in any of the three unique genes of this complex (PBRM1, ARID2 and BRD7) are known to occur in a variety of human cancers (Kadoch et al. (2015) *Sci. Adv.* 1:e1500447). For example, inactivating mutations in PBRM1 are prevalent in clear cell renal cancer (~41% of patients) (Varela et al. (2011) *Nature* 469:539-542). A study by Miao et al demonstrated that PBRM1 mutations in metastatic renal cancers are associated with improved clinical responses to PD-1/PD-L1 blockade (Miao et al. (2017) *Science* 359:801-806). Mutations in ARID2 and BRD7 are also observed in a variety of other human cancers, including ARID2 mutations in melanoma (Hodis et al. (2012) *Cell* 150:251-263). Human tumors with inactivating mutations in PBRM1, ARID2 and BRD7 are therefore believed to be more sensitive to PD-1 blockade, as well as to other forms of immunotherapy in which cytotoxic T cells serve as the main effector mechanism, including cancer vaccines and adoptive T cell therapies. The results described herein provide a mechanistic understanding for these exciting clinical findings by demonstrating that PBAF-deficient tumor cells are more sensitive to T cell-mediated cytotoxicity. It is also demonstrated herein that PBAF-deficient tumor cells produce higher levels of chemokines (Cxcl9 and Cxcl10) in response to IFNγ, resulting in more efficient recruitment of effector T cells into tumors (Groom et al. (2011) *Immunol. Cell Biol.* 89:207-215).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of sensitizing cancer cells in a subject afflicted with a cancer to cytotoxic T cell-mediated killing comprising administering to the subject a therapeutically effective amount of a nucleic acid that downregulates the copy number, amount, and/or activity of at least one biomarker in the cancer cells, thereby sensitizing the cancer cells in the subject to cytotoxic T cell-mediated killing; or a method of sensitizing cancer cells to cytotoxic T cell-mediated killing comprising contacting the cancer cells with 1) a nucleic acid that downregulates the copy number, amount, and/or activity of at least one biomarker in the cancer cells; and 2) cytotoxic T cells, thereby sensitizing the cancer cells to cytotoxic T cell-mediated killing;

wherein the at least one biomarker is selected from the group consisting of Arid2 and Brd7;

wherein the cancer is resistant to blockade of at least one immune checkpoint.

2. The method of claim 1, wherein the nucleic acid is a CRISPR guide RNA (gRNA), RNA interfering agent, antisense oligonucleotide, or aptamer, optionally wherein the RNA interfering agent is a small interfering RNA (siRNA) or a small hairpin RNA (shRNA).

3. The method of claim 1, further comprising treating the cancer in the subject by administering to the subject or contacting the cancer cells with at least one immunotherapy, optionally wherein (a) the immunotherapy is cell-based;
(b) the immunotherapy comprises a cancer vaccine, adoptive T cell therapies, and/or oncolytic virus; and/or
(c) the immunotherapy inhibits an immune checkpoint and/or inhibits TNF alpha, optionally wherein the immune checkpoint is selected from the group consisting of CTLA-4, PD-1, VISTA, B7-H2, B7-H3, PD-L1, B7-H4, B7-H6, ICOS, HVEM, PD-L2, C160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR.

4. The method of claim 1, wherein
the nucleic acid the agent reduces the number of proliferating cells in the cancer and/or reduces the volume or size of a tumor comprising the cancer cells;

the nucleic acid increases the amount of CD8+ T cells, CD4+ T cells, granzyme B+CD8+ T cells, and/or CD45+ immune cells infiltrating a tumor comprising the cancer cells;

the nucleic acid induces CD45+ immune cells to express higher levels of genes associated with productive antitumor immunity, optionally wherein the genes are related to IFN-γ response, IFN-α response, and/or tumor necrosis factor α signaling via NF-κB;

the nucleic acid increases the percentage of dendritic cells within the CD45+ immune cells;

the nucleic acid increases the ratio of tumor-inhibitory M1-like macrophages to tumor-promoting M2-like macrophages within the CD45+ immune cells;

the nucleic acid increases the responsiveness of cancer cells to IFN-γ and/or IFN-α;

the nucleic acid increases the production of chemokines in response to IFN-γ in cancer cells, optionally wherein the chemokine is CXCL9 and/or CXCL10;

the nucleic acid increases cancer cell surface levels of $H2-K^b$ and/or PD-L1 in response to IFN-γ;

the nucleic acid increases chromatin accessibility for IFN-γ-responsive genes in cancer cells;

the nucleic acid downregulates genes associated with mTORC1 pathway and/or cholesterol homeostasis in cancer cells;

the nucleic acid sensitizes cancer cells to immune checkpoint blockade therapy, optionally wherein the immune checkpoint is PD-1 and/or CTLA-4; and/or the nucleic acid is administered in a pharmaceutically acceptable formulation.

5. The method of claim 1, further comprising administering to the subject or contacting the cancer cells with at least one additional therapeutic agent or regimen for treating the cancer.

6. The method of claim 1, wherein
the cancer is selected form the group consisting of melanoma, head and neck squamous carcinoma, kidney cancer, colorectal cancer, gliomas, neuroblastoma, prostate cancer, breast cancer, pancreatic ductal carcinoma, epithelial ovarian cancer, B-CLL, leukemia, B cell lymphoma, renal cell carcinoma, lung adenocarcinoma and squamous carcinoma;

and/or the subject is a mammal, optionally wherein the mammal is a mouse or human.

* * * * *

```
                         SEQUENCE LISTING

<160> NUMBER OF SEQ ID NOS: 993

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      OVA peptide sequence

<400> SEQUENCE: 1

Ser Ile Ile Asn Phe Glu Lys Leu
1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 2
acatgatgct gcagtaccgg                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 3
aggttgtatt atcttcggaa                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 4
ccggagctcg cacttccccg                                                    20
```

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 5
ctcgccttca agttccagca                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 6
aacagaaccc aggttaagtg                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 7
agtatacctg gatcaagcag                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 8
ggaacttcac agcttcgtag                                                    20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 9
tgataactac tgtgcactga                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 10
ctcagcacag caacttcagg                                                    20
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 11
gcttgcgtta gtggtgtact                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 12
tccaaaggac ttgtacgtgg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 13
tgctgcataa tcagctacgg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 14
atgtggcacc ctcggcaaag                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 15
caagatccat gtccaacgtg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 16
gaagccagtg atgcactcga                                              20
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 17
tcacacatac cccgtgacgg                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 18
aaaggggacg aagacgacaa                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 19
ccgtgaagac ctgtgtagca                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 20
ctgcaaccag gtagtgacct                                                   20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 21
gaactgcaat gagaagattg                                                   20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 22
aagctggagc gcgtgcagag                                                   20

<210> SEQ ID NO 23

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 23
gcgcctggac gacttcgagg                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 24
tagatcgtgt cggcgcagcg                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 25
ttcgtttgct cacgcgctcg                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 26
gattccgcta taaatgcgag                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 27
gcccagaccg cagtatccat                                                   20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 28
tatcaaaaat cggatgtgag                                                   20

<210> SEQ ID NO 29
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 29
tcaccaagga tccacctcac                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 30
acagattgcc acattagccc                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 31
acagctggct aacaatggta                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 32
actgctagtt tggtaaatgg                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 33
gaagggaaat cctttcaagg                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 34
aaaaagaaat gctctaccag                                                   20

<210> SEQ ID NO 35
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 35
agctcacatc tcgaaccatg                                                   20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 36
agtacagtga agttcaagat                                                   20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 37
atctttcttg accatatcgg                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 38
cacaatcatg agcgcacaga                                                   20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 39
cccgatgcac tcacacgttg                                                   20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 40
cttaccaact accacctgac                                                   20

<210> SEQ ID NO 41
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 41
gaggtagctc tcgggcagcg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 42
acatacctgt agcaattcta                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 43
agaactggga tctcagattg                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 44
gatgagagac ttggctagag                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 45
gctgcagctc ttcggacagg                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 46
gaattcagag acttacctcc                                                    20

<210> SEQ ID NO 47
<211> LENGTH: 20
<212> TYPE: DNA
<213> ORGANISM: Artificial Sequence
<220> FEATURE:
```

<223> OTHER INFORMATION: Description of Artificial Sequence: Synthetic
      sgRNA targeting sequence

<400> SEQUENCE: 47
ggatgtccag aggagcccgg                                                  20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 48
tcctccaccc aaggatgacg                                                  20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 49
tttctcttag tccctaagtg                                                  20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 50
acagctctcg cagcacatgt                                                  20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 51
caggcactga acgagctccg                                                  20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 52
catcatgaac acttgaagca                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic sgRNA targeting sequence

<400> SEQUENCE: 53
tgtacagccc acgcaaatca                                          20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 54
acagccagca ctcctagacc                                          20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 55
aggaagagca tgaatctcca                                          20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 56
ccattcgacc ctcatagtgg                                          20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 57
ggatgatccc agtgtcacca                                          20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 58
agaacttgga cttgccgtag                                          20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 59
atcttcaccg atgcgcccag                                                20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 60
ctgggggttc ccgtacacgg                                                20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 61
ttaactctat agtagtccag                                                20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 62
aagaagttac atcttaacac                                                20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 63
cactctatga ggatagtcat                                                20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 64
ctcacttcca ttataccacc                                                20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 65
tgcagtgatc cattgcagtg                                                   20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 66
catactcctg cgcaacagga                                                   20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 67
ctcgcgagat gaaatcctca                                                   20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 68
ggccggctac ttgaccacgc                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 69
tggtgttggg caatacacat                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 70
acctgctaaa ccagccaggg                                                   20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 71
```
gtcccattgt aaggcaggag                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 72
tgaggacgat tctgatagtg                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 73
ttctccagat aaaacctgtg                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 74
aggactcctg ggtcacatcg                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 75
caggcccagc ctcttcgtgt                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 76
gtaattgtgg cagcgctgga                                               20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 77
taggactgac cgatcatgtg                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 78
aagttctgca cgttccgtga                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 79
aatgaagtgg tgatcgacag                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 80
agctacaatc accctatccg                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 81
taaactcaca tgatggtctg                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 82
aaagttatgg attatgtacc                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 83
ctctccggaa gaatgagttg                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 84
ctgaatttga ccaactacga                                          20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 85
tgcctgtcct gattcctgat                                          20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 86
acgttagaag gacatgcgta                                          20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 87
cctcttacca caatagcgtg                                          20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 88
gacatcctga ctcttgcatg                                          20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 89
gagagtctgt aaacgccgtg                                          20

```
<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 90
acaaccccag tggatcactg                                                   20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 91
ccaagcggct aggcaaacgc                                                   20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 92
ccacgctaag ctggtcccgg                                                   20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 93
ccacggccgt ctacaaggtg                                                   20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 94
acctcagtct gactgaacag                                                   20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 95
cactaggcaa cgatgagcca                                                   20
```

```
<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 96
cgagtgtctt aggaaacagt                                                    20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 97
gcacacacac ttcacatggg                                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 98
agcaacagtg aaatagcaca                                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 99
catgctttag ttcaacagaa                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 100
tatggttaga gaacgacagt                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 101 tttgtctttta tccgttcaag                                                   20

<210> SEQ ID NO 102
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 102
cagaaagtac tctcttagag                                                 20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 103
caggcaacac ataaacacat                                                 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 104
gctccgtcga ttcagaaacc                                                 20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 105
taacctcgcc tatgtgaagg                                                 20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 106
atgcgggata cacatactgt                                                 20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 107
gagagtgcac atcgagacag                                                 20

<210> SEQ ID NO 108
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 108
tcaatacgaa gatcatacag                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 109
acttgcagta aattagctcg                                              20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 110
gctgaaccgt ctgaccggca                                              20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 111
gttgccttaa cgacttcaca                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 112
tttactgctc gctaatgcgg                                              20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 113
cttacgttga aaagcttgtg                                              20

<210> SEQ ID NO 114
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 114
gggcgccggt tcgattaagg                                                 20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 115
ggtccccgat cttaaagcgg                                                 20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 116
ataataacca attagcaaca                                                 20

<210> SEQ ID NO 117
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 117
cctgcatgga gcatactcaa                                                 20

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 118
tcatggaccg aggttccgat                                                 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 119
caagacacag aatgtccacg                                                 20

<210> SEQ ID NO 120
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 120
ccatcaagtg acactcgtca                                              20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 121
ccatgacatc tggcatacga                                              20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 122
aactctggtc caaagaagcg                                              20

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 123
cgtgccctgt acttacggtg                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 124
ctttctgtag agccttcccg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 125
caatgaactc ctgaatcctg                                              20

<210> SEQ ID NO 126
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 126
catgagcatt accttgtatg                                                   20

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 127
gcaggagtac ccgaccctca                                                   20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 128
aaggagctga aatacgacgt                                                   20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 129
agagaacgaa gtctccgggg                                                   20

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 130
agtattacat ggaacaccat                                                   20

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 131
atgatcaagc agattcctag                                                   20

<210> SEQ ID NO 132
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 132
ccaaaattac ttactggact                                        20

<210> SEQ ID NO 133
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 133
cttacctata atcagaaacc                                        20

<210> SEQ ID NO 134
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 134
tgggttatgt catgtgactt                                        20

<210> SEQ ID NO 135
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 135
aggctctaaa gtatgtgcga                                        20

<210> SEQ ID NO 136
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 136
gcacgcaatt tgaatatgcc                                        20

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 137
ggttcgaagc aaatacaatg                                        20

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence -continued

<400> SEQUENCE: 138
gacacacctg tccacactac                                              20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 139
gttcacgatt tcccgccgtg                                              20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 140
tgggttgggt ccaactacgc                                              20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 141
tggtatggca gatcactgac                                              20

<210> SEQ ID NO 142
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 142
agttcgtgga gcgctacgag                                              20

<210> SEQ ID NO 143
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 143
ctgctatcga agatgtaaag                                              20

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 144
tagttcaggg tcacaagcgg                                              20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 145
tgaatcccag ttccagaacg                                              20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 146
agctcgttag ccaaacaaga                                              20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 147
caggaggcaa gctaacacgg                                              20

<210> SEQ ID NO 148
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 148
ctggagtgaa cactctgcag                                              20

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 149
gtgattgtta agctgcgcgt                                              20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 150
```
tctgtcctgg accataaccg                                           20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 151
tggaggggtt gaatccaaag                                           20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 152
ttaactacaa taacccattg                                           20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 153
acttaccgtg ttcgtagaca                                           20

<210> SEQ ID NO 154
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 154
cggcaaagat gtgatgccgg                                           20

<210> SEQ ID NO 155
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 155
gtacactggc aaatccatca                                           20

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 156
ttagagacaa accagacacg                                              20

<210> SEQ ID NO 157
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 157
agagaaatgc ccatactgtg                                              20

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 158
cagtggtgtc cggtccactt                                              20

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 159
cgtagctaat actgacgtag                                              20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 160
gttcatcatt ggacccggag                                              20

<210> SEQ ID NO 161
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 161
acgcttcatc aatgttggga                                              20

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 162
caccattgag aggatctatg                                              20

```
<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 163
cggcaagagg cggatggaca                                              20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 164
gttacagcac catatgaagg                                              20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 165
aaatgtactg tgatgttcca                                              20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 166
aagagtcagc tatttgacgt                                              20

<210> SEQ ID NO 167
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 167
ccttctacac tgtccatcca                                              20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 168
aataaaagag cagtccaagg                                              20
```

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 169
acaagcagct ttatactcag                                                     20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 170
caatgccagg cactacaatg                                                     20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 171
agtactgtat actaacagat                                                     20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 172
atacgtttca gcagtatgtg                                                     20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 173
cggtcttact ggaatcactc                                                     20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 174
gtcatagtaa ctgtccccag                                                     20

```
<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 175
aatgcgtgtg agaaaatatg                                                   20

<210> SEQ ID NO 176
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 176
cagaccatct aagttaccag                                                   20

<210> SEQ ID NO 177
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 177
ctagtaccat aacggcttgg                                                   20

<210> SEQ ID NO 178
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 178
atgaagacac tctgtaatgg                                                   20

<210> SEQ ID NO 179
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 179
caaattagtg atcaatctag                                                   20

<210> SEQ ID NO 180
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 180
cctcgaagcg gcctctcaag                                                   20

<210> SEQ ID NO 181
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 181 tgtaggggt cagctcgaca                                                    20

<210> SEQ ID NO 182
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 182
ataggactta caagaccagc                                                   20

<210> SEQ ID NO 183
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 183
cagtccgtca agctaggtgg                                                   20

<210> SEQ ID NO 184
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 184
ggcccaacag tcctttaaca                                                   20

<210> SEQ ID NO 185
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 185
ttacaccatc cagtcactaa                                                   20

<210> SEQ ID NO 186
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 186
acaatccctt tgaacaagaa                                                   20

<210> SEQ ID NO 187
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 187
aggaaccgcg aaagactggg                                               20

<210> SEQ ID NO 188
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 188
cagctggaaa ttgtgaccgg                                               20

<210> SEQ ID NO 189
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 189
tgcgtcgaaa taatctgaca                                               20

<210> SEQ ID NO 190
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 190
aaattgctga ttatctgacc                                               20

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 191
aggtagccga ttctgagttg                                               20

<210> SEQ ID NO 192
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 192
ggtcacaaaa tggtcagttg                                               20

<210> SEQ ID NO 193
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 193
tttgccaata gtcctagaca                                              20

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 194
acaggtcaat gaactcccgt                                              20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 195
actgggcgaa tatacttgag                                              20

<210> SEQ ID NO 196
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 196
ttaggttatg tggtccaccg                                              20

<210> SEQ ID NO 197
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 197
ttcagcaatg acacaaccaa                                              20

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 198
atcacagagt ctttagtcag                                              20

<210> SEQ ID NO 199
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 199
tccatcaagg caatctggcg                                                    20

<210> SEQ ID NO 200
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 200
tggcggcgag cggctcggtg                                                    20

<210> SEQ ID NO 201
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 201
acagctggct gggactaaga                                                    20

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 202
agtcagtata attcacaggt                                                    20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 203
gttctctgga ccaaaaccga                                                    20

<210> SEQ ID NO 204
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 204
tcagattaca tgttccagtg                                                    20

<210> SEQ ID NO 205
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 205
acagccgact cgttgtaaca                                                     20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 206
gaaacgctgt cttacacaag                                                     20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 207
tcgagccaga agaaccaatg                                                     20

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 208
tgggtaccat acccatattg                                                     20

<210> SEQ ID NO 209
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 209
atgggagacc aatttcaact                                                     20

<210> SEQ ID NO 210
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 210
ccaccaccga tgccagacaa                                                     20

<210> SEQ ID NO 211
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued sgRNA targeting sequence

<400> SEQUENCE: 211
tttgacgccc acattaacaa                                           20

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 212
tttgcactgc atcagcgccg                                           20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 213
ctacctcaac accctatcca                                           20

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 214
gaactatgag ttgttggacg                                           20

<210> SEQ ID NO 215
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 215
ggaggaacca aggtgttgtg                                           20

<210> SEQ ID NO 216
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 216
aaagatgatc gacctcatgc                                           20

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 217
gatcagctga tagacgatgc                                              20

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 218
ggttccccaa gaatcggacg                                              20

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 219
ttcatcagcc tcaataatct                                              20

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 220
agaggcgggc gttataattg                                              20

<210> SEQ ID NO 221
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 221
agtggtaact gaggccaggt                                              20

<210> SEQ ID NO 222
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 222
gaagatacgc caaagcgtcg                                              20

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 223
tggatggaaa agcgacaccg                                                      20

<210> SEQ ID NO 224
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 224
acggaagtca atgtacggat                                                      20

<210> SEQ ID NO 225
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 225
gaaacggctg attaacacct                                                      20

<210> SEQ ID NO 226
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 226
ggcaccccga aaaactcgtg                                                      20

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 227
tacttaaagg aacctaaggt                                                      20

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 228
attctggcag agcacgtcag                                                      20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 229
```
ctgcaagcag acacttccgc                                          20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 230
ctgcgggaca ccattgacca                                          20

<210> SEQ ID NO 231
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 231
acgggtacag taatagacag                                          20

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 232
atgacaccga tgggtcaaag                                          20

<210> SEQ ID NO 233
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 233
taatagtggc caattcgcca                                          20

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 234
tttccaagga ctgctcagga                                          20

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 235
aaatgtgacc aggtatggct                                              20

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 236
agtgtggaaa ggcctttgat                                              20

<210> SEQ ID NO 237
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 237
caacaccaac agattcatag                                              20

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 238
gcaccagcga actcatactg                                              20

<210> SEQ ID NO 239
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 239
cctgctggcc atacgcactg                                              20

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 240
gcagctgcga agatatcggg                                              20

<210> SEQ ID NO 241
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 241
tacccaaata tgaatcaagg                                              20

<210> SEQ ID NO 242
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 242
tggtcgtgcg agttctgctg                                                 20

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 243
atgctactga agtcaatccg                                                 20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 244
gagcccggag agaacaagaa                                                 20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 245
tcagcaagga caactcatgc                                                 20

<210> SEQ ID NO 246
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 246
tctgtcacct gagtcgacaa                                                 20

<210> SEQ ID NO 247
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 247
ctccaataca acagacgtcg                                                 20

```
<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 248
taccatgatg ccagccgatg                                              20

<210> SEQ ID NO 249
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 249
ttgagggcaa tattgcaagt                                              20

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 250
cggagctggg ccattcacac                                              20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 251
ctgtaggtta tacagatcag                                              20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 252
ttaattccaa ccaaatccca                                              20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 253
caaatccatc ccctccacac                                              20
```

<210> SEQ ID NO 254
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 254
ggtccccaag aaccatgtac                                              20

<210> SEQ ID NO 255
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 255
tggccgtcac tgacctccca                                              20

<210> SEQ ID NO 256
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 256
atggctcacc tgctcagact                                              20

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 257
ctaacaaacg gtctgctcgg                                              20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 258
tgagaagcag ctgtttcatg                                              20

<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 259
aagtccgata tctacagtgt                                              20

<210> SEQ ID NO 260

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 260
gagagtatgt gacagtacga                                                     20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 261
gatacggtac tatattggga                                                     20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 262
gtcacatcat ttatggcgta                                                     20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 263
ctatgagtcc atatccctg                                                      20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 264
tatcgactag tatctgactg                                                     20

<210> SEQ ID NO 265
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 265
tgttagtaat cgggatgatg                                                     20

<210> SEQ ID NO 266
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 266
caggctgtac tcaagggtat                                              20

<210> SEQ ID NO 267
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 267
ccctgatgga gcatctcatg                                              20

<210> SEQ ID NO 268
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 268
ttgattgagg gaaccatcga                                              20

<210> SEQ ID NO 269
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 269
gaacgggagc agaaacggaa                                              20

<210> SEQ ID NO 270
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 270
tctatgaact ctagtctacc                                              20

<210> SEQ ID NO 271
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 271
tgggtacacg acgggcatcg                                              20

<210> SEQ ID NO 272
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 272
acctggcgat tgtgactcag                                                  20

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 273
gagagactcg agttattact                                                  20

<210> SEQ ID NO 274
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 274
gccgaataag caaaggactg                                                  20

<210> SEQ ID NO 275
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 275
gggtgtagag tatctgtgct                                                  20

<210> SEQ ID NO 276
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 276
aagtacaagg cactttacag                                                  20

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 277
aggtgagcgt tgctatagcg                                                  20

<210> SEQ ID NO 278
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 278
gaggctacgt agcagtcgag                                                     20

<210> SEQ ID NO 279
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 279
agttccacgg agctatcact                                                     20

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 280
gcacaatgcg acgtgacatg                                                     20

<210> SEQ ID NO 281
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 281
tgagtctgac tactcagatg                                                     20

<210> SEQ ID NO 282
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 282
aaggcgttgg acataaggcg                                                     20

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 283
agtgatctcg atgcgatgca                                                     20

<210> SEQ ID NO 284
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 284
ctcactcaag aaagttgtga                                              20

<210> SEQ ID NO 285
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 285
ggacaacgcc ccgaccaccg                                              20

<210> SEQ ID NO 286
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 286
gcaggacagt agcaattcgg                                              20

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 287
gctgcatagt ggatcttgtg                                              20

<210> SEQ ID NO 288
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 288
tgtctcactc agataaacca                                              20

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 289
ggaaagcgga caccttggag                                              20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 290
ggctgcacgg agaattaaga                                                  20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 291
taaagccaag caaagtatca                                                  20

<210> SEQ ID NO 292
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 292
aaatggcaga agaagaggcg                                                  20

<210> SEQ ID NO 293
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 293
aaggcatgaa acatggacag                                                  20

<210> SEQ ID NO 294
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 294
cagaaatgca gcgcttgtcg                                                  20

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 295
cttaccttct ccattacagt                                                  20

<210> SEQ ID NO 296
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 296
acacagaagg taccatctag                                                 20

<210> SEQ ID NO 297
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 297
agcttgtcca ccacacgggg                                                 20

<210> SEQ ID NO 298
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 298
ggagcagagg aaagtcatag                                                 20

<210> SEQ ID NO 299
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 299
cctggtagat ggctacacta                                                 20

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 300
cgaaaactca atgaaagtcg                                                 20

<210> SEQ ID NO 301
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 301
cgcctgagac ccgacttcgg                                                 20

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence
```

<400> SEQUENCE: 302
cttcacactc caccaatacg                                                  20

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 303
taccgaagca gcgttccgag                                                  20

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 304
tgggcaagga agccagtatg                                                  20

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 305
agtttaagga gtcggcctgg                                                  20

<210> SEQ ID NO 306
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 306
taacatgacc aataagcgtg                                                  20

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 307
tcagggacta gaacctgtcg                                                  20

<210> SEQ ID NO 308
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 308
aaggataaga aactcaacat                                          20

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 309
aggttctagt ctcatgccag                                          20

<210> SEQ ID NO 310
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 310
gaatcactta caggccaaga                                          20

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 311
ggtgacacag gattagggga                                          20

<210> SEQ ID NO 312
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 312
gacggtaaaa gaaggtccag                                          20

<210> SEQ ID NO 313
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 313
gatgaggcca ctgttgcaga                                          20

<210> SEQ ID NO 314
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 314
ggaaggctac tcccacacca                                          20

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 315
tgtctacctg ttcaacctgg                                          20

<210> SEQ ID NO 316
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 316
cctcggagaa gctctctaag                                          20

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 317
cttcctgtta gatttcgttg                                          20

<210> SEQ ID NO 318
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 318
gattaatgtg atgaatcgtg                                          20

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 319
tcagtgtccc acctgagccg                                          20

<210> SEQ ID NO 320
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 320
caaacatgga accaccgcta                                          20

<210> SEQ ID NO 321
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 321
cctgctcatc aatcgtaacg                                            20

<210> SEQ ID NO 322
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 322
gtgtcaccta cagctctacg                                            20

<210> SEQ ID NO 323
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 323
acacagcggg tgatccacat                                            20

<210> SEQ ID NO 324
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 324
ggaagaggct aactcaggag                                            20

<210> SEQ ID NO 325
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 325
ggatgacgaa ctcaagagtg                                            20

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 326
tgtggaaaag aaccgcaagg                                            20

<210> SEQ ID NO 327
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 327
cgaacagccc cccatagtgg                                            20

<210> SEQ ID NO 328
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 328
ttgaagcaca ggcgcacgtg                                            20

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 329
aaaacgttgt aggagcccgt                                            20

<210> SEQ ID NO 330
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 330
atgaagtctg tcactgagca                                            20

<210> SEQ ID NO 331
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 331
gttgcattat ctaggaattg                                            20

<210> SEQ ID NO 332
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 332
tttctggttg cgaagcattg                                            20

-continued

```
<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 333
acccgtctgg aatcaacaca                                                    20

<210> SEQ ID NO 334
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 334
gcagttccag aaacacgagg                                                    20

<210> SEQ ID NO 335
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 335
ggtgtgggcc agcaatcttg                                                    20

<210> SEQ ID NO 336
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 336
ccttcaagac aacctcccag                                                    20

<210> SEQ ID NO 337
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 337
cggtctccag tcatcgtagt                                                    20

<210> SEQ ID NO 338
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 338
gagctgtaaa cagtacttcg                                                    20

<210> SEQ ID NO 339
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 339
ccagaacctg ctcataaaca                                                 20

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 340
tgagtagaca gatctcccgg                                                 20

<210> SEQ ID NO 341
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 341
tgtgttcaag gctaaaaacc                                                 20

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 342
aacacatttg tttctaaacg                                                 20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 343
agtttacaag tccacctgtg                                                 20

<210> SEQ ID NO 344
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 344
ttacctaaga ggattgccat                                                 20

<210> SEQ ID NO 345
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 345
cacagggtga taatgaacag                                              20

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 346
ctgatcctag cacacatgtg                                              20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 347
tgaaccacat ggctatgacg                                              20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 348
aactacaata cttacgacac                                              20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 349
gacacttcgt catgtaagga                                              20

<210> SEQ ID NO 350
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 350
gcgctgccga gggcaagcca                                              20

<210> SEQ ID NO 351
<211> LENGTH: 20
<212> TYPE: DNA
```

<213> ORGANISM: Artificial Sequence
<220> FEATURE:
<223> OTHER INFORMATION: Description of Artificial Sequence: Synthetic
      sgRNA targeting sequence

<400> SEQUENCE: 351
ggacaggaaa agcagcacgc                                               20

<210> SEQ ID NO 352
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 352
agtgatcctt gaaagttcga                                               20

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 353
cgttcgtcac ttgaaccgaa                                               20

<210> SEQ ID NO 354
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 354
ctcagagtca aacccatcag                                               20

<210> SEQ ID NO 355
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 355
cagtgctgac atcgatcaag                                               20

<210> SEQ ID NO 356
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 356
gaacgaacta tcacttacag                                               20

<210> SEQ ID NO 357
<211> LENGTH: 20
<212> TYPE: DNA
<213> ORGANISM: Artificial Sequence

```
<220> FEATURE:
<223> OTHER INFORMATION: Description of Artificial Sequence: Synthetic
      sgRNA targeting sequence

<400> SEQUENCE: 357
cgggaacaac tcaataccgt                                                 20

<210> SEQ ID NO 358
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 358
cttctcgcta caacacatga                                                 20

<210> SEQ ID NO 359
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 359
tgccgtttag acccttcgag                                                 20

<210> SEQ ID NO 360
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 360
caataaaatc cacaccatcg                                                 20

<210> SEQ ID NO 361
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 361
gttaaaagtc ctggcacaca                                                 20

<210> SEQ ID NO 362
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 362
tctacgaaac cactctgcaa                                                 20

<210> SEQ ID NO 363
<211> LENGTH: 20
<212> TYPE: DNA
<213> ORGANISM: Artificial Sequence
<220> FEATURE:
```

<223> OTHER INFORMATION: Description of Artificial Sequence: Synthetic
      sgRNA targeting sequence

<400> SEQUENCE: 363
ctgtagagga gcatcaggag                                              20

<210> SEQ ID NO 364
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 364
gcaagagatc tcaaacctgg                                              20

<210> SEQ ID NO 365
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 365
tttgatacag gggattagag                                              20

<210> SEQ ID NO 366
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 366
accccataca ggtactatcg                                              20

<210> SEQ ID NO 367
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 367
cacgagcatg acaacaatcg                                              20

<210> SEQ ID NO 368
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 368
cggtgcccag cattacagtg                                              20

<210> SEQ ID NO 369
<211> LENGTH: 20
<212> TYPE: DNA
<213> ORGANISM: Artificial Sequence
<220> FEATURE:
<223> OTHER INFORMATION: Description of Artificial Sequence: Synthetic sgRNA targeting sequence

<400> SEQUENCE: 369
ctcgcgaaga aatcgccgtg                    20

<210> SEQ ID NO 370
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 370
gggccagcaa ggaaagaatg                    20

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 371
ggtttggttc aagaatcgcc                    20

<210> SEQ ID NO 372
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 372
aggcaaaatg attcgctggg                    20

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 373
tgtcactgct ccataagtca                    20

<210> SEQ ID NO 374
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 374
acgaagacaa tgtagaccta                    20

<210> SEQ ID NO 375
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 375
gttggggaaa atctgaagag                                                          20

<210> SEQ ID NO 376
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 376
tgagagatag atgtatctac                                                          20

<210> SEQ ID NO 377
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 377
cattgccaat gtccacactg                                                          20

<210> SEQ ID NO 378
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 378
ccggattgtg cgtaaagagt                                                          20

<210> SEQ ID NO 379
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 379
tgtgaaactt cacaaaactc                                                          20

<210> SEQ ID NO 380
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 380
ctgagagtag gactgatact                                                          20

<210> SEQ ID NO 381
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 381
gccgcgcaca gtctgcacgt                                               20

<210> SEQ ID NO 382
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 382
ggaggaatga gtcatctccg                                               20

<210> SEQ ID NO 383
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 383
acatcaccaa cgccttccga                                               20

<210> SEQ ID NO 384
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 384
ctgtaaaacc cagatgcgat                                               20

<210> SEQ ID NO 385
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 385
ggcgatagtg aaatccactg                                               20

<210> SEQ ID NO 386
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 386
ggttgagaac aaacttggtg                                               20

<210> SEQ ID NO 387
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 387
```
acaaacctga gccctaaggg                                            20

<210> SEQ ID NO 388
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 388
atgatctgcg cgttaatgtg                                            20

<210> SEQ ID NO 389
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 389
cctgcactga agttcaatgg                                            20

<210> SEQ ID NO 390
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 390
cctggggaga gccacatcag                                            20

<210> SEQ ID NO 391
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 391
ctcttacctg cagcaccgag                                            20

<210> SEQ ID NO 392
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 392
ttagcttctc ctgctctgag                                            20

<210> SEQ ID NO 393
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 393
ctgaaggaca tacagctgat					20

<210> SEQ ID NO 394
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 394
gagtgggact gaaaagcgca					20

<210> SEQ ID NO 395
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 395
tcatcaagga ggtgtgcgat					20

<210> SEQ ID NO 396
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 396
cagggtacat caactagcaa					20

<210> SEQ ID NO 397
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 397
ctggaggcat catagtgcga					20

<210> SEQ ID NO 398
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 398
gaagctattg gatgagcgat					20

<210> SEQ ID NO 399
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 399
aagctccttc tccatcacac					20

```
<210> SEQ ID NO 400
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 400
atcactagca taagacaatg                                              20

<210> SEQ ID NO 401
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 401
gatggtctta ccaaaagctg                                              20

<210> SEQ ID NO 402
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 402
aaagagtatt tgcaacatgt                                              20

<210> SEQ ID NO 403
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 403
agggcgcgtc catgtacgag                                              20

<210> SEQ ID NO 404
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 404
ctctgccgct ggacacatcg                                              20

<210> SEQ ID NO 405
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 405
tttgagcgag gggtactggg                                              20
```

<210> SEQ ID NO 406
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 406
actggggtgt cacttcaacg                                           20

<210> SEQ ID NO 407
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 407
ctgatgctaa gactctggcg                                           20

<210> SEQ ID NO 408
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 408
gagcgcagca gactataacc                                           20

<210> SEQ ID NO 409
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 409
accaggatac cacacttcgg                                           20

<210> SEQ ID NO 410
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 410
gacttgggta gtctacatgg                                           20

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 411
gctcctggga ggtccacccg                                           20

```
<210> SEQ ID NO 412
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 412
ggtggaaagt aatagtcgat                                              20

<210> SEQ ID NO 413
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 413
gagtccatca atacctaaca                                              20

<210> SEQ ID NO 414
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 414
tggaacgact gaatgaggca                                              20

<210> SEQ ID NO 415
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 415
ttaattctgt actgaccaag                                              20

<210> SEQ ID NO 416
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 416
cagagagagc tctattccgg                                              20

<210> SEQ ID NO 417
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 417
gcagtacctg tctaatagca                                              20

<210> SEQ ID NO 418
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 418
taccatctac aggcctgacg                                                  20

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 419
gcgtaaccca cactcgtggg                                                  20

<210> SEQ ID NO 420
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 420
taacaactgc agatacaagg                                                  20

<210> SEQ ID NO 421
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 421
tgatttcatc tcataaaggg                                                  20

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 422
gaagatcccg ttcatcaggg                                                  20

<210> SEQ ID NO 423
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 423
gtacaggctc gcgccctcgg                                                  20

<210> SEQ ID NO 424
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 424
tgtggtccaa gatcgagcgc                                              20

<210> SEQ ID NO 425
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 425
aaataccaca gagtagacag                                              20

<210> SEQ ID NO 426
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 426
agcactctga aagggcatag                                              20

<210> SEQ ID NO 427
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 427
tgggcagaat ccgacagtaa                                              20

<210> SEQ ID NO 428
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 428
catacttacg aagacatacg                                              20

<210> SEQ ID NO 429
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 429
cgaactgcac aagaagcgtg                                              20

<210> SEQ ID NO 430
<211> LENGTH: 20
<212> TYPE: DNA
```

<213> ORGANISM: Artificial Sequence
<220> FEATURE:
<223> OTHER INFORMATION: Description of Artificial Sequence: Synthetic
      sgRNA targeting sequence

<400> SEQUENCE: 430
gaaactgagg aaaactactg                                              20

<210> SEQ ID NO 431
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 431
ctgatggcac tcgagccgta                                              20

<210> SEQ ID NO 432
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 432
gcaggctctt ctcgacatcg                                              20

<210> SEQ ID NO 433
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 433
gctggggcac gacactactg                                              20

<210> SEQ ID NO 434
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 434
cccagacatt tacaccaggg                                              20

<210> SEQ ID NO 435
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 435
gttaatggac ccagtacctg                                              20

<210> SEQ ID NO 436
<211> LENGTH: 20
<212> TYPE: DNA
<213> ORGANISM: Artificial Sequence

```
<220> FEATURE:
<223> OTHER INFORMATION: Description of Artificial Sequence: Synthetic
      sgRNA targeting sequence

<400> SEQUENCE: 436
tgccgccgat ggcaccaggt                                                 20

<210> SEQ ID NO 437
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 437
catgtaccag attgacagcg                                                 20

<210> SEQ ID NO 438
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 438
ggcacgctca tagaggcaca                                                 20

<210> SEQ ID NO 439
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 439
gggccgcctc atctacacag                                                 20

<210> SEQ ID NO 440
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 440
tcaaatacga ctgcccgcag                                                 20

<210> SEQ ID NO 441
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 441
agataacgct gcccgcagag                                                 20

<210> SEQ ID NO 442
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 442
agtacaaacc ttgttactca                                              20

<210> SEQ ID NO 443
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 443
cacaggttaa gggaaacttg                                              20

<210> SEQ ID NO 444
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 444
cggaccaggc ctttacatgc                                              20

<210> SEQ ID NO 445
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 445
caaatccatg cacacaatca                                              20

<210> SEQ ID NO 446
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 446
gaatgatatc acttccgtag                                              20

<210> SEQ ID NO 447
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 447
gagcttggta aagaaaaacg                                              20

<210> SEQ ID NO 448
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 448
gtcataagca tatcggacga                                          20

<210> SEQ ID NO 449
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 449
gacaattcat cagtctgccc                                          20

<210> SEQ ID NO 450
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 450
gaggacaaga cttcaatcag                                          20

<210> SEQ ID NO 451
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 451
gtgttggtca tagacttggg                                          20

<210> SEQ ID NO 452
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 452
ggaggagcag agtcccacgt                                          20

<210> SEQ ID NO 453
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 453
ggctgaacac gataccatcg                                          20

<210> SEQ ID NO 454
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 454
tggaaactaa gggcctcgcg                                          20

<210> SEQ ID NO 455
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 455
taaacaaaat caccatgacc                                          20

<210> SEQ ID NO 456
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 456
tgtgatgtgg ctggacacac                                          20

<210> SEQ ID NO 457
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 457
gcaacaccga gaccgagaca                                          20

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 458
ttccctagga aactgcacgt                                          20

<210> SEQ ID NO 459
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 459
ctgaaggaga aggcccacga                                          20

<210> SEQ ID NO 460
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 460
cttaaccctg agcgctacac                                               20

<210> SEQ ID NO 461
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 461
aacaggagga aatccttcgg                                               20

<210> SEQ ID NO 462
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 462
ggtgatatca tgaaaatgtg                                               20

<210> SEQ ID NO 463
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 463
tgacacagac ctagttactg                                               20

<210> SEQ ID NO 464
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 464
catggctcca cggtaatagg                                               20

<210> SEQ ID NO 465
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 465
ctggatgaaa agcatcaaag                                               20

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 466
```
tgatttcaag atccgaaccg                                              20

<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 467
ctgcagcagc accctacaag                                              20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 468
gctaccagtt catcaaacac                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 469
tccatccgta gtagtgcact                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 470
ttggagctat tgtagaaaca                                              20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 471
cctgtgtacc cacagaaatg                                              20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 472
cttgggccga aaatgccatg                                               20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 473
taggcttcat ggcgtaaggg                                               20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 474
gaagatttaa gtgcaacaca                                               20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 475
gttatcatgt aaatactagg                                               20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 476
tggagaaagg ccccaccctg                                               20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 477
aatagaaggt gttatgctcc                                               20

<210> SEQ ID NO 478
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 478
acatatccac tattgtgaca                                               20

<210> SEQ ID NO 479
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 479
gtattcgaca acactactgg                                              20

<210> SEQ ID NO 480
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 480
tgtagacata gagcagccga                                              20

<210> SEQ ID NO 481
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 481
aaatacaagt actcacgcgt                                              20

<210> SEQ ID NO 482
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 482
gcaggattaa gcattgtgct                                              20

<210> SEQ ID NO 483
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 483
gggagcacac cttcacgccg                                              20

<210> SEQ ID NO 484
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 484
ttccaccaac atttcaacca                                              20

<210> SEQ ID NO 485
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 485
actactcgga tagcatctga                                               20

<210> SEQ ID NO 486
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 486
ggatagcctc gtgtatgatg                                               20

<210> SEQ ID NO 487
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 487
tgaactagga atttacctga                                               20

<210> SEQ ID NO 488
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 488
tttgggctaa tgccttacaa                                               20

<210> SEQ ID NO 489
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 489
agaactgtgc cggatcaatg                                               20

<210> SEQ ID NO 490
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 490
cctggagttc ctgcgacccg                                               20

```
<210> SEQ ID NO 491
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 491
gcctgtgggc cccgccactg                                                    20

<210> SEQ ID NO 492
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 492
gctcgactct cacgtgcacg                                                    20

<210> SEQ ID NO 493
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 493
cctgcgctgt ccgggcagtg                                                    20

<210> SEQ ID NO 494
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 494
gaattgcaag cctaagaacc                                                    20

<210> SEQ ID NO 495
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 495
ggtggctttc aagaagacgt                                                    20

<210> SEQ ID NO 496
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 496
cgtgggccgc aagtacccgg                                                    20

<210> SEQ ID NO 497
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 497
gaagcgctgg aacagtatcg                                             20

<210> SEQ ID NO 498
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 498
ggagatggag agttatgatg                                             20

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 499
ggcagtgtac tacactaacc                                             20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 500
accgcccagg ttgtacgcag                                             20

<210> SEQ ID NO 501
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 501
gtagttaact ggttagggag                                             20

<210> SEQ ID NO 502
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 502
tatcgagaac atcatcgcta                                             20

<210> SEQ ID NO 503
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 503
actggaatga tgttcaaggc                                              20

<210> SEQ ID NO 504
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 504
gccgagactc cttagaaaag                                              20

<210> SEQ ID NO 505
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 505
tttgttatta cacttactga                                              20

<210> SEQ ID NO 506
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 506
aagtacactt ataacctcgg                                              20

<210> SEQ ID NO 507
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 507
ctgagccctg ctgtaaatgg                                              20

<210> SEQ ID NO 508
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 508
gatacaaacc ctgtggactg                                              20

<210> SEQ ID NO 509
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 509
gctgcacata tgcctgactg                                                  20

<210> SEQ ID NO 510
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 510
gaaaagctgt acaactccag                                                  20

<210> SEQ ID NO 511
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 511
gagaagccaa taaattaccg                                                  20

<210> SEQ ID NO 512
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 512
ggaatatcta gacaaaaggg                                                  20

<210> SEQ ID NO 513
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 513
cctaacaccc tctacgaagg                                                  20

<210> SEQ ID NO 514
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 514
tcagattctt gaccaaaatg                                                  20

<210> SEQ ID NO 515
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 515
tgagtccgac ctctacaact                                               20

<210> SEQ ID NO 516
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 516
acaggcagac cagaaaacca                                               20

<210> SEQ ID NO 517
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 517
gaagagacac aagtctaatg                                               20

<210> SEQ ID NO 518
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 518
gggctacgta ctgacaaacg                                               20

<210> SEQ ID NO 519
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 519
agaattctca tcgggaatag                                               20

<210> SEQ ID NO 520
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 520
ctaccataac tcgcttgaca                                               20

<210> SEQ ID NO 521
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 521
ctggacaagt ctaacccggt                                              20

<210> SEQ ID NO 522
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 522
ggacatagga tgtctccacg                                              20

<210> SEQ ID NO 523
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 523
tgagcataaa gaatgcaccg                                              20

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 524
aacacaagac aagatcgtgt                                              20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 525
gagaagtcct ggggcaaaca                                              20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 526
gagtacgcca tgatgtacac                                              20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 527
tggccgagtt catttccgag                                                    20

<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 528
acctgcttat caatgcagag                                                    20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 529
caagttgacg ggagaagttg                                                    20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 530
catgagtgta agttcggaca                                                    20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 531
ccaagtgttg gaaacgcccg                                                    20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 532
tgtgtatctg catgaagagg                                                    20

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 533
ttgggtttag gaaatccatg                                               20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 534
catgcccgat atgctgagtg                                               20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 535
cgtgtgcatc gtcaccaacg                                               20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 536
tggtctggca ggcaccatgg                                               20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 537
accaaaccgt accagtcacg                                               20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 538
tctaacatag gctcttcacg                                               20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 539
tgcagtgaac gacttaggag                                              20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 540
tgggcgccat cgtcagaaag                                              20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 541
ccaagcgaag caggcactcg                                              20

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 542
ggagaaaagc tgggagcgtg                                              20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 543
ggcccgaggc cgtagatcca                                              20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 544
gatgaacctt gcaaaaagtg                                              20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 545
```
gtgtgggtcg aactttaaga                                           20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 546
tggccccagc catcgagagt                                           20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 547
cctgtgaagt ataacatcgt                                           20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 548
cttgtcgggt tgtaatcagg                                           20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 549
gcagagcaat accagaacca                                           20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 550
ctatcgaaca tactatccag                                           20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 551
ctggacccat atttacatgg                                                    20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 552
ttcatgccca ggattgccta                                                    20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 553
ataacttgta aggatttgag                                                    20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 554
tgtacaaact acacagctca                                                    20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 555
acggttccag tctcttggtg                                                    20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 556
cgacagactt gttaccatgc                                                    20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 557
ggaagttctc gggatcccgg                                                    20

```
<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 558
acaccgtgga gatacagacc                                             20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 559
agccaccata cagagtacct                                             20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 560
cttccatgga ctcttaccga                                             20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 561
agaaccgaca tgagggaaaa                                             20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 562
agtcagtcag aaccgacatg                                             20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 563
gtcagtcaga accgacatga                                             20
```

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 564
cagtttgcaa gacctaacaa                                              20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 565
gtggagcaga tacgcagccg                                              20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 566
taacaaaagg aattgtgaag                                              20

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 567
aaaattctac taacaatacg                                              20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 568
actttgctaa gcacaaacag                                              20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 569
tggcatttga agtatcaggg                                              20

```
<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 570
aggtttacaa taccttaggg                                                   20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 571
ccttcatacg gtgtgtctgg                                                   20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 572
gtcattgcaa gcgctgttgg                                                   20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 573
taatattagt tccgtcacag                                                   20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 574
aggaactatt gtgagcatag                                                   20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 575
ggtgtgctca aaatcagatg                                                   20

<210> SEQ ID NO 576
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 576
tatctctgca gatttacaca                                                  20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 577
atatcttact cacgtccccg                                                  20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 578
tgtgcttggt gccaataacg                                                  20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 579
aagtagttaa cttaccctca                                                  20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 580
taccagaaac atcatagagt                                                  20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 581
tcagttcgtc ccaatatgga                                                  20

<210> SEQ ID NO 582
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 582
tggtccatcc cccaatgaca                                               20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 583
gatcacagtc cactctgcac                                               20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 584
gcagccattg tatccaagag                                               20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 585
gtgatgatgc agacaggaca                                               20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 586
aatcttgtca aattggacaa                                               20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 587
gagttcttga tacggatgaa                                               20

<210> SEQ ID NO 588
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 588
ggctgaacag gaacactagg                                              20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 589
tgaatgccac ctcgttccag                                              20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 590
cttacctaaa tcctaataca                                              20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 591
tcaagcctag gctcaacgaa                                              20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 592
cgatgactcc gattatccgg                                              20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 593
gactccttaa gaatcaaacg                                              20

<210> SEQ ID NO 594
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 594
tgagttccga tctggacaag                                                     20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 595
cagactctcg caaagctccg                                                     20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 596
cgagccgtag catgtcaaag                                                     20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 597
tggatagacc gagtcagtgg                                                     20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 598
ttcatggtcc agaaggaacg                                                     20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 599
cttacttctt aatcacgaag                                                     20

<210> SEQ ID NO 600
<211> LENGTH: 20
<212> TYPE: DNA
<213> ORGANISM: Artificial Sequence
<220> FEATURE:
```

<223> OTHER INFORMATION: Description of Artificial Sequence: Synthetic
      sgRNA targeting sequence

<400> SEQUENCE: 600
tcactcctca gaaggcaacg                                                   20

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 601
tcttgggatt ccataccacg                                                   20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 602
gcagccttaa acctcgaaga                                                   20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 603
tgacgaggat acacgaacgc                                                   20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 604
agagactgaa gtcggtgcaa                                                   20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 605
ggacaatagc ctaatagaca                                                   20

<210> SEQ ID NO 606
<211> LENGTH: 20
<212> TYPE: DNA
<213> ORGANISM: Artificial Sequence
<220> FEATURE:
<223> OTHER INFORMATION: Description of Artificial Sequence: Synthetic -continued sgRNA targeting sequence

<400> SEQUENCE: 606
ggtaggaccg gccactcttg                                           20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 607
tcagccagtt tgggtgcctg                                           20

<210> SEQ ID NO 608
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 608
tccgaaccgg agattccgaa                                           20

<210> SEQ ID NO 609
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 609
tgaaggcgac aatggatgca                                           20

<210> SEQ ID NO 610
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 610
caggccgtat ctctcctcgg                                           20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 611
gagcccacat aaatgccggt                                           20

<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 612
gctcggccgt gacactacca                                        20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 613
tgacgccact cagaacgctg                                        20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 614
aaggatcggc aagctttaga                                        20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 615
aggctgcctt gcgaatggag                                        20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 616
gctcaggtga catcattgct                                        20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 617
aaagttccct acaagcccaa                                        20

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 618
gaatataccg aagttcaaag                                                20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 619
ctcctacacg gtaactacgg                                                20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 620
gaggaggcac actacagacg                                                20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 621
agttgtcacg acaaacaagt                                                20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 622
gaccaccctg cacatatgga                                                20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 623
gcagcttccc gatataccga                                                20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 624
```
tcagagcctc ccgatcgcct                                               20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 625
gagatcacca taggacgacc                                               20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 626
tatgtgacgt tccaacacct                                               20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 627
tcgtgcccgg aatacccgat                                               20

<210> SEQ ID NO 628
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 628
aataattcca aggactgagg                                               20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 629
ctgaacacgt agctggagcg                                               20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 630
tgacgtctaa cacgccagag                                              20

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 631
taggatatgg aaccaaactg                                              20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 632
catctgtgcg agctgaaggt                                              20

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 633
ctcacctagc tgtcttggca                                              20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 634
tggaccgggc aaggcagtac                                              20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 635
caggcttaaa gacagatacc                                              20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 636
cttggtaaag ggtttcgacg                                              20

<210> SEQ ID NO 637
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 637
gacggcaata ctttatctgt                                              20

<210> SEQ ID NO 638
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 638
ttcgtgtccg atgagcctaa                                              20

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 639
ccccacggtg ggcttcaacg                                              20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 640
cgaccgcgac cgcatcgacg                                              20

<210> SEQ ID NO 641
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 641
tctggcggca ttactacacc                                              20

<210> SEQ ID NO 642
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 642
cagtccggga gatactgtag                                              20

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 643
tctgtgcggg cagaaacccg                                             20

<210> SEQ ID NO 644
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 644
gaaagcacga ctgcccaacg                                             20

<210> SEQ ID NO 645
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 645
gacttacaaa tttaagaatg                                             20

<210> SEQ ID NO 646
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 646
gatattggat gcgaacagca                                             20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 647
aggtgagagg gatcccaatg                                             20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 648
atgtcagagt atgaaacacc                                             20

```
<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 649
caatctgaca gaccgcatcg                                                    20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 650
ggttctgcag gatcgcacgc                                                    20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 651
tgagtacttc cggcaacctg                                                    20

<210> SEQ ID NO 652
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 652
acatagtatg tatacaccct                                                    20

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 653
ggcattagaa tgcttcggga                                                    20

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 654
gtcatcatag tgtccgaact                                                    20

<210> SEQ ID NO 655
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 655
gccatggagt ctatccaggg                                              20

<210> SEQ ID NO 656
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 656
tggtggcaag aacatccgcg                                              20

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 657
ttaccaaata gtcatctgga                                              20

<210> SEQ ID NO 658
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 658
actgaaagca atgatctccg                                              20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 659
tcaataataa aaggcccct                                               20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 660
tcttaccttt gtattcactt                                              20

<210> SEQ ID NO 661
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 661
caaaccattt gttgtcaagg                                                    20

<210> SEQ ID NO 662
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 662
ctctatactt actctgagga                                                    20

<210> SEQ ID NO 663
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 663
gcggctatgt gaattgctaa                                                    20

<210> SEQ ID NO 664
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 664
gcattcgctt aatatcccgg                                                    20

<210> SEQ ID NO 665
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 665
tgctcatgct cagagtgacg                                                    20

<210> SEQ ID NO 666
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 666
ttgcttatga tcgaatccaa                                                    20

<210> SEQ ID NO 667
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 667
actgactgac cccgaaagga                                                   20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 668
cagacttggc gaagacgtgg                                                   20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 669
ctctctctct aacctcggtg                                                   20

<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 670
caaagagtca catgccacgt                                                   20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 671
gtttaccacg aaagtcaggt                                                   20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 672
aaaaggccca ttacccaatg                                                   20

<210> SEQ ID NO 673
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 673
aagcattacc tgaatccatg                                              20

<210> SEQ ID NO 674
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 674
ggtgaaatgg atgatagtcg                                              20

<210> SEQ ID NO 675
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 675
acgtccaact caaagaacgc                                              20

<210> SEQ ID NO 676
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 676
cctcttgtta aacgagatca                                              20

<210> SEQ ID NO 677
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 677
gctccacacg attgttagag                                              20

<210> SEQ ID NO 678
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 678
ttgcagctca aagatatatg                                              20

<210> SEQ ID NO 679
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 679
agcctcatta tcgatgcagt                                                20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 680
aggtaataaa tatgtgccta                                                20

<210> SEQ ID NO 681
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 681
ctccatggta acttccagtg                                                20

<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 682
cgtcgtctgg tatttccgtg                                                20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 683
ggtgaatgta agacaatctg                                                20

<210> SEQ ID NO 684
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 684
ggaacccgga gagtatactg                                                20

<210> SEQ ID NO 685
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 685
tatacttact cactaagctg					20

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 686
aatgcaattg tgcatatggg					20

<210> SEQ ID NO 687
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 687
cctctacaag ctgaaactcg					20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 688
gaagagccta atcggcaaga					20

<210> SEQ ID NO 689
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 689
tgatcgggag cgagtgaacg					20

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 690
ttcacagtct gggacgtagg					20

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 691
ccgcaggatg ccatacacgt                                               20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 692
gtccctccac tgtcacatcg                                               20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 693
gtggaggcac taaccctacg                                               20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 694
agacattact aggtgtcggt                                               20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 695
atggtatcca agatccactg                                               20

<210> SEQ ID NO 696
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 696
gctgtggaag gtctttacga                                               20

<210> SEQ ID NO 697
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence
```

```
<400> SEQUENCE: 697
tagcctttga tcgaagcggg                                          20

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 698
atactttatc cacgacacag                                          20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 699
gcaggcgaca gagcacgcgc                                          20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 700
tggtggagat tgaaacagcg                                          20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 701
ttaccatgac atgatgaaca                                          20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 702
atgctacgga aagagatacg                                          20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 703
```
cggtacctcc gtgtgaacga                                              20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 704
ctaatggaaa atacctacga                                              20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 705
ggggactcta tccaaagacc                                              20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 706
acatagaatc aagagttgtg                                              20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 707
cctggcttta tagtccaagg                                              20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 708
gagatattga catagagttg                                              20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 709
gggagcctac ctgactgact                                               20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 710
aggagaaggt ctcagtctcg                                               20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 711
aggagcggtt aaaaaacgag                                               20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 712
taccacagaa cgaaatcgta                                               20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 713
tgtctttata actagaaatg                                               20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 714
cggccgacgc ggtgacgtcg                                               20

<210> SEQ ID NO 715
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 715
cgtgcagcgc aaccacgaga                                               20

```
<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 716
ctcctccgga gacacgatgg                                              20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 717
cagacatgta tacaaaggag                                              20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 718
catctcagga cggagtgcgt                                              20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 719
cttgcatcca gctccgcgtg                                              20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 720
tcaatagcaa cttctacctg                                              20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 721
tcctcagtca cgtcggccgg                                              20
```

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 722
accataatgc caccccagcg                                                    20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 723
ctacctaagc tggacttgag                                                    20

<210> SEQ ID NO 724
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 724
gatctctcgc tcatgcacaa                                                    20

<210> SEQ ID NO 725
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 725
gggcgacctg gactatgcga                                                    20

<210> SEQ ID NO 726
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 726
aatgtgccat agaaccctcg                                                    20

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 727
ccctccaacc cacaacatcg                                                    20

```
<210> SEQ ID NO 728
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 728
tcctgcgtac tctaagagag                                                    20

<210> SEQ ID NO 729
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 729
aaagagtgac gacggaacac                                                    20

<210> SEQ ID NO 730
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 730
gttccaagac cttcaaacca                                                    20

<210> SEQ ID NO 731
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 731
tacatagata ggttcctcgg                                                    20

<210> SEQ ID NO 732
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 732
ttattgttgt gtaatacaca                                                    20

<210> SEQ ID NO 733
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 733
cgcacctgaa cagcacgccc                                                    20

<210> SEQ ID NO 734
```

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 734
ctaacaggtc tagactccag                                              20

<210> SEQ ID NO 735
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 735
gagtccgggt ctttcaagag                                              20

<210> SEQ ID NO 736
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 736
tgtgtgctca tccggaaaca                                              20

<210> SEQ ID NO 737
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 737
cggcaggaac aggaccgggt                                              20

<210> SEQ ID NO 738
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 738
gcttcaggaa cagacaaccc                                              20

<210> SEQ ID NO 739
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 739
ggtggccgag gcgctaacca                                              20

<210> SEQ ID NO 740
<211> LENGTH: 20

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 740
tctgagcgag gacatacgca                                              20

<210> SEQ ID NO 741
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 741
aggagactac ttatcttcgg                                              20

<210> SEQ ID NO 742
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 742
ctcagacacc cgggaccgcg                                              20

<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 743
agtgactgca cgtggcctcg                                              20

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 744
caggttcacg tgctgtaccg                                              20

<210> SEQ ID NO 745
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 745
gctttgagat cgagattgag                                              20

<210> SEQ ID NO 746
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 746
acacacgctc tcgagacagg                                                   20

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 747
acggttctca gtaagcgtgt                                                   20

<210> SEQ ID NO 748
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 748
ctcacccagt gacaactcag                                                   20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 749
aatctcgaag atatccaaag                                                   20

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 750
acaactatct tggatttgcg                                                   20

<210> SEQ ID NO 751
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 751
gttgtgtttg aagattcgaa                                                   20

<210> SEQ ID NO 752
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 752
tgagagcaat cacttcagga                                                    20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 753
aagggaccgt ctgtggactg                                                    20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 754
gaagcgctgt gagtttgtca                                                    20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 755
tctacacctt caatcaaagc                                                    20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 756
acatcttaat aagaagtcct                                                    20

<210> SEQ ID NO 757
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 757
gcctccaatg cagtacatca                                                    20

<210> SEQ ID NO 758
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 758
acaggccaca aagttccctg                                               20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 759
ggacgccaga aaagcatgcg                                               20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 760
atagatgaca gccgaacacg                                               20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 761
cagcgtccga aagtggaacg                                               20

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 762
gggcaaccgg ttgtaccgtg                                               20

<210> SEQ ID NO 763
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 763
agcagacaga gaacctacag                                               20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued sgRNA targeting sequence

<400> SEQUENCE: 764
gaatacaaca tgcctaaaga                                            20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 765
gctggctggt ggaatatggt                                            20

<210> SEQ ID NO 766
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 766
caacccgtgt gactttgact                                            20

<210> SEQ ID NO 767
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 767
gccagccatc gagaaagccg                                            20

<210> SEQ ID NO 768
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 768
gtcactgtgg agcaacatgt                                            20

<210> SEQ ID NO 769
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 769
tcagtgtgca tactcacttg                                            20

<210> SEQ ID NO 770
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 770
agagggaaag gaagaaccgg                                              20

<210> SEQ ID NO 771
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 771
gctcccacaa gagacttgag                                              20

<210> SEQ ID NO 772
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 772
ggtccacaaa ggcctccgag                                              20

<210> SEQ ID NO 773
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 773
acagttcgag ttggaacagt                                              20

<210> SEQ ID NO 774
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 774
tgtggggcga tctatgtgtg                                              20

<210> SEQ ID NO 775
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 775
aatttggcag aaatcgagag                                              20

<210> SEQ ID NO 776
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence
```

```
<400> SEQUENCE: 776
taagctgtcc catggatccg                                              20

<210> SEQ ID NO 777
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 777
tctaagaagc ttccatgtcg                                              20

<210> SEQ ID NO 778
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 778
caagaatgtg ctgatcaaca                                              20

<210> SEQ ID NO 779
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 779
gcggccagac aacacctatg                                              20

<210> SEQ ID NO 780
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 780
tatgtttgga ttcgacccag                                              20

<210> SEQ ID NO 781
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 781
caatatgatt ccaccaacgc                                              20

<210> SEQ ID NO 782
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 782
```
tagccaaaag attcttgact                                              20

<210> SEQ ID NO 783
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 783
tgctactgag cagctcgcaa                                              20

<210> SEQ ID NO 784
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 784
caagtgggtc aacaacctag                                              20

<210> SEQ ID NO 785
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 785
ggagaagaag tacccgtacg                                              20

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 786
tcgtgtgaca gggtcaacaa                                              20

<210> SEQ ID NO 787
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 787
atagacatat ccatagcatg                                              20

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 788
catgctcatc gtttatagga                                          20

<210> SEQ ID NO 789
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 789
gcctgccttc accattcatg                                          20

<210> SEQ ID NO 790
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 790
aaacatgtca tagtcttccg                                          20

<210> SEQ ID NO 791
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 791
agaggcgaaa aattatgaag                                          20

<210> SEQ ID NO 792
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 792
ctctcgcaag tgtctccgag                                          20

<210> SEQ ID NO 793
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 793
acataaggaa tggtccagag                                          20

<210> SEQ ID NO 794
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 794
gcaggggtcc tcggaagtaa                                          20

<210> SEQ ID NO 795
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 795
gggtgcaccg attattcccg                                              20

<210> SEQ ID NO 796
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 796
gggtgtatgg aacatctgca                                              20

<210> SEQ ID NO 797
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 797
aaagctcaaa ttcagcgatg                                              20

<210> SEQ ID NO 798
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 798
gaggaatcat catccagcgg                                              20

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 799
tcagtacgat tctctctccg                                              20

<210> SEQ ID NO 800
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 800
cagcattgac aatacgacca                                              20

<210> SEQ ID NO 801
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 801
gctgttactc cagagacaca                                               20

<210> SEQ ID NO 802
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 802 ttaccccta ctacactgga                                                20

<210> SEQ ID NO 803
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 803
tttacaatcc tccaaagtcg                                               20

<210> SEQ ID NO 804
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 804
gaagtaaagg gatttaacag                                               20

<210> SEQ ID NO 805
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 805
ttagttctgg caaagcgccg                                               20

<210> SEQ ID NO 806
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 806
cggcccgccg atgtcgtgtg                                               20

```
<210> SEQ ID NO 807
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 807
gccaacatct gcttactcgc                                              20

<210> SEQ ID NO 808
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 808
tcttgaaaac tatagtactc                                              20

<210> SEQ ID NO 809
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 809
gccctttact ttcagtacgg                                              20

<210> SEQ ID NO 810
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 810
ggaatccctg tgctgatcgt                                              20

<210> SEQ ID NO 811
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 811
tgtaatgtag gtctcccagg                                              20

<210> SEQ ID NO 812
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 812
gagatctgca cattccgcac                                              20

<210> SEQ ID NO 813
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 813
gctgcagagg cagtttgatg                                              20

<210> SEQ ID NO 814
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 814
ggacaccaag ttattccgtg                                              20

<210> SEQ ID NO 815
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 815
ccatatccaa atagccacag                                              20

<210> SEQ ID NO 816
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 816
cctgggctag cacataacca                                              20

<210> SEQ ID NO 817
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 817
tactgatcat aaacgaacca                                              20

<210> SEQ ID NO 818
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 818
ttattgagtc aagaaaaggt                                              20

<210> SEQ ID NO 819
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 819
aaaaattcaa cgttgaaaca                                              20

<210> SEQ ID NO 820
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 820
agattgtcaa caatggaact                                              20

<210> SEQ ID NO 821
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 821
tgtttgcagt tagcaaaacg                                              20

<210> SEQ ID NO 822
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 822
agttggatcg cgaataaaga                                              20

<210> SEQ ID NO 823
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 823
catagccaga acagttgacc                                              20

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 824
catgcaatac atgccaaagg                                              20

<210> SEQ ID NO 825
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 825
atagcaccaa agcctaacaa                                              20

<210> SEQ ID NO 826
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 826
gaacactcag caaattacag                                              20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 827
tcttaaagct acggtgtaag                                              20

<210> SEQ ID NO 828
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 828
tgcacagcat acactagtga                                              20

<210> SEQ ID NO 829
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 829
cctccgacat tccgtaactg                                              20

<210> SEQ ID NO 830
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 830
ctcagctgga tacaaccagg                                              20

<210> SEQ ID NO 831
<211> LENGTH: 20
<212> TYPE: DNA
<213> ORGANISM: Artificial Sequence
```

<220> FEATURE:
<223> OTHER INFORMATION: Description of Artificial Sequence: Synthetic
      sgRNA targeting sequence

<400> SEQUENCE: 831
ctgagcatgt ctaacacgag                                              20

<210> SEQ ID NO 832
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 832
cttcagatct ctctcgaatg                                              20

<210> SEQ ID NO 833
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 833
cttgtgacgg taattctgaa                                              20

<210> SEQ ID NO 834
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 834
ttcaaagcaa ggctctactg                                              20

<210> SEQ ID NO 835
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 835
gctcaagtac tcgcccgacc                                              20

<210> SEQ ID NO 836
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 836
ggttccttgc gggactccgt                                              20

<210> SEQ ID NO 837
<211> LENGTH: 20
<212> TYPE: DNA
<213> ORGANISM: Artificial Sequence
<220> FEATURE:

```
<223> OTHER INFORMATION: Description of Artificial Sequence: Synthetic
      sgRNA targeting sequence

<400> SEQUENCE: 837
acagcctccc aatatctcag                                                20

<210> SEQ ID NO 838
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 838
agtttggagc ccagtaggca                                                20

<210> SEQ ID NO 839
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 839
ccgcagcaga tagacaccat                                                20

<210> SEQ ID NO 840
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 840
ttgtccgcgt tacttccctg                                                20

<210> SEQ ID NO 841
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 841
agagatctgc gccatttaag                                                20

<210> SEQ ID NO 842
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 842
gatatgctac aggaccttcg                                                20

<210> SEQ ID NO 843
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 843
tgatgctggc ctctatactg                                         20

<210> SEQ ID NO 844
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 844
aatgctgacg actttcaatg                                         20

<210> SEQ ID NO 845
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 845
gcaggggtct ccttatgtcg                                         20

<210> SEQ ID NO 846
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 846
ggttcgcttc ttccaaacca                                         20

<210> SEQ ID NO 847
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 847
ccattgtata actgtctgcg                                         20

<210> SEQ ID NO 848
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 848
gagttgcagc cagatacgcg                                         20

<210> SEQ ID NO 849
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 849
ttactgaggc tcgattggga                                              20

<210> SEQ ID NO 850
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 850
atgggattga tcgttactgg                                              20

<210> SEQ ID NO 851
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 851
ccaaacaccc cacatatggt                                              20

<210> SEQ ID NO 852
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 852
gtataagcca ttacgacgca                                              20

<210> SEQ ID NO 853
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 853
caccggatcg tccaattccg                                              20

<210> SEQ ID NO 854
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 854
caggacttct ggtctatccg                                              20

<210> SEQ ID NO 855
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence
```

```
<400> SEQUENCE: 855
taagcgttgt tgactacatg                                              20

<210> SEQ ID NO 856
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 856
cctgggtacc aactgacgaa                                              20

<210> SEQ ID NO 857
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 857
tgataataga taaacgacca                                              20

<210> SEQ ID NO 858
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 858
ttgtgcctaa acaaaaaaca                                              20

<210> SEQ ID NO 859
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 859
ctgttacctt catagataag                                              20

<210> SEQ ID NO 860
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 860
gctgccccgc aggatcatca                                              20

<210> SEQ ID NO 861
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 861
```
taaaagtccc tccctcaaag                                                20

<210> SEQ ID NO 862
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 862
cagcagcaag ttcacaggtg                                                20

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 863
tgaagctaat gaccatgagc                                                20

<210> SEQ ID NO 864
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 864
tgtgaatgct atgacgagct                                                20

<210> SEQ ID NO 865
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 865
atttcaagag attctatgct                                                20

<210> SEQ ID NO 866
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 866
gtttctggca tccaaagtag                                                20

<210> SEQ ID NO 867
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 867

```
tctgttgaaa gagcgccaaa                                              20
```

<210> SEQ ID NO 868
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 868

```
tggtctagtt accatgcaag                                              20
```

<210> SEQ ID NO 869
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 869

```
aaaacggtct caagccaatg                                              20
```

<210> SEQ ID NO 870
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 870

```
aagacatata gttatcagca                                              20
```

<210> SEQ ID NO 871
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 871

```
ggtcatactt aaaagcacaa                                              20
```

<210> SEQ ID NO 872
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 872

```
gccagctttc tcgcacgtgg                                              20
```

<210> SEQ ID NO 873
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 873

```
tggaacctcc tgatccgctg                                              20
```

<210> SEQ ID NO 874
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 874
tggaattatg gtcaaagtag                                                 20

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 875
caagagccag accttggatg                                                 20

<210> SEQ ID NO 876
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 876
cctttagtag cagaagccgc                                                 20

<210> SEQ ID NO 877
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 877
gtcttgtgca aaaagcccga                                                 20

<210> SEQ ID NO 878
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 878
tcagcaactg agaactcact                                                 20

<210> SEQ ID NO 879
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 879
acacaacgct aagacagtcg                                                 20

```
<210> SEQ ID NO 880
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 880
gcaagaggtt atcaaacacg                                              20

<210> SEQ ID NO 881
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 881
gcctgtacca cgcagccaag                                              20

<210> SEQ ID NO 882
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 882
taattgctga gaatgtactc                                              20

<210> SEQ ID NO 883
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 883
acgacgagga gttcgaatac                                              20

<210> SEQ ID NO 884
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 884
gaatctgaat ggaggaacct                                              20

<210> SEQ ID NO 885
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 885
ttcagattca gacatcagat                                              20
```

```
<210> SEQ ID NO 886
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 886
ttcggacaaa tacgacgacg                                               20

<210> SEQ ID NO 887
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 887
ctgcagcata tcgtcaacca                                               20

<210> SEQ ID NO 888
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 888
gaatgatatt atagcgacga                                               20

<210> SEQ ID NO 889
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 889
ggatcctggc gattcaacat                                               20

<210> SEQ ID NO 890
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 890
tcatagccag agcatactct                                               20

<210> SEQ ID NO 891
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 891
acgcaatgaa aaggtttagg                                               20

<210> SEQ ID NO 892
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 892
aggtcacaat gtaccaaccc                                              20

<210> SEQ ID NO 893
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 893
cagtgtcaca acccaccgga                                              20

<210> SEQ ID NO 894
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 894
gaaaaatctg tacaccaccg                                              20

<210> SEQ ID NO 895
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 895
cccggactgg atcaacaccg                                              20

<210> SEQ ID NO 896
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 896
gctcgatgga tagcattcac                                              20

<210> SEQ ID NO 897
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 897
cacaccctta ctgcccgtcg                                              20

<210> SEQ ID NO 898
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 898
gaattgcaac gcccacaccg                                                   20

<210> SEQ ID NO 899
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 899
gatgtgtccc tagtctaccg                                                   20

<210> SEQ ID NO 900
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 900
tgttctagga aactacatgg                                                   20

<210> SEQ ID NO 901
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 901
acagggaaag catgggacac                                                   20

<210> SEQ ID NO 902
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 902
agaaggcagg cagagtggtg                                                   20

<210> SEQ ID NO 903
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 903
ttgtgaggca aactgaacga                                                   20

<210> SEQ ID NO 904
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 904
gcgtcgtcga cttatgactt                                              20

<210> SEQ ID NO 905
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 905
aacttcagta gcgggcgacg                                              20

<210> SEQ ID NO 906
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 906
atagaaatct gacactgccg                                              20

<210> SEQ ID NO 907
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 907
atgcagataa tccgccaaag                                              20

<210> SEQ ID NO 908
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 908
acttctgatt ggcgattctg                                              20

<210> SEQ ID NO 909
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 909
atacacaact atgatgccat                                              20

<210> SEQ ID NO 910
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      sgRNA targeting sequence

<400> SEQUENCE: 910
ccttcaataa cgttaaacag                                              20

<210> SEQ ID NO 911
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 911
acttcaaagt ccatggcaca                                              20

<210> SEQ ID NO 912
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 912
cccgggaata gcgtacagct                                              20

<210> SEQ ID NO 913
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 913
gcaaatgtag aaatgtcgtg                                              20

<210> SEQ ID NO 914
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 914
atgaggtaca gcagaaaggt                                              20

<210> SEQ ID NO 915
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 915
cagcctgctg aggatccaga                                              20

<210> SEQ ID NO 916
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      sgRNA targeting sequence

<400> SEQUENCE: 916
gaatacgaag cagaaaaggt                                              20

<210> SEQ ID NO 917
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 917
ccgctcgaag aagcactcct                                              20

<210> SEQ ID NO 918
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 918
cttcctggac atcgacgtgg                                              20

<210> SEQ ID NO 919
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 919
ggacaagaca tggagacaga                                              20

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 920
aaacaagagc acactccccg                                              20

<210> SEQ ID NO 921
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 921
acattgatac gcacactcac                                              20

<210> SEQ ID NO 922
<211> LENGTH: 20
<212> TYPE: DNA
<213> ORGANISM: Artificial Sequence
<220> FEATURE:
<223> OTHER INFORMATION: Description of Artificial Sequence: Synthetic
``` sgRNA targeting sequence

<400> SEQUENCE: 922
acctccgaat gatcaatggg                                          20

<210> SEQ ID NO 923
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 923
agcgtataat cttcgatcag                                          20

<210> SEQ ID NO 924
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 924
catgaggtag aatagttcgt                                          20

<210> SEQ ID NO 925
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 925
tatggagcgg tgtatgcccg                                          20

<210> SEQ ID NO 926
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 926
tcactgcgta cgcgtcactg                                          20

<210> SEQ ID NO 927
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 927
ctgcaccaat gttggtcacg                                          20

<210> SEQ ID NO 928
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence -continued

<400> SEQUENCE: 928
gctcaccacg ggctgcaacg                                                20

<210> SEQ ID NO 929
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 929
aagggccact tacaattagg                                                20

<210> SEQ ID NO 930
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 930
cttggtcaaa tacactacag                                                20

<210> SEQ ID NO 931
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 931
tcaggatgct gtgataagcg                                                20

<210> SEQ ID NO 932
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 932
gacaagatga caaacctggt                                                20

<210> SEQ ID NO 933
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 933
ggaaacgtgg catgtctcgg                                                20

<210> SEQ ID NO 934
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

```
<400> SEQUENCE: 934
ggacgagagc aacataaaca                                                    20

<210> SEQ ID NO 935
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 935
caaagtctgc tgtccgacct                                                    20

<210> SEQ ID NO 936
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 936
caataatgct ggtctacgtg                                                    20

<210> SEQ ID NO 937
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 937
gaagaccaaa gaagttcatg                                                    20

<210> SEQ ID NO 938
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 938
gctggggaac tcaattatag                                                    20

<210> SEQ ID NO 939
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 939
agaagccact cggactactg                                                    20

<210> SEQ ID NO 940
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 940
```

-continued gctgtgggga ctgctaaaag                                          20

<210> SEQ ID NO 941
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 941
ttacacgacc cgaatagcga                                          20

<210> SEQ ID NO 942
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 942
actaatggac tcgcacacgt                                          20

<210> SEQ ID NO 943
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 943
gtctctagca aagtccacgc                                          20

<210> SEQ ID NO 944
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 944
tggacatgag ccatatgttg                                          20

<210> SEQ ID NO 945
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 945
actcgtacag ctcctgtggt                                          20

<210> SEQ ID NO 946
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 946
cactgcgaga ccaatctaga                                                20

<210> SEQ ID NO 947
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 947
ccgagacccc aatagtgcaa                                                20

<210> SEQ ID NO 948
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 948
ctcttccaac acgtccaagt                                                20

<210> SEQ ID NO 949
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 949
atcacctgga gcatgcagga                                                20

<210> SEQ ID NO 950
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 950
gaatcctcca gaaggaatcg                                                20

<210> SEQ ID NO 951
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 951
gcactgctct cataacccat                                                20

<210> SEQ ID NO 952
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 952
tcatcttcgg agggctcaag                                                20

<210> SEQ ID NO 953
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 953
atgttgccat cgtcactgca                                              20

<210> SEQ ID NO 954
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 954
cccacgaatt cgtcacaggg                                              20

<210> SEQ ID NO 955
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 955
cggatggcca cacgtaacag                                              20

<210> SEQ ID NO 956
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 956
gtagacaaca acattcgcag                                              20

<210> SEQ ID NO 957
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 957
aagtcctaga taaagcacat                                              20

<210> SEQ ID NO 958
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 958
acagatacgg agtgtcccgt                                              20

<210> SEQ ID NO 959
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 959
cgggtattac agactaactg                                              20

<210> SEQ ID NO 960
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 960
tcttcaggag agaataccat                                              20

<210> SEQ ID NO 961
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 961
cgacgcaagt gggagcagag                                              20

<210> SEQ ID NO 962
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 962
ggccccgact cagacccgcg                                              20

<210> SEQ ID NO 963
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 963
gtgagcctga ggaacctgct                                              20

<210> SEQ ID NO 964
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 964
tagccgacag agatgtaccg                                              20

```
<210> SEQ ID NO 965
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 965
actcactctg gatagcatac                                                      20

<210> SEQ ID NO 966
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 966
atttggattt caatgtgagg                                                      20

<210> SEQ ID NO 967
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 967
tcggcttccc attctccggt                                                      20

<210> SEQ ID NO 968
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 968
tgagtatact tgaatttgag                                                      20

<210> SEQ ID NO 969
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 969
ggtattccca gcatacgaca                                                      20

<210> SEQ ID NO 970
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 970
tataccaata cgcaaatacc                                                      20

<210> SEQ ID NO 971
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 971
tatgtggagc ataaccggag                                              20

<210> SEQ ID NO 972
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 972
ttcagggtga aatacgagga                                              20

<210> SEQ ID NO 973
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 973
agggaacctc acttccaagt                                              20

<210> SEQ ID NO 974
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 974
tccctttgat gtgttccacg                                              20

<210> SEQ ID NO 975
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 975
tgatgagcag attctaactt                                              20

<210> SEQ ID NO 976
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 976
tggacctccg aaaaacatct                                              20

<210> SEQ ID NO 977
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 977
gaaaagcaag cgtaatctcc                                              20

<210> SEQ ID NO 978
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 978
ggatagacgc ccagccactg                                              20

<210> SEQ ID NO 979
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 979
tgtgatgtta gataaacaga                                              20

<210> SEQ ID NO 980
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 980
ttaatgacga gctcgtggag                                              20

<210> SEQ ID NO 981
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 981
aaacatatag tgtacctcta                                              20

<210> SEQ ID NO 982
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 982
cgatgccatt cgaatgacag                                              20

<210> SEQ ID NO 983
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      sgRNA targeting sequence

<400> SEQUENCE: 983
tccgaaccga atcatcactg                                              20

<210> SEQ ID NO 984
<211> LENGTH: 20
<212> TYPE: DNA
<213> ORGANISM: Artificial Sequence
<220> FEATURE:
<223> OTHER INFORMATION: Description of Artificial Sequence: Synthetic
      sgRNA targeting sequence

<400> SEQUENCE: 984
tgaataaatc catcagacag                                              20

<210> SEQ ID NO 985
<211> LENGTH: 20
<212> TYPE: DNA
<213> ORGANISM: Artificial Sequence
<220> FEATURE:
<223> OTHER INFORMATION: Description of Artificial Sequence: Synthetic
      Synthetic primer sequence

<400> SEQUENCE: 985
agtccgctgt tcttttcctc                                              20

<210> SEQ ID NO 986
<211> LENGTH: 23
<212> TYPE: DNA
<213> ORGANISM: Artificial Sequence
<220> FEATURE:
<223> OTHER INFORMATION: Description of Artificial Sequence: Synthetic
      Synthetic primer sequence

<400> SEQUENCE: 986
tgaggtcttt gagggatttg tag                                          23

<210> SEQ ID NO 987
<211> LENGTH: 21
<212> TYPE: DNA
<213> ORGANISM: Artificial Sequence
<220> FEATURE:
<223> OTHER INFORMATION: Description of Artificial Sequence: Synthetic
      Synthetic primer sequence

<400> SEQUENCE: 987
gtgttcctac ccccaatgtg t                                            21

<210> SEQ ID NO 988
<211> LENGTH: 24
<212> TYPE: DNA
<213> ORGANISM: Artificial Sequence
<220> FEATURE:
<223> OTHER INFORMATION: Description of Artificial Sequence: Synthetic
      Synthetic primer sequence

<400> SEQUENCE: 988
attgtcatac caggaaatga gctt                                         24

<210> SEQ ID NO 989
<211> LENGTH: 12
<212> TYPE: DNA
<213> ORGANISM: Artificial Sequence
```

```
<220> FEATURE:
<223> OTHER INFORMATION: Description of Artificial Sequence: Synthetic
      IRF2 motif consensus sequence
<220> FEATURE:
<221> NAME/KEY: modified_base
<222> LOCATION: (6)..(6)
<223> OTHER INFORMATION: a, c, g, or t
<220> FEATURE:
<221> NAME/KEY: modified_base
<222> LOCATION: (12)..(12)
<223> OTHER INFORMATION: a, c, g, or t

<400> SEQUENCE: 989
rraavnrraa vn                                                           12

<210> SEQ ID NO 990
<211> LENGTH: 12
<212> TYPE: DNA
<213> ORGANISM: Artificial Sequence
<220> FEATURE:
<223> OTHER INFORMATION: Description of Artificial Sequence: Synthetic
      IRSE motif consensus sequence
<220> FEATURE:
<221> NAME/KEY: modified_base
<222> LOCATION: (8)..(8)
<223> OTHER INFORMATION: a, c, g, or t

<400> SEQUENCE: 990
dstttcdntt yy                                                           12

<210> SEQ ID NO 991
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: I or V
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (10)..(10)
<223> OTHER INFORMATION: S or T

<400> SEQUENCE: 991

Xaa His Cys Xaa Ala Gly Xaa Xaa Arg Xaa Gly
1               5                   10

<210> SEQ ID NO 992
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
rraavwgaaa sh                                                           12

<210> SEQ ID NO 993
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
dstttcdstt tc                                                    12
```